United States Patent
Estrada et al.

(10) Patent No.: US 10,028,942 B2
(45) Date of Patent: *Jul. 24, 2018

(54) 3-SUBSTITUTED PYRAZOLES AND USES THEREOF

(71) Applicant: Genentech, Inc., South San Francisco, CA (US)

(72) Inventors: Anthony Estrada, South San Francisco, CA (US); Wen Liu, South San Francisco, CA (US); Snahel Patel, South San Francisco, CA (US); Michael Siu, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/374,047

(22) Filed: Dec. 9, 2016

(65) Prior Publication Data

US 2017/0087137 A1  Mar. 30, 2017

Related U.S. Application Data

(60) Division of application No. 14/800,829, filed on Jul. 16, 2015, now Pat. No. 9,550,777, which is a continuation of application No. PCT/EP2014/050860, filed on Jan. 17, 2014.

(60) Provisional application No. 61/754,501, filed on Jan. 18, 2013.

(51) Int. Cl.
*A61K 31/4439* (2006.01)
*A61K 31/437* (2006.01)
*A61K 31/4545* (2006.01)

(52) U.S. Cl.
CPC ........ *A61K 31/4439* (2013.01); *A61K 31/437* (2013.01); *A61K 31/4545* (2013.01)

(58) Field of Classification Search
CPC .. C07D 401/04; C07D 471/04; C07D 401/14; C07D 405/14
USPC ........................................................ 546/112
See application file for complete search history.

(56) References Cited

U.S. PATENT DOCUMENTS

| | | | |
|---|---|---|---|
| 9,365,583 B2 * | 6/2016 | Siu ...................... | C07D 401/04 |
| 2006/0046991 A1 | 3/2006 | Cui et al. | |
| 2006/0128724 A1 | 6/2006 | Cui et al. | |
| 2009/0118305 A1 | 5/2009 | Barlaam et al. | |
| 2009/0221608 A1 | 9/2009 | Cui et al. | |
| 2010/0286142 A1 | 11/2010 | Ibrahim et al. | |
| 2011/0082140 A1 | 4/2011 | Dorsch et al. | |
| 2011/0183988 A1 | 7/2011 | Ibrahim et al. | |
| 2011/0281888 A1 | 11/2011 | Mulvihill et al. | |
| 2012/0077828 A1 | 3/2012 | Axten et al. | |
| 2013/0018038 A1 | 1/2013 | Axten et al. | |
| 2014/0328805 A1 | 11/2014 | Estrada et al. | |
| 2015/0080367 A1 | 3/2015 | Cohen et al. | |
| 2015/0175619 A1 | 6/2015 | Siu et al. | |
| 2016/0046608 A1 | 2/2016 | Cohen et al. | |

FOREIGN PATENT DOCUMENTS

| | | |
|---|---|---|
| JP | 2011-530485 | 12/2011 |
| WO | 95/34563 | 12/1995 |
| WO | 03/008412 | 1/2003 |
| WO | 2009/146343 | 12/2009 |
| WO | 2011/138751 | 11/2011 |
| WO | 2011/149950 A2 | 12/2011 |
| WO | 2012/158413 | 11/2012 |

OTHER PUBLICATIONS

Agid; Nature Reviews Drug Discovery 2007, 6, 189-201.*
Bloom; Genes & Development 2007, 21, 2593-2606.*
Brinkmann; Nature Reviews Drug Discovery 2010, 9, 883-897.*
Chen; Journal of Neuroscience 2008, 28, 672-680.*
Chico; Nature Reviews Drug Discovery 2009, 8, 892-909.*
Cook; Nature 2012, 483, 213-217.*
Fan; The Journal of Biological Chemistry 1996, 271, 24788-24793.*
Ferraris; Future Med. Chem. 2013, 5, 1923-1934 (Oct. 2013).*
Hirai; Journal of Neuroscience 2006, 26, 11992-12002.*
Huntwork-Rodriguez; The Journal of Cell Biology, 2013, 202, 747-763.*
Itoh; Biochemical and Biophysical Research Communications 2009, 383, 258-262.*
Judge; Pharmacology & Therapeutics 2006, 111, 224-259.*
Sengupta; The Journal of Cell Biology, 2011, 194, 751-764.*
Shin; Neuron, 2012, 74, 1015-1022.*

(Continued)

*Primary Examiner* — Daniel R Carcanague
(74) *Attorney, Agent, or Firm* — Jonathan Duffield

(57) ABSTRACT

The present invention provides for compounds of Formula (I) and various embodiments thereof, and compositions comprising compounds of Formula (I) and various embodiments thereof.

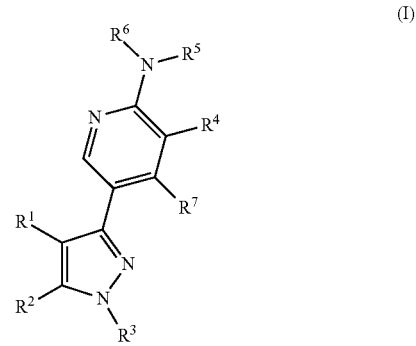

(I)

In compounds of Formula I, the groups $R^1$, $R^2$, $R^3$, $R^4$, $R^5$, $R^6$ and $R^7$ have the meaning as described herein. The present invention also provides for methods of using compounds of Formula I and compositions comprising compounds of Formula (I) as DLK inhibitors and for treating neurodegeneration diseases and disorders.

69 Claims, No Drawings

(56) References Cited

OTHER PUBLICATIONS

Welsbie; PNAS, 2013, 110, 4045-4050.*
Zakrzewska; Postgraduate Medical Journal, 2011, 87, 410-416.*
Patel; J. Med. Chem., 2017, 60, 8083-8102.*
Curtin et al., "Thienopyridine ureas as dual inhibitors of the VEGF and Aurora kinase families" Bioorganic & Medicinal Chemistry Letters 22:3208-3212 ( 2012).
International Search Report issued in International Application No. PCT/EP2014/050860, dated Mar. 3, 2014, in 2 pages.
Palmer et al., "Structural modifications of a 3-methoxy-2-aminopyridine compound to reduce potential for mutagenicity and time-dependent drug-drug interaction" Bioorganic & Medicinal Chemistry Letters 22:7605-7609 ( 2012).
Torti et al., "Epithelial Tissue Hyperplasia Induced by the RAF Inhibitor PF-04880594 is Attenuated by a Clinically Well-Tolerated Dose of the MEK Inhibitor PD-0325901" Molecular Cancer Therapeutics 11(10):2274 ( 2012).

* cited by examiner

3-SUBSTITUTED PYRAZOLES AND USES THEREOF

CROSS-REFERENCE TO RELATED APPLICATIONS

This application is a divisional application of U.S. patent application Ser. No. 14/800,829, filed on Jul. 16, 2015, which is a continuation application of International Application No. PCT/EP2014/050860, filed on Jan. 17, 2014, which claims priority to U.S. Patent Application No. 61/754,501, filed on Jan. 18, 2013, the entire contents of which are incorporated herein by reference.

FIELD OF THE INVENTION

The present invention relates to organic compounds useful for therapy and/or prophylaxis in a mammal, and in particular to inhibitors of DLK useful for treating neurodegeneration diseases and disorders.

BACKGROUND OF THE INVENTION

Neuron or axon degeneration plays a central role in the proper development of the nervous system and is a hall mark of many neurodegenerative diseases including for example, amyotrophic lateral sclerosis (ALS), glaucoma, Alzheimer's disease, and Parkinson's disease, as well a traumatic injury to the brain and spinal cord. Recent patent publication WO2011/050192, incorporated herein by reference, describes the role of the Dual Leucine Zipper Kinase (DLK), also referred to as MAP3K12, to cause neuronal cell death. Neurodegenerative diseases and injuries are devastating to patients and caregivers, and also result in great financial burdens, with annual costs currently exceeding several hundred billion dollars in the United States alone. Most current treatments for these diseases and conditions are inadequate. Adding to the urgency of the problems created by these diseases is the fact that many such diseases are age related, and thus their incidence is increasing rapidly as population demographics change. There is a great need for the development of effective approaches to treating neurodegenerative diseases and nervous system injuries, including for example, through the inhibitors of DLK in neurons.

SUMMARY OF THE INVENTION

In one aspect the present invention provides for novel compounds. In a first embodiment of such compounds (Embodiment 1; abbreviated as "E1") the invention provides for compounds of Formula I

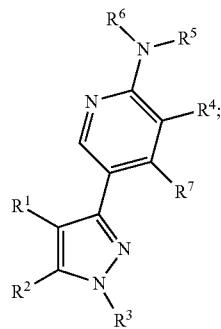

(I)

and salts thereof; wherein in Formula (I)
$R^1$ is selected from the group consisting of hydrogen, —F, —Cl, —Br, —I, —NO$_2$, —CN, $C_{1-12}$ alkyl and $C_{1-12}$ haloalkyl;
$R^2$ is selected from the group consisting of 3 to 12 membered cycloalkyl, C-linked 3 to 12 membered heterocycloalkyl, and —C($R^{A2}$)($C_{1-6}$(halo)alkyl)$_2$, wherein $R^{A2}$ is hydrogen, —F, —Cl, —Br, —I, —CN, —OH, —NH$_2$, —SF$_5$, —OSF$_5$, $C_{1-12}$ alkylthio, $C_{1-12}$ alkoxy, $C_{1-12}$ alkylamino and $C_{1-12}$ dialkylamino; and wherein $R^2$ is optionally substituted 1 to 5 $R^{2-A}$ substituents selected from the group consisting of $C_{1-12}$ alkyl, $C_{1-12}$ haloalkyl, $C_{1-12}$ heteroalkyl, $C_{2-12}$ alkenyl, $C_{2-12}$ alkynyl, —F, —Cl, —Br, —I, —$(X^2)_{0-1}$—CN, —$(X^2)_{0-1}$—NO$_2$, —$(X^2)_{0-1}$—SF$_5$, —$(X^2)_{0-1}$—OSF$_5$, —$(X^2)_{0-1}$—OR$^{2A}$, —$(X^2)_{0-1}$—N(R$^{2A}$)$_2$, —$(X^2)_{0-1}$—SR$^{2A}$, —$(X^2)_{0-1}$-CF$_3$, 3 to 12 membered cycloalkyl-$(X^2)_{0-1}$—, 3 to 12 membered heterocycloalkyl-$(X^2)_{0-1}$—, 5 to 6 membered heteroaryl-$(X^2)_{0-1}$—, phenyl-$(X^2)_{0-1}$—, —$(X^2)_{0-1}$—C(═O)N(R$^{2A}$)(R$^{2A}$), —$(X^2)_{0-1}$—C(═O)OR$^{2A}$, —$(X^2)_{0-1}$—N(R$^{2A}$)C(═O) (R$^{2A}$, —$(X^2)_{0-1}$—N(R$^{2A}$)C(═O)OR$^{2A}$, —$(X^2)_{0-1}$—S (═O)$_{1-2}$—R$^{2A}$, —$(X^2)_{0-1}$—N(R$^{2A}$)S(═O)$_{1-2}$—R$^{2A}$, —$(X^2)_{0-1}$—S(═O)$_{1-22}$N(R$^{2A}$)$_2$, —$(X^2)_{0-1}$—C(═O) R$^{2A}$, —$(X^2)_{0-1}$—C(═NOR$^{2A}$)R$^{2A}$, —$(X^2)_{0-1}$—N(R$^{2A}$) C(═O)N(R$^{2A}$)$_2$ and —$(X^2)_{0-1}$—OC(═O)R$^{2A}$, —$(X^2)_{0-1}$—OP(═O)(OR$^{2A}$)$_2$, —$(X^2)$—SC(═O)OR$^{2A}$ and —$(X^2)$—SC(═O)N(R$^{2A}$)$_2$; wherein $X^2$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{2A}$ at each occurrence is each independently selected from the group consisting of hydrogen, $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl, 3-7 membered heterocycloalkyl, 3-7 membered heterocycloalkyl-$C_{1-4}$ alkyl, 5-6 membered heteroaryl, 5-6 membered heteroaryl-$C_{1-4}$ alkyl, phenyl and phenyl-$C_{1-4}$ alkyl, or any two $R^{2A}$ groups attached to the same nitrogen atom are optionally combined to form a 3 to 6 membered heterocyclic ring comprising 1 to 2 additional heteroatom selected from N, O and S; and wherein a $R^{2-A}$ substituent at each occurrence is independently optionally further substituted with 1 to 5 $R^{2A-1}$ substituents selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ dialkylamino;
$R^3$ is selected from the group consisting of $C_{1-12}$ alkyl-, $C_{1-12}$ haloalkyl-, $C_{1-12}$ heteroalkyl-$(L)_{0-1}$, $C_{2-12}$ alkenyl-$(L)_{0-1}$, $C_{2-12}$alkynyl-$(L)_{0-1}$, 3 to 12 membered cycloalkyl-$(L)_{0-1}$-, 3 to 12 membered heterocycloalkyl-$(L)_{0-1}$, wherein L is selected from the group consisting of $C_{1-4}$ alkylene, $C_{1-4}$ haloalkylene, $C_{1-4}$ heteroalkylene, $C_{2-4}$ alkenylene, $C_{2-4}$ alkynylene, —C(═O)—, —C(═O)—N(H)—, —C(═O)N($C_{1-6}$ alkyl)-, —C(═O)O—, —S(O)$_{1-2}$- and —S(O)$_{1-2}$—N(H)—; wherein a $R^3$ group is optionally further substituted with 1 to 5 $R^{3A}$ substituents selected from the group consisting of —F, —Cl, —Br, —I, —OH, —CN, —NO$_2$, —SF$_5$, —OSF$_5$, —NH$_2$, $C_{1-6}$ alkyl, $C_{1-6}$ haloalkyl, 3 to 5 membered cycloalkyl, 3 to 5 membered heterocycloalkyl, $C_{1-6}$ alkoxy, $C_{1-6}$ alkylthio, $C_{1-6}$ alkylamino and $C_{1-6}$ dialkylamino;
$R^4$ is selected from the group consisting of $C_{1-12}$ alkyl, $C_{1-12}$ haloalkyl, $C_{2-12}$ alkenyl, $C_{2-12}$ alkynyl, —F, —Cl, —Br, —I, —$(X^4)_{0-1}$—CN, —$(X^4)_{0-1}$—NO$_2$, —$(X^4)_{0-1}$—SF$_5$, —$(X^4)_{0-1}$—OSF$_5$, —$(X^4)_{0-1}$—OR$^{4A}$, —$(X^4)_{0-1}$—$N(R^{4A})_2$, —$(X^4)_{0-1}$—$SR^{4A}$, —$(X^4)_{0-1}$-$CF_3$, 3 to 7 membered cycloalkyl-$(X^4)_{0-1}$—, 3 to 7 membered heterocycloalkyl-$(X^4)_{0-1}$—, 5 to 6 membered heteroaryl-$(X^4)_{0-1}$—, phenyl-$(X^4)_{0-1}$—, —$(X^4)_{0-1}$—C(=O)N($R^{4A}$)($R^{4A}$), —$(X^4)_{0-1}$—C(=O)O$R^{4A}$, —$(X^4)_{0-1}$—N($R^{4A}$)C(=O)($R^{4A}$, —$(X^4)_{0-1}$—N($R^{4A}$)C(=O)O$R^{4A}$, —$(X^4)_{0-1}$—S(=O)$_{1-2}$—$R^{4A}$, —$(X^4)_{0-1}$—N($R^{4A}$)S(=O)$_{1-2}$—$R^{4A}$, —$(X^4)_{0-1}$—S(=O)$_{1-2}$N($R^{4A}$)$_2$, —$(X^4)_{0-1}$—C(=O)$R^{4A}$, —$(X^4)_{0-1}$—C(=NO$R^{4A}$)$R^{4A}$, —$(X^4)_{0-1}$—N($R^{4A}$)C(=O)N($R^{4A}$)$_2$, —$(X^4)_{0-1}$—OC(=O)$R^{4A}$, —$(X^4)_{0-1}$—OP(=O)(O$R^{4A}$)$_2$, —$(X^4)$—SC(=O)O$R^{4A}$ and —$(X^4)$—SC(=O)N($R^{4A}$)$_2$, $X^4$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{4A}$ at each occurrence is each independently selected from the group consisting of hydrogen, $C_{1-6}$ alkyl, $C_{1-6}$ haloalkyl and $C_{1-6}$ heteroalkyl, or any two $R^{4A}$ groups attached to the same nitrogen atom are optionally combined to form a 3 to 6 membered heterocyclic ring comprising 1 to 2 additional heteroatom selected from N, O and S; and wherein a $R^4$ group is independently optionally further substituted with 1 to 5 $R^{4A-1}$ substituents selected from the group consisting of —F, —Cl, —Br, —I, —OH, —CN, —NO$_2$, —SF$_5$, —NH$_2$, $C_{1-6}$ alkoxy, $C_{1-6}$ alkylamino and $C_{1-6}$ dialkylamino;

$R^5$ and $R^6$ are each independently selected from the group consisting of hydrogen, $C_{1-12}$ alkyl, and $C_{1-12}$ haloalkyl; and in the alternative $R^4$ and $R^5$ are combined to form a 5 to 7 membered heteroaryl or 5 to 7 membered heterocycloalkyl ring optionally comprising 1 additional heteroatom selected from N, O and S, and wherein said 5 to 7 membered heteroaryl or 5 to 7 membered heterocycloalkyl ring is further optionally substituted with 1 to 3 $R^{4/5cy}$ substituents selected from the group consisting of $C_{1-12}$ alkyl, $C_{1-12}$ haloalkyl, $C_{2-12}$ alkenyl, $C_{2-12}$ alkynyl, —F, —Cl, —Br, —I, —$(X^{4/5})_{0-1}$—CN, —$(X^{4/5})_{0-1}$—NO$_2$, —$(X^{4/5})_{0-1}$—SF$_5$, —$(X^{4/5})_{0-1}$—OSF$_5$, —$(X^{4/5})_{0-1}$—O$R^{45A}$, —$(X^{4/5})_{0-1}$—N($R^{45A}$)$_2$, —$(X^{4/5})_{0-1}$—S$R^{45A}$, —$(X^{4/5})_{0-1}$—CF$_3$, 3 to 12 membered cycloalkyl-$(X^{4/5})_{0-1}$—, 3 to 12 membered heterocycloalkyl-$(X^{4/5})_{0-1}$—, 5 to 6 membered heteroaryl-$(X^{4/5})_{0-1}$—, phenyl-$(X^{4/5})_{0-1}$—, —$(X^{4/5})_{0-1}$—C(=O)N($R^{45A}$)($R^{45A}$), —$(X^{4/5})_{0-1}$—C(=O)O$R^{45A}$, —$(X^{4/5})_{0-1}$—N($R^{45A}$)C(=O)($R^{45A}$), —$(X^{4/5})_{0-1}$—N($R^{45A}$)C(=O)O$R^{45A}$, —$(X^{4/5})_{0-1}$—S(=O)$_{1-2}$—$R^{45A}$, —$(X^{4/5})_{0-1}$—N($R^{45A}$)S(=O)$_{1-2}$—$R^{45A}$, —$(X^{4/5})_{0-1}$—S(=O)$_{1-2}$N($R^{45A}$)$_2$, —$(X^{4/5})_{0-1}$—C(=O)$R^{45A}$, —$(X^{4/5})_{0-1}$—C(=NO$R^{45A}$)$R^{45A}$, —$(X^{4/5})_{0-1}$—N($R^{45A}$)C(=O)N($R^{45A}$)$_2$ and —$(X^{4/5})_{0-1}$—OC(=O)$R^{45A}$, —$(X^{4/5})_{0-1}$—OP(=O)(O$R^{45A}$)$_2$, —$(X^{4/5})$—SC(=O)O$R^{45A}$ and —$(X^{4/5})$—SC(=O)N($R^{45A}$)$_2$, $X^{4/5}$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{45A}$ at each occurrence is each independently selected from the group consisting of hydrogen, $C_{1-6}$ alkyl, $C_{1-6}$ haloalkyl and $C_{1-6}$ heteroalkyl; or any two $R^{45A}$ groups attached to the same nitrogen atom are optionally combined to form a 3 to 6 membered heterocyclic ring comprising 1 to 2 additional heteroatom selected from N, O and S; and wherein a $R^{4/5cy}$ substituent at each occurrence is independently optionally further substituted with 1 to 5 $R^{4/5cy-1}$ substituents selected from the group consisting of —F, —Cl, —Br, —I, —OH, —CN, —NO$_2$, —SF$_5$, —NH$_2$, $C_{1-6}$ alkoxy, $C_{1-6}$ alkylamino and $C_{1-6}$ dialkylamino; and $R^7$ is hydrogen, or in the alternative $R^4$ and $R^7$ are optionally combined to form a 5 to 7 membered heteroaryl or 5 to 7 membered heterocycloalkyl ring optionally comprising 1 additional heteroatom selected from N, O and S.

Further embodiments (E) of the first embodiment of compounds of the invention, are described below.

E2 A compound of E1, wherein $R^5$ and $R^6$ are each H.

E3 A compound of E1 or E2, wherein $R^4$ is selected from the group consisting of $C_{1-12}$ alkyl, $C_{1-12}$ haloalkyl, —F, —Cl, —$(X^4)_{0-1}$—CN, —$(X^4)_{0-1}$—O$R^{4A}$, —$(X^4)_{0-1}$-S$R^{4A}$, 3 to 7 membered cycloalkyl-$(X^4)_{0-1}$—, —$(X^4)_{0-1}$—S(=O)$_{1-2}$—$R^{4A}$ and is further optionally substituted.

E4 A compound of any one of E1-E3, wherein $R^4$ is selected from the group consisting of —F, —Cl, $C_{1-4}$ alkyl, $C_{1-4}$ haloalkyl, —($C_{1-4}$ alkylene)$_{01}$-CN, $C_{1-4}$ alkyloxy, $C_{1-4}$ haloalkyloxy, $C_{1-4}$ alkylthio, $C_{1-4}$ haloalkylthio, 3 to 5 membered cycloalkyl-($C_{1-4}$ alkyloxy)-, 3 to 6 membered cycloalkyl, and ($C_{1-4}$ alkyl)-S(O)$_2$—, wherein $R^4$ is further optionally substituted.

E5 A compound of any one of E1-E4, wherein $R^4$ is selected from the group consisting of —F, Cl, —CN, methyl, monofluoromethyl, difluoromethyl, trifluoromethyl, ethyl, 2-fluoroeth-1-yl, 1-fluoroeth-1-yl, 2,2-difluoroeth-1-yl, 1,2-difluoroeth-1-yl, 1,1-difluoroeth-1-yl, 2,2,2-trifluoroeth-1-yl, 1,2,2-trifluoroeth-1-yl, 1,1,2-trifluoroeth-1-yl, methoxy, monofluoromethoxy, difluoromethoxy, trifluoromethoxy, 2-fluoroethan-1-oxy, 2,2-difluoroethan-1 oxy, 1,2-difluoroethan-1-oxy, 1,1-difluoroethan-1-oxy, 2,2,2-trifluoroethan-1-oxy, 1,2,2-trifluoroethan-1-oxy, 1,1,2-trifluoroethan-1-oxy, isopropoxy, 1-fluoro-propan-2-oxy, 1,1-difluoro-propan-2-oxy, 1,3-difluoro-propan-2-oxy, 1,1,1-trifluoro-propan-2-oxy, 1,1,3-trifluoro-propan-2-oxy, 1,1,1,3,3,3-hexafluoro-propan-2-oxy, monofluoromethylthio, difluoromethylthio, trifluromethylthio, cyclopropylmethoxy and cyclopropyl.

E6 A compound of E1, wherein $R^6$ is H; and $R^4$ and $R^5$ are combined to form a 5 to 7 membered ring selected from the group consisting of pyrrole, imidazole, pyrazole, pyrrolidone, pyrrolidine, morpholine, piperdine and piperazine, wherein $R^4$ and $R^5$ combined are optionally substituted with 1 to 3 $R^{4/5cy}$ substituents.

E7 A compound of E1 or E6, wherein $R^{4/5cy}$ is selected from the group consisting of $C_{1-12}$ alkyl, $C_{1-12}$ haloalkyl, —F, —Cl, —$(X^{4/5})_{0-1}$—CN, —$(X^{4/5})_{0-1}$-O$R^{45A}$, 3 to 7 membered cycloalkyl-$(X^{4/5})_{0-1}$, —$(X^{4/5})_{0-1}$—S(=O)$_{1-2}$—$R^{45A}$, wherein $R^{4/5cy}$ is optionally substituted with 1 to 3 $R^{4/5cy-1}$ substituents.

E8 A compound of E1, E6 or E7, wherein $R^{4/5cy}$ is selected from the group consisting of —F, —Cl, $C_{1-4}$ alkyl, $C_{1-4}$ haloalkyl, —($C_{1-4}$ alkylene)$_{0-1}$-CN, $C_{1-4}$ alkyloxy, $C_{1-4}$ haloalkyloxy, $C_{1-4}$ alkylthio, $C_{1-4}$ haloalkylthio, 3-6 membered cycloalkyl-($C_{1-4}$ alkyloxy)-, 3 to 6 membered cycloalkyl, and ($C_{1-4}$ alkyl)-S(O)$_2$—, wherein $R^{4/5cy}$ is optionally substituted with 1 to 5 $R^{4/5cy-1}$ substituents.

E9 A compound of E1, E6, E7 or E8, wherein $R^{4/5cy}$ is selected from the group consisting of —F, Cl, —CN, methyl, monofluoromethyl, difluoromethyl, trifluoromethyl, ethyl, 2-fluoroeth-1-yl, 1-fluoroeth-1-yl, 2,2-difluoroeth-1-yl, 1,2-difluoroeth-1-yl, 1,1-difluoroeth-1-yl, 2,2,2-trifluoroeth-1-yl, 1,2,2-trifluoroeth-1-yl, 1,1,2-trifluoroeth-1-yl, methoxy, monofluoromethoxy, difluoromethoxy, trifluoromethoxy, 2-fluoroethan-1-oxy, 2,2-difluoroethan-1 oxy, 1,2-difluoroethan-1-oxy, 1,1-difluoroethan-1-oxy, 2,2,2-trifluoroethan-1-oxy, 1,2,2-trifluoroethan-1-oxy, 1,1,2-trifluoroethan-1-oxy, isopropoxy, 1-fluoro-propan-2-oxy, 1,1-difluoro-propan-2-oxy, 1,3-difluoro-propan-2-oxy, 1,1,1-trifluoro-propan-2-oxy, 1,1,3-trifluoro-propan-2-oxy, 1,1,1,3,3,3-hexafluoro-propan-2-oxy, monofluoromethylthio, difluoromethylthio, trifluromethylthio, cyclopropylmethoxy and cyclopropyl.

E10 A compound of any one of E1-E9, wherein $R^1$ is selected from the group consisting of hydrogen, $C_{1-4}$ alkyl and $C_{1-4}$ haloalkyl.

E11 A compound of any one of E1-E10, wherein $R^1$ is hydrogen, monofluoromethyl, difluoromethyl, trifluormethyl and methyl.

E12 A compound of any one of E1-E11, wherein $R^1$ is hydrogen.

E13 A compound of any one of E1-E12, wherein $R^2$ is a fused or bridged 3 to 12 membered cycloalkyl or a fused or bridged bicyclic or tricyclic C-linked 3 to 12 membered heterocycloalkyl ring, wherein $R^2$ is optionally substituted with 1-5 $R^{2-A}$ substituents.

E14 A compound of any one of E1-E13, wherein $R^2$ is selected from the group consisting of 3-azabicyclo[3.1.0]hexane, 3-azabicyclo[3.2.1]octane, 3-azabicyclo[3.1.1]heptane, 1,1a,5,5a-tetrahydro-4a-aza-cyclopropa[a]pentalene, 1,1a,5,5a-tetrahydro-2,4a-diaza-cyclopropa[a]pentalene, 1,1a,5,5a-tetrahydro-3,4a-diaza-cyclopropa[a]pentalene, 1,1a,5,5a-tetrahydro-2,3,4a-triaza-cyclopropa[a]pentalene, 1,1a,5,5a-tetrahydro-4,4a-diaza-cyclopropa[a]pentalene, octahydro-4a-aza-cyclopropa[a]pentalene, 3-oxabicyclo[3.2.1]octane, 3-oxabicyclo[3.1.1]heptane and 3-oxabicyclo[3.1.0]hexane, and wherein $R^2$ is optionally substituted with 1 to 5 $R^{2-A}$ substituents.

E15 A compound of any one of E1-E14, wherein $R^2$ is selected from the group consisting of

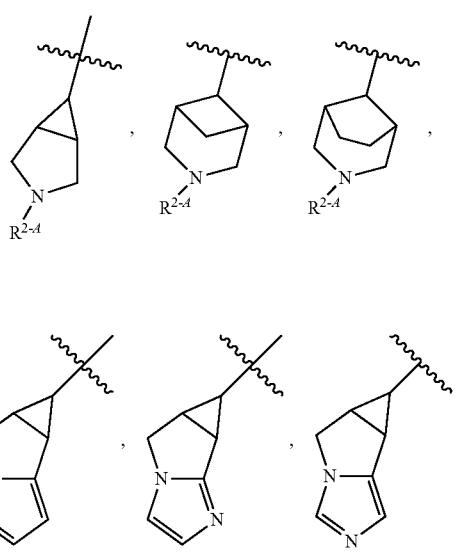

E16 A compound of any one of E1-E15, wherein $R^2$ is selected from the group consisting of

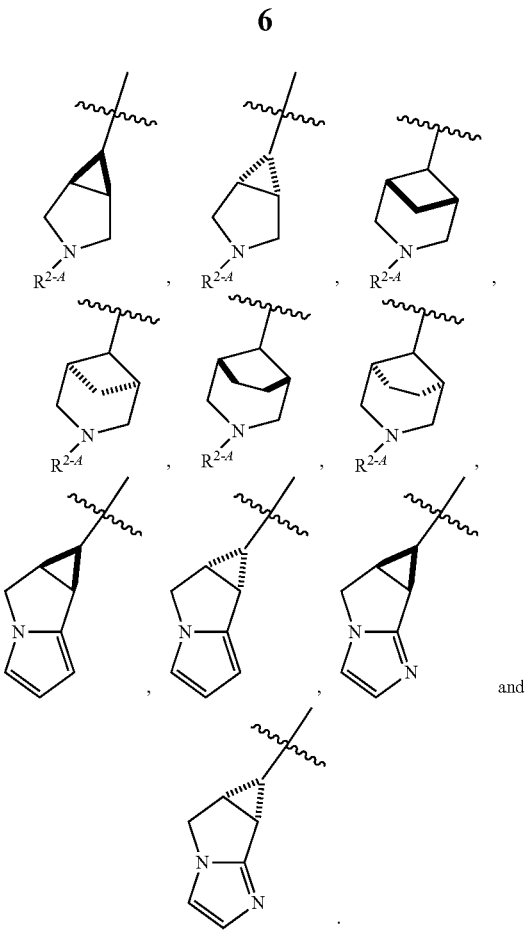

and

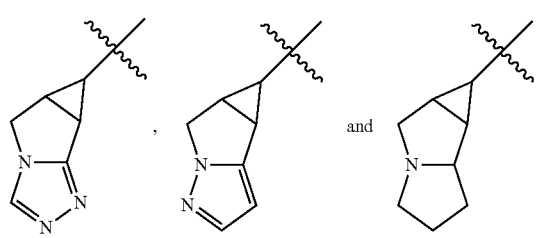

E17 A compound of any one of E1-E12, wherein $R^2$ is a monocyclic ring, wherein $R^2$ is optionally substituted with 1 to 5 $R^{2-A}$ substituents.

E18 A compound of any one of E1-E12 or E17, wherein $R^2$ is a monocyclic ring selected from the group consisting of azetidine, pyrrolidine, pyrrolidone, piperidine, piperidone, azepane, azepanone, tetrahydrofuran, tetrahydrofuranone, tetrahydropyan, tetrahydropyanone, oxetane, oxetanone, oxepane and oxepanone, wherein $R^2$ is optionally substituted with 1 to 5 $R^{2-A}$ substituents and wherein $R^{2-A}$ is further optionally substituted.

E19 A compound of any one of E1-E12, E17 or E18, wherein $R^2$ is selected from the group consisting of

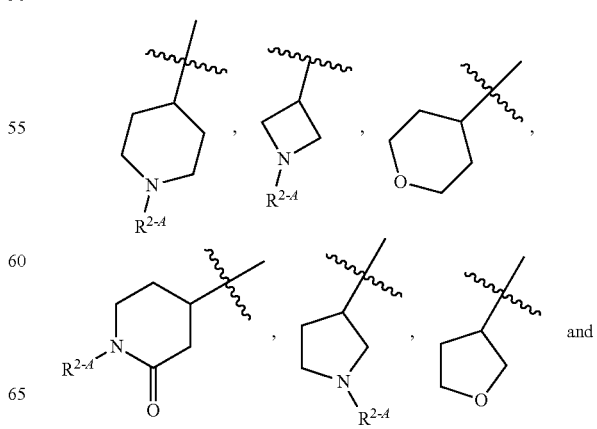

and

E20 A compound of any one of E1-E19, wherein $R^{2-A}$ is selected from the group consisting of $C_{1-12}$ alkyl, $C_{1-12}$ haloalkyl, $C_{1-12}$ heteroalkyl, $-(X^2)_{0-1}-CN$, $-(X^2)_{0-1}-OR^{2A}$, 3 to 12 membered cycloalkyl-$(X^2)_{0-1}-$, 3 to 12 membered heterocycloalkyl-$(X^2)_{0-1}-$, $-(X^2)_{0-1}-S(=O)_{1-2}-R^{2A}$ and $-(X^2)_{0-1}-C(=O)R^{2A}$, wherein $R^{2-A}$ is optionally substituted.

E21 A compound of any one of E1-E20, wherein $R^{2-A}$ is selected from the group consisting of OH, ($C_{1-6}$ alkyl)-C(=O)—, ($C_{1-6}$ alkyl)-S(=O)$_2$—, oxepane, azetidine, $C_{1-6}$ alkyl, $C_{1-6}$ haloalkyl, $C_{1-6}$ heteroalkyl and —($C_{1-6}$ alkyl)-CN, wherein $R^{2-A}$ is optionally substituted.

E22 A compound of any one of E1-E21, wherein $R^{2-A}$ is selected from the group consisting of $CH_3-C(=O)-$, oxetanyl, methyl, monofluoromethyl, difluoromethyl, trifluoromethyl, ethyl, 2-fluoroeth-1-yl, 1-fluoroeth-1-yl, 1,2-difluoroeth-1-yl, 2,2-difluoroeth-1-yl, 1,1,2-trifluoroeth-1-yl 2,2,2-trifluoroeth-1-yl, 1,2,2-trifluoroeth-1-yl, cyanomethyl, cyanoethyl, methoxyethyl, hydroxy, $(CH_3)_2(OH)CC(H)_2-$, $CH_3OCH_2C(H)(CH_3)-$, $CH_3OC(CH_3)_2CH_2-$, $NCC(H)(CH_3)CH_2-$, $NCC(H)(CH_3)_2CH_2-$, $CH_3OC(H)(CH_3)CH_2-$, $NCCH_2C(H)(CH_3)-$, $NCCCH_2C(CH_3)_2-$, $CH_3-S(O)_2-$ and isopropyl-OC(=O)—.

E23 A compound of any one of E1-E12, wherein $R^2$ is $-C(R^{A2})(C_{1-6}$ alkyl$)_2$, wherein $R^{A2}$ is hydrogen, —F, —Cl, —Br, —I, —CN, —OH, —NH$_2$, —SF$_5$, —OSF$_5$, $C_{1-4}$ alkylthio, $C_{1-4}$ alkoxy, $C_{1-4}$ alkylamino and $C_{1-4}$ dialkylamino and wherein $R^2$ is optionally substituted with 1 to 5 $R^{2-A}$ substituents.

E24 A compound of any one of E1-E23, wherein $R^3$ is selected from the group consisting of $C_{1-6}$ alkyl, 3 to 6 membered cycloalkyl-$C_{1-4}$ alkyl, 3 to 6 membered cycloalkyl, 3 to 6 membered heterocycloalkyl-$C_{1-4}$ alkyl, and 3-6 membered heterocycloalkyl, wherein $R^3$ is optionally substituted with $R^{3A}$.

E25 A compound of any one of E1-E24, wherein $R^3$ is selected from the group consisting of methyl, monofluoromethyl, difluoromethyl, ethyl, 1,1,1-trifluoroeth-2-yl, propyl, isopropyl, butyl, sec-butyl, tert-butyl, cyclopropyl, cyclopropylmethyl, cyclobutyl, cyclobutylmethyl, cyclopentyl, cyclopentylmethyl, cyclohexyl, cyclohexylmethyl, 1,1-difluorocyclobut-3-yl, 1,1-difluorocyclopent-3-yl, oxetan-2-yl, oxetan-2-yl-methyl, oxetan-3-yl, oxetan-3-yl-methyl, tetrahydrofuran-3-yl, tetrahydrofuran-3-yl-methyl, tetrahydropyran-3-yl, tetrahydropyran-3-yl-methyl, tetrahydropyran-4-yl, tetrahydropyran-4-yl-methyl, azetindin-3-yl, azetindin-3-yl-methyl, pyrrolidin-3-yl, pyrrolidin-3-yl-methyl, piperidin-4yl, piperidin-4-yl-methyl, piperidin-3-yl and piperidin-3-yl-methyl.

E26 A compound of E1, E2, E3, E4, E5, E10, E11, E12, E20, E21, E22, E23, E24 or E25, wherein said compound has a formula selected from the group consisting of:

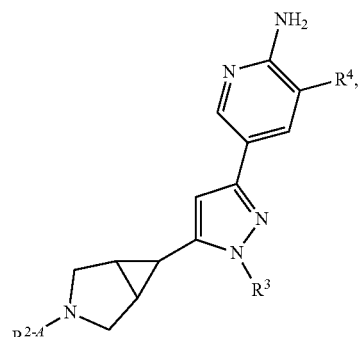

(II-a)

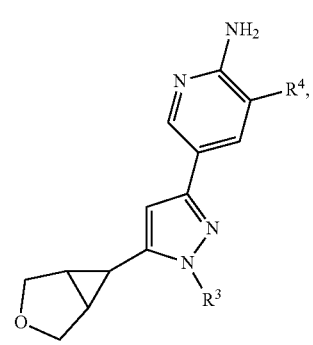

(II-b)

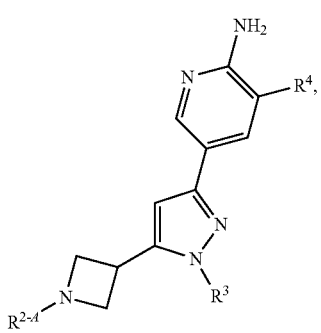

(II-c)

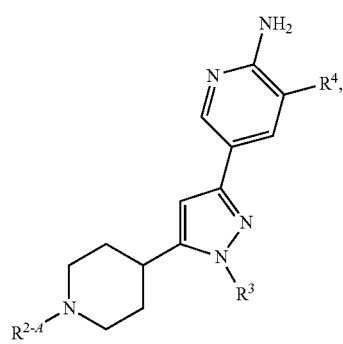

(II-d

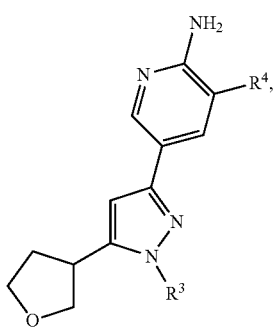
(II-e)
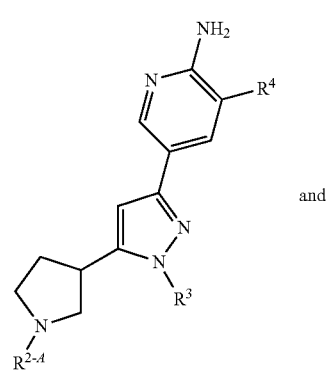
(II-f)
and
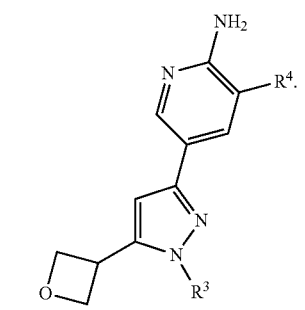
(II-g)
E27 A compound of E1, E6, E7, E8, E9, E10, E11, E20, E21, E22, E23, E24 or E25, wherein said compound has the formula selected from the group consisting of
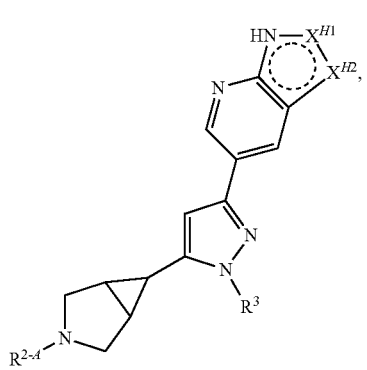
(III-a)
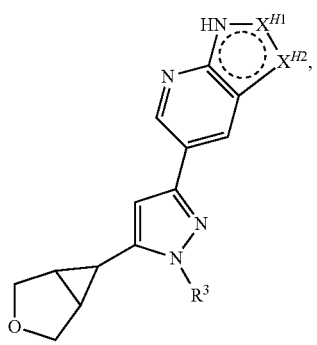
(III-b)
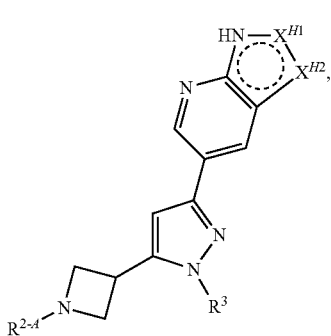
(III-c)
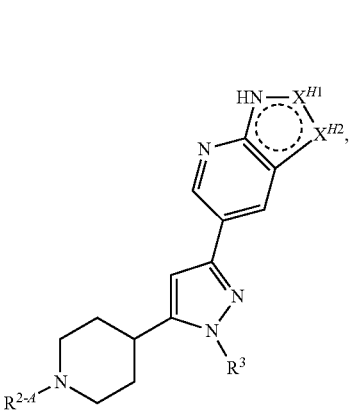
(III-d)
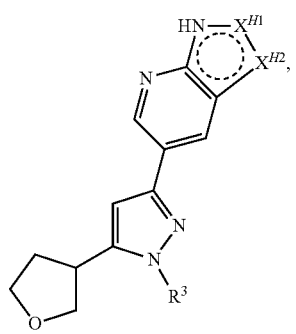
(III-e)

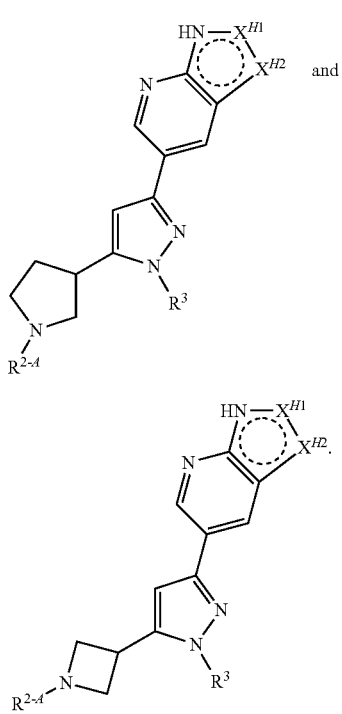

wherein in formula III-a, III-b, III-c, III-d, III-e, III-f and III-g, $X^{H1}$ and $X^{H2}$ at each occurrence is independently selected from the group consisting of N, NH, $N(R^{4/5cy})$, CH or $C(R^{4/5cy})$.

E28 A compound of E27, wherein $X^{H1}$ and $X^{H2}$ are independently CH or $C(R^{4/5cy})$.

E29 A compound of claim E1, selected from the group consisting of compounds set forth in Table 1 presented herein.

E30 A compound of claim E1, wherein
$R^1$ is hydrogen;
$R^2$ is selected from the group consisting of C-linked 3 to 12 membered heterocycloalkyl and —$C(R^{A2})(C_{1-6}(\text{halo})$alkyl$)_2$, wherein $R^{A2}$ is hydrogen, —CN or —OH; and wherein $R^2$ is optionally substituted by 1 to 5 $R^{2-A}$ substituents selected from the group consisting of $C_{1-2}$ alkyl, —$(X^2)_{0-1}$—CN, —$(X^2)_{0-1}$—$OR^{2A}$, 3 to 12 membered cycloalkyl-$(X^2)_{0-1}$—, 3 to 12 membered heterocycloalkyl-$(X^2)_{0-1}$—, —$(X^2)_{0-1}$—$S(=O)_{1-2}$—$R^{2A}$ and —$(X^2)_{0-1}$—$C(=O)R^{2A}$, wherein $X^2$ is $C_{1-4}$ alkylene and wherein $R^{2A}$ at each occurrence is each independently selected from the group consisting of hydrogen, $C_{1-6}$ alkyl and $C_{1-6}$ haloalkyl;
$R^3$ is 3 to 12 membered heterocycloalkyl-$(L)_{0-1}$-, wherein L is $C_{1-4}$ alkylene; wherein a $R^3$ group is optionally further substituted 3 to 5 membered heterocycloalkyl;
$R^4$ is selected from the group consisting of $C_{1-12}$ alkyl, $C_{1-12}$ haloalkyl, —F, —Cl, —$(X^4)_{0-1}$—CN, —$(X^4)_{0-1}$—$OR^{4A}$, 3 to 7 membered cycloalkyl-$(X^4)_{0-1}$-and —$(X^4)_{0-1}$—$S(=O)_{1-2}$—$R^{4A}$, wherein $X^4$ is $C_{1-4}$ heteroalkylene, $R^{4A}$ at each occurrence is each independently selected from the group consisting of $C_{1-6}$ alkyl and $C_{1-6}$ haloalkyl;
$R^5$ and $R^6$ are each independently hydrogen;
in the alternative $R^4$ and $R^5$ are combined to form a 5 to 7 membered heteroaryl or 5 to 7 membered heterocycloalkyl ring optionally comprising 1 additional heteroatom selected from N and O, and wherein said 5 to 7 membered heteroaryl or 5 to 7 membered heterocycloalkyl ring is further optionally substituted with 1 to 3 $R^{4/5cy}$ substituents selected from the group consisting of $C_{1-12}$ alkyl, $C_{1-12}$ haloalkyl, —F, —Cl and —$(X^{4/5})_{0-1}$—CN; and
$R^7$ is hydrogen,
or in the alternative $R^4$ and $R^7$ are optionally combined to form a 5 to 7 membered heteroaryl optionally comprising 1 additional heteroatom N.

In another aspect the present invention provides for a pharmaceutical composition comprising a compound of formula I or any embodiment thereof and a pharmaceutically acceptable carrier, diluent or excipient.

In another aspect the present invention provides a method for inhibiting or preventing degeneration of a central nervous system (CNS) neuron or a portion thereof, the method comprising administering to the CNS neuron a compound of formula I or any embodiment thereof.

In another aspect the present invention provides a method for inhibiting or preventing degeneration of a central nervous system (CNS) neuron in a patient having or at risk of developing a neurodegenerative disease or condition comprising administering to said patient a therapeutically effective amount of a compound of formula I or any embodiment thereof, or a pharmaceutically acceptable salt thereof.

In another aspect the present invention provides a method for decreasing or preventing one or more symptoms of a neurodegenerative disease or condition in a patient suffering therefrom comprising administering to said patient a therapeutically effective amount of a compound of formula I or any embodiment thereof, or a pharmaceutically acceptable salt thereof.

In another aspect the present invention provides method for decreasing the progression of a neurodegenerative disease or condition in a patient suffering therefrom comprising administering to said patient a therapeutically effective amount of a compound of formula I or any embodiment thereof, or a pharmaceutically acceptable salt thereof.

In another aspect the present invention provides a compound of formula I or any embodiment thereof, or a pharmaceutically acceptable salt thereof for use in medical therapy.

In another aspect the present invention provides the use of a compound of formula I or any embodiment thereof, or a pharmaceutically acceptable salt thereof for the preparation of a medicament for inhibiting or preventing degeneration of a central nervous system (CNS) neuron in a patient having or at risk of developing a neurodegenerative disease or condition.

In another aspect the present invention provides use of a compound of formula I or any embodiment thereof, or a pharmaceutically acceptable salt thereof for the preparation of a medicament for decreasing or preventing one or more symptoms of a neurodegenerative disease or condition in a patient suffering therefrom.

In another aspect the present invention provides the use of a compound of formula I or any embodiment thereof, or a pharmaceutically acceptable salt thereof for the preparation of a medicament for decreasing the progression of a neurodegenerative disease or condition in a patient suffering.

In another aspect the present invention provides a compound of formula I or any embodiment thereof, or a pharmaceutically acceptable salt thereof for the therapeutic or prophylactic treatment of central nervous system (CNS) neuron degeneration.

In another aspect the present invention provides a compound of formula I or any embodiment thereof, or a pharmaceutically acceptable salt thereof for the therapeutic or prophylactic treatment of a neurodegenerative disease or condition.

DETAILED DESCRIPTION OF THE INVENTION

A. Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include linear and branched groups including vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl," "carbocyclic," or "carbocycle" refers to hydrocarbon ring system having specified overall number of ring atoms (e.g., 3 to 12 ring atoms in a 3 to 12 membered cycloalkyl or $C_{3-12}$ cycloalkyl) and being fully saturated or having no more than one double bond between ring vertices for a 3-5 membered cycloalkyl and being saturated or having no more than two double bonds between ring vertices for 6 or larger membered cycloalkyl. The monocyclic or polycyclic ring may be optionally substituted with one or more oxo groups. The terms "cycloalkyl," "carbocyclic," or "carbocycle" also include polycyclic ring systems wherein the ring radical attached to the remainder of the molecule is a saturated or partially unsaturated ring as defined above and wherein such polycyclic ring systems can also include fused aryl rings and fused heteroaryl rings as defined herein within the polycyclic ring systems. As used herein, "cycloalkyl," "carbocyclic," or "carbocycle" is also meant to refer to polycyclic (including fused and bridged bicyclic, fused and bridged polyclic and spirocyclic) hydrocarbon ring system such as, for example, bicyclo[2.2.1]heptane, pinane, bicyclo [2.2.2]octane, adamantane, norborene, spirocyclic $C_{5-12}$ alkane, etc. As used herein, the terms, "alkenyl," "alkynyl," "cycloalkyl,", "carbocycle," and "carbocyclic," are meant to include mono and polyhalogenated variants thereof.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include —$CH_2$—$CH_2$—O—$CH_3$, —$CH_2$—$CH_2$—O—$CF_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=N($CH_3$)—$CH_3$. Up to two heteroatoms can be consecutive, such as, for example, —$CH_2$—NH—$OCH_3$ and —$CH_2$—O—Si($CH_3$)$_3$.

The term "heterocycloalkyl," "heterocyclic," or "heterocycle" refers to a saturated or partially unsaturated ring system radical having from the indicated number of overall number of stated ring atoms and containing from one to five heteroatoms selected from N, O, and S, wherein the nitrogen and sulfur atoms are optionally oxidized, nitrogen atom(s) are optionally quaternized, as ring atoms (e.g., a 3 to 12 membered heterocycloalkyl that would have 3 to 12 ring atoms and include at least one heteroatom, which also could be referred to as a $C_{2-11}$ heterocycloalkyl). Unless otherwise stated, a "heterocycloalkyl," "heterocyclic," or "heterocycle" ring system can be a monocyclic or a fused, bridged, or spirocyclic polycyclic (including a fused bicyclic, bridged bicyclic or spirocyclic) ring system. The monocyclic or polycyclic ring may be optionally substituted with one or more oxo groups. The terms "heterocycloalkyl," "heterocyclic," and "heterocycle" also include polycyclic ring systems wherein the ring radical attached to the remainder of the molecule is a saturated or partially unsaturated ring that contains from one to five heteroatoms selected from N, O, and S, as defined above and wherein such polycyclic ring systems can also include fused aryl rings and fused heteroaryl rings as defined herein within the polycyclic ring systems. A "heterocycloalkyl," "heterocyclic," or "heterocycle" group can be attached to the remainder of the molecule through one or more ring carbons or heteroatoms. Non limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, tropane, 2-azaspiro[3.3] heptane, (1R,5 S)-3-azabicyclo[3.2.1]octane, (1s,4s)-2-azabicyclo[2.2.2]octane, (1R,4R)-2-oxa-5-azabicyclo[2.2.2] octane and the like. A "heterocycloalkyl," "heterocyclic," or "heterocycle" can include mono- and poly-halogenated variants thereof.

The term "alkylene" by itself or as part of another substituent means a divalent radical derived from an alkane, as exemplified by —$CH_2CH_2CH_2CH_2$—, and can be branched. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively. "Alkylene", "alkenylene" and "alkynylene" are also meant to include mono and poly-halogenated variants.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like). The term "heteroalkylene" is also meant to include mono and poly-halogenated variants.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively, and further include mono- and poly-halogenated variants thereof. Additionally, for dialkylamino groups, the alkyl portions can be the same or different.

The terms "alkoxy," "alkylamino" and "alkylthio", are used in their conventional sense, and refer to those alkyl groups attached to the remainder of the molecule via an oxygen atom ("oxy"), an amino group ("amino") or thio group, and further include mono- and poly-halogenated variants thereof. Additionally, for dialkylamino groups, the alkyl portions can be the same or different.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like. The term "(halo)alkyl" as used herein includes optionally halogenated alkyl. Thus the term "(halo)alkyl" includes both alkyl and haloalkyl (e.g., monohaloalkyl and polyhaloalkyl).

The term "aryl" means, unless otherwise stated, a polyunsaturated, typically aromatic, hydrocarbon ring, which can be a single ring or multiple rings (up to three rings) which are fused together. The term "heteroaryl" refers to aryl ring(s) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from the group of acceptable substituents described further below.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl and cycloalkyl) can be a variety of groups including, but not limited to, -halogen, =O, —OR', —NR'R", —SR', —SiR'R"R'", —OC(O)R', —C(O)R', —CO$_2$R', —CONR'R", —OC(O)NR'R", —NR"C(O)R', —NR"'C(O)NR'R", —NR"C(O)$_2$R', —NHC(NH$_2$)=NH, —NRC(NH$_2$)=NH, —NHC(NH$_2$)=NR', —NR"'C(NR'R")=N—CN, —NR"'C(NR'R")=NOR', —NHC(NH$_2$)=NR', —S(O)R', —S(O)$_2$R', —S(O)$_2$NR'R", —NR'S(O)$_2$R", —NR"'S(O)$_2$NR'R", —CN, —NO$_2$, —(CH$_2$)$_{1-4}$—OR', —(CH$_2$)$_{1-4}$—NR'R", —(CH$_2$)$_{1-4}$—SR', —(CH$_2$)$_{1-4}$—SiR'R"R'", —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R", in a number ranging from zero to (2m'+1), where m' is the total number of carbon atoms in such radical. R', R" and R'" each independently refer groups including, for example, hydrogen, unsubstituted $C_{1-6}$ alkyl, unsubstituted heteroalkyl, unsubstituted aryl, aryl substituted with 1-3 halogens, unsubstituted $C_{1-6}$ alkyl, $C_{1-6}$ alkoxy or $C_{1-6}$ thioalkoxy groups, or unsubstituted aryl-$C_{1-4}$ alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substituents for alkyl radicals, including heteroalkyl, alkylene, include for example, =O, =NR', =N—OR', =N—CN, =NH, wherein R' include substituents as described above. When a substituent for the alkyl radicals (including those groups often referred to as alkylene, alkenyl, alkynyl, heteroalkyl and cycloalkyl) contains an alkylene, alkenylene, alkynylene linker (e.g., —(CH$_2$)$_{1-4}$—NR'R" for alkylene), the alkylene linker includes halo variants as well. For example, the linker "—(CH$_2$)$_{1-4}$-" when used as part of a substituent is meant to include difluoromethylene, 1,2-difluoroethylene, etc.

Similarly, substituents for the aryl and heteroaryl groups are varied and are generally selected from the group including, but not limited to, -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'C(O)NR"R'", —NHC(NH$_2$)=NH, —NR'C(NH$_2$)=NH, —NHC(NH$_2$)=NR', —S(O)R', —S(O)$_2$R', —S(O)$_2$NR'R", —NR'S(O)$_2$R", —N$_3$, perfluoro-$C_{1-4}$ alkoxy, and perfluoro-$C_{1-4}$ alkyl, —(CH$_2$)$_{1-4}$—OR', —(CH$_2$)$_{1-4}$—NR'R", —(CH$_2$)$_{1-4}$—SR', —(CH$_2$)$_{1-4}$—SiR'R"R'", —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R", in a number ranging from zero to the total number of open valences on the aromatic ring system; and where R', R" and R'" are independently selected from hydrogen, $C_{1-6}$ alkyl, $C_{3-6}$ cycloalkyl, $C_{2-6}$ alkenyl, $C_{2-6}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms. When a substituent for the aryl or heteroaryl group contains an alkylene, alkenylene, alkynylene linker (e.g., —(CH$_2$)$_{1-4}$—NR'R" for alkylene), the alkylene linker includes halo variants as well. For example, the linker "—(CH$_2$)$_{1-4}$-" when used as part of a substituent is meant to include difluoromethylene, 1,2-difluoroethylene, etc.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "〜〜" that intersects a bond in a chemical structure fragment indicates the point of attachment of the bond to which the wavy bond intersects in the chemical structure fragment to the remainder of a molecule or structural formula.

As used herein, the representation of a group (e.g., $X^d$) in parenthesis followed by a subscript integer range (e.g., $(X^d)_{0-2}$) means that the group can have the number of occurrences as designated by the integer range. For example, $(X^d)_{0-1}$ means the group $X^d$ can be absent or can occur one time.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$)alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include istopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically labeled compounds of the present invention (e.g., those labeled with $^3$H or $^{14}$C) are useful in compound and/or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In some embodiments, a therapeutically effective amount is an amount of a chemical entity described herein sufficient to significantly decrease or delay neuronal cell death.

The term "administering" as used herein refers to contacting a neuron or portion thereof with a compound described herein. This includes administration of the compound to a subject in which the neuron or portion thereof is present, as well as introducing the inhibitor into a medium in which a neuro or portion thereof is cultured.

The term "patient" as used herein refers to any mammal, including humans, higher non-human primates, rodents domestic and farm animals such as cow, horses, dogs and cats. In one embodiment, the patient is a human patient.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The phrases "preventing axon degeneration," "preventing neuron degeneration," "preventing CNS neuron degeneration," "inhibiting axon degeneration," "inhibiting neuron degeneration" "inhibiting CNS neuron degeneration "as used herein include (i) the ability to inhibit or preserve axon or neuron degeneration in patients diagnosed as having a neurodegerative disease or risk of developing a neurodegenerative disease and (ii) the ability to inhibit or prevent further axon or neuron degeneration in patients who are already suffering from, or have symptoms of a neurodegenerative disease. Preventing axon or neuron degeneration includes decreasing or inhibiting axon or neuron degeneration, which may be characterized by complete or partial inhibition or neuron or axon degeneration. This can be assessed, for example, by analysis of neurological function. The above-listed terms also include in vitro and ex vivo methods. Further, the phrases "preventing neuron degeneration" and "inhibiting neuron degeneration" in clued such inhibition with respect to the entire neuron or a portion thereof, such as the neuron ell body, axons and dendrites. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90% or even 100% decrease in one or more symptoms of a disorder of the nervous system, a condition of the nervous system that is secondary to a disease, condition, or therapy having a primary effect outside of the nervous system; an injury to the nervous system caused by physical, mechanical or chemical trauma, pain; and ocular related neurodegeneration; memory loss; or a psychiatric disorder (e.g., tremors, slowness of movement, ataxia, loss of balance, depression, decreased cognitive function, short term memory loss, long term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity) in a subject or population compared to a control subject or population that does not receive the one or more agent described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the agents described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the likelihood of developing a disorder of the nervous system; a condition of the nervous system that is secondary to a disease, condition, or therapy having a primary effect outside of the nervous system; an injury to the nervous system caused by physical, mechanical, or chemical trauma, pain; an ocular-related neurodegeneration; memory loss; or a psychiatric disorder in a subject or a subject population compared to a control subject or population not treated with the one or more compounds described herein.

The term "neuron" as used herein denotes nervous system cells that include a central cell body or soma, and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the invention include cerebellar granule neurons, dorsal root ganglion neurons, and cortical neurons.

B. Compounds

In one aspect the invention are provided compounds of Formula (I)

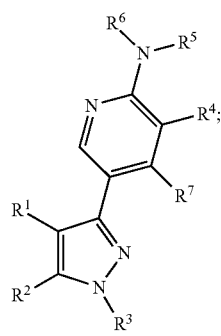

(I)

and salts thereof; wherein in Formula (I)

$R^1$ is selected from the group consisting of hydrogen, —F, —Cl, —Br, —I, —NO$_2$, —CN, $C_{1-12}$ alkyl and $C_{1-12}$ haloalkyl;

$R^2$ is selected from the group consisting of 3 to 12 membered cycloalkyl, C-linked 3 to 12 membered heterocycloalkyl, and —C($R^{A2}$)($C_{1-6}$(halo)alkyl)$_2$, wherein $R^{A2}$ is hydrogen, —F, —Cl, —Br, —I, —CN, —OH, —NH$_2$, —SF$_5$, —OSF$_5$, $C_{1-12}$ alkylthio, $C_{1-12}$ alkoxy, $C_{1-12}$ alkylamino and $C_{1-12}$ dialkylamino; and wherein $R^2$ is optionally substituted 1 to 5 $R^{2-A}$ substituents selected from the group consisting of $C_{1-12}$ alkyl, $C_{1-12}$ haloalkyl, $C_{1-12}$ heteroalkyl, $C_{2-12}$ alkenyl, $C_{2-12}$ alkynyl, —F, —Cl, —Br, —I, —(X)$_{0-1}$—CN, —(X)$_{0-1}$—NO$_2$, —(X$^2$)$_{0-1}$—SF$_5$, —(X$^2$)$_{0-1}$—OSF$_5$, —(X$^2$)$_{0-1}$—OR$^{2A}$, —(X$^2$)$_{0-1}$—N(R$^{2A}$)$_2$, —(X$^2$)$_{0-1}$—SR$^{2A}$, —(X$^2$)$_{0-1}$—CF$_3$, 3 to 12 membered cycloalkyl-(X$^2$)$_{0-1}$—, 3 to 12 membered heterocycloalkyl-(X$^2$)$_{0-1}$—, 5 to 6 membered heteroaryl-(X$^2$)$_{0-1}$—, phenyl-(X$^2$)$_{0-1}$—, —(X$^2$)$^{0-1}$—C(=O)N(R$^{2A}$)(R$^{2A}$), —(X$^2$)$_{0-1}$—C(=O)OR$^{2A}$, —(X$^2$)$_{0-1}$—N(R$^{2A}$)C(=O)(R$^{2A}$), —(X$^2$)$_{0-1}$—N(R$^{2A}$)C(=O)OR$^{2A}$, —(X$^2$)$_{0-1}$—S(=O)$_{1-2}$—R$^{2A}$, —(X$^2$)$_{0-1}$—N(R$^{2A}$)S(=O)$_{1-2}$—R$^{2A}$, —(X$^2$)$_{0-1}$—S(=O)$_{1-2}$N(R$^{2A}$)$_2$, —(X$^2$)$_{0-1}$—C(=O)R$^{2A}$, —(X$^2$)$_{0-1}$—C(=NOR$^{2A}$)R$^{2A}$, —(X$^2$)$_{0-1}$—N(R$^{2A}$)C(=O)N(R$^{2A}$)$_2$ and —(X$^2$)$_{0-1}$—OC(=O)R$^{2A}$, —(X$^2$)$_{0-1}$—OP(=O)(OR$^{2A}$)$_2$, —(X$^2$)—SC(=O)OR$^{2A}$ and —(X$^2$)—SC(=O)N(R$^{2A}$)$_2$; wherein X$^2$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{2A}$ at each occurrence is each independently selected from the group consisting of hydrogen, $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl, 3-7 membered heterocycloalkyl, 3-7 membered heterocycloalkyl-$C_{1-4}$ alkyl, 5-6 membered heteroaryl, 5-6 membered heteroaryl-$C_{1-4}$ alkyl, phenyl and phenyl-$C_{1-4}$ alkyl, or any two $R^{2A}$ groups attached to the same nitrogen atom are optionally combined to form a 3 to 6 membered heterocyclic ring comprising 1 to 2 additional heteroatom selected from N, O and S; and wherein a $R^{2-A}$ substituent at each occurrence is independently optionally further substituted with 1 to 5 $R^{2A-1}$ substituents selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_1$-6 dialkylamino;

$R^3$ is selected from the group consisting of $C_{1-12}$ alkyl-, $C_{1-12}$ haloalkyl-, $C_{1-12}$ heteroalkyl-(L)$_{0-1}$-, $C_{2-12}$ alkenyl-(L)$_{0-1}$-, $C_{2-12}$alkynyl-(L)$_{0-1}$-, 3 to 12 membered cycloalkyl-(L)$_{0-1}$-, 3 to 12 membered heterocycloalkyl-(L)$_{0-1}$-, wherein L is selected from the group consisting of $C_{1-4}$ alkylene, $C_{1-4}$ haloalkylene, $C_{1-4}$ heteroalkylene, $C_{2-4}$ alkenylene, $C_{2-4}$ alkynylene, —C(=O)—, —C(=O)—N(H)—, —C(=O)N($C_{1-6}$ alkyl)-, —C(=O)O—, —S(O)$_{1-2}$—and —S(O)$_{1-2}$—N(H)—; wherein a $R^3$ group is optionally further substituted with 1 to 5 $R^{3A}$ substituents selected from the group consisting of —F, —Cl, —Br, —I, —OH, —CN, —NO$_2$, —SF$_5$, —OSF$_5$, —NH$_2$, $C_{1-6}$ alkyl, $C_{1-6}$ haloalkyl, 3 to 5 membered cycloalkyl, 3 to 5 membered heterocycloalkyl, $C_{1-6}$ alkoxy, $C_{1-6}$ alkylthio, $C_{1-6}$ alkylamino and $C_{1-6}$ dialkylamino;

$R^4$ is selected from the group consisting of $C_{1-12}$ alkyl, $C_{1-12}$ haloalkyl, $C_{2-12}$ alkenyl, $C_{2-12}$ alkynyl, —F, —Cl, —Br, —I, —(X$^4$)$_{0-1}$—CN, —(X$^4$)$_{0-1}$—NO$_2$, —(X$^4$)$_{0-1}$—SF$_5$, —(X$^4$)$_{0-1}$—OSF$_5$, —(X$^4$)$_{0-1}$—OR$^{4A}$, —(X$^4$)$_{0-1}$—N(R$^{4A}$)$_2$, —(X$^4$)$_{0-1}$—SR$^{4A}$, —(X$^4$)$_{0-1}$-CF$_3$, 3 to 7 membered cycloalkyl-(X$^4$)$_{0-1}$—, 3 to 7 membered heterocycloalkyl-(X$^4$)$_{0-1}$—, 5 to 6 membered heteroaryl-(X$^4$)$_{0-1}$—, phenyl-(X$^4$)$_{0-1}$—, —(X$^4$)$_{0-1}$—C(=O)N(R$^{4A}$)(R$^{4A}$), —(X$^4$)$_{0-1}$—C(=O)OR$^{4A}$, —(X$^4$)$_{0-1}$—N(R$^{4A}$)C(=O)R$^{4A}$, —(X$^4$)$_{0-1}$—N(R$^{4A}$)C(=O)OR$^{4A}$, —(X$^4$)$_{0-1}$—S(=O)$_{1-2}$—R$^{4A}$, —(X$^4$)$_{0-1}$—N(R$^{4A}$)S(=O)$_{1-2}$—R$^{4A}$, —(X$^4$)$_{0-1}$—S(=O)$_{1-2}$N(R$^{4A}$)$_2$, —(X$^4$)$_{0-1}$—C(=O)R$^{4A}$, —(X$^4$)$_{0-1}$—C(=NOR$^{4A}$)R$^{4A}$, —(X$^4$)$_{0-1}$—N(R$^{4A}$)C(=O)N(R$^{4A}$)$_2$, —(X$^4$)$_{0-1}$—OC(=O)R$^{4A}$, —(X$^4$)$_{0-1}$—OP(=O)(OR$^{4A}$)$_2$, —(X$^4$)—SC(=O)OR$^{4A}$ and —(X$^4$)—SC(=O)N(R$^{4A}$)$_2$, X$^4$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{4A}$ at each occurrence is each independently selected from the group consisting of hydrogen, $C_{1-6}$ alkyl, $C_{1-6}$ haloalkyl and $C_{1-6}$ heteroalkyl, or any two $R^{4A}$ groups attached to the same nitrogen atom are optionally combined to form a 3 to 6 membered heterocyclic ring comprising 1 to 2 additional heteroatom selected from N, O and S; and wherein a $R^4$ group is independently optionally further substituted with 1 to 5 $R^{4A-1}$ substituents selected from the group consisting of —F, —Cl, —Br, —I, —OH, —CN, —NO$_2$, —SF$_5$, —NH$_2$, $C_{1-6}$ alkoxy, $C_{1-6}$ alkylamino and $C_{1-6}$ dialkylamino;

$R^5$ and $R^6$ are each independently selected from the group consisting of hydrogen, $C_{1-12}$ alkyl, and $C_{1-12}$ haloalkyl; and in the alternative $R^4$ and $R^5$ are combined to form a 5 to 7 membered heteroaryl or 5 to 7 membered heterocycloalkyl ring optionally comprising 1 additional heteroatom selected from N, O and S, and wherein said 5 to 7 membered heteroaryl or 5 to 7 membered heterocycloalkyl ring is further optionally substituted with 1 to 3 $R^{4/5cy}$ substituents selected from the group consisting of $C_{1-12}$ alkyl, $C_{1-12}$ haloalkyl, $C_{2-12}$ alkenyl, $C_{2-12}$ alkynyl, —F, —Cl, —Br, —I, —$(X^{4/5})_{0-1}$—CN, —$(X^{4/5})_{0-1}$—$NO_2$, —$(X^{4/5})_{0-1}$—$SF_5$, —$(X^{4/5})_{0-1}$—$OSF_5$, —$(X^{4/5})_{0-1}$—$OR^{45A}$, —$(X^{4/5})_{0-1}$—$N(R^{45A})_2$, —$(X^{4/5})_{0-1}$—$SR^{45A}$, —$(X^{4/5})_{0-1}$—$CF_3$, 3 to 12 membered cycloalkyl-$(X^{4/5})_{0-1}$—, 3 to 12 membered heterocycloalkyl-$(X^{4/5})_{0-1}$—, 5 to 6 membered heteroaryl-$(X^{4/5})_{0-1}$—, phenyl-$(X^{4/5})_{0-1}$—, —$(X^{4/5})_{0-1}$—C(=O)N$(R^{45A})(R^{45A})$, —$(X^{4/5})_{0-1}$—C(=O)$OR^{45A}$, —$(X^{4/5})_{0-1}$N$(R^{45A})$C(=O)$(R^{45A})$, —$(X^{4/5})_{0-1}$—N$(R^{45A})$C(=O)$OR^{45A}$, —$(X^{4/5})_{0-1}$—S(=O)$_{1-2}$—$R^{45A}$, —$(X^{4/5})_{0-1}$—N$(R^{45A})$S(=O)$_{1-2}$—$R^{45A}$, —$(X^{4/5})_{0-1}$—S(=O)$_{1-2}$N$(R^{45A})_2$, —$(X^{4-5})_{0-1}$—C(=O)$R^{45A}$, —$(X^{4/5})_{0-1}$—C(=NO$R^{45A}$)$R^{45A}$, —$(X^{4/5})_{0-1}$—N$(R^{45A})$C(=O)N$(R^{45A})_2$ and —$(X^{4/5})_{0-1}$—OC(=O)$R^{45A}$, —$(X^{4/5})_{0-1}$—OP(=O)$(OR^{45A})_2$, —$(X^{4/5})$—SC(=O)$OR^{45A}$ and —$(X^{4/5})$—SC(=O)N$(R^{45A})_2$, $X^{4/5}$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{45A}$ at each occurrence is each independently selected from the group consisting of hydrogen, $C_{1-6}$ alkyl, $C_{1-6}$ haloalkyl and $C_{1-6}$ heteroalkyl; or any two $R^{45A}$ groups attached to the same nitrogen atom are optionally combined to form a 3 to 6 membered heterocyclic ring comprising 1 to 2 additional heteroatom selected from N, O and S; and wherein a $R^{4/5cy}$ substituent at each occurrence is independently optionally further substituted with 1 to 5 $R^{4/5cy-1}$ substituents selected from the group consisting of —F, —Cl, —Br, —I, —OH, —CN, —$NO_2$, —$SF_5$, —$NH_2$, $C_{1-6}$ alkoxy, $C_{1-6}$ alkylamino and $C_{1-6}$ dialkylamino; and $R^7$ is hydrogen, or in the alternative $R^4$ and $R^7$ are optionally combined to form a 5 to 7 membered heteroaryl or 5 to 7 membered heterocycloalkyl ring optionally comprising 1 additional heteroatom selected from N, O and S.

In another embodiment, in compounds of formula (I), $R^5$ and $R^6$ are each H.

In another embodiment, in compounds of formula (I), $R^4$ is selected from the group consisting of $C_{1-12}$ alkyl, $C_{1-12}$ haloalkyl, —F, —Cl, —$(X^4)_{0-1}$—CN, —$(X^4)_{0-1}$—$OR^{4A}$, —$(X^4)_{0-1}$—$SR^{4A}$, 3 to 7 membered cycloalkyl-$(X^4)_{0-1}$—, —$(X^4)_{0-1}$—S(=O)$_{1-2}$—$R^{4A}$ and is further optionally substituted.

In another embodiment, in compounds of formula (I), $R^4$ is selected from the group consisting of —F, —Cl, $C_{1-4}$ alkyl, $C_{1-4}$ haloalkyl, —$(C_{1-4}$ alkylene)$_{0-1}$-CN, $C_{1-4}$ alkyloxy, $C_{1-4}$ haloalkyloxy, $C_{1-4}$ alkylthio, $C_{1-4}$ haloalkylthio, 3 to 5 membered cycloalkyl-$(C_{1-4}$ alkyloxy)-, 3 to 6 membered cycloalkyl, and $(C_{1-4}$ alkyl)-S(O)$_2$—, wherein $R^4$ is further optionally substituted.

In another embodiment, in compounds of formula (I), $R^4$ is selected from the group consisting of —F, Cl, —CN, methyl, monofluoromethyl, difluoromethyl, trifluoromethyl, ethyl, 2-fluoroeth-1-yl, 1-fluoroeth-1-yl, 2,2-difluoroeth-1-yl, 1,2-difluoroeth-1-yl, 1,1-difluoroeth-1-yl, 2,2,2-trifluoroeth-1-yl, 1,2,2-trifluoroeth-1-yl, 1,1,2-trifluoroeth-1-yl, methoxy, monofluoromethoxy, difluoromethoxy, trifluoromethoxy, 2-fluoroethan-1-oxy, 2,2-difluoroethan-1 oxy, 1,2-difluoroethan-1-oxy, 1,1-difluoroethan-1-oxy, 2,2,2-trifluoroethan-1-oxy, 1,2,2-trifluoroethan-1-oxy, 1,1,2-trifluoroethan-1-oxy, isopropoxy, 1-fluoro-propan-2-oxy, 1,1-difluoro-propan-2-oxy, 1,3-difluoro-propan-2-oxy, 1,1,1-trifluoro-propan-2-oxy, 1,1,3-trifluoro-propan-2-oxy, 1,1,1,3,3,3-hexafluoro-propan-2-oxy, monofluoromethylthio, difluoromethylthio, trifluromethylthio, cyclopropylmethoxy and cyclopropyl.

In another embodiment, in compounds of formula (I), $R^6$ is H; and $R^4$ and $R^5$ are combined to form a 5 to 7 membered ring selected from the group consisting of pyrrole, imidazole, pyrazole, pyrrolidone, pyrrolidine, morpholine, piperdine and piperazine, wherein $R^4$ and $R^5$ combined are optionally substituted with 1 to 3 $R^{4/5cy}$ substituents.

In another embodiment, in compounds of formula (I), $R^{4/5cy}$ is selected from the group consisting of $C_{1-12}$ alkyl, $C_{1-12}$ haloalkyl, —F, —Cl, —$(X^{4/5})_{0-1}$—CN, —$(X^{4/5})_{0-1}$—$OR^{45A}$, 3 to 7 membered cycloalkyl-$(X^{4/5})_{0-1}$—, —$(X^{4/5})_{0-1}$S(=O)$_{1-2}$—$R^{45A}$, wherein $R^{4/5cy}$ is optionally substituted with 1 to 3 $R^{4/5cy-1}$ substituents.

In another embodiment, in compounds of formula (I), $R^{4/5cy}$ is selected from the group consisting of —F, —Cl, $C_{1-4}$ alkyl, $C_{1-4}$ haloalkyl, —$(C_{1-4}$ alkylene)$_{0-1}$-CN, $C_{1-4}$ alkyloxy, $C_{1-4}$ haloalkyloxy, $C_{1-4}$ alkylthio, $C_{1-4}$ haloalkylthio, 3-6 membered cycloalkyl-$(C_{1-4}$ alkyloxy)-, 3 to 6 membered cycloalkyl, and $(C_{1-4}$ alkyl)-S(O)$_2$—, wherein $R^{4/5cy}$ is optionally substituted with 1 to 5 $R^{4/5cy-1}$ substituents.

In another embodiment, in compounds of formula (I), $R^{4/5cy}$ is selected from the group consisting of —F, Cl, —CN, methyl, monofluoromethyl, difluoromethyl, trifluoromethyl, ethyl, 2-fluoroeth-1-yl, 1-fluoroeth-1-yl, 2,2-difluoroeth-1-yl, 1,2-difluoroeth-1-yl, 1,1-difluoroeth-1-yl, 2,2,2-trifluoroeth-1-yl, 1,2,2-trifluoroeth-1-yl, 1,1,2-trifluoroeth-1-yl, methoxy, monofluoromethoxy, difluoromethoxy, trifluoromethoxy, 2-fluoroethan-1-oxy, 2,2-difluoroethan-1 oxy, 1,2-difluoroethan-1-oxy, 1,1-difluoroethan-1-oxy, 2,2,2-trifluoroethan-1-oxy, 1,2,2-trifluoroethan-1-oxy, 1,1,2-trifluoroethan-1-oxy, isopropoxy, 1-fluoro-propan-2-oxy, 1,1-difluoro-propan-2-oxy, 1,3-difluoro-propan-2-oxy, 1,1,1-trifluoro-propan-2-oxy, 1,1,3-trifluoro-propan-2-oxy, 1,1,1,3,3,3-hexafluoro-propan-2-oxy, monofluoromethylthio, difluoromethylthio, trifluromethylthio, cyclopropylmethoxy and cyclopropyl.

In another embodiment, in compounds of formula (I), $R^1$ is selected from the group consisting of hydrogen, $C_{1-4}$ alkyl and $C_{1-4}$ haloalkyl.

In another embodiment, in compounds of formula (I), $R^1$ is hydrogen, monofluoromethyl, difluoromethyl, trifluormethyl and methyl.

In another embodiment, in compounds of formula (I), $R^1$ is hydrogen.

In another embodiment, in compounds of formula (I), $R^2$ is a fused or bridged 3 to 12 membered cycloalkyl or a fused or bridged bicyclic or tricyclic C-linked 3 to 12 membered heterocycloalkyl ring, wherein $R^2$ is optionally substituted with 1-5 $R^{2-A}$ substituents.

In another embodiment, in compounds of formula (I), $R^2$ is selected from the group consisting of 3-azabicyclo[3.1.0]hexane, 3-azabicyclo[3.2.1]octane, 3-azabicyclo[3.1.1]heptane, 1,1a,5,5a-tetrahydro-4a-aza-cyclopropa[a]pentalene, 1,1a,5,5a-tetrahydro-2,4a-diaza-cyclopropa[a]pentalene, 1,1a,5,5a-tetrahydro-3,4a-diaza-cyclopropa[a]pentalene, 1,1a,5,5a-tetrahydro-2,3,4a-triaza-cyclopropa[a]pentalene, 1,1a,5,5a-tetrahydro-4,4a-diaza-cyclopropa[a]pentalene, octahydro-4a-aza-cyclopropa[a]pentalene, 3-oxabicyclo

[3.2.1]octane, 3-oxabicyclo[3.1.1]heptane and 3-oxabicyclo[3.1.0]hexane, and wherein $R^2$ is optionally substituted with 1 to 5 $R^{2-A}$ substituents.

In another embodiment, in compounds of formula (I), $R^2$ is selected from the group consisting of

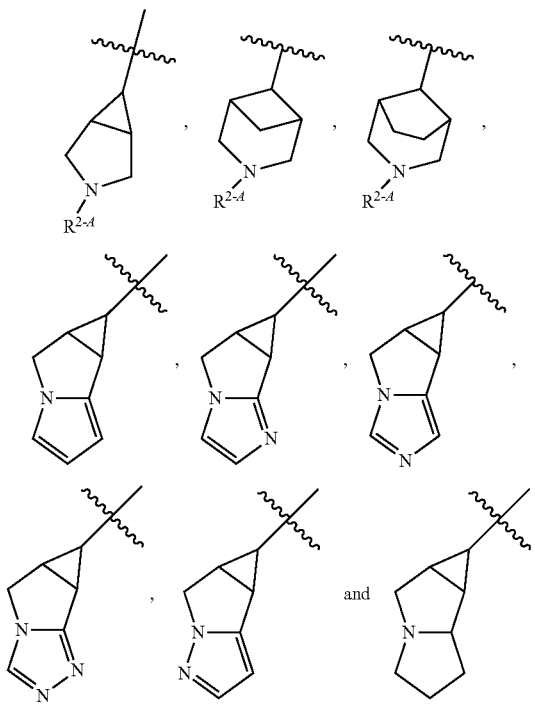

In another embodiment, in compounds of formula (I), $R^2$ is selected from the group consisting of

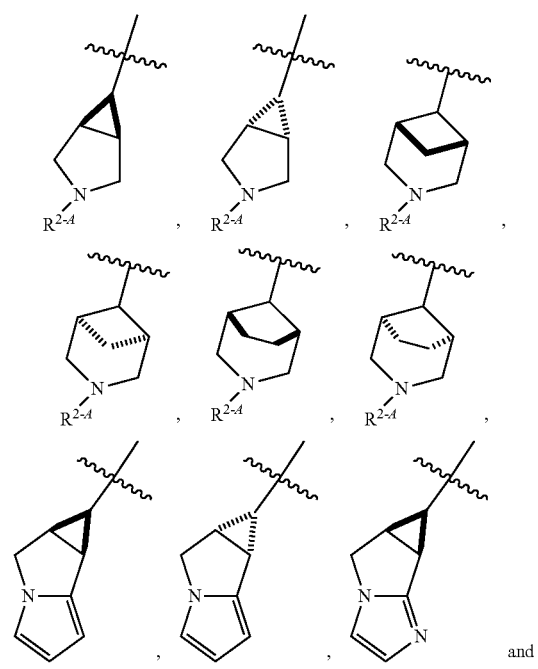

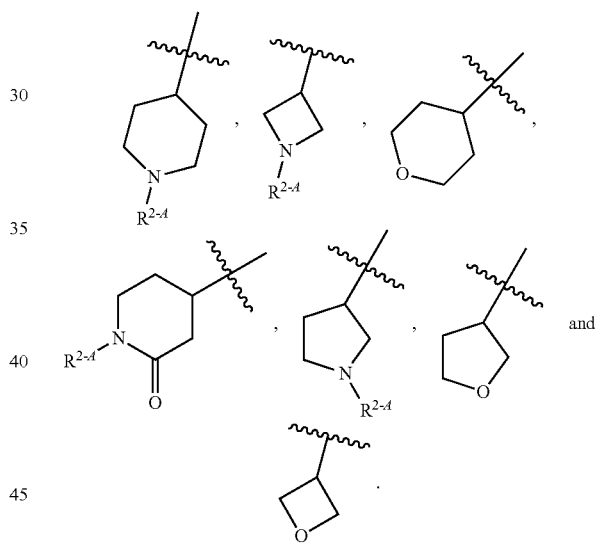

In another embodiment, in compounds of formula (I), $R^2$ is a monocyclic ring, wherein $R^2$ is optionally substituted with 1 to 5 $R^{2-A}$ substituents.

In another embodiment, in compounds of formula (I), $R^2$ is a monocyclic ring selected from the group consisting of azetidine, pyrrolidine, pyrrolidone, piperidine, piperidone, azepane, azepanone, tetrahydrofuran, tetrahydrofuranone, tetrahydropyan, tetrahydropyanone, oxetane, oxetanone, oxepane and oxepanone, wherein $R^2$ is optionally substituted with 1 to 5 $R^{2-A}$ substituents and wherein $R^{2-A}$ is further optionally substituted.

In another embodiment, in compounds of formula (I), $R^2$ is selected from the group consisting of In another embodiment, in compounds of formula (I), $R^{2-A}$ is selected from the group consisting of $C_{1-12}$ alkyl, $C_{1-12}$ haloalkyl, $C_{1-12}$ heteroalkyl, —$(X^2)_{0-1}$—CN, —$(X^2)_{0-1}$—$OR^{2A}$, 3 to 12 membered cycloalkyl-$(X^2)_{0-1}$—, 3 to 12 membered heterocycloalkyl-$(X^2)_{0-1}$—, —$(X^2)_{0-1}$—S(=O)$_{1-2}$—$R^{2A}$ and —$(X^2)_{0-1}$—C(=O)$R^{2A}$, wherein $R^{2-A}$ is optionally substituted.

In another embodiment, in compounds of formula (I), $R^{2-A}$ is selected from the group consisting of OH, ($C_{1-6}$ alkyl)-C(=O)—, ($C_{1-6}$ alkyl)-S(=O)$_2$—, oxepane, azetidine, $C_{1-6}$ alkyl, $C_{1-6}$ haloalkyl, $C_{1-6}$ heteroalkyl and —($C_{1-6}$ alkyl)-CN, wherein $R^{2-A}$ is optionally substituted.

In another embodiment, in compounds of formula (I), $R^{2-A}$ is selected from the group consisting of $CH_3$—C(=O)—, oxetanyl, methyl, monofluoromethyl, difluoromethyl, trifluoromethyl, ethyl, 2-fluoroeth-1-yl, 1-fluoroeth-1-yl, 1,2-difluoroeth-1-yl, 2,2-difluoroeth-1-yl, 1,1,2-trifluoroeth-1-yl 2,2,2-trifluoroeth-1-yl, 1,2,2-trifluoroeth-1-yl, cyanomethyl, cyanoethyl, methoxyethyl, hydroxy, (CH₃)₂(OH)CC(H)₂—, CH₃OCH₂C(H)(CH₃)—, CH₃OC(CH₃)₂CH₂—, NCC(H)(CH₃)CH₂—, NCC(H)(CH₃)₂CH₂—, CH₃OC(H)(CH₃)CH₂—, NCCH₂C(H)(CH₃)—, NCCH₂C(CH₃)₂—, CH₃—S(O)₂— and isopropyl-OC(=O)—.

In another embodiment, in compounds of formula (I), $R^2$ is —C($R^{A2}$)($C_{1-6}$ alkyl)₂, wherein $R^{A2}$ is hydrogen, —F, —Cl, —Br, —I, —CN, —OH, —NH₂, —SF₅, —OSF₅, $C_{1-4}$ alkylthio, $C_{1-4}$ alkoxy, $C_{1-4}$ alkylamino and $C_{1-4}$ dialkylamino and wherein $R^2$ is optionally substituted with 1 to 5 $R^{2-A}$ substituents.

In another embodiment, in compounds of formula (I), $R^3$ is selected from the group consisting of $C_{1-6}$ alkyl, 3 to 6 membered cycloalkyl-$C_{1-4}$ alkyl, 3 to 6 membered cycloalkyl, 3 to 6 membered heterocycloalkyl-$C_{1-4}$ alkyl, and 3-6 membered heterocycloalkyl, wherein $R^3$ is optionally substituted with $R^{3.A}$.

In another embodiment, in compounds of formula (I), $R^3$ is selected from the group consisting of methyl, monofluoromethyl, difluoromethyl, ethyl, 1,1,1-trifluoroeth-2-yl, propyl, isopropyl, butyl, sec-butyl, tert-butyl, cyclopropyl, cyclopropylmethyl, cyclobutyl, cyclobutylmethyl, cyclopentyl, cyclopentylmethyl, cyclohexyl, cyclohexylmethyl, 1,1-difluorocyclobut-3-yl, 1,1-difluorocyclopent-3-yl, oxetan-2-yl, oxetan-2-yl-methyl, oxetan-3-yl, oxetan-3-yl-methyl, tetrahydrofuran-3-yl, tetrahydrofuran-3-yl-methyl, tetrahydropyran-3-yl, tetrahydropyran-3-yl-methyl, tetrahydropyran-4-yl, tetrahydropyran-4-yl-methyl, azetindin-3-yl, azetindin-3-yl-methyl, pyrrolidin-3-yl, pyrrolidin-3-yl-methyl, piperidin-4yl, piperidin-4-yl-methyl, piperidin-3-yl and piperidin-3-yl-methyl.

In another embodiment, in compounds of formula (I), the compound has a formula selected from the group consisting of:

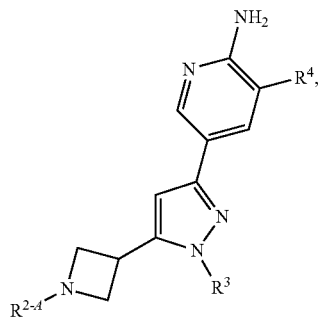
(II-a)

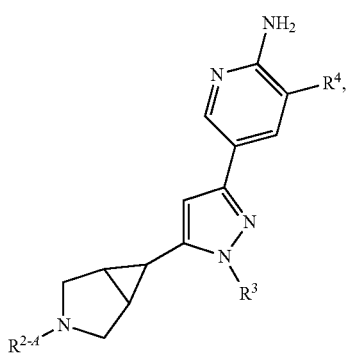
(II-b)

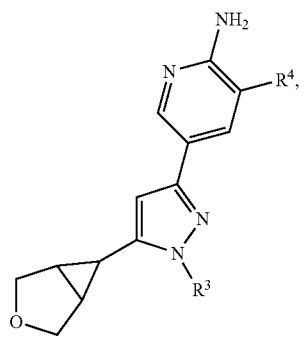
(II-c)

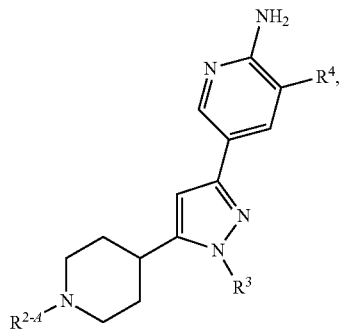
(II-d)

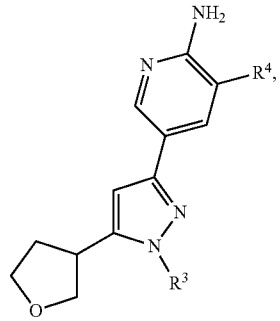
(II-e)

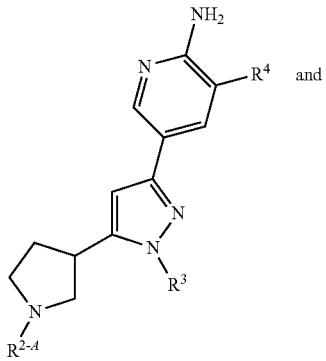
(II-f)

and

-continued (II-g)
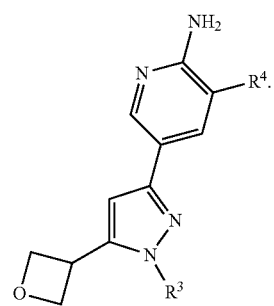

In another embodiment, in compounds of formula (I), the compound has the formula selected from the group consisting of (III-a)
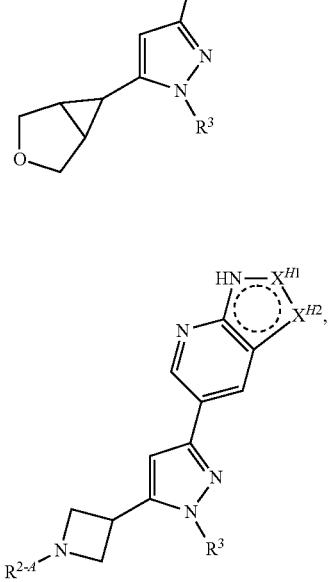

(III-b)

(III-c)

-continued (III-d)
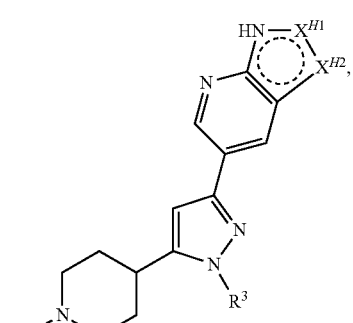

(III-e)
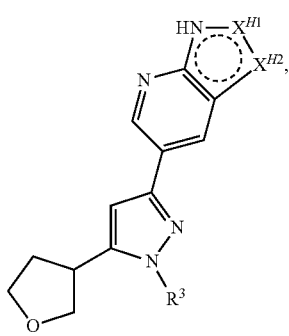

(III-f) and
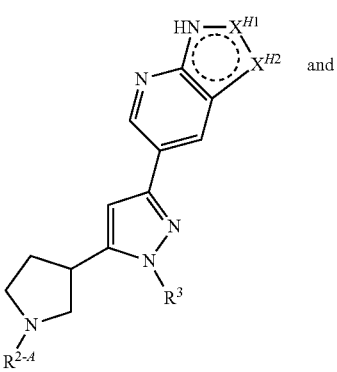

(III-g)
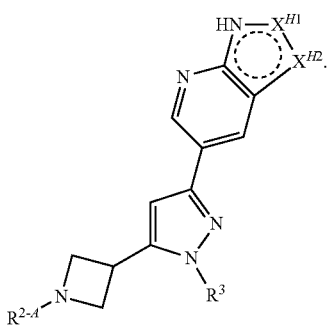

wherein in formula III-a, III-b, III-c, III-d, III-e, III-f and III-g, $X^{H1}$ and $X^{H2}$ at each occurrence is independently selected from the group consisting of N, NH, N($R^{4/5cy}$), CH or C($R^{4/5cy}$).

In another embodiment, in compounds of formula III-a, III-b, III-c, III-d, III-e, III-f and III-g, $X^{H1}$ and $X^{H2}$ are independently CH or C($R^{4/5cy}$).

In another embodiment the compound of Formula (I), is selected from the group consisting of:
5-(5-isopropyl-1-(1-(oxetan-3-yl)azetidin-3-yl)-1H-pyrazol-3-yl)-3-(trifluoromethyl)-1H-pyrrolo[2,3-b]pyridine, 2-(3-(6-amino-5-(trifluoromethyl)pyridin-3-yl)-1-isopropyl-1H-pyrazol-5-yl)propan-2-ol,
2-(3-(6-amino-5-(difluoromethoxy)pyridin-3-yl)-1-isopropyl-1H-pyrazol-5-yl)propan-2-ol,
2-(3-(6-amino-5-(trifluoromethyl)pyridin-3-yl)-1-isopropyl-1H-pyrazol-5-yl)-2-methylpropanenitrile,
2-(3-(6-amino-5-(difluoromethyl)pyridin-3-yl)-1-isopropyl-1H-pyrazol-5-yl)-2-methylpropanenitrile,
2-(3-(6-amino-5-(trifluoromethoxy)pyridin-3-yl)-1-isopropyl-1H-pyrazol-5-yl)-2-methylpropanenitrile,
5-(1-isopropyl-5-(1-methylazetidin-3-yl)-1H-pyrazol-3-yl)-3-(trifluoromethyl)pyridin-2-amine,
1-(3-(1-(cyclopropylmethyl)-3-(3-(trifluoromethyl)-1H-pyrrolo[2,3-b]pyridin-5-yl)-1H-pyrazol-5-yl)azetidin-1-yl)ethanone,
1-(3-(1-(cyclopropylmethyl)-3-(3-methyl-1H-pyrrolo[2,3-b]pyridin-5-yl)-1H-pyrazol-5-yl)azetidin-1-yl)ethanone,
1-(3-(1-isopropyl-3-(3-(trifluoromethyl)-1H-pyrrolo[2,3-b]pyridin-5-yl)-1H-pyrazol-5-yl)azetidin-1-yl)ethanone,
1-(3-(1-methyl-3-(3-(trifluoromethyl)-1H-pyrrolo[2,3-b]pyridin-5-yl)-1H-pyrazol-5-yl)azetidin-1-yl)ethanone,
1-(3-(1-isopropyl-3-(3-methyl-1H-pyrrolo[2,3-b]pyridin-5-yl)-1H-pyrazol-5-yl)azetidin-1-yl)ethanone,
racemic-5-(1-(cyclopropylmethyl)-5-(tetrahydrofuran-3-yl)-1H-pyrazol-3-yl)-3-methyl-1H-pyrrolo[2,3-b]pyridine,
5-(1-(3,3-difluorocyclopentyl)-5-(tetrahydrofuran-3-yl)-1H-pyrazol-3-yl)-3-methyl-1H-pyrrolo[2,3-b]pyridine,
5-(1,5-bis(tetrahydrofuran-3-yl)-1H-pyrazol-3-yl)-3-(trifluoromethyl)-1H-pyrrolo[2,3-b]pyridine,
5-(1-(3,3-difluorocyclopentyl)-5-(tetrahydrofuran-3-yl)-1H-pyrazol-3-yl)-3-(trifluoromethyl)-1H-pyrrolo[2,3-b]pyridine,
(R)-5-(1-(cyclopropylmethyl)-5-(tetrahydrofuran-3-yl)-1H-pyrazol-3-yl)-3-methyl-1H-pyrrolo[2,3-b]pyridine,
(S)-5-(1-(cyclopropylmethyl)-5-(tetrahydrofuran-3-yl)-1H-pyrazol-3-yl)-3-methyl-1H-pyrrolo[2,3-b]pyridine,
5-(1-(3,3-difluorocyclobutyl)-5-(tetrahydrofuran-3-yl)-1H-pyrazol-3-yl)-3-methyl-1H-pyrrolo[2,3-b]pyridine,
5-(1-(3,3-difluorocyclobutyl)-5-(tetrahydrofuran-3-yl)-1H-pyrazol-3-yl)-3-ethyl-1H-pyrrolo[2,3-b]pyridine,
5-(1,5-bis(tetrahydrofuran-3-yl)-1H-pyrazol-3-yl)-3-chloropyridin-2-amine,
5-(1,5-bis(tetrahydrofuran-3-yl)-1H-pyrazol-3-yl)-3-fluoropyridin-2-amine,
3-chloro-5-(1-(3,3-difluorocyclopentyl)-5-(tetrahydrofuran-3-yl)-1H-pyrazol-3-yl)pyridin-2-amine,
5-(1-(3,3-difluorocyclopentyl)-5-(tetrahydrofuran-3-yl)-1H-pyrazol-3-yl)-3-fluoropyridin-2-amine,
3-chloro-5-(1-(3,3-difluorocyclobutyl)-5-(tetrahydrofuran-3-yl)-1H-pyrazol-3-yl)pyridin-2-amine,
5-(1-((R)-tetrahydrofuran-3-yl)-5-((S)-tetrahydrofuran-3-yl)-1H-pyrazol-3-yl)-3-(trifluoromethyl)-1H-pyrrolo[2,3-b]pyridine,
5-(1-((R)-3,3-difluorocyclopentyl)-5-((R)-tetrahydrofuran-3-yl)-1H-pyrazol-3-yl)-3-methyl-1H-pyrrolo[2,3-b]pyridine,
5-(5-((R)-tetrahydrofuran-3-yl)-1-((S)-tetrahydrofuran-3-yl)-1H-pyrazol-3-yl)-3-(trifluoromethyl)-1H-pyrrolo[2,3-b]pyridine,
5-(1,5-bis((S)-tetrahydrofuran-3-yl)-1H-pyrazol-3-yl)-3-(trifluoromethyl)-1H-pyrrolo[2,3-b]pyridine,
5-(1,5-bis((R)-tetrahydrofuran-3-yl)-1H-pyrazol-3-yl)-3-(trifluoromethyl)-1H-pyrrolo[2,3-b]pyridine,
5-(1-((S)-3,3-difluorocyclopentyl)-5-((S)-tetrahydrofuran-3-yl)-1H-pyrazol-3-yl)-3-methyl-1H-pyrrolo[2,3-b]pyridine,
5-(1-((R)-3,3-difluorocyclopentyl)-5-((S)-tetrahydrofuran-3-yl)-1H-pyrazol-3-yl)-3-methyl-1H-pyrrolo[2,3-b]pyridine,
5-(1-((S)-3,3-difluorocyclopentyl)-5-((R)-tetrahydrofuran-3-yl)-1H-pyrazol-3-yl)-3-methyl-1H-pyrrolo[2,3-b]pyridine,
1-(3-(6-amino-5-(trifluoromethyl)pyridin-3-yl)-1-isopropyl-1H-pyrazol-5-yl)cyclopentanol,
5-(1-(3,3-difluorocyclobutyl)-5-(tetrahydro-2H-pyran-4-yl)-1H-pyrazol-3-yl)-3-methyl-1H-pyrrolo[2,3-b]pyridine,
5-(1-(3,3-difluorocyclobutyl)-5-(tetrahydro-2H-pyran-4-yl)-1H-pyrazol-3-yl)-3-ethyl-1H-pyrazolo[3,4-b]pyridine,
5-(1-(3,3-difluorocyclobutyl)-5-(tetrahydro-2H-pyran-4-yl)-1H-pyrazol-3-yl)-3-fluoropyridin-2-amine,
5-(1-(3,3-difluorocyclobutyl)-5-(tetrahydro-2H-pyran-4-yl)-1H-pyrazol-3-yl)-3-(trifluoromethyl)-1H-pyrrolo[2,3-b]pyridine,
3-chloro-5-(1-(3,3-difluorocyclobutyl)-5-(tetrahydro-2H-pyran-4-yl)-1H-pyrazol-3-yl)pyridin-2-amine,
5-(1-isopropyl-5-(1-methylpiperidin-4-yl)-1H-pyrazol-3-yl)-3-(trifluoromethyl)-1H-pyrrolo[2,3-b]pyridine,
5-(1-isopropyl-5-(1-methylpiperidin-4-yl)-1H-pyrazol-3-yl)-3-(trifluoromethyl)pyridin-2-amine,
4-(1-(3,3-difluorocyclobutyl)-3-(3-methyl-1H-pyrrolo[2,3-b]pyridin-5-yl)-1H-pyrazol-5-yl)-1-methylpiperidin-2-one,
4-(3-(6-amino-5-chloropyridin-3-yl)-1-(3,3-difluorocyclobutyl)-1H-pyrazol-5-yl)-1-methylpiperidin-2-one,
4-(3-(6-amino-5-fluoropyridin-3-yl)-1-(3,3-difluorocyclobutyl)-1H-pyrazol-5-yl)-1-methylpiperidin-2-one,
4-(1-(3,3-difluorocyclobutyl)-3-(3-(trifluoromethyl)-1H-pyrrolo[2,3-b]pyridin-5-yl)-1H-pyrazol-5-yl)-1-methylpiperidin-2-one,
5-(1-isopropyl-5-(1-(2,2,2-trifluoroethyl)piperidin-4-yl)-1H-pyrazol-3-yl)-1H-pyrrolo[2,3-b]pyridine-3-carbonitrile,
1-(4-(1-methyl-3-(3-methyl-1H-pyrrolo[2,3-b]pyridin-5-yl)-1H-pyrazol-5-yl)piperidin-1-yl)ethanone,
1-(4-(1-methyl-3-(3-(trifluoromethyl)-1H-pyrrolo[2,3-b]pyridin-5-yl)-1H-pyrazol-5-yl)piperidin-1-yl)ethanone,
1-(4-(1-isopropyl-3-(3-methyl-1H-pyrrolo[2,3-b]pyridin-5-yl)-1H-pyrazol-5-yl)piperidin-1-yl)ethanone,
1-(4-(1-isopropyl-3-(3-(trifluoromethyl)-1H-pyrrolo[2,3-b]pyridin-5-yl)-1H-pyrazol-5-yl)piperidin-1-yl)ethanone,
2-(4-(1-isopropyl-3-(3-(trifluoromethyl)-1H-pyrrolo[2,3-b]pyridin-5-yl)-1H-pyrazol-5-yl)piperidin-1-yl)acetonitrile,
2-(4-(3-(6-amino-5-(trifluoromethyl)pyridin-3-yl)-1-isopropyl-1H-pyrazol-5-yl)piperidin-1-yl)acetonitrile,
5-(1-isopropyl-5-(1-(2-methoxyethyl)piperidin-4-yl)-1H-pyrazol-3-yl)-3-(trifluoromethyl)pyridin-2-amine,
5-(1-isopropyl-5-(1-(oxetan-3-yl)azetidin-3-yl)-H-pyrazol-3-yl)-3-(trifluoromethyl)-1H-pyrrolo[2,3-b]pyridine,
5-(5-(1-(oxetan-3-yl)azetidin-3-yl)-1-(tetrahydrofuran-3-yl)-1H-pyrazol-3-yl)-3-(trifluoromethyl)-1H-pyrrolo[2,3-b]pyridine,
5-(1-(3,3-difluorocyclopentyl)-5-(1-(oxetan-3-yl)azetidin-3-yl)-1H-pyrazol-3-yl)-3-(trifluoromethyl)-1H-pyrrolo[2,3-b]pyridine,
3-chloro-5-(1-isopropyl-5-(1-(oxetan-3-yl)azetidin-3-yl)-1H-pyrazol-3-yl)-1H-pyrrolo[2,3-b]pyridine,
3-fluoro-5-(1-isopropyl-5-(1-(oxetan-3-yl)azetidin-3-yl)-1H-pyrazol-3-yl)-1H-pyrrolo[2,3-b]pyridine,
5-(1-isopropyl-5-(1-(oxetan-3-yl)azetidin-3-yl)-1H-pyrazol-3-yl)-1H-pyrrolo[2,3-b]pyridine-3-carbonitrile, 5-(1-isopropyl-5-(1-(oxetan-3-yl)azetidin-3-yl)-1H-pyrazol-3-yl)-3-(trifluoromethyl)pyridin-2-amine,
5-(1-isopropyl-5-(1-(oxetan-3-yl)azetidin-3-yl)-1H-pyrazol-3-yl)-3,3-dimethyl-1H-pyrrolo[2,3-b]pyridin-2(3H)-one,
6-(1-isopropyl-5-(1-(oxetan-3-yl)azetidin-3-yl)-1H-pyrazol-3-yl)-3H-imidazo[4,5-b]pyridine,
3-methyl-5-(1-methyl-5-(1-(oxetan-3-yl)pyrrolidin-3-yl)-1H-pyrazol-3-yl)-1H-pyrrolo[2,3-b]pyridine,
5-(1-isopropyl-5-(1-(oxetan-3-yl)pyrrolidin-3-yl)-1H-pyrazol-3-yl)-3-methyl-1H-pyrrolo[2,3-b]pyridine,
3-chloro-5-(1-isopropyl-5-(1-(oxetan-3-yl)pyrrolidin-3-yl)-1H-pyrazol-3-yl)-1H-pyrrolo[2,3-b]pyridine,
3-fluoro-5-(1-isopropyl-5-(1-(oxetan-3-yl)pyrrolidin-3-yl)-1H-pyrazol-3-yl)-1H-pyrrolo[2,3-b]pyridine,
5-(1-isopropyl-5-(1-(oxetan-3-yl)pyrrolidin-3-yl)-1H-pyrazol-3-yl)-3-(trifluoromethyl)pyridin-2-amine,
5-(1-methyl-5-(1-(oxetan-3-yl)piperidin-4-yl)-1H-pyrazol-3-yl)-3-(trifluoromethyl)-1H-pyrrolo[2,3-b]pyridine,
5-(1-isopropyl-5-(1-(oxetan-3-yl)piperidin-4-yl)-1H-pyrazol-3-yl)-3-methyl-1H-pyrrolo[2,3-b]pyridine,
5-(1-isopropyl-5-(1-(oxetan-3-yl)piperidin-4-yl)-1H-pyrazol-3-yl)-3-(trifluoromethyl)-1H-pyrrolo[2,3-b]pyridine,
3-chloro-5-(1-cyclopentyl-5-(1-(oxetan-3-yl)piperidin-4-yl)-1H-pyrazol-3-yl)pyridin-2-amine,
3-chloro-5-(1-isopropyl-5-(1-(oxetan-3-yl)piperidin-4-yl)-1H-pyrazol-3-yl)-1H-pyrrolo[2,3-b]pyridine,
5-(1-isopropyl-5-(1-(oxetan-3-yl)piperidin-4-yl)-1H-pyrazol-3-yl)-1H-pyrrolo[2,3-b]pyridin-2(3H)-one,
3-chloro-5-(5-(1-(oxetan-3-yl)piperidin-4-yl)-1-(tetrahydrofuran-3-yl)-1H-pyrazol-3-yl)pyridin-2-amine,
3-fluoro-5-(1-isopropyl-5-(1-(oxetan-3-yl)piperidin-4-yl)-1H-pyrazol-3-yl)-1H-pyrrolo[2,3-b]pyridine,
5-(1-isopropyl-5-(1-(oxetan-3-yl)piperidin-4-yl)-1H-pyrazol-3-yl)-3-(trifluoromethyl)pyridin-2-amine,
5-(1-isopropyl-5-(1-(oxetan-3-yl)piperidin-4-yl)-1H-pyrazol-3-yl)-1H-pyrrolo[2,3-b]pyridine-3-carbonitrile,
3-chloro-5-(1-isopropyl-5-(1-(oxetan-3-yl)piperidin-4-yl)-1H-pyrazol-3-yl)pyridin-2-amine,
6-(1-isopropyl-5-(1-(oxetan-3-yl)piperidin-4-yl)-1H-pyrazol-3-yl)-3H-imidazo[4,5-b]pyridine,
5-(1-isopropyl-5-(1-(oxetan-3-yl)piperidin-4-yl)-1H-pyrazol-3-yl)-3,3-dimethyl-1H-pyrrolo[2,3-b]pyridin-2(3H)-one,
5-(1-cyclopentyl-5-(1-(oxetan-3-yl)piperidin-4-yl)-1H-pyrazol-3-yl)-3-(trifluoromethyl)pyridin-2-amine,
5-(1-isopropyl-5-(1-(oxetan-3-yl)piperidin-4-yl)-1H-pyrazol-3-yl)-3-methylpyridin-2-amine,
3-ethoxy-5-(1-isopropyl-5-(1-(oxetan-3-yl)piperidin-4-yl)-1H-pyrazol-3-yl)pyridin-2-amine,
3-isopropoxy-5-(1-isopropyl-5-(1-(oxetan-3-yl)piperidin-4-yl)-1H-pyrazol-3-yl)pyridin-2---amine,
5-(1-(3,3-difluorocyclopentyl)-5-(1-(oxetan-3-yl)piperidin-4-yl)-1H-pyrazol-3-yl)-3-ethoxypyridin-2-amine,
5-(1-(3,3-difluorocyclopentyl)-5-(1-(oxetan-3-yl)piperidin-4-yl)-1H-pyrazol-3-yl)-3-isopropoxypyridin-2-amine,
3-(cyclopropylmethoxy)-5-(1-(3,3-difluorocyclopentyl)-5-(1-(oxetan-3-yl)piperidin-4-yl)-1H-pyrazol-3-yl)pyridin-2-amine,
5-(1-cyclopentyl-5-(1-(oxetan-3-yl)piperidin-4-yl)-1H-pyrazol-3-yl)-3-methoxypyridin-2-amine,
5-(1-isopropyl-5-(1-(oxetan-3-yl)piperidin-4-yl)-1H-pyrazol-3-yl)-3-methoxypyridin-2-amine,
5-(1-cyclopentyl-5-(1-(oxetan-3-yl)piperidin-4-yl)-1H-pyrazol-3-yl)-3-isopropoxypyridin-2-amine,
3-chloro-5-(1-(3,3-difluorocyclopentyl)-5-(1-(oxetan-3-yl)piperidin-4-yl)-1H-pyrazol-3-yl)pyridin-2-amine,
2-amino-5-(1-isopropyl-5-(1-(oxetan-3-yl)piperidin-4-yl)-1H-pyrazol-3-yl)nicotinonitrile,
2-amino-5-(1-cyclopentyl-5-(1-(oxetan-3-yl)piperidin-4-yl)-1H-pyrazol-3-yl)nicotinonitrile,
7-(1-isopropyl-5-(1-(oxetan-3-yl)piperidin-4-yl)-1H-pyrazol-3-yl)-3,4-dihydro-2H-pyrido[3,2-b][1,4]oxazine,
5-(1-isopropyl-5-(1-(oxetan-3-yl)piperidin-4-yl)-1H-pyrazol-3-yl)-3,3-dimethyl-2,3-dihydro-1H-pyrrolo[2,3-b]pyridine,
6-(1-isopropyl-5-(1-(oxetan-3-yl)piperidin-4-yl)-1H-pyrazol-3-yl)-1,2,3,4-tetrahydro-,1,8-naphthyridine,
5-(5-(1-(oxetan-3-yl)piperidin-4-yl)-1-(tetrahydrofuran-3-yl)-1H-pyrazol-3-yl)-3-(trifluoromethyl)pyridin-2-amine,
3-cyclopropyl-5-(1-isopropyl-5-(1-(oxetan-3-yl)piperidin-4-yl)-1H-pyrazol-3-yl)pyridin-2-amine,
3-(difluoromethoxy)-5-(1-isopropyl-5-(1-(oxetan-3-yl)piperidin-4-yl)-1H-pyrazol-3-yl)pyridin-2-amine,
5-(1-(3,3-difluorocyclopentyl)-5-(1-(oxetan-3-yl)piperidin-4-yl)-1H-pyrazol-3-yl)-3-methoxypyridin-2-amine,
5-(5-(1-cyclobutylpiperidin-4-yl)-1-isopropyl-1H-pyrazol-3-yl)-3-(trifluoromethyl)-1H-pyrrolo[2,3-b]pyridine,
5-(5-(1-cyclobutylpiperidin-4-yl)-1-isopropyl-1H-pyrazol-3-yl)-3-(trifluoromethyl)pyridin-2-amine,
5-(1-isopropyl-5-(4-methoxy-1-(oxetan-3-yl)piperidin-4-yl)-1H-pyrazol-3-yl)-3-(trifluoromethyl)pyridin-2-amine,
5-(5-((1R,5S,6s)-3-oxabicyclo[3.1.0]hexan-6-yl)-1-isopropyl-1H-pyrazol-3-yl)-3-(trifluoromethyl)pyridin-2-amine,
5-(5-((1R,5 S,6s)-3-oxabicyclo[3.1.0]hexan-6-yl)-1-cyclopentyl-1H-pyrazol-3-yl)-3-chloropyridin-2-amine,
5-(5-((1R,5 S,6s)-3-oxabicyclo[3.1.0]hexan-6-yl)-1-isopropyl-1H-pyrazol-3-yl)-3-fluoro-1H-pyrrolo[2,3-b]pyridine,
5-(5-((1R,5 S,6r)-3-azabicyclo[3.1.0]hexan-6-yl)-1-(2,2,2-trifluoroethyl)-1H-pyrazol-3-yl)-3-(trifluoromethyl)pyridin-2-amine,
5-(1-isopropyl-5-((1R,5S,6r)-3-(methylsulfonyl)-3-azabicyclo[3.1.0]hexan-6-yl)-1H-pyrazol-3-yl)-3-(trifluoromethyl)pyridin-2-amine
5-(5-((1R,5S,6r)-3-(2,2-difluoroethyl)-3-azabicyclo[3.1.0]hexan-6-yl)-1-isopropyl-1H-pyrazol-3-yl)-3-(trifluoromethyl)pyridin-2-amine,
3-(difluoromethoxy)-5-(1-isopropyl-5-((1R,5S,6r)-3-(2,2,2-trifluoroethyl)-3-azabicyclo[3.1.0]hexan-6-yl)-1H-pyrazol-3-yl)pyridin-2-amine,
3-chloro-5-(1-(oxetan-3-yl)-5-((1R,5S,6r)-3-(2,2,2-trifluoroethyl)-3-azabicyclo[3.1.0]hexan-6-yl)-1H-pyrazol-3-yl)pyridin-2-amine,
3-chloro-5-(1-((3-methyloxetan-3-yl)methyl)-5-((1R,5S,6r)-3-(2,2,2-trifluoroethyl)-3-azabicyclo[3.1.0]hexan-6-yl)-1H-pyrazol-3-yl)pyridin-2-amine,
2-amino-5-(1-(cyclopropylmethyl)-5-((1R,5S,6r)-3-(2,2,2-trifluoroethyl)-3-azabicyclo[3.1.0]hexan-6-yl)-1H-pyrazol-3-yl)nicotinonitrile,
7-(1-isopropyl-5-((1R,5 S,6r)-3-(2,2,2-trifluoroethyl)-3-azabicyclo[3.1.0]hexan-6-yl)-1H-pyrazol-3-yl)-1H-pyrazolo[4,3-c]pyridin-4-amine,
1-((1R,5 S,6r)-6-(3-(6-amino-5-(trifluoromethyl)pyridin-3-yl)-1-isopropyl-1H-pyrazol-5-yl)-3-azabicyclo[3.1.0]hexan-3-yl)ethanone,
3-chloro-5-(5-((1R,5 S,6r)-3-(2-methoxyethyl)-3-azabicyclo[3.1.0]hexan-6-yl)-1-(2,2,2-trifluoroethyl)-1H-pyrazol-3-yl)pyridin-2-amine,
5-(1-isopropyl-5-((1R,5 S,6r)-3-(2-methoxyethyl)-3-azabicyclo[3.1.0]hexan-6-yl)-1H-pyrazol-3-yl)-3-(trifluoromethyl)pyridin-2-amine, 3-chloro-5-(1-isopropyl-5-((1R,5S,6r)-3-(2-methoxyethyl)-3-azabicyclo[3.1.0]hexan-6-yl)-1H-pyrazol-3-yl)pyridin-2-amine, 3-(difluoromethoxy)-5-(1-isopropyl-5-((1R,5S,6r)-3-(2-methoxyethyl)-3-azabicyclo[3.1.0]hexan-6-yl)-1H-pyrazol-3-yl)pyridin-2-amine, 3-chloro-5-(1-isobutyl-5-((1R,5S,6r)-3-(2-methoxyethyl)-3-azabicyclo[3.1.0]hexan-6-yl)-1H-pyrazol-3-yl)pyridin-2-amine, 3-chloro-5-(1-((2,2-difluorocyclopropyl)methyl)-5-((1R,5S,6r)-3-(2-methoxyethyl)-3-azabicyclo[3.1.0]hexan-6-yl)-1H-pyrazol-3-yl)pyridin-2-amine, 5-(1-(cyclopropylmethyl)-5-((1R,5S,6r)-3-(2-methoxyethyl)-3-azabicyclo[3.1.0]hexan-6-yl)-1H-pyrazol-3-yl)-3-(trifluoromethyl)pyridin-2-amine, 3-chloro-5-(1-(cyclopropylmethyl)-5-((1R,5S,6r)-3-(2-methoxyethyl)-3-azabicyclo[3.1.0]hexan-6-yl)-1H-pyrazol-3-yl)pyridin-2-amine, 5-(1-(cyclobutylmethyl)-5-((1R,5S,6r)-3-(2-methoxyethyl)-3-azabicyclo[3.1.0]hexan-6-yl)-1H-pyrazol-3-yl)-3-(trifluoromethyl)pyridin-2-amine, 5-(1-isopropyl-5-((1R,5S,6r)-3-(2-methoxyethyl)-3-azabicyclo[3.1.0]hexan-6-yl)-1H-pyrazol-3-yl)-3-(trifluoromethoxy)pyridin-2-amine, 5-(5-((1R,5S,6r)-3-(2-methoxyethyl)-3-azabicyclo[3.1.0]hexan-6-yl)-1-(2,2,2-trifluoroethyl)-1H-pyrazol-3-yl)-3-(trifluoromethyl)pyridin-2-amine, 3-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)propanenitrile, 1-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)-2-methylpropan-2-ol, 5-(1-isopropyl-5-((1R,5S,6r)-3-(1-methoxypropan-2-yl)-3-azabicyclo[3.1.0]hexan-6-yl)-1H-pyrazol-3-yl)-3-(trifluoromethyl)pyridin-2-amine, (1R,5S,6r)-isopropyl-6-(3-(6-amino-5-(trifluoromethyl)pyridin-3-yl)-1-isopropyl-1H-pyrazol-5-yl)-3-azabicyclo[3.1.0]hexane-3-carboxylate, 3-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)butanenitrile, 5-(1-isopropyl-5-((1R,5S,6r)-3-(oxetan-3-yl)-3-azabicyclo[3.1.0]hexan-6-yl)-1H-pyrazol-3-yl)-1H-pyrrolo[2,3-b]pyridine-3-carbonitrile, 5-(1-isopropyl-5-((1R,5S,6r)-3-(oxetan-3-yl)-3-azabicyclo[3.1.0]hexan-6-yl)-1H-pyrazol-3-yl)-3-(trifluoromethyl)-1H-pyrrolo[2,3-b]pyridine, 5-(1-isopropyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 3-chloro-5-(1-cyclopentyl-5-((1R,5S,6r)-3-(oxetan-3-yl)-3-azabicyclo[3.1.0]hexan-6-yl)-1H-pyrazol-3-yl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-(difluoromethoxy)pyridin-2-amine, 2-amino-5-(1-cyclopentyl-5-((1R,5S,6r)-3-(oxetan-3-yl)-3-azabicyclo[3.1.0]hexan-6-yl)-1H-pyrazol-3-yl)nicotinonitrile, 5-(1-cyclopentyl-5-((1R,5S,6r)-3-(oxetan-3-yl)-3-azabicyclo[3.1.0]hexan-6-yl)-1H-pyrazol-3-yl)-3-cyclopropylpyridin-2-amine, 3-chloro-5-(1-isopropyl-5-((1R,5S,6r)-3-(oxetan-3-yl)-3-azabicyclo[3.1.0]hexan-6-yl)-1H-pyrazol-3-yl)pyridin-2-amine, 3-(difluoromethoxy)-5-(1-isopropyl-5-((1R,5S,6r)-3-(oxetan-3-yl)-3-azabicyclo[3.1.0]hexan-6-yl)-1H-pyrazol-3-yl)pyridin-2-amine, 3-cyclopropyl-5-(1-isopropyl-5-((1R,5S,6r)-3-(oxetan-3-yl)-3-azabicyclo[3.1.0]hexan-6-yl)-1H-pyrazol-3-yl)pyridin-2-amine, 5-(1-isopropyl-5-((1R,5S,6r)-3-(oxetan-3-yl)-3-azabicyclo[3.1.0]hexan-6-yl)-1H-pyrazol-3-yl)-3,3-dimethyl-2,3-dihydro-1H-pyrrolo[2,3-b]pyridine, 2-amino-5-(1-isopropyl-5-((1R,5S,6r)-3-(oxetan-3-yl)-3-azabicyclo[3.1.0]hexan-6-yl)-1H-pyrazol-3-yl)nicotinonitrile, 5-(1-isopropyl-5-((1R,5S,6r)-3-(oxetan-3-yl)-3-azabicyclo[3.1.0]hexan-6-yl)-1H-pyrazol-3-yl)-3-methoxypyridin-2-amine, 3-isopropoxy-5-(1-isopropyl-5-((1R,5S,6r)-3-(oxetan-3-yl)-3-azabicyclo[3.1.0]hexan-6-yl)-1H-pyrazol-3-yl)pyridin-2-amine, 3-chloro-5-(1-cyclobutyl-5-((1R,5S,6r)-3-(oxetan-3-yl)-3-azabicyclo[3.1.0]hexan-6-yl)-1H-pyrazol-3-yl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-isopropoxypyridin-2-amine, 3-chloro-5-(5-((1R,5S,6r)-3-(oxetan-3-yl)-3-azabicyclo[3.1.0]hexan-6-yl)-1-(2,2,2-trifluoroethyl)-1H-pyrazol-3-yl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-(difluoromethoxy)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-cyclopropylpyridin-2-amine, 3-chloro-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-(methylsulfonyl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-isopropoxypyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-methoxypyridin-2-amine, 3-(difluoromethyl)-5-(1-isopropyl-5-((1R,5S,6r)-3-(oxetan-3-yl)-3-azabicyclo[3.1.0]hexan-6-yl)-1H-pyrazol-3-yl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-methoxypyridin-2-amine, 5-(1-(cyclobutylmethyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 3-cyclopropyl-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine, 5-(1-(cyclobutylmethyl)-5-(((1R,5S,6r)-3-(oxetan-3-yl)-3-azabicyclo[3.1.0]hexan-6-yl)-1H-pyrazol-3-yl)-3-cyclopropylpyridin-2-amine,
5-(1-cyclobutyl-5-(((1R,5S,6r)-3-(oxetan-3-yl)-3-azabicyclo[3.1.0]hexan-6-yl)-1H-pyrazol-3-yl)-3-(trifluoromethoxy)pyridin-2-amine,
5-(1-(cyclobutylmethyl)-5-(((1R,5S,6r)-3-(oxetan-3-yl)-3-azabicyclo[3.1.0]hexan-6-yl)-1H-pyrazol-3-yl)-3-(difluoromethoxy)pyridin-2-amine,
5-(1-isopropyl-5-(((1R,5 S,6r)-3-(oxetan-3-yl)-3-azabicyclo[3.1.0]hexan-6-yl)-1H-pyrazol-3-yl)-3-(trifluoromethoxy)pyridin-2-amine,
5-(1-cyclopentyl-5-(((1R,5S,6r)-3-(oxetan-3-yl)-3-azabicyclo[3.1.0]hexan-6-yl)-1H-pyrazol-3-yl)-3-(trifluoromethoxy)pyridin-2-amine,
5-(1-(tert-butyl)-5-(((1R,5S,6r)-3-(oxetan-3-yl)-3-azabicyclo[3.1.0]hexan-6-yl)-1H-pyrazol-3-yl)-3-(trifluoromethyl)pyridin-2-amine,
5-(1-cyclopropyl-5-(((1R,5S,6r)-3-(oxetan-3-yl)-3-azabicyclo[3.1.0]hexan-6-yl)-1H-pyrazol-3-yl)-3-(trifluoromethyl)pyridin-2-amine,
5-(1-(cyclopropylmethyl)-5-(((1R,5S,6r)-3-(oxetan-3-yl)-3-azabicyclo[3.1.0]hexan-6-yl)-1H-pyrazol-3-yl)-3-(difluoromethyl)pyridin-2-amine,
5-(1-cyclopropyl-5-(((1R,5S,6r)-3-(oxetan-3-yl)-3-azabicyclo[3.1.0]hexan-6-yl)-1H-pyrazol-3-yl)-3-(difluoromethyl)pyridin-2-amine,
5-(1-cyclopentyl-5-(((1R,5S,6r)-3-(oxetan-3-yl)-3-azabicyclo[3.1.0]hexan-6-yl)-1H-pyrazol-3-yl)-3-(difluoromethyl)pyridin-2-amine,
7-(1-isopropyl-5-(((1R,5 S,6r)-3-(oxetan-3-yl)-3-azabicyclo[3.1.0]hexan-6-yl)-1H-pyrazol-3-yl)-1H-pyrazolo[4,3-c]pyridin-4-amine,
5-(1-(cyclopropylmethyl)-5-(((1R,5S,6r)-3-(oxetan-3-yl)-3-azabicyclo[3.1.0]hexan-6-yl)-1H-pyrazol-3-yl)-3-(difluoromethoxy)pyridin-2-amine,
5-(5-(((1R,5S,6r)-3-(oxetan-3-yl)-3-azabicyclo[3.1.0]hexan-6-yl)-1-(2,2,2-trifluoroethyl)-1H-pyrazol-3-yl)-3-(trifluoromethyl)pyridin-2-amine,
3-(1,1-difluoroethyl)-5-(1-isopropyl-5-(((1R,5S,6r)-3-(oxetan-3-yl)-3-azabicyclo[3.1.0]hexan-6-yl)-1H-pyrazol-3-yl)pyridin-2-amine,
3-(1,1-difluoroethoxy)-5-(1-isopropyl-5-(((1R,5S,6r)-3-(oxetan-3-yl)-3-azabicyclo[3.1.0]hexan-6-yl)-1H-pyrazol-3-yl)pyridin-2-amine,
5-(1-((1-methylcyclopropyl)methyl)-5-(((1R,5S,6r)-3-(oxetan-3-yl)-3-azabicyclo[3.1.0]hexan-6-yl)-1H-pyrazol-3-yl)-3-(trifluoromethyl)pyridin-2-amine,
5-(5-(((1R,5 S,6r)-3-cyclobutyl-3-azabicyclo[3.1.0]hexan-6-yl)-1-cyclopentyl-1H-pyrazol-3-yl)-3-(methylsulfonyl)pyridin-2-amine,
5-(1-isopropyl-5-(3-(oxetan-3-yl)-3-azabicyclo[3.1.1]heptan-6-yl)-1H-pyrazol-3-yl)-3-(trifluoromethyl)pyridin-2-amine,
3-chloro-5-(1-isopropyl-5-(3-(oxetan-3-yl)-3-azabicyclo[3.1.1]heptan-6-yl)-1H-pyrazol-3-yl)pyridin-2-amine,
3-(difluoromethoxy)-5-(1-isopropyl-5-(3-(oxetan-3-yl)-3-azabicyclo[3.1.1]heptan-6-yl)-1H-pyrazol-3-yl)pyridin-2-amine, and
5-(1-isopropyl-5-(3-(oxetan-3-yl)-3-azabicyclo[3.1.1]heptan-6-yl)-1H-pyrazol-3-yl)-3-(trifluoromethoxy)pyridin-2-amine,
and salts thereof.

In another embodiment, the compounds of Formula (I) are selected from the group of compounds in Table 1.

TABLE 1

| No | Structure | Name | M + H |
|---|---|---|---|
| 1 | 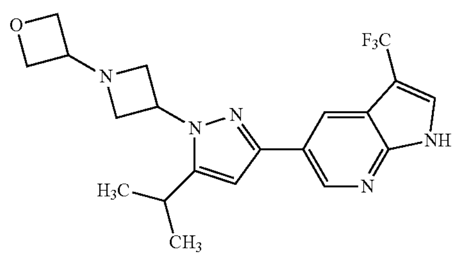 [SMILES: CC(C)c1cc(-c2cnc3[nH]cc(C(F)(F)F)c3c2)nn1C1CN(C2COC2)C1] | 5-(5-isopropyl-1-(1-(oxetan-3-yl)azetidin-3-yl)-1H-pyrazol-3-yl)-3-(trifluoromethyl)-1H-pyrrolo[2,3-b]pyridine | 406.2 |
| 2 | 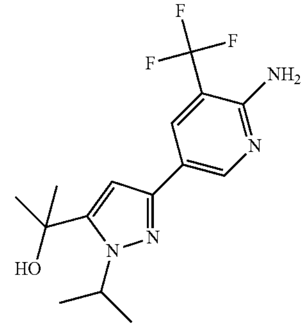 [SMILES: CC(C)n1nc(-c2cnc(N)c(C(F)(F)F)c2)cc1C(C)(C)O] | 2-(3-(6-amino-5-(trifluoromethyl)pyridin-3-yl)-1-isopropyl-1H-pyrazol-5-yl)propan-2-ol | |

| No | Structure | Name | M + H |
|---|---|---|---|
| 3 | 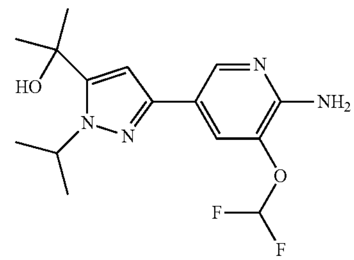 [SMILES: CC(C)n1nc(-c2cnc(N)c(OC(F)F)c2)cc1C(C)(C)O] | 2-(3-(6-amino-5-(difluoromethoxy)pyridin-3-yl)-1-isopropyl-1H-pyrazol-5-yl)propan-2-ol | |
| 4 | 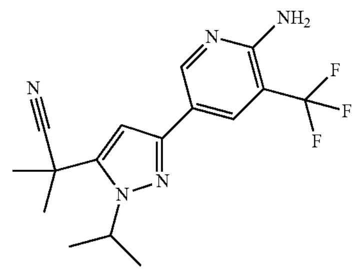 [SMILES: CC(C)n1nc(-c2cnc(N)c(C(F)(F)F)c2)cc1C(C)(C)C#N] | 2-(3-(6-amino-5-(trifluoromethyl)pyridin-3-yl)-1-isopropyl-1H-pyrazol-5-yl)-2-methylpropanenitrile | |
| 5 | 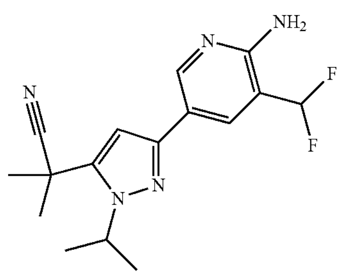 [SMILES: CC(C)n1nc(-c2cnc(N)c(C(F)F)c2)cc1C(C)(C)C#N] | 2-(3-(6-amino-5-(difluoromethyl)pyridin-3-yl)-1-isopropyl-1H-pyrazol-5-yl)-2-methylpropanenitrile | |
| 6 | 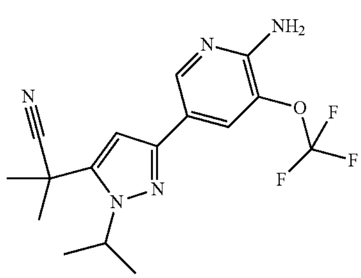 [SMILES: CC(C)n1nc(-c2cnc(N)c(OC(F)(F)F)c2)cc1C(C)(C)C#N] | 2-(3-(6-amino-5-(trifluoromethoxy)pyridin-3-yl)-1-isopropyl-1H-pyrazol-5-yl)-2-methylpropanenitrile | |
| 7 | 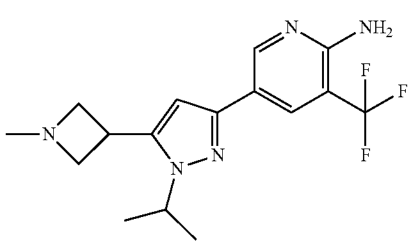 [SMILES: CC(C)n1nc(-c2cnc(N)c(C(F)(F)F)c2)cc1C1CN(C)C1] | 5-(1-isopropyl-5-(1-methylazetidin-3-yl)-1H-pyrazol-3-yl)-3-(trifluoromethyl)pyridin-2-amine | 339.9 |
| 8 | 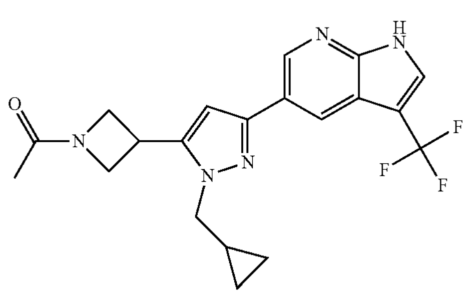 [SMILES: CC(=O)N1CC(c2cc(-c3cnc4[nH]cc(C(F)(F)F)c4c3)nn2CC2CC2)C1] | 1-(3-(1-(cyclopropylmethyl)-3-(3-(trifluoromethyl)-1H-pyrrolo[2,3-b]pyridin-5-yl)-1H-pyrazol-5-yl)azetidin-1-yl)ethanone | 404.2 |

TABLE 1-continued

| No | Structure | Name | M + H |
|---|---|---|---|
| 9 | 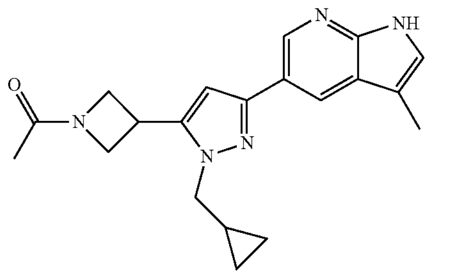 [SMILES: CC(=O)N1CC(c2cc(-c3cnc4[nH]cc(C)c4c3)nn2CC2CC2)C1] | 1-(3-(1-(cyclopropylmethyl)-3-(3-methyl-1H-pyrrolo[2,3-b]pyridin-5-yl)-1H-pyrazol-5-yl)azetidin-1-yl)ethanone | 349.9 |
| 10 | 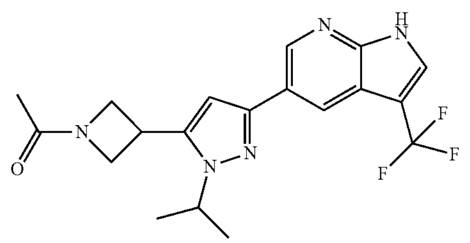 [SMILES: CC(=O)N1CC(c2cc(-c3cnc4[nH]cc(C(F)(F)F)c4c3)nn2C(C)C)C1] | 1-(3-(1-isopropyl-3-(3-(trifluoromethyl)-1H-pyrrolo[2,3-b]pyridin-5-yl)-1H-pyrazol-5-yl)azetidin-1-yl)ethanone | 392.1 |
| 11 | 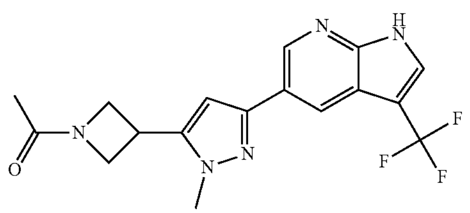 [SMILES: CC(=O)N1CC(c2cc(-c3cnc4[nH]cc(C(F)(F)F)c4c3)nn2C)C1] | 1-(3-(1-methyl-3-(3-(trifluoromethyl)-1H-pyrrolo[2,3-b]pyridin-5-yl)-1H-pyrazol-5-yl)azetidin-1-yl)ethanone | 363.9 |
| 12 | 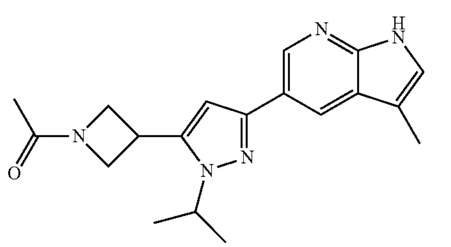 [SMILES: CC(=O)N1CC(c2cc(-c3cnc4[nH]cc(C)c4c3)nn2C(C)C)C1] | 1-(3-(1-isopropyl-3-(3-methyl-1H-pyrrolo[2,3-b]pyridin-5-yl)-1H-pyrazol-5-yl)azetidin-1-yl)ethanone | 337.9 |
| 13 | 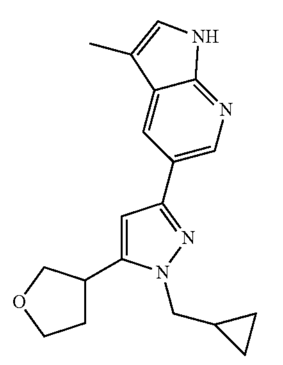 [SMILES: Cc1c[nH]c2ncc(-c3cc(C4CCOC4)n(CC4CC4)n3)cc12] | Racemic-5-(1-(cyclopropylmethyl)-5-(tetrahydrofuran-3-yl)-1H-pyrazol-3-yl)-3-methyl-1H-pyrrolo[2,3-b]pyridine | 323.0 |

TABLE 1-continued

| No | Name | M + H |
|---|---|---|
| 14 | 5-(1-(3,3-difluorocyclopentyl)-5-(tetrahydrofuran-3-yl)-1H-pyrazol-3-yl)-3-methyl-1H-pyrrolo[2,3-b]pyridine | 373.0 |
| 15 | 5-(1,5-bis(tetrahydrofuran-3-yl)-1H-pyrazol-3-yl)-3-(trifluoromethyl)-1H-pyrrolo[2,3-b]pyridine | 392.8 |
| 16 | 5-(1-(3,3-difluorocyclopentyl)-5-(tetrahydrofuran-3-yl)-1H-pyrazol-3-yl)-3-(trifluoromethyl)-1H-pyrrolo[2,3-b]pyridine | 427.0 |
| 17 | (R)-5-(1-(cyclopropylmethyl)-5-(tetrahydrofuran-3-yl)-1H-pyrazol-3-yl)-3-methyl-1H-pyrrolo[2,3-b]pyridine | 323.2 |

TABLE 1-continued

| No | Structure | Name | M + H |
|----|-----------|------|-------|
| 18 | 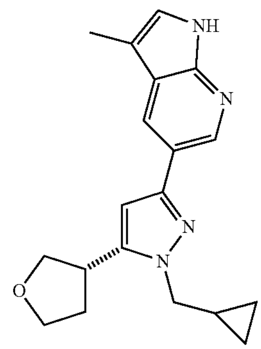 [SMILES: Cc1c[nH]c2ncc(-c3cc([C@@H]4CCOC4)n(CC4CC4)n3)cc12] | (S)-5-(1-(cyclopropylmethyl)-5-(tetrahydrofuran-3-yl)-1H-pyrazol-3-yl)-3-methyl-1H-pyrrolo[2,3-b]pyridine | 323.2 |
| 19 | 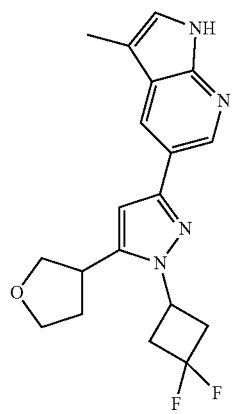 [SMILES: Cc1c[nH]c2ncc(-c3cc(C4CCOC4)n(C4CC(F)(F)C4)n3)cc12] | 5-(1-(3,3-difluorocyclobutyl)-5-(tetrahydrofuran-3-yl)-1H-pyrazol-3-yl)-3-methyl-1H-pyrrolo[2,3-b]pyridine | 358.9 |
| 20 | 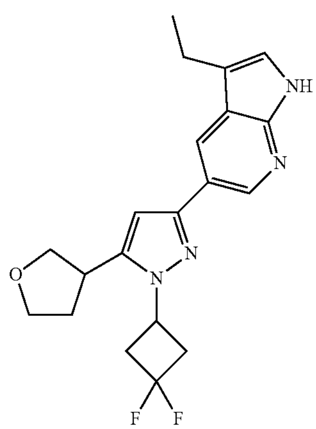 [SMILES: CCc1c[nH]c2ncc(-c3cc(C4CCOC4)n(C4CC(F)(F)C4)n3)cc12] | 5-(1-(3,3-difluorocyclobutyl)-5-(tetrahydrofuran-3-yl)-1H-pyrazol-3-yl)-3-ethyl-1H-pyrrolo[2,3-b]pyridine | 373.2 |
| 21 | 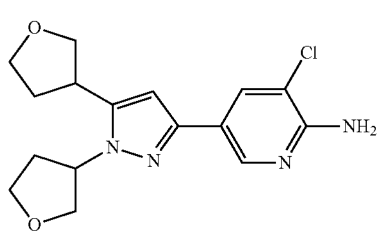 [SMILES: Nc1ncc(-c2cc(C3CCOC3)n(C3CCOC3)n2)cc1Cl] | 5-(1,5-bis(tetrahydrofuran-3-yl)-1H-pyrazol-3-yl)-3-chloropyridin-2-amine | |

TABLE 1-continued

| No | Structure | Name | M + H |
|----|-----------|------|-------|
| 22 | 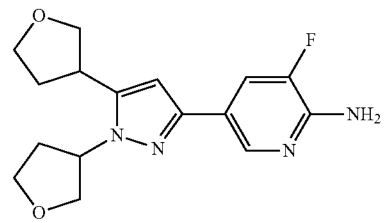 [SMILES: Nc1ncc(-c2cc(C3CCOC3)n(C3CCOC3)n2)cc1F] | 5-(1,5-bis(tetrahydrofuran-3-yl)-1H-pyrazol-3-yl)-3-fluoropyridin-2-amine | |
| 23 | 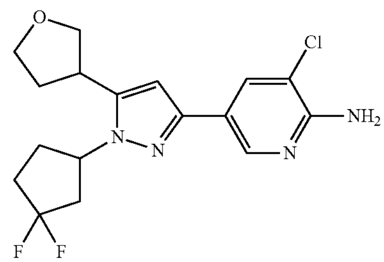 [SMILES: Nc1ncc(-c2cc(C3CCOC3)n(C3CCC(F)(F)C3)n2)cc1Cl] | 3-chloro-5-(1-(3,3-difluorocyclopent-yl)-5-(tetrahydrofuran-3-yl)-1H-pyrazol-3-yl)pyridin-2-amine | 369.0 |
| 24 | 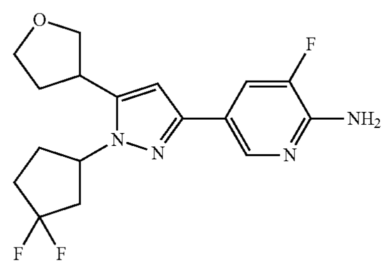 [SMILES: Nc1ncc(-c2cc(C3CCOC3)n(C3CCC(F)(F)C3)n2)cc1F] | 5-(1-(3,3-difluorocyclopentyl)-5-(tetrahydrofuran-3-yl)-1H-pyrazol-3-yl)-3-fluoropyridin-2-amine | |
| 25 | 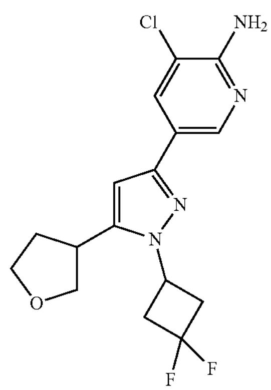 [SMILES: Nc1ncc(-c2cc(C3CCOC3)n(C3CC(F)(F)C3)n2)cc1Cl] | 3-chloro-5-(1-(3,3-difluorocyclobut-yl)-5-(tetrahydrofuran-3-yl)-1H-pyrazol-3-yl)pyridin-2-amine | 354.9 |
| 26 | 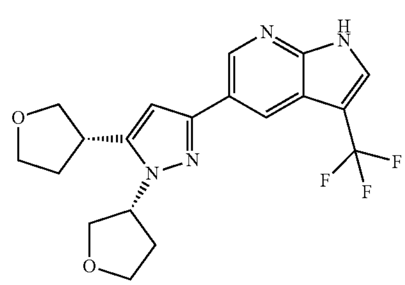 [SMILES: FC(F)(F)c1c[nH]c2ncc(-c3cc([C@@H]4CCOC4)n([C@@H]4CCOC4)n3)cc12] | 5-(1-((R)-tetrahydrofuran-3-yl)-5-((S)-tetrahydrofuran-3-yl)-1H-pyrazol-3-yl)-3-(trifluoromethyl)-1H-pyrrolo[2,3-b]pyridine | 393.2 |

TABLE 1-continued

| No | Structure | Name | M + H |
|---|---|---|---|
| 27 | 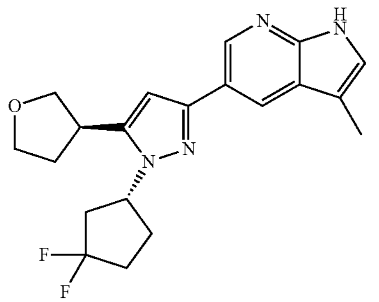 [SMILES: Cc1c[nH]c2ncc(-c3cc([C@H]4CCOC4)n([C@@H]4CCC(F)(F)C4)n3)cc12] | 5-(1-((R)-3,3-difluorocyclopentyl)-5-((R)-tetrahydrofuran-3-yl)-1H-pyrazol-3-yl)-3-methyl-1H-pyrrolo[2,3-b]pyridine | 373.2 |
| 28 | 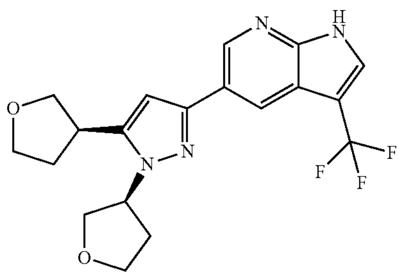 [SMILES: FC(F)(F)c1c[nH]c2ncc(-c3cc([C@H]4CCOC4)n([C@H]4CCOC4)n3)cc12] | 5-(5-((R)-tetrahydrofuran-3-yl)-1-((S)-tetrahydrofuran-3-yl)-1H-pyrazol-3-yl)-3-(trifluoromethyl)-1H-pyrrolo[2,3-b]pyridine | 393.2 |
| 29 | 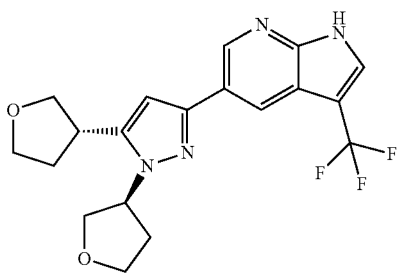 [SMILES: FC(F)(F)c1c[nH]c2ncc(-c3cc([C@@H]4CCOC4)n([C@H]4CCOC4)n3)cc12] | 5-(1,5-bis((S)-tetrahydrofuran-3-yl)-1H-pyrazol-3-yl)-3-(trifluoromethyl)-1H-pyrrolo[2,3-b]pyridine | 393.2 |
| 30 | 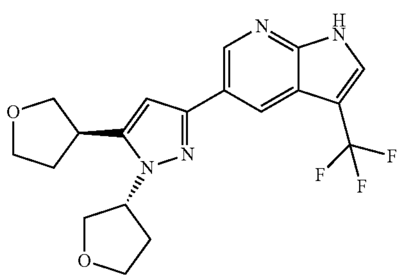 [SMILES: FC(F)(F)c1c[nH]c2ncc(-c3cc([C@H]4CCOC4)n([C@@H]4CCOC4)n3)cc12] | 5-(1,5-bis((R)-tetrahydrofuran-3-yl)-1H-pyrazol-3-yl)-3-(trifluoromethyl)-1H-pyrrolo[2,3-b]pyridine | 393.2 |
| 31 | 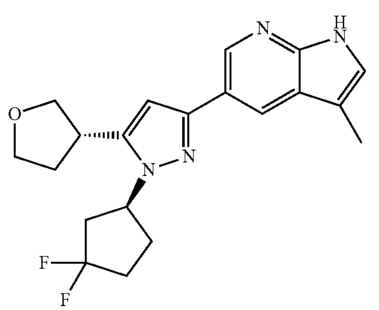 [SMILES: Cc1c[nH]c2ncc(-c3cc([C@@H]4CCOC4)n([C@H]4CCC(F)(F)C4)n3)cc12] | 5-(1-((S)-3,3-difluorocyclopentyl)-5-((S)-tetrahydrofuran-3-yl)-1H-pyrazol-3-yl)-3-methyl-1H-pyrrolo[2,3-b]pyridine | 373.2 |

| No | Structure | Name | M + H |
|----|-----------|------|-------|
| 32 | 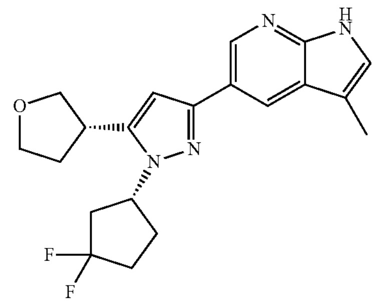 [SMILES: Cc1c[nH]c2ncc(-c3cc([C@@H]4CCOC4)n([C@@H]4CCC(F)(F)C4)n3)cc12] | 5-(1-((R)-3,3-difluorocyclopentyl)-5-((S)-tetrahydrofuran-3-yl)-1H-pyrazol-3-yl)-3-methyl-1H-pyrrolo[2,3-b]pyridine | 373.2 |
| 33 | 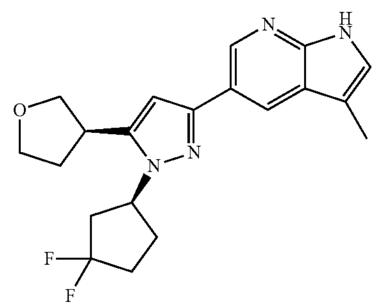 [SMILES: Cc1c[nH]c2ncc(-c3cc([C@H]4CCOC4)n([C@H]4CCC(F)(F)C4)n3)cc12] | 5-(1-((S)-3,3-difluorocyclopentyl)-5-((R)-tetrahydrofuran-3-yl)-1H-pyrazol-3-yl)-3-methyl-1H-pyrrolo[2,3-b]pyridine | 373.2 |
| 34 | 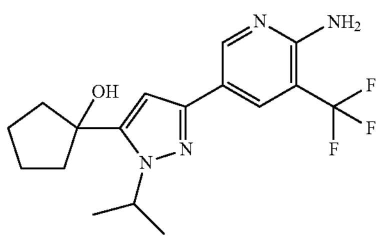 [SMILES: CC(C)n1nc(-c2cnc(N)c(C(F)(F)F)c2)cc1C1(O)CCCC1] | 1-(3-(6-amino-5-(trifluoromethyl)pyridin-3-yl)-1-isopropyl-1H-pyrazol-5-yl)cyclopentanol | |
| 35 | 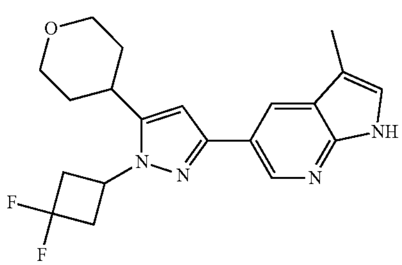 [SMILES: Cc1c[nH]c2ncc(-c3cc(C4CCOCC4)n(C4CC(F)(F)C4)n3)cc12] | 5-(1-(3,3-difluorocyclobutyl)-5-(tetrahydro-2H-pyran-4-yl)-1H-pyrazol-3-yl)-3-methyl-1H-pyrrolo[2,3-b]pyridine | 373.2 |
| 36 | 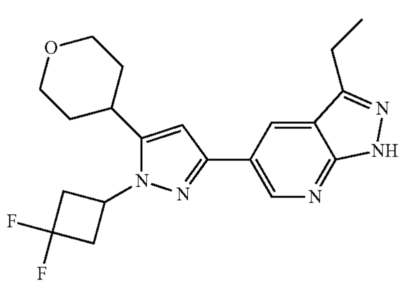 [SMILES: CCc1n[nH]c2ncc(-c3cc(C4CCOCC4)n(C4CC(F)(F)C4)n3)cc12] | 5-(1-(3,3-difluorocyclobutyl)-5-(tetrahydro-2H-pyran-4-yl)-1H-pyrazol-3-yl)-3-methyl-1H-pyrazolo[3,4-b]pyridine | |

TABLE 1-continued

| No | Name | M + H |
|---|---|---|
| 37 | 5-(1-(3,3-difluorocyclobutyl)-5-(tetrahydro-2H-pyran-4-yl)-1H-pyrazol-3-yl)-3-fluoropyridin-2-amine | |
| 38 | 5-(1-(3,3-difluroocyclobutyl)-5-(tetrahydro-2H-pyran-4-yl)-1H-pyrazol-3-yl)-3-(trifluoromethyl)-1H-pyrrolo[2,3-b]pyridine | 427.2 |
| 39 | 3-chloro-5-(1-(3,3-difluorocyclobutyl)-5-(tetrahydro-2H-pyran-4-yl)-1H-pyrazol-3-yl)pyridin-2-amine | 369.2 |
| 40 | 5-(1-isopropyl-5-(1-methylpiperidin-4-yl)-1H-pyrazol-3-yl)-3-(trifluoromethyl)-1H-pyrrolo[2,3-b]pyridine | 391.9 |
| 41 | 5-(1-isopropyl-5-(1-methylpiperidin-4-yl)-1H-pyrazol-3-yl)-3-(trifluoromethyl)pyridin-2-amine | 367.9 |

TABLE 1-continued

| No | Structure | Name | M + H |
|---|---|---|---|
| 42 | 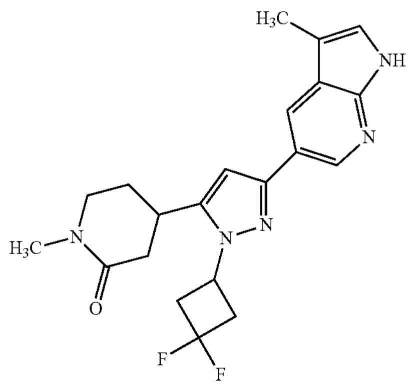 [SMILES: Cc1c[nH]c2ncc(-c3cc(C4CCN(C)C(=O)C4)n(C4CC(F)(F)C4)n3)cc12] | 4-(1-(3,3-difluorocyclobutyl)-3-(3-methyl-1H-pyrrolo[2,3-b]pyridin-5-yl)-1H-pyrazol-5-yl)-1-methylpiperidin-2-one | 400.2 |
| 43 | 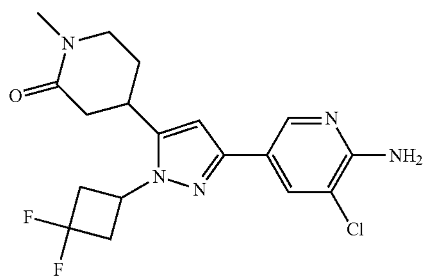 [SMILES: CN1CCC(c2cc(-c3cnc(N)c(F)c3)nn2C2CC(F)(F)C2)CC1=O] | 4-(3-(6-amino-5-chloropyridin-3-yl)-1-(3,3-difluorocyclobutyl)-1H-pyrazol-5-yl)-1-methylpiperidin-2-one | 396.2 |
| 44 | 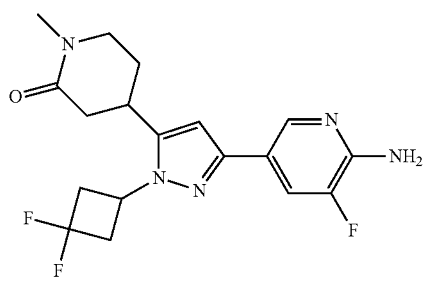 | 4-(3-(6-amino-5-fluoropyridin-3-yl)-1-(3,3-difluorocyclobutyl)-1H-pyrazol-5-yl)-1-methylpiperidin-2-one | |
| 45 | 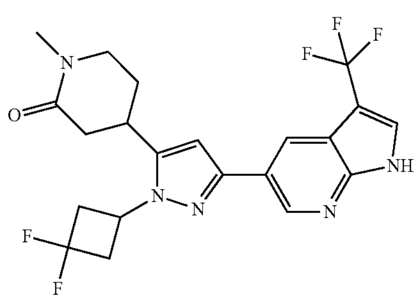 [SMILES: CN1CCC(c2cc(-c3cnc4[nH]cc(C(F)(F)F)c4c3)nn2C2CC(F)(F)C2)CC1=O] | 4-(1-(3,3-difluorocyclobutyl)-3-(3-(trifluoromethyl)-1H-pyrrolo[2,3-b]pyridin-5-yl)-1H-pyrazol-5-yl)-1-methylpiperidin-2-one | 454.2 |
| 46 | 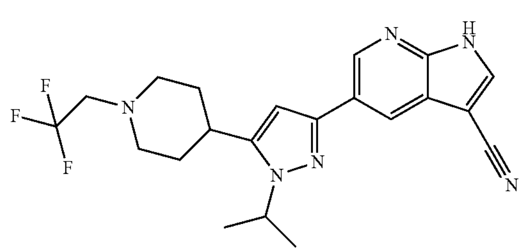 [SMILES: CC(C)n1nc(-c2cnc3[nH]cc(C#N)c3c2)cc1C1CCN(CC(F)(F)F)CC1] | 5-(1-isopropyl-5-(1-(2,2,2-trifluoromethyl)piperidin-4-yl)-1H-pyrazol-3-yl)-1H-pyrrolo[2,3-b]pyridine-3-carbonitrile | 416.9 |

TABLE 1-continued

| No | Structure | Name | M + H |
|---|---|---|---|
| 47 | 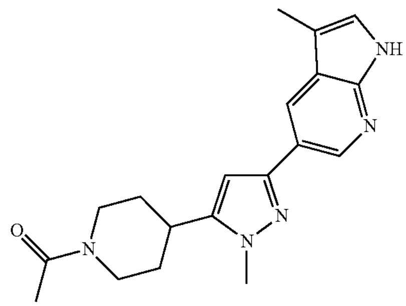 [SMILES: CC(=O)N1CCC(c2cc(-c3cnc4[nH]cc(C)c4c3)nn2C)CC1] | 1-(4-(1-methyl-3-(3-methyl-1H-pyrrolo[2,3-b]pyridin-5-yl)-1H-pyrazol-5-yl)piperidin-1-yl)ethanone | 338.2 |
| 48 | 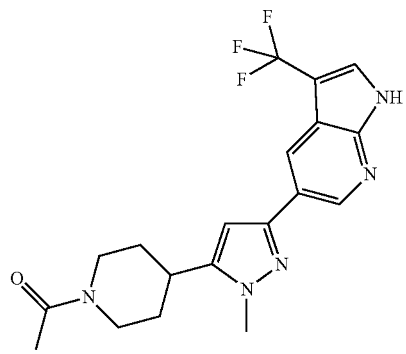 [SMILES: CC(=O)N1CCC(c2cc(-c3cnc4[nH]cc(C(F)(F)F)c4c3)nn2C)CC1] | 1-(4-(1-methyl-3-(3-(trifluoromethyl)-1H-pyrrolo[2,3-b]pyridin-5-yl)-1H-pyrazol-5-yl)piperidin-1-yl)ethanone | 392.2 |
| 49 | 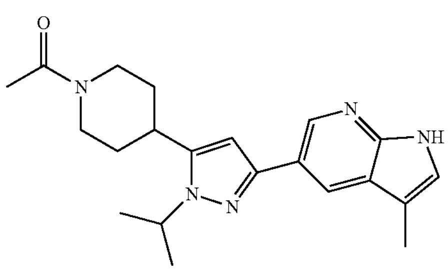 [SMILES: CC(=O)N1CCC(c2cc(-c3cnc4[nH]cc(C)c4c3)nn2C(C)C)CC1] | 1-(4-(1-isopropyl-3-(3-methyl-1H-pyrrolo[2,3-b]pyridin-5-yl)-1H-pyrazol-5-yl)piperidin-1-yl)ethanone | 366.0 |
| 50 | 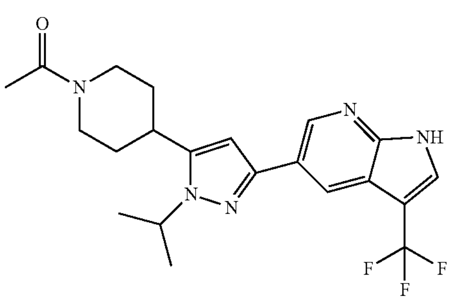 [SMILES: CC(=O)N1CCC(c2cc(-c3cnc4[nH]cc(C(F)(F)F)c4c3)nn2C(C)C)CC1] | 1-(4-(1-isopropyl-3-(3-(trifluoromethyl)-1H-pyrrolo[2,3-b]pyridin-5-yl)-1H-pyrazol-5-yl)piperidin-1-yl)ethanone | 419.9 |
| 51 | 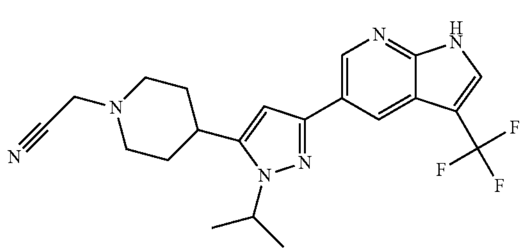 [SMILES: CC(C)n1nc(-c2cnc3[nH]cc(C(F)(F)F)c3c2)cc1C1CCN(CC#N)CC1] | 2-(4-(1-isopropyl-3-(3-(trifluoromethyl)-1H-pyrrolo[2,3-b]pyridin-5-yl)-1H-pyrazol-5-yl)piperidin-1-yl)acetonitrile | 417.1 |

TABLE 1-continued

| No | Structure | Name | M + H |
|---|---|---|---|
| 52 | 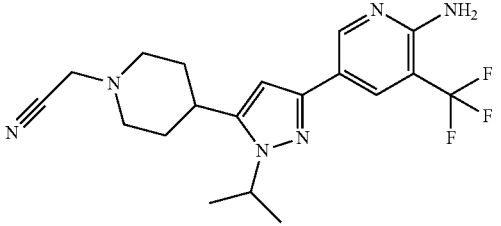 [SMILES: CC(C)n1nc(-c2cnc(N)c(C(F)(F)F)c2)cc1C1CCN(CC#N)CC1] | 2-(4-(3-(6-amino-5-(trifluoromethyl) pyridin-3-yl)-1-isopropyl-1H-pyrazol-5-yl)piperidin-1-yl)acetonitrile | 393.1 |
| 53 | 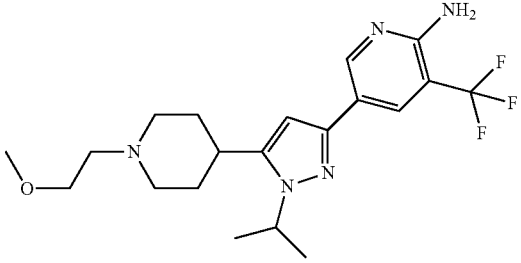 [SMILES: COCCN1CCC(c2cc(-c3cnc(N)c(C(F)(F)F)c3)nn2C(C)C)CC1] | 5-(1-isopropyl-5-(1-(2-methoxyethyl) piperidin-4-yl)-1H-pyrazol-3-yl)-3-(trifluoromethyl)pyridin-2-amine | 412.0 |
| 54 | 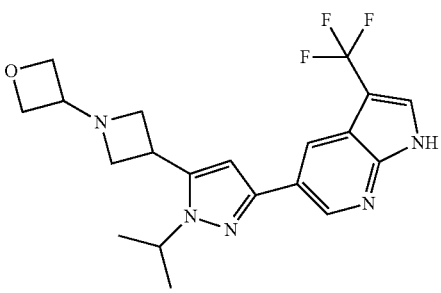 [SMILES: CC(C)n1nc(-c2cnc3[nH]cc(C(F)(F)F)c3c2)cc1C1CN(C2COC2)C1] | 5-(1-isopropyl-5-(1-(oxetan-3-yl)azetidin-3-yl)-1H-pyrazol-3-yl)-3-(trifluoromethyl)-1H-pyrrolo[2,3-b]pyridine | 405.9 |
| 55 | 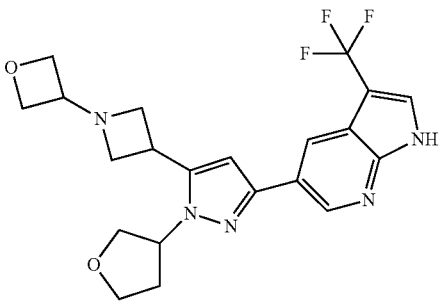 [SMILES: FC(F)(F)c1c[nH]c2ncc(-c3cc(C4CN(C5COC5)C4)n(C4CCOC4)n3)cc12] | 5-(5-(1-(oxetan-3-yl)azetidin-3-yl)-1-(tetrahydrofuran-3-yl)-1H-pyrazol-3-yl)-3-(trifluoromethyl)-1H-pyrrolo[2,3-b]pyridine | 433.8 |
| 56 | 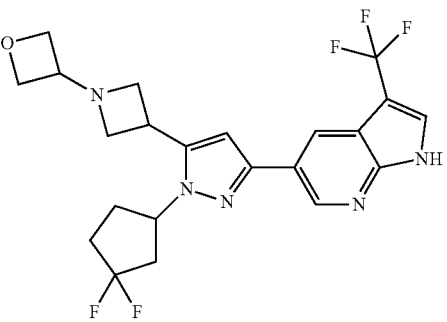 [SMILES: FC1(F)CCC(n2nc(-c3cnc4[nH]cc(C(F)(F)F)c4c3)cc2C2CN(C3COC3)C2)C1] | 5-(1-(3,3-difluorocyclopentyl)-5-(1-(oxetan-3-yl)azetidin-3-yl)-1H-pyrazol-3-yl)-3-(trifluoromethyl)-1H-pyrrolo[2,3-b]pyridine | 468.0 |

TABLE 1-continued

| No | Structure | Name | M + H |
|----|-----------|------|-------|
| 57 | 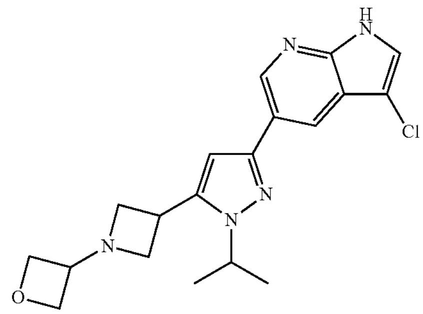 [SMILES: CC(C)n1nc(-c2cnc3[nH]cc(Cl)c3c2)cc1C1CN(C2COC2)C1] | 3-chloro-5-(1-isopropyl-5-(1-(oxetan-3-yl)azetidin-3-yl)-1H-pyrazol-3-yl)-1H-pyrrolo[2,3-b]pyridine | 372.1 |
| 58 | 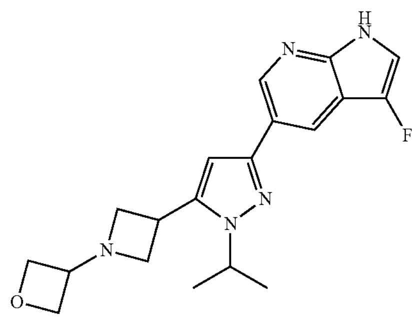 [SMILES: CC(C)n1nc(-c2cnc3[nH]cc(F)c3c2)cc1C1CN(C2COC2)C1] | 3-fluoro-5-(1-isopropyl-5-(1-(oxetan-3-yl)azetidin-3-yl)-1H-pyrazol-3-yl)-1H-pyrrolo[2,3-b]pyridine | 356.1 |
| 59 | 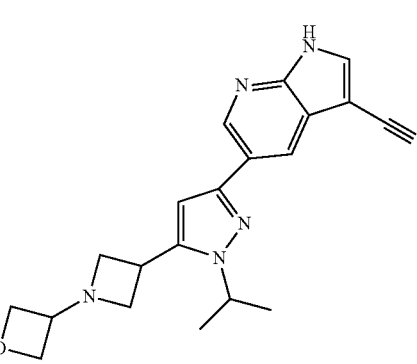 | 5-(1-isopropyl-5-(1-(oxetan-3-yl)azetidin-3-yl)-1H-pyrazol-3-yl)-1H-pyrrolo[2,3-b]pyridine-3-carbonitrile | 362.9 |
| 60 | 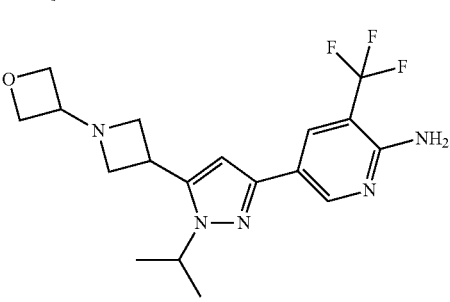 | 5-(1-isopropyl-5-(1-(oxetan-3-yl)azetidin-3-yl)-1H-pyrazol-3-yl)-3-(trilfuoromethyl)pyridin-2-amine | 381.9 |
| 61 | 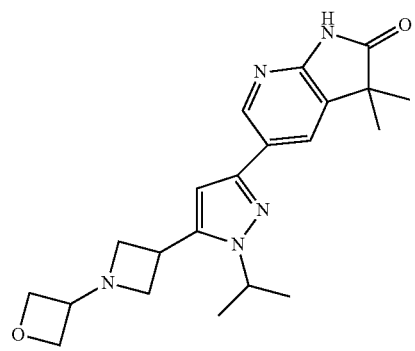 [SMILES: CC(C)n1nc(-c2cnc3c(c2)C(C)(C)C(=O)N3)cc1C1CN(C2COC2)C1] | 5-(1-isopropyl-5-(1-(oxetan-3-yl)azetidin-3-yl)-1H-pyrazol-3-yl)-3,3-dimethyl-1H-pyrrolo[2,3-b]pyridin-2(3H)-one | |

TABLE 1-continued

| No | Structure | Name | M + H |
|---|---|---|---|
| 62 | 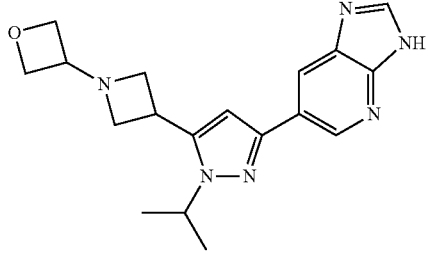 [SMILES: CC(C)n1nc(-c2cnc3[nH]cnc3c2)cc1C1CN(C2COC2)C1] | 6-(1-isopropyl-5-(1-(oxetan-3-yl)azetidin-3-yl)-1H-pyrazol-3-yl)-3H-imidazo[4,5-b]pyridine | |
| 63 | 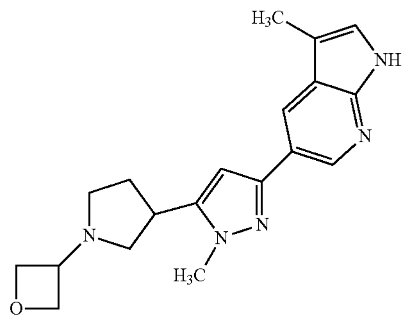 [SMILES: Cc1c[nH]c2ncc(-c3cc(C4CCN(C5COC5)C4)n(C)n3)cc12] | 3-methyl-5-(1-methyl-5-(1-(oxetan-3-yl)pyrrolidin-3-yl)-1H-pyrazol-3-yl)-1H-pyrrolo[2,3-b]pyridine | 338.2 |
| 64 | 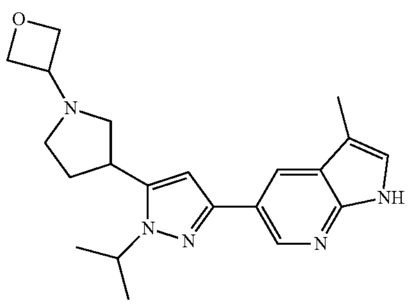 [SMILES: Cc1c[nH]c2ncc(-c3cc(C4CCN(C5COC5)C4)n(C(C)C)n3)cc12] | 5-(1-isopropyl-5-(1-(oxetan-3-yl)pyrrolidin-3-yl)-1H-pyrazol-3-yl)-3-methyl-1H-pyrrolo[2,3-b]pyridine | 366.3 |
| 65 | 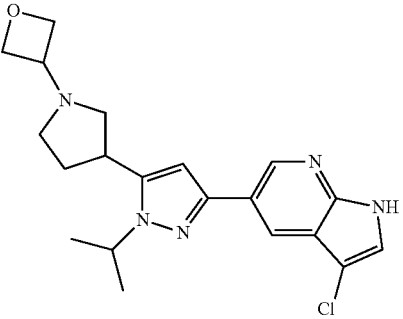 [SMILES: CC(C)n1nc(-c2cnc3[nH]cc(Cl)c3c2)cc1C1CCN(C2COC2)C1] | 3-chloro-5-(1-isopropyl-5-(1-(oxetan-3-yl)pyrrolidin-3-yl)-1H-pyrazol-3-yl)-1H-pyrrolo[2,3-b]pyridine | 386.2 |
| 66 | 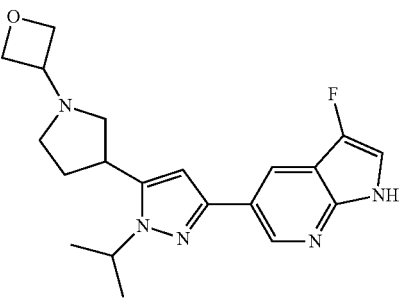 [SMILES: CC(C)n1nc(-c2cnc3[nH]cc(F)c3c2)cc1C1CCN(C2COC2)C1] | 3-fluoro-5-(1-isopropyl-5-(1-(oxetan-3-yl)pyrrolidin-3-yl)-1H-pyrazol-3-yl)-1H-pyrrolo[2,3-b]pyridine | 370.2 |

TABLE 1-continued

| No | Structure | Name | M + H |
|---|---|---|---|
| 67 | 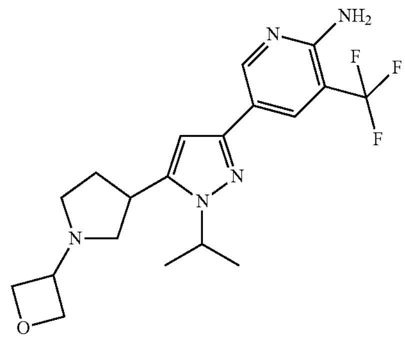 [SMILES: CC(C)n1nc(-c2cnc(N)c(C(F)(F)F)c2)cc1C1CCN(C2COC2)C1] | 5-(1-isopropyl-5-(1-(oxetan-3-yl)pyrrolidin-3-yl)-1H-pyrazol-3-yl)-3-(trifluoromethyl)pyridin-2-amine | 396.2 |
| 68 | 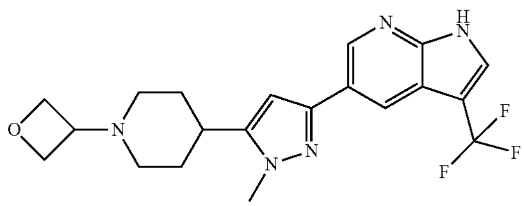 [SMILES: Cn1nc(-c2cnc3[nH]cc(C(F)(F)F)c3c2)cc1C1CCN(C2COC2)CC1] | 5-(1-methyl-5-(1-(oxetan-3-yl)piperidin-4-yl)-1H-pyrazol-3-yl)-3-(trifluoromethyl)-1H-pyrrolo[2,3-b]pyridine | 405.9 |
| 69 | 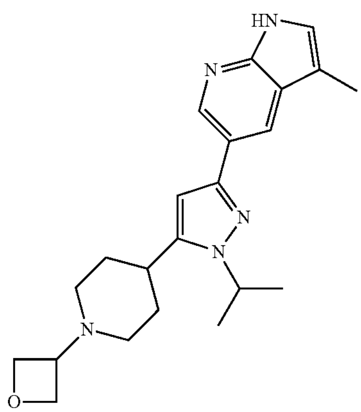 [SMILES: Cc1c[nH]c2ncc(-c3cc(C4CCN(C5COC5)CC4)n(C(C)C)n3)cc12] | 5-(1-isopropyl-5-(1-(oxetan-3-yl)piperidin-4-yl)-1H-pyrazol-3-yl)-3-methyl-1H-pyrrolo[2,3-b]pyridine | 380.0 |
| 70 | 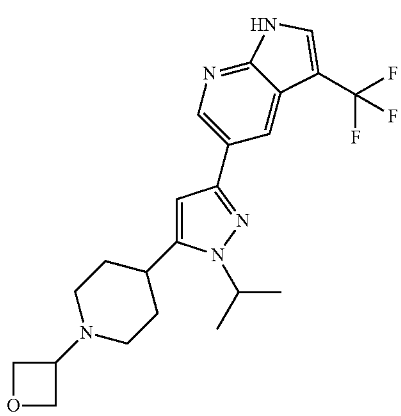 [SMILES: CC(C)n1nc(-c2cnc3[nH]cc(C(F)(F)F)c3c2)cc1C1CCN(C2COC2)CC1] | 5-(1-isopropyl-5-(1-(oxetan-3-yl)piperidin-4-yl)-1H-pyrazol-3-yl)-3-(trifluoromethyl)-1H-pyrrolo[2,3-b]pyridine | 433.9 |

TABLE 1-continued

| No | Structure | Name | M + H |
|---|---|---|---|
| 71 | 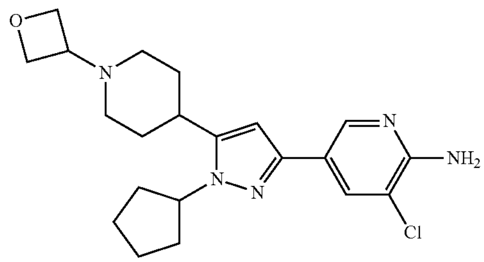 [SMILES: Nc1ncc(-c2cc(C3CCN(C4COC4)CC3)n(C3CCCC3)n2)cc1Cl] | 3-chloro-5-(1-cyclopentyl-5-(1-(oxetan-3-yl)piperidin-4-yl)-1H-pyrazol-3-yl)pyridin-2-amine | 402 |
| 72 | 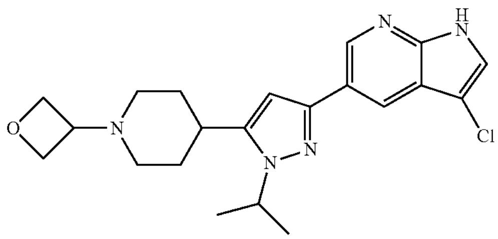 [SMILES: CC(C)n1nc(-c2cnc3[nH]cc(Cl)c3c2)cc1C1CCN(C2COC2)CC1] | 3-chloro-5-(1-isopropyl-5-(1-(oxetan-3-yl)piperidin-4-yl)-1H-pyrazol-3-yl)-1H-pyrrolo[2,3-b]pyridine | 399.9 |
| 73 | 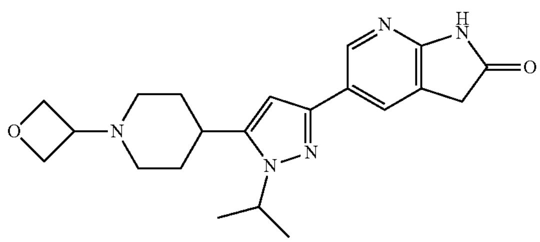 [SMILES: CC(C)n1nc(-c2cnc3c(c2)CC(=O)N3)cc1C1CCN(C2COC2)CC1] | 5-(1-isopropyl-5-(1-(oxetan-3-yl)piperidin-4-yl)-1H-pyrazol-3-yl)-1H-pyrrolo[2,3-b]pyridin-2(3H)-one | |
| 74 | 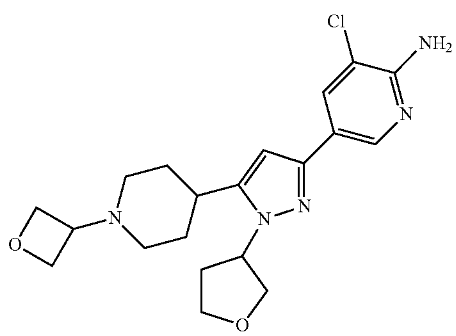 [SMILES: Nc1ncc(-c2cc(C3CCN(C4COC4)CC3)n(C3CCOC3)n2)cc1Cl] | 3-chloro-5-(5-(1-(oxetan-3-yl)piperidin-4-yl)-1-(tetrahydrofuran-3-yl)-1H-pyrazol-3-yl)pyridin-2-amine | 404.0 |
| 75 | 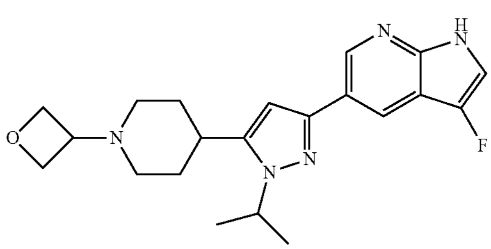 [SMILES: CC(C)n1nc(-c2cnc3[nH]cc(F)c3c2)cc1C1CCN(C2COC2)CC1] | 3-fluoro-5-(1-isopropyl-5-(1-(oxetan-3-yl)piperidin-4-yl)-1H-pyrazol-3-yl)-1H-pyrrolo[2,3-b]pyridine | 384.0 |

TABLE 1-continued

| No | Structure | Name | M + H |
|----|-----------|------|-------|
| 76 | 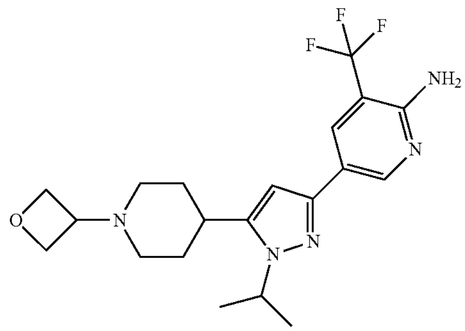 [SMILES: CC(C)n1nc(-c2cnc(N)c(C(F)(F)F)c2)cc1C1CCN(C2COC2)CC1] | 5-(1-isopropyl-5-(1-(oxetan-3-yl)piperidin-4-yl)-1H-pyrazol-3-yl)-3-(trifluoromethyl)pyridin-2-amine | 410.0 |
| 77 | 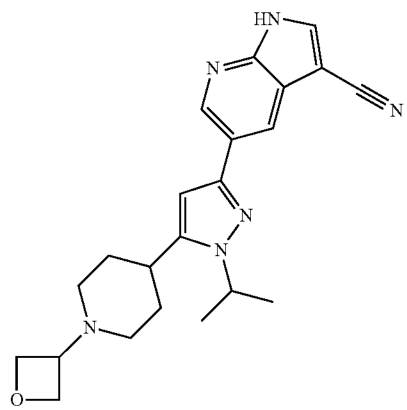 [SMILES: CC(C)n1nc(-c2cnc3[nH]cc(C#N)c3c2)cc1C1CCN(C2COC2)CC1] | 5-(1-isopropyl-5-(1-(oxetan-3-yl)piperidin-4-yl)-1H-pyrazol-3-yl)-1H-pyrrolo[2,3-b]pyridine-3-carbonitrile | 391.0 |
| 78 | 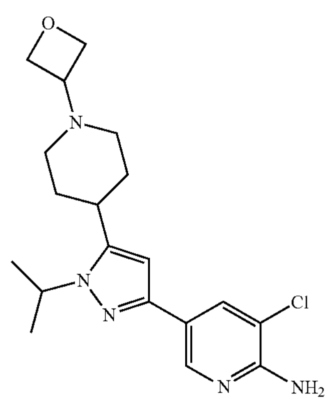 [SMILES: CC(C)n1nc(-c2cnc(N)c(Cl)c2)cc1C1CCN(C2COC2)CC1] | 3-chloro-5-(1-isopropyl-5-(1-(oxetan-3-yl)piperidin-4-yl)-1H-pyrazol-3-yl)pyridin-2-amine | 376.0 |
| 79 | 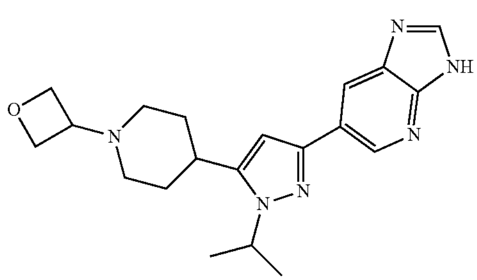 [SMILES: CC(C)n1nc(-c2cnc3[nH]cnc3c2)cc1C1CCN(C2COC2)CC1] | 6-(1-isopropyl-5-(1-(oxetan-3-yl)piperidin-4-yl)-1H-pyrazol-3-yl)-3H-imidazo[4,5-b]pyridine | |

TABLE 1-continued

| No | Structure | Name | M + H |
|---|---|---|---|
| 80 | 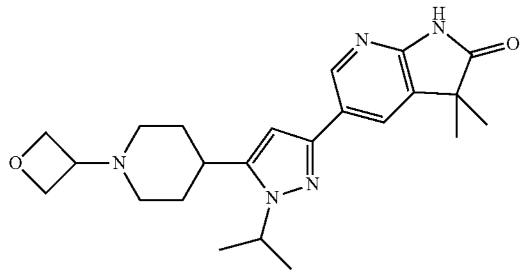 [SMILES: CC(C)n1nc(-c2cnc3c(c2)C(C)(C)C(=O)N3)cc1C1CCN(C2COC2)CC1] | 5-(1-isopropyl-5-(1-(oxetan-3-yl)piperidin-4-yl)-1H-pyrazol-3-yl)-3,3-dimethyl-1H-pyrrolo[2,3-b]pyridin-2(3H)-one | |
| 81 | 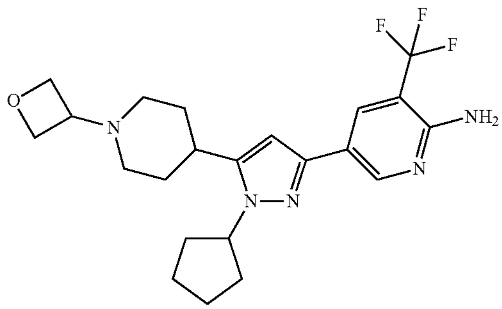 [SMILES: Nc1ncc(-c2cc(C3CCN(C4COC4)CC3)n(C3CCCC3)n2)cc1C(F)(F)F] | 5-(1-cyclopentyl-5-(1-(oxetan-3-yl)piperidin-4-yl)-1H-pyrazol-3-yl)-3-(trifluoromethyl)pyridin-2-amine | 436.0 |
| 82 | 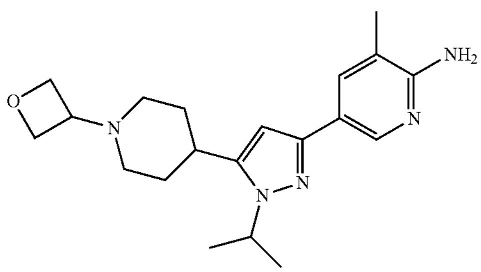 [SMILES: Cc1cc(-c2cc(C3CCN(C4COC4)CC3)n(C(C)C)n2)cnc1N] | 5-(1-isopropyl-5-(1-(oxetan-3-yl)piperidin-4-yl)-1H-pyrazol-3-yl)-3-methylpyridin-2-amine | |
| 83 | 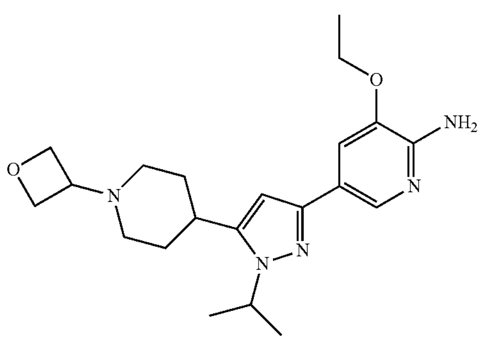 [SMILES: CCOc1cc(-c2cc(C3CCN(C4COC4)CC3)n(C(C)C)n2)cnc1N] | 3-ethoxy-5-(1-isopropyl-5-(1-(oxetan-3-yl)piperidin-4-yl)-1H-pyrazol-3-yl)pyridin-2-amine | 386.1 |
| 84 | 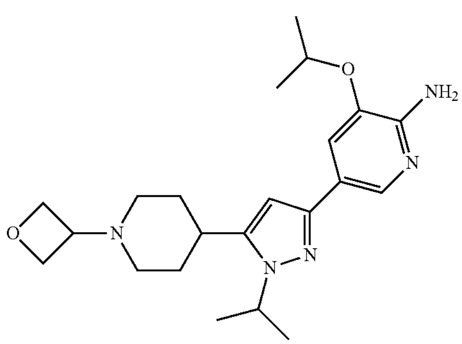 [SMILES: CC(C)Oc1cc(-c2cc(C3CCN(C4COC4)CC3)n(C(C)C)n2)cnc1N] | 3-isopropoxy-5-(1-isopropyl-5-(1-(oxetan-3-yl)piperidin-4-yl)-1H-pyrazol-3-yl)pyridin-2-amine | 400.1 |

TABLE 1-continued

| No | Structure | Name | M + H |
|---|---|---|---|
| 85 | 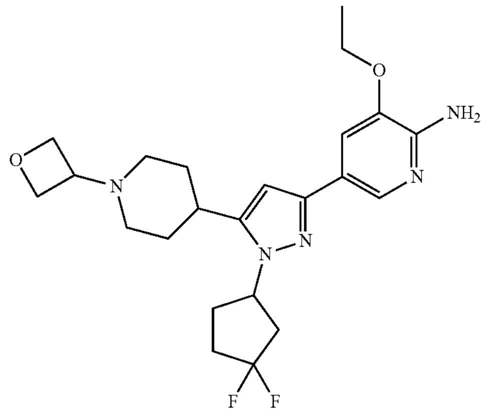 [SMILES: CCOc1cc(-c2cc(C3CCN(C4COC4)CC3)n(C3CCC(F)(F)C3)n2)cnc1N] | 5-(1-(3,3-difluorocyclopentyl)-5-(1-(oxetan-3-yl)piperidin-4-yl)-1H-pyrazol-3-yl)-3-ethoxypyridin-2-amine | 448.2 |
| 86 | 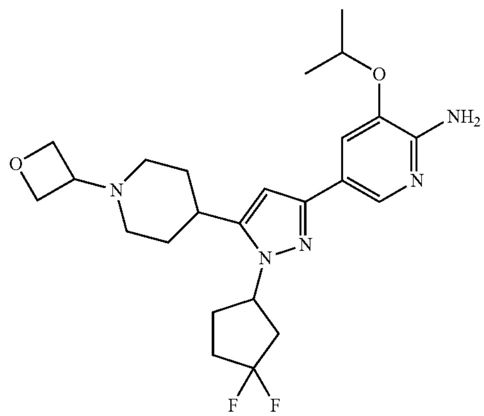 [SMILES: CC(C)Oc1cc(-c2cc(C3CCN(C4COC4)CC3)n(C3CCC(F)(F)C3)n2)cnc1N] | 5-(1-(3,3-difluorocyclopentyl)-5-(1-(oxetan-3-yl)piperidin-4-yl)-1H-pyrazol-3-yl)-3-isopropoxypyridin-2-amine | 462.0 |
| 87 | 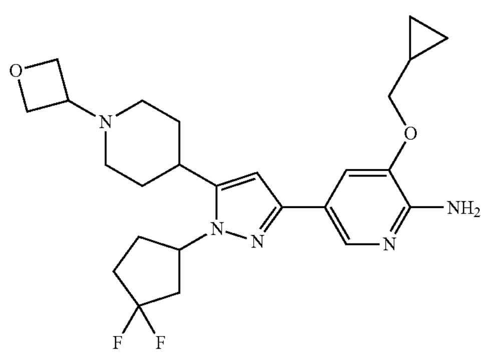 [SMILES: Nc1ncc(-c2cc(C3CCN(C4COC4)CC3)n(C3CCC(F)(F)C3)n2)cc1OCC1CC1] | 3-(cyclopropylmethoxy)-5-(1-(3,3-difluorocyclopentyl)-5-(1-(oxetan-3-yl)piperidin-4-yl)-1H-pyrazol-3-yl)pyridin-2-amine | 474.1 |
| 88 | 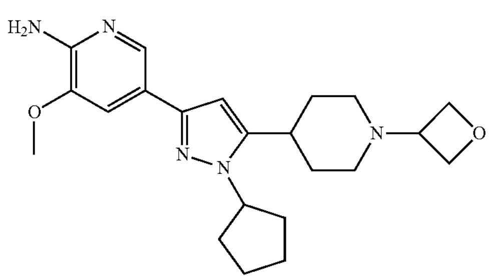 [SMILES: COc1cc(-c2cc(C3CCN(C4COC4)CC3)n(C3CCCC3)n2)cnc1N] | 5-(1-cyclopentyl-5-(1-(oxetan-3-yl)piperidin-4-yl)-1H-pyrazol-3-yl)-3-methoxypyridin-2-amine | 398.3 |

TABLE 1-continued

| No | Structure | Name | M + H |
|---|---|---|---|
| 89 | 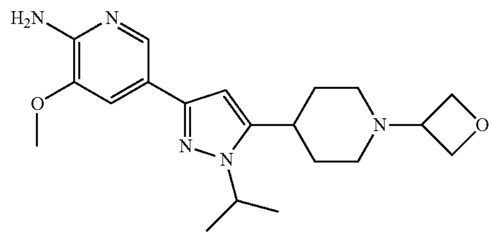 [SMILES: COc1cc(-c2cc(C3CCN(C4COC4)CC3)n(C(C)C)n2)cnc1N] | 5-(1-isopropyl-5-(1-(oxetan-3-yl)piperidin-4-yl)-1H-pyrazol-3-yl)-3-methoxypyridin-2-amine | 372.3 |
| 90 | 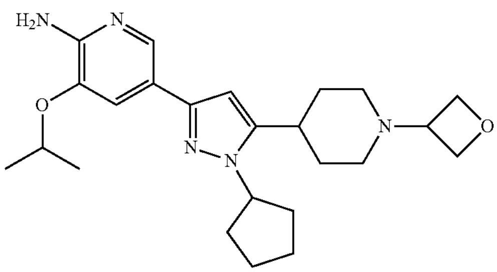 [SMILES: CC(C)Oc1cc(-c2cc(C3CCN(C4COC4)CC3)n(C3CCCC3)n2)cnc1N] | 5-(1-cyclopentyl-5-(1-(oxetan-3-yl)piperidin-4-yl)-1H-pyrazol-3-yl)-3-isopropoxypyridin-2-amine | 426.3 |
| 91 | 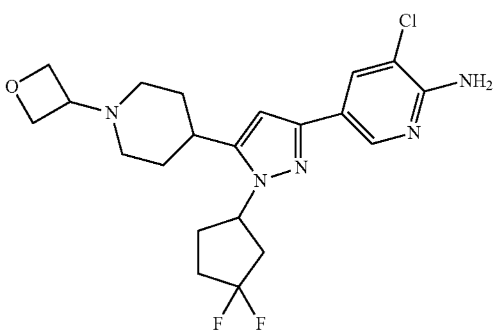 [SMILES: Nc1ncc(-c2cc(C3CCN(C4COC4)CC3)n(C3CCC(F)(F)C3)n2)cc1Cl] | 3-chloro-5-(1-(3,3-difluorocyclopentyl)-5-(1-(oxetan-3-yl)piperidin-4-yl)-1H-pyrazol-3-yl)pyridin-2-amine | 438.2 |
| 92 | 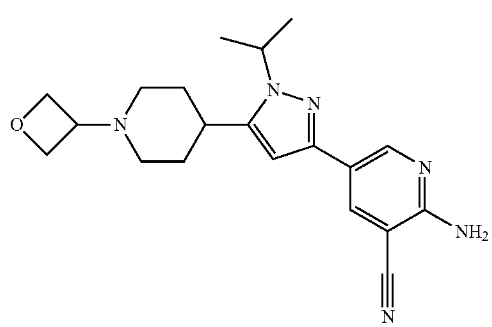 [SMILES: CC(C)n1nc(-c2cnc(N)c(C#N)c2)cc1C1CCN(C2COC2)CC1] | 2-amino-5-(1-isopropyl-5-(1-(oxetan-3-yl)piperidin-4-yl)-1H-pyrazol-3-yl)nicotinonitrile | 367.2 |
| 93 | 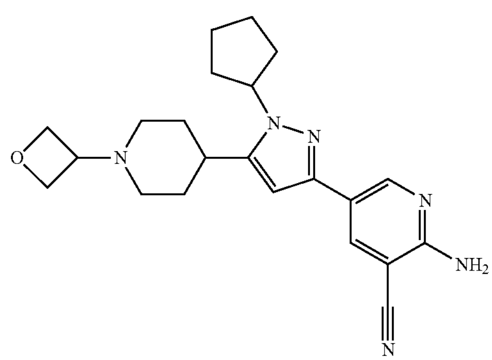 [SMILES: N#Cc1cc(-c2cc(C3CCN(C4COC4)CC3)n(C3CCCC3)n2)cnc1N] | 2-amino-5-(1-cyclopentyl-5-(1-(oxetan-an-3-yl)piperidin-4-yl)-1H-pyrazol-3-yl)nicotinonitrile | 393.3 |

TABLE 1-continued

| No | Structure | Name | M + H |
|---|---|---|---|
| 94 | 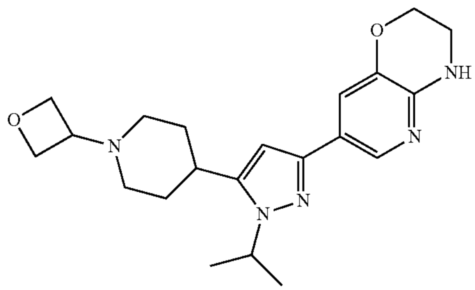 [SMILES: CC(C)n1nc(-c2cnc3c(c2)OCCN3)cc1C1CCN(C2COC2)CC1] | 7-(1-isopropyl-5-(1-(oxetan-3-yl)piperidin-4-yl)-1H-pyrazol-3-yl)-3,4-dihydro-2H-pyrido[3,2-b][1,4]oxazine | |
| 95 | 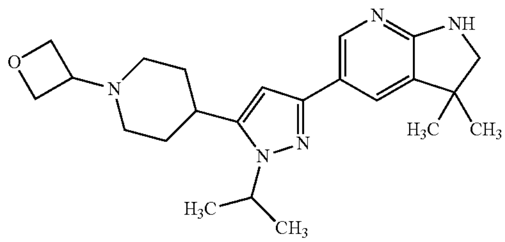 [SMILES: CC(C)n1nc(-c2cnc3c(c2)C(C)(C)CN3)cc1C1CCN(C2COC2)CC1] | 5-(1-isopropyl-5-(1-(oxetan-3-yl)piperidin-4-yl)-1H-pyrazol-3-yl)-3,3-dimethyl-2,3-dihydro-1H-pyrrolo[2,3-b]pyridine | 396.3 |
| 96 | 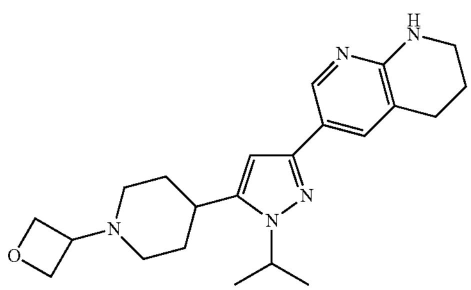 [SMILES: CC(C)n1nc(-c2cnc3c(c2)CCCN3)cc1C1CCN(C2COC2)CC1] | 6-(1-isopropyl-5-(1-(oxetan-3-yl)piperidin-4-yl)-1H-pyrazol-3-yl)-1,2,3,4-tetrahydro-1,8-naphthyridine | |
| 97 | 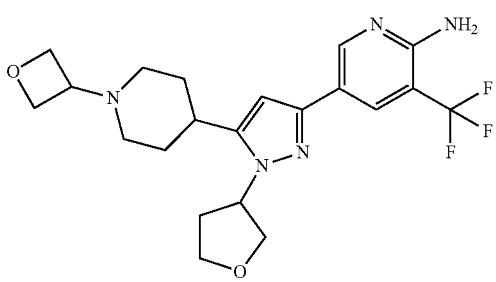 [SMILES: Nc1ncc(-c2cc(C3CCN(C4COC4)CC3)n(C3CCOC3)n2)cc1C(F)(F)F] | 5-(5-(1-(oxetan-3-yl)piperidin-4-yl)-1-(tetrahydrofuran-3-yl)-1H-pyrazol-3-yl)-3-(trifluoromethyl)pyridin-2-amine | 438.2 |
| 98 | 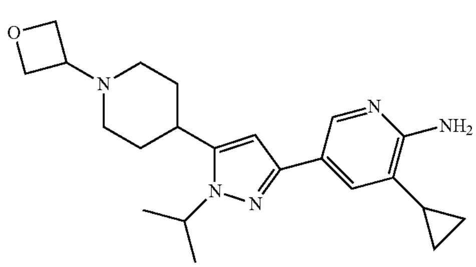 [SMILES: CC(C)n1nc(-c2cnc(N)c(C3CC3)c2)cc1C1CCN(C2COC2)CC1] | 3-cyclopropyl-5-(1-isopropyl-5-(1-(oxetan-3-yl)piperidin-4-yl)-1H-pyrazol-3-yl)pyridin-2-amine | 382.2 |

TABLE 1-continued

| No | Structure | Name | M + H |
|---|---|---|---|
| 99 | 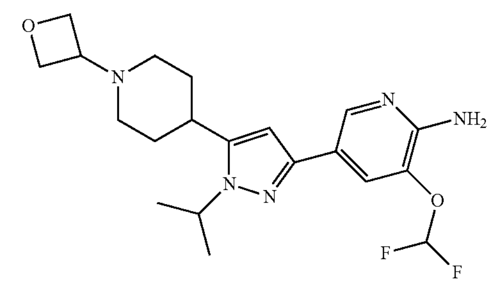 [SMILES: CC(C)n1nc(-c2cnc(N)c(OC(F)F)c2)cc1C1CCN(C2COC2)CC1] | 3-(difluoromethoxy)-5-(1-isopropyl-5-(1-(oxetan-3-yl)piperidin-4-yl)-1H-pyrazol-3-yl)pyridin-2-amine | 408.0 |
| 100 | 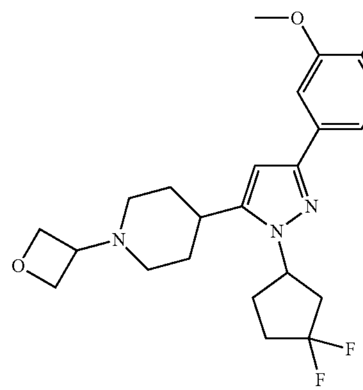 | 5-(1-(3,3-difluorocyclopentyl)-5-(1-(oxetan-3-yl)piperidin-4-yl)-1H-pyrazol-3-yl)-3-methoxypyridin-2-amine | |
| 101 | 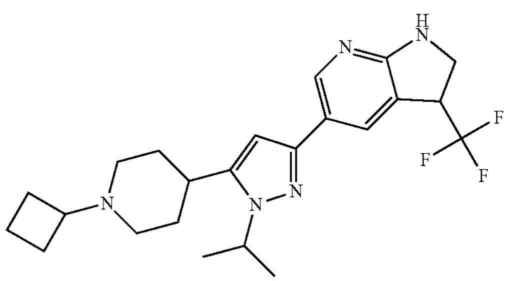 [SMILES: CC(C)n1nc(-c2cnc3c(c2)C(C(F)(F)F)CN3)cc1C1CCN(C2CCC2)CC1] | 5-(5-(1-cyclobutylpiperidin-4-yl)-1-isopropyl-1H-pyrazol-3-yl)-3-(trifluoromethyl)-1H-pyrrolo[2,3-b]pyridine | 432.0 |
| 102 | 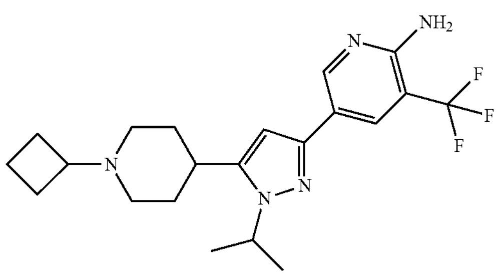 [SMILES: CC(C)n1nc(-c2cnc(N)c(C(F)(F)F)c2)cc1C1CCN(C2CCC2)CC1] | 5-(5-(1-cyclobutylpiperidin-4-yl)-1-isopropyl-1H-pyrazol-3-yl)-3-(trifluoromethyl)pyridin-2-amine | 408.0 |
| 103 | 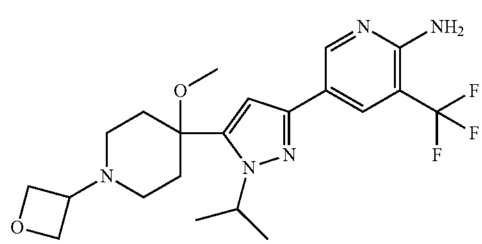 [SMILES: COC1(c2cc(-c3cnc(N)c(C(F)(F)F)c3)nn2C(C)C)CCN(C2COC2)CC1] | 5-(1-isopropyl-5-(4-methoxy-1-(oxetan-3-yl)piperidin-4-yl)-1H-pyrazol-3-yl)-3-(trifluoromethyl)pyridin-2-amine | |

TABLE 1-continued

| No | Structure | Name | M + H |
|---|---|---|---|
| 104 | 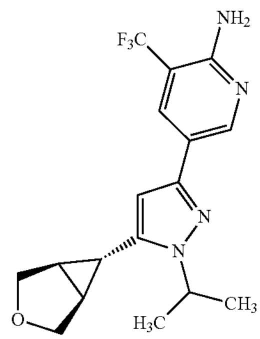 [SMILES: CC(C)n1nc(-c2cnc(N)c(C(F)(F)F)c2)cc1[C@H]1[C@@H]2COC[C@@H]21] | 5-(5-((1R,5S,6s)-3-oxabicyclo[3.1.0]hexan-6-yl)-1-isopropyl-1H-pyrazol-3-yl)-3-(trifluoromethyl)pyridin-2-amine | 353.2 |
| 105 | 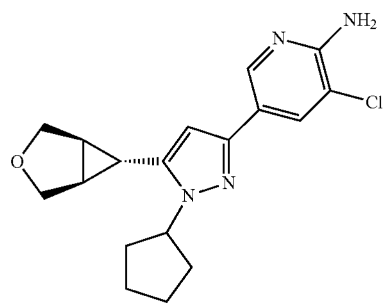 [SMILES: Nc1ncc(-c2cc([C@H]3[C@@H]4COC[C@@H]43)n(C3CCCC3)n2)cc1Cl] | 5-(5-((1R,5S,6s)-3-oxabicyclo[3.1.0]hexan-6-yl)-1-cyclopentyl-1H-pyrazol-3-yl)-3-chloropyridin-2-amine | 345.1 |
| 106 | 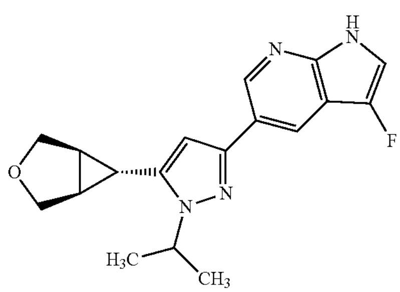 [SMILES: CC(C)n1nc(-c2cnc3[nH]cc(F)c3c2)cc1[C@H]1[C@@H]2COC[C@@H]21] | 5-(5-((1R,5S,6s)-3-oxabicyclo[3.1.0]hexan-6-yl)-1-isopropyl-1H-pyrazol-3-yl)-3-fluoro-1H-pyrrolo[2,3-b]pyridine | 327.2 |
| 107 | 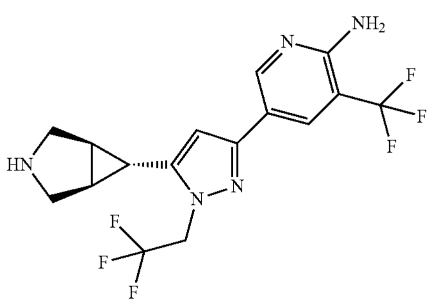 [SMILES: Nc1ncc(-c2cc([C@H]3[C@@H]4CNC[C@@H]43)n(CC(F)(F)F)n2)cc1C(F)(F)F] | 5-(5-((1R,5S,6r)-3-azabicyclo[3.1.0]hexan-6-yl)-1-(2,2,2-trifluoroethyl)-1H-pyrazol-3-yl)-3-(trifluoromethyl)pyridin-2-amine | |
| 108 | 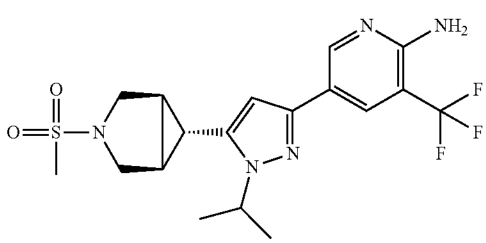 [SMILES: CC(C)n1nc(-c2cnc(N)c(C(F)(F)F)c2)cc1[C@H]1[C@@H]2CN(S(C)(=O)=O)C[C@@H]21] | 5-(1-isopropyl-5-((1R,5S,6r)-3-(methylsulfonyl)-3-azabicyclo[3.1.0]hexan-6-yl)-1H-pyrazol-3-yl)-3-(trifluoromethyl)pyridin-2-amine | |

TABLE 1-continued

| No | Structure | Name | M + H |
|---|---|---|---|
| 109 | 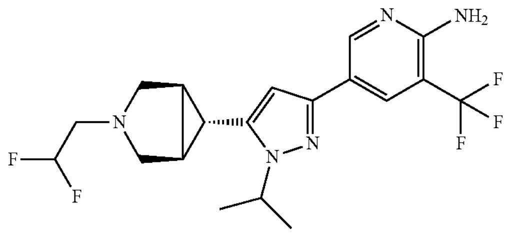 [SMILES: CC(C)n1nc(-c2cnc(N)c(C(F)(F)F)c2)cc1[C@H]1[C@@H]2CN(CC(F)F)C[C@@H]21] | 5-(5-((1R,5S,6r)-3-(2,2-difluoroethyl)-3-azabicyclo[3.1.0]hexan-6-yl)-1-isopropyl-1H-pyrazol-3-yl)-3-(trifluoromethyl)pyridin-2-amine | |
| 110 | 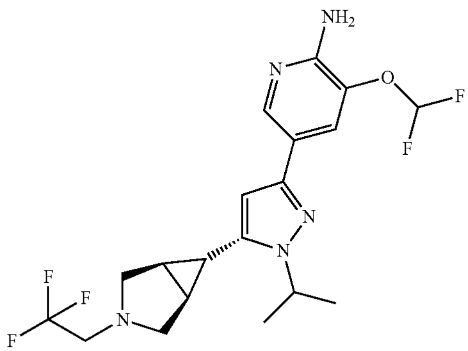 | 3-(difluoromethoxy)-5-(1-isopropyl-5-((1R,5S,6r)-3-(2,2,2-trifluoroethyl)-3-azabicyclo[3.1.0]hexan-6-yl)-1H-pyrazol-3-yl)pyridin-2-amine | |
| 111 | 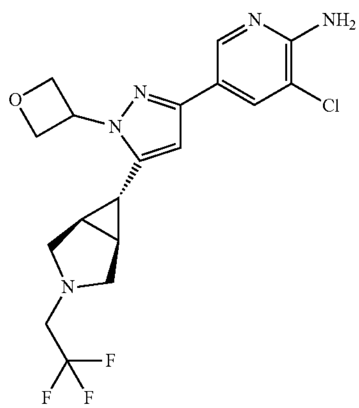 [SMILES: Nc1ncc(-c2cc([C@H]3[C@@H]4CN(CC(F)(F)F)C[C@@H]43)n(C3COC3)n2)cc1Cl] | 3-chloro-5-(1-(oxetan-3-yl)-5-((1R,5S,6r)-3-(2,2,2-trifluoroethyl)-3-azabicyclo[3.1.0]hexan-6-yl)-1H-pyrazol-3-yl)pyridin-2-amine | |
| 112 | 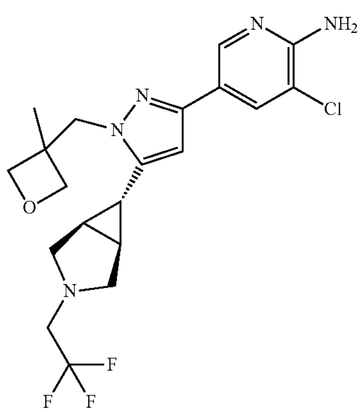 [SMILES: CC1(Cn2nc(-c3cnc(N)c(Cl)c3)cc2[C@H]2[C@@H]3CN(CC(F)(F)F)C[C@@H]32)COC1] | 3-chloro-5-(1-((3-methyloxetan-3-yl)methyl)-5-((1R,5S,6r)-3-(2,2,2-trifluoroethyl)-3-azabicyclo[3.1.0]hexan-6-yl)-1H-pyrazol-3-yl)pyridin-2-amine | |

TABLE 1-continued

| No | Structure | Name | M + H |
|----|-----------|------|-------|
| 113 | 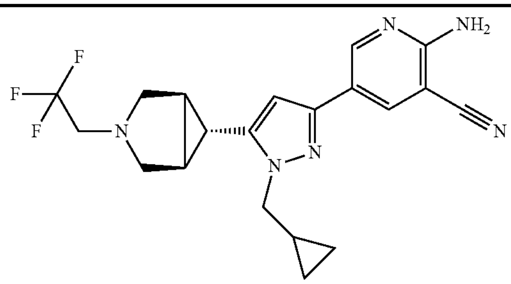 | 2-amino-5-(1-(cyclopropylmethyl)-5-((1R,5S,6r)-3-(2,2,2-trifluoroethyl)-3-azabicyclo[3.1.0]hexan-6-yl)-1H-pyrazol-3-yl)nicotinonitrile | |
| 114 | 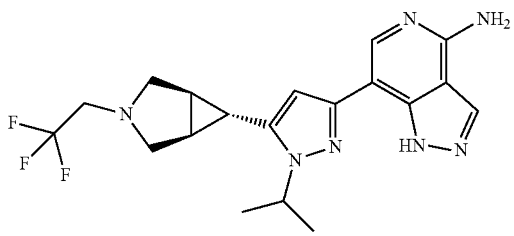 [SMILES: CC(C)n1nc(-c2cnc(N)c3cn[nH]c23)cc1[C@H]1[C@@H]2CN(CC(F)(F)F)C[C@@H]21] | 7-(1-isopropyl-5-((1R,5S,6r)-3-(2,2,2-trifluoroethyl)-3-azabicyclo[3.1.0]hexan-6-yl)-1H-pyrazol-3-yl)-1H-pyrazolo[4,3-c]pyridin-4-amine | |
| 115 | 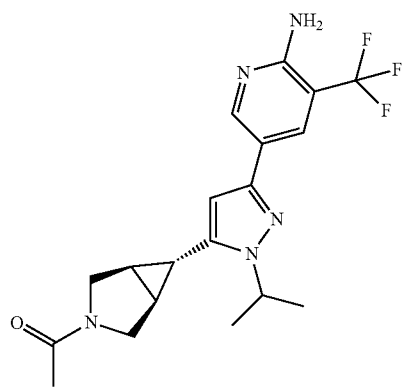 [SMILES: CC(=O)N1C[C@@H]2[C@H](C1)[C@H]2c1cc(-c2cnc(N)c(C(F)(F)F)c2)nn1C(C)C] | 1-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)ethanone | |
| 116 | 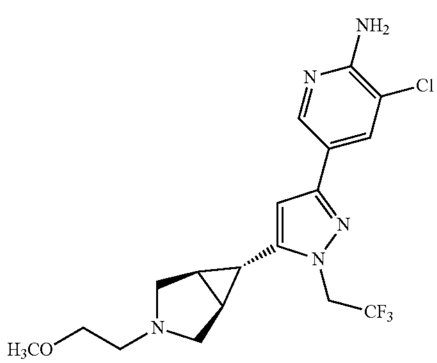 [SMILES: COCCN1C[C@@H]2[C@H](C1)[C@H]2c1cc(-c2cnc(N)c(Cl)c2)nn1CC(F)(F)F] | 3-chloro-5-(5-((1R,5S,r)-3-(2-methoxyethyl)-3-azabicyclo[3.1.0]hexan-6-yl)-1-(2,2,2-trifluoroehtyl)-1H-pyrazol-3-yl)pyridin-2-amine | 416 |
| 117 | 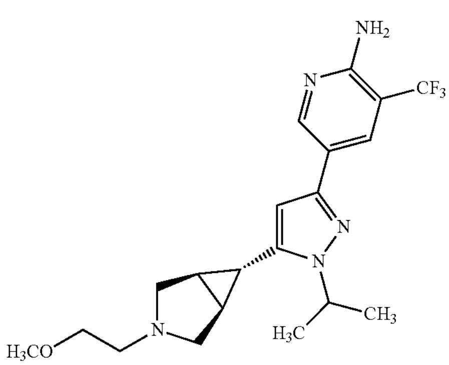 [SMILES: COCCN1C[C@@H]2[C@H](C1)[C@H]2c1cc(-c2cnc(N)c(C(F)(F)F)c2)nn1C(C)C] | 5-(1-isopropyl-5-((1R,5S,6r)-3-(2-methoxyethyl)-3-azabicyclo[3.1.0]hexan-6-yl)-1H-pyrazol-3-yl)-3-(trifluoromethyl)pyridin-2-amine | 410 |

TABLE 1-continued

| No | Structure | Name | M + H |
|---|---|---|---|
| 118 | 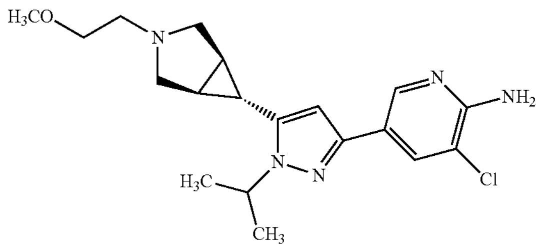 [SMILES: COCCN1C[C@@H]2[C@H](C1)[C@H]2c1cc(-c2cnc(N)c(Cl)c2)nn1C(C)C] | 3-chloro-5-(1-isopropyl-5-((1R,5S,6r)-3-(2-methoxyethyl)-3-azabicyclo[3.1.0]hexan-6-yl)-1H-pyrazol-3-yl)pyridin-2-amine | 375.9 |
| 119 | 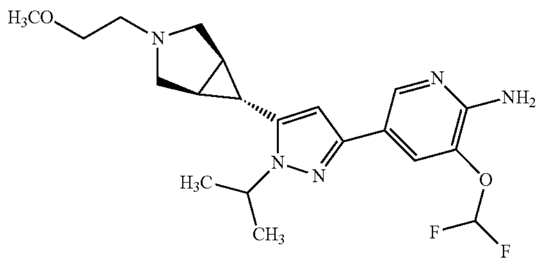 [SMILES: COCCN1C[C@@H]2[C@H](C1)[C@H]2c1cc(-c2cnc(N)c(OC(F)F)c2)nn1C(C)C] | 3-(difluoromethoxy)-5-(1-isopropyl-5-((1R,5S,6r)-3-(2-methoxyethyl)-3-azabicyclo[3.1.0]hexan-6-yl)-1H-pyrazol-3-yl)pyridin-2-amine | 408.1 |
| 120 | 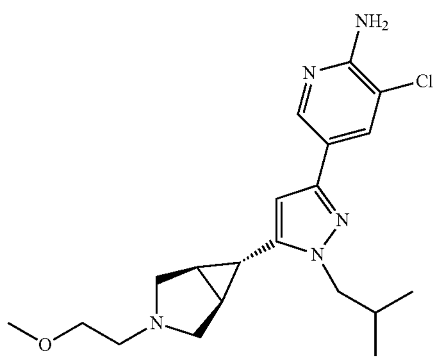 [SMILES: COCCN1C[C@@H]2[C@H](C1)[C@H]2c1cc(-c2cnc(N)c(Cl)c2)nn1CC(C)C] | 3-chloro-5-(1-isobutyl-5-((1R,5S,6r)-3-(2-methoxyethyl)-3-azabicyclo[3.1.0]hexan-6-yl)-1H-pyrazol-3-yl)pyridin-2-amine | |
| 121 | 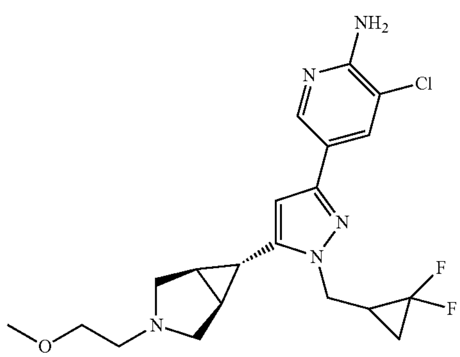 [SMILES: COCCN1C[C@@H]2[C@H](C1)[C@H]2c1cc(-c2cnc(N)c(Cl)c2)nn1CC1CC1(F)F] | 3-chloro-5-(1-((2,2-difluorocyclopropyl)methyl)-5-((1R,5S,6r)-3-(2-methoxyethyl)-3-azabicyclo[3.1.0]hexan-6-yl)-1H-pyrazol-3-yl)pyridin-2-amine | |
| 122 | 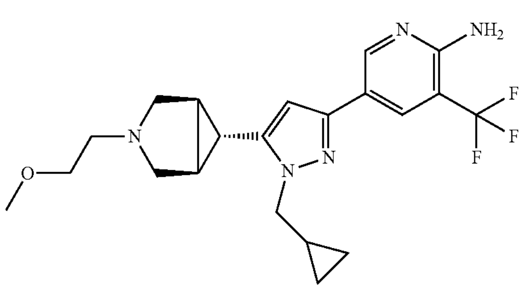 [SMILES: COCCN1C[C@@H]2[C@H](C1)[C@H]2c1cc(-c2cnc(N)c(C(F)(F)F)c2)nn1CC1CC1] | 5-(1-(cyclopropylmethyl)-5-((1R,5S,6r)-3-(2-methoxyethyl)-3-azabicyclo[3.1.0]hexan-6-yl)-1H-pyrazol-3-yl)-3-(trifluoromethyl)pyridin-2-amine | |

TABLE 1-continued

| No | Structure | Name | M + H |
|---|---|---|---|
| 123 | 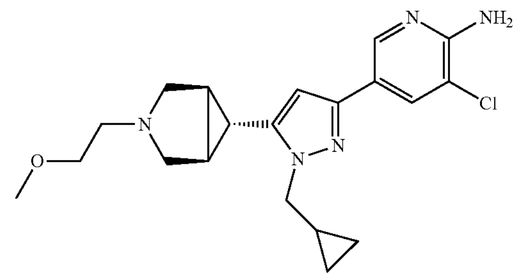 [SMILES: COCCN1C[C@@H]2[C@H](C1)[C@H]2c1cc(-c2cnc(N)c(Cl)c2)nn1CC1CC1] | 3-chloro-5-(1-(cyclopropylmethyl)-5-((1R,5S,6r)-3-(2-methoxyethyl)-3-azabicyclo[3.1.0]hexan-6-yl)-1H-pyrazol-3-yl)pyridin-2-amine | |
| 124 | 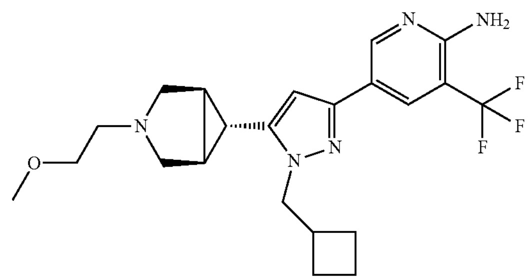 [SMILES: COCCN1C[C@@H]2[C@H](C1)[C@H]2c1cc(-c2cnc(N)c(C(F)(F)F)c2)nn1CC1CCC1] | 5-(1-(cyclobutylmethyl)-5-((1R,5S,6r)-3-(2-methoxyethyl)-3-azabicyclo[3.1.0]hexan-6-yl)-1H-pyrazol-3-yl)-3-(trifluoromethyl)pyridin-2-amine | |
| 125 | 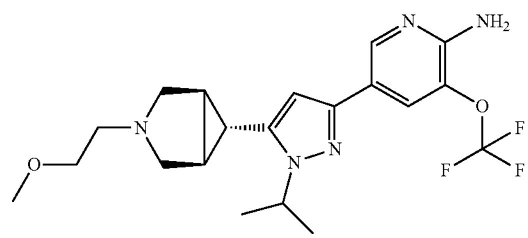 [SMILES: COCCN1C[C@@H]2[C@H](C1)[C@H]2c1cc(-c2cnc(N)c(OC(F)(F)F)c2)nn1C(C)C] | 5-(1-isopropyl-5-((1R,5S,6r)-3-(2-methoxyethyl)-3-azabicyclo[3.1.0]hexan-6-yl)-1H-pyrazol-3-yl)-3-(trifluoromethoxy)pyridin-2-amine | |
| 126 | 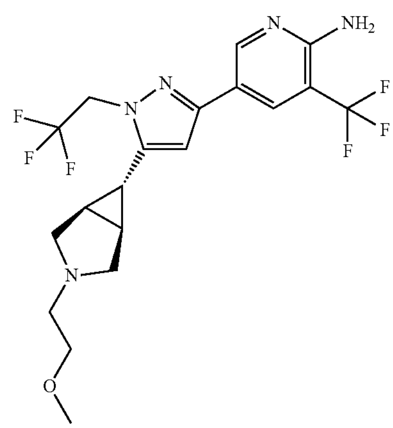 [SMILES: COCCN1C[C@@H]2[C@H](C1)[C@H]2c1cc(-c2cnc(N)c(C(F)(F)F)c2)nn1CC(F)(F)F] | 5-(5-((1R,5S,6r)-3-(2-methoxyethyl)-3-azabicyclo[3.1.0]hexan-6-yl)-1-(2,2,2-trifluoroethyl)-1H-pyrazol-3-yl)-3-(trifluoromethyl)pyridin-2-amine | |
| 127 | 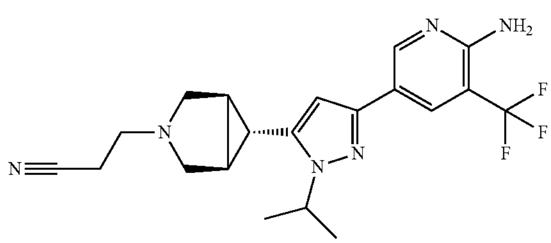 [SMILES: CC(C)n1nc(-c2cnc(N)c(C(F)(F)F)c2)cc1[C@H]1[C@@H]2CN(CCC#N)C[C@@H]21] | 3-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)propanenitrile | |

TABLE 1-continued

| No | Structure | Name | M + H |
|---|---|---|---|
| 128 | 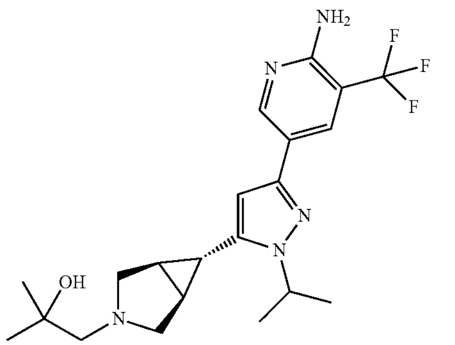 [SMILES: CC(C)n1nc(-c2cnc(N)c(C(F)(F)F)c2)cc1[C@H]1[C@@H]2CN(CC(C)(C)O)C[C@@H]21] | 1-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)-2-methylpropan-2-ol | |
| 129 | 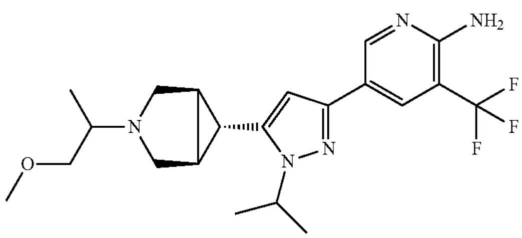 [SMILES: COCC(C)N1C[C@@H]2[C@H](C1)[C@H]2c1cc(-c2cnc(N)c(C(F)(F)F)c2)nn1C(C)C] | 5-(1-isopropyl-5-((1R,5S,6r)-3-(1-methoxypropan-2-yl)-3-azabicyclo[3.1.0]hexan-6-yl)-1H-pyrazol-3-yl)-3-(trifluoromethyl)pyridin-2-amine | |
| 130 | 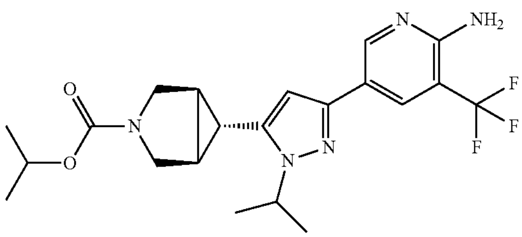 [SMILES: CC(C)OC(=O)N1C[C@@H]2[C@H](C1)[C@H]2c1cc(-c2cnc(N)c(C(F)(F)F)c2)nn1C(C)C] | (1R,5S,6r)-isopropyl 6-(3-(6-amino-5-(trifluoromethyl)pyridin-3-yl)-1-isopropyl-1H-pyrazol-5-yl)-3-azabicyclo[3.1.0]hexane-3-carboxylate | |
| 131 | 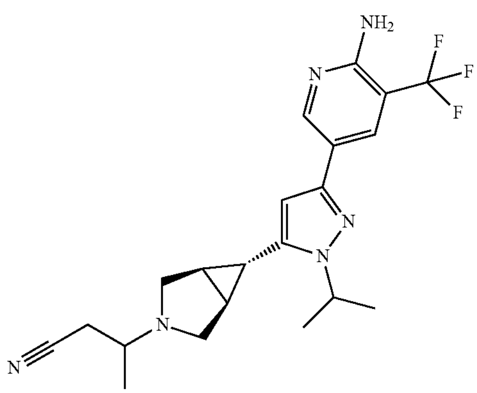 [SMILES: CC(CC#N)N1C[C@@H]2[C@H](C1)[C@H]2c1cc(-c2cnc(N)c(C(F)(F)F)c2)nn1C(C)C] | 3-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)butanenitrile | |
| 132 | 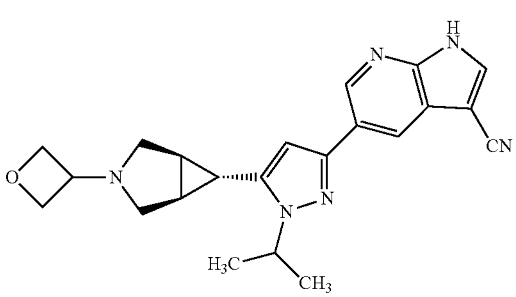 [SMILES: CC(C)n1nc(-c2cnc3[nH]cc(C#N)c3c2)cc1[C@H]1[C@@H]2CN(C3COC3)C[C@@H]21] | 5-(1-isopropyl-5-((1R,5S,6r)-3-(oxetan-3-yl)-3-azabicyclo[3.1.0]hexan-6-yl)-1H-pyrazol-3-yl)-1H-pyrrolo[2,3-b]pyridine-3-carbonitrile | 389.0 |

| No | Structure | Name | M + H |
|---|---|---|---|
| 133 | 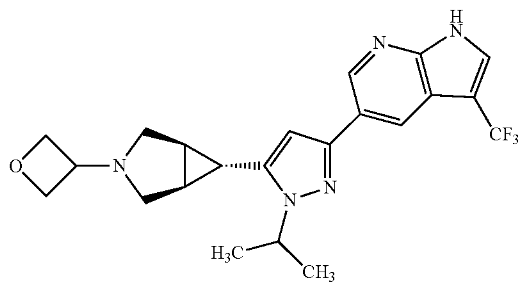 [SMILES: CC(C)n1nc(-c2cnc3[nH]cc(C(F)(F)F)c3c2)cc1[C@H]1[C@@H]2CN(C3COC3)C[C@@H]21] | 5-(1-isopropyl-5-((1R,5S,6r)-3-(oxetan-3-yl)-3-azabicyclo[3.1.0]hexan-6-yl)-1H-pyrazol-3-yl)-3-(trifluoromethyl)-1H-pyrrolo[2,3-b]pyridine | 432.1 |
| 134 | 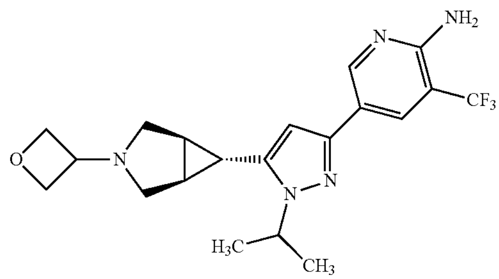 [SMILES: CC(C)n1nc(-c2cnc(N)c(C(F)(F)F)c2)cc1[C@H]1[C@@H]2CN(C3COC3)C[C@@H]21] | 5-(1-isopropyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine | 408.0 |
| 135 | 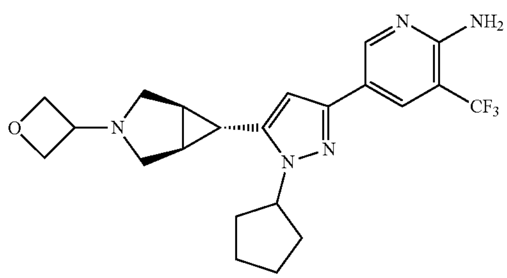 [SMILES: Nc1ncc(-c2cc([C@H]3[C@@H]4CN(C5COC5)C[C@@H]43)n(C3CCCC3)n2)cc1C(F)(F)F] | 5-(1-cyclopentyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine | 433.9 |
| 136 | 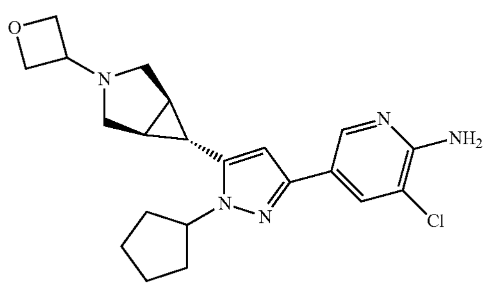 [SMILES: Nc1ncc(-c2cc([C@H]3[C@@H]4CN(C5COC5)C[C@@H]43)n(C3CCCC3)n2)cc1Cl] | 3-chloro-5-(1-cyclopentyl-5-((1R,5S,6r)-3-(oxetan-3-yl)-3-azabicyclo[3.1.0]hexan-6-yl)-1H-pyrazol-3-yl)pyridin-2-amine | 399.9 |
| 137 | 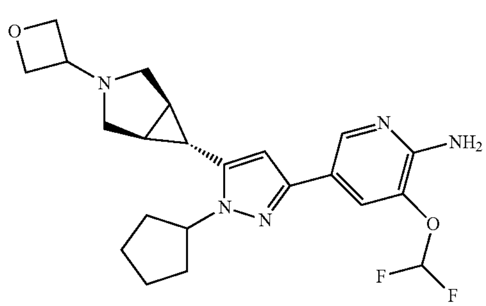 [SMILES: Nc1ncc(-c2cc([C@H]3[C@@H]4CN(C5COC5)C[C@@H]43)n(C3CCCC3)n2)cc1OC(F)F] | 5-(1-cyclopentyl-5-((1R,5S,6r)-3-(oxetan-3-yl)-3-azabicyclo[3.1.0]hexan-6-yl)-1H-pyrazol-3-yl)-3-(difluoromethoxy)pyridin-2-amine | 432.0 |

TABLE 1-continued

| No | Structure | Name | M + H |
|---|---|---|---|
| 138 | 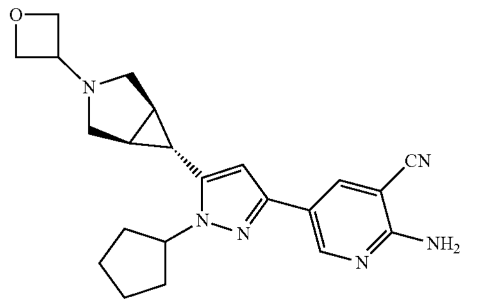 [SMILES: N#Cc1cc(-c2cc([C@H]3[C@@H]4CN(C5COC5)C[C@@H]43)n(C3CCCC3)n2)cnc1N] | 2-amino-5-(1-cyclopentyl-5-((1R,5S,6r)-3-(oxetan-3-yl)-3-azabicyclo[3.1.0]hexan-6-yl)-1H-pyrazol-3-yl)nicotinitrile | 391.2 |
| 139 | 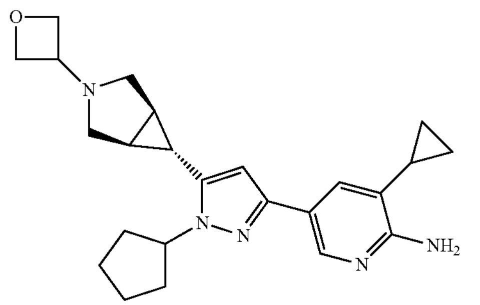 [SMILES: Nc1ncc(-c2cc([C@H]3[C@@H]4CN(C5COC5)C[C@@H]43)n(C3CCCC3)n2)cc1C1CC1] | 5-(1-cyclopentyl-5-((1R,5S,6r)-3-(oxetan-3-yl)-3-azabicyclo[3.1.0]hexan-6-yl)-1H-pyrazol-3-yl)-3-cyclopropylpyridin-2-amine | 406.3 |
| 140 | 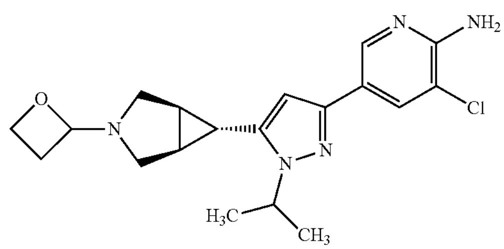 [SMILES: CC(C)n1nc(-c2cnc(N)c(Cl)c2)cc1[C@H]1[C@@H]2CN(C3CCO3)C[C@@H]21] | 3-chloro-5-(1-isopropyl-5-((1R,5S,6r)-3-(oxetan-3-yl)-3-azabicyclo[3.1.0]hexan-6-yl)-1H-pyrazol-3-yl)pyridin-2-amine | 373.9 |
| 141 | 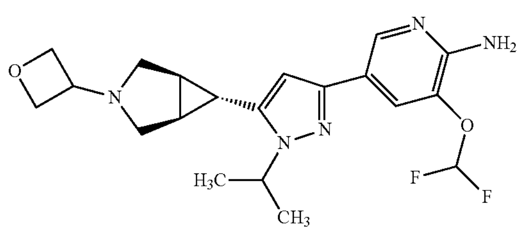 [SMILES: CC(C)n1nc(-c2cnc(N)c(OC(F)F)c2)cc1[C@H]1[C@@H]2CN(C3COC3)C[C@@H]21] | 3-(difluoromethoxy)-5-(1-isopropyl-5-((1R,5S,6r)-3-(oxetan-3-yl)-3-azabicyclo[3.1.0]hexan-6-yl)-1H-pyrazol-3-yl)pyridin-2-amine | 406.0 |
| 142 | 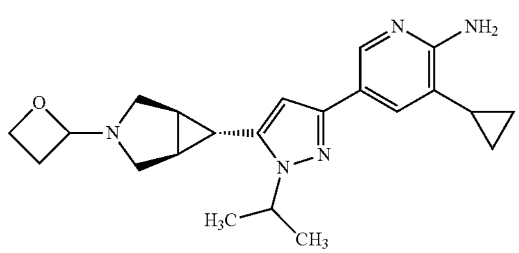 [SMILES: CC(C)n1nc(-c2cnc(N)c(C3CC3)c2)cc1[C@H]1[C@@H]2CN(C3CCO3)C[C@@H]21] | 3-cyclopropyl-5-(1-isopropyl-5-((1R,5S,6r)-3-(oxetan-3-yl)-3-azabicyclo[3.1.0]hexan-6-yl)-1H-pyrazol-3-yl)pyridin-2-amine | 380.0 |

TABLE 1-continued

| No | Structure | Name | M + H |
|----|-----------|------|-------|
| 143 | 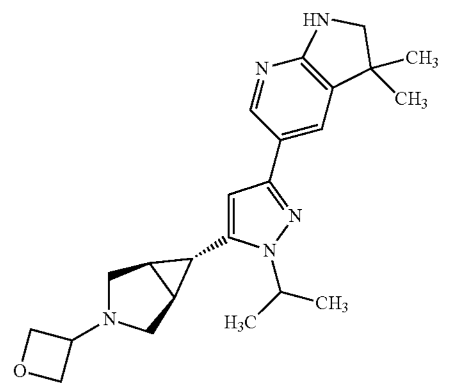 [SMILES: CC(C)n1nc(-c2cnc3c(c2)C(C)(C)CN3)cc1[C@H]1[C@@H]2CN(C3COC3)C[C@@H]21] | 5-(1-isopropyl-5-((1R,5S,6r)-3-(oxetan-3-yl)-3-azabicyclo[3.1.0]hexan-6-yl)-1H-pyrazol-3-yl)-3,3-dimethyl-2,3-dihydro-1H-pyrrolo[2,3-b]pyridine | 394.0 |
| 144 | 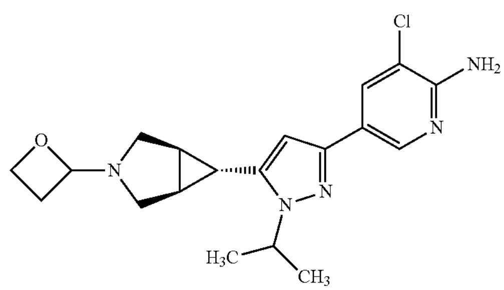 [SMILES: CC(C)n1nc(-c2cnc(N)c(Cl)c2)cc1[C@H]1[C@@H]2CN(C3CCO3)C[C@@H]21] | 2-amino-5-(1-isopropyl-5-((1R,5S,6r)-3-(oxetan-3-yl)-3-azabicyclo[3.1.0]hexan-6-yl)-1H-pyrazol-3-yl)nicotinonitrile | 365.2 |
| 145 | 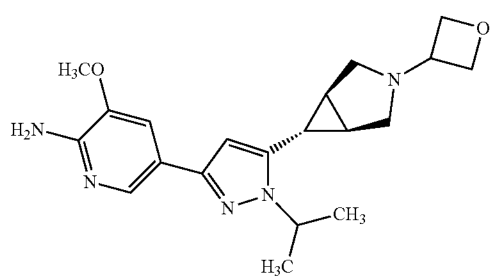 [SMILES: COc1cc(-c2cc([C@H]3[C@@H]4CN(C5COC5)C[C@@H]43)n(C(C)C)n2)cnc1N] | 5-(1-isopropyl-5-((1R,5S,6r)-3-(oxetan-3-yl)-3-azabicyclo[3.1.0]hexan-6-yl)-1H-pyrazol-3-yl)-3-methoxypyridin-2-amine | 370.2 |
| 146 | 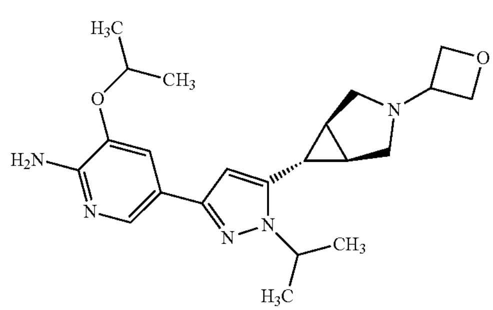 [SMILES: CC(C)Oc1cc(-c2cc([C@H]3[C@@H]4CN(C5COC5)C[C@@H]43)n(C(C)C)n2)cnc1N] | 3-isopropoxy-5-(1-isopropyl-5-((1R,5S,6r)-3-(oxetan-3-yl)-3-azabicyclo[3.1.0]hexan-6-yl)-1H-pyrazol-3-yl)pyridin-2-amine | 398.3 |
| 147 | 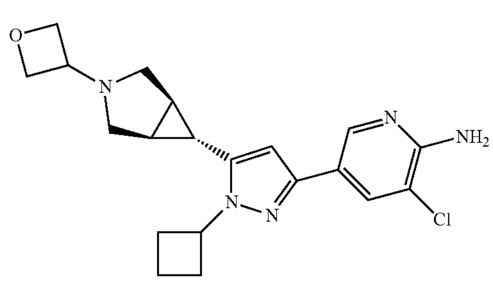 [SMILES: Nc1ncc(-c2cc([C@H]3[C@@H]4CN(C5COC5)C[C@@H]43)n(C3CCC3)n2)cc1Cl] | 3-chloro-5-(1-cyclobutyl-5-((1R,5S,6r)-3-(oxetan-3-yl)-3-azabicyclo[3.1.0]hexan-6-yl)-1H-pyrazol-3-yl)pyridin-2-amine | 386.2 |

TABLE 1-continued

| No | Structure | Name | M + H |
|---|---|---|---|
| 148 | 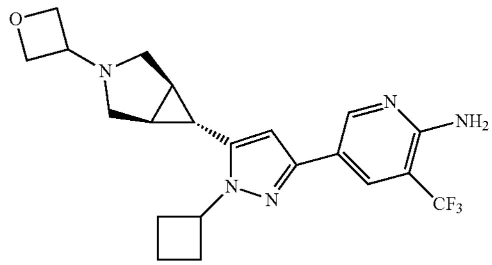 [SMILES: Nc1ncc(-c2cc([C@H]3[C@@H]4CN(C5COC5)C[C@@H]43)n(C3CCC3)n2)cc1C(F)(F)F] | 5-(1-cyclobutyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine | 420.2 |
| 149 | 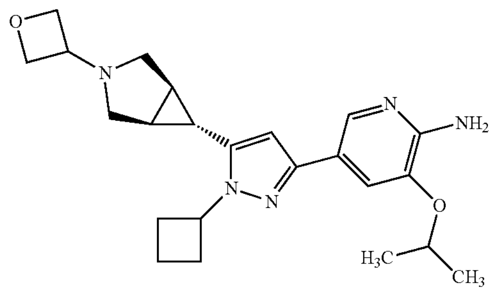 [SMILES: CC(C)Oc1cc(-c2cc([C@H]3[C@@H]4CN(C5COC5)C[C@@H]43)n(C3CCC3)n2)cnc1N] | 5-(1-cyclobutyl-5-((1R,5S,6r)-3-(oxetan-3-yl)-3-azabicyclo[3.1.0]hexan-6-yl)-1H-pyrazol-3-yl)-3-isopropoxypyridin-2-amine | 410.2 |
| 150 | 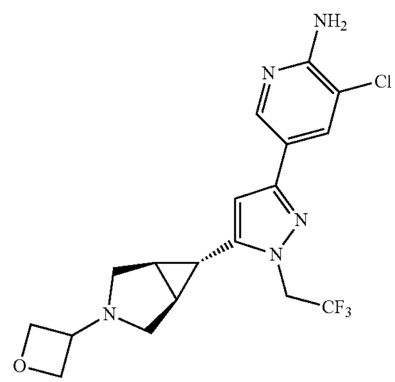 [SMILES: Nc1ncc(-c2cc([C@H]3[C@@H]4CN(C5COC5)C[C@@H]43)n(CC(F)(F)F)n2)cc1Cl] | 3-chloro-5-(5-((1R,5S,6r)-3-(oxetan-3-yl)-3-azabicyclo[3.1.0]hexan-6-yl)-1-(2,2,2-trifluoroethyl)-1H-pyrazol-3-yl)pyridin-2-amine | 414 |
| 151 | 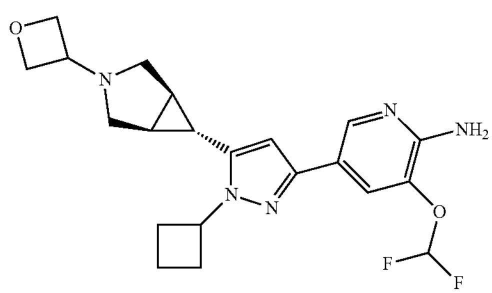 [SMILES: Nc1ncc(-c2cc([C@H]3[C@@H]4CN(C5COC5)C[C@@H]43)n(C3CCC3)n2)cc1OC(F)F] | 5-(1-cyclobutyl-5-((1R,5S,6r)-3-(oxetan-3-yl)-3-azabicyclo[3.1.0]hexan-6-yl)-1H-pyrazol-3-yl)-3-(difluoromethoxy)pyridin-2-amine | 418.2 |
| 152 | 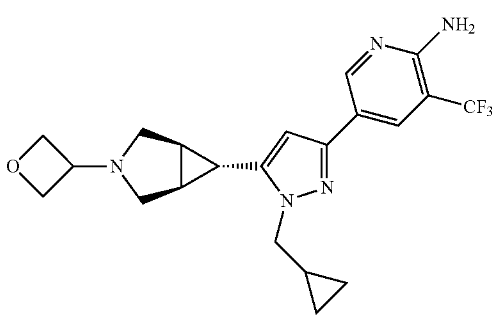 [SMILES: Nc1ncc(-c2cc([C@H]3[C@@H]4CN(C5COC5)C[C@@H]43)n(CC3CC3)n2)cc1C(F)(F)F] | 5-(1-(cyclopropylmethyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine | 419.9 |

TABLE 1-continued

| No | Structure | Name | M + H |
|----|-----------|------|-------|
| 153 | 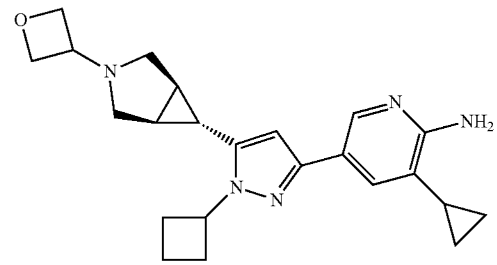 [SMILES: Nc1ncc(-c2cc([C@H]3[C@@H]4CN(C5COC5)C[C@@H]43)n(C3CCC3)n2)cc1C1CC1] | 5-(1-cyclobutyl-5-((1R,5S,6r)-3-(oxetan-3-yl)-3-azabicyclo[3.1.0]hexan-6-yl)-1H-pyrazol-3-yl)-3-cyclopropyl-pyridin-2-amine | 392.2 |
| 154 | 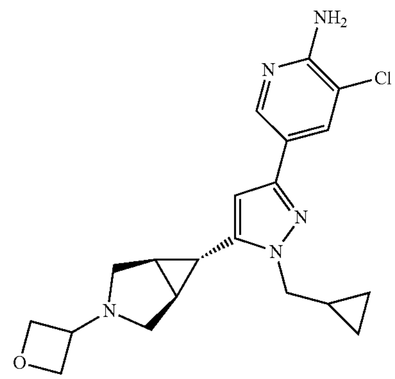 [SMILES: Nc1ncc(-c2cc([C@H]3[C@@H]4CN(C5COC5)C[C@@H]43)n(CC3CC3)n2)cc1Cl] | 3-chloro-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine | 386 |
| 155 | 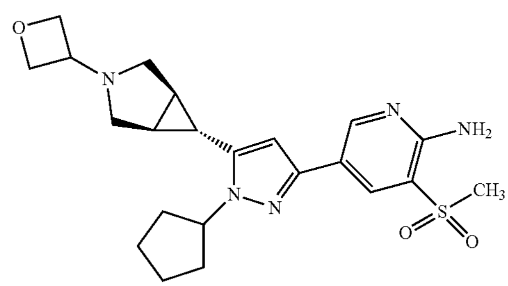 [SMILES: CS(=O)(=O)c1cc(-c2cc([C@H]3[C@@H]4CN(C5COC5)C[C@@H]43)n(C3CCCC3)n2)cnc1N] | 5-(1-cyclopentyl-5-((1R,5S,6r)-3-(oxetan-3-yl)-3-azabicyclo[3.1.0]hexan-6-yl)-1H-pyrazol-3-yl)-3-(methylsulfonyl)pyridin-2-amine | 444.0 |
| 156 | 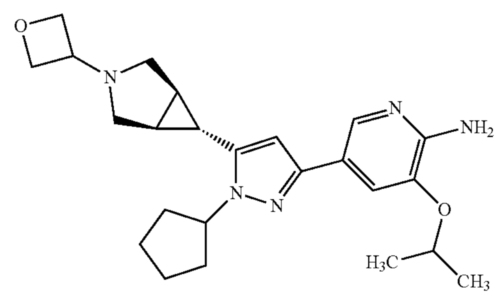 [SMILES: CC(C)Oc1cc(-c2cc([C@H]3[C@@H]4CN(C5COC5)C[C@@H]43)n(C3CCCC3)n2)cnc1N] | 5-(1-cyclopentyl-5-((1R,5S,6r)-3-(oxetan-3-yl)-3-azabicyclo[3.1.0]hexan-6-yl)-1H-pyrazol-3-yl)-3-isopropoxy-pyridin-2-amine | 424.1 |
| 157 | 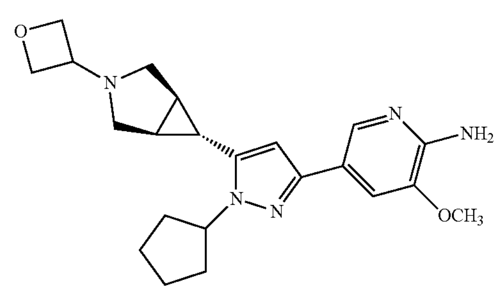 [SMILES: COc1cc(-c2cc([C@H]3[C@@H]4CN(C5COC5)C[C@@H]43)n(C3CCCC3)n2)cnc1N] | 5-(1-cyclopentyl-5-((1R,5S,6r)-3-(oxetan-3-yl)-3-azabicyclo[3.1.0]hexan-6-yl)-1H-pyrazol-3-yl)-3-methoxy-pyridin-2-amine | 396.2 |

TABLE 1-continued

| No | Structure | Name | M + H |
|---|---|---|---|
| 158 | 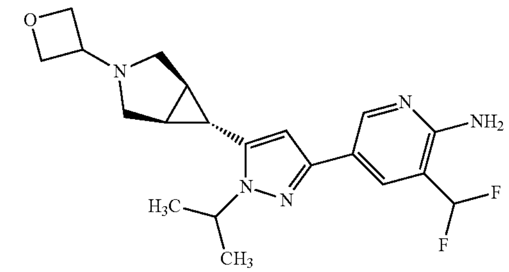 [SMILES: CC(C)n1nc(-c2cnc(N)c(C(F)F)c2)cc1[C@H]1[C@@H]2CN(C3COC3)C[C@@H]21] | 3-(difluoromethyl)-5-(1-isopropyl-5-((1R,5S,6r)-3-(oxetan-3-yl)-3-azabicyclo[3.1.0]hexan-6-yl)-1H-pyrazol-3-yl)pyridin-2-amine | 390.2 |
| 159 | 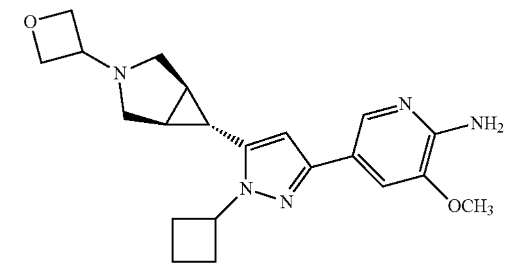 [SMILES: COc1cc(-c2cc([C@H]3[C@@H]4CN(C5COC5)C[C@@H]43)n(C3CCC3)n2)cnc1N] | 5-(1-cyclobutyl-5-((1R,5S,6r)-3-(oxetan-3-yl)-3-azabicyclo[3.1.0]hexan-6-yl)-1H-pyrazol-3-yl)-3-methoxypyridin-2-amine | 382.2 |
| 160 | 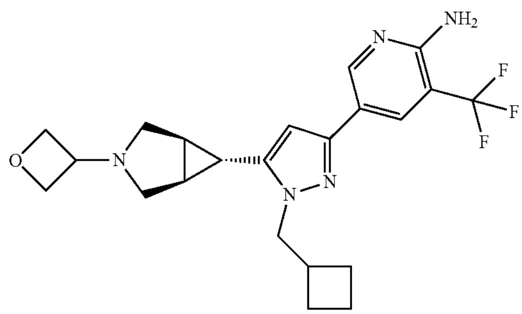 [SMILES: Nc1ncc(-c2cc([C@H]3[C@@H]4CN(C5COC5)C[C@@H]43)n(CC3CCC3)n2)cc1C(F)(F)F] | 5-(1-(cyclobutylmethyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine | |
| 161 | 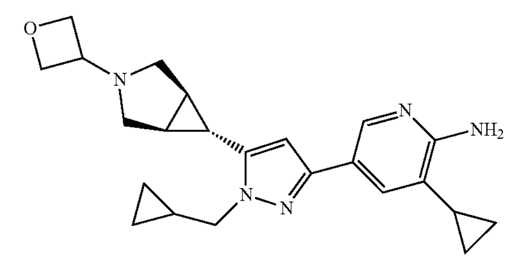 [SMILES: Nc1ncc(-c2cc([C@H]3[C@@H]4CN(C5COC5)C[C@@H]43)n(CC3CC3)n2)cc1C1CC1] | 3-cyclopropyl-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine | 392.2 |
| 162 | 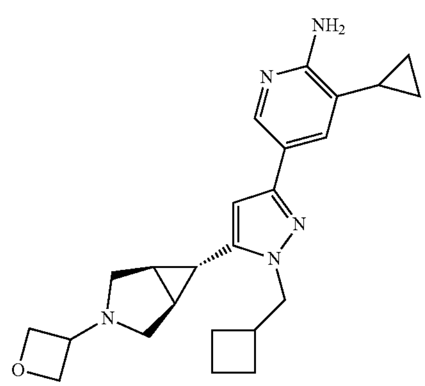 [SMILES: Nc1ncc(-c2cc([C@H]3[C@@H]4CN(C5COC5)C[C@@H]43)n(CC3CCC3)n2)cc1C1CC1] | 5-(1-(cyclobutylmethyl)-5-((1R,5S,6r)-3-(oxetan-3-yl)-3-azabicyclo[3.1.0]hexan-6-yl)-1H-pyrazol-3-yl)-3-cyclopropylpyridin-2-amine | |

TABLE 1-continued

| No | Structure | Name | M + H |
|---|---|---|---|
| 163 | 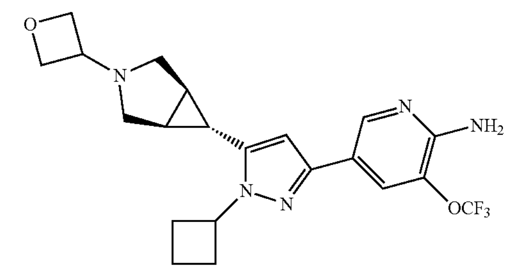 [SMILES: Nc1ncc(-c2cc([C@H]3[C@@H]4CN(C5COC5)C[C@@H]43)n(C3CCC3)n2)cc1OC(F)(F)F] | 5-(1-cyclobutyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine | 436.1 |
| 164 | 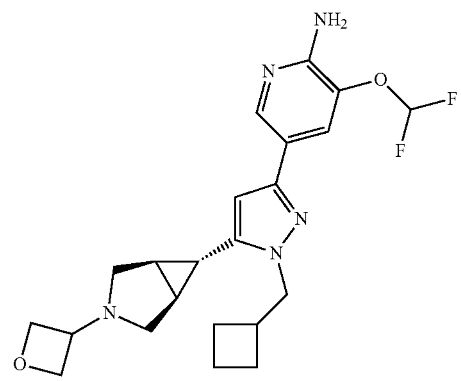 [SMILES: Nc1ncc(-c2cc([C@H]3[C@@H]4CN(C5COC5)C[C@@H]43)n(CC3CCC3)n2)cc1OC(F)F] | 5-(1-(cyclobutylmethyl)-5-((1R,5S,6r)-3-(oxetan-3-yl)-3-azabicyclo[3.1.0]hexan-6-yl)-1H-pyrazol-3-yl)-3-(difluoromethoxy)pyridin-2-amine | |
| 165 | 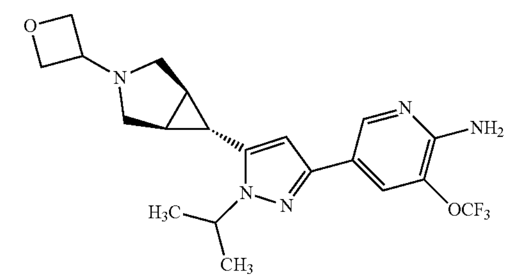 [SMILES: CC(C)n1nc(-c2cnc(N)c(OC(F)(F)F)c2)cc1[C@H]1[C@@H]2CN(C3COC3)C[C@@H]21] | 5-(1-isopropyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine | 424.1 |
| 166 | 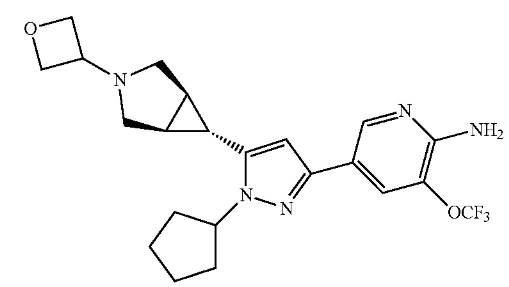 [SMILES: Nc1ncc(-c2cc([C@H]3[C@@H]4CN(C5COC5)C[C@@H]43)n(C3CCCC3)n2)cc1OC(F)(F)F] | 5-(1-cyclopentyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine | 450.2 |
| 167 | 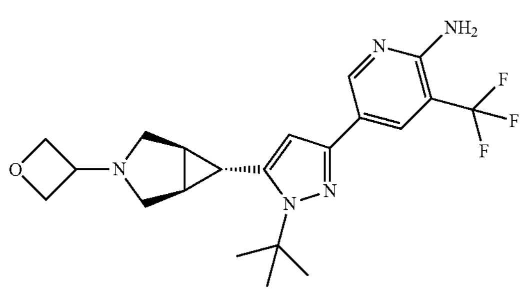 [SMILES: CC(C)(C)n1nc(-c2cnc(N)c(C(F)(F)F)c2)cc1[C@H]1[C@@H]2CN(C3COC3)C[C@@H]21] | 5-(1-(tert-butyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine | |

| No | Structure | Name | M + H |
|----|-----------|------|-------|
| 168 | 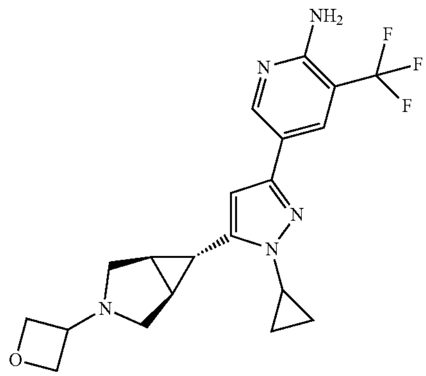 [SMILES: Nc1ncc(-c2cc([C@H]3[C@@H]4CN(C5COC5)C[C@@H]43)n(C3CC3)n2)cc1C(F)(F)F] | 5-(1-cyclopropyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine | |
| 169 | 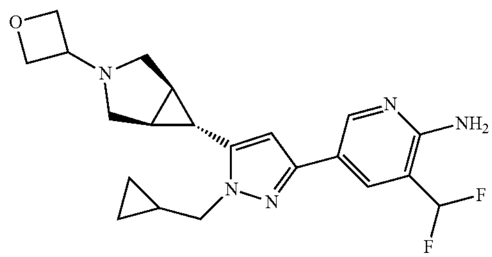 [SMILES: Nc1ncc(-c2cc([C@H]3[C@@H]4CN(C5COC5)C[C@@H]43)n(CC3CC3)n2)cc1C(F)F] | 5-(1-(cyclopropylmethyl)-5-((1R,5S,6r)-3-(oxetan-3-yl)-3-azabicyclo[3.1.0]hexan-6-yl)-1H-pyrazol-3-yl)-3-(difluoromethyl)pyridin-2-amine | 402.2 |
| 170 | 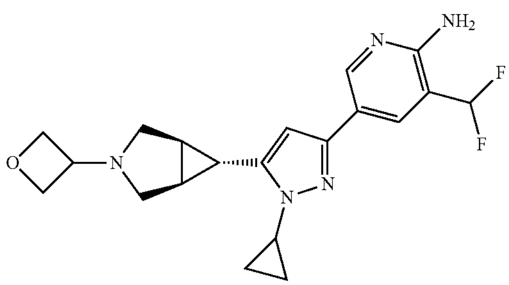 [SMILES: Nc1ncc(-c2cc([C@H]3[C@@H]4CN(C5COC5)C[C@@H]43)n(C3CC3)n2)cc1C(F)F] | 5-(1-cyclopropyl-5-((1R,5S,6r)-3-(oxetan-3-yl)-3-azabicyclo[3.1.0]hexan-6-yl)-1H-pyrazol-3-yl)-3-(difluoromethyl)pyridin-2-amine | |
| 171 | 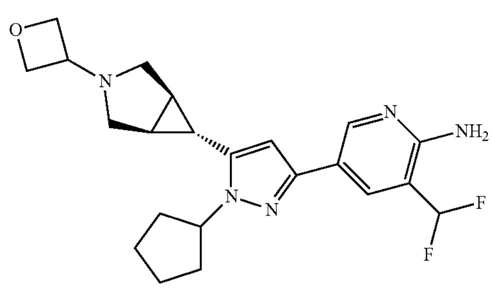 [SMILES: Nc1ncc(-c2cc([C@H]3[C@@H]4CN(C5COC5)C[C@@H]43)n(C3CCCC3)n2)cc1C(F)F] | 5-(1-cyclopentyl-5-((1R,5S,6r)-3-(oxetan-3-yl)-3-azabicyclo[3.1.0]hexan-6-yl)-1H-pyrazol-3-yl)-3-(difluoromethyl)pyridin-2-amine | 416.2 |
| 172 | 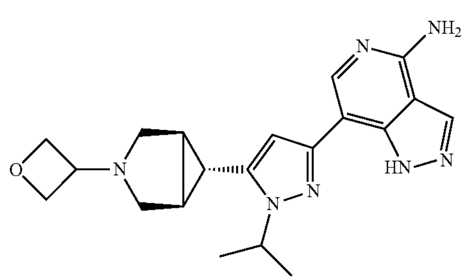 [SMILES: CC(C)n1nc(-c2cnc(N)c3cn[nH]c23)cc1[C@H]1[C@@H]2CN(C3COC3)C[C@@H]21] | 7-(1-isopropyl-5-((1R,5S,6r)-3-(oxetan-3-yl)-3-azabicyclo[3.1.0]hexan-6-yl)-1H-pyrazol-3-yl)-1H-pyrazolo[4,3-c]pyridin-4-amine | |

…

| No | Structure | Name | M + H |
|---|---|---|---|
| 173 | 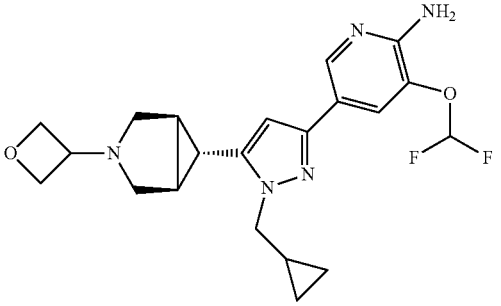 [SMILES: Nc1ncc(-c2cc([C@H]3[C@@H]4CN(C5COC5)C[C@@H]43)n(CC3CC3)n2)cc1OC(F)F] | 5-(1-(cyclopropylmethyl)-5-((1R,5S,6r)-3-(oxetan-3-yl)-3-azabicyclo[3.1.0]hexan-6-yl)-1H-pyrazol-3-yl)-3-(difluoromethoxy)pyridin-2-amine | |
| 174 | 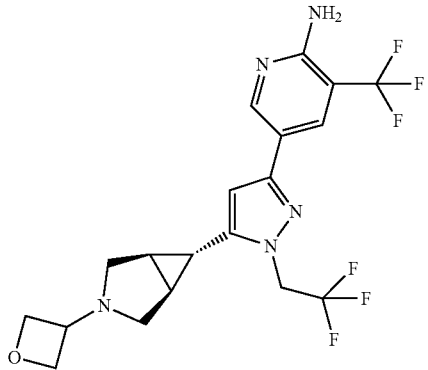 [SMILES: Nc1ncc(-c2cc([C@H]3[C@@H]4CN(C5COC5)C[C@@H]43)n(CC(F)(F)F)n2)cc1C(F)(F)F] | 5-(5-((1R,5S,6r)-3-(oxetan-3-yl)-3-azabicyclo[3.1.0]hexan-6-yl)-1-(2,2,2-trifluoroethyl)-1H-pyrazol-3-yl)-3-(trifluoromethyl)pyridin-2-amine | |
| 175 | 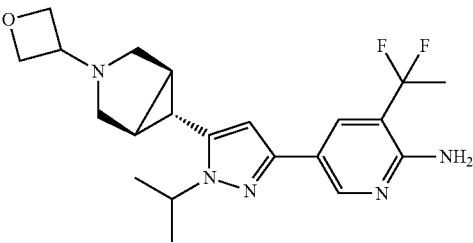 [SMILES: CC(C)n1nc(-c2cnc(N)c(C(C)(F)F)c2)cc1[C@H]1[C@@H]2CN(C3COC3)C[C@@H]21] | 3-(1,1-difluoroethyl)-5-(1-isopropyl-5-((1R,5S,6r)-3-(oxetan-3-yl)-3-azabicyclo[3.1.0]hexan-6-yl)-1H-pyrazol-3-yl)pyridin-2-amine | |
| 176 | 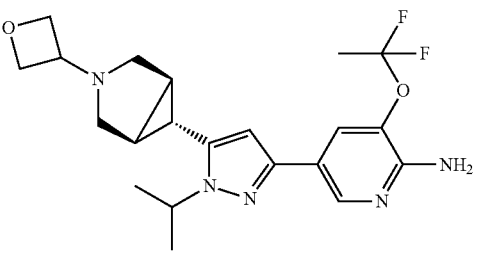 [SMILES: CC(C)n1nc(-c2cnc(N)c(OC(C)(F)F)c2)cc1[C@H]1[C@@H]2CN(C3COC3)C[C@@H]21] | 3-(1,1-difluoroethoxy)-5-(1-isopropyl-5-((1R,5S,6r)-3-(oxetan-3-yl)-3-azabicyclo[3.1.0]hexan-6-yl)-1H-pyrazol-3-yl)pyridin-2-amine | |
| 177 | 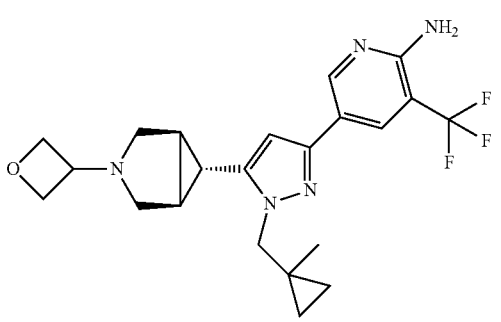 [SMILES: CC1(Cn2nc(-c3cnc(N)c(C(F)(F)F)c3)cc2[C@H]2[C@@H]3CN(C4COC4)C[C@@H]32)CC1] | 5-(1-((1-methylcyclopropyl)methyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine | |

TABLE 1-continued

| No | Structure | Name | M + H |
|---|---|---|---|
| 178 | 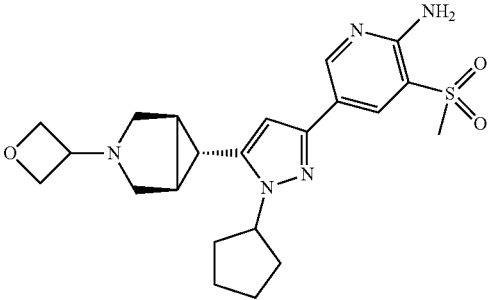 [SMILES: CS(=O)(=O)c1cc(-c2cc([C@H]3[C@@H]4CN(C5COC5)C[C@@H]43)n(C3CCCC3)n2)cnc1N] | 5-(5-(((1R,5S,6r)-3-cyclobutyl-3-aza-bicyclo[3.1.0]hexan-6-yl)-1-cyclo-pentyl-1H-pyrazol-3-yl)-3-(methyl-sulfonyl)pyridin-2-amine | |
| 179 | 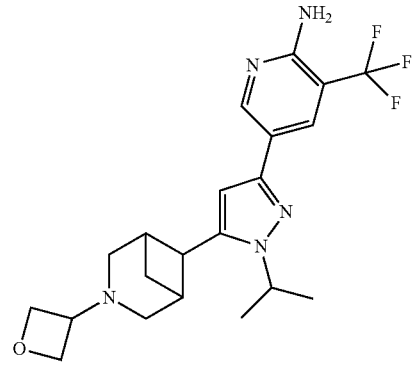 [SMILES: CC(C)n1nc(-c2cnc(N)c(C(F)(F)F)c2)cc1C1C2CC1CN(C1COC1)C2] | 5-(1-isopropyl-5-(3-(oxetan-3-yl)-3-azabicyclo[3.1.1]heptan-6-yl)-1H-py-razol-3-yl)-3-(trifluoromethyl)pyridin-2-amine | |
| 180 | 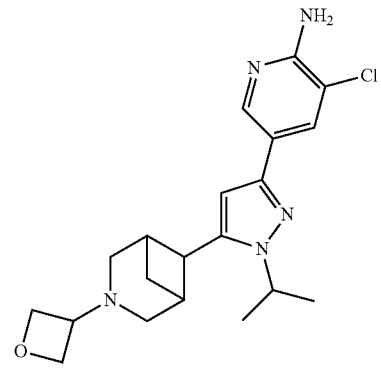 [SMILES: CC(C)n1nc(-c2cnc(N)c(Cl)c2)cc1C1C2CC1CN(C1COC1)C2] | 3-chloro-5-(1-isopropyl-5-(3-(oxetan-3-yl)-3-azabicyclo[3.1.1]heptan-6-yl)-1H-pyrazol-3-yl)pyridin-2-amine | |
| 181 | 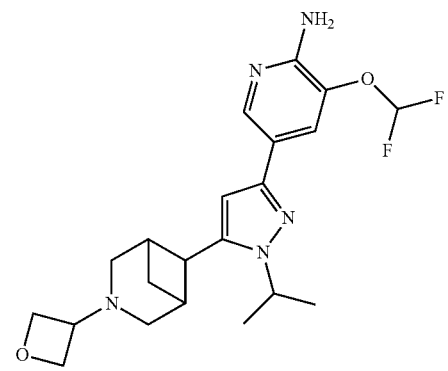 [SMILES: CC(C)n1nc(-c2cnc(N)c(OC(F)F)c2)cc1C1C2CC1CN(C1COC1)C2] | 3-(difluoromethoxy)-5-(1-isopropyl-5-(3-(oxetan-3-yl)-3-azabicyclo[3.1.1]heptan-6-yl)-1H-pyrazol-3-yl)pyri-din-2-amine | |

TABLE 1-continued

| No | Structure | Name | M + H |
|---|---|---|---|
| 182 | 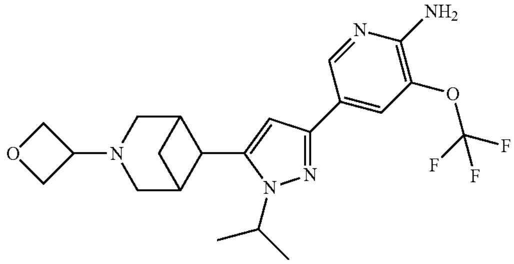 [SMILES: CC(C)n1nc(-c2cnc(N)c(OC(F)(F)F)c2)cc1C1C2CC1CN(C1COC1)C2] | 5-(1-isopropyl-5-(3-(oxetan-3-yl)-3-azabicyclo[3.1.]heptan-6-yl)-1H-pyrazol-3-yl)-3-(trifluoromethoxy)pyridin-2-amine | |

C. Synthesis of Compounds

Compound of the invention can be synthesized according to the general Methods A-AH described in the Examples section.

D. Pharmaceutical Compositions and Administrations

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of Formula I or any subformula thereof and at least one pharmaceutically acceptable carrier, diluent or excipient. The compositions of the invention can be used for inhibiting DLK activity in patients (e.g., humans)

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of Formula I or I-I (or stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of Formula I or I—I and compositions comprising compounds of Formula I or any embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit DLK activity as required to prevent or treat the undesired disease or disorder, such as for example, neurodegeneration, amyloidosis, formation of neurofibrillary tangles, or undesired cell growth. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of Formula I any embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of Formula I or any embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21$^{st}$ Edition, Lippincott Williams & Wilkins, Philidelphia, Pa.

Sustained-release preparations of a compound of the invention (e.g., compound of Formula I or any embodiment thereof) can be prepared. Suitable examples of sustained-release preparations include semipermeable matrices of solid hydrophobic polymers containing a compound of Formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21$^{st}$ Edition, Lippincott Williams & Wilkins, Philidelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of Formula I or any embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of Formula I or an embodiment thereof is formulated in an acetate buffer, at pH 5. In another embodiment, the compounds of Formula I or an embodiment thereof are sterile. The compound may be stored, for example, as a solid or amorphous composition, as a lyophilized formulation or as an aqueous solution.

Formulations of a compound of the invention (e.g., compound of Formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention (e.g., compound of Formula I or an embodiment thereof) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of Formula I or I-I) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford. Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I or I-I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I or I-I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

A compound of formula I (or an embodiment thereof) used in the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. A compound of formula I (or an embodiment thereof) need not be, but is optionally formulated with one or more agent currently used to prevent or treat the disorder in question. The effective amount of such other agents depends on the amount of a compound of the invention present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of formula I or I-I (or an embodiment thereof) (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 µg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 µg kg to 100 mg/kg or more, depending on the factors mentioned above. For repeated administrations over several days or longer, depending on the condition, the treatment would generally be sustained until a desired suppression of disease symptoms occurs. One exemplary dosage of a compound of formula I (or an embodiment thereof) would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 µg kg to 1 mg/kg, about 1 µg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

E. Indications and Methods of Treatment

In another aspect, the invention provides for methods of inhibiting the Dual Leucine Zipper Kinase (DLK) in an in vitro (e.g., a nerve graft of nerve transplant) or in vivo setting (e.g., in a patient) by contacting DLK present in an in vitro or in vivo setting with compounds of Formula I or an embodiment thereof. In these methods of the invention, the inhibition of DLK signaling or expression with a compound of formula I or an embodiment thereof results in a downstream decrease in JNK phosphorylation (e.g., a decrease in JNK2 and/or JNK3 phosphorylation), JNK activity (e.g., a decrease in JNK2 and/or JNK3 activity), and/or JNK expression (e.g., a decrease in JNK2 and/or JNK3 expression). Accordingly, administering one or more compounds of Formula I or an embodiment thereof according to the methods of the invention can result in decrease in activity of kinase targets downstream of the DLK signalling cascade, e.g, (i) a decrease in JNK phosphorylation, JNK activity, and/or JNK expression, (ii) a decrease in cJun phosphorylation, cJun activity, and/or cJun expression, and/or (iii) a decrease in p38 phosphorylation, p38 activity, and/or p38 expression.

Compounds of the invention can be used in methods for inhibiting neuron or axon degeneration. The inhibitors are, therefore, useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) pain, (v) ocular-related neurodegeneration, (vi) memory loss, and (vii) psychiatric disorders. Non-limiting examples of some of these diseases, conditions, and injuries are provided below.

Examples of neurodegenerative diseases and conditions that can be prevented or treated according to the invention include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson's-plus diseases (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS dementia complex (also known as HIV dementia, HIV encephalopathy, and HIV-associated dementia).

The methods of the invention can also be used in the prevention and treatment of ocular-related neurodegeneration and related diseases and conditions, such as glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis. Non-limiting examples of different types of glaucoma that can be prevented or treated according to the invention include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neo-vascular glaucoma, drug-induced glaucoma (e.g., corticosteroid induced glaucoma and alpha-chymotrypsin glaucoma), toxic glaucoma, and glaucoma associated with intraocular tumors, retinal detachments, severe chemical burns of the eye, and iris atrophy.

Examples of types of pain that can be treated according to the methods of the invention include those associated with the following conditions: chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neurogenic or neuropathic pain, nerve inflammation or damage, shingles, herniated disc, torn ligament, and diabetes.

Certain diseases and conditions having primary effects outside of the nervous system can lead to damage to the nervous system, which can be treated according to the methods of the present invention. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the methods of the invention can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine. Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexiline), and Metronidazole.

The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage).

Further, the methods of the invention can be used in the prevention or treatment of memory loss such as, for example, age-related memory loss. Types of memory that can be affected by loss, and thus treated according to the invention, include episodic memory, semantic memory, short-term memory, and long-term memory. Examples of diseases and conditions associated with memory loss, which can be treated according to the present invention, include mild cognitive impairment, Alzheimer's disease, Parkinson's disease, Huntington's disease, chemotherapy, stress, stroke, and traumatic brain injury (e.g., concussion).

The methods of the invention can also be used in the treatment of psychiatric disorders including, for example, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

In addition to the in vivo methods described above, the methods of the invention can be used to treat nerves ex vivo, which may be helpful in the context of nerve grafts or nerve transplants. Thus, the inhibitors described herein can be useful as components of culture media for use in culturing nerve cells in vitro.

Accordingly, in another aspect, the invention provides for a method for inhibiting or preventing degeneration of a central nervous system (CNS) neuron or a portion thereof, the method comprising administering to the CNS neuron a compound of formula I or an embodiment thereof.

In one embodiment, of the method for inhibiting or preventing degeneration of a central nervous system neuron or a portion thereof, the administering to the CNS neuron is performed in vitro.

In another embodiment, of the method for inhibiting or preventing degeneration of a central nervous system neuron or a portion thereof, the method further comprises grafting or implanting the CNS neuron into a human patient after administration of the agent.

In another embodiment, of the method for inhibiting or preventing degeneration of a central nervous system neuron or a portion thereof, the CNS neuron is present in a human patient.

In another embodiment, of the method for inhibiting or preventing degeneration of a central nervous system neuron or a portion thereof, the administering to the CNS neuron comprises administration of said compound of formula I or an embodiment thereof in a pharmaceutically acceptable carrier, diluent or excipient.

In another embodiment, of the method for inhibiting or preventing degeneration of a central nervous system neuron or a portion thereof, the administering to the CNS neuron is carried out by an administration route selected from the group consisting of parenteral, subcutaneous, intravenous, intraperitoneal, intracerebral, intralesional, intramuscular, intraocular, intraarterial interstitial infusion and implanted delivery device.

In another embodiment, of the method for inhibiting or preventing degeneration of a central nervous system neuron or a portion thereof, the method further comprises administering one or more additional pharmaceutical agents.

The inhibitors can be optionally combined with or administered in concert with each other or other agents known to be useful in the treatment of the relevant disease or condition. Thus, in the treatment of ALS, for example, inhibitors can be administered in combination with Riluzole (Rilutek), minocycline, insulin-like growth factor 1 (IGF-1), and/or methylcobalamin. In another example, in the treatment of Parkinson's disease, inhibitors can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, inhibitors can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The invention also includes pharmaceutical compositions and kits comprising combinations as described herein.

In addition to the combinations noted above, other combinations included in the invention are combinations of inhibitors of degeneration of different neuronal regions. Thus, the invention includes combinations of agents that (i) inhibit degeneration of the neuron cell body, and (ii) inhibit axon degeneration. For example, inhibitors of GSK and transcription are found to prevent degeneration of neuron cell bodies, while inhibitors of EGFR and p38 MAPK are found to prevent degeneration of axons. Thus, the invention includes combinations of inhibitors of GSK and EGFR (and/or p38 MAPK), combinations of transcription inhibitors and EGF (and/or p38 MAPK), and further combinations of inhibitors of dual leucine zipper-bearing kinase (DLK), glycogen synthase kinase 3β (GSK3), p38 MAPK, EGFF, phosphoinositide 3-kinase (PI3K), cyclin-dependent kinase 5 (cdk5), adenylyl cyclase, c-Jun N-terminal kinase (JNK), BCL2-associated X protein (Bax), In channel, calcium/calmodulin-dependent protein kinase (CaMKK), a G-protein, a G-protein coupled receptor, transcription factor 4 (TCF4), and β-catenin. The inhibitors used in these combinations can be any of those described herein, or other inhibitors of these targets as described in WO 2011/050192, incorporated herein by reference.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

F. Examples

The invention will be more fully understood by reference to the following examples. They should not, however, be construed as limiting the scope of the invention. These examples are not intended to limit the scope of the present invention, but rather to provide guidance to a skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention. Accordingly, the following examples are provided to illustrate but not limit the invention.

In the Examples described below, unless otherwise indicated all temperatures are set forth in degrees Celsius. Commercially available reagents were purchased from suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters); or alternatively column chromatography was carried out using on an ISCO chromatography system (Manufacturer: Teledyne ISCO) having a silica gel column. $^1$H NMR spectra were recorded on a Varian instrument operating at 400 MHz. $^1$H NMR spectra were obtained in deuterated CDCl$_3$, d$_6$-DMSO, CH$_3$OD or d$_6$-acetone solutions (reported in ppm), using tetramethylsilane (TMS) as the reference standard (0 ppm). When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

When possible, product formed in the reaction mixtures were monitored by LC/MS. High Pressure Liquid Chromatography—Mass Spectrometry (LCMS) experiments to performed either on an Agilent 1200 Series LC coupled to a 6140 quadrupole mass spectrometer using a Supelco Ascentis Express C18 column with a linear gradient of 5%-95% acetonitrile/water (with 0.1% trifluoroacetic acid in each mobile phase) within 1.4 minutes and held at 95% for 0.3 minute, or on a PE Sciex API 150 EX using a Phenomenex DNYC monolithic C18 column with a linear gradient of 5%-95% acetonitrile/water (with 0.1% trifluoroacetic acid in each mobile phase) within 5 minutes and held at 95% for 1 minute to determine retention times ($R_T$) and associated mass ions.

All abbreviations used to described reagents, reaction conditions, or equipment used are consistent with the definitions set forth in the "List of standard abbreviations and acronyms" published yearly by the Journal of Organic Chemistry (an American Chemical Society journal). The chemical names of discrete compounds of the invention were obtained using the structure naming feature ChemBioDraw Version 11.0 or from Accelrys' Pipeline Pilot IUPAC compound naming program.

EXAMPLE 1

Preparation of Intermediates

Preparation of 3-(cyclopropylmethoxy)-5-(4,4,5,5-tetramethyl-1,3,2-dioxaborolan-2-yl)pyridin-2-amine

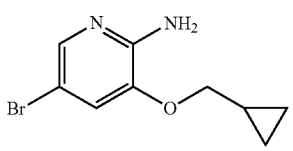 [SMILES: Nc1ncc(Br)cc1OCC1CC1]

Step 1:
5-bromo-3-(cyclopropylmethoxy)pyridin-2-amine

To a stirred solution of 2-amino-5-bromopyridine-3-ol (25 g, 132.9 mmol) in dichloromethane (150 mL) was added (bromomethyl)cyclopropane (35.88 g, 265.8 mmol), aliquat (7.5 g) and 40% aqueous sodium hydroxide (150 mL) at RT, followed by stirring for 16 h. The reaction mixture was diluted with water (500 mL) and extracted with dichloromethane (2×500 mL). The combined organic layers were concentrated to dryness in vacuo and the resulting residue was purified by column chromatography (silica gel, 100-200 mesh, 25% ethyl acetate in hexane) affording 5-bromo-3-(cyclopropylmethoxy)pyridin-2-amine as and off white solid (15 g, 47%): $^1$H NMR (300 MHz, DMSO-d6) δ 7.61 (s, 1H), 7.19 (s, 1H), 5.81 (s, 2H), 4-3.8 (m, 2H), 1.35-1.1 (m, 1H), 0.65-0.55 (m, 2H), 0.2-0.4 (m, 2H).

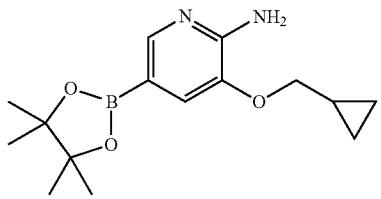 [SMILES: CC1(C)OB(c2cnc(N)c(OCC3CC3)c2)OC1(C)C]

Step 2: 3-(cyclopropylmethoxy)-5-(4,4,5,5-tetramethyl-1,3,2-dioxaborolan-2-yl)pyridin-2-amine To a stirred solution of 5-bromo-3-(cyclopropylmethoxy) pyridin-2-amine (10 g, 41.32 mmol) in 1,4-dioxane (120 mL) was added 4,4,4',4',5,5,5',5'-octamethyl-2,2'-bi(1,3,2-dioxaborolane) (11.54 g, 45.45 mmol), and potassium acetate (8.09 g, 82.64 mmol). The mixture was purged with argon gas for 15 min and tris(dibenzylideneacetone)dipalladium (756 mg, 0.82 mmol) and tricyclohexylphosphine (579 mg, 0.206 mmol) was added. The mixture was purged with argon gas for 15 min and the reaction mixture was stirred at 110° C. for 14 h. The reaction mixture was filtered through celite bed and washed with ethyl acetate (500 mL). The filtrate was concentrated to dryness in vacuo and the crude was crystallized (1:3, ethanol:water). The resulting solid was filtered and triturated with hexane, filtered and dried affording 3-(cyclopropylmethoxy)-5-(4,4,5,5-tetramethyl-1,3,2-dioxaborolan-2-yl)pyridin-2-amine as a pale yellow solid (6.5 g, 54%): $^1$H NMR (300 MHz, DMSO-d6) δ 7.81 (s, 1H), 7.1 (s, 1H), 6 (s, 2H), 3.9-3.7 (m, 2H), 1.4-1.2 (m, 13H), 0.6-0.5 (m, 2H), 0.4-0.3 (m, 2H).

Preparation of 3-ethoxy-5-(4,4,5,5-tetramethyl-1,3,2-dioxaborolan-2-yl)pyridin-2-amine

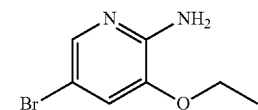

Step 1: 5-bromo-3-ethoxypyridin-2-amine

To a stirred solution of 2-amino-5-bromopyridine-3-ol (25 g, 132.9 mmol) in dichloromethane (150 mL) was added iodoethane (41.43 g, 265 mmol), aliquat (7.5 g) and 40% aqueous sodium hydroxide (150 mL) at RT, followed by stirring for 16 h. The reaction mixture was diluted with water (150 mL) and extracted with dichloromethane (2×300 mL). The combined organic layers were concentrated to dryness in vacuo and the resulting residue was purified by column chromatography (silica gel, 100-200 mesh, 20% ethyl acetate in hexane) affording 5-bromo-3-ethoxypyridin-2-amine as and off white solid (17 g, 59%): $^1$H NMR (300 MHz, DMSO-d6) δ 7.58 (s, 1H), 7.18 (s, 1H), 5.85 (s, 2H), 4.2-3.8 (m, 2H), 1.20-1.40 (m, 1H), 0.65-0.55 (m, 2H).

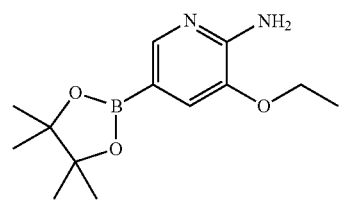 [SMILES: CCOc1cc(B2OC(C)(C)C(C)(C)O2)cnc1N]

Step 2: 3-ethoxy-5-(4,4,5,5-tetramethyl-1,3,2-dioxaborolan-2-yl)pyridin-2-amine

To a stirred solution of 5-bromo-3-ethoxypyridin-2-amine (12 g, 55.29 mmol) in 1,4-dioxane (120 mL) was added 4,4,4',4',5,5,5',5'-octamethyl-2,2'-bi(1,3,2-dioxaborolane) (15.44 g, 60.08 mmol), and potassium acetate (10.83 g, 110.58 mmol). The mixture was purged with argon gas for 15 min and tris(dibenzylideneacetone)dipalladium (1.0 g, 1.1 mmol) and tricyclohexylphosphine (775 mg, 2.76 mmol) was added. The mixture was purged with argon gas for 15 min and the reaction mixture was stirred at 110° C. for 14 h. The reaction mixture was filtered through celite bed and washed with ethyl acetate (500 mL). The filtrate was concentrated to dryness in vacuo and the crude was crystallized (1:3, ethanol:water). The resulting solid was filtered and triturated with hexane, filtered and dried affording 3-(cyclopropylmethoxy)-5-(4,4,5,5-tetramethyl-1,3,2-dioxaborolan-2-yl)pyridin-2-amine as a of white solid (7.5 g, 51%): $^1$H NMR (300 MHz, DMSO-d6) δ 7.80 (s, 1H), 7.0 (s, 1H), 6.05 (s, 2H), 4.1-3.9 (m, 2H), 1.4-1.2 (m, 15H).

Preparation of 3-isopropoxy-5-(4,4,5,5-tetramethyl-1,3,2-dioxaborolan-2-yl)pyridin-2-amine

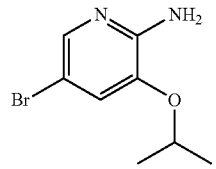

Step 1: 5-bromo-3-isopropoxypyridin-2-amine

To a stirred solution of 2-amino-5-bromopyridine-3-ol (25 g, 132.9 mmol) in dichloromethane (150 mL) was added 2-iodo-propane (45.15 g, 265.8 mmol), aliquat (7.5 g) and 40% aqueous sodium hydroxide (500 mL) at RT, followed by stirring for 16 h. The reaction mixture was diluted with water (150 mL) and extracted with dichloromethane (2×250 mL). The combined organic layers were concentrated to dryness in vacuo and the resulting residue was purified by column chromatography (silica gel, 100-200 mesh, 20% ethyl acetate in hexane) affording 5-bromo-3-isopropoxy-pyridin-2-amine as a pale yellow solid (15 g, 49%): $^1$H NMR (300 MHz, Chloroform-d) δ 7.7 (s, 1H), 7.0 (s, 1H), 4.80-4.60 (s, 2H), 4.58-4.4 (m, 1H), 1.35 (s, 1H).

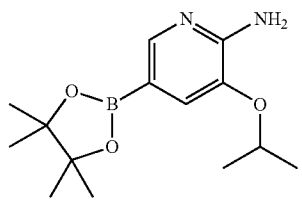 [SMILES: CC(C)Oc1cc(B2OC(C)(C)C(C)(C)O2)cnc1N]

Step 2: 3-isopropoxy-5-(4,4,5,5-tetramethyl-1,3,2-dioxaborolan-2-yl)pyridin-2-amine To a stirred solution of 5-bromo-3-isopropoxypyridin-2-amine (10 g, 43.29 mmol) in 1,4-dioxane (120 mL) was added 4,4,4',4',5,5,5',5'-octamethyl-2,2'-bi(1,3,2-dioxaborolane) (12.09 g, 47.61 mmol), and potassium acetate (8.48 g, 86.58 mmol). The mixture was purged with argon gas for 15 min and tris(dibenzylideneacetone)dipalladium (792 mg, 0.865 mmol) and tricyclohexylphosphine (605 mg, 2.16 mmol) was added. The mixture was purged with argon gas for 15 min, the reaction mixture was sealed and stirred at 110° C. for 14 h. The reaction mixture was filtered through celite bed and washed with ethyl acetate (500 mL). The filtrate was concentrated to dryness in vacuo and the crude was crystallized (1:3, ethanol:water). The resulting solid was filtered and triturated with hexane, filtered and dried affording 3-isopropoxy-5-(4,4,5,5-tetramethyl-1,3,2-dioxaborolan-2-yl)pyridin-2-amine as a pale yellow solid (6 g, 50%): $^1$H NMR (300 MHz, DMSO-d6) δ 7.80 (s, 1H), 7.0 (s, 1H), 6.0 (s, 2H), 4.6-4.4 (m, 1H), 1.4-1.2 (m, 18H).

Preparation of 3-methyl-5-(4,4,5,5-tetramethyl-1,3,2-dioxaborolan-2-yl)-1H-pyrrolo[2,3-b]pyridine

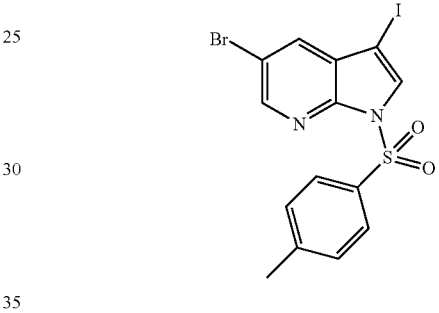

Step 1: 5-bromo-3-iodo-1-tosyl-1H-pyrrolo[2,3-b]pyridine

A stirred solution of sodium hydride (14.4 g, 0.36 mol) in tetrahydrofuran (800 mL) was added 5-bromo-3-iodo-1H-pyrrolo[2,3-b]pyridine (60 g, 0.186 mol) at 0° C. The reaction mixture was stirred for 0.5 h, 4-toluenesulfonyl chloride was added at 0° C., warmed to RT and stirred for 1 h. The reaction mixture was poured into ice water, the solid was filtered, washed with water, acetone and dried to give 5-bromo-3-iodo-1-tosyl-1H-pyrrolo[2,3-b]pyridine as a light yellow solid (79 g, 88.8%): $^1$H NMR (DMSO-d6, 400 MHz): δ 8.642-8.647 (d, J=2 Hz, 1H), 8.375 (s, 1H), 8.158 (s, 1H), 8.119-8.124 (d, J=2 Hz, 2H), 7.559-7.579 (d, J=8 Hz, 2H), 2.654 (s, 3H).

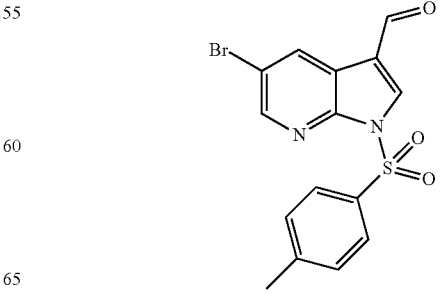

Step 2: 5-bromo-1-tosyl-1H-pyrrolo[2,3-b]pyridine-3-carbaldehyde

To a stirred solution of 5-bromo-3-iodo-1-tosyl-1H-pyrrolo[2,3-b]pyridine 3 (45 g, 0.094 mol) in tetrahydrofuran (600 mL), isopropylmagnesium bromide (103.75 mL, 0.103 mol) was added dropwise at 0° C. and the mixture was stirred for 0.5 h. N,N-dimethylformamide was added and stirred at RT for 2 h. The reaction was quenched with aqueous ammonium chloride, extracted with (3×1000 mL). The combined organic layers were washed with brine, dried over sodium sulfate and concentrated to dryness in vacuo. The resulting residue was purified by column chromatography (silica gel, 9% to 50% ethyl acetate in petroleum ether) affording 5-bromo-1-tosyl-1H-pyrrolo[2,3-b]pyridine-3-carbaldehyde as a white solid (48 g, 67.1%): $^1$H NMR (400 MHz, Chloroform-d): δ 10.010 (s, 1H), 8.665 (s, 1H), 8.518 (s, 1H), 8.379 (s, 1H), 8.114-8.135 (d, J=8.4 Hz, 2H), 7.330-7.351 (d, J=8.4 Hz, 2H), 2.170 (s, 3H).

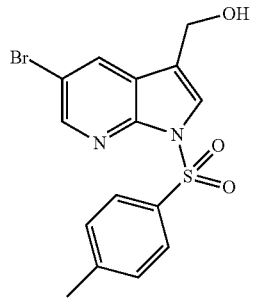 [SMILES: Cc1ccc(S(=O)(=O)n2cc(CO)c3cc(Br)cnc32)cc1]

Step 3: (5-bromo-1-tosyl-1H-pyrrolo[2,3-b]pyridin-3-yl)methanol

To a solution of 5-bromo-1-tosyl-1H-pyrrolo[2,3-b]pyridine-3-carbaldehyde (45 g, 0.12 mol) in methanol (600 mL) was added sodium borohydride at 0° C., and the mixture was stirred at RT overnight. The reaction mixture was quenched with aqueous ammonium chloride, and extracted with ethyl acetate (3×1000 mL). The combined organic layers were washed with brine, dried over sodium sulfate and concentrated to dryness in vacuo affording (5-bromo-1-tosyl-1H-pyrrolo[2,3-b]pyridin-3-yl)methanol as a white solid. (45 g, 99.5%): $^1$H NMR (400 MHz, Chloroform-d): δ 8.443-8.449 (d, J=2.4 Hz, 1H), 8.096 (s, 1H), 8.018-8.040 (d, J=8.8 Hz, 2H), 7.687 (s, 1H), 7.258-7.282 (d, J=8.8 Hz, 2H), 4.776-4.789 (d, J=5.2 Hz, 2H), 2.373 (s, 3H).

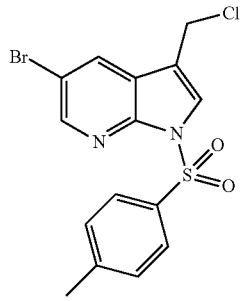 [SMILES: Cc1ccc(S(=O)(=O)n2cc(CCl)c3cc(Br)cnc32)cc1]

Step 4: 5-bromo-3-(chloromethyl)-1-tosyl-1H-pyrrolo[2,3-b]pyridine

To a solution of (5-bromo-1-tosyl-1H-pyrrolo[2,3-b]pyridin-3-yl)methanol (45 g, 0.12 mol) in dichloromethane (500 mL), thionyl chloride (28.1 g, 0.24 mol) was added at 0° C. and the mixture was stirred at RT for 0.5 h. The reaction mixture was quenched with water and adjusted to pH 8 with aqueous sodium carbonate. The resulting mixture was extracted with dichloromethane (3×800 mL). The combined organic layers were washed with brine, dried over sodium sulfate and concentrated to dryness in vacuo affording 5-bromo-3-(chloromethyl)-1-tosyl-1H-pyrrolo[2,3-b]pyridine as a white solid (47 g, 100%): $^1$H NMR (400 MHz, Chloroform-d), δ 8.471-8.477 (d, J=2.4 Hz, 1H), 8.101 (s, 1H), 8.044-8.065 (d, J=8.4 Hz, 2H), 7.765 (s, 1H), 7.283-7.303 (d, J=8.4 Hz, 2H), 4.680 (s, 2H), 2.383 (s, 3H).

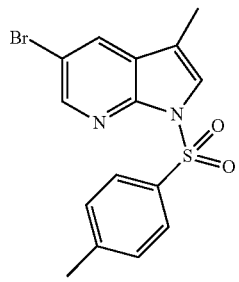 [SMILES: Cc1ccc(S(=O)(=O)n2cc(C)c3cc(Br)cnc32)cc1]

Step 5: 5-bromo-3-methyl-1-tosyl-1H-pyrrolo[2,3-b]pyridine

To a solution of 5-bromo-3-(chloromethyl)-1-tosyl-1H-pyrrolo[2,3-b]pyridine (47 g, 0.12 mol) in dimethyl sulfoxide (400 mL) was added sodium borohydride (8.97 g, 0.24 mol) and the mixture was stirred at 50° C. for 2 h. The reaction mixture was quenched with water and extracted with ethyl acetate (3×800 mL). The combined organic layers were washed with brine, dried over sodium sulfate and concentrated to dryness in vacuo. The resulting crude product was washed with ethyl acetate affording 5-bromo-3-methyl-1-tosyl-1H-pyrrolo[2,3-b]pyridine (35 g, 81.4%) as a white solid: $^1$H NMR (400 MHz, Chloroform-d), δ 8.424-8.429 (d, J=2 Hz, 1H), 7.995-8.016 (d, J=8.4 Hz, 2H), 7.889 (s, 1H), 7.477 (s, 1H), 7.248-7.260 (d, J=4.8 Hz, 2H), 2.366 (s, 3H), 2.217 (s, 3H).

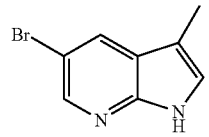

Step 6: 5-bromo-3-methyl-1H-pyrrolo[2,3-b]pyridine

To a solution of 5-bromo-3-methyl-1-tosyl-1H-pyrrolo[2,3-b]pyridine (35 g, 96.2 mmol) in methanol (200 mL) was added a solution of 6N sodium hydroxide (200 mL) and the mixture was heated at reflux for 2 h. The reaction mixture was concentrated in vacuo to remove methanol and adjusted to pH 7 with citric acid. The resulting solid was filtered, washed with water, dried to afford 5-bromo-3-methyl-1H-pyrrolo[2,3-b]pyridine as a yellow solid (20 g, 98.5%): ¹H NMR (400 MHz, DMSO-d6), δ 11.462 (s, 1H), 8.134 (s, 1H), 8.045 (s, 1H), 7.210 (s, 1H), 2.135 (s, 3H).

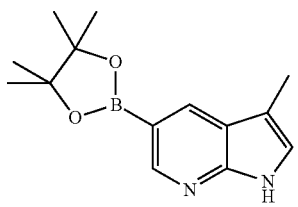 [SMILES: Cc1c[nH]c2ncc(B3OC(C)(C)C(C)(C)O3)cc12]

Step 7: 3-methyl-5-(4,4,5,5-tetramethyl-1,3,2-dioxaborolan-2-yl)-1H-pyrrolo[2,3-b]pyridine To a solution of 5-bromo-3-methyl-1H-pyrrolo[2,3-b]pyridine (20 g, 94.8 mmol) in N,N-dimethylformamide (200 mL) was added potassium acetate (27.9 g, 284.4 mmol) and 4,4,4',4',5,5,5',5'-octamethyl-2,2'-bi(1,3,2-dioxaborolane) (28.8 g, 113.74 mmol). The resulting mixture was degassed with nitrogen for 5 min, 1,1'-Bis(diphenylphosphino)ferrocene-palladium(II)dichloride (6.65 g, 9.48 mmol) was added and the mixture was degassed with nitrogen once more for 5 min. The reaction mixture was stirred overnight at 80-90° C. The reaction mixture was poured into water, extracted with (3×200 mL). The combined organic layers were washed with brine, dried over sodium sulfate and concentrated to dryness in vacuo. The resulting residue was purified by column chromatography (silica gel, 100-200 mesh, 9% to 50% ethyl acetate in petroleum ether) affording 3-methyl-5-(4,4,5,5-tetramethyl-1,3,2-dioxaborolan-2-yl)-1H-pyrrolo[2,3-b]pyridine as a white solid (10.5 g, 43%): ¹H NMR (400 MHz, DMSO-d6), δ 11.360 (s, 1H), 8.371-8.375 (d, J=1.6 Hz, 1H), 8.097-8.100 (s, J=1.2 Hz, 2H), 7.17 (s, 1H), 3.296 (s, 3H), 1.245 (s, 12H).

Preparation of 3-isopropyl-5-(4,4,5,5-tetramethyl-1,3,2-dioxaborolan-2-yl)-1H-pyrrolo[2,3-b]pyridine

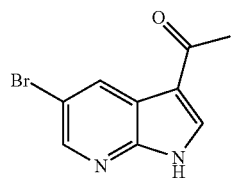

Step 1: 1-(5-bromo-1H-pyrrolo[2,3-b]pyridin-3-yl)ethanone

To a solution of 5-bromo-1H-pyrrolo[2,3-b]pyridine (30 g, 0.15 mol) and aluminium chloride (100 g, 0.75 mol) in dichloromethane (2000 mL) was added dropwise acetyl chloride (102 mL, 1.44 mol) over 1 h under nitrogen atmosphere at 0° C. The reaction mixture was warmed to RT and stirred overnight. Methanol (150 mL) was added dropwise at 0° C., and the resulting mixture was concentrated to dryness in vacuo. The resulting crude was dissolved in ice-water, basified with saturated sodium bicarbonate to pH 4~5 and extracted with ethyl acetated (3×3000 mL). The combined organic layer were washed with brine, dried over sodium sulfate and concentrated to dryness in vacuo affording crude 1-(5-bromo-1H-pyrrolo[2,3-b]pyridin-3-yl)ethanone as a yellow solid (330 g, 93% after 10 batch repeat) used for the next step without any further purification: 1H NMR (DMSO, 400 MHz): δ 12.675 (s, 1H), 8.537-8.543 (d, J=2.4 Hz, 1H), 8.506 (s, 1H), 8.371-8.377 (d, J=2.4 Hz, 1H), 2.445 (s, 3H).

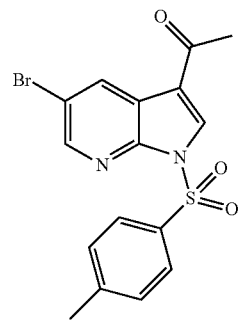 [SMILES: CC(=O)c1cn(S(=O)(=O)c2ccc(C)cc2)c2ncc(Br)cc12]

Step 2: 1-(5-bromo-1-tosyl-1H-pyrrolo[2,3-b]pyridin-3-yl)ethanone

To a solution of 1-(5-bromo-1H-pyrrolo[2,3-b]pyridin-3-yl)ethanone (50 g, 0.21 mol) in tetrahydrofuran (1400 mL) was added sodium hydride (8.8 g, 0.22 mol, 60%) at 0° C. After the mixture was stirred for 1 h at 0° C. a solution of 4-methylbenzene-1-sulfonyl chloride (48.3 g, 0.25 mol) in tetrahydrofuran (300 mL) was added dropwise at 0° C. The resulting mixture was warmed up to RT and stirred overnight. The reaction mixture was poured into ice water and extracted with ethyl acetate (3×1000 mL). The combined organic layers were washed with brine, dried over sodium sulfate and concentrated to dryness in vacuo affording crude 1-(5-bromo-1-tosyl-1H-pyrrolo[2,3-b]pyridin-3-yl)ethanone as yellow solid (75 g, yield: 90%), which was used for the next step without further purification: ¹H NMR (400 MHz, DMSO-d6): δ 8.884 (s, 1H), 8.532-8.573 (m, 2H), 8.054-8.075 (d, J=12 Hz, 2H), 7.442-7.463 (d, J=8.4 Hz, 2H), 2.578 (s, 3H), 2.347 (s, 3H).

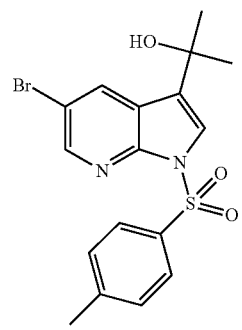 [SMILES: Cc1ccc(S(=O)(=O)n2cc(C(C)(C)O)c3cc(Br)cnc32)cc1]

Step 3: 2-(5-bromo-1-tosyl-1H-pyrrolo[2,3-b]pyridin-3-yl)propan-2-ol

To a solution of 1-(5-bromo-1-tosyl-1H-pyrrolo[2,3-b]pyridin-3-yl)ethanone (50 g, 0.13 mol) in tetrhydrofuran (1700 mL) was added dropwise methylmagnesium bromide (213 mL, 0.64 mol, 3M in ether) at 0° C. After addition the resulting mixture was stirred at 0° C. for 2 h. The mixture was poured into ice water and extracted with ethyl acetate (3×1000 mL). The combined organic layers were washed with brine, dried over sodium sulfate and concentrated to dryness in vacuo. The resulting residue was purified by column chromatography (silica gel, 100-200 mesh, 5% to 17% ethyl acetate in petroleum ether) affording 2-(5-bromo-1-tosyl-1H-pyrrolo[2,3-b]pyridin-3-yl)propan-2-ol as yellow solid (36 g, 69%). The yellow solid was used as is in the next step.

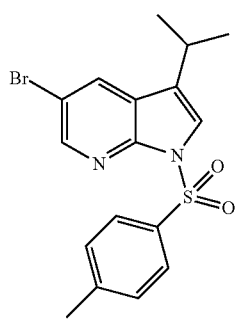 [SMILES: Cc1ccc(S(=O)(=O)n2cc(C(C)C)c3cc(Br)cnc32)cc1]

Step 4: 5-bromo-3-isopropyl-1-tosyl-1H-pyrrolo[2,3-b]pyridine

To a solution of 2-(5-bromo-1-tosyl-1H-pyrrolo[2,3-b]pyridin-3-yl)propan-2-ol (50 g, 0.122 mol) in dry dichloromethane (1000 mL) was added dropwise triethylsilane (42.6 g, 0.366 mol) and trifluoroacetic acide (71 g, 0.623 mol) at 0° C. The resulting mixture was warmed up to RT and stirred overnight. The mixture was poured into ice-water and basified with saturated sodium bicarbonate to pH 4~5 and extracted with dichloromethane (3×1000 mL). The combined organic layers were washed with brine, dried over sodium sulfate and concentrated to dryness in vacuo. The resulting residue was purified by column chromatography (silica gel, 100-200 mesh, 3% to 10% ethyl acetate in petroleum ether) affording 5-bromo-3-isopropyl-1-tosyl-1H-pyrrolo[2,3-b]pyridine (33.3 g, 69%): $^1$H NMR (400 MHz, Chloroform-d), δ 8.409-8.415 (d, J=2.4 Hz, 1H), 8.010-8.041 (m, 2H), 7.945-7.950 (d, J=2 Hz, 1H), 7.454-7.456 (d, J=0.8 Hz, 1H), 7.257-7.280 (m, 2H), 2.994-3.031 (m, 1H), 2.371 (s, 3H), 1.298-1.321 (dd, J=6.8 Hz, 6H).

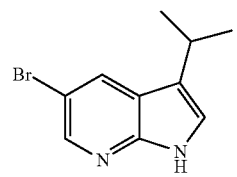

Step 5: 5-bromo-3-isopropyl-1H-pyrrolo[2,3-b]pyridine

To a solution of 5-bromo-3-isopropyl-1-tosyl-1H-pyrrolo[2,3-b]pyridine (30 g, 76.3 mmol) in methanol (1000 mL) was added a solution of 6N sodium hydroxide (600 mL) at RT. The resulting mixture was heated to reflux and stirred for 2 h. The mixture was concentrated in vacuo to remove methanol and residue was poured into ice water. The mixture was adjusted pH 5 by adding a saturated solution of critic acid and filtered. The filtered cake was dissolved in ethyl acetate, dried over sodium sulfate and concentrated to dryness in vacuo affording 5-bromo-3-isopropyl-1H-pyrrolo[2,3-b]pyridine (16.6 g, 91%), which was used for the next step without further purification.

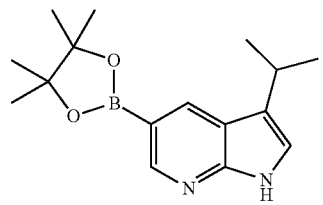 [SMILES: CC(C)c1c[nH]c2ncc(B3OC(C)(C)C(C)(C)O3)cc12]

Step 6: 3-isopropyl-5-(4,4,5,5-tetramethyl-1,3,2-dioxaborolan-2-yl)-1H-pyrrolo[2,3-b]pyridine To a solution of 5-bromo-3-isopropyl-1H-pyrrolo[2,3-b]pyridine (15 g, 62.7 mmol) in acetonitrile (350 mL) was added 4,4,4',4',5,5,5',5'-octamethyl-2,2'-bi(1,3,2-dioxaborolane) (20.6 g, 81.5 mmol), potassium acetate (30.7 g, 0.313 mol) and 1,1'-bis(diphenylphosphino)ferrocene-palladium (II)dichloride (3.75 g, 5.12 mmol) at ambient temperature under nitrogen atmosphere. The resulting mixture was heated to reflux under nitrogen atmosphere and stirred overnight. The resulting mixture was filtered and the filter cake was washed with ethyl acetate. The filtrate was concentrated to dryness in vacuo and the resulting residue was purified by column chromatography (silica gel, 100-200 mesh, 5% to 17% ethyl acetate in petroleum ether) affording 3-isopropyl-5-(4,4,5,5-tetramethyl-1,3,2-dioxaborolan-2-yl)-1H-pyrrolo[2,3-b]pyridine (12.2 g, yield: 33%, after 2 repeat batches): $^1$H NMR (400 MHz, Chloroform-d), δ: 10.500-11.100 (s, 1H), 8.702-8.709 (m, 1H), 8.401 (s, 1H), 7.097 (s, 1H), 3.211-3.212 (m, 1H), 1.359-1.391 (m, 18H).

Preparation of 5-(4,4,5,5-tetramethyl-1,3,2-dioxaborolan-2-yl)-3-(trifluoromethyl)-1H-pyrrolo[2,3-b]pyridine

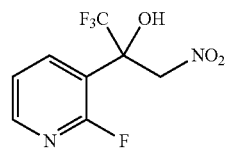 [SMILES: O=[N+]([O-])CC(O)(c1cccnc1F)C(F)(F)F]

Step 1: 1,1,1-trifluoro-2-(2-fluoropyridin-3-yl)-3-nitropropan-2-ol

To a solution of freshly prepared lithium diisopropylamide (42.5 g, 0.55 mol) in tetrahydrofuran (1200 mL) at −75 OC was added 2-fluoropyridine (45 g, 0.46 mol) and the mixture was stirred for 4 h at this temperature. To the resulting stirred suspension, ethyl trifluoroacetate (91.4 g, 0.64 mol) was added while ensuring the temperature did not rise above −45 OC. The reaction mixture was warmed to RT., nitromethane (56.1 g, 0.92 mol) was added, and the reaction was stirred overnight. The solution was poured into 2N aqueous hydrochloric acid (6 L), and the mixture was extracted with ethyl acetate (3×500 mL). The combined organic layers were washed with brine, dried over sodium sulfate and concentrated to dryness in vacuo. The resulting residue was triturated with petroleum ether, and the product was collected by suction filtration to give 1,1,1-trifluoro-2-(2-fluoropyridin-3-yl)-3-nitropropan-2-ol (100 g, 85%): $^1$H NMR (400 MHz, DMSO-d6): δ 8.22-8.35 (m, 3H), 7.47-7.51 (m, 1H), 5.65 (d, J=13.2 Hz, 1H), 5.11 (d, J=13.2 Hz, 1H).

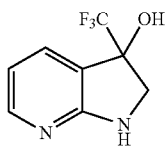

Step 2: 3-(trifluoromethyl)-2,3-dihydro-1H-pyrrolo[2,3-b]pyridin-3-ol 1,1,1-trifluoro-2-(2-fluoropyridin-3-yl)-3-nitropropan-2-ol (25 g, 98.4 mmol) was dissolved in ethanol (600 mL) and stirred under hydrogen (1 atm) with nickel catalyst (20 g). After theoretical consumption of hydrogen, the solution was filtered, the filtrate was refluxed for 48 h, triethylamine (11.5 g, 0.11 mol) was added, and reflux was continued overnight. The reaction mixture was allowed to cool and concentrated to dryness in vacuo. The resulting residue was dissolved in dichloromethane and washed with a solution of aqueous saturated sodium carbonate. The aqueous phase was extracted with dichloromethane (3×500 mL) and the combined organic layers were dried over sodium sulfate and concentrated to dryness in vacuo. The resulting residue was triturated with dichloromethane and the crystalline product was collected by suction filtration and washed with dichloromethane to give 3-(trifluoromethyl)-2,3-dihydro-1H-pyrrolo[2,3-b]pyridin-3-ol (15.4 g, 77%): $^1$H NMR (400 MHz, Chloroform-d): δ 7.98 (s, 1H), 7.62 (s, 1H), 6.65 (s, 1H), 4.74 (s, 1H), 3.91-3.95 (m, 1H), 3.65 (d, J=3.2 Hz, 1H).

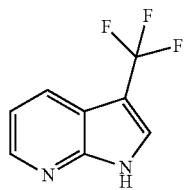 [SMILES: FC(F)(F)c1c[nH]c2ncccc12]

Step 3: 3-(trifluoromethyl)-1H-pyrrolo[2,3-b]pyridine

To a solution of 3-(trifluoromethyl)-2,3-dihydro-1H-pyrrolo[2,3-b]pyridin-3-ol (84 g, 0.411 mol) in dichloromethane (1500 mL) was added pyridine (32.4 g, 0.82 mmol), thionyl chloride (97.5 g, 0.82 mmol) and the reaction was stirred for 2 h. Ice was added and the reaction was neutralized to pH 5.7 with aqueous sodium hydroxide solution. The mixture was extracted with dichloromethane (2×500 mL), the combined organic layers were washed with water, dried over sodium sulfate and concentrated to dryness in vacuo to yield tan crystals. The crude product was triturated with petroleum ether for 15 min, and the crystals were collected by suction filtration affording 3-(trifluoromethyl)-1H-pyrrolo[2,3-b]pyridine (65 g, 80%): $^1$H NMR (400 MHz, Chloroform-d), δ12.52 (s, 1H), 8.43 (t, J=3.6 Hz, 1H), 8.12-8.14 (m, 1H), 7.77 (s, 1H), 7.24-7.27 (m, 1H).

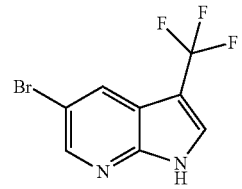 [SMILES: FC(F)(F)c1c[nH]c2ncc(Br)cc12]

Step 4: 5-bromo-3-(trifluoromethyl)-1H-pyrrolo[2,3-b]pyridine

To dry dichloromethane (200 mL) cooled to −5° C. was added dropwise bromine (36.2 g, 0.2 mol) over a period of 1 h. After a solution of 3-(trifluoromethyl)-1H-pyrrolo[2,3-b]pyridine (25 g, 0.13 mol) and pyridine (17 mL) in dichloromethne (500 mL) was added dropwise and the reaction mixture was stirred 0° C. for 45 min. The reaction mixture was poured into saturated aqueous sodium bicarbonate and sodium thiosulfate, extracted with ethyl acetate (3×1000 mL), the organic layer was washed with brine, dried over sodium sulfate, and concentrated to dryness in vacuo. The resulting residue was re-crystallized (8:1, ethyl acetate: petroleum ether) to afford 5-bromo-3-(trifluoromethyl)-1H-pyrrolo[2,3-b]pyridine (7.55 g, 21%): $^1$H NMR (400 MHz, DMSO-d6), δ12.76 (s, 1H), 8.44 (s, 1H), 8.23 (m, 2H).

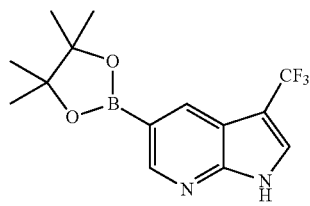 [SMILES: CC1(C)OB(c2cnc3[nH]cc(C(F)(F)F)c3c2)OC1(C)C]

Step 5: 5-(4,4,5,5-tetramethyl-1,3,2-dioxaborolan-2-yl)-3-(trifluoromethyl)-1H-pyrrolo[2,3-b]pyridine To a solution of 5-bromo-3-(trifluoromethyl)-1H-pyrrolo[2,3-b]pyridine (19 g, 72.3 mmol) in 1,4-dioxane (400 mL) was added potassium acetate (21.27 g, 220 mmol) and 4,4,4',4',5,5,5',5'-octamethyl-2,2'-bi(1,3,2-dioxaborolane) (21.9 g, 86.7 mmol). The resulting mixture was degassed with nitrogen for 5 times, 1,1'-bis(diphenylphosphino)ferrocene-palladium(II)dichloride (5.3 g, 7.23 mmol) was added and the mixture was degassed again. The reaction mixture was stirred at 80-90° C. and overnight. The reaction mixture was poured into water, extracted with ethyl acetate (3×500 mL), washed with brine, dried over sodium sulphate and concentrated to dryness in vacuo. The resulting residue was purified by column chromatography (silica gel, 100-200 mesh, 10% to 20% ethyl acetate in petroleum ether) affording 5-(4,4,5,5-tetramethyl-1,3,2-dioxaborolan-2-yl)-3-(trifluoromethyl)-1H-pyrrolo[2,3-b]pyridine (11.1 g, 49%): $^1$H NMR (400 MHz, DMSO-d6), δ 12.62 (s, 1H), 8.58 (s, 1H), 8.21 (s, 1H), 8.18 (s, 1H), 1.31 (s, 12H).

Preparation of 3-chloro-5-(4,4,5,5-tetramethyl-1,3,2-dioxaborolan-2-yl)pyridin-2-amine

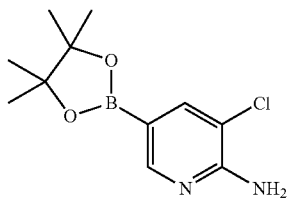 [SMILES: CC1(C)OB(c2cnc(N)c(Cl)c2)OC1(C)C]

To a solution of 5-bromo-3-chloro-pyridin-2-ylamine (2.0 g, 9.64 mmol) in 1,4-dioxane (20 mL) were added 4,4,4',4',5,5,5',5'-octamethyl-2,2'-bi(1,3,2-dioxaborolane) (2.94 g, 11.57 mmol), potassium acetate (2.84 g, 28.92 mmol) and 1,1'-bis(diphenylphosphino)ferrocene-palladium(II)dichloride (705 mg, 0.96 mmol). The reaction mixture was purged with nitrogen for 2 min and heated to 100° C. for 4 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 30% ethyl acetate in hexane) affording 3-chloro-5-(4,4,5,5-tetramethyl-1,3,2-dioxaborolan-2-yl)pyridin-2-amine (2.0 g, 84%): $^1$H NMR (400 MHz, Chloroform-d) δ 8.32 (d, J=1.6 Hz, 1H), 7.84 (d, J=1.6 Hz, 1H), 5.09 (s, 2H), 1.32 (s, 12H).

Preparation of 3-fluoro-5-(4,4,5,5-tetramethyl-1,3,2-dioxaborolan-2-yl)pyridin-2-amine

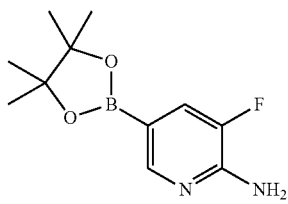 [SMILES: CC1(C)OB(c2cnc(N)c(F)c2)OC1(C)C]

To a solution of 5-bromo-3-fluoro-pyridin-2-ylamine (1.9 g, 9.95 mmol) in 1,4-dioxane (20 mL) were added 4,4,4',4',5,5,5',5'-octamethyl-2,2'-bi(1,3,2-dioxaborolane) (3.03 g, 11.94 mmol), potassium acetate (2.93 g, 29.84 mmol) and 1,1'-bis(diphenylphosphino)ferrocene-palladium(II)dichloride (728 mg, 0.99 mmol). The reaction mixture was purged with nitrogen for 2 min and heated to 100° C. for 4 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 30% ethyl acetate in hexane) affording 3-fluoro-5-(4,4,5,5-tetramethyl-1,3,2-dioxaborolan-2-yl)pyridin-2-amine (2.0 g, 84%): $^1$H NMR (400 MHz, Chloroform-d) δ 8.20 (t, J=1.2 Hz, 1H), 7.84 (dd, J=11.2 Hz 1.2 Hz, 1H), 4.89 (s, 2H), 1.32 (s, 12H).

Preparation of 3-(difluoromethoxy)-5-(4,4,5,5-tetramethyl-1,3,2-dioxaborolan-2-yl)pyridin-2-amine

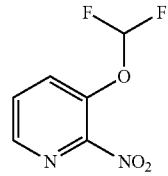 [SMILES: O=[N+]([O-])c1ncccc1OC(F)F]

Step 1: 3-(difluoromethoxy)-2-nitropyridine

To a stirred solution of 2-nitropyridin-3-ol (5 g, 35.69 mmol) and sodium 2,2-dichloro-2-fluoroacetate (8.16 g, 53.53 mmol) in N,N-dimethylmethanamide (20 mL) and water (15 mL) was added potassium carbonate (9.86 g, 71.38 mmol) slowly. The reaction mixture was heated to 105° C. for 20 h. After cooling down the reaction mixture was diluted with water (150 mL), and the mixture was extracted with ethyl acetate (3×50 mL). The combined organic layers were dried over sodium sulfate and concentrated to dryness in vacuo affording 3-(difluoromethoxy)-2-nitropyridine (5 g, 74%). The residue was used in next step directly without further purification. $^1$H NMR (400 MHz, DMSO-d6) δ 8.48 (dd, J$_1$=4.4 Hz, J$_2$=1.2 Hz, 1H), 8.18 (dd, J$_1$=4.4 Hz, J$_2$=0.8 Hz, 1H), 7.95-7.91 (m, 1H), 7.45 (t, J=72.0 Hz, 1H).

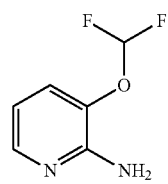

Step 2: 3-(difluoromethoxy)pyridin-2-amine

To a stirred solution of 3-(difluoromethoxy)-2-nitropyridine (5 g, 2.63 mmol) and ammonium chloride (4.22 g, 78.9 mmol) in ethanol (40 mL) and water (30 mL) was added iron powder (7.34 g, 131.51 mmol). The reaction mixture was heated to 90° C. for 1 h. After cooling down the reaction mixture was filtered and the solid was washed with ethyl acetate. The mother liquid was concentrated to dryness in vacuo. The residue was diluted with water and extracted with ethyl acetate (3×70 mL). The combined organic layers were dried over sodium sulfate and concentrated to dryness in vacuo affording 3-(difluoromethoxy)pyridin-2-amine (2.3 g, 55%). The residue was used in next step directly without further purification. $^1$H NMR (400 MHz, DMSO-d6) δ 7.90 (dd, J=4.8 Hz, J$_2$=1.6 Hz, 1H), 7.28 (dd, J=8.0 Hz, J$_2$=0.8 Hz, 1H), 7.07 (t, J=74.0 Hz, 1H), 6.53 (dd, J=8.0 Hz, J$_2$=0.8 Hz, 1H), 6.01 (s, 2H).

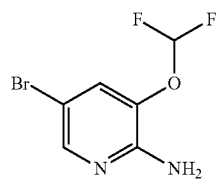

Step 3: 5-bromo-3-(difluoromethoxy)pyridin-2-amine

To a solution of 3-(difluoromethoxy)pyridin-2-amine (2.3 g, 14.36 mmol) in acetonitrile (15 mL) was added N-bromosuccinimide (2.61 g, 14.65 mmol) over 3 min at 0° C. The reaction mixture was stirred at the same temperature for another 20 min and subsequently concentrated to dryness in vacuo. The resulting viscous mass was diluted with water and extracted with ethyl acetate (3×60 mL). The combined organic layers were dried over sodium sulfate and concentrated to dryness in vacuo. The resulting residue was purified by column chromatography (silica gel, 100-200 mesh, 20% ethyl acetate in hexane) affording 5-bromo-3-(difluoromethoxy)pyridin-2-amine (3.2 g, 93%): $^1$H NMR (400 MHz, DMSO-d6) δ 7.89 (s, 1H), 7.51 (s, 1H), 7.16 (t, J=73.6 Hz, 1H), 6.34 (s, 2H).

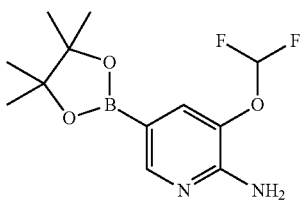 [SMILES: CC1(C)OB(c2cnc(N)c(OC(F)F)c2)OC1(C)C]

Step 4: 3-(difluoromethoxy)-5-(4,4,5,5-tetramethyl-1,3,2-dioxaborolan-2-yl)pyridin-2-amine To a solution of 5-bromo-3-(difluoromethoxy)pyridin-2-amine (3.2 g, 13.39 mmol) in 1,4-dioxane (60 mL) were added 4,4,4',4',5,5,5',5'-octamethyl-2,2'-bi(1,3,2-dioxaborolane) (3.74 g, 14.73 mmol), tricyclohexylphosphine (525 mg, 1.87 mmol), potassium acetate (3.28 g, 33.47 mmol) and tris(dibenzylideneacetone)dipalladium(0) (490 mg, 0.53 mmol). The reaction mixture was purged with nitrogen for 2 min and heated to 110° C. for 16 h and subsequently concentrated to dryness in vacuo. The resulting viscous mass was diluted with water and extracted with ethyl acetate (3×75 mL). The combined organic layers were dried over sodium sulfate and concentrated to dryness in vacuo. The resulting residue was purified by column chromatography (silica gel, 100-200 mesh, 25% ethyl acetate in hexane) affording 3-(difluoromethoxy)-5-(4,4,5,5-tetramethyl-1,3,2-dioxaborolan-2-yl)pyridin-2-amine (1.3 g, 34%): 1H NMR (400 MHz, DMSO-d6) δ 8.03 (s, 1H), 7.33 (s, 1H), 7.11 (t, J=73.6 Hz, 1H), 6.44 (s, 2H), 1.25 (s, 12H).

Preparation of 3-cyclopropyl-5-(4,4,5,5-tetramethyl-1,3,2-dioxaborolan-2-yl)pyridin-2-amine

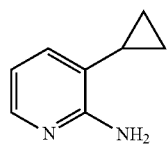

Step 1: 3-cyclopropylpyridin-2-amine

To a solution of 3-bromopyridin-2-amine (10.0 g, 58.13 mmol) in toluene (100 mL) and water (10 mL) were added cyclopropylboronic acid (6.49 g, 75.57 mmol), tricyclohexylphosphine (1.63 g, 5.81 mmol), tri-potassium phosphate trihydrate (54 g, 0.2 mol) and palladium(II) acetate (652 mg, 2.91 mmol). The reaction mixture was purged with nitrogen for 2 min and heated to 90° C. for 16 h and subsequently concentrated to dryness in vacuo. The resulting viscous mass was diluted with water and extracted with ethyl acetate (3×150 mL). The combined organic layers were dried over sodium sulfate and concentrated to dryness in vacuo. The resulting residue was purified by column chromatography (silica gel, 100-200 mesh, 10% to 30% ethyl acetate in hexane) affording 3-cyclopropylpyridin-2-amine (7.0 g, 90%): $^1$H NMR (400 MHz, Chloroform-d) δ 7.93-7.91 (m, 1H), 7.24-7.21 (m, 1H), 6.59-6.56 (m, 1H), 4.76 (s, 2H), 1.63-1.57 (m, 1H), 0.92-0.87 (m, 2H), 0.59-0.57 (m, 2H).

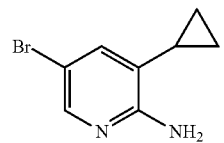

Step 2: 5-bromo-3-cyclopropylpyridin-2-amine

To a solution of 3-cyclopropylpyridin-2-amine (7.0 g, 52.17 mmol) in acetonitrile (100 mL) was added N-bromosuccinimide (9.75 g, 54.78 mmol). The reaction mixture was stirred at 25° C. for 30 min and subsequently concentrated to dryness in vacuo. The resulting viscous mass was diluted with water and extracted with ethyl acetate (3×100 mL). The combined organic layers were dried over sodium sulfate and concentrated to dryness in vacuo. The resulting residue was purified by column chromatography (silica gel, 100-200 mesh, 10% ethyl acetate in hexane) affording 5-bromo-3-cyclopropylpyridin-2-amine (9.5 g, 86%): $^1$H NMR (400 MHz, Chloroform-d) δ 7.94 (s, 1H), 7.31 (s, 1H), 4.85 (s, 2H), 1.62-1.55 (m, 1H), 0.95-0.90 (m, 2H), 0.60-0.56 (m, 2H).

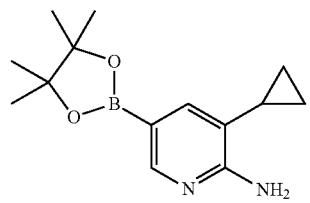 [SMILES: CC1(C)OB(c2cnc(N)c(C3CC3)c2)OC1(C)C]

Step 3: 3-cyclopropyl-5-(4,4,5,5-tetramethyl-1,3,2-dioxaborolan-2-yl)pyridin-2-amine To a solution of 5-bromo-3-cyclopropylpyridin-2-amine (2.13 g, 10 mmol) in 1,4-dioxane (60 mL) were added 4,4,4',4',5,5,5',5'-octamethyl-2,2'-bi(1,3,2-dioxaborolane) (2.8 g, 11 mmol), tricyclohexylphosphine (140 mg, 0.5 mmol), potassium acetate (1.96 g, 20 mmol) and tris(dibenzylideneacetone)dipalladium(0) (183 mg, 0.2 mmol). The reaction mixture was purged with nitrogen for 2 min and heated to 110° C. for 16 h and subsequently concentrated to dryness in vacuo. The resulting viscous mass was diluted with water and extracted with ethyl acetate (3×75 mL). The combined organic layers were dried over sodium sulfate and concentrated to dryness in vacuo. The resulting residue was purified by column chromatography (silica gel, 100-200 mesh, ethyl acetate) affording 3-cyclopropyl-5-(4,4,5,5-tetramethyl-1,3,2-dioxaborolan-2-yl)pyridin-2-amine (1.5 g, 57%): $^1$H NMR (400 MHz, Chloroform-d) δ 8.16 (s, 1H), 7.59 (s, 1H), 6.14 (s, 2H), 1.55-1.47 (m, 1H), 1.27 (s, 12H), 0.89-0.87 (m, 2H), 0.59-0.57 (m, 2H).

Preparation of 5-(4,4,5,5-tetramethyl-1,3,2-dioxaborolan-2-yl)-1H-pyrrolo[2,3-b]pyridin-2(3H)-one

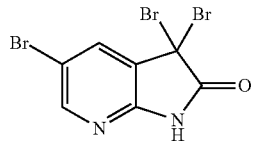

Step 1: 3,3,5-tribromo-1H-pyrrolo[2,3-b]pyridin-2(3H)-one

To a solution of 7-azaindole (20 g, 169.3 mmol) in tert-butanol (1000 mL) and water (1000 mL) was added bromine (86 mL, 1.69 mol) dropwise at 25° C. The reaction mixture was stirred at 25° C. for 16 h. The organic solvent was removed in vacuo and the aqueous suspension was treated with aqueous sodium bicarbonate to pH 8. The mixture was filtered and the filter cake was washed with water. The filter cake was dried in vacuo to afford 3,3,5-tribromo-1H-pyrrolo[2,3-b]pyridin-2(3H)-one (51 g, 81%): $^1$H NMR (400 MHz, Chloroform-d) δ 9.67 (s, 1H), 8.30 (d, J=2 Hz, 1H), 7.96 (d, J=2 Hz, 1H).

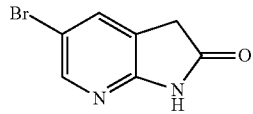

Step 2: 5-bromo-1H-pyrrolo[2,3-b]pyridin-2(3H)-one

To a solution of 3,3,5-tribromo-1H-pyrrolo[2,3-b]pyridin-2(3H)-one (20 g, 53.93 mmol) in acetic acid (150 mL) was added zinc dust (17.64 g, 269.67 mmol). The reaction mixture was stirred at RT for 5 h and subsequently concentrated to dryness in vacuo. The residue was diluted with ethyl acetate (200 mL) and washed with water. The organic layer was dried over anhydrous sodium sulfate and filtered. The filtrate was concentrated to dryness in vacuo to afford 5-bromo-1H-pyrrolo[2,3-b]pyridin-2(3H)-one (4.6 g, 40%): $^1$H NMR (400 MHz, DMSO-d6) δ 11.15 (s, 1H), 8.16 (s, 1H), 7.77 (s, 1H), 3.58 (s, 2H).

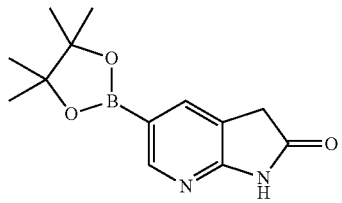 [SMILES: CC1(C)OB(c2cnc3c(c2)CC(=O)N3)OC1(C)C]

Step 3: 5-(4,4,5,5-tetramethyl-1,3,2-dioxaborolan-2-yl)-1H-pyrrolo[2,3-b]pyridin-2(3H)-one To a solution of 5-bromo-1H-pyrrolo[2,3-b]pyridin-2(3H)-one (3 g, 14.08 mmol) in 1,4-dioxane (60 mL) were added 4,4,4',4',5,5,5',5'-octamethyl-2,2'-bi(1,3,2-dioxaborolane) (4.29 g, 16.9 mmol), potassium acetate (2.07 g, 21.12 mmol) and 1,1'-bis(diphenylphosphino)ferrocene-palladium (II)dichloride (1.02 g, 1.41 mmol). The reaction mixture was purged with nitrogen for 2 min and heated to 110° C. for 1 h. After cooling down the mixture was filtered and the solid was washed with ethyl acetate. The mother liquid was diluted with methanol and the precipitate was filtered and dried in vacuo to afford 5-(4,4,5,5-tetramethyl-1,3,2-dioxaborolan-2-yl)-1H-pyrrolo[2,3-b]pyridin-2(3H)-one (1.1 g, 30%): $^1$H NMR (400 MHz, DMSO-d6) δ 11.14 (s, 1H), 8.29 (s, 1H), 7.68 (s, 1H), 3.54 (s, 2H), 1.29 (s, 12H).

Preparation of 3,3-dimethyl-5-(4,4,5,5-tetramethyl-1,3,2-dioxaborolan-2-yl)-1-((2-(trimethylsilyl)ethoxy)methyl)-1H-pyrrolo[2,3-b]pyridin-2(3H)-one

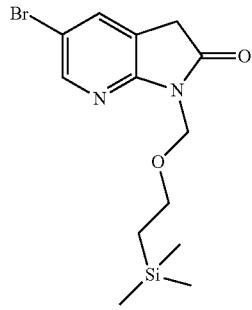

Step 1: 5-bromo-1-((2-(trimethylsilyl)ethoxy)methyl)-1H-pyrrolo[2,3-b]pyridin-2(3H)-one To a stirred solution of 5-bromo-1H-pyrrolo[2,3-b]pyridin-2(3H)-one (8.52 g, 40 mmol) in tetrahydrofuran (100 mL) and N,N-dimethylmethanamide (100 mL) was added sodium hydride (1.6 g, 40 mmol, 60% in mineral oil) under nitrogen at 0° C., and the reaction mixture was stirred at the same temperature for 30 min. (2-(chloromethoxy)ethyl)trimethylsilane (8.67 g, 52 mmol) was added dropwise into the reaction mixture. The resulting solution was stirred at RT for 24 h. The reaction mixture was poured into ice-water (1000 mL) and extracted four times with ethyl acetate. The combined organic phases were washed with saturated sodium bicarbonate, water, brine, dried over sodium sulfate and concentrated to dryness in vacuo. The resulting residue was purified by column chromatography (silica gel, 100-200 mesh, 40% ethyl acetate in hexane) affording 5-bromo-1-((2-(trimethylsilyl)ethoxy)methyl)-1H-pyrrolo[2,3-b]pyridin-2(3H)-one (6.5 g, 47%): $^1$H NMR (400 MHz, DMSO-d6) δ 8.27 (m, 1H), 7.88 (m, 1H), 5.04 (s, 2H), 3.72 (s, 2H), 3.59-3.55 (m, 2H), 0.86-0.82 (m, 2H), −0.08 (s, 9H).

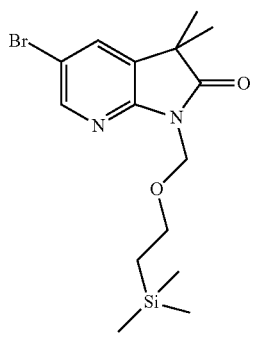 [SMILES: CC1(C)C(=O)N(COCC[Si](C)(C)C)c2ncc(Br)cc21]

Step 2: 5-bromo-3,3-dimethyl-1-((2-(trimethylsilyl)ethoxy)methyl)-1H-pyrrolo[2,3-b]pyridin-2(3H)-one To a stirred solution of 5-bromo-1-((2-(trimethylsilyl)ethoxy)methyl)-1H-pyrrolo[2,3-b]pyridin-2(3H)-one (6.4 g, 18.64 mmol) in N,N-dimethylmethanamide (50 mL), was added cesium carbonate (18.22 g, 56 mmol) and slow addition of iodomethane (2.84 mL, 56 mmol). The reaction mixture was stirred at 25° C. for 1 h and quenched with water. The mixture was extracted with ethyl acetate (3×60 mL). The combined organic layers were dried over sodium sulfate and concentrated to dryness in vacuo. The resulting residue was purified by column chromatography (silica gel, 100-200 mesh, 15% ethyl acetate in hexane) affording 5-bromo-3,3-dimethyl-1-((2-(trimethylsilyl)ethoxy)methyl)-1H-pyrrolo[2,3-b]pyridin-2(3H)-one (5.0 g, 72%): $^1$H NMR (400 MHz, DMSO-d6) δ 8.28 (s, 1H), 8.10 (s, 1H), 5.06 (s, 2H), 3.55 (t, J=8.0 Hz, 2H), 1.33 (s, 6H), 0.82 (t, J=8.0 Hz, 2H), −0.10 (s, 9H).

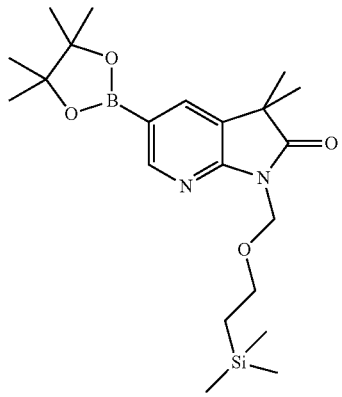 [SMILES: CC1(C)C(=O)N(COCC[Si](C)(C)C)c2ncc(B3OC(C)(C)C(C)(C)O3)cc21]

Step 3: 3,3-dimethyl-5-(4,4,5,5-tetramethyl-1,3,2-dioxaborolan-2-yl)-1-((2-(trimethylsilyl)ethoxy)methyl)-1H-pyrrolo[2,3-b]pyridin-2(3H)-one To a solution of 5-bromo-3,3-dimethyl-1-((2-(trimethylsilyl)ethoxy)methyl)-1H-pyrrolo[2,3-b]pyridin-2(3H)-one (1.4 g, 3.77 mmol) in 1,4-dioxane (20 mL) were added 4,4,4',4',5,5,5',5'-octamethyl-2,2'-bi(1,3,2-dioxaborolane) (1.05 g, 4.15 mmol), potassium acetate (1.11 g, 11.31 mmol) and 1,1'-bis(diphenylphosphino)ferrocene-palladium(II)dichloride (138 mg, 0.19 mmol). The reaction mixture was purged with nitrogen for 2 min and heated to 90° C. for 4 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 10% ethyl acetate in hexane) affording 3,3-dimethyl-5-(4,4,5,5-tetramethyl-1,3,2-dioxaborolan-2-yl)-1-((2-(trimethylsilyl)ethoxy)methyl)-1H-pyrrolo[2,3-b]pyridin-2(3H)-one (1.1 g, 70%): $^1$H NMR (400 MHz, DMSO-d6) δ 8.38 (s, 1H), 7.93 (s, 1H), 5.10 (s, 2H), 3.56 (t, J=8.0 Hz, 2H), 1.33 (s, 6H), 1.30 (s, 12H), 0.82 (t, J=8.0 Hz, 2H), −0.09 (s, 9H).

Preparation of tert-butyl 3,3-dimethyl-5-(4,4,5,5-tetramethyl-1,3,2-dioxaborolan-2-yl)-2,3-dihydro-1H-pyrrolo[2,3-b]pyridine-1-carboxylate

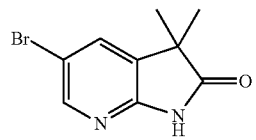

Step 1: 5-bromo-3,3-dimethyl-1H-pyrrolo[2,3-b]pyridin-2(3H)-one

To a solution of 5-bromo-3,3-dimethyl-1-((2-(trimethylsilyl) ethoxy)methyl)-1H-pyrrolo[2,3-b]pyridin-2(3H)-one (1.11 g, 3 mmol) in dichlormethane (20 mL) was added trifluoroacetic acid (5 mL). The reaction mixture was stirred at 25° C. for 2 h and subsequently concentrated to dryness in vacuo. The resulting viscous mass was diluted with methanol (10 mL) and ammonium hydroxide (10 mL). The mixture was stirred at 25° C. for 30 min and subsequently concentrated to dryness in vacuo affording crude 5-bromo-3,3-dimethyl-1H-pyrrolo[2,3-b]pyridin-2(3H)-one. The crude residue was used without further purification.

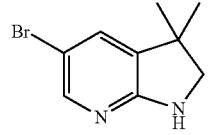

Step 2: 5-bromo-3,3-dimethyl-2,3-dihydro-1H-pyrrolo[2,3-b]pyridine

To a solution of 5-bromo-3,3-dimethyl-1H-pyrrolo[2,3-b]pyridin-2(3H)-one (2 g, 8.3 mmol) in tetrahydrofuran (5 mL) was added borane-tetrahydrofuran complex (83 mL, 83 mmol, 1 M solution). The reaction mixture was heated to 80° C. for 16 h and quenched with methanol carefully. The mixture was concentrated to dryness in vacuo. The resulting viscous mass was purified by column chromatography (silica gel, 100-200 mesh, 30% ethyl acetate in hexane) affording 5-bromo-3,3-dimethyl-2,3-dihydro-1H-pyrrolo[2, 3-b]pyridine (1.1 g, 59%): $^1$H NMR (400 MHz, Chloroform-d) δ 7.86 (s, 1H), 7.23 (s, 1H), 3.36 (s, 2H), 1.31 (s, 6H).

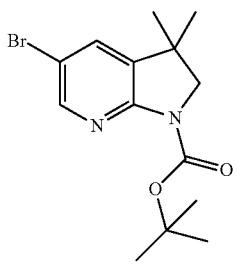 [SMILES: CC(C)(C)OC(=O)N1CC(C)(C)c2cc(Br)cnc21]

Step 3: tert-butyl-5-bromo-3,3-dimethyl-2,3-dihydro-1H-pyrrolo[2,3-b]pyridine-1-carboxylate To a solution of 5-bromo-3,3-dimethyl-2,3-dihydro-1H-pyrrolo[2,3-b]pyridine (500 mg, 2.2 mmol) in tetrahydrofuran (10 mL) was added lithium bis(trimethylsilyl)azanide (2 M, in terahydrofuran, 1.32 mL, 2.64 mmol) at −10°C. The reaction mixture was stirred at the same temperature for 30 min and di-tert-butyl-dicarbonate (576 mg, 2.64 mmol) was added dropwise. The reaction mixture was stirred at 25° C. for 1 h and quenched with aqueous ammonium chloride. The mixture was extracted with ethyl acetate (2×50 mL). The combined organic layers were dried over sodium sulfate and concentrated to dryness in vacuo. The resulting residue was purified by column chromatography (silica gel, 100-200 mesh, 10% ethyl acetate in hexane) affording tert-butyl 5-bromo-3,3-dimethyl-2,3-dihydro-1H-pyrrolo[2,3-b]pyridine-1-carboxylate (400 mg, 56%): $^1$H NMR (400 MHz, Chloroform-d) δ 8.26 (s, 1H), 7.43 (s, 1H), 3.72 (s, 2H), 1.55 (s, 3H), 1.31 (s, 6H).

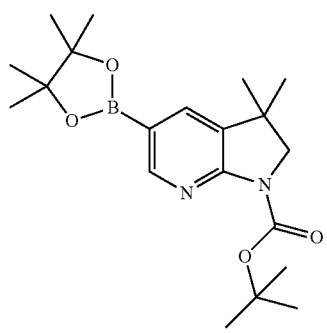 [SMILES: CC(C)(C)OC(=O)N1CC(C)(C)c2cc(B3OC(C)(C)C(C)(C)O3)cnc21]

Step 4: tert-butyl 3,3-dimethyl-5-(4,4,5,5-tetramethyl-1,3,2-dioxaborolan-2-yl)-2,3-dihydro-1H-pyrrolo[2,3-b]pyridine-1-carboxylate To a solution of tert-butyl 5-bromo-3,3-dimethyl-2,3-dihydro-1H-pyrrolo[2,3-b]pyridine-1-carboxylate (400 mg, 1.22 mmol) in 1,4-dioxane (10 mL) were added 4,4,4',4',5,5,5',5'-octamethyl-2,2'-bi(1,3,2-dioxaborolane) (403 mg, 1.59 mmol), potassium acetate (359 mg, 3.66 mmol) and 1,1'-bis(diphenylphosphino)ferrocene-palladium(II)dichloride (88 mg, 0.12 mmol). The reaction mixture was purged with nitrogen for 2 min and heated to 100° C. for 10 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 10% ethyl acetate in hexane) affording: tert-butyl 3,3-dimethyl-5-(4,4,5,5-tetramethyl-1,3,2-dioxaborolan-2-yl)-2,3-dihydro-1H-pyrrolo[2,3-b]pyridine-1-carboxylate (200 mg, 44%): $^1$H NMR (400 MHz, DMSO-d6) δ 8.32 (s, 1H), 7.71 (s, 1H), 3.65 (s, 2H), 1.49 (s, 9H), 1.29 (s, 12H), 1.16 (s, 6H).

Preparation of 3-chloro-5-(4,4,5,5-tetramethyl-1,3,2-dioxaborolan-2-yl)-1H-pyrrolo[2,3-b]pyridine

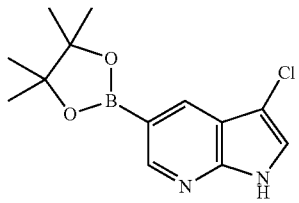 [SMILES: CC1(C)OB(c2cnc3[nH]cc(Cl)c3c2)OC1(C)C]

To a solution of 5-bromo-3-chloro-1H-pyrrolo[2,3-b]pyridine (1.0 g, 4.32 mmol) in 1,4-dioxane (20 mL) was added 4,4,4',4',5,5,5',5'-octamethyl-2,2'-bi(1,3,2-dioxaborolane) (1.32 g, 5.18 mmol), potassium acetate (1.27 g, 12.96 mmol) and 1,1'-bis(diphenylphosphino)ferrocene-palladium(II)dichloride (315 mg, 0.43 mmol). The reaction mixture was purged with nitrogen for 2 min and heated to 100° C. for 2 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 30% ethyl acetate in petroleum ether) affording 3-chloro-5-(4,4,5,5-tetramethyl-1,3,2-dioxaborolan-2-yl)-1H-pyrrolo[2,3-b]pyridine (770 mg, 64%): $^1$H NMR (400 MHz, Chloroform-d) δ 11.61 (s, 1H), 8.76 (s, 1H), 8.45 (s, 1H), 7.33 (s, 1H), 1.40 (s, 12H).

Preparation of 3-fluoro-5-(4,4,5,5-tetramethyl-1,3,2-dioxaborolan-2-yl)-1H-pyrrolo[2,3-b]pyridine

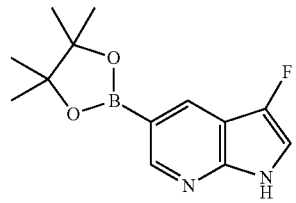 [SMILES: CC1(C)OB(c2cnc3[nH]cc(F)c3c2)OC1(C)C]

To a solution of 5-bromo-3-fluoro-1H-pyrrolo[2,3-b]pyridine (1.0 g, 4.65 mmol) in 1,4-dioxane (20 mL) was added 4,4,4',4',5,5,5',5'-octamethyl-2,2'-bi(1,3,2-dioxaborolane) (1.77 g, 6.98 mmol), potassium acetate (1.37 g, 13.95 mmol) and 1,1'-bis(diphenylphosphino)ferrocene-palladium(II)dichloride (340 mg, 0.46 mmol). The reaction mixture was purged with nitrogen for 2 min and heated to 100° C. for 2 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 30% ethyl acetate in petroleum ether) affording 3-fluoro-5-(4,4,5,5-tetramethyl-1,3,2-dioxaborolan-2-yl)-1H-pyrrolo[2,3-b]pyridine (240 mg, 20%): ¹H NMR (400 MHz, Chloroform-d) δ 11.44 (m, 1H), 8.73 (d, J=1.6 Hz, 1H), 8.46 (d, J=1.2 Hz, 1H), 7.10 (m, 1H), 1.39 (s, 12H).

Preparation of 5-(4,4,5,5-tetramethyl-1,3,2-dioxaborolan-2-yl)-1H-pyrrolo[2,3-b]pyridine-3-carbonitrile

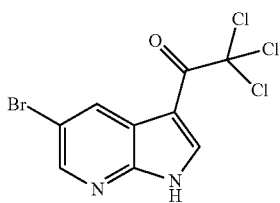 [SMILES: O=C(c1c[nH]c2ncc(Br)cc12)C(Cl)(Cl)Cl]

Step 1: 1-(5-bromo-1H-pyrrolo[2,3-b]pyridin-3-yl)-2,2,2-trichloroethanone

To a suspension of aluminum trichloride (4.06 g, 30.45 mmol) in dichloromethane (200 mL) was added 5-bromo-1H-pyrrolo[2,3-b]pyridine (2 g, 10.15 mmol) at 0° C. The resulting mixture was stirred for 3 h at the same temperature. After this period 2,2,2-trichloroacetyl chloride (1.13 mL, 10.15 mmol) was added dropwise. After addition, the mixture was stirred at 25° C. for 16 h. The reaction mixture was poured onto ice, the resulting solid was collected by filtration and dried in vacuo to give 1-(5-bromo-1H-pyrrolo[2,3-b]pyridin-3-yl)-2,2,2-trichloroethanone (2.5 g, 72%). The solid was used without further purification: MS (ESI+) m/z: 343 [M+3]⁺.

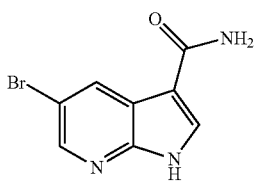 [SMILES: NC(=O)c1c[nH]c2ncc(Br)cc12]

Step 2: 5-bromo-1H-pyrrolo[2,3-b]pyridine-3-carboxamide

A mixture of 1-(5-bromo-1H-pyrrolo[2,3-b]pyridin-3-yl)-2,2,2-trichloroethanone (2.5 g, 7.3 mmol) in a 4M solution of ammonia in tetrahydrofuran (80 mL) was stirred at 100° C. for 16 h in a sealed vessel. After cooling down, the mixture filtered and the solid was dried to give 5-bromo-1H-pyrrolo[2,3-b]pyridine-3-carboxamide (1.6 g, 91%). The solid was used without further purification.

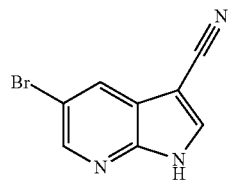 [SMILES: N#Cc1c[nH]c2ncc(Br)cc12]

Step 3: 5-bromo-1H-pyrrolo[2,3-b]pyridine-3-carbonitrile

To the suspension of 5-bromo-1H-pyrrolo[2,3-b]pyridine-3-carboxamide (1.5 g, 6.3 mmol) and triethylamine (8.7 mL, 63 mmol) in acetonitrile (60 mL) was added trifluoroacetic anhydride (2.6 mL, 19 mmol) dropwise at 0° C. After addition, the mixture was stirred for another 20 min and subsequently concentrated to dryness in vacuo. The resulting residue was purified by flash column chromatography (silica gel, 100-200 mesh, 10% ethyl acetate in hexane) to give 5-bromo-1H-pyrrolo[2,3-b]pyridine-3-carbonitrile (1 g, 72%). The residue was used as is in the next step.

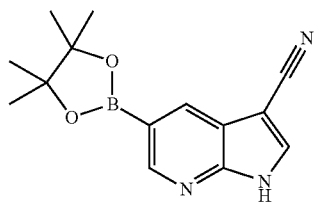 [SMILES: CC1(C)OB(c2cnc3[nH]cc(C#N)c3c2)OC1(C)C]

Step 4: 5-(4,4,5,5-tetramethyl-1,3,2-dioxaborolan-2-yl)-1H-pyrrolo[2,3-b]pyridine-3-carbonitrile To a solution of 5-bromo-1H-pyrrolo[2,3-b]pyridine-3-carbonitrile (700 mg, 3.15 mmol) in 1,4-dioxane (40 mL) were added 4,4,4',4',5,5,5',5'-octamethyl-2,2'-bi(1,3,2-dioxaborolane) (1.2 g, 4.73 mmol), potassium acetate (930 mg, 9.46 mmol) and 1,1'-bis(diphenylphosphino)ferrocene-palladium(II)dichloride (100 mg, 0.14 mmol). The reaction mixture was purged with nitrogen for 2 min and heated to 80° C. for 10 h and subsequently concentrated to dryness in vacuo. The residue was diluted with ethyl acetate (60 mL), filtered and the filtrate was washed with brine (60 mL). The organic layer was dried over sodium sulfate, filtered and concentrated to dryness in vacuo. The residue was purified by flash column chromatography (silica gel, 100-200 mesh, ethyl acetate) to afford 5-(4,4,5,5-tetramethyl-1,3,2-dioxaborolan-2-yl)-1H-pyrrolo[2,3-b]pyridine-3-carbonitrile (400 mg, 47%): ¹H NMR (400 MHz, DMSO-d6) δ 12.93 (s, 1H), 8.58 (s, 1H), 8.46 (s, 1H), 8.24 (s, 1H), 1.30 (s, 12H).

Preparation of 5-(4,4,5,5-tetramethyl-1,3,2-dioxaborolan-2-yl)-3-(trifluoromethoxy)pyridin-2-amine

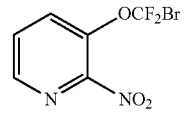

Step 1: 3-(bromodifluoromethoxy)-2-nitropyridine

To a stirred solution of sodium hydride (856 mg, 21.41 mmol) in N-methylpyrrolidinone (20 mL) was added a solution of 2-nitropyridin-3-ol (2 g, 14.28 mmol) in N-methylpyrrolidinone (10 mL). The reaction mixture was stirred at 20° C. for 30 min followed by heating at 50° C. for another 30 min before cooling to 20° C. CF₂Br₂ (4.49 g, 21.41 mmol) was added dropwise and the resulting mixture was stirred at 20° C. for 18 h. Then CF$_2$Br$_2$ (8.99 g, 42.83 mmol) was added dropwise and the mixture was stirred at 20° C. for another 18 h. The reaction mixture was slowly quenched into saturated aqueous ammonium chloride solution (30 mL) and extracted with ethyl acetate (2×50 mL). The combined organic layers were washed with water (2×50 mL), brine (2×50 mL), dried over anhydrous sodium sulfate and concentrated in vacuo. The resulting residue was purified by column chromatography (silica gel, 100-200 mesh, 15% ethyl acetate in petroleum ether) affording product (890 mg, 23%): $^1$H NMR (400 MHz, chloroform-d) δ 8.53-8.51 (m, 1H), 7.99-7.97 (m, 1H), 7.72-7.69 (m, 1H).

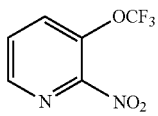 [SMILES: O=[N+]([O-])c1ncccc1OC(F)(F)F]

Step 2: 2-nitro-3-(trifluoromethoxy)pyridine

A solution of 3-(bromodifluoromethoxy)-2-nitropyridine (500 mg, 1.86 mmol) in dichloromethane (10 mL) was cooled to −78° C., then silver tetrafluoroborate (796 mg, 4.09 mmol) was added. The resulting mixture was slowly warmed to 20° C. and allowed to stir for 18 h. Saturated sodium bicarbonate solution (10 mL) was added, and the mixture was filtered. The filtrate was extracted with dichloromethane (3×10 mL). The combined organic layers were dried over anhydrous sodium sulfate and concentrated to dryness in vacuo. The residue was used in the next step directly without further purification (300 mg, 78%): LCMS (ESI) m/z 209.0 [M+H]$^+$.

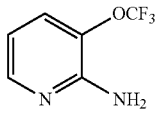

Step 3: 3-(trifluoromethoxy)pyridin-2-amine

To a stirred solution of 2-nitro-3-(trifluoromethoxy)pyridine (370 mg, 1.78 mmol) in ethanol (5 mL) were added aqueous ammonium chloride (951 mg, 17.78 mmol, in 10 mL of water) and iron powder (993 mg, 17.78 mmol). The reaction mixture was heated to 70° C. for 2 h. After cooling down the reaction mixture was filtered and the solid was washed with ethyl acetate. The mother liquid was concentrated to dryness in vacuo. The residue was diluted with water and extracted with ethyl acetate (3×15 mL). The combined organic layers were dried over anhydrous sodium sulfate and concentrated to dryness in vacuo. The residue was used in next step directly without further purification (250 mg, 79%): $^1$H NMR (400 MHz, DMSO-d$_6$) δ 7.93-7.91 (m, 1H), 7.48-7.46 (m, 1H), 6.59-6.56 (m, 1H), 6.35 (brs, 2H).

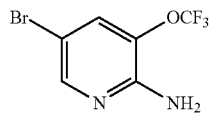

Step 4:
5-bromo-3-(trifluoromethoxy)pyridin-2-amine

To a solution of 3-(trifluoromethoxy)pyridin-2-amine (300 mg, 1.68 mmol) in dichloromethane (8 mL) was added N-bromosuccinimide (450 mg, 2.53 mmol) at 20° C. The reaction mixture was stirred at the same temperature for another 5 min and subsequently concentrated to dryness in vacuo. The resulting residue was purified by column chromatography (silica gel, 100-200 mesh, 15% ethyl acetate in petroleum ether) affording product (220 mg, 51%): $^1$H NMR (400 MHz, DMSO-d$_6$) δ 8.03 (d, J=2.0 Hz, 1H), 7.75-7.74 (m, 1H), 6.68 (brs, 2H).

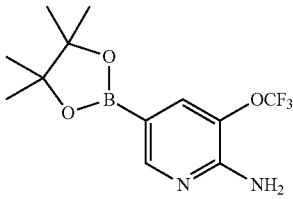 [SMILES: CC1(C)OB(c2cnc(N)c(OC(F)(F)F)c2)OC1(C)C]

Step 5: 5-(4,4,5,5-tetramethyl-1,3,2-dioxaborolan-2-yl)-3-(trifluoromethoxy)pyridin-2-amine To a solution of 5-bromo-3-(trifluoromethoxy)pyridin-2-amine (220 mg, 0.856 mmol) in dioxane (5 mL) were added 4,4,4',4',5,5,5',5'-octamethyl-2,2'-bi(1,3,2-dioxaborolane) (261 mg, 1.03 mmol), 1,1'-bis(diphenylphosphino)ferrocene-palladium(II)dichloride (63 mg, 0.0856 mmol) and potassium acetate (252 mg, 2.57 mmol). The reaction mixture was purged with nitrogen for 2 min and heated to 80° C. for 2 h and subsequently concentrated to dryness in vacuo. The resulting residue was purified by column chromatography (silica gel, 100-200 mesh, 15% ethyl acetate in petroleum ether) affording product (220 mg, 84%): $^1$H NMR (400 MHz, DMSO-d$_6$) δ 8.14 (d, J=2.0 Hz, 1H), 7.46-7.45 (m, 1H), 6.86 (brs, 2H), 1.27 (s, 12H).

Preparation of 3-(difluoromethyl)-5-(4,4,5,5-tetramethyl-1,3,2-dioxaborolan-2-yl)pyridin-2-amine

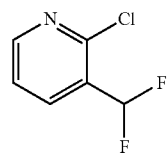

Step 1: 2-chloro-3-(difluoromethyl)pyridine

To a solution of 2-chloronicotinaldehyde (5 g, 35 mmol) in dichloromethane (30 mL) was added DAST (13 mL, 100 mmol) and stirred for 4 h at 25° C. When the starting material was consumed, the reaction was quenched with aqueous sodium bicarbonate (20 mL) at 0° C. The mixture was extracted with dichloromethane (2×20 mL) and the organic layer was washed with brine (2×20 mL). The organic layer was dried over anhydrous sodium sulfate, filtered and evaporated in vacuo. The resulting residue was purified by column chromatography (silica gel, 100-200 mesh, 5% ethyl acetate in hexane) affording product (3.12 g, 55%): $^1$H NMR (400 MHz, chloroform-d) δ 8.50-8.48 (m, 1H), 8.01-7.97 (m, 1H), 7.39-7.35 (m, 1H), 7.04-6.76 (t, J=54.8 Hz, 1H).

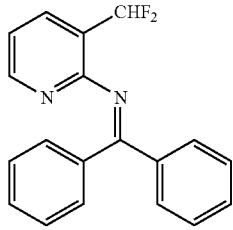 [SMILES: FC(F)c1cccnc1N=C(c1ccccc1)c1ccccc1]

Step 2: 3-(difluoromethyl)-N-(diphenylmethylene) pyridin-2-amine

To a solution of 2-chloro-3-(difluoromethyl)pyridine (2.36 g, 14.4 mmol) in toluene (30 mL) were added benzophenone imine (3.4 g, 18.7 mmol), potassium tert-butoxide (3.2 g, 28.8 mmol), tris(dibenzylideneacetone)dipalladium (0) (650 mg, 1.44 mmol) 4,5-bis(diphenylphosphino)-9,9-dimethylxanthene (833 mg, 0.72 mmol) and purged with nitrogen for 2 min. Then the mixture was stirred at 90° C. for 3 h. When the starting material was consumed, the mixture was concentrated in vacuo and the resulting residue was purified by column chromatography (silica gel, 100-200 mesh, 10% ethyl acetate in hexane) affording product (3.7 g, 84%), which was used in the next step without further purification.

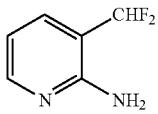

Step 3: 3-(difluoromethyl)pyridin-2-amine

A solution of 3-(difluoromethyl)-N-(diphenylmethylene) pyridin-2-amine (3.7 g, 12.7 mmol) in tetrahydrofuran (20 mL) was added hydrochloride (1 M, 50 mL) and then the mixture was stirred at 20° C. for 16 h. Tetrahydrofuran was removed in vacuo, and the residue was basified by aqueous sodium bicarbonate, and then the resulting mixture was extracted with ethyl acetate (2×20 mL). The organic layer was washed with brine (2×20 mL), dried over anhydrous sodium sulfate and evaporated. The resulting residue was purified by column chromatography (silica gel, 100-200 mesh, 20%-50% ethyl acetate in hexane) affording product (1.3 g, 72%): $^1$H NMR (400 MHz, DMSO-d$_6$) δ 8.08-8.06 (m, 1H), 7.62-7.60 (m, 1H), 7.14-6.86 (t, J=54.8 Hz, 1H), 6.64-6.60 (m, 1H), 6.19 (s, 2H).

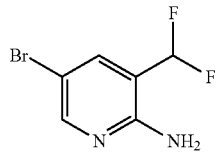

Step 4: 5-bromo-3-(difluoromethyl)pyridin-2-amine

To a solution of 3-(difluoromethyl)pyridin-2-amine (1.3 g, 9 mmol) in acetonitrile (15 mL) was added N-bromosuccinimide (2.0 g, 11.2 mmol) over 3 min at 0° C. The reaction mixture was stirred at the same temperature for another 20 min and subsequently concentrated to dryness in vacuo. The residue was diluted with water and extracted with ethyl acetate (3×20 mL). The combined organic layers were dried over anhydrous sodium sulfate and concentrated to dryness in vacuo. The resulting residue was purified by column chromatography (silica gel, 100-200 mesh, 20% ethyl acetate in hexane) affording product (1.29 g, 64%): $^1$H NMR (400 MHz, DMSO-d$_6$) δ 8.16-8.15 (m, 1H), 7.75-7.74 (m, 1H), 7.11-6.83 (t, J=54.4 Hz, 1H), 6.49 (s, 2H).

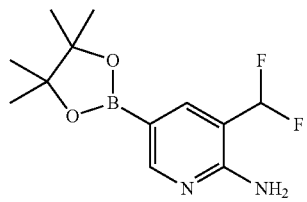

Step 5: 3-(difluoromethyl)-5-(4,4,5,5-tetramethyl-1, 3,2-dioxaborolan-2-yl)pyridin-2-amine To a solution of 5-bromo-3-(difluoromethyl)pyridin-2-amine (1.0 g, 4.5 mmol) in dioxane (15 mL) were added 4,4,4',4',5,5,5',5'-octamethyl-2,2'-bi(1,3,2-dioxaborolane) (1.48 g, 5.8 mmol), potassium acetate (882 mg, 9 mmol) and 1,1'-bis(diphenylphosphino)ferrocene-palladium(II)dichloride (330 mg, 0.45 mmol). The reaction mixture was purged with nitrogen for 2 min and heated to 80° C. for 5 h and subsequently concentrated to dryness in vacuo. The resulting viscous mass was diluted with water and extracted with ethyl acetate (3×30 mL). The combined organic layers were dried over anhydrous sodium sulfate and concentrated to dryness in vacuo. The resulting residue was purified by column chromatography (silica gel, 100-200 mesh, 30% ethyl acetate in hexane) affording product (814 mg, 67%): $^1$H NMR (400 MHz, chloroform-d) δ 8.44 (s, 1H), 7.86-7.85 (m, 1H), 6.68-6.39 (t, J=54.8 Hz, 1H), 5.63 (s, 2H), 1.31 (s, 12H).

Preparation of 3-(methylsulfonyl)-5-(4,4,5,5-tetramethyl-1,3,2-dioxaborolan-2-yl)pyridin-2-amine

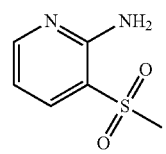

Step 1: 3-(methylsulfonyl)pyridin-2-amine

To a solution of 3-bromopyridin-2-amine (1.0 g, 5.78 mmol) in dimethylsulfoxide (10 mL) were added sodium methanesulfinate (766 mg, 7.52 mmol), L-proline (132 mg, 1.12 mmol), copper (I) iodide (110 mg, 0.58 mmol) and sodium hydroxide (44 mg, 1.12 mmol). The reaction mixture was purged with nitrogen for 2 min and irradiated in microwave at 160° C. for 40 min, and subsequently quenched with water. The resulting mixture was extracted with ethyl acetate (3×25 mL). The combined organic layers were dried over sodium sulfate and concentrated to dryness in vacuo. The resulting residue was purified by column chromatography (silica gel, 100-200 mesh, 10% to 25% ethyl acetate in hexane) affording product (1 g, 50%): ¹H NMR (400 MHz, DMSO-$d_6$) δ 8.26-8.24 (m, 1H), 7.89-7.87 (m, 1H), 6.77-6.74 (m, 1H), 6.69 (s, 2H), 3.16 (s, 3H).

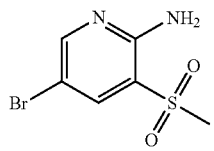

Step 2: 5-bromo-3-(methylsulfonyl)pyridin-2-amine

To a solution of 3-(methylsulfonyl)pyridin-2-amine (1.0 g, 5.81 mmol) in acetonitrile (15 mL) was added N-bromosuccinimide (1.09 g, 6.1 mmol) at 25° C. The reaction mixture was stirred at 25° C. for 30 min and subsequently concentrated to dryness in vacuo. The resulting viscous mass was diluted with water and extracted with ethyl acetate (3×100 mL). The combined organic layers were dried over anhydrous sodium sulfate and concentrated to dryness in vacuo. The resulting residue was purified by column chromatography (silica gel, 100-200 mesh, 10% ethyl acetate in hexane) affording product (750 mg, 51%): ¹H NMR (400 MHz, DMSO-$d_6$) δ 8.35 (d, J=2.4 Hz, 1H), 7.95 (d, J=2.4 Hz, 1H), 6.93 (s, 2H), 3.23 (s, 3H).

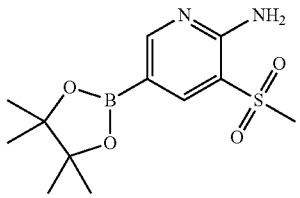

Step 3: 3-(methylsulfonyl)-5-(4,4,5,5-tetramethyl-1,3,2-dioxaborolan-2-yl)pyridin-2-amine To a solution of 5-bromo-3-(methylsulfonyl)pyridin-2-amine (600 mg, 2.39 mmol) in dioxane (10 mL) were added 4,4,4',4',5,5,5',5'-octamethyl-2,2'-bi(1,3,2-dioxaborolane) (668 mg, 2.63 mmol), 1,1'-bis(diphenylphosphino)ferrocene-palladium(II)dichloride (175 mg, 0.24 mmol) and potassium acetate (468 mg, 4.78 mmol). The reaction mixture was purged with nitrogen for 2 min and heated to 90° C. for 16 h and subsequently concentrated to dryness in vacuo. The resulting viscous mass was diluted with water and extracted with ethyl acetate (3×25 mL). The combined organic layers were dried over sodium sulfate and concentrated to dryness in vacuo. The resulting residue was purified by column chromatography (silica gel, 100-200 mesh, 10% to 25% ethyl acetate in hexane) affording product (350 mg, 49%): ¹H NMR (400 MHz, DMSO-$d_6$) δ 8.42 (d, J=2.0 Hz, 1H), 8.06 (d, J=2.0 Hz, 1H), 7.12 (s, 2H), 3.19 (s, 3H), 1.29 (s, 12H).

EXAMPLE 2

General Methods A-AH

Method A

Preparation of 5-(1-isopropyl-5-((1R,5 S,6r)-3-(oxetan-3-yl)-3-azabicyclo[3.1.0]hexan-6-yl)-1H-pyrazol-3-yl)-3-(trifluoromethyl)pyridin-2-amine (134)

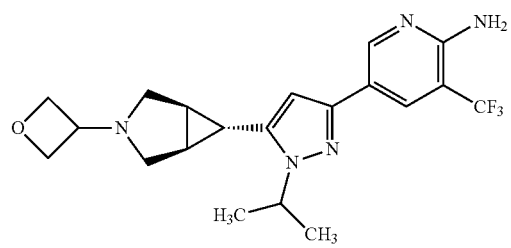

Step 1—Synthesis of (1R,5S,6r)-3-tert-butyl 6-ethyl 3-azabicyclo[3.1.0]hexane-3,6-dicarboxylate

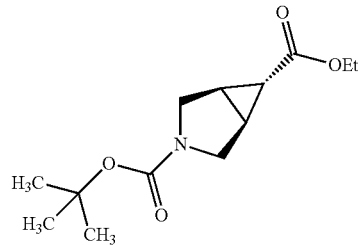 [SMILES: CCOC(=O)[C@H]1[C@@H]2CN(C(=O)OC(C)(C)C)C[C@@H]21]

To a solution of tert-butyl 2,5-dihydro-1H-pyrrole-1-carboxylate (0.100 kg, 0.592 mol) and rhodium(II) acetate dimer (3 g, 0.007 mol) in anhydrous dichloromethane (1.5 L) was added a solution of ethyl diazoacetate (101 g, 0.888 mol) in dichloromethane (500 mL) over 10 h. The reaction was filtered through Celite®, and the filtrate was concentrated in vacuo. Purification of the resulting residue by flash column chromatography (solvent gradient: petroleum ether→50% ethyl acetate in petroleum ether) afforded (1R, 5S,6r)-3-tert-butyl 6-ethyl 3-azabicyclo[3.1.0]hexane-3,6-dicarboxylate (71 g, 47% yield) as a clear yellow oil.

¹H NMR (400 MHz, CDCl₃): δ 4.12 (q, J=7.2 Hz, 2 H), 3.58-3.69 (m, 2 H), 3.40 (m, 2 H), 2.05 (m, 2 H), 1.46 (t, J=3.2 Hz, 1 H), 1.42 (s, 9 H), 1.25 (t, J=7.2 Hz, 3 H).

Step 2—Synthesis of (1R,5S,6r)-tert-butyl 6-(2-cyanoacetyl)-3-azabicyclo[3.1.0]hexane-3-carboxylate

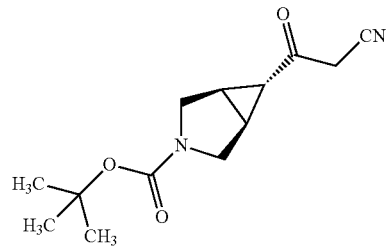 [SMILES: CC(C)(C)OC(=O)N1C[C@@H]2[C@H](C1)[C@H]2C(=O)CC#N]

To an ice-cooled solution of (1R,5S,6r)-3-tert-butyl 6-ethyl 3-azabicyclo[3.1.0]hexane-3,6-dicarboxylate (27.0 g, 0.106 mol) and acetonitrile (21.7 g, 0.529 mol) in tetrahydrofuran (500 mL) was added potassium tert-butoxide (21.1 g, 0.188 mmol) portionwise. The resulting mixture was warmed to room temperature. After 1 h, the reaction mixture was poured into aqueous hydrochloric acid (0.5 M, 200 mL), and the resulting solution was extracted with ethyl acetate (3×400 mL). The combined organic was washed with saturated aqueous sodium chloride solution (150 mL), dried over anhydrous sodium sulfate, and concentrated in vacuo (25 g, crude).

Step 3—Synthesis of (1R,5S,6r)-tert-butyl 6-(3-amino-1H-pyrazol-5-yl)-3-azabicyclo[3.1.0]hexane-3-carboxylate

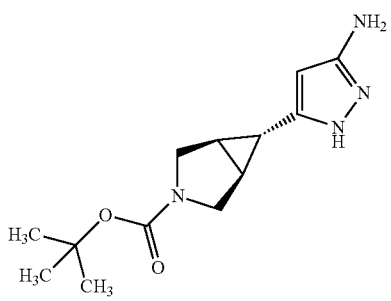 [SMILES: CC(C)(C)OC(=O)N1C[C@@H]2[C@H](C1)[C@H]2c1cc(N)n[nH]1]

To a solution of (1R,5S,6r)-tert-butyl 6-(2-cyanoacetyl)-3-azabicyclo[3.1.0]hexane-3-carboxylate (25 g, crude) in 2-propanol (500 mL) was added hydrazine monohydrate (20 mL). The mixture was heated to 80° C. After 16 h, the reaction mixture was concentrated in vacuo. The resulting residue was dissolved in dichloromethane (300 mL), and the organic solution was washed sequentially with water (300 mL) and saturated aqueous sodium chloride solution (300 mL). The organic layer was dried over anhydrous sodium sulfate, filtered, and concentrated. Purification by flash column chromatography (solvent gradient: 1→3% methanol in ethyl acetate) provided (1R,5S,6r)-tert-butyl 6-(3-amino-1H-pyrazol-5-yl)-3-azabicyclo[3.1.0]hexane-3-carboxylate (21 g, 75% yield over 2-steps). LRMS (ESI): [MH]⁺=265.1; ¹H NMR (400 MHz, DMSO-d₆): δ 5.03 (s, 1 H), 4.50 (br s, 2 H), 3.47-3.50 (m, 2 H), 3.27-3.33 (m, 2 H), 1.71 (m, 1 H), 1.42 (m, 1 H), 1.41 (s, 9 H).

Step 4—Synthesis of (1R,5S,6r)-tert-butyl 6-(3-iodo-1H-pyrazol-5-yl)-3-azabicyclo[3.1.0]hexane-3-carboxylate

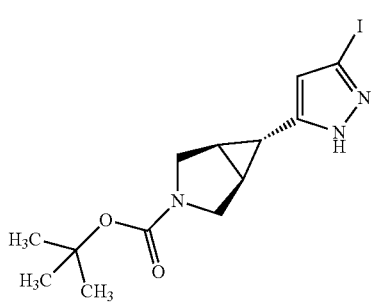 [SMILES: CC(C)(C)OC(=O)N1C[C@@H]2[C@H](C1)[C@H]2c1cc(I)n[nH]1]

To an ice-cooled solution of (1R,5S,6r)-tert-butyl 6-(3-amino-1H-pyrazol-5-yl)-3-azabicyclo[3.1.0]hexane-3-carboxylate (10.5 g, 39.77 mmol) in acetonitrile/water (5:1, 120 mL) was added p-toluenesulfonic acid (20.3 g, 119.4 mmol) and sodium nitrite (8.2 g, 119.4 mmol). After 30 min, sodium iodide (17.9 g, 119.4 mmol) was added, and the reaction mixture was warmed to room temperature. After 1 h, the reaction mixture was poured into water (50 mL), and the resulting solution was extracted with ethyl acetate (3×30 mL). The combined organic layer was washed with saturated aqueous sodium chloride solution (30 mL), dried over anhydrous sodium sulfate, filtered, and concentrated. Purification by flash column chromatography yielded a yellow solid (3.8 g, 26% yield). ¹H NMR (400 MHz, CDCl₃): δ 6.05 (s, 1 H), 3.80-3.66 (m, 2 H), 3.49-3.41 (m, 2 H), 1.96-1.94 (m, 1 H), 1.82-1.80 (m, 1 H), 1.78-1.70 (m, 1 H), 1.46-1.44 (m, 9 H).

Step 5—Synthesis of (1R,5S,6r)-tert-butyl 6-(3-iodo-1-isopropyl-1H-pyrazol-5-yl)-3-azabicyclo[3.1.0]hexane-3-carboxylate

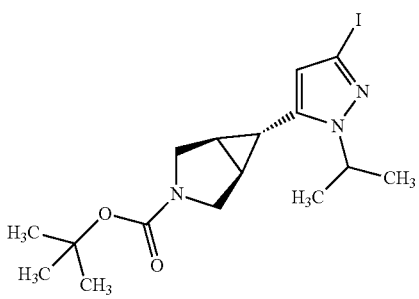 [SMILES: CC(C)n1nc(I)cc1[C@H]1[C@@H]2CN(C(=O)OC(C)(C)C)C[C@@H]21]

To a solution of (1R,5S,6r)-tert-butyl 6-(3-iodo-1H-pyrazol-5-yl)-3-azabicyclo[3.1.0]hexane-3-carboxylate (7 g, 18.7 mmol) in N,N-dimethylformamide (80 mL) was added 2-bromopropane (4.6 g, 37.3 mmol) and cesium carbonate (12.2 g, 37.3 mmol). The mixture was stirred at room temperature for 10 h. Ethyl acetate (60 mL) was added to the reaction mixture, and the resulting suspension was filtered. The filtrate was concentrated in vacuo. Purification by flash column chromatography afforded (1R,5S,6r)-tert-butyl 6-(3-iodo-1-isopropyl-1H-pyrazol-5-yl)-3-azabicyclo[3.1.0]hexane-3-carboxylate (1.8 g, 23% yield, R_f=0.4 in 5:1 petroleum ether/ethyl acetate)¹H NMR (400 MHz, CDCl₃): δ 5.95 (s, 1 H), 4.60-4.53 (m, 1 H), 3.77-3.74 (m, 1 H), 3.67-3.64 (m, 1 H), 3.47-3.44 (m, 2 H), 1.80-1.75 (m, 1 H), 1.59-1.55 (m, 1 H), 1.48-1.46 (m, 15 H) and the regioisomer (1R,5S,6r)-tert-butyl 6-(5-iodo-1-isopropyl-1H-pyrazol-3-yl)-3-azabicyclo[3.1.0]hexane-3-carboxylate (2.8 g, R_f=0.6 in 5:1 petroleum ether/ethyl acetate).

Step 6—Synthesis of (1R,5S,6r)-6-(3-iodo-1-isopropyl-1H-pyrazol-5-yl)-3-azabicyclo[3.1.0]hexane

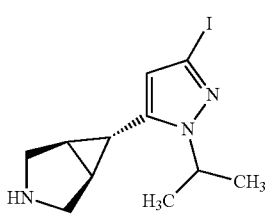

To an ice-cooled solution of (1R,5S,6r)-tert-butyl 6-(3-iodo-1H-pyrazol-5-yl)-3-azabicyclo[3.1.0]hexane-3-carboxylate (1.0 g, 2.4 mmol) in dichloromethane (20 mL) was added trifluoroacetic acid (3 mL). The mixture was warmed to room temperature. After 3 h, the reaction mixture was concentrated in vacuo. The resulting residue was used without further purification (0.78 g, crude).

Step 7—Synthesis of (1R,5S,6r)-6-(3-iodo-1-isopropyl-1H-pyrazol-5-yl)-3-(oxetan-3-yl)-3-azabicyclo[3.1.0]hexane

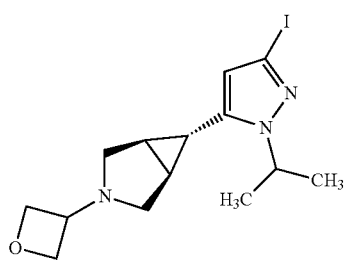 [SMILES: CC(C)n1nc(I)cc1[C@H]1[C@@H]2CN(C3COC3)C[C@@H]21]

To a solution of (1R,5S,6r)-6-(3-iodo-1-isopropyl-1H-pyrazol-5-yl)-3-azabicyclo[3.1.0]hexane (0.78 g, 2.46 mmol) in methanol (10 mL) was added oxetan-3-one (0.88 g, 12.3 mmol). The mixture was stirred at room temperature for 1 h after which sodium cyanoborohydride (30 mg, 0.47 mmol) was added under nitrogen. After 3 h, the mixture was diluted with water (15 mL), and the resulting solution was extracted with ethyl acetate (3×20 mL). The organic layer was dried over anhydrous sodium sulfate, filtered, and concentrated. Purification by flash column chromatography (80% ethyl acetate in hexanes) afforded product (0.62 g, yield 67.5%). LRMS (ESI) [MH]$^+$=373.8; $^1$H NMR (400 MHz, CDCl$_3$): δ 5.94 (s, 1 H), 4.71-4.59 (m, 5 H), 3.81-3.75 (m, 1 H), 3.14-3.12 (m, 2 H), 2.47-2.45 (m, 2 H), 2.21-2.20 (m, 1 H), 1.70-1.67 (m, 2 H), 1.49 (d, J=6.8 Hz, 6 H).

Step 8—Synthesis of 5-(1-isopropyl-5-((1R,5S,6R)-3-(oxetan-3-yl)-3-azabicyclo[3.1.0]hexan-6-yl)-1H-pyrazol-3-yl)-3-(trifluoromethyl)pyridin-2-amine To a solution of (1R,5S,6r)-6-(3-iodo-1-isopropyl-1H-pyrazol-5-yl)-3-azabicyclo[3.1.0]hexane (500 mg, 1.34 mmol), 5-(4,4,5,5-tetramethyl-1,3-dioxolan-2-yl)-3-(trifluoromethyl)pyridin-2-amine (463 mg, 1.61 mmol) and cesium carbonate (655 mg, 2.01 mmol) in 1,4-dioxane/water (10:1, 5 mL) was added 1,1'-bis(diphenylphosphino)ferrocene-palladium(II)dichloride (196 mg, 0.27 mmol) under nitrogen. The mixture was irradiated in the microwave at 100° C. for 20 min. The reaction mixture was concentrated in vacuo, and resulting residue was purified by flash column chromatography (6% ethyl acetate in hexanes) to provide product (297 mg, yield 54%). LRMS (ESI): [MH]$^+$=408.0; $^1$H NMR (CDCl$_3$, 400 MHz): δ 8.54 (d, J=2.1 Hz, 1 H), 7.98 (d, J=2.1 Hz, 1 H), 6.50 (br s, 2 H), 6.39 (s, 1 H), 4.67 (m, 1 H), 4.56 (t, J=6.6 Hz, 2 H), 4.48 (t, J=6.0 Hz, 2 H), 3.75 (m, 1 H), 3.12 (d, J=8.7 Hz, 2 H), 2.42 (m, 2 H), 2.15 (m, 1 H), 1.81 (m, 2 H), 1.42 (d, J=6.5 Hz, 6 H).

Method B

Preparation of 5-(1-cyclobutyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine (148)

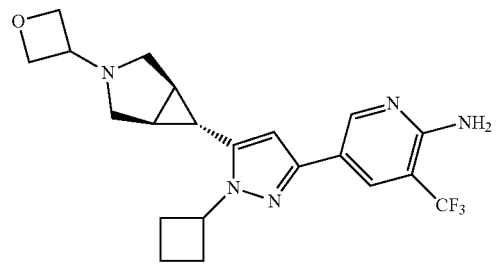 [SMILES: Nc1ncc(-c2cc([C@H]3[C@@H]4CN(C5COC5)C[C@@H]43)n(C3CCC3)n2)cc1C(F)(F)F]

Step 1—Synthesis of (1R,5S,6r)-tert-butyl 6-(3-iodo-1-cyclobutyl-1H-pyrazol-5-yl)-3-azabicyclo[3.1.0]hexane-3-carboxylate

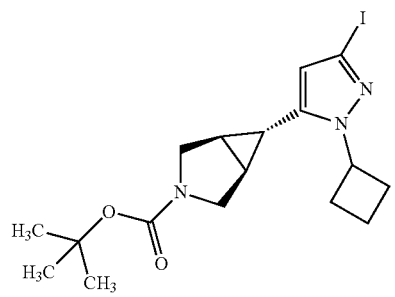 [SMILES: CC(C)(C)OC(=O)N1C[C@@H]2[C@H](C1)[C@H]2c1cc(I)nn1C1CCC1]

Prepared following the method described for the synthesis of (1R,5S,6r)-tert-butyl 6-(3-iodo-1-isopropyl-1H-pyrazol-5-yl)-3-azabicyclo[3.1.0]hexane-3-carboxylate using bromocyclobutane afforded product (350 mg, 16% yield, R$_f$=0.3 in 12:1 petroleum ether/ethyl acetate)$^1$H NMR (400 MHz, CDCl$_3$): δ 5.97 (s, 1 H), 4.81-4.76 (m, 1 H), 3.79-3.65 (m, 2 H), 3.47-3.44 (m, 2 H), 2.74-2.70 (m, 2 H), 2.42-2.34 (m, 2 H), 1.90-1.54 (m, 5 H), 1.47 (s, 9 H).

Step 2—Synthesis of (1R,5S,6r)-6-(3-iodo-1-cyclobutyl-1H-pyrazol-5-yl)-3-azabicyclo[3.1.0]hexane

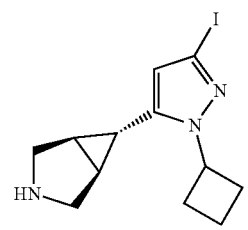 [SMILES: Ic1cc([C@H]2[C@@H]3CNC[C@@H]32)n(C2CCC2)n1]

Prepared following the method described for the synthesis of (1R,5S,6r)-6-(3-iodo-1-isopropyl-1H-pyrazol-5-yl)-3-azabicyclo[3.1.0]hexane using (1R,5S,6r)-tert-butyl 6-(3-iodo-1-cyclobutyl-1H-pyrazol-5-yl)-3-azabicyclo[3.1.0]hexane-3-carboxylate (270 mg, 100% crude yield). LCMS (ESI): [MH]$^+$=330.1. The resulting residue was used without further purification.

Step 3—Synthesis of (1R,5S,6r)-6-(3-iodo-1-cyclobutyl-1H-pyrazol-5-yl)-3-(oxetan-3-yl)-3-azabicyclo[3.1.0]hexane

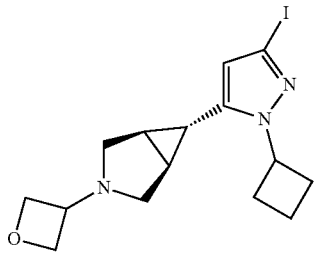 [SMILES: Ic1cc([C@H]2[C@@H]3CN(C4COC4)C[C@@H]32)n(C2CCC2)n1]

Prepared following the method described for the synthesis of (1R,5S,6r)-6-(3-iodo-1-isopropyl-1H-pyrazol-5-yl)-3-(oxetan-3-yl)-3-azabicyclo[3.1.0]hexane using (1R,5S,6r)-6-(3-iodo-1-cyclobutyl-1H-pyrazol-5-yl)-3-(oxetan-3-yl)-3-azabicyclo[3.1.0]hexane afforded product (250 mg, 80% yield over 2-steps). LCMS (ESI) [MH]$^+$=385.9.

Step 4—Synthesis of 5-(1-cyclobutyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine Prepared following the method described for the synthesis of 5-(1-isopropyl-5-((1R,5S,6R)-3-(oxetan-3-yl)-3-azabicyclo[3.1.0]hexan-6-yl)-1H-pyrazol-3-yl)-3-(trifluoromethyl)pyridin-2-amine using (1R,5S,6r)-6-(3-iodo-1-cyclobutyl-1H-pyrazol-5-yl)-3-(oxetan-3-yl)-3-azabicyclo[3.1.0]hexane yielded product (5.4 mg, 13% yield). LCMS (ESI) [MH]$^+$=420.2. $^1$H NMR (400 MHz, CD$_3$OD): δ 8.53 (s, 1 H), 8.14 (s, 1 H), 6.25 (s, 1 H), 5.03-4.99 (m, 1 H), 4.76-4.73 (m, 2 H), 4.66-4.63 (m, 2 H), 3.91-3.87 (m, 1 H), 3.32-3.30 (m, 2 H), 2.78-2.62 (m, 4 H), 2.50-2.43 (m, 2 H), 2.28-2.26 (m, 1 H), 1.95-1.90 (m, 4 H).

Method C

Preparation of 5-(1-cyclopentyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine (135)

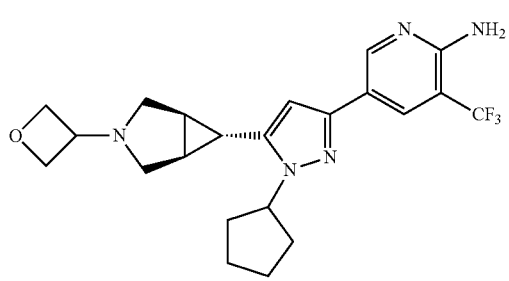 [SMILES: Nc1ncc(-c2cc([C@H]3[C@@H]4CN(C5COC5)C[C@@H]43)n(C3CCCC3)n2)cc1C(F)(F)F]

Step 1—Synthesis of (1R,5S,6r)-tert-butyl 6-(1-cyclopentyl-3-iodo-1H-pyrazol-5-yl)-3-azabicyclo[3.1.0]hexane-3-carboxylate

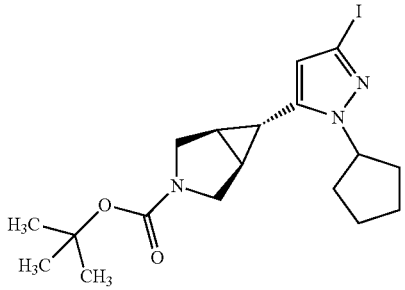 [SMILES: CC(C)(C)OC(=O)N1C[C@@H]2[C@H](C1)[C@H]2c1cc(I)nn1C1CCCC1]

Prepared following the method described for the synthesis of (1R,5S,6r)-tert-butyl 6-(3-iodo-1-isopropyl-1H-pyrazol-5-yl)-3-azabicyclo[3.1.0]hexane-3-carboxylate using bromocyclopentane afforded product (0.81 g, 30% yield, R$_f$=0.4 in 6:1 petroleum ether/ethyl acetate)$^1$H NMR (400 MHz, CDCl$_3$): δ 5.95 (s, 1 H), 4.60-4.53 (m, 1 H), 3.77-3.74 (m, 1 H), 3.67-3.64 (m, 1 H), 3.47-3.44 (m, 2 H), 1.80-1.75 (m, 2 H), 1.59-1.55 (m, 1 H), 1.48-1.46 (m, 15H).

Step 2—Synthesis of (1R,5S,6r)-6-(1-cyclopentyl-3-iodo-1H-pyrazol-5-yl)-3-azabicyclo[3.1.0]hexane

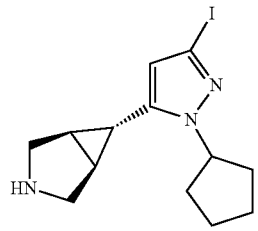 [SMILES: Ic1cc([C@H]2[C@@H]3CNC[C@@H]32)n(C2CCCC2)n1]

Prepared following the method described for the synthesis of (1R,5S,6r)-6-(3-iodo-1-isopropyl-1H-pyrazol-5-yl)-3-azabicyclo[3.1.0]hexane using (1R,5S,6r)-tert-butyl 6-(1-cyclopentyl-3-iodo-1H-pyrazol-5-yl)-3-azabicyclo[3.1.0]hexane-3-carboxylate (120 mg, crude, 100% yield). LCMS (ESI): [MH]$^+$=343.8. The resulting residue was used without further purification.

Step 3—Synthesis of (1R,5S,6r)-6-(1-cyclopentyl-3-iodo-1H-pyrazol-5-yl)-3-(oxetan-3-yl)-3-azabicyclo[3.1.0]hexane

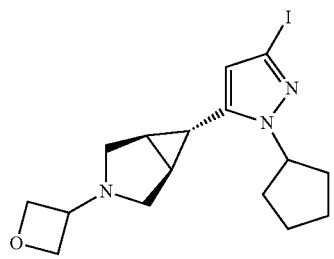 [SMILES: Ic1cc([C@H]2[C@@H]3CN(C4COC4)C[C@@H]32)n(C2CCCC2)n1]

Prepared following the method described for the synthesis of (1R,5S,6r)-6-(3-iodo-1-isopropyl-1H-pyrazol-5-yl)-3-(oxetan-3-yl)-3-azabicyclo[3.1.0]hexane using (1R,5S,6r)-6-(1-cyclopentyl-3-iodo-1H-pyrazol-5-yl)-3-azabicyclo[3.1.0]hexane afforded product (138 mg, 97% yield). LCMS (ESI) [MH]+=400.0.

Step 4—Synthesis of 5-(1-cyclopentyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine Prepared following the method described for the synthesis of 5-(1-isopropyl-5-((1R,5S,6R)-3-(oxetan-3-yl)-3-azabicyclo[3.1.0]hexan-6-yl)-1H-pyrazol-3-yl)-3-(t rifluoromethyl)pyridin-2-amine using (1R,5 S,6r)-6-(1-cyclopentyl-3-iodo-1H-pyrazol-5-yl)-3-(oxetan-3-yl)-3-azabicyclo[3.1.0]hexane yielded product (52 mg, 44% yield). LCMS (ESI): [MH]+=433.9; 1H NMR (400 MHz, CD3OD): δ 8.52 (s, 1 H), 8.12 (s, 1 H), 6.24 (s, 1 H), 4.94-4.90 (m, 1 H), 4.76-4.73 (m, 2 H), 4.67-4.64 (m, 2 H), 3.88-3.82 (m, 1 H), 3.26 (d, J=9.2 Hz, 2 H), 2.59-2.56 (m, 2 H), 2.34-2.32 (m, 1 H), 2.18-2.09 (m, 4 H), 2.04-1.98 (m, 2 H), 1.90 (s, 2 H), 1.89-1.74 (m, 2 H).

Method D

Preparation of 5-(1-isopropyl-5-(1-methylazetidin-3-yl)-1H-pyrazol-3-yl)-3-(trifluoromethyl)pyridin-2-amine (7)

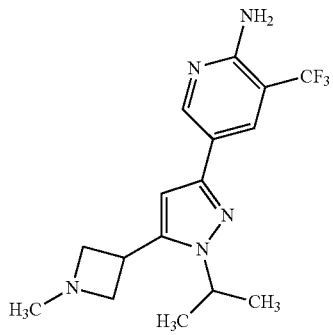 [SMILES: CC(C)n1nc(-c2cnc(N)c(C(F)(F)F)c2)cc1C1CN(C)C1]

Step 1—Synthesis of 1-tert-butyl 3-methyl azetidine-1,3-dicarboxylate

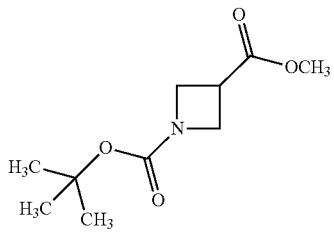

To a solution of 1-(tert-butoxycarbonyl)azetidine-3-carboxylic acid (0.30 kg, 1.5 mol) and cesium carbonate (978 g, 3.0 mol) in anhydrous N,N-dimethylacetamide (1.5 L) was added iodomethane (537 g, 3.8 mol) over 10 h. The reaction was filtered through Celite®, and the filtrate was extracted with ethyl acetate (3×300 mL). The combined organic layer was washed with saturated aqueous sodium chloride solution (300 mL), dried over anhydrous sodium sulfate, filtered, and concentrated to afford a clear yellow oil (303 g, crude, 94% yield). 1H NMR (400 MHz, CDCl3): δ 4.09-4.07 (m, 4H), 3.73 (s, 3H), 3.35-3.31 (m, 1H), 1.42 (s, 9H).

Step 2—Synthesis of tert-butyl 3-(2-cyanoacetyl)azetidine-1-carboxylate

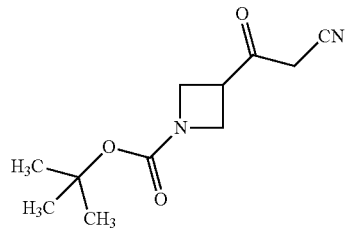 [SMILES: CC(C)(C)OC(=O)N1CC(C(=O)CC#N)C1]

To an ice-cooled solution of 1-tert-butyl 3-methyl azetidine-1,3-dicarboxylate (10.0 g, 46.5 mmol) and acetonitrile (2.9 g, 69.8 mmol) in tetrahydrofuran (250 mL) was added potassium tert-butoxide (70 mL, 69.8 mmol) dropwise under the atmosphere of nitrogen. The resulting mixture was warmed to room temperature. After 1 h, the reaction mixture was poured into saturated aqueous ammonium chloride (500 mL), and the resulting solution was extracted with ethyl acetate (3×500 mL). The combined organic was washed with saturated aqueous sodium chloride solution (500 mL), dried over anhydrous sodium sulfate, and concentrated in vacuo (10 g, 96% crude yield). 1H NMR (400 MHz, CDCl3): δ 4.16-4.09 (m, 4H), 3.72-3.64 (m, 1H), 3.50-3.48 (m, 2H), 1.43 (s, 9H).

Step 3—Synthesis of tert-butyl 3-(3-amino-1H-pyrazol-5-yl)azetidine-1-carboxylate

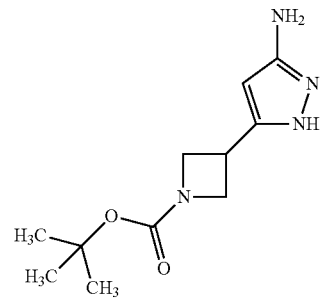 [SMILES: CC(C)(C)OC(=O)N1CC(c2cc(N)n[nH]2)C1]

To a solution of tert-butyl 3-(2-cyanoacetyl)azetidine-1-carboxylate (10 g, crude, 44.6 mmol) in 2-propanol (200 mL) was added hydrazine monohydrate (40 mL). The mixture was heated to 80° C. After 16 h, the reaction mixture was concentrated in vacuo. The resulting residue was dissolved in dichloromethane (500 mL), and the organic solution was washed sequentially with water (500 mL) and saturated aqueous sodium chloride solution (500 mL). The organic layer was dried over anhydrous sodium sulfate, filtered, and concentrated in vacuo to afford product (10 g, crude, 94% crude yield). 1H NMR (400 MHz, DMSO-d6):

δ 11.30 (br s, 1 H), 5.28 (s, 1 H), 4.70 (br s, 2 H), 4.12-4.08 (m, 2 H), 3.90-3.79 (m, 2 H), 3.63-3.56 (m, 1 H), 1.38 (s, 9 H).

Step 4—Synthesis of tert-butyl 3-(3-iodo-1H-pyrazol-5-yl)azetidine-1-carboxylate

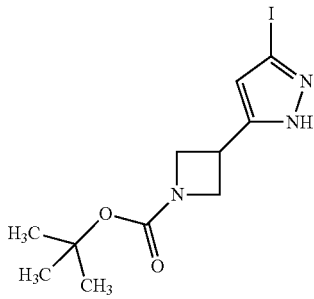 [SMILES: CC(C)(C)OC(=O)N1CC(c2cc(I)n[nH]2)C1]

To an ice-cooled solution of tert-butyl 3-(3-amino-1H-pyrazol-5-yl)azetidine-1-carboxylate (4.0 g, 16.8 mmol) in acetonitrile/water (5:1, 120 mL) was added p-toluenesulfonic acid (7.8 g, 50.4 mmol) and sodium nitrite (2.32 g, 33.6 mmol). After 30 min, sodium iodide (5.04 g, 33.6 mmol) was added, and the reaction mixture was warmed to room temperature. After 1 h, the reaction mixture was poured into water (100 mL), and the resulting solution was extracted with ethyl acetate (3×50 mL). The combined organic layer was washed with saturated aqueous sodium chloride solution (50 mL), dried over anhydrous sodium sulfate, filtered, and concentrated. Purification by flash column chromatography (100% petroleum ether→30% ethyl acetate in petroleum ether) yielded a yellow solid (2.0 g, 36% yield).

Step 5—Synthesis of tert-butyl 3-(3-iodo-1-isopropyl-1H-pyrazol-5-yl)azetidine-1-carboxylate

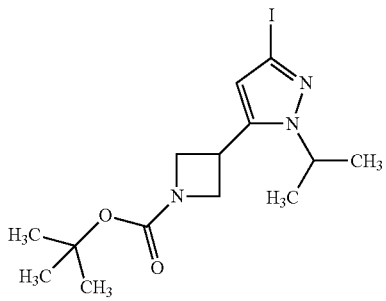 [SMILES: CC(C)n1nc(I)cc1C1CN(C(=O)OC(C)(C)C)C1]

To a solution of tert-butyl 3-(3-iodo-1H-pyrazol-5-yl)azetidine-1-carboxylate (2 g, 5.7 mmol) in N,N-dimethylformamide (10 mL) was added 2-bromopropane (2.1 g, 17.2 mmol) and cesium carbonate (3.7 g, 11.5 mmol). The mixture was stirred at 50-60° C. for 10 h. Ethyl acetate (50 mL) was added to the reaction mixture, and the resulting suspension was filtered. The filtrate was concentrated in vacuo. Purification by flash column chromatography (100% petroleum ether→30% ethyl acetate in petroleum ether) afforded product (0.6 g, 26% yield, $R_f$=0.5 in 3:1 petroleum ether/ethyl acetate). $^1$H NMR (400 MHz, CD$_3$OD): δ 6.45 (s, 1 H), 4.37-4.31 (m, 3 H), 4.00-3.96 (m, 1 H), 3.96-3.89 (m, 2 H), 1.45 (s, 9 H), 1.41 (d, J=6.8 Hz, 3 H).

Step 6—Synthesis of 5-(azetidin-3-yl)-3-iodo-1-isopropyl-1H-pyrazole

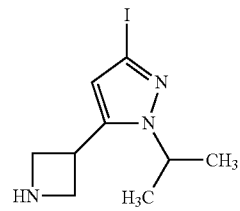

To an ice-cooled solution of tert-butyl 3-(3-iodo-1-isopropyl-1H-pyrazol-5-yl)azetidine-1-carboxylate (650 mg, 1.66 mmol) in dichloromethane (20 mL) was added trifluoroacetic acid (3 mL). The mixture was warmed to room temperature. After 1 h, the reaction mixture was concentrated in vacuo to afford crude product (300 mg). LCMS (ESI): [MH]$^+$=291.9. The resulting residue was used without further purification.

Step 7—Synthesis of 3-iodo-1-isopropyl-5-(1-methylazetidin-3-yl)-1H-pyrazole

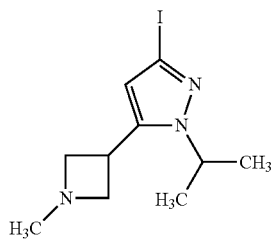

To a solution of 5-(azetidin-3-yl)-3-iodo-1-isopropyl-1H-pyrazole (300 mg, 1.03 mmol) in methanol (20 mL) was added paraformaldehyde (305 mg, 10.3 mmol) at room temperature. After stirring at 60° C. for 1 h, sodium cyanoborohydride (324 mg, 5.15 mmol) was added under nitrogen. After another 2 h, the mixture was diluted with water (15 mL), and the resulting solution was extracted with ethyl acetate (3×20 mL). The organic layer was dried over anhydrous sodium sulfate, filtered, and concentrated. Purification by flash column chromatography (80% ethyl acetate in hexanes) afforded product (150 mg, 48% yield). LCMS (ESI): [MH]$^+$=305.8.

Step 8—Synthesis of 5-(1-isopropyl-5-(1-methylazetidin-3-yl)-1H-pyrazol-3-yl)-3-(trifluoromethyl)pyridin-2-amine To a microwave vial charged with 3-iodo-1-isopropyl-5-(1-methylazetidin-3-yl)-1H-pyrazole (150 mg, 0.492 mmol), 5-(4,4,5,5-tetramethyl-1,3-dioxolan-2-yl)-3-(trifluoromethyl)pyridin-2-amine (566 mg, 1.97 mmol) and cesium carbonate (321 mg, 0.984 mmol) in 1,4-dioxane/water (5:1, 4 mL) was added 1,1'-bis(diphenylphosphino)ferrocene-palladium(II) dichloride (36 mg, 0.0492 mmol) under nitrogen. The vial was sealed and heated by microwave irradiation at 110° C. for 30 min. The reaction mixture was concentrated in vacuo, and resulting residue was purified by HPLC to provide product (27 mg, 16% yield). LCMS (ESI):

[MH]⁺=339.9; ¹H NMR (400 MHz, CDCl₃): δ 8.61 (s, 1 H), 8.15 (s, 1 H), 6.33 (s, 1 H), 4.96 (s, 2 H), 4.29-4.22 (m, 1 H), 3.81-3.78 (m, 2 H), 3.73-3.65 (m, 1 H), 3.17-3.14 (m, 2 H), 2.38 (s, 3 H), 1.47 (d, J=6.8 Hz, 6 H).

Method E

Preparation of 5-(1-isopropyl-5-(1-(oxetan-3-yl) azetidin-3-yl)-1H-pyrazol-3-yl)-3-(trifluoromethyl) pyridin-2-amine (60)

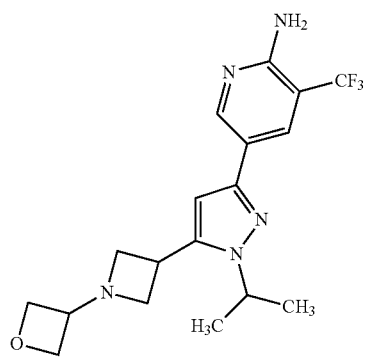 [SMILES: CC(C)n1nc(-c2cnc(N)c(C(F)(F)F)c2)cc1C1CN(C2COC2)C1]

Step 1—Synthesis of 3-iodo-1-isopropyl-5-(1-(oxetan-3-yl)azetidin-3-yl)-1H-pyrazole

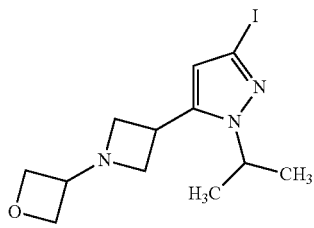 [SMILES: CC(C)n1nc(I)cc1C1CN(C2COC2)C1]

To a solution of 5-(azetidin-3-yl)-3-iodo-1-isopropyl-1H-pyrazole (110 mg, crude, 0.38 mmol) in methanol (10 mL) was added oxetan-3-one (136 mg, 1.9 mmol) and acetic acid (3 drops) at room temperature. After 1 h, sodium cyanoborohydride (119 mg, 1.9 mmol) was added under nitrogen. After another 3 h, the mixture was diluted with water (15 mL), and the resulting solution was extracted with ethyl acetate (3×20 mL). The organic layer was dried over anhydrous sodium sulfate, filtered, and concentrated. Purification by flash column chromatography (80% ethyl acetate in hexanes) afforded product (70 mg, 53% yield). LCMS (ESI): [MH]⁺=347.8.

Step 2—Synthesis of 5-(1-isopropyl-5-(1-(oxetan-3-yl)azetidin-3-yl)-1H-pyrazol-3-yl)-3-(trifluoromethyl)pyridin-2-amine Prepared following the method described for the synthesis of 5-(1-isopropyl-5-(1-methylazetidin-3-yl)-1H-pyrazol-3-yl)-3-(trifluoromethyl)pyridin-2-amine using 3-iodo-1-isopropyl-5-(1-(oxetan-3-yl)azetidin-3-yl)-1H-pyrazole yielded product (17 mg, 22% yield). LCMS (ESI): [MH]⁺=381.9; ¹H NMR (400 MHz, CD₃OD): δ 8.58 (s, 1 H), 8.17 (s, 1 H), 6.70 (s, 1 H), 4.87-4.85 (m, 2 H), 4.59-4.56 (m, 2 H), 4.41-4.37 (m, 1 H), 4.32-4.27 (m, 3 H), 4.19-4.15 (m, 1 H), 3.93-3.89 (m, 2 H), 1.47 (d, J=6.8 Hz, 6 H).

Method F

Preparation of 1-(3-(1-isopropyl-3-(3-methyl-1H-pyrrolo[2,3-b]pyridin-5-yl)-1H-pyrazol-5-yl)azetidin-1-yl)ethanone (12)

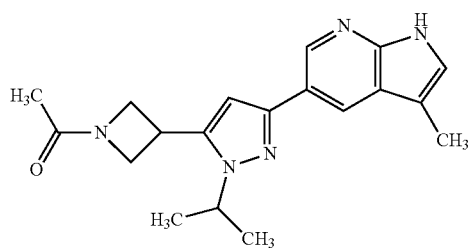 [SMILES: CC(=O)N1CC(c2cc(-c3cnc4[nH]cc(C)c4c3)nn2C(C)C)C1]

Step 1—Synthesis of 1-(3-(3-iodo-1-isopropyl-1H-pyrazol-5-yl)azetidin-1-yl)ethanone

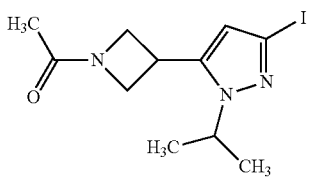 [SMILES: CC(=O)N1CC(c2cc(I)nn2C(C)C)C1]

To an ice-cooled solution of 5-(azetidin-3-yl)-3-iodo-1-isopropyl-1H-pyrazole (112 mg, 0.38 mmol) and diisopropylethylamine (130 mg, 1 mmol) in dichloromethane (15 mL) was added acetyl chloride (59 mg, 0.76 mmol) dropwise. The reaction mixture was warmed to room temperature. After 30 min, the reaction mixture was concentrated in vacuo, and the residue was diluted with saturated aqueous sodium bicarbonate and extracted with ethyl acetate (3×15 mL). The collected organic was washed with saturated aqueous sodium chloride solution (20 mL). The resultant organic was dried over anhydrous sodium sulfate, filtered, and concentrated to afford crude product (70 mg, 55% crude yield). LCMS (ESI): [MH]⁺=333.8.

Step 2—Synthesis of 1-(3-(1-isopropyl-3-(3-methyl-1H-pyrrolo[2,3-b]pyridin-5-yl)-1H-pyrazol-5-yl) azetidin-1-yl)ethanone Prepared following the method described for the synthesis of 5-(1-isopropyl-5-(1-methylazetidin-3-yl)-1H-pyrazol-3-yl)-3-(trifluoromethyl)pyridin-2-amine using 1-(3-(3-iodo-1-isopropyl-1H-pyrazol-5-yl)azetidin-1-yl)ethanone and 3-methyl-5-(4,4,5,5-tetramethyl-1,3,2-dioxaborolan-2-yl)-1H-pyrrolo[2,3-b]pyridine yielded product (19 mg, 27% yield). LCMS (ESI): [MH]⁺=337.9; ¹H NMR (400 MHz, CDCl₃): δ 9.48 (s, 1 H), 8.74 (s, 1 H), 8.28 (s, 1 H), 7.10 (s, 1 H), 6.55 (s, 1 H), 4.58 (t, J=8.4 Hz, 1 H), 4.47 (t, J=8.8 Hz, 1 H), 4.30-4.23 (m, 2 H), 4.19-4.15 (m, 1 H), 3.97-3.91 (m, 1 H), 2.36 (s, 3 H), 1.94 (s, 3 H), 1.55 (d, J=6.8 Hz, 6 H).

Method G

Preparation of 5-(5-(1-(oxetan-3-yl)azetidin-3-yl)-1-(tetrahydrofuran-3-yl)-1H-pyrazol-3-yl)-3-(trifluoromethyl)-1H-pyrrolo[2,3-b]pyridine (55)

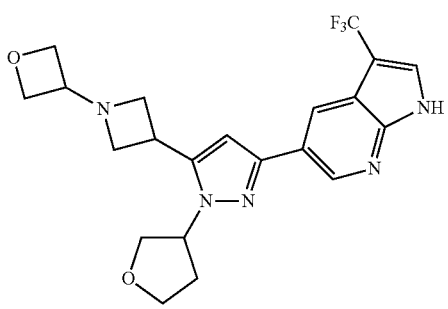 [SMILES: FC(F)(F)c1c[nH]c2ncc(-c3cc(C4CN(C5COC5)C4)n(C4CCOC4)n3)cc12]

Step 1—Synthesis of tert-butyl 3-(3-iodo-1-(tetrahydrofuran-3-yl)-1H-pyrazol-5-yl)azetidine-1-carboxylate

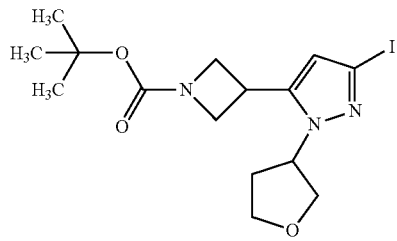 [SMILES: CC(C)(C)OC(=O)N1CC(c2cc(I)nn2C2CCOC2)C1]

To an ice-cooled solution of tert-butyl 3-(3-iodo-1H-pyrazol-5-yl)azetidine-1-carboxylate (2 g, 5.7 mmol) in N,N-dimethylformamide (10 mL) was added sodium hydride (276 mg, 11.5 mmol, 60% in mineral oil). After 15 min, tetrahydrofuran-3-yl methanesulfonate (1.9 g, 11.5 mmol) was added dropwise, and the mixture was warmed at room temperature for 10 h. Ethyl acetate (50 mL) was added to the reaction mixture, and the resulting suspension was filtered. The filtrate was concentrated in vacuo. Purification by flash column chromatography (100% petroleum ether→30% ethyl acetate in petroleum ether) afforded product (400 mg, 17% yield, $R_f$=0.3 in 3:1 petroleum ether/ethyl acetate).

Step 2—Synthesis of 5-(azetidin-3-yl)-3-iodo-1-(tetrahydrofuran-3-yl)-1H-pyrazole

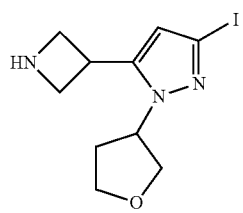 [SMILES: Ic1cc(C2CNC2)n(C2CCOC2)n1]

Prepared following the method described for the synthesis of 5-(azetidin-3-yl)-3-iodo-1-isopropyl-1H-pyrazole using tert-butyl 3-(3-iodo-1-(tetrahydrofuran-3-yl)-1H-pyrazol-5-yl)azetidine-1-carboxylate to yield product (153 mg, 100% crude yield). LCMS (ESI): [MH]⁺=319.7.

Step 3—Synthesis of 3-iodo-5-(1-(oxetan-3-yl)azetidin-3-yl)-1-(tetrahydrofuran-3-yl)-1H-pyrazole

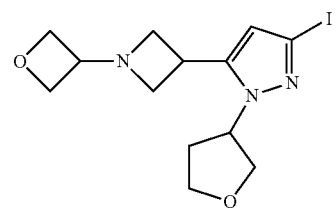 [SMILES: Ic1cc(C2CN(C3COC3)C2)n(C2CCOC2)n1]

To a solution of 5-(azetidin-3-yl)-3-iodo-1-(tetrahydrofuran-3-yl)-1H-pyrazole (153 mg, 0.48 mmol) and oxetan-3-one (104 mg, 1.44 mmol) in methanol (10 mL) was heated at 60° C. After 1 h, sodium cyanoborohydride (89 mg, 1.44 mmol) was added under nitrogen. After 3 h, the mixture was diluted with water (15 mL), and the resulting solution was extracted with ethyl acetate (3×20 mL). The organic layer was dried over anhydrous sodium sulfate, filtered, and concentrated. Purification by flash column chromatography (80% ethyl acetate in hexanes) afforded product (90 mg, 50% yield). LCMS (ESI): [MH]⁺=375.8.

Step 4—Synthesis 5-(5-(1-(oxetan-3-yl)azetidin-3-yl)-1-(tetrahydrofuran-3-yl)-1H-pyrazol-3-yl)-3-(trifluoromethyl)-1H-pyrrolo[2,3-b]pyridine Prepared following the method described for the synthesis of 5-(1-isopropyl-5-(1-methylazetidin-3-yl)-1H-pyrazol-3-yl)-3-(trifluoromethyl)pyridin-2-amine using 3-iodo-5-(1-(oxetan-3-yl)azetidin-3-yl)-1-(tetrahydrofuran-3-yl)-1H-pyrazole and 3-trifluoromethyl-5-(4,4,5,5-tetramethyl-1,3,2-dioxaborolan-2-yl)-1H-pyrrolo[2,3-b]pyridine yielded product (6 mg, 6% yield). LCMS (ESI): [MH]⁺=433.8; ¹H NMR (400 MHz, CD₃OD): δ 8.83 (s, 1 H), 8.43 (s, 1 H), 7.87 (s, 1 H), 6.78 (s, 1 H), 4.99-4.95 (m, 1 H), 4.77 (t, J=6.8 Hz, 2 H), 4.56-4.55 (m, 2 H), 4.28-4.22 (m, 1 H), 4.14-4.10 (m, 1 H), 4.05-3.88 (m, 6 H), 3.46-3.41 (m, 2 H), 2.44-2.39 (m, 2 H).

Method H

Preparation of 5-(1-(3,3-difluorocyclopentyl)-5-(1-(oxetan-3-yl)azetidin-3-yl)-1H-pyrazol-3-yl)-3-(trifluoromethyl)-1H-pyrrolo[2,3-b]pyridine (56)

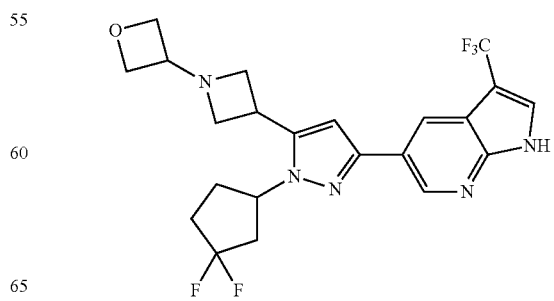

Step 1—Synthesis of tert-butyl 3-(3-iodo-1-(3-oxocyclopentyl)-1H-pyrazol-5-yl)azetidine-1-carboxylate and tert-butyl 3-(5-iodo-1-(3-oxocyclopentyl)-1H-pyrazol-3-yl)azetidine-1-carboxylate.

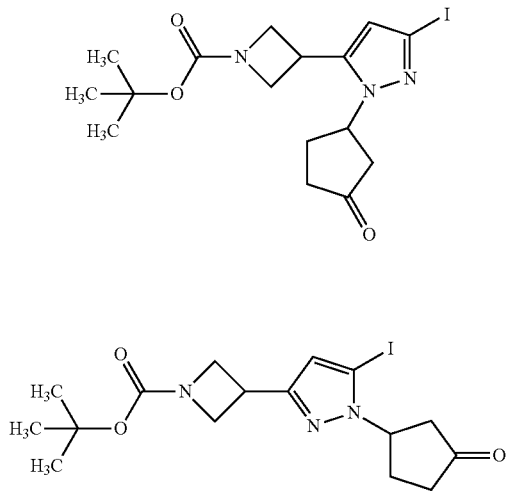

To a solution of tert-butyl 3-(3-iodo-1H-pyrazol-5-yl) azetidine-1-carboxylate (2 g, 5.73 mmol) in dichloromethane (20 mL) was added hafnium(IV) chloride (183 mg, 0.6 mmol) and cyclopent-2-enone (1.4 g, 17.2 mmol). The mixture was stirred at room temperature for 12 h. The reaction mixture was filtrated, and the filtrate was used for next step without further purification. LCMS (ESI): [MH-100]$^+$=331.8.

Step 2—Synthesis of tert-butyl 3-(1-(3,3-difluorocyclopentyl)-3-iodo-1H-pyrazol-5-yl)azetidine-1-carboxylate

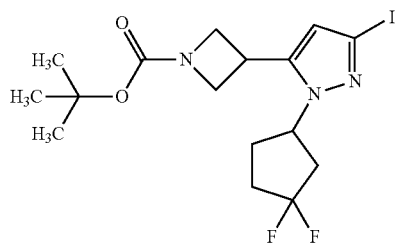 [SMILES: CC(C)(C)OC(=O)N1CC(c2cc(I)nn2C2CCC(F)(F)C2)C1]

To an ice-cooled solution of crude tert-butyl 3-(3-iodo-1-(3-oxocyclopentyl)-1H-pyrazol-5-yl)azetidine-1-carboxylate and tert-butyl 3-(5-iodo-1-(3-oxocyclopentyl)-1H-pyrazol-3-yl)azetidine-1-carboxylate from previous reaction in dichloromethane (20 mL) was added DAST (15 mL). The reaction mixture was warmed to room temperature. After 4 h, the reaction mixture was cooled to 0° C., and saturated aqueous sodium bicarbonate solution (30 mL) was added dropwise. The resulting mixture was extracted with ethyl acetate (3×30 mL) and saturated aqueous sodium chloride solution (30 mL). The collected organic was dried over anhydrous sodium sulfate, filtered, and concentrated. Purification by flash column chromatography (100% petroleum ether→20% ethyl acetate in petroleum ether) provided product (400 mg, 15% yield, $R_f$=0.3 in 5:1 petroleum ether/ethyl acetate). LCMS (ESI): [MH-56]$^+$=397.8.

Step 3—Synthesis of 5-(azetidin-3-yl)-1-(3,3-difluorocyclopentyl)-3-iodo-1H-pyrazole

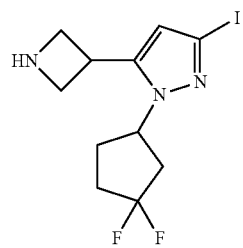 [SMILES: FC1(F)CCC(n2nc(I)cc2C2CNC2)C1]

Prepared following the method described for the synthesis of 5-(azetidin-3-yl)-3-iodo-1-isopropyl-1H-pyrazole using tert-butyl 3-(1-(3,3-difluorocyclopentyl)-3-iodo-1H-pyrazol-5-yl)azetidine-1-carboxylate afforded crude product (155 mg). LCMS (ESI): [MH-56]$^+$=353.8.

Step 4—Synthesis of 1-(3,3-difluorocyclopentyl)-3-iodo-5-(1-(oxetan-3-yl)azetidin-3-yl)-1H-pyrazole

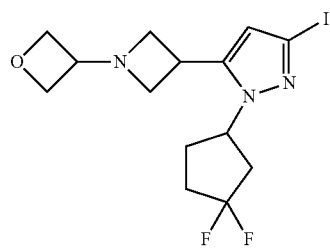 [SMILES: FC1(F)CCC(n2nc(I)cc2C2CN(C3COC3)C2)C1]

Prepared following the method described for the synthesis of 3-iodo-5-(1-(oxetan-3-yl)azetidin-3-yl)-1-(tetrahydrofuran-3-yl)-1H-pyrazole to afford product (100 mg, 56% yield). LCMS (ESI): [MH-56]$^+$=409.8.

Step 5—Synthesis of 5-(1-(3,3-difluorocyclopentyl)-5-(1-(oxetan-3-yl)azetidin-3-yl)-1H-pyrazol-3-yl)-3-(trifluoromethyl)-1H-pyrrolo[2,3-b]pyridine Prepared following the method described for the synthesis of 5-(1-isopropyl-5-(1-methylazetidin-3-yl)-1H-pyrazol-3-yl)-3-(trifluoromethyl)pyridin-2-amine using 1-(3,3-difluorocyclopentyl)-3-iodo-5-(1-(oxetan-3-yl)azetidin-3-yl)-1H-pyrazole and 3-trifluoromethyl-5-(4,4,5,5-tetramethyl-1,3,2-dioxaborolan-2-yl)-1H-pyrrolo[2,3-b]pyridine to yield product (5 mg, 4% yield). LCMS (ESI): [MH]$^+$=468.0; $^1$H NMR (400 MHz, CDCl$_3$): δ 9.87 (s, 1 H), 8.90 (s, 1 H), 8.39 (s, 1 H), 7.70 (s, 1 H), 6.52 (s, 1 H), 4.74 (t, J=6.8 Hz, 2 H), 4.59-4.56 (m, 3 H), 3.89-3.80 (m, 4 H), 3.36-3.35 (m, 2 H), 2.94-2.82 (m, 1 H), 2.61-2.40 (m, 3 H), 2.27-2.18 (m, 2 H).

Method I

Preparation of 1-(3-(1-(cyclopropylmethyl)-3-(3-(trifluoromethyl)-1H-pyrrolo[2,3-b]pyridin-5-yl)-1H-pyrazol-5-yl)azetidin-1-yl)ethanone (8)

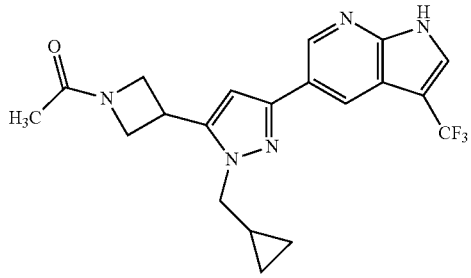 [SMILES: CC(=O)N1CC(c2cc(-c3cnc4[nH]cc(C(F)(F)F)c4c3)nn2CC2CC2)C1]

Step 1—Synthesis of tert-butyl 3-(1-(cyclopropylmethyl)-3-iodo-1H-pyrazol-5-yl)azetidine-1-carboxylate

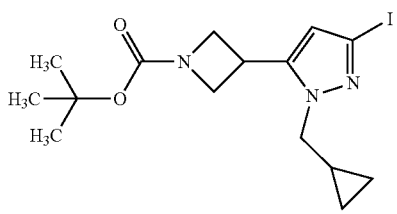 [SMILES: CC(C)(C)OC(=O)N1CC(c2cc(I)nn2CC2CC2)C1]

Prepared following the method described for the synthesis of tert-butyl 3-(3-iodo-1-isopropyl-1H-pyrazol-5-yl)azetidine-1-carboxylate using bromomethylcyclopropane to afford product (0.5 g, 21% yield, $R_f$=0.5 in 5:1 petroleum ether/ethyl acetate).

Step 2—Synthesis of 5-(azetidin-3-yl)-1-(cyclopropylmethyl)-3-iodo-1H-pyrazole

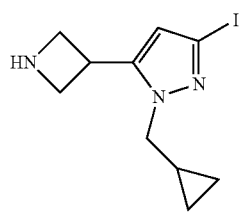 [SMILES: Ic1cc(C2CNC2)n(CC2CC2)n1]

Prepared following the method described for the synthesis of 5-(azetidin-3-yl)-3-iodo-1-isopropyl-1H-pyrazole using tert-butyl 3-(1-(cyclopropylmethyl)-3-iodo-1H-pyrazol-5-yl)azetidine-1-carboxylate to afford crude product (112 mg, 99% crude yield). LCMS (ESI): [MH]⁺=303.8.

Step 3—Synthesis of 1-(3-(1-(cyclopropylmethyl)-3-iodo-1H-pyrazol-5-yl)azetidin-1-yl)ethanone

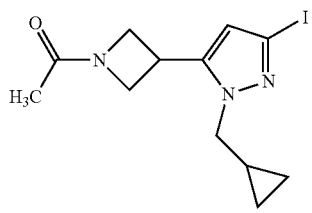 [SMILES: CC(=O)N1CC(c2cc(I)nn2CC2CC2)C1]

Prepared following the method described for the synthesis of 1-(3-(3-iodo-1-isopropyl-1H-pyrazol-5-yl)azetidin-1-yl)ethanone using 5-(azetidin-3-yl)-1-(cyclopropylmethyl)-3-iodo-1H-pyrazole to provide product (70 mg, 54% yield). LCMS (ESI): [MH]⁺=345.9.

Step 4—Synthesis of 1-(3-(1-(cyclopropylmethyl)-3-(3-(trifluoromethyl)-1H-pyrrolo[2,3-b]pyridin-5-yl)-1H-pyrazol-5-yl)azetidin-1-yl)ethanone Prepared following the method described for the synthesis of 5-(1-isopropyl-5-(1-methylazetidin-3-yl)-1H-pyrazol-3-yl)-3-(trifluoromethyl)pyridin-2-amine using 1-(3-(1-(cyclopropylmethyl)-3-iodo-1H-pyrazol-5-yl)azetidin-1-yl)ethanone and 3-trifluoromethyl-5-(4,4,5,5-tetramethyl-1,3,2-dioxaborolan-2-yl)-1H-pyrrolo[2,3-b]pyridine to yield product (10 mg, yield 12%). LCMS (ESI): [MH]⁺=404.2; ¹H NMR (400 MHz, DMSO-d₆): δ 12.53 (s, 1 H), 8.86 (s, 1 H), 8.34 (s, 1 H), 8.16 (s, 1 H), 7.09 (s, 1 H), 4.55 (t, J=8.4 Hz, 1 H), 4.30-4.19 (m, 2 H), 4.06-4.01 (m, 1 H), 3.95-3.90 (m, 3 H), 1.81 (s, 3 H), 1.22-1.19 (m, 1 H), 0.52-0.50 (m, 2 H), 0.37-0.36 (m, 2 H).

Method J

Preparation of 1-(3-(1-methyl-3-(3-(trifluoromethyl)-1H-pyrrolo[2,3-b]pyridin-5-yl)-1H-pyrazol-5-yl)azetidin-1-yl)ethanone (11)

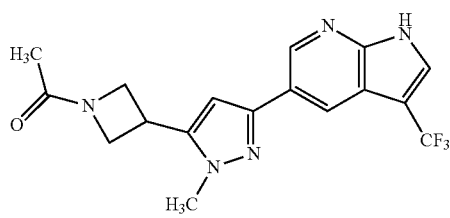 [SMILES: CC(=O)N1CC(c2cc(-c3cnc4[nH]cc(C(F)(F)F)c4c3)nn2C)C1]

Step 1—Synthesis of tert-butyl 3-(3-iodo-1-methyl-1H-pyrazol-5-yl)azetidine-1-carboxylate and tert-butyl 3-(5-iodo-1-methyl-1H-pyrazol-3-yl)azetidine-1-carboxylate

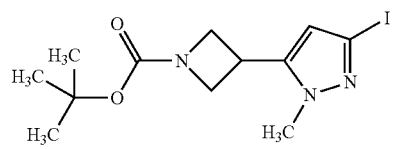

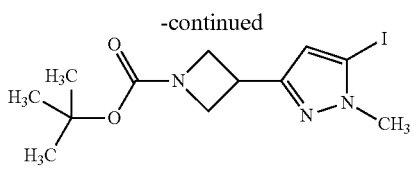

To a solution of tert-butyl 3-(3-iodo-1H-pyrazol-5-yl)azetidine-1-carboxylate (2 g, 5.7 mmol) in N,N-dimethylformamide (10 mL) was added iodomethane (2.4 g, 17.2 mmol) and cesium carbonate (3.7 g, 11.5 mmol). The mixture was stirred at room temperature for 10 h. Ethyl acetate (60 mL) was added to the reaction mixture, and the resulting suspension was filtered. The filtrate was concentrated in vacuo. Purification by flash column chromatography (100% petroleum ether→30% ethyl acetate in petroleum ether) afforded the mixture of products (1.4 g, 67% yield, $R_f$=0.3 in 3:1 petroleum ether/ethyl acetate).

Step 2—Synthesis of 5-(azetidin-3-yl)-3-iodo-1-methyl-1H-pyrazole and 3-(azetidin-3-yl)-5-iodo-1-methyl-1H-pyrazole

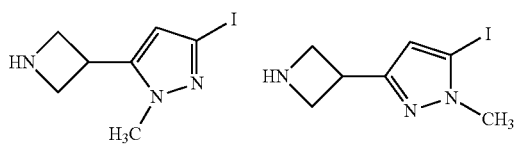

Prepared following the method described for the synthesis of 5-(azetidin-3-yl)-3-iodo-1-isopropyl-1H-pyrazole using tert-butyl 3-(3-iodo-1-methyl-1H-pyrazol-5-yl)azetidine-1-carboxylate and tert-butyl 3-(5-iodo-1-methyl-1H-pyrazol-3-yl)azetidine-1-carboxylate to afford crude product (0.71 g, 98% crude yield). LCMS (ESI): [MH]$^+$=263.7.

Step 3—Synthesis of 1-(3-(3-iodo-1-methyl-1H-pyrazol-5-yl)azetidin-1-yl)ethanone and 1-(3-(5-iodo-1-methyl-1H-pyrazol-3-yl)azetidin-1-yl)ethanone

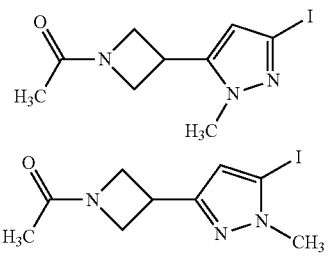

Prepared following the method described for the synthesis of 1-(3-(3-iodo-1-isopropyl-1H-pyrazol-5-yl)azetidin-1-yl)ethanone using 5-(azetidin-3-yl)-3-iodo-1-methyl-1H-pyrazole and 3-(azetidin-3-yl)-5-iodo-1-methyl-1H-pyrazole to provide the mixture of products (310 mg, 36% yield). LCMS (ESI): [MH]$^+$=305.7.

Step 4—Synthesis of 1-(3-(1-methyl-3-(3-(trifluoromethyl)-1H-pyrrolo[2,3-b]pyridin-5-yl)-1H-pyrazol-5-yl)azetidin-1-yl)ethanone Prepared following the method described for the synthesis of 5-(1-isopropyl-5-(1-methylazetidin-3-yl)-1H-pyrazol-3-yl)-3-(trifluoromethyl)pyridin-2-amine using a mixture of 1-(3-(3-iodo-1-methyl-1H-pyrazol-5-yl)azetidin-1-yl)ethanone and 1-(3-(5-iodo-1-methyl-1H-pyrazol-3-yl)azetidin-1-yl)ethanone and 3-trifluoromethyl-5-(4,4,5,5-tetramethyl-1,3,2-dioxaborolan-2-yl)-1H-pyrrolo[2,3-b]pyridine to yield product (16 mg, 4% yield). LCMS (ESI): [MH]$^+$=363.9; $^1$H NMR (400 MHz, CD$_3$OD): δ 8.79 (s, 1 H), 8.43 (s, 1 H), 7.88 (s, 1 H), 6.87 (s, 1 H), 4.70-4.66 (m, 1 H), 4.49-4.43 (m, 1H), 4.38-4.34 (m, 1 H), 4.11-4.06 (m, 2 H), 3.83 (s, 3 H), 1.93 (s, 3 H).

Method K

Preparation of 5-(5-((1R,5 S,6s)-3-oxabicyclo[3.1.0]hexan-6-yl)-1-isopropyl-1H-pyrazol-3-yl)-3-(trifluoromethyl)pyridin-2-amine

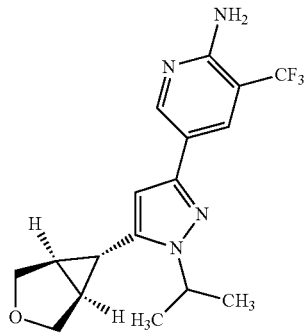 [SMILES: CC(C)n1nc(-c2cnc(N)c(C(F)(F)F)c2)cc1[C@H]1[C@@H]2COC[C@@H]21]

Step 1—Synthesis of (1R,5S,6r)-3-oxabicyclo[3.1.0]hexane-6-carboxylic acid

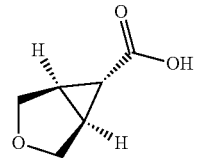

To a stirred suspension of 2,5-dihydrofuran (40.0 g, 571 mmol) and copper(II) acetylacetonate (3.0 g, 11 mmol) in toluene (1.2 L) at 90° C. was added ethyl 2-diazoacetate (78.0 g, 686 mmol) over 1 h (color of the solution changed from blue to brown). After complete addition, the reaction was cooled to room temperature and allowed to stir for 16 h. The reaction was filtered through Celite, and the filtrate was concentrated in vacuo. The resulting residue was dissolved in ethyl acetate (1 L), and the solution was washed with water (3×1 L). The organic layers were dried over magnesium sulfate, filtered and concentrated. To a stirred solution of the crude product in ethanol (500 mL) was added aqueous sodium hydroxide solution (34.3 g, 857 mmol in 100 mL of water). After 2 h at room temperature, organic solvent was removed in vacuo, and the resulting aqueous solution was diluted with water (200 mL) and acidified with 2 M hydrochloric acid to pH=2. The mixture was extracted with ethyl acetate (2×400 mL) and the combined organic extracts were washed with saturated aqueous sodium chloride solution, dried over anhydrous sodium sulfate, filtered and concentrated to afford crude (1R,5S,6r)-3-oxabicyclo

[3.1.0]hexane-6-carboxylic acid (15 g, 20% crude yield) as a white solid. ¹H NMR (400 MHz, DMSO-d6) δ 12.25 (s, 1 H), 3.83-3.56 (m, 4 H), 2.08 (s, 2 H), 1.29 (s, 1 H).

Step 2—Synthesis of (1R,5S,6r)-N-methoxy-N-methyl-3-oxabicyclo[3.1.0]hexane-6-carboxamide

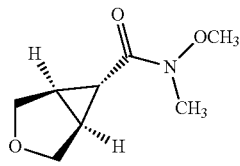

An ice-cooled solution of (1R,5 S,6r)-3-oxabicyclo[3.1.0]hexane-6-carboxylic acid (14.2 g, 111 mmol), triethylamine (44.9 g, 443 mmol) and N-(3-dimethylaminopropyl)-N'-ethylcarbodiimide hydrochloride (25.4 g, 133 mmol) in dichloromethane (150 mL) was stirred 30 min. N,O-dimethylhydroxylamine hydrochloride (16.2 g, 166 mmol) was slowly added to the mixture, and the reaction was warmed to room temperature. After 16 h, water (150 mL) was added to the reaction, and the resulting solution was extracted with dichloromethane (3×150 mL). The combined organic extracts were washed with saturated aqueous sodium chloride solution (150 mL), dried over anhydrous sodium sulfate, filtered and concentrated. Purification by flash column chromatography (10-50% ethyl acetate in petroleum ether) afforded (1R,5S,6r)-N-methoxy-N-methyl-3-oxabicyclo[3.1.0]hexane-6-carboxamide (9.6 g, 51% yield) as yellow oil. ¹H NMR (400 MHz, Chloroform-d) δ 3.91 (d, J=8.4 Hz, 2 H), 3.76 (d, J=8.4 Hz, 2 H), 3.70 (s, 3 H), 3.17 (s, 3 H), 2.13-2.11 (m, 2 H), 2.10-2.08 (m, 1 H).

Step 3—Synthesis of 1-((1R,5S,6r)-3-oxabicyclo[3.1.0]hexan-6-yl)ethanone

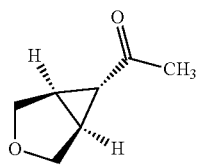

To a solution of (1R,5S,6r)-N-methoxy-N-methyl-3-oxabicyclo[3.1.0]hexane-6-carboxamide (9.6 g, 56 mmol) in tetrahydrofuran (150 mL) was slowly added methylmagnesium bromide (94 mL, 280 mmol, 3 M) at −78° C. The mixture was warmed to room temperature for 16 h. Saturated aqueous ammonium chloride solution (100 mL) was added to the reaction, and tetrahydrofuran was removed in vacuo. The resulting aqueous solution was extracted with ethyl acetate (3×100 mL). The combined organic extracts were washed saturated aqueous sodium chloride solution (100 mL), dried over anhydrous sodium sulfate, filtered and concentrated to give 1-((1R,5S,6r)-3-oxabicyclo[3.1.0]hexan-6-yl)-ethanone (6.6 g, 93% crude yield) as a yellow oil. The crude product was used directly to next step. ¹H NMR (400 MHz, Chloroform-d) δ 3.91 (d, J=8.8 Hz, 2 H), 3.74 (d, J=8.4 Hz, 2 H), 2.25 (s, 3 H), 2.17-2.16 (m, 2 H), 1.94-1.93 (m, 1 H).

Step 4—Synthesis of ethyl 4-((1R,5 S,6r)-3-oxabicyclo[3.1.0]hexan-6-yl)-2,4-dioxobutanoate

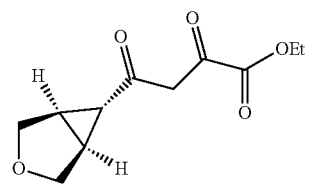 [SMILES: CCOC(=O)C(=O)CC(=O)[C@H]1[C@@H]2COC[C@@H]21]

To an ice-cooled solution of 1-((1R,5S,6r)-3-oxabicyclo[3.1.0]hexan-6-yl)ethanone (6.5 g, 51 mmol) and diethyl oxalate (11.3 g, 77.3 mmol) in anhydrous tetrahydrofuran (500 mL) was added lithium bis(trimethylsilyl)amide (25.9 g, 154 mmol, 1 M in tetrahydrofuran). After 6 h, the mixture was acidified with 2 M hydrochloric acid to pH between 1-2. The solution was concentrated in vacuo, and the resulting aqueous solution was extracted with ethyl acetate (3×500 mL). The combined organic extracts were washed with water (200 mL), dried over anhydrous sodium sulfate, filtered, and concentrated to afford ethyl 4-((1R,5S,6r)-3-oxabicyclo[3.1.0]hexan-6-yl)-2,4-dioxobutanoate (7.84 g, 67% crude yield) as a yellow solid. LRMS (ESI): [MH]+=225.9. The crude product was used directly in the next step.

Step 5—Synthesis of ethyl 5-((1R,5S,6s)-3-oxabicyclo[3.1.0]hexan-6-yl)-1-isopropyl-1H-pyrazole-3-carboxylate

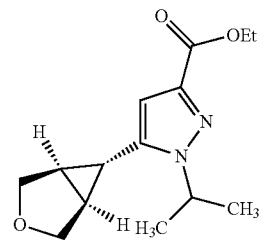 [SMILES: CCOC(=O)c1cc([C@H]2[C@@H]3COC[C@@H]32)n(C(C)C)n1]

To a solution of ethyl 4-((1R,5S,6r)-3-oxabicyclo[3.1.0]hexan-6-yl)-2,4-dioxobutanoate (7.84 g, 34.6 mmol) in ethanol (150 mL) was added isopropylhydrazine hydrochloride (4.22 g, 38.1 mmol). The reaction mixture was heated at 50° C. After 2 h, the solution was concentrated in vacuo, and the resulting residue was purified by flash column chromatography (30-50% ethyl acetate in petroleum ether) to give ethyl 5-((1R,5 S,6s)-3-oxabicyclo[3.1.0]hexan-6-yl)-1-isopropyl-1H-pyrazole-3-carboxylate (7.2 g, 78% yield) as a white solid. LRMS (ESI): [MH]+=265.4. ¹H NMR (400 MHz, Chloroform-d) δ 6.39 (s, 1 H), 4.70-4.64 (m, 1 H), 4.39-4.34 (m, 2 H), 4.09-4.02 (m, 2 H), 3.80 (d, J=8.4 Hz, 2 H), 1.93-1.92 (m, 2 H), 1.78-1.76 (m, 1 H), 1.54 (d, J=6.8 Hz, 6 H), 1.37 (t, J=7.2 Hz, 3 H).

Step 6—Synthesis of 5-((1R,5S,6s)-3-oxabicyclo[3.1.0]hexan-6-yl)-1-isopropyl-1H-pyrazole-3-carboxylic acid

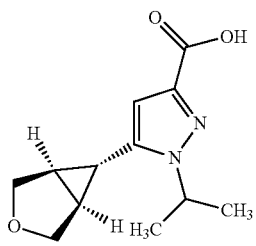 [SMILES: CC(C)n1nc(C(=O)O)cc1[C@H]1[C@@H]2COC[C@@H]21]

A solution of ethyl 5-((1R,5 S,6s)-3-oxabicyclo[3.1.0]hexan-6-yl)-1-isopropyl-1H-pyrazole-3-carboxylate (7.2 g, 27 mmol) in ethanol (150 mL) was added a solution of sodium hydroxide (4.22 g, 105 mmol) in water (50 mL). After 2 h, the mixture was concentrated under in vacuo, and the resulting aqueous solution was acidified with 2 M aqueous hydrochloric acid to pH=1-2. The mixture was extracted with ethyl acetate (3×100 mL). The combined organic layers were washed with saturated aqueous sodium chloride (100 mL), dried over anhydrous sodium sulfate, filtered, and concentrated to provide 5-((1R,5 S,6s)-3-oxabicyclo[3.1.0]hexan-6-yl)-1-isopropyl-1H-pyrazole-3-carboxylic acid (5.3 g, 82% crude yield) as a yellow solid. The crude product was used directly in the next step.

Step 7—Synthesis of tert-butyl (5-((1R,5 S,6s)-3-oxabicyclo[3.1.0]hexan-6-yl)-1-isopropyl-1H-pyrazol-3-yl)carbamate

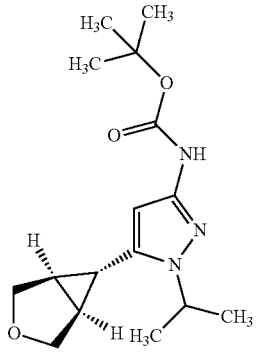 [SMILES: CC(C)n1nc(NC(=O)OC(C)(C)C)cc1[C@H]1[C@@H]2COC[C@@H]21]

A solution of 5-((1R,5S,6s)-3-oxabicyclo[3.1.0]hexan-6-yl)-1-isopropyl-1H-pyrazole-3-carboxylic acid (5.3 g, 22 mmol), 2-methylpropan-2-ol (13.5 g, 182 mmol) and N-ethyl-N-isopropylpropan-2-amine (3.5 g, 27 mmol) in toluene (130 mL) was purged with nitrogen and heated to 90° C. A solution of diphenyl phosphoryl azide (7.51 g, 27.3 mmol) in toluene (30 mL) was added to the heated reaction. After 4 h, the mixture was concentrated under in vacuo. Purification of the resulting residue by flash column chromatography (3-60% ethyl acetate in petroleum ether) afforded tert-butyl (5-((1R,5S,6s)-3-oxabicyclo[3.1.0]hexan-6-yl)-1-isopropyl-1H-pyrazol-3-yl)carbamate (3.7 g, 54% yield) as a white solid. $^1$H NMR (400 MHz, Chloroform-d) δ 6.97 (s, 1 H), 6.06 (s, 1 H), 4.54-4.44 (m, 1 H), 3.99 (d, J=8.4 Hz, 2 H), 3.77 (d, J=8.4 Hz, 2 H), 1.92-1.91 (m, 2 H), 1.81-1.80 (m, 1 H), 1.47 (s, 9 H), 1.39 (d, J=6.8 Hz, 6 H).

Step 8—Synthesis of 5-((1R,5S,6s)-3-oxabicyclo[3.1.0]hexan-6-yl)-1-isopropyl-1H-pyrazol-3-amine

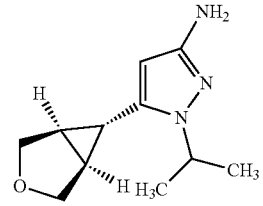

To a solution of tert-butyl (5-((1R,5 S,6s)-3-oxabicyclo[3.1.0]hexan-6-yl)-1-isopropyl-1H-pyrazol-3-yl)carbamate (3.7 g, 12 mmol) in dichloromethane (60 mL) was added 4 M hydrogen chloride in dioxane (60 mL) at room temperature. After 2 h, the reaction mixture was concentrated in vacuo to yield 5-((1R,5 S,6s)-3-oxabicyclo[3.1.0]hexan-6-yl)-1-isopropyl-1H-pyrazol-3-amine (2.9 g, 98% crude yield) as a brown solid.

Step 9—Synthesis of 5-((1R,5S,6s)-3-oxabicyclo[3.1.0]hexan-6-yl)-3-iodo-1-isopropyl-1H-pyrazole

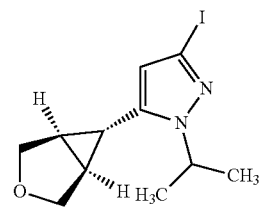

To a stirred solution of crude 5-((1R,5S,6s)-3-oxabicyclo[3.1.0]hexan-6-yl)-1-isopropyl-1H-pyrazol 3-amine (2.5 g, 12 mmol) in acetonitrile (100 mL) was added a solution of 4-methylbenzenesulfonic acid (6.23 g, 36.2 mmol) in water (20 mL) at room temperature. After 30 min, a solution of sodium nitrite (2.08 g, 30.2 mmol) and sodium iodide (4.52 g, 30.2 mmol) in water (20 mL) was added to the reaction mixture. After 3 h, the reaction mixture was poured into water (50 mL), and the resulting solution was extracted with ethyl acetate (3×80 mL). The combined organic extracts were washed with saturated aqueous sodium chloride solution (50 mL), dried over anhydrous sodium sulfate, filtered, and concentrated. Purification by flash column chromatography (2→10% ethyl acetate in petroleum ether) afforded 5-((1R,5S,6s)-3-oxabicyclo[3.1.0]hexan-6-yl)-3-iodo-1-isopropyl-1H-pyrazole (3.4 g, 90% yield) as a brown oil LRMS (ESI): [MH]+=318.7. $^1$H NMR (400 MHz, Chloroform-d) δ 5.97 (s, 1 H), 4.61-4.51 (m, 1 H), 4.01 (d, J=8.4 Hz, 2 H), 3.78 (d, J=8.8 Hz, 2 H), 1.88-1.87 (m, 2 H), 1.73-1.71 (m, 1 H), 1.47 (d, J=6.4 Hz, 6 H).

Step 10—Synthesis of 5-(5-((1R,5S,6s)-3-oxabicyclo[3.1.0]hexan-6-yl)-1-isopropyl-1H-pyrazol-3-yl)-3-(trifluoromethyl)pyridin-2-amine To a microwave vial charged with 5-(4,4,5,5-tetramethyl-1,3,2-dioxaborolan-2-yl)-3-(trifluoromethyl)pyridin-2- amine (86 mg, 0.30 mmol), 5-((1R,5S,6s)-3-oxabicyclo[3.1.0]-hexan-6-yl)-3-iodo-1-isopropyl-1H-pyrazole (64 mg, 0.20 mmol) and cesium carbonate (98 mg, 0.30 mmol) in 5:1 1,4-dioxane/water (6 mL) was added 1,1'-bis(diphenylphosphino)ferrocene-palladium(II) dichloride (15 mg, 0.020 mmol) under nitrogen. The vial was sealed and heated by microwave irradiation at 110° C. for 40 min. The reaction mixture was concentrated in vacuo, and resulting residue was purified by preparative HPLC (base) to afford 5-(5-((1R,5S,6s)-3-oxabicyclo[3.1.0]hexan-6-yl)-1-isopropyl-1H-pyrazol-3-yl)-3-(trifluoromethyl)pyridin-2-amine (23 mg, 32% yield) as a white solid. LRMS (ESI): [MH]$^+$=352.8. $^1$H NMR (400 MHz, Chloroform-d) δ 8.56 (s, 1 H), 8.12 (s, 1 H), 6.07 (s, 1 H), 4.99 (br.s, 2 H), 4.70-4.60 (m, 2 H), 4.06 (d, J=8.8 Hz, 2 H), 3.82 (d, J=8.8 Hz, 2 H), 1.96 (s, 2 H), 1.79-1.75 (m, 1 H), 1.53 (d, J=6.4 Hz, 6 H).

Method L

Preparation of 5-(1-isopropyl-5-(1-(oxetan-3-yl)piperidin-4-yl)-1H-pyrazol-3-yl)-3-(trifluoromethyl)pyridin-2-amine (76)

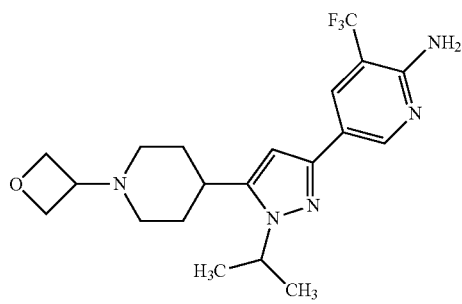 [SMILES: CC(C)n1nc(-c2cnc(N)c(C(F)(F)F)c2)cc1C1CCN(C2COC2)CC1]

Step 1—Synthesis of tert-butyl 4-(2-cyanoacetyl)piperidine-1-carboxylate

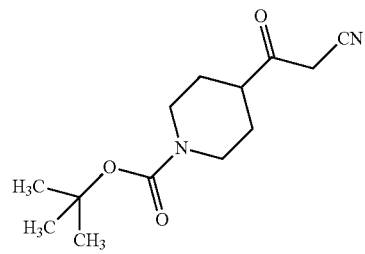 [SMILES: CC(C)(C)OC(=O)N1CCC(C(=O)CC#N)CC1]

To an ice-cooled solution of 1-tert-butyl 4-methyl piperidine-1,4-dicarboxylate (50 g, 206 mmol) in tetrahydrofuran (1 L) and acetonitrile (53 mL, 1027 mmol) was added potassium tert-butoxide (69 g, 616 mmol) portion-wise. The resulting mixture was warmed to room temperature. After 1 h, the reaction mixture was added to saturated aqueous ammonium chloride solution (2 L). The solution was extracted with ethyl acetate (3×500 mL). The combined organic was washed with saturated aqueous sodium chloride solution. The collected organic was dried over anhydrous sodium sulfate, filtered, and concentrated to afford a pale yellow oil (40 g, 77%). TLC(R$_f$=0.5 in 2:1 petroleum ether/ethyl acetate).

Step 2—Synthesis of tert-butyl 4-(3-amino-1H-pyrazol-5-yl)piperidine-1-carboxylate

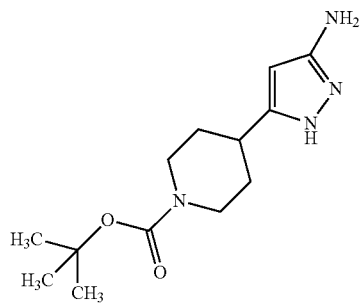 [SMILES: CC(C)(C)OC(=O)N1CCC(c2cc(N)n[nH]2)CC1]

A solution of tert-butyl 4-(2-cyanoacetyl) piperidine-1-carboxylate (40 g, 158 mmol) and hydrazine monohydrate (39.6 mL, 792 mmol) in 2-propanol (500 mL) was added heated to 80° C. overnight. The reaction mixture was concentrated in vacuo, and the resulting residue was dissolved in dichloromethane (1 L). The solution was washed sequentially with water (500 mL) and saturated aqueous sodium chloride solution (500 mL). The collected organic layer was dried over anhydrous sodium sulfate, filtered, and concentrated to provide a pale yellow oil (35 g, 83%). LCMS (ESI): [MH]$^+$=267.2. $^1$H NMR (400 MHz, DMSO-d$_6$): δ 11.14 (br s, 1 H), 5.15 (s, 1 H), 4.41 (br s, 2 H), 3.93-3.90 (m, 2 H), 2.76-2.74 (m, 2 H), 2.65-2.55 (m, 1 H), 1.78-1.74 (m, 2 H), 1.39-1.36 (m, 11 H).

Step 3—Synthesis of tert-butyl 4-(3-(1,3-dioxoisoindolin-2-yl)-1H-pyrazol-5-yl)piperidine-1-carboxylate

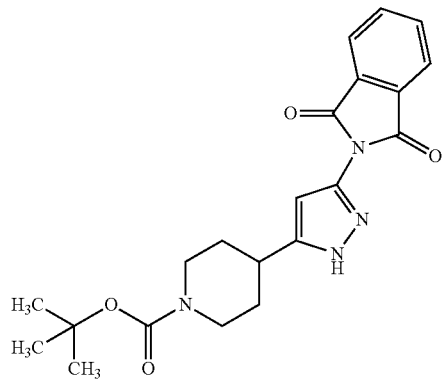 [SMILES: CC(C)(C)OC(=O)N1CCC(c2cc(N3C(=O)c4ccccc4C3=O)n[nH]2)CC1]

To a stirred solution of tert-butyl 4-(3-amino-1H-pyrazol-5-yl)piperidine-1-carboxylate (35 g, 131.4 mmol) in dioxane (700 mL) was added phthalic anhydride (19.4 g, 131.4 mmol). The resulting reaction mixture was heated to 90° C. overnight. The reaction mixture was poured in to water (2 L) and extracted with ethyl acetate (3×1 L). The combined organic layers were washed with saturated aqueous sodium chloride solution, dried over anhydrous sodium sulfate, filtered, and concentrated. The resulting pale yellow viscous oil was triturated with ether to afford a white solid (40 g, 76.8%), LCMS (ESI): [M-1]$^-$=395.3.

Step 4—Synthesis of tert-butyl 4-(3-(1,3-dioxoisoindolin-2-yl)-1-isopropyl-1H-pyrazol-5-yl)piperidine-1-carboxylate

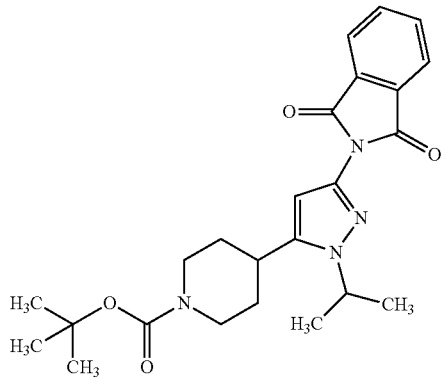 [SMILES: CC(C)n1nc(N2C(=O)c3ccccc3C2=O)cc1C1CCN(C(=O)OC(C)(C)C)CC1]

A sealed tube charged with tert-butyl 4-(3-(1,3-dioxoisoindolin-2-yl)-1H-pyrazol-5-yl)piperidine-1-carboxylate (10 g, 25.25 mmol), cesium carbonate (24.6 g, 75.75 mmol) and isopropyl iodide (12.6 mL, 126.5 mmol) in N,N-dimethylformamide (200 mL) was heated to 60° C. for 3 h. The reaction mixture was poured in to water (100 mL) and extracted with ethyl acetate (3×100 mL). The combined organic layers were washed with saturated aqueous sodium chloride solution, dried over anhydrous sodium sulfate, filtered, and concentrated. Purification by flash column chromatography using silica gel (230-400) gave desired product (2.2 g, 20%). LCMS (ESI): $[MH]^+=439.5$.

Step 5—Synthesis of tert-butyl 4-(3-amino-1-isopropyl-1H-pyrazol-5-yl)piperidine-1-carboxylate

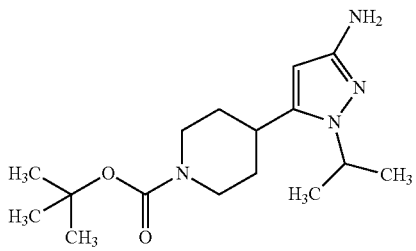 [SMILES: CC(C)n1nc(N)cc1C1CCN(C(=O)OC(C)(C)C)CC1]

To an ice-cooled solution of tert-butyl 4-(3-(1,3-dioxoisoindolin-2-yl)-1-isopropyl-1H-pyrazol-5-yl)piperidine-1-carboxylate (28 g, 63.9 mmol) in methanol (1 L) was added hydrazine hydrate (9.5 mL, 191.7 mmol). After 30 min, the reaction mixture was concentrated in vacuo. The resulting oil was triturated with ethyl acetate, and the solid was filtered. The filtrate was washed with water and concentrated. The resulting oil was triturated with ether to provide a white solid (10.5 g 53.3%). LCMS (ESI): $[MH]^+=309.3$; $^1$H NMR (400 MHz, DMSO-$d_6$): δ 5.15 (s, 1 H), 4.40 (br s, 2 H), 4.31 (m, 1 H), 4.00 (m, 2 H), 2.70-2.89 (m, 3 H), 1.74 (m, 2 H), 1.41 (s, 9 H), 1.32 (m, 2 H), 1.27 (d, 6 H).

Step 6—Synthesis of tert-butyl 4-(3-iodo-1-isopropyl-1H-pyrazol-5-yl)piperidine-1-carboxylate

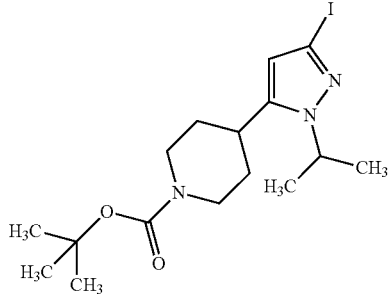 [SMILES: CC(C)n1nc(I)cc1C1CCN(C(=O)OC(C)(C)C)CC1]

To an ice-cooled solution of tert-butyl 4-(3-amino-1-isopropyl-1H-pyrazol-5-yl)piperidine-1-carboxylate (600 mg, 2 mmol) in acetonitrile/water (8:1, 15 mL) was added p-toluenesulfonic acid (1140 mg, 6 mmol) and sodium nitrite (280 mg, 4 mmol). After 30 min, sodium iodide, sodium iodide (600 mg, 4 mmol) was added, and the reaction mixture was warmed to room temperature. After 3 h, the reaction mixture was poured into water (50 mL), and the resulting solution was extracted with ethyl acetate (3×50 mL). The combined organic layer was washed with saturated aqueous sodium chloride solution (30 mL), dried over anhydrous sodium sulfate, filtered, and concentrated. Purification of the resulting residue by flash column chromatography (100% petroleum ether→15% ethyl acetate in petroleum ether) afforded product (500 mg, 60% yield). LCMS (ESI): $[MH]^+=420.1$.

Step 7—Synthesis of 4-(3-iodo-1-isopropyl-1H-pyrazol-5-yl)piperidine

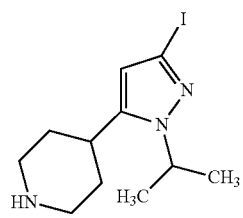

To an ice-cooled solution of tert-butyl 4-(3-iodo-1-isopropyl-1H-pyrazol-5-yl)piperidine-1-carboxylate (150 mg, 0.36 mmol) in dichloromethane (20 mL) was added trifluoroacetic acid (3 mL). The mixture was warmed to room temperature. After 3 h, the reaction mixture was concentrated in vacuo to afford crude product (115 mg, crude, 100% crude yield). LCMS (ESI): $[MH]^+=319.9$. The resulting residue was used without further purification.

Step 8—Synthesis of 4-(3-iodo-1-isopropyl-1H-pyrazol-5-yl)-1-(oxetan-3-yl)piperidine

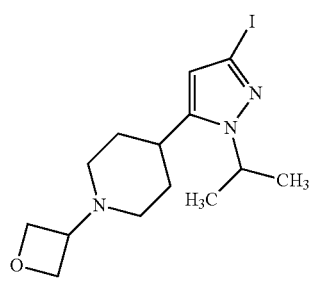 [SMILES: CC(C)n1nc(I)cc1C1CCN(C2COC2)CC1]

To a solution of 4-(3-iodo-1-isopropyl-1H-pyrazol-5-yl)piperidine (115 mg, crude, 0.36 mmol) in methanol (10 mL) was added oxetan-3-one (135 mg, 1.88 mmol) and acetic acid (5 drops) at room temperature. After 1 h, sodium cyanoborohydride (71 mg, 1.13 mmol) was added to the reaction mixture under nitrogen. After 3 h, the mixture was diluted with water (15 mL), and the resulting solution was extracted with ethyl acetate (3×20 mL). The collected organic was dried over anhydrous sodium sulfate, filtered, and concentrated. Purification by flash column chromatography (60% ethyl acetate in hexanes) afforded product (110 mg, 79% yield). LCMS (ESI): [MH]$^+$=376.0.

Step 9—Synthesis of 5-(1-isopropyl-5-(1-(oxetan-3-yl)piperidin-4-yl)-1H-pyrazol-3-yl)-3-(trifluoromethyl)pyridin-2-amine To a microwave vial charged with 4-(3-iodo-1-isopropyl-1H-pyrazol-5-yl)-1-(oxetan-3-yl)piperidine (110 mg, 0.293 mmol), 5-(4,4,5,5-tetramethyl-1,3,2-dioxaborolan-2-yl)-3-(trifluoromethyl)pyridin-2-amine (101 mg, 0.352 mmol) and cesium carbonate (143 mg, 0.44 mmol) in 1,4-dioxane/water (10:1, 5 mL) was added 1,1'-bis(diphenylphosphino)ferrocene-palladium(II) dichloride (21 mg, 0.029 mmol) under nitrogen. The vial was sealed and heated by microwave irradiation at 100° C. for 20 min. The reaction mixture was concentrated in vacuo, and resulting residue was purified by preparative HPLC to provide product (24.5 mg, 20% yield). LCMS (ESI): [MH]$^+$=410.0; $^1$H NMR (400 MHz, CD$_3$OD): δ 8.53 (s, 1 H), 8.13 (s, 1 H), 6.42 (s, 1 H), 4.79-4.76 (m, 2 H), 4.72-4.69 (m, 2 H), 4.62-4.55 (m, 1 H), 3.92-3.86 (m, 1 H), 3.18-3.15 (m, 2 H), 2.97-2.87 (m, 1 H), 2.46-2.39 (m, 2 H), 2.06-2.03 (m, 2 H), 1.92-1.82 (m, 2 H), 1.48 (d, J=6.8 Hz, 6 H).

Method M

Preparation of 5-(1-isopropyl-5-(1-(2-methoxyethyl)piperidin-4-yl)-1H-pyrazol-3-yl)-3-(trifluoromethyl)pyridin-2-amine (53)

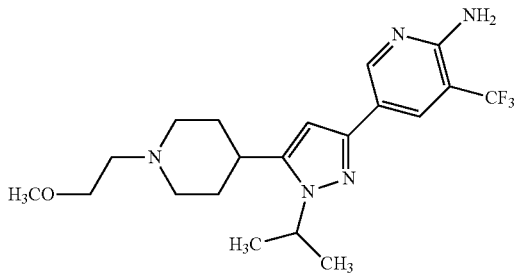 [SMILES: COCCN1CCC(c2cc(-c3cnc(N)c(C(F)(F)F)c3)nn2C(C)C)CC1]

Step 1—Synthesis of 4-(3-iodo-1-isopropyl-1H-pyrazol-5-yl)-1-(2-methoxyethyl)piperidine

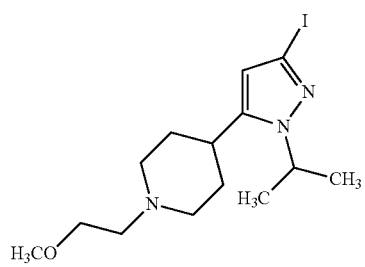 [SMILES: COCCN1CCC(c2cc(I)nn2C(C)C)CC1]

A solution of 4-(3-iodo-1-isopropyl-1H-pyrazol-5-yl)piperidine (115 mg, 036 mmol), 1-bromo-2-methoxyethane (149 mg, 1.08 mmol), and cesium carbonate (235 mg, 0.72 mmol) in N,N-dimethylformamide (10 mL) was heated to 60° C. for 5 h. Ethyl acetate (15 mL) was added to the reaction mixture, and the resulting suspension was filtered. The filtrate was concentrated in vacuo. Purification by flash column chromatography (30% methanol in ethyl acetate) afforded product (110 mg, 81% yield). LCMS (ESI): [MH]$^+$=377.9.

Step 2—Synthesis of 5-(1-isopropyl-5-(1-(2-methoxyethyl)piperidin-4-yl)-1H-pyrazol-3-yl)-3-(trifluoromethyl)pyridin-2-amine Prepared following the method described for the synthesis of 5-(1-isopropyl-5-(1-(oxetan-3-yl)piperidin-4-yl)-1H-pyrazol-3-yl)-3-(trifluoromethyl)pyridin-2-amine using 4-(3-iodo-1-isopropyl-1H-pyrazol-5-yl)-1-(2-methoxyethyl)piperidine to yield product (4.8 mg, 15% yield). LCMS (ESI): [MH]$^+$=412.0; $^1$H NMR (400 MHz, CD$_3$OD): δ 8.56 (s, 1 H), 8.16 (s, 1 H), 6.44 (s, 1 H), 4.67-4.60 (m, 1 H), 3.73-3.70 (m, 2 H), 3.52-3.49 (m, 2 H), 3.43 (s, 3 H), 3.17-3.14 (m, 2 H), 3.07-3.02 (m, 1 H), 3.02-3.87 (m, 2 H), 2.13-2.10 (m, 2 H), 2.02-1.91 (m, 2 H), 1.53 (d, J=6.8 Hz, 6 H).

Method N

Preparation of 5-(5-(1-cyclobutylpiperidin-4-yl)-1-isopropyl-1H-pyrazol-3-yl)-3-(trifluoromethyl)pyridin-2-amine (102)

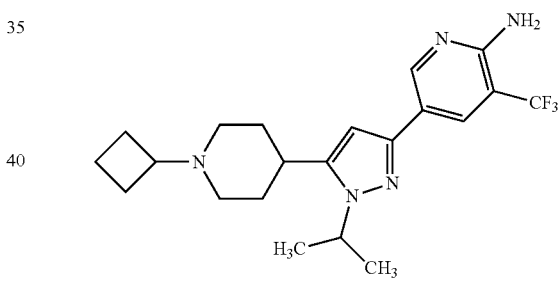

Step 1—Synthesis of 1-cyclobutyl-4-(3-iodo-1-isopropyl-1H-pyrazol-5-yl)piperidine

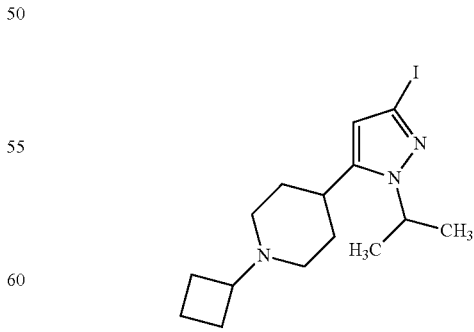

Prepared following the method described for the synthesis of 4-(3-iodo-1-isopropyl-1H-pyrazol-5-yl)-1-(oxetan-3-yl)piperidine using cyclobutanone to yield product (30 mg, 19% yield). LCMS (ESI) [MH]$^+$=374.1.

Step 2—Synthesis of 5-(5-(1-cyclobutylpiperidin-4-yl)-1-isopropyl-1H-pyrazol-3-yl)-3-(trifluoromethyl)pyridin-2-amine Prepared following the method described for the synthesis of 5-(1-isopropyl-5-(1-(oxetan-3-yl)piperidin-4-yl)-1H-pyrazol-3-yl)-3-(trifluoromethyl)pyridin-2-amine using 1-cyclobutyl-4-(3-iodo-1-isopropyl-1H-pyrazol-5-yl)piperidine to yield product (29.6 mg, 90% yield). LCMS (ESI) [MH]$^+$=408.0; $^1$H NMR (400 MHz, CD$_3$OD): δ 8.54 (s, 1 H), 8.14 (s, 1 H), 6.44 (s, 1 H), 4.63-4.60 (m, 1 H), 3.66-3.62 (m, 1 H), 3.54-3.50 (m, 2 H), 3.15-3.07 (m, 1 H), 2.92-2.85 (m, 2 H), 2.38-2.32 (m, 2 H), 2.27-2.17 (m, 4 H), 1.97-1.86 (m, 4 H), 1.51 (d, J=6.4 Hz, 6 H).

Method O

Preparation of 5-(1-isopropyl-5-(1-methylpiperidin-4-yl)-1H-pyrazol-3-yl)-3-(trifluoromethyl)pyridin-2-amine (41)

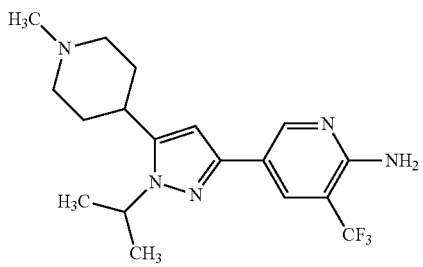 [SMILES: CC(C)n1nc(-c2cnc(N)c(C(F)(F)F)c2)cc1C1CCN(C)CC1]

Step 1—Synthesis of 4-(3-iodo-1-isopropyl-1H-pyrazol-5-yl)-1-methylpiperidine

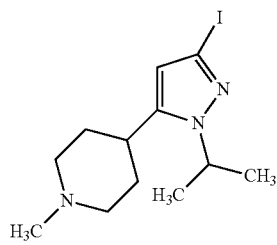 [SMILES: CC(C)n1nc(I)cc1C1CCN(C)CC1]

To a solution of 4-(3-iodo-1-isopropyl-1H-pyrazol-5-yl)piperidine (130 mg, 0.41 mmol) in methanol (5 mL) was added paraformaldehyde (358 mg, 4.3 mmol) at room temperature. After 1 h, sodium cyanoborohydride (81 mg, 1.29 mmol) was added. After another 1 h, the mixture was diluted with water (5 mL), and the resulting solution was extracted with ethyl acetate (3×15 mL). The organic layer was dried over anhydrous sodium sulfate, filtered, and concentrated. Purification by flash column chromatography (80% ethyl acetate in hexanes) afforded product (30 mg, 21% yield). LCMS (ESI) [MH]$^+$=334.0.

Step 2—Synthesis of 5-(1-isopropyl-5-(1-methylpiperidin-4-yl)-1H-pyrazol-3-yl)-3-(trifluoromethyl)pyridin-2-amine Prepared following the method described for the synthesis of 5-(1-isopropyl-5-(1-(oxetan-3-yl)piperidin-4-yl)-1H-pyrazol-3-yl)-3-(trifluoromethyl)pyridin-2-amine using 4-(3-iodo-1-isopropyl-1H-pyrazol-5-yl)-1-methylpiperidine to yield (33 mg, 90% yield). LCMS (ESI) [MH]$^+$=367.9; $^1$H NMR (400 MHz, CD$_3$OD): δ 8.55 (s, 1 H), 8.14 (s, 1 H), 6.45 (s, 1H), 4.66-4.59 (m, 1 H), 3.55-3.52 (m, 2 H), 3.32-3.31 (m, 3 H), 2.85 (s, 3 H), 2.17-2.14 (m, 2H), 2.01-1.98 (m, 2 H), 1.51 (d, J=7.6 Hz, 6 H).

Method P

Preparation of 2-(4-(3-(6-amino-5-(trifluoromethyl)pyridin-3-yl)-1-isopropyl-1H-pyrazol-5-yl)piperidin-1-yl)acetonitrile (52)

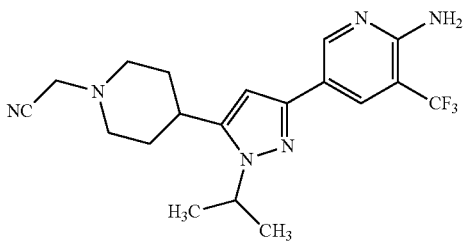 [SMILES: CC(C)n1nc(-c2cnc(N)c(C(F)(F)F)c2)cc1C1CCN(CC#N)CC1]

Step 1—Synthesis of 2-(4-(3-iodo-1-isopropyl-1H-pyrazol-5-yl)piperidin-1-yl)acetonitrile

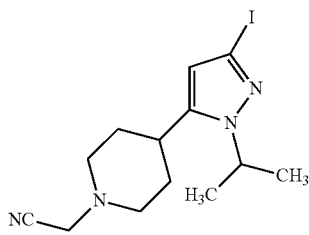 [SMILES: CC(C)n1nc(I)cc1C1CCN(CC#N)CC1]

To a solution of 4-(3-iodo-1-isopropyl-1H-pyrazol-5-yl)piperidine (130 mg, crude, 0.41 mmol) in N,N-dimethylformamide was added cesium carbonate (280 mg, 0.86 mmol). After stirring for 15 min, 2-bromoacetonitrile (154 mg, 1.29 mmol) was added. The reaction mixture was stirred at room temperature for 5 h. Purification by flash column chromatography (80% ethyl acetate in hexanes) afforded product (30 mg, 25% yield). LCMS (ESI) [MH]$^+$=359.1.

Step 2—Synthesis of 2-(4-(3-(6-amino-5-(trifluoromethyl)pyridin-3-yl)-1-isopropyl-1H-pyrazol-5-yl)piperidin-1-yl)acetonitrile Prepared following the method described for the synthesis of 5-(1-isopropyl-5-(1-(oxetan-3-yl)piperidin-4-yl)-1H-pyrazol-3-yl)-3-(trifluoromethyl)pyridin-2-amine using 2-(4-(3-iodo-1-isopropyl-1H-pyrazol-5-yl)piperidin-1-yl)acetonitrile to yield product (9.8 mg, 30% yield). LCMS (ESI) [MH]$^+$=393.1; $^1$H NMR (400 MHz, CD$_3$OD): δ 8.54 (s, 1 H), 8.14 (s, 1 H), 6.39 (s, 1 H), 4.61-4.58 (m, 1 H), 3.70 (s, 2 H), 3.00-2.97 (m, 2 H), 2.80-2.74 (m, 1 H), 2.52-2.46 (m, 2 H), 2.03-1.96 (m, 2 H), 1.84-1.81 (m, 2 H), 1.50 (d, J=6.8 Hz, 6 H).

Method Q

Preparation of 5-(1-isopropyl-5-(1-(2,2,2-trifluoroethyl)piperidin-4-yl)-1H-pyrazol-3-yl)-1H-pyrrolo[2,3-b]pyridine-3-carbonitrile (46)

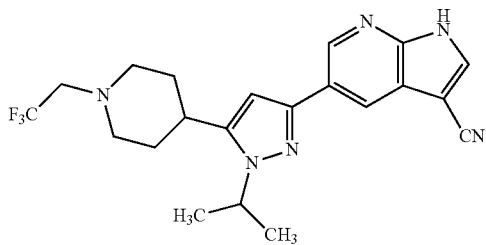 [SMILES: CC(C)n1nc(-c2cnc3[nH]cc(C#N)c3c2)cc1C1CCN(CC(F)(F)F)CC1]

Step 1—Synthesis of tert-butyl 4-(3-(3-cyano-1H-pyrrolo[2,3-b]pyridin-5-yl)-1-isopropyl-1H-pyrazol-5-yl)piperidine-1-carboxylate

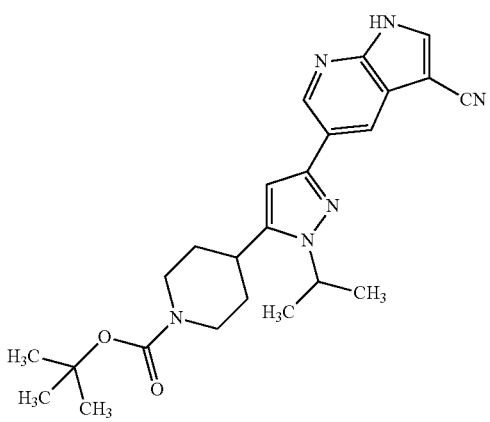 [SMILES: CC(C)n1nc(-c2cnc3[nH]cc(C#N)c3c2)cc1C1CCN(C(=O)OC(C)(C)C)CC1]

Prepared following the method described for the synthesis of 5-(1-isopropyl-5-(1-(oxetan-3-yl)piperidin-4-yl)-1H-pyrazol-3-yl)-3-(trifluoromethyl)pyridin-2-amine using tert-butyl 4-(3-iodo-1-isopropyl-1H-pyrazol-5-yl)piperidine-1-carboxylate and 5-(4,4,5,5-tetramethyl-1,3-dioxolan-2-yl)-1H-pyrrolo[2,3-b]pyridine-3-carbonitrile to yield product (120 mg, 59% yield). LCMS (ESI): [MH]$^+$=435.2.

Step 2—Synthesis of 5-(1-isopropyl-5-(piperidin-4-yl)-1H-pyrazol-3-yl)-1H-pyrrolo[2,3-b]pyridine-3-carbonitrile

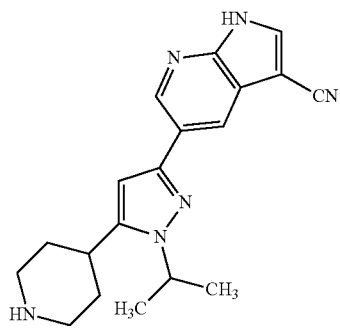 [SMILES: CC(C)n1nc(-c2cnc3[nH]cc(C#N)c3c2)cc1C1CCNCC1]

Prepared following the method described for the synthesis of 4-(3-iodo-1-isopropyl-1H-pyrazol-5-yl)piperidine using tert-butyl 4-(3-(3-cyano-1H-pyrrolo[2,3-b]pyridin-5-yl)-1-isopropyl-1H-pyrazol-5-yl)piperidine-1-carboxylate to afford product (80 mg, 87% crude yield). LCMS (ESI): [MH]$^+$=335.2. The resulting residue was used without further purification.

Step 3—Synthesis of 5-(1-isopropyl-5-(1-(2,2,2-trifluoroethyl)piperidin-4-yl)-1H-pyrazol-3-yl)-1H-pyrrolo[2,3-b]pyridine-3-carbonitrile To a solution of 5-(1-isopropyl-5-(piperidin-4-yl)-1H-pyrazol-3-yl)-1H-pyrrolo[2,3-b]pyridine-3-carbonitrile (80 mg, crude, 0.24 mmol) and disopropylethylamine (93 mg, 0.72 mmol) in tetrahydrofuran (5 mL) was added 2,2,2-trifluoroethyl trifluoromethanesulfonate (166 mg, 0.72 mmol) at room temperature. After 20 h, the mixture was concentrated in vacuo. Purification by preparative HPLC afforded product (6 mg, 6% yield). LCMS (ESI): [MH]$^+$=416.9; $^1$H NMR (400 MHz, CD$_3$OD): δ 8.82 (s, 1 H), 8.43 (s, 1 H), 8.13 (s, 1 H), 6.55 (s, 1 H), 4.65-4.61 (m, 1 H), 3.16-3.08 (m, 4 H), 2.80-2.76 (m, 1 H), 2.59-2.54 (m, 2 H), 1.94-1.84 (m, 4 H), 1.54 (d, J=6.4 Hz, 6 H).

Method R

Preparation of 1-(4-(1-isopropyl-3-(3-methyl-1H-pyrrolo[2,3-b]pyridin-5-yl)-1H-pyrazol-5-yl)piperidin-1-yl)ethanone (49)

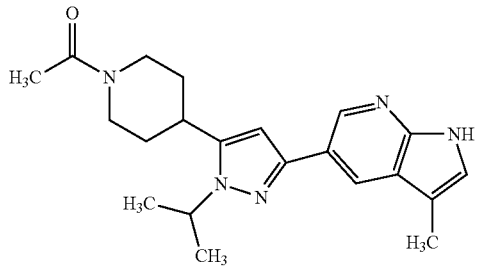 [SMILES: CC(=O)N1CCC(c2cc(-c3cnc4[nH]cc(C)c4c3)nn2C(C)C)CC1]

Step 1—Synthesis of 1-(4-(3-iodo-1-isopropyl-1H-pyrazol-5-yl)piperidin-1-yl)ethanone

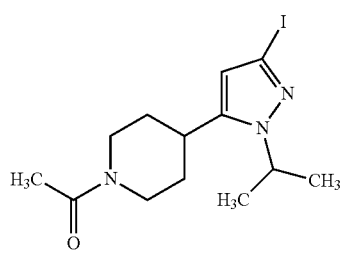 [SMILES: CC(=O)N1CCC(c2cc(I)nn2C(C)C)CC1]

To an ice-cooled solution of 4-(3-iodo-1-isopropyl-1H-pyrazol-5-yl)piperidine (150 mg, 0.47 mmol) and diisopropylethylamine (130 mg, 1 mmol) in dichloromethane (15 mL) was added acetyl chloride (80 mg, 1 mmol). The reaction mixture was warmed to room temperature for 30 min. The reaction mixture was concentrated in vacuo, and the resulting residue was dissolved in ethyl acetate (30 mL).

The organic solution was washed with water (2×20 mL), dried over anhydrous sodium sulfate, filtered, and concentrated to afford product (160 mg, 95% yield). LCMS (ESI): [MH]$^+$=362.1. The resulting residue was used without further purification.

Step 2—Synthesis of 1-(4-(1-isopropyl-3-(3-methyl-1H-pyrrolo[2,3-b]pyridin-5-yl)-1H-pyrazol-5-yl)piperidin-1-yl)ethanone Prepared following the method described for the synthesis of 5-(1-isopropyl-5-(1-(oxetan-3-yl)piperidin-4-yl)-1H-pyrazol-3-yl)-3-(trifluoromethyl)pyridin-2-amine using 1-(4-(3-iodo-1-isopropyl-1H-pyrazol-5-yl)piperidin-1-yl)ethanone and 3-methyl-5-(4,4,5,5-tetramethyl-1,3,2-dioxaborolan-2-yl)-1H-pyrrolo[2,3-b]pyridine to yield product (17.8 mg, 11% yield). LCMS (ESI) [MH]$^+$=366.0; $^1$H NMR (400 MHz, CD$_3$OD): δ 8.59 (s, 1 H), 8.32 (s, 1 H), 7.18 (s, 1 H), 6.49 (s, 1 H), 4.72-4.68 (m, 2 H), 4.10-4.01 (m, 1 H), 3.50-3.47 (m, 1 H), 3.10-3.02 (m, 1 H), 2.85-2.75 (m, 1 H), 2.37 (s, 3 H), 2.17 (s, 3 H), 2.03-1.95 (m, 2 H), 1.80-1.60 (m, 2 H), 1.57 (d, J=6.0 Hz, 6 H).

Method S

Preparation of 5-(1-cyclopentyl-5-(1-(oxetan-3-yl)piperidin-4-yl)-1H-pyrazol-3-yl)-3-(trifluoromethyl)pyridin-2-amine (81)

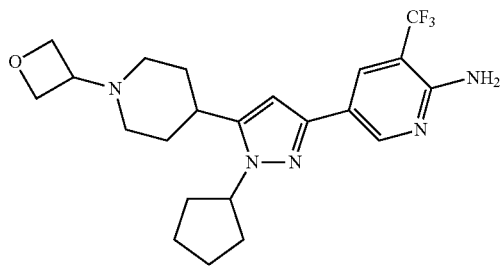 [SMILES: Nc1ncc(-c2cc(C3CCN(C4COC4)CC3)n(C3CCCC3)n2)cc1C(F)(F)F]

Step 1—Synthesis of tert-butyl 4-(3-iodo-1H-pyrazol-5-yl)piperidine-1-carboxylate

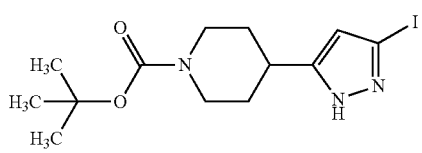 [SMILES: CC(C)(C)OC(=O)N1CCC(c2cc(I)n[nH]2)CC1]

To an ice-cooled solution of tert-butyl 4-(3-amino-1H-pyrazol-5-yl)piperidine-1-carboxylate (35.5 g, 133 mmol) in acetonitrile/water (5:1, 500 mL) was added p-toluenesulfonic acid monohydrate (70.3 g, 414 mmol) and sodium nitrite (17.2 g, 250 mmol). After 30 min, sodium iodide (60.0 g, 400 mmol) in water (85 mL) was added. After 30 min, the reaction mixture was warmed to room temperature. After another 1 h, the reaction mixture was poured into water (1500 mL), and the resulting solution was extracted with ethyl acetate (3×1500 mL). The combined organic layer was washed with saturated aqueous sodium chloride solution (1000 mL), dried over anhydrous sodium sulfate, filtered, and concentrated. Purification by flash column chromatography (25% ethyl acetate in petroleum ether) yielded product (11.4 g, 22.7% yield) as yellow solid. $^1$H NMR (400 MHz, CDCl$_3$): δ 6.21 (s, 1 H), 4.14-4.12 (m, 2 H), 2.90-2.80 (m, 3 H), 1.92-1.89 (m, 2 H), 1.62-1.52 (m, 2 H), 1.46 (s, 9 H).

Step 2—Synthesis of tert-butyl 4-(1-cyclopentyl-3-iodo-1H-pyrazol-5-yl)piperidine-1-carboxylate

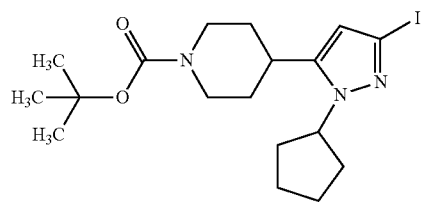 [SMILES: CC(C)(C)OC(=O)N1CCC(c2cc(I)nn2C2CCCC2)CC1]

To a solution of tert-butyl 4-(3-iodo-1H-pyrazol-5-yl)piperidine-1-carboxylate (2.0 g, 5.3 mmol) in N,N-dimethylformamide (20 mL) was added bromocyclopentane (1.18 g, 7.95 mmol) and cesium carbonate (2.6 g, 7.95 mmol). The mixture was stirred at room temperature for 4 h. Ethyl acetate (80 mL) was added to the reaction mixture, and the resulting suspension was filtered. The filtrate was concentrated in vacuo. Purification by flash column chromatography (100% petroleum ether→10% ethyl acetate in petroleum ether) provided desired product (511.9 mg, 25% yield, R$_f$=0.4 in 8:1 petroleum ether/ethyl acetate). LCMS (ESI): [MH]$^+$=445.9; $^1$H NMR (400 MHz, CDCl$_3$): δ 6.11 (s, 1 H), 4.54-4.46 (m, 1 H), 4.30-4.12 (m, 2 H), 2.80-2.71 (m, 3 H), 2.13-1.93 (m, 6 H), 1.85-1.81 (m, 2 H), 1.75-1.60 (m, 2 H), 1.59-1.52 (m, 2 H), 1.37 (s, 9 H).

Step 3—Synthesis of 4-(1-cyclopentyl-3-iodo-1H-pyrazol-5-yl)piperidine

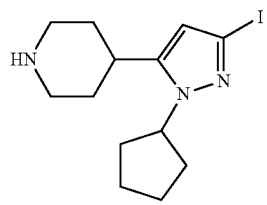 [SMILES: Ic1cc(C2CCNCC2)n(C2CCCC2)n1]

Prepared following the method described for the synthesis of 4-(3-iodo-1-isopropyl-1H-pyrazol-5-yl)piperidine using tert-butyl 4-(1-cyclopentyl-3-iodo-1H-pyrazol-5-yl)piperidine-1-carboxylate to afford product (310 mg, 100% crude yield)). LCMS (ESI): [MH]$^+$=346.1. The resulting residue was used without further purification.

Step 4—Synthesis of 4-(1-cyclopentyl-3-iodo-1H-pyrazol-5-yl)-1-(oxetan-3-yl)piperidine

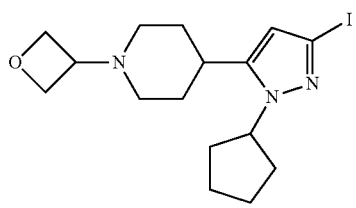 [SMILES: Ic1cc(C2CCN(C3COC3)CC2)n(C2CCCC2)n1]

Prepared following the method described for the synthesis of 4-(3-iodo-1-isopropyl-1H-pyrazol-5-yl)-1-(oxetan-3-yl)piperidine using 4-(1-cyclopentyl-3-iodo-1H-pyrazol-5-yl)piperidine to afford product (200 mg, 58% yield). LCMS (ESI): [MH]⁺=401.9.

Step 5—Synthesis of 5-(1-cyclopentyl-5-(1-(oxetan-3-yl)piperidin-4-yl)-1H-pyrazol-3-yl)-3-(trifluoromethyl)pyridin-2-amine Prepared following the method described for the synthesis of 5-(1-isopropyl-5-(1-(oxetan-3-yl)piperidin-4-yl)-1H-pyrazol-3-yl)-3-(trifluoromethyl)pyridin-2-amine using 4-(1-cyclopentyl-3-iodo-1H-pyrazol-5-yl)-1-(oxetan-3-yl)piperidine to afford product (5.1 mg, 4.5% yield). LCMS (ESI): [MH]⁺=436.0; ¹H NMR (400 MHz, CD₃OD) δ 8.54 (s, 1 H), 8.13 (s, 1 H), 6.42 (s, 1 H), 4.78-4.74 (m, 3 H), 4.69-4.66 (m, 2 H), 3.77-3.70 (m, 1 H), 3.06-3.03 (m, 2 H), 2.94-2.86 (m, 1 H), 2.28-2.23 (m, 2 H), 2.16-1.97 (m, 8 H), 1.88-1.81 (m, 4 H).

Method T

Preparation of 3-chloro-5-(1-(3,3-difluorocyclopentyl)-5-(1-(oxetan-3-yl)piperidin-4-yl)-1H-pyrazol-3-yl)pyridin-2-amine (91)

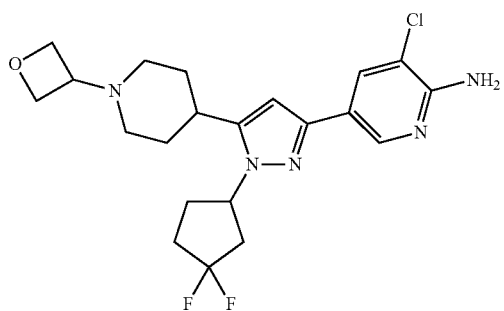 [SMILES: Nc1ncc(-c2cc(C3CCN(C4COC4)CC3)n(C3CCC(F)(F)C3)n2)cc1Cl]

Step 1—Synthesis of tert-butyl 4-(3-iodo-1-(3-oxocyclopentyl)-1H-pyrazol-5-yl)piperidine-1-carboxylate and tert-butyl 4-(5-iodo-1-(3-oxocyclopentyl)-1H-pyrazol-3-yl)piperidine-1-carboxylate

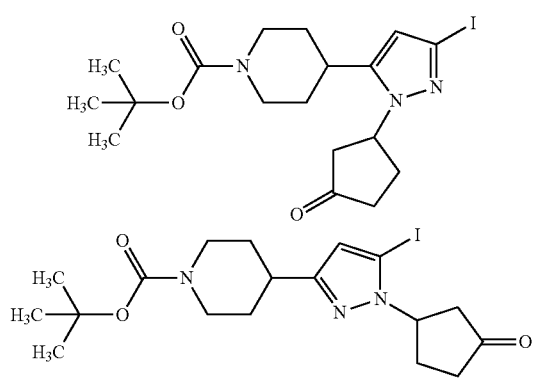

To a solution of tert-butyl 4-(3-iodo-1H-pyrazol-5-yl)piperidine-1-carboxylate (2 g, 5.3 mmol) in dichloromethane (20 mL) was added hafnium(IV) chloride (170 mg, 0.5 mmol) and cyclopent-2-enone (1.3 g, 15.9 mmol). The mixture was stirred at room temperature for 12 h. The reaction mixture was filtrated, and the filtrate was used for next step without further purification. LCMS (ESI): [MH-100]⁺=359.8; [MH-56+39]⁺=441.9.

Step 2—Synthesis of tert-butyl 4-(1-(3,3-difluorocyclopentyl)-3-iodo-1H-pyrazol-5-yl)piperidine-1-carboxylate

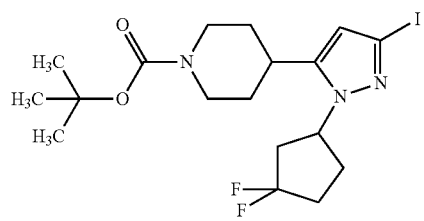 [SMILES: CC(C)(C)OC(=O)N1CCC(c2cc(I)nn2C2CCC(F)(F)C2)CC1]

To an ice-cooled solution of tert-butyl 4-(3-iodo-1-(3-oxocyclopentyl)-1H-pyrazol-5-yl)piperidine-1-carboxylate and tert-butyl 4-(5-iodo-1-(3-oxocyclopentyl)-1H-pyrazol-3-yl)piperidine-1-carboxylate (crude) in dichloromethane (20 mL) was added DAST (15 mL). The reaction mixture was stirred at 20° C. for 12 h. Saturated aqueous sodium bicarbonate solution (30 mL) was added drop-wise, and the resulting mixture was extracted with ethyl acetate (3×30 mL) and saturated aqueous sodium chloride solution (30 mL). The organic layer was dried over anhydrous sodium sulfate, filtered, and concentrated. Purification by flash column chromatography (100% petroleum ether→20% ethyl acetate in petroleum ether) provided product (400 mg, 15.6% yield, R_f=0.3 in 5:1 petroleum ether/ethyl acetate). ¹H NMR (400 MHz, CDCl₃): δ 6.14 (s, 1 H), 4.69-4.65 (m, 1 H), 4.23-4.20 (m, 2 H), 2.85-2.67 (m, 4 H), 2.55-2.46 (m, 2 H), 2.40-2.35 (m, 1 H), 2.26-2.14 (m, 2 H), 2.81-2.78 (m, 2 H), 1.63-1.53 (m, 2 H), 1.47 (s, 9 H).

Step 3—Synthesis of 4-(1-(3,3-difluorocyclopentyl)-3-iodo-1H-pyrazol-5-yl)piperidine

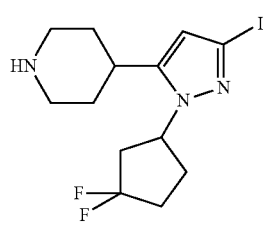 [SMILES: FC1(F)CCC(n2nc(I)cc2C2CCNCC2)C1]

Prepared following the method described for the synthesis of 4-(3-iodo-1-isopropyl-1H-pyrazol-5-yl)piperidine using tert-butyl 4-(1-(3,3-difluorocyclopentyl)-3-iodo-1H-pyrazol-5-yl)piperidine-1-carboxylate to afford product (160 mg, crude, 100% yield). LCMS (ESI): [MH]⁺=381.8. The resulting residue was used without further purification.

Step 4—Synthesis of 4-(1-(3,3-difluorocyclopentyl)-3-iodo-1H-pyrazol-5-yl)-1-(oxetan-3-yl)piperidine

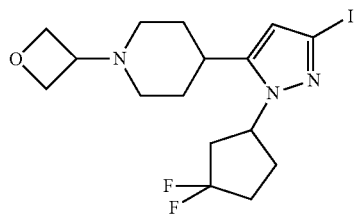 [SMILES: FC1(F)CCC(n2nc(I)cc2C2CCN(C3COC3)CC2)C1]

Prepared following the method described for the synthesis of 4-(3-iodo-1-isopropyl-1H-pyrazol-5-yl)-1-(oxetan-3-yl)piperidine using 4-(1-(3,3-difluorocyclopentyl)-3-iodo-1H-pyrazol-5-yl)piperidine to afford product (70 mg, yield 38.3%). LCMS (ESI): [MH]$^+$=437.9.

Step 5—Synthesis of 3-chloro-5-(1-(3,3-difluorocyclopentyl)-5-(1-(oxetan-3-yl)piperidin-4-yl)-1H-pyrazol-3-yl)pyridin-2-amine Prepared following the method described for the synthesis of 5-(1-isopropyl-5-(1-(oxetan-3-yl)piperidin-4-yl)-1H-pyrazol-3-yl)-3-(trifluoromethyl)pyridin-2-amine using 4-(1-cyclopentyl-3-iodo-1H-pyrazol-5-yl)-1-(oxetan-3-yl)piperidine and 5-(4,4,5,5-tetramethyl-1,3,2-dioxaborolan-2-yl)-3-chloropyridin-2-amine to afford product (15.6 mg, yield 22.3%). MS (ESI): [MH]$^+$=438.2; $^1$H NMR (400 MHz, CD$_3$OD): δ 8.28 (s, 1 H), 7.98 (s, 1 H), 6.40 (s, 1 H), 4.97-4.93 (m, 1 H), 4.71 (t, J=6.8 Hz, 2 H), 4.63 (t, J=6.8 Hz, 2 H), 3.58-3.53 (m, 1 H), 2.92-2.89 (m, 2 H), 2.84-2.71 (m, 2 H), 2.63-2.51 (m, 2 H), 2.34-2.14 (m, 3 H), 2.08-2.01 (m, 2 H), 1.95-1.92 (m, 2 H), 1.83-1.73 (m, 2 H).

Method U

Preparation of 5-(5-(1-(oxetan-3-yl)piperidin-4-yl)-1-(tetrahydrofuran-3-yl)-1H-pyrazol-3-yl)-3-(trifluoromethyl)pyridin-2-amine (97)

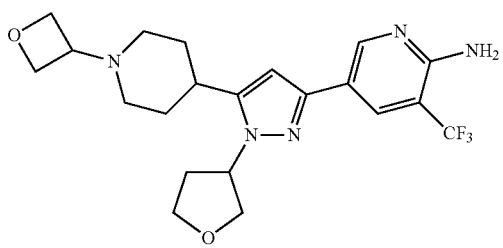 [SMILES: Nc1ncc(-c2cc(C3CCN(C4COC4)CC3)n(C3CCOC3)n2)cc1C(F)(F)F]

Step 1—Synthesis of tert-butyl 4-(3-iodo-1-(tetrahydrofuran-3-yl)-1H-pyrazol-5-yl)piperidine-1-carboxylate

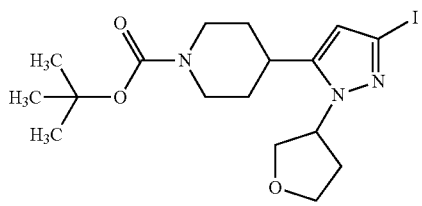 [SMILES: CC(C)(C)OC(=O)N1CCC(c2cc(I)nn2C2CCOC2)CC1]

To an ice-cooled solution of tert-butyl 4-(3-iodo-1H-pyrazol-5-yl)piperidine-1-carboxylate (2.0 g, 5.3 mmol) in N,N-dimethylformamide (30 mL) was added sodium hydride (637 mg, 26.5 mmol, 60% in mineral oil. After 15 min, tetrahydrofuran-3-yl methanesulfonate (2.03 g, 12.2 mmol) was added to dropwise, and the reaction mixture was warmed to room temperature. After 1 h, the mixture was warmed to 90° C. for 2 h. Excess sodium hydride was quenched with the addition of methonol (20 mL) at room temperature. The reaction mixture was extracted with ethyl acetate (3×60 mL). The combined organic layer was washed with saturated aqueous sodium chloride solution (300 mL), dried over anhydrous sodium sulfate, filtered, and concentrated. Purification by flash column chromatography (100% petroleum ether→30% ethyl acetate in petroleum ether) afforded product (730 mg, 31.2% yield, R$_f$=0.3 in 2:1 petroleum ether/ethyl acetate).

Step 2—Synthesis of 4-(3-iodo-1-(tetrahydrofuran-3-yl)-1H-pyrazol-5-yl)piperidine

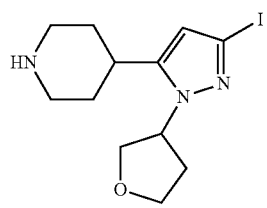

Prepared following the method described for the synthesis of 4-(3-iodo-1-isopropyl-1H-pyrazol-5-yl)piperidine using tert-butyl 4-(3-iodo-1-(tetrahydrofuran-3-yl)-1H-pyrazol-5-yl)piperidine-1-carboxylate to afford product (202 mg, 100% crude yield). LCMS (ESI): [MH]$^+$=347.8. The resulting residue was used without further purification.

Step 3—Synthesis of 4-(3-iodo-1-(tetrahydrofuran-3-yl)-1H-pyrazol-5-yl)-1-(oxetan-3-yl)piperidine

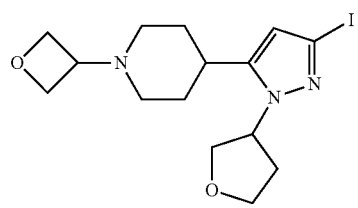 [SMILES: Ic1cc(C2CCN(C3COC3)CC2)n(C2CCOC2)n1]

Prepared following the method described for the synthesis of 4-(3-iodo-1-isopropyl-1H-pyrazol-5-yl)-1-(oxetan-3-yl)piperidine using 4-(3-iodo-1-(tetrahydrofuran-3-yl)-1H-pyrazol-5-yl)piperidine to afford product (100 mg, 86% yield). LCMS (ESI) [MH]$^+$=404.0.

Step 4—Synthesis of 5-(5-(1-(oxetan-3-yl)piperidin-4-yl)-1-(tetrahydrofuran-3-yl)-1H-pyrazol-3-yl)-3-(trifluoromethyl)pyridin-2-amine Prepared following the method described for the synthesis of 5-(1-isopropyl-5-(1-(oxetan-3-yl)piperidin-4-yl)-1H-pyrazol-3-yl)-3-(trifluoromethyl)pyridin-2-amine using 4-(1-cyclopentyl-3-iodo-1H-pyrazol-5-yl)-1-(oxetan-3-yl)

piperidine to afford product (34.5 mg, 32% yield). MS (ESI) [MH]⁺=438.2; ¹H NMR (400 MHz, Methanol-d₄): δ 8.58 (s, 1 H), 8.18 (s, 1 H), 6.49 (s, 1 H), 5.16-5.10 (m, 1 H), 4.81-4.77 (m, 2 H), 4.72-4.68 (m, 2 H), 4.29-4.27 (m, 1 H), 4.25-4.23 (m, 1 H), 4.17-3.96 (m, 2 H), 3.81-3.77 (m, 1 H), 3.11-3.08 (m, 2 H), 2.98-2.92 (m, 1 H), 2.45-2.39 (m, 2 H), 2.38-2.28 (m, 2 H), 2.09-2.01 (m, 2 H), 1.91-1.80 (m, 2 H).

Method V

Preparation of 5-(1-methyl-5-(1-(oxetan-3-yl)piperidin-4-yl)-1H-pyrazol-3-yl)-3-(trifluoromethyl)-1H-pyrrolo[2,3-b]pyridine (68)

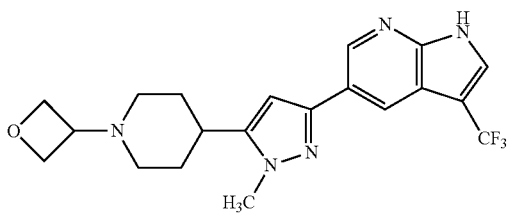 [SMILES: Cn1nc(-c2cnc3[nH]cc(C(F)(F)F)c3c2)cc1C1CCN(C2COC2)CC1]

Step 1—Synthesis of tert-butyl 4-(3-iodo-1-methyl-1H-pyrazol-5-yl)piperidine-1-carboxylate

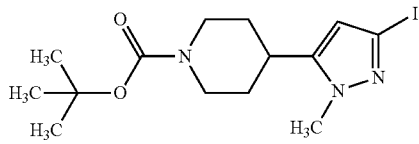 [SMILES: Cn1nc(I)cc1C1CCN(C(=O)OC(C)(C)C)CC1]

Prepared following the method described for the synthesis of tert-butyl 4-(1-cyclopentyl-3-iodo-1H-pyrazol-5-yl)piperidine-1-carboxylate using of tert-butyl 4-(3-iodo-1H-pyrazol-5-yl)piperidine-1-carboxylate and iodomethane to afford product (300 mg, 16% yield, R$_f$=0.3 in 3:1 petroleum ether/ethyl acetate) LCMS (ESI): [MH]⁺=391.8.

Step 2—Synthesis of 4-(3-iodo-1-methyl-1H-pyrazol-5-yl)piperidine

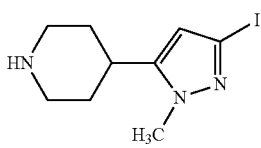

Prepared following the method described for the synthesis of 4-(3-iodo-1-isopropyl-1H-pyrazol-5-yl)piperidine using tert-butyl 4-(3-iodo-1-methyl-1H-pyrazol-5-yl)piperidine-1-carboxylate to afford product (220 mg, 99% crude yield). LCMS (ESI): [MH]⁺=291.9. The resulting residue was used without further purification.

Step 3—Synthesis of 4-(3-iodo-1-methyl-1H-pyrazol-5-yl)-1-(oxetan-3-yl)piperidine

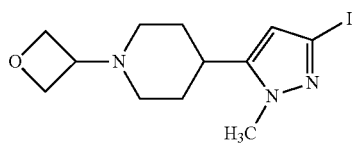 [SMILES: Cn1nc(I)cc1C1CCN(C2COC2)CC1]

Prepared following the method described for the synthesis of 4-(3-iodo-1-isopropyl-1H-pyrazol-5-yl)-1-(oxetan-3-yl)piperidine using 4-(3-iodo-1-methyl-1H-pyrazol-5-yl)piperidine to afford product (160 mg, 61.0% yield). LCMS (ESI): [MH]⁺=347.9.

Step 4—Synthesis of 5-(1-methyl-5-(1-(oxetan-3-yl)piperidin-4-yl)-1H-pyrazol-3-yl)-3-(trifluoromethyl)-1H-pyrrolo[2,3-b]pyridine Prepared following the method described for the synthesis of 5-(1-isopropyl-5-(1-(oxetan-3-yl)piperidin-4-yl)-1H-pyrazol-3-yl)-3-(trifluoromethyl)pyridin-2-amine using 4-(3-iodo-1-methyl-1H-pyrazol-5-yl)-1-(oxetan-3-yl)piperidine and 3-trifluoromethyl-5-(4,4,5,5-tetramethyl-1,3,2-dioxaborolan-2-yl)-1H-pyrrolo[2,3-b]pyridine to afford product (10 mg, 13.1% yield). LCMS (ESI): [MH]⁺=405.9; ¹H NMR (400 MHz, CD₃OD): δ 8.75 (s, 1 H), 8.39 (s, 1 H), 7.84 (s, 1 H), 6.58 (s, 1 H), 4.77-4.74 (m, 2 H), 4.69-4.66 (m, 2 H), 3.89 (s, 3 H), 3.71-3.68 (m, 1 H), 3.04-3.01 (m, 2 H), 2.88-2.82 (m, 1 H), 2.24-2.17 (m, 2 H), 2.07-2.04 (m, 2 H), 1.89-1.82 (m, 2 H).

Method W

Preparation of 1-(4-(1-methyl-3-(3-(trifluoromethyl)-1H-pyrrolo[2,3-b]pyridin-5-yl)-1H-pyrazol-5-yl)piperidin-1-yl)ethanone (48)

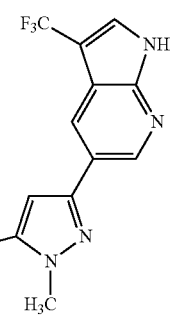

Step 1—Synthesis of 1-(4-(3-iodo-1-methyl-1H-pyrazol-5-yl)piperidin-1-yl)ethanone

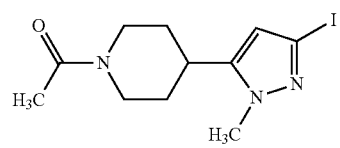

To a solution of 4-(3-iodo-1-methyl-1H-pyrazol-5-yl)piperidine (50 mg, 0.153 mmol) in tetrahydrofuran (5 mL) was added pyridine (0.5 mL) followed acetyl chloride (36 mg, 0.459 mmol). The reactions mixture was stirred at room temperature for 1 h. The reaction mixture was concentrated in vacuo, and the residue was dissolved in ethyl acetate (15 mL). The organic solution was washed with water (2×10 mL). The organic layer was dried over anhydrous sodium sulfate, filtered, and concentrated in vacuo to afford product (50 mg, 88% crude yield). LCMS (ESI): [MH]$^+$=333.8. The resulting residue was used without further purification.

Step2—Synthesis of 1-(4-(1-methyl-3-(3-(trifluoromethyl)-1H-pyrrolo[2,3-b]pyridin-5-yl)-1H-pyrazol-5-yl)piperidin-1-yl)ethanone Prepared following the method described for the synthesis of 5-(1-isopropyl-5-(1-(oxetan-3-yl)piperidin-4-yl)-1H-pyrazol-3-yl)-3-(trifluoromethyl)pyridin-2-amine using 1-(4-(3-iodo-1-methyl-1H-pyrazol-5-yl)piperidin-1-yl)ethanone and 3-trifluoromethyl-5-(4,4,5,5-tetramethyl-1,3,2-dioxaborolan-2-yl)-1H-pyrrolo[2,3-b]pyridine to afford product (20 mg, 40% yield). LCMS (ESI): [MH]$^+$=392.2; $^1$H NMR (400 MHz, CD$_3$OD): δ 8.77 (s, 1 H), 8.41 (s, 1 H), 7.89 (s, 1 H), 6.61 (s, 1 H), 4.71-4.68 (m, 1 H), 4.10-4.05 (m, 1 H), 3.94 (s, 3 H), 3.33-3.29 (m, 1 H), 3.12-3.05 (m, 1 H), 2.85-2.79 (m, 1 H), 2.17 (s, 3 H), 2.10-2.03 (m, 2 H), 1.80-1.64 (m, 2 H).

Method X

Preparation of 5-(1-(cyclopropylmethyl)-5-(tetrahydrofuran-3-yl)-1H-pyrazol-3-yl)-3-methyl-1H-pyrrolo[2,3-b]pyridine (13)

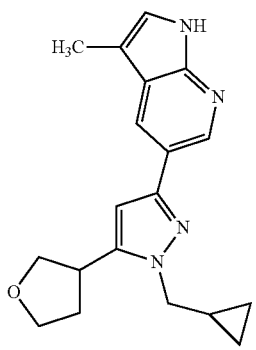 [SMILES: Cc1c[nH]c2ncc(-c3cc(C4CCOC4)n(CC4CC4)n3)cc12]

Step 1—Synthesis of methyl tetrahydrofuran-3-carboxylate

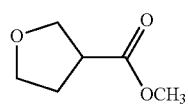

To a solution of tetrahydrofuran-3-carboxylic acid (50 g, 0.431 mol) and potassium carbonate (89.2 g, 0.647 mol) in N,N-dimethylformamide (500 mL) was added iodomethane (73.4 g, 0.517 mol) at 32° C. and stirred for 5 h. The reaction solution was filtered, and the filtrate was concentrated in vacuo to afford crude product (53 g, 95% yield). $^1$H NMR (400 MHz, CDCl$_3$): δ 3.98-3.76 (m, 4 H), 3.69 (s, 3 H), 3.11-3.04 (m, 1 H), 2.23-2.09 (m, 2 H).

Step 2—Synthesis of 3-oxo-3-(tetrahydrofuran-3-yl)propanenitrile

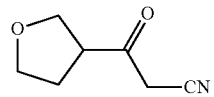

To an ice-cooled solution of methyl tetrahydrofuran-3-carboxylate (50 g, 0.385 mol) and acetonitrile (47 g, 1.154 mol) in tetrahydrofuran (500 mL) was added potassium tert-butoxide (129 g, 1.15 mol) portion-wise. The resulting mixture was warmed to room temperature and stirred for 1 h. The reaction mixture was poured into saturated aqueous ammonium chloride solution (1 L) and extracted with ethyl acetate (3×400 mL). The collected organic layers were washed with saturated aqueous sodium chloride solution (400 mL), dried over sodium sulfate, and concentrated in vacuo to afford product (41 g, crude, 76.6% yield).

Step 3—Synthesis of 5-(tetrahydrofuran-3-yl)-1H-pyrazol-3-amine

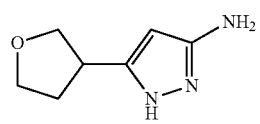 [SMILES: Nc1cc(C2CCOC2)[nH]n1]

To a stirred solution of 3-oxo-3-(tetrahydrofuran-3-yl)propanenitrile (41 g, 0.295 mol) in 2-propanol (400 mL) was added hydrazine mono hydrate (44.2 g, 0.885 mol). The reaction mixture was heated to 80° C. for 10 h. After removal of the solvent, the residue was dissolved in dichloromethane (500 mL), washed with water (3×150 mL). The organic layer was dried over anhydrous sodium sulfate, filtered, and concentrated in vacuo to afford product (38.5 g, crude, 85.4% yield).

Step 4—Synthesis of 3-iodo-5-(tetrahydrofuran-3-yl)-1H-pyrazole

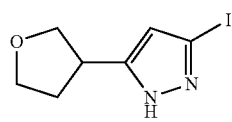 [SMILES: Ic1cc(C2CCOC2)[nH]n1]

To an ice-cooled solution of 5-(tetrahydrofuran-3-yl)-1H-pyrazol-3-amine (18 g, 0.118 mmol) in acetonitrile/water (5:1, 240 mL) was added p-toluenesulfonic acid monohydrate (30 g, 0.176 mmol) and sodium nitrite (12.2 g, 0.176 mmol). After 30 min, sodium iodide (26.5 g, 0.176 mmol) was slowly added, and the reaction mixture was warmed to room temperature for 1 h. The reaction mixture was poured into water (600 mL) and extracted with ethyl acetate (3×300 mL). The organic layers were washed with saturated aqueous sodium chloride solution (500 mL), dried over anhydrous sodium sulfate, and concentrated. Purification of the resulting residue by flash column chromatography (100% petroleum ether→30% ethyl acetate in petroleum ether) afforded a yellow solid (11 g, 35% yield). $^1$H NMR (400 MHz, CDCl$_3$): δ 5.73 (s, 1 H), 3.99-3.92 (m, 2 H), 3.86-3.80 (m, 1 H), 3.78-3.72 (m, 1 H), 3.50-3.38 (m, 1 H), 2.40-2.26 (m, 1 H), 1.98-1.95 (m, 1 H).

Step 5—Synthesis of 1-(cyclopropylmethyl)-3-iodo-5-(tetrahydrofuran-3-yl)-1H-pyrazole

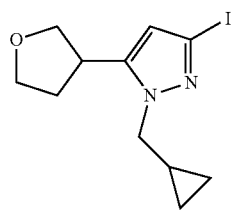 [SMILES: Ic1cc(C2CCOC2)n(CC2CC2)n1]

To a solution of 3-iodo-5-(tetrahydrofuran-3-yl)-1H-pyrazole (0.4 g, 1.52 mmol) in N,N-dimethylformamide (10 mL) was added (bromomethyl)cyclopropane (0.61 g, 4.55 mmol) and potassium carbonate (0.63 g, 4.55 mmol). The reaction mixture was stirred at 80° C. for 3 h under N$_2$. Ethyl acetate (60 mL) was added to the reaction mixture, and the resulting suspension was filtered. The filtrate was concentrated in vacuo. Purification by flash column chromatography (12% ethyl acetate in petroleum ether) afforded product (0.14 g, yield 29%, R$_f$=0.4 in 8:1 petroleum ether/ethyl acetate): $^1$H NMR (400 MHz, CDCl$_3$): δ 9.11 (br s, 1 H), 6.39 (s, 1 H), 4.19 (d, J=6.8 Hz, 2 H), 4.09-3.99 (m, 2 H), 3.94-3.88 (m, 1 H), 3.47-3.43 (m, 1 H), 2.42-2.35 (m, 1 H), 2.00-1.93 (m, 1 H), 1.25-1.23 (m, 1 H), 0.63-0.61 (m, 2 H), 0.53-0.49 (m, 2 H).

Step 6—Synthesis of 5-(1-(cyclopropylmethyl)-5-(tetrahydrofuran-3-yl)-1H-pyrazol-3-yl)-3-methyl-1H-pyrrolo[2,3-b]pyridine To a microwave vial charged with 1-(cyclopropylmethyl)-3-iodo-5-(tetrahydrofuran-3-yl)-1H-pyrazole (50 mg, 0.157 mmol), and 3-methyl-5-(4,4,5,5-tetramethyl-1,3,2-dioxaborolan-2-yl)-1H-pyrrolo[2,3-b]pyridine (48 mg, 0.189 mmol) and cesium carbonate (154 mg, 0.472 mmol) in 1,4-dioxane/water (10:1, 3 mL) was added 1,1'-bis(diphenylphosphino)ferrocene-palladium(II) dichloride (23 mg, 0.031 mmol) under nitrogen. The vial was sealed and heated by microwave irradiation at 100° C. for 20 min. The reaction mixture was concentrated in vacuo, and resulting residue was purified by preparative HPLC to provide racemic product (45 mg, 88% yield). LCMS (ESI): [MH]$^+$=323.0; $^1$H NMR (400 MHz, CD$_3$OD): δ 8.60 (s, 1 H), 8.31 (s, 1 H), 7.17 (s, 1 H), 6.60 (s, 1 H), 4.16 (t, J=8.0 Hz, 1 H), 4.10-4.05 (m, 3H), 3.97-3.92 (m, 1 H), 3.82-3.79 (m, 1 H), 3.64-3.60 (m, 1 H), 2.49-2.35 (m, 1 H), 2.25 (s, 3 H), 2.12-2.03 (m, 1 H), 1.35-1.29 (m, 1 H), 0.65-0.58 (m 2 H), 0.49-0.38 (m, 2 H). The racemic product was further purified by chiral supercritical fluid chromatography (Berger MG II, 21.1×150 mm, 5 uM, 70 mL/min, 35% methanol in 0.1% ammonium hydroxide, Column: Chiralpak AD) Enantiomer 1 retention time=0.61 min; Enantiomer 2 retention time=0.90 min.

Method Y

Preparation of 3-chloro-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine (154)

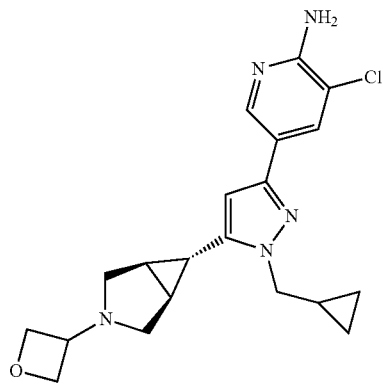 [SMILES: Nc1ncc(-c2cc([C@H]3[C@@H]4CN(C5COC5)C[C@@H]43)n(CC3CC3)n2)cc1Cl]

Step 1—Synthesis of (1R,5S,6r)-tert-butyl 6-(1-(cyclopropylmethyl)-3-iodo-1H-pyrazol-5-yl)-3-azabicyclo[3.1.0]hexane-3-carboxylate

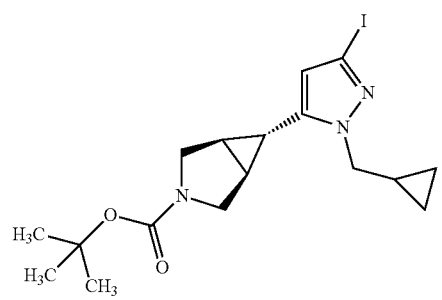 [SMILES: CC(C)(C)OC(=O)N1C[C@@H]2[C@H](C1)[C@H]2c1cc(I)nn1CC1CC1]

Prepared following the method described for the synthesis of (1R,5S,6r)-tert-butyl 6-(3-iodo-1-isopropyl-1H-pyrazol-5-yl)-3-azabicyclo[3.1.0]hexane-3-carboxylate using (bromomethyl)cyclopropane to afford product. LCMS (ESI): [MH]$^+$=430.2.

Step 2—Synthesis of (1R,5S,6r)-tert-butyl 6-(3-(6-amino-5-chloropyridin-3-yl)-1-(cyclopropylmethyl)-1H-pyrazol-5-yl)-3-azabicyclo[3.1.0]hexane-3-carboxylate

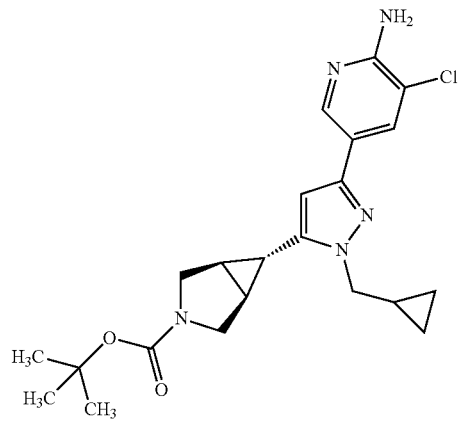 [SMILES: CC(C)(C)OC(=O)N1C[C@@H]2[C@H](C1)[C@H]2c1cc(-c2cnc(N)c(Cl)c2)nn1CC1CC1]

Prepared following the method described for the synthesis of 5-(1-isopropyl-5-((1R,5S,6R)-3-(oxetan-3-yl)-3-azabicyclo[3.1.0]hexan-6-yl)-1H-pyrazol-3-yl)-3-(t rifluoromethyl) pyridin-2-amine using (1R,5S,6r)-tert-butyl 6-(1-(cyclopropylmethyl)-3-iodo-1H-pyrazol-5-yl)-3-azabicyclo[3.1.0]hexane-3-carboxylate and 5-(4,4,5,5-tetramethyl-1,3-dioxolan-2-yl)-3-(chloro)pyridin-2-amine to afford product. LCMS (ESI): [MH]⁺=431.2; ¹H NMR (400 MHz, CDCl₃): δ 8.29 (s, 1H), 7.94 (s, 1H), 6.03 (s, 1H), 4.99 (s, 2H), 4.04 (d, J=6.8 Hz, 2H), 3.83-3.73 (m, 1H), 3.73-3.62 (m, 1H), 3.54-3.46 (m, 2H), 1.93-1.79 (m, 2H), 1.64-1.57 (m, 1H), 1.46 (s, 9H), 1.30-1.25 (m, 1H), 0.63-0.56 (m, 2H), 0.45-0.38 (m, 2H)

Step 3—Synthesis of 5-(5-((1R,5S,6r)-3-azabicyclo[3.1.0]hexan-6-yl)-1-(cyclopropylmethyl)-1H-pyrazol-3-yl)-3-chloropyridin-2-amine

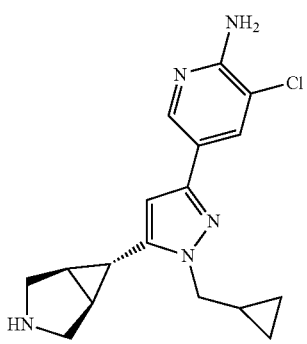 [SMILES: Nc1ncc(-c2cc([C@H]3[C@@H]4CNC[C@@H]43)n(CC3CC3)n2)cc1Cl]

Prepared following the method described for the synthesis of (1R,5S,6r)-6-(3-iodo-1-isopropyl-1H-pyrazol-5-yl)-3-azabicyclo[3.1.0]hexane using of (1R,5S,6r)-tert-butyl 6-(3-(6-amino-5-chloropyridin-3-yl)-1-(cyclopropylmethyl)-1H-pyrazol-5-yl)-3-azabicyclo[3.1.0]hexane-3-carboxylate to afford product. LCMS (ESI): [MH]⁺=330.2;

Step 4—Synthesis of 3-chloro-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine Prepared following the method described for the synthesis of (1R,5S,6r)-6-(3-iodo-1-isopropyl-1H-pyrazol-5-yl)-3-(oxetan-3-yl)-3-azabicyclo[3.1.0]hexane using of 5-(5-((1R,5S,6r)-3-azabicyclo[3.1.0]hexan-6-yl)-1-(cyclopropylmethyl)-1H-pyrazol-3-yl)-3-chloropyridin-2-amine to afford product. LCMS (ESI): [MH]⁺=386; ¹H NMR (400 MHz, CDCl₃): δ 8.30 (d, J=2.0 Hz, 1H), 7.95 (d, J=2.0 Hz, 1H), 6.01 (s, 1H), 4.88 (s, 2H), 4.71 (t, J=6.6 Hz, 2H), 4.63 (t, J=6.1 Hz, 2H), 4.07 (d, J=6.8 Hz, 2H), 3.81 (p, J=6.3 Hz, 1H), 3.16 (d, J=8.8 Hz, 2H), 2.50 (d, J=8.7 Hz, 2H), 2.29-2.19 (m, 1H), 1.83-1.74 (m, 2H), 1.44-1.23 (m, 1H), 0.65-0.53 (m, 2H), 0.47-0.38 (m, 2H).

Method Z

Preparation of 3-chloro-5-(5-((1R,5 S,6r)-3-(2-methoxyethyl)-3-azabicyclo[3.1.0]hexan-6-yl)-1-(2,2,2-trifluoroethyl)-1H-pyrazol-3-yl)pyridin-2-amine (116)

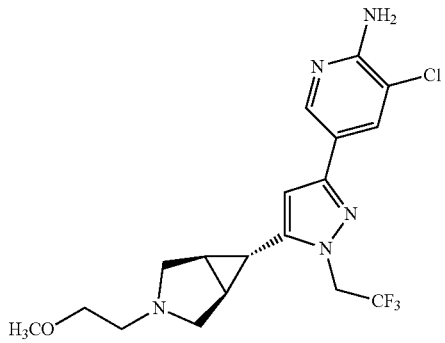 [SMILES: COCCN1C[C@@H]2[C@H](C1)[C@H]2c1cc(-c2cnc(N)c(Cl)c2)nn1CC(F)(F)F]

Step 1—Synthesis of (1R,5S,6r)-tert-butyl 6-(3-iodo-1-(2,2,2-trifluoroethyl)-1H-pyrazol-5-yl)-3-azabicyclo[3.1.0]hexane-3-carboxylate

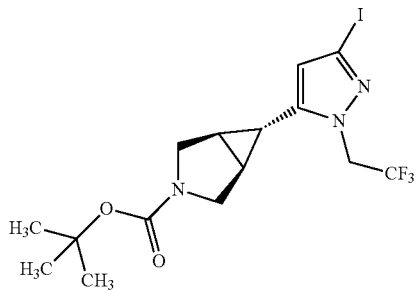 [SMILES: CC(C)(C)OC(=O)N1C[C@@H]2[C@H](C1)[C@H]2c1cc(I)nn1CC(F)(F)F]

Prepared following the method described for the synthesis of (1R,5S,6r)-tert-butyl 6-(3-iodo-1-isopropyl-1H-pyrazol-5-yl)-3-azabicyclo[3.1.0]hexane-3-carboxylate using 1,1,1-trifluoro-2-iodoethane to afford product. LCMS (ESI): [MH]⁺=458.4; ¹H NMR (400 MHz, CDCl₃): δ 6.06 (s, 1H), 4.72 (q, J=8.2 Hz, 2H), 3.80-3.72 (m, 1H), 3.72-3.62 (m, 1H), 3.52-3.41 (m, 2H), 1.88-1.78 (m, 2H), 1.58-1.54 (m, 1H), 1.47 (s, 9H).

Step 2—Synthesis of (1R,5S,6r)-tert-butyl 6-(3-(6-amino-5-chloropyridin-3-yl)-1-(2,2,2-trifluoroethyl)-1H-pyrazol-5-yl)-3-azabicyclo[3.1.0]hexane-3-carboxylate

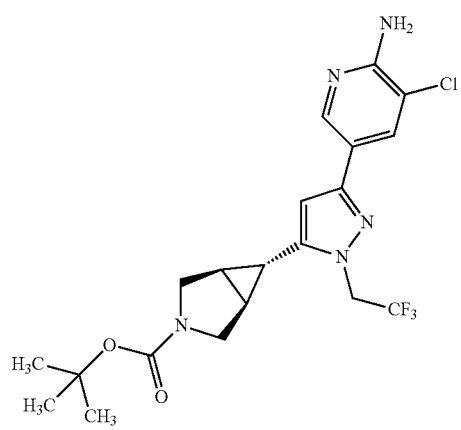 [SMILES: CC(C)(C)OC(=O)N1C[C@@H]2[C@H](C1)[C@H]2c1cc(-c2cnc(N)c(Cl)c2)nn1CC(F)(F)F]

Prepared following the method described for the synthesis of 5-(1-isopropyl-5-((1R,5S,6R)-3-(oxetan-3-yl)-3-azabicyclo[3.1.0]hexan-6-yl)-1H-pyrazol-3-yl)-3-(t rifluoromethyl)pyridin-2-amine using (1R,5S,6r)-tert-butyl 6-(3-iodo-1-(2,2,2-trifluoroethyl)-1H-pyrazol-5-yl)-3-azabicyclo[3.1.0]hexane-3-carboxylate and 5-(4,4,5,5-tetramethyl-1,3-dioxolan-2-yl)-3-(chloro)pyridin-2-amine to afford product. LCMS (ESI): [MH]⁺=458.1.

Step 3—Synthesis of 5-(5-((1R,5S,6r)-3-azabicyclo[3.1.0]hexan-6-yl)-1-(2,2,2-trifluoroethyl)-1H-pyrazol-3-yl)-3-chloropyridin-2-amine

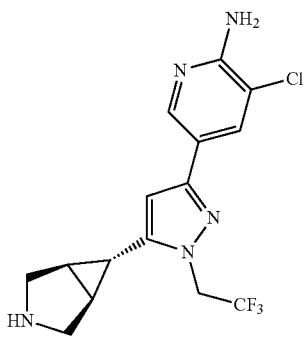 [SMILES: Nc1ncc(-c2cc([C@H]3[C@@H]4CNC[C@@H]43)n(CC(F)(F)F)n2)cc1Cl]

Prepared following the method described for the synthesis of (1R,5S,6r)-6-(3-iodo-1-isopropyl-1H-pyrazol-5-yl)-3-azabicyclo[3.1.0]hexane using of (1R,5S,6r)-tert-butyl 6-(3-(6-amino-5-chloropyridin-3-yl)-1-(2,2,2-trifluoroethyl)-1H-pyrazol-5-yl)-3-azabicyclo[3.1.0]hexane-3-carboxylate to afford product. LCMS (ESI): [MH]⁺=358.1.

Step 4—Synthesis of 3-chloro-5-(5-((1R,5 S,6r)-3-(2-methoxyethyl)-3-azabicyclo[3.1.0]hexan-6-yl)-1-(2,2,2-trifluoroethyl)-1H-pyrazol-3-yl)pyridin-2-amine To an ice-cooled solution of 5-(5-((1R,5S,6r)-3-azabicyclo[3.1.0]hexan-6-yl)-1-(2,2,2-trifluoroethyl)-1H-pyrazol-3-yl)-3-chloropyridin-2-amine (156 mg) and diisopropylethylamine (2.33 mL) in N,N-dimethylformamide (10 mL) was added 2-bromoethyl methyl ether (0.432 mL). The reaction mixture was warm to room temperature. After 10 h, the reaction solution was diluted with ethyl acetate and sequentially washed with saturated aqueous sodium bicarbonate solution, water, and saturated aqueous sodium chloride solution. The collected organic was dried over anhydrous sodium sulfate, filtered, and concentrated. Purification by flash column chromatography (10% methanol in dichloromethane with 1% (v/v) aqueous ammonium hydroxide)) provided a yellow solid (100 mg). LCMS (ESI): [MH]⁺=416; ¹H NMR (400 MHz, CDCl₃): δ 8.29 (d, J=2.0 Hz, 1H), 7.93 (d, J=2.0 Hz, 1H), 6.06 (s, 1H), 4.89 (s, 2H), 4.81-4.66 (m, 1H), 3.49 (t, 2H), 3.37 (s, 3H), 3.26-3.13 (m, 2H), 2.77-2.61 (m, 2H), 2.54-2.40 (m, 2H), 2.25-2.11 (m, 1H), 1.79-1.67 (m, 2H).

Method AA

Preparation of 3-chloro-5-(5-((1R,5 S,6r)-3-(oxetan-3-yl)-3-azabicyclo[3.1.0]hexan-6-yl)-1-(2,2,2-trifluoroethyl)-1H-pyrazol-3-yl)pyridin-2-amine (150)

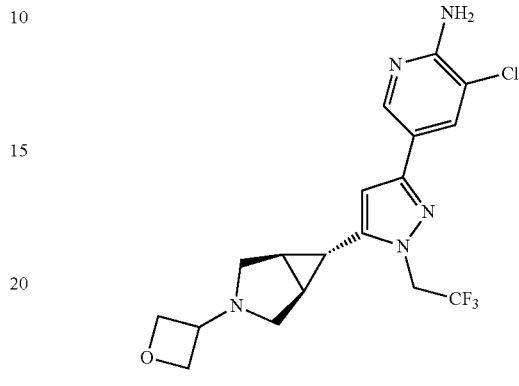

Prepared following the method described for the synthesis of (1R,5S,6r)-6-(3-iodo-1-isopropyl-1H-pyrazol-5-yl)-3-(oxetan-3-yl)-3-azabicyclo[3.1.0]hexane using 5-(5-((1R,5S,6r)-3-azabicyclo[3.1.0]hexan-6-yl)-1-(2,2,2-trifluoroethyl)-1H-pyrazol-3-yl)-3-chloro pyridin-2-amine to afford product. LCMS (ESI): [MH]⁺=414; ¹H NMR (400 MHz, CDCl₃): δ 8.30 (d, J=2.0 Hz, 1H), 7.94 (d, J=2.0 Hz, 1H), 6.07 (d, J=0.62 Hz, 1H), 4.91 (s, 2H), 4.77 (q, J=8.3 Hz, 2H), 4.69 (t, J=6.6 Hz, 2H), 4.62 (t, J=6.1 Hz, 2H), 3.81 (tt, J=6.8, 5.8 Hz, 1H), 3.15 (d, J=8.8 Hz, 2H), 2.50 (ddt, J=8.8, 2.0, 0.9 Hz, 2H), 2.24 (t, J=3.3 Hz, 1H), 1.81 (ddd, J=3.3, 2.0, 1.1 Hz, 2H).

Method AB

Preparation of 5-(1-(3,3-difluorocyclobutyl)-5-(tetrahydrofuran-3-yl)-1H-pyrazol-3-yl)-3-methyl-1H-pyrrolo[2,3-b]pyridine (19)

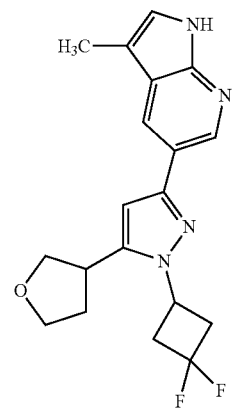 [SMILES: Cc1c[nH]c2ncc(-c3cc(C4CCOC4)n(C4CC(F)(F)C4)n3)cc12]

Step 1—Synthesis of 3-(3-iodo-5-(tetrahydrofuran-3-yl)-1H-pyrazol-1-yl)cyclobutanone

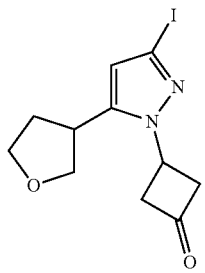 [SMILES: O=C1CC(n2nc(I)cc2C2CCOC2)C1]

To a solution of 3-iodo-5-(tetrahydrofuran-3-yl)-1H-pyrazole (2 g, 7.5 mmol) in N,N-dimethylformamide (20 mL) was added 3-bromocyclobutanone (2.24 g, 15.1 mmol) and potassium carbonate (2 g, 15.1 mmol). The mixture was stirred at 25° C. for 10 h. Ethyl acetate (50 mL) was added to the reaction mixture, and the resulting suspension was filtered. The filtrate was concentrated in vacuo. Purification by flash column chromatography afforded product (800 mg, 32% yield, $R_f$=0.3 in 30% ethyl acetate in hexanes) LCMS (EI): $[MH]^+$=332.8.

Step 2—Synthesis of 1-(3,3-difluorocyclobutyl)-3-iodo-5-(tetrahydrofuran-3-yl)-1H-pyrazole

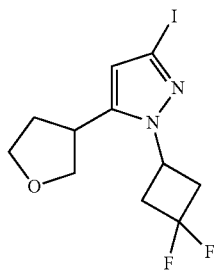 [SMILES: FC1(F)CC(n2nc(I)cc2C2CCOC2)C1]

To an ice-cooled solution of 3-(3-iodo-5-(tetrahydrofuran-3-yl)-1H-pyrazol-1-yl)cyclobutanone (800 mg, 2.4 mmol) in dichloromethane (50 mL) was added DAST (15 mL). The reaction mixture was warmed to room temperature. After 4 h, the reaction mixture was cooled to 0° C., and saturated sodium bicarbonate aqueous solution (30 mL) was added drop-wise. The resulting mixture was extracted with ethyl acetate (3×30 mL), and the collected organic was washed with saturated aqueous sodium chloride solution (30 mL), dried over anhydrous sodium sulfate, filtered, and concentrated. Purification by flash column chromatography (100% petroleum ether→20% ethyl acetate in petroleum ether) provided product (320 mg, 37.5% yield). LCMS (ESI): $[MH]=354.9$; $^1H$ NMR (400 MHz, Acetone-$d_6$): δ 6.36 (s, 1 H), 5.03-4.98 (m, 1 H), 4.07-4.04 (m, 1 H), 3.92-3.87 (m, 1 H), 3.84-3.78 (m, 1 H), 3.68-3.59 (m, 2 H), 3.10-3.26 (m, 4 H), 2.41-2.34 (m, 1 H), 1.96-1.80 (m, 1 H).

Step 3—Synthesis of 5-(1-(3,3-difluorocyclobutyl)-5-(tetrahydrofuran-3-yl)-1H-pyrazol-3-yl)-3-methyl-1H-pyrrolo[2,3-b]pyridine Prepared following the method described for the synthesis of 5-(1-(cyclopropylmethyl)-5-(tetrahydrofuran-3-yl)-1H-pyrazol-3-yl)-3-methyl-1H-pyrrolo[2,3-b]pyridine using 1-(3,3-difluorocyclobutyl)-3-iodo-5-(tetrahydrofuran-3-yl)-1H-pyrazole. LCMS (ESI): $[MH]^+$=358.9; $^1H$ NMR (400 MHz, $CD_3OD$): δ 9.02 (s, 1 H), 8.81 (s, 1 H), 7.48 (s, 1 H), 6.82 (s, 1H), 5.10-4.90 (m, 1 H), 4.18-4.14 (m, 1 H), 4.05-4.03 (m, 1 H), 3.97-3.94 (m, 1 H), 3.80-3.79 (m, 1 H), 3.77-3.68 (m, 1 H), 3.50-3.30 (m, 2 H), 3.17-3.14 (m, 2 H), 2.60-2.40 (m, 4 H), 2.07-2.03 (m, 1 H).

Method AC

Preparation of 5-(1-(3,3-difluorocyclopentyl)-5-(tetrahydrofuran-3-yl)-1H-pyrazol-3-yl)-3-(trifluoromethyl)-1H-pyrrolo[2,3-b]pyridine (16)

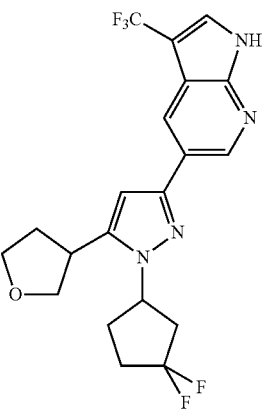 [SMILES: FC1(F)CCC(n2nc(-c3cnc4[nH]cc(C(F)(F)F)c4c3)cc2C2CCOC2)C1]

Step 1—Synthesis of 1-(3,3-difluorocyclopentyl)-3-iodo-5-(tetrahydrofuran-3-yl)-1H-pyrazole

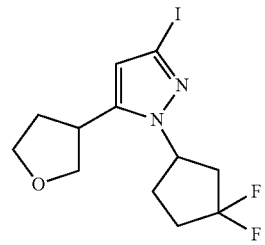 [SMILES: FC1(F)CCC(n2nc(I)cc2C2CCOC2)C1]

To a solution of 3-iodo-5-(tetrahydrofuran-3-yl)-1H-pyrazole (1 g, 3.8 mmol) in dichloromethane (20 mL) was added cyclopent-2-enone (0.93 g, 11.36 mmol), hafnium(IV) chloride (0.12 g, 0.38 mmol). The mixture was stirred at 25° C. for 10 h under $N_2$. LCMS (ESI) [MH]=346.8.

The reaction mixture was filtered, and DAST (5 mL) was added to the filtrate at 0° C. The reaction mixture was warmed to 20° C. After 4 h, the reaction mixture was cooled to 0° C., and saturated sodium bicarbonate aqueous solution (30 mL) was added drop-wise. The resulting mixture was extracted with ethyl acetate (3×30 mL). The collected organic was washed with saturated aqueous sodium chloride solution (30 mL), dried over anhydrous sodium sulfate, filtered, and concentrated. Purification by flash column chromatography (100% petroleum ether→15% ethyl acetate in petroleum ether) provided product (0.3 g, 21.5% yield 2-steps) LCMS (ESI) $[MH]^+$=368.9.

Step 2—Synthesis of 5-(1-(3,3-difluorocyclopentyl)-5-(tetrahydrofuran-3-yl)-1H-pyrazol-3-yl)-3-(trifluoromethyl)-1H-pyrrolo[2,3-b]pyridine Prepared following the method described for the synthesis of 5-(1-(cyclopropylmethyl)-5-(tetrahydrofuran-3-yl)-1H-pyrazol-3-yl)-3-methyl-1H-pyrrolo[2,3-b]pyridine using 1-(3,3-difluorocyclopentyl)-3-iodo-5-(tetrahydrofuran-3-yl)-1H-pyrazole and 3-trifluoromethyl-5-(4,4,5,5-tetramethyl-1,3,2-dioxaborolan-2-yl)-1H-pyrrolo[2,3-b]pyridine to afford product as a mixture of 4 stereoisomers. The mixture was further purified by chiral supercritical fluid chromatography following similar conditions as described in Method AD. LCMS (ESI): [MH]$^+$=427.0; $^1$H NMR (400 MHz, CD$_3$OD): δ 8.83 (s, 1 H), 8.42 (s, 1 H), 7.88 (s, 1 H), 6.64 (s, 1 H), 5.09-5.05 (m, 1 H), 4.21-4.17 (m, 1 H), 4.10-4.04 (m, 1 H), 3.99-3.93 (m, 1 H), 3.85-3.80 (m, 1 H), 3.71-3.67 (m, 1 H), 2.88-2.81 (m, 1 H), 2.79-2.66 (m, 1 H), 2.60-2.45 (m, 2 H), 2.43-2.22 (m, 3 H), 2.11-2.06 (m, 1 H).

Method AD

Preparation of 5-(1,5-bis(tetrahydrofuran-3-yl)-1H-pyrazol-3-yl)-3-(trifluoromethyl)-1H-pyrrolo[2,3-b]pyridine (15)

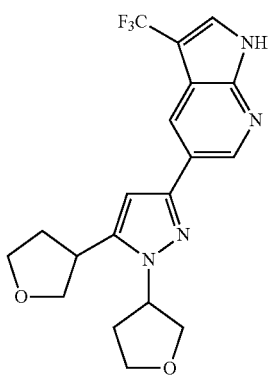 [SMILES: FC(F)(F)c1c[nH]c2ncc(-c3cc(C4CCOC4)n(C4CCOC4)n3)cc12]

Step 1—Synthesis of 3-iodo-1,5-bis(tetrahydrofuran-3-yl)-1H-pyrazole and 5-iodo-1,3-bis(tetrahydrofuran-3-yl)-1H-pyrazole

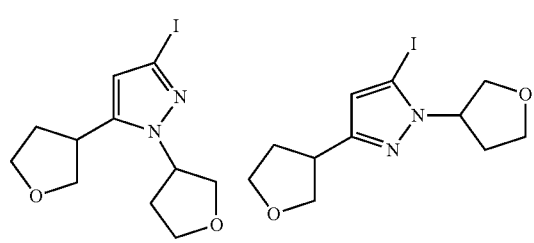

To an ice-cooled solution of 3-iodo-5-(tetrahydrofuran-3-yl)-1H-pyrazole (500 mg, 1.89 mol) in N,N-dimethylformamide (10 mL) was added sodium hydride (68 mg, 2.83 mmol, 60% in mineral oil). After 5 min, 3-iodo-5-(tetrahydrofuran-3-yl)-1H-pyrazole (470 mg, 2.83 mmol) was added. The reaction mixture was warmed to 90° C. for 3 h. The reaction mixture was poured into ice water (50 mL) and extracted with ethyl acetate (3×20 mL). The organic layer was dried over anhydrous sodium sulfate, filtered, and concentrated. Purification of the resulting residue by flash column chromatography (100% petroleum ether→25% ethyl acetate in petroleum ether) afforded the mixture of products (300 mg, 47.4% yield). LCMS (ESI): [MH]$^+$=334.8.

Step 2—Synthesis of 5-(1,5-bis(tetrahydrofuran-3-yl)-1H-pyrazol-3-yl)-3-(trifluoromethyl)-1H-pyrrolo[2,3-b]pyridine Prepared following the method described for the synthesis of 5-(1-(cyclopropylmethyl)-5-(tetrahydrofuran-3-yl)-1H-pyrazol-3-yl)-3-methyl-1H-pyrrolo[2,3-b]pyridine using a mixture of 3-iodo-1,5-bis(tetrahydrofuran-3-yl)-1H-pyrazole and 5-iodo-1,3-bis(tetrahydrofuran-3-yl)-1H-pyrazole and 3-trifluoromethyl-5-(4,4,5,5-tetramethyl-1,3,2-dioxaborolan-2-yl)-1H-pyrrolo[2,3-b]pyridine to afford product as mixture of 4 stereoisomers. LCMS (ESI): [MH]$^+$=392.8; $^1$H NMR (400 MHz, CD$_3$OD): δ 8.78 (s, 1 H), 8.39 (s, 1 H), 7.84 (s, 1 H), 6.61 (s, 1 H), 5.18-5.16 (m, 1 H), 4.29-4.24 (m, 1 H), 4.20-4.13 (m, 2 H), 4.08-3.90 (m, 4 H), 3.80-3.77 (m, 1 H), 3.69-3.65 (m, 1 H), 2.45-2.40 (m, 3 H), 2.07-2.04 (m, 1 H). The mixture was further purified by chiral supercritical fluid chromatography: (Berger MG II, 21.1×150 mm, 5 uM, 70 mL/min, 25% methanol in 0.1% ammonium hydroxide; Chiralpak AD) to provide separately Stereoisomer 1 ($R_T$=0.4 min), Stereoisomer 2 ($R_T$=0.45 min), Stereoisomer 3 ($R_T$=0.52 min), and Stereoisomer 4 ($R_T$=0.56 min).

Method AE

Preparation of 5-(1-isopropyl-5-((1R,5 S,6r)-3-(2-methoxyethyl)-3-azabicyclo[3.1.0]hexan-6-yl)-1H-pyrazol-3-yl)-3-(trifluoromethyl)pyridin-2-amine (117)

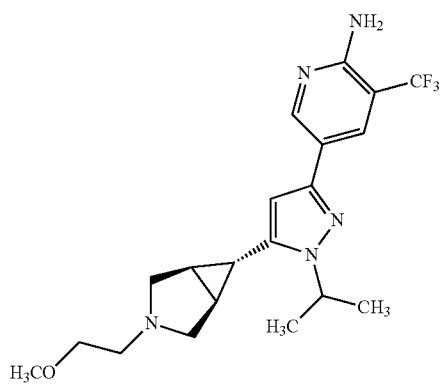 [SMILES: COCCN1C[C@@H]2[C@H](C1)[C@H]2c1cc(-c2cnc(N)c(C(F)(F)F)c2)nn1C(C)C]

Step 1—Synthesis of (1R,5S,6r)-tert-butyl 6-(3-(6-amino-5-(trifluoromethyl)pyridin-3-yl)-1-isopropyl-1H-pyrazol-5-yl)-3-azabicyclo[3.1.0]hexane-3-carboxylate

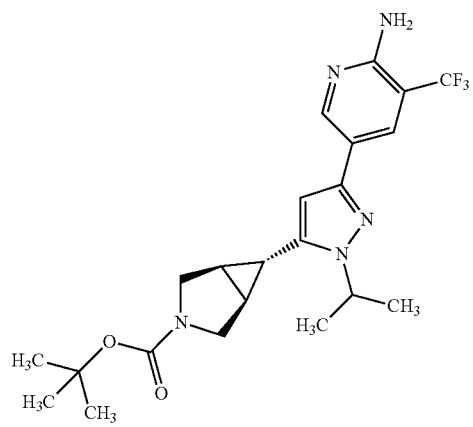 [SMILES: CC(C)n1nc(-c2cnc(N)c(C(F)(F)F)c2)cc1[C@H]1[C@@H]2CN(C(=O)OC(C)(C)C)C[C@@H]21]

Prepared following the method described for the synthesis of 5-(1-isopropyl-5-((1R,5S,6R)-3-(oxetan-3-yl)-3-azabicyclo[3.1.0]hexan-6-yl)-1H-pyrazol-3-yl)-3-(t rifluoromethyl)pyridin-2-amine using (1R,5S,6r)-tert-butyl 6-(3-iodo-1-isopropyl-1H-pyrazol-5-yl)-3-azabicyclo[3.1.0]hexane-3-carboxylate. LCMS (ESI): [MH]$^+$=452.4.

Step 2—Synthesis of 5-(5-((1R,5S,6r)-3-azabicyclo[3.1.0]hexan-6-yl)-1-isopropyl-1H-pyrazol-3-yl)-3-(trifluoromethyl)pyridin-2-amine

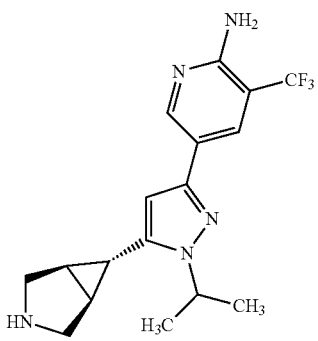 [SMILES: CC(C)n1nc(-c2cnc(N)c(C(F)(F)F)c2)cc1[C@H]1[C@@H]2CNC[C@@H]21]

Prepared following the method described for the synthesis of (1R,5S,6r)-6-(3-iodo-1-isopropyl-1H-pyrazol-5-yl)-3-azabicyclo[3.1.0]hexane using ((1R,5S,6r)-tert-butyl 6-(3-(6-amino-5-(trifluoromethyl)pyridin-3-yl)-1-isopropyl-1H-pyrazol-5-yl)-3-azabicyclo[3.1.0]hexane-3-carboxylate. LCMS (ESI): [MH]$^+$=352.2.

Step 3—Synthesis of 5-(1-isopropyl-5-((1R,5S,6r)-3-(2-methoxyethyl)-3-azabicyclo[3.1.0]hexan-6-yl)-1H-pyrazol-3-yl)-3-(trifluoromethyl)pyridin-2-amine To an ice-cooled solution of 5-(5-((1R,5S,6r)-3-azabicyclo[3.1.0]hexan-6-yl)-1-isopropyl-1H-pyrazol-3-yl)-3-(trifluoromethyl)pyridin-2-amine (19 mg, 0.055 mmol) and diisopropylethylamine (295 µL, 1.66 mmol) in N,N-dimethylformamide (1 mL) was added 2-bromoethyl methyl ether (55 µL, 0.55 mmol). The reaction mixture was warm to room temperature. After 10 h, the reaction solution was diluted with ethyl acetate and sequentially washed with saturated aqueous sodium bicarbonate solution, water, and saturated aqueous sodium chloride solution. The collected organic was dried over anhydrous sodium sulfate, filtered, and concentrated.

Purification by flash column chromatography (10% methanol in dichloromethane with 1% (v/v) aqueous ammonium hydroxide)) provided product (15 mg, 66% yield). LCMS (ESI): [MH]$^+$=410.3; $^1$H NMR (400 MHz, CDCl$_3$): δ 8.55 (d, J=2.1, 0.8 Hz, 1H), 8.11 (d, J=2.2, 0.7 Hz, 1H), 6.01 (d, J=0.6 Hz, 1H), 4.95 (s, 2H), 4.69 (hept, J=6.7 Hz, 1H), 3.56-3.49 (m, 2H), 3.37 (s, 3H), 3.33-3.17 (m, 2H), 2.82-2.62 (m, 3H), 2.57-2.43 (m, 2H), 2.27-2.13 (m, 1H), 1.79-1.65 (m, 2H), 1.51 (d, J=6.7 Hz, 6H).

Method AF

Preparation of 2-amino-5-(1-isopropyl-5-((1R,5 S,6r)-3-(oxetan-3-yl)-3-azabicyclo[3.1.0]hexan-6-yl)-1H-pyrazol-3-yl)nicotinonitrile (144)

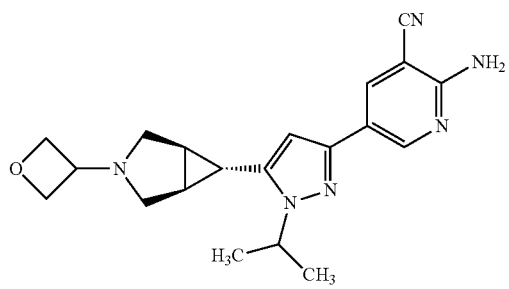 [SMILES: CC(C)n1nc(-c2cnc(N)c(C#N)c2)cc1[C@H]1[C@@H]2CN(C3COC3)C[C@@H]21]

To a microwave vial equipped with a stirbar was dissolve 2-amino-5-bromonicotinonitrile (0.087 g, 0.44 mmol) in anhydrous acetonitrile (4 mL). To the solution was added potassium acetate (0.086 g, 0.86 mmol), 4,4,4',4',5,5,5',5'-octamethyl-2,2'-bi(1,3,2-dioxaborolane (0.223 g, 0.86 mmol) and 1,1'-bis(diphenylphosphino)ferrocene-palladium (II)dichloride (0.016 g, 0.022 mmol). The resulting mixture was microwaved at 150° C. for 15 min. To the mixture was added (1R,5 S,6r)-6-(3-iodo-1-isopropyl-1H-pyrazol-5-yl)-3-(oxetan-3-yl)-3-azabicyclo[3.1.0]hexane (0.100 g, 0.26 mmol), 1M potassium carbonate (4 mL) and further 1,1'-bis(diphenylphosphino)ferrocene-palladium(II)dichloride (0.008 g, 0.011 mmol) and the resulting mixture was microwave at 110° C. for 15 min. The reaction mixture was diluted with 10 mL water and extracted with ethyl acetate (3×15 mL). The combined organic layers were dried over magnesium sulfate, filtered and concentrated to dryness in vacuo. This crude material was purified by RP-HPLC affording 2-amino-5-(1-isopropyl-5-((1R,5S,6r)-3-(oxetan-3-yl)-3-azabicyclo[3.1.0]hexan-6-yl)-1H-pyrazol-3-yl)nicotinonitrile (20.1 mg, 21%): $^1$H NMR (400 MHz, DMSO-d$_6$) δ: 8.57 (s, 1H), 8.08 (s, 1H), 6.91 (s, 2H), 6.35 (s, 1H), 4.73-4.62 (m, 1H), 4.60-4.44 (m, 4H), 3.81-3.70 (m, 1H), 3.12 (d, J=8.8 Hz, 2H), 2.46-2.39 (m, 2H), 2.19-2.12 (m, 1H), 1.82-1.76 (m, 2H), 1.42 (d, J=6.5 Hz, 6H).

Method AG

Preparation of 5-(1-isopropyl-5-(1-(oxetan-3-yl) piperidin-4-yl)-1H-pyrazol-3-yl)-3,3-dimethyl-2,3-dihydro-1H-pyrrolo[2,3-b]pyridine (95)

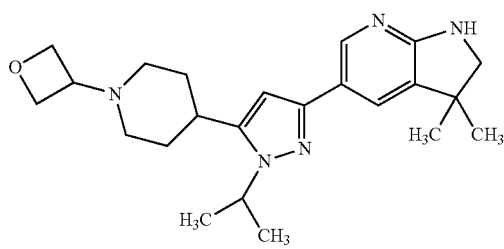 [SMILES: CC(C)n1nc(-c2cnc3c(c2)C(C)(C)CN3)cc1C1CCN(C2COC2)CC1]

To a microwave vial equipped with a stirbar was dissolve 5-(1-isopropyl-5-(1-(oxetan-3)piperidin-4-yl)-H-pyrazol-3-yl)-3,3-dimethyl-1H-pyrrolo[2,3-b]pyridin-2(3H)-one (0.055 g, 0.13 mmol) in anhydrous tetrahydrofuran (4 mL). To the solution was added lithium aluminium hydride and the resulting mixture was microwaved at 150° C. for 20 min. The mixture was filtered through celite and concentrated to dryness in vacuo. This crude material was purified by RP-HPLC affording 5-(1-isopropyl-5-(1-(oxetan-3-yl)piperidin-4-yl)-1H-pyrazol-3-yl)-3,3-dimethyl-2,3-dihydro-1H-pyrrolo[2,3-b]pyridine (18.7 mg, 36%): $^1$H NMR (400 MHz, DMSO-$d_6$) δ: 8.09 (s, 1H), 7.70 (s, 1H), 7.01 (s, 1H), 6.40 (s, 1H), 4.75-4.70 (m, 2H), 4.70-4.62 (m, 2H), 4.62-4.50 (m, 1H), 4.08 (s, 1H), 2.99-2.94 (m, 1H), 2.02-1.94 (m, 2H), 1.90-1.85 (m, 2H), 1.41 (d, J=6.4 Hz, 6H), 1.30 (s, 6H).

Method AH

Preparation of 5-(5-isopropyl-1-(1-(oxetan-3-yl) azetidin-3-yl)-1H-pyrazol-3-yl)-3-(trifluoromethyl)-1H-pyrrolo[2,3-b]pyridine (1)

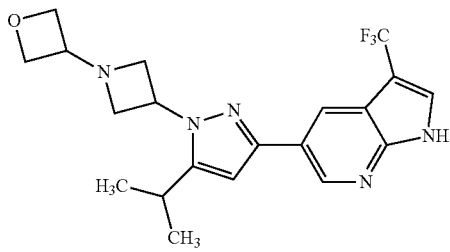 [SMILES: CC(C)c1cc(-c2cnc3[nH]cc(C(F)(F)F)c3c2)nn1C1CN(C2COC2)C1]

Step 1—Synthesis of 3-iodo-5-isopropyl-1H-pyrazole

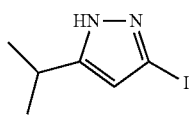

To a cooled solution of 5-isopropyl-1H-pyrazol-3-amine (1 g, 7.9 mmol) in acetonitrile (50 mL) was added 4-methylbenzenesulfonic acid (2.8 g, 20 mmol) and at 0° C. dropwise solution of sodium nitrite in water (10 mL). Upon completion the reaction mixture was stirred a further 30 min at 0° C. A solution of sodium iodide (6 g, 40 mmol) in water (10 mL) was slowly added dropwise at 0° C. to the reaction mixture and stirred at RT for 3 h. The mixture was concentrated to dryness in vacuo, dissolved in ethyl acetate (150 mL), washed with water, brine and dried over sodium sulphate. The organic layer was concentrated to dryness in vacuo and the resulting residue was purified by column chromatography (silica gel, 100-200 mesh, 20% ethyl acetate in hexane) affording 3-iodo-5-isopropyl-1H-pyrazole (1.2 g, 64%): 1H NMR (400 MHz, DMSO-d6) δ: 6.20 (s, 1H), 3.10-2.75 (m, 1H), 1.19 (d, J=7.0 Hz, 6H).

Step 2—Synthesis of tert-butyl 3-(3-iodo-5-isopropyl-1H-pyrazol-1-yl)azetidine-1-carboxylate compound with tert-butyl 3-(5-iodo-3-isopropyl-1H-pyrazol-1-yl)azetidine-1-carboxylate (1:1)

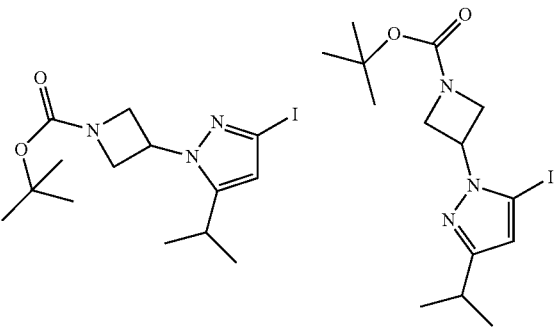 [SMILES: CC(C)c1cc(I)nn1C1CN(C(=O)OC(C)(C)C)C1 ; CC(C)c1cc(I)n(C2CN(C(=O)OC(C)(C)C)C2)n1]

To a solution of 3-iodo-5-isopropyl-1H-pyrazole (0.500 g, 2.1 mmols) dissolved in N,N-dimethylformamide was added tert-butyl 3-iodoazetidine-1-carboxylate (0.900 g, 3.2 mmol) and the mixture was shaken at 50° C. overnight. The reaction mixture was concentrated to dryness in vacuo, redissolved in ethyl acetate (200 mL), washed with water (2×100 mL), brine and dried over sodium sulphate. The organic was concentrated to dryness in vacuo and the resulting residue was purified by column chromatography (silica gel, 100-200 mesh, 20 to 35% ethyl acetate in hexane) affording tert-butyl 3-(3-iodo-5-isopropyl-1H-pyrazol-1-yl) azetidine-1-carboxylate compound with tert-butyl 3-(5-iodo-3-isopropyl-1H-pyrazol-1-yl)azetidine-1-carboxylate (1:1) (0.405 g) used in the step without further purification.

Step 3—Synthesis of 5-(5-isopropyl-1-(1-(oxetan-3-yl)azetidin-3-yl)-1H-pyrazol-3-yl)-3-(trifluoromethyl)-1H-pyrrolo[2,3-b]pyridine To a microwave vial equipped with a stirbar was dissolve tert-butyl 3-(3-iodo-5-isopropyl-1H-pyrazol-1-yl)azetidine-1-carboxylate compound with tert-butyl 3-(5-iodo-3-isopropyl-1H-pyrazol-1-yl)azetidine-1-carboxylate (0.405 mg, 1 mmol) in a 1:1 mixture of acetonitrile: 1M potassium carbonate (5 mL) and transferred to a microwave vial equipped with a stirbar. To the solution was added 5-(4,4,5,5-tetramethyl-1,3,2-dioxaborolan-2-yl)-3-(trifluoromethyl)-1H-pyrrolo[2,3-b]pyridine (0.387 g, 1.2 mmol), 1,1'-bis(diphenylphosphino)ferrocene-palladium(II)dichloride (0.037 g, 0.05 mmol) and the mixture was microwaved at 110° C. for 5 min. The reaction mixture was diluted with 10 mL water and extracted with ethyl acetate (3×15 ml). The combined organic layers were dried over magnesium sulfate, filtered and concentrated to dryness in vacuo. The resulting residue was dissolved in methanol (10 mL), a 4M solution of hydrogen chloride in 1,4-dioxane (3.75 mL, 15 mmol) was added and the mixture was stirred for 2 h. The reaction mixture was concentrated to dryness in vacuo with the resulting residue redissolved in anhydrous dichloromethane, triethylamine added (0.300 mL) and the mixture was allowed to stir at RT for 10 min. To the mixture was added oxetan-3-one (0.223 g, 3 mmols), sodium triacetoxy borohyride (1.1 g, 5.19 mmol) and stirred at 40° C. overnight. The reaction mixture was diluted with dichloromethane (100 mL) washed with 1M sodium hydroxide (2×50 mL), water, brine and dried over sodium sulfate. The organic was concentrated to dryness in vacuo and the resulting residue was purified by RP-HPLC affording 5-(5-isopropyl-1-(1-(oxetan-3-yl)azetidin-3-yl)-1H-pyrazol-3-yl)-3-(trifluormethyl)-1H-pyrrolo[2, 3-b]pyridine (3.6 mg, 2%): LCMS $R_T$=4.63 min, m/z=406.2 [M+H]$^+$.

EXAMPLE 3

The compounds disclosed in Table A were prepared following the General Methods A-AH as described above in Example 2 with modifying the starting reactants in those methods as would be known to one skilled in the art as necessary to arrive at the compounds in Table A.

TABLE A

| No. | Structure | $^1$H NMR | MS [MH]$^+$ | Method |
| --- | --- | --- | --- | --- |
| 117 | 5-(1-isopropyl-5-((1R,5S,6r)-3-(2-methoxyethyl)-3-azabicyclo[3.1.0]hexan-6-yl)-1H-pyrazol-3-yl)-3-(trifluoromethyl) pyridin-2-amine | (400 MHz, CDCl$_3$): δ 8.55 (d, J = 2.1, 0.8 Hz, 1H), 8.11 (d, J = 2.2, 0.7 Hz, 1H), 6.01 (d, J = 0.6 Hz, 1H), 4.95 (s, 2H), 4.69 (hept, J = 6.7 Hz, 1H), 3.56-3.49 (m, 2H), 3.37 (s, 3H), 3.33-3.17 (m, 2H), 2.82-2.62 (m, 3H), 2.57-2.43 (m, 2H), 2.27-2.13 (m, 1H), 1.79-1.65 (m, 2H), 1.51 (d, J = 6.7 Hz, 6H) | 410 | AE |
| 153 | 5-(1-cyclobutyl-5-((1R,5S,6r)-3-(oxetan-3-yl)-3-azabicyclo[3.1.0]hexan-6-yl)-1H-pyrazol-3-yl)-3-cyclopropylpyridin-2-amine | (400 MHz, CD$_3$OD): δ 8.13-8.08 (m, 1 H), 7.95 (s, 1 H), 6.26 (s, 1H), 5.03-4.99 (m, 1 H), 4.75-4.72 (m, 2 H), 4.66-4.63 (m, 2 H), 3.88-3.85 (m, 1 H), 3.32-3.31 (m, 1 H), 3.30-3.27 (m, 1 H), 2.73-2.68 (m, 2 H), 2.61-2.58 (m, 2 H), 2.48-2.45 (m, 2 H), 2.28-2.27 (m, 1 H), 1.95-1.90 (m, 4 H), 1.86-1.76 (m, 1 H), 1.20-1.08 (m, 2 H), 0.80-0.70 (m, 2 H) | 392.2 | B |

TABLE A-continued

| No. | Structure | ¹H NMR | MS [MH]⁺ | Method |
|---|---|---|---|---|
| 152 | 5-(1-(cyclopropylmethyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine | (400 MHz, CDCl₃): δ 8.56 (s, 1 H), 8.10 (s, 1 H), 6.04 (s, 1 H), 4.96 (s, 2 H), 4.72-4.69 (m, 2 H), 4.65-4.62 (m, 2 H), 4.08 (d, J = 6.8 Hz, 2 H), 3.84-3.78 (m, 1 H), 3.16 (d, J = 8.8 Hz, 2 H), 2.51-2.49 (m, 2 H), 2.27-2.26 (m, 1 H), 1.80-1.79 (m, 2 H), 1.37-1.33 (m, 1 H), 0.64-0.59 (m, 2 H), 0.46-0.44 (m, 2 H) | 419.9 | Y |
| 151 | 5-(1-(cyclobutyl-5-((1R,5S,6r)-3-(oxetan-3-yl)-3-azabicyclo[3.1.0]hexan-6-yl)-1H-pyrazol-3-yl)-3-(difluoromethoxy)pyridin-2-amine | (400 MHz, CD₃OD): δ 8.16 (s, 1 H), 7.75 (s, 1 H), 6.89 (t, J = 73.6 Hz, 1 H), 6.19 (s, 1 H), 5.02-4.98 (m, 1 H), 4.74-4.71 (m, 2 H), 4.64-4.57 (m, 2 H), 3.82-3.79 (m, 1 H), 3.21 (d, J = 9.2 Hz, 2 H), 2.74-2.69 (m, 2 H), 2.52-2.44 (m, 4 H), 2.27-2.25 (m, 1 H), 1.94-1.91 (m, 2 H), 1.91-1.83 (m, 2 H) | 418.2 | B |
| 150 | 3-chloro-5-(5-((1R,5S,6r)-3-(oxetan-3-yl)-3-azabicyclo[3.1.0]hexan-6-yl)-1-(2,2,2-trifluoroethyl)-1H-pyrazol-3-yl)pyridin-2-amine | (400 MHz, CDCl₃): δ 8.30 (d, J = 2.0 Hz, 1H), 7.94 (d, J = 2.0 Hz, 1H), 6.07 (d, J = 0.62 Hz, 1H), 4.91 (s, 2H), 4.77 (q, J = 8.3 Hz, 2H), 4.69 (t, J = 6.6 Hz, 2H), 4.62 (t, J = 6.1 Hz, 2H), 3.81 (tt, J = 6.8, 5.8 Hz, 1H), 3.15(d, J = 8.8 Hz, 2H), 2.50 (ddt, J = 8.8, 2.0, 0.9 Hz, 2H), 2.24 (t, J = 3.3 Hz, 1H), 1.81 (ddd, J = 3.3, 2.0, 1.1 Hz, 2H) | 414 | AA |

TABLE A-continued

| No. | Structure | ¹H NMR | MS [MH]⁺ | Method |
|---|---|---|---|---|
| 116 | 3-chloro-5-(5-((1R,5S,6r)-3-(2-methoxyethyl)-3-azabicyclo[3.1.0]hexan-6-yl)-1-(2,2,2-trifluoroethyl)-1H-pyrazol-3-yl)pyridin-2-amine | (400 MHz, CDCl₃): δ 8.29 (d, J = 2.0 Hz, 1H), 7.93 (d, J = 2.0 Hz, 1H), 6.06 (s, 1H), 4.89 (s, 2H), 4.81-4.66 (m, 1H), 3.49 (t, 2H), 3.37 (s, 3H), 3.26-3.13 (m, 2H), 2.77-2.61 (m, 2H), 2.54-2.40 (m, 2H), 2.25-2.11 (m, 1H), 1.79-1.67 (m, 2H) | 416 | Z |
| 149 | 5-(1-cyclobutyl-5-((1R,5S,6r)-3-(oxetan-3-yl)-3-azabicyclo[3.1.0]hexan-6-yl)-1H-pyrazol-3-yl)-3-isopropoxypyridin-2-amine | (400 MHz, CD₃OD): δ 7.82 (s, 1 H), 7.56 (s, 1 H), 6.22 (s, 1 H), 5.03-4.99 (m, 1 H), 4.74-4.71 (m, 3 H), 4.65-4.62 (m, 2 H), 3.84-3.81 (m, 1 H), 3.24 (d, J = 9.2 Hz, 2 H), 2.74-2.69 (m, 2 H), 2.55-2.45 (m, 4 H), 2.27-2.26 (m, 1 H), 1.95-1.91 (m, 2 H), 1.89-1.84 (m, 2 H), 1.41 (d, J = 6.0 Hz, 6 H) | 410.2 | B |
| 148 | 5-(1-cyclobutyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine | (400 MHz, CD₃OD): δ 8.53 (s, 1 H), 8.14 (s, 1 H), 6.25 (s, 1 H), 5.03-4.99 (m, 1 H), 4.76-4.73 (m, 2 H), 4.66-4.63 (m, 2 H), 3.91-3.87 (m, 1 H), 3.32-3.30 (m, 2 H), 2.78-2.62 (m, 4 H), 2.50-2.43 (m, 2 H), 2.28-2.26 (m, 1 H), 1.95-1.90 (m, 4 H) | 420.2 | B |
| 147 | 3-chloro-5-(1-cyclobutyl-5-((1R,5S,6r)-3-(oxetan-3-yl)-3-azabicyclo[3.1.0]hexan-6-yl)-1H-pyrazol-3-yl)pyridin-2-amine | (400 MHz, CD₃OD): δ 8.25 (s, 1 H), 8.08 (s, 1 H), 6.21 (s, 1 H), 5.02-4.98 (m, 1 H), 4.77-4.73 (m, 2 H), 4.66-4.63 (m, 2 H), 3.92-3.88 (m, 1 H), 3.32-3.31 (m, 2 H), 2.72-2.69 (m, 2 H), 2.66-2.64 (m, 2 H), 2.47-2.45 (m, 2 H), 2.27-2.25 (m, 1 H), 1.95-1.88 (m, 4 H) | 386.2 | B |

TABLE A-continued

| No. | Structure | ¹H NMR | MS [MH]⁺ | Method |
|---|---|---|---|---|
| 146 | 3-isopropoxy-5-(1-isopropyl-5-((1R,5S,6r)-3-(oxetan-3-yl)-3-azabicyclo[3.1.0]hexan-6-yl)-1H-pyrazol-3-yl)pyridin-2-amine | (400 MHz, DMSO-d₆) δ: 7.88 (s, 1H), 7.33 (s, 1H), 6.29 (s, 1H), 5.77 (s, 2H), 4.72-4.46 (m, 6H), 3.83-3.78 (m, 1H), 3.16 (s, 2H), 2.20-2.14 (m, 1H), 1.85-1.80 (m, 2H), 1.43 (d, J = 6.5 Hz, 6H), 1.30 (d, J = 6.0 Hz, 6H) | 398.3 | A |
| 145 | 5-(1-isopropyl-5-((1R,5S,6r)-3-(oxetan-3-yl)-3-azabicyclo[3.1.0]hexan-6-yl)-1H-pyrazol-3-yl)-3-methoxypyridin-2-amine | (400 MHz, DMSO-d₆) δ: 7.87 (s, 1H), 7.32 (s, 1H), 6.29 (s, 1H), 5.89 (s, 2H), 4.72-4.61 (m, 1H), 4.64-4.46 (m, 4H), 3.84 (s, 4H), 3.18 (s, 2H), 2.18 (s, 1H), 1.84 (s, 2H), 1.43 (d, J = 6.6 Hz, 6H) | 370.2 | A |
| 144 | 2-amino-5-(1-isopropyl-5-((1R,5S,6r)-3-(oxetan-3-yl)-3-azabicyclo[3.1.0]hexan-6-yl)-1H-pyrazol-3-yl)nicotinonitrile | (400 MHz, DMSO-d₆) δ: 8.57 (s, 1H), 8.08 (s, 1H), 6.91 (s, 2H), 6.35 (s, 1H), 4.73-4.62 (m, 1H), 4.60-4.44 (m, 4H), 3.81-3.70 (m, 1H), 3.12 (d, J = 8.8 Hz, 2H), 2.46-2.39 (m, 2H), 2.19-2.12 (m, 1H), 1.82-1.76 (m, 2H), 1.42 (d, J = 6.5 Hz, 6H) | 365.2 | AF |

TABLE A-continued

| No. | Structure | ¹H NMR | MS [MH]⁺ | Method |
|---|---|---|---|---|
| 143 | 5-(1-isopropyl-5-((1R,5S,6r)-3-(oxetan-3-yl)-3-azabicyclo[3.1.0]hexan-6-yl)-1H-pyrazol-3-yl)-3,3-dimethyl-2,3-dihydro-1H-pyrrolo[2,3-b]pyridine | (400 MHz, CD₃OD): δ 8.01-7.97 (m, 1 H), 7.80 (s, 1 H), 6.19 (s, 1 H), 4.76-4.71 (m, 3 H), 4.65-4.62 (m, 2 H), 3.86-3.79 (m, 1 H), 3.47 (s, 2 H), 3.25 (d, J = 9.2 Hz, 2 H), 2.58-2.56 (m, 2 H), 2.31-2.29 (m, 1 H), 1.89-1.87 (m, 2 H), 1.52 (d, J = 6.4 Hz, 6H), 1.38 (s, 6 H) | 394.0 | A |
| 142 | 3-cyclopropyl-5-(1-isopropyl-5-((1R,5S,6r)-3-(oxetan-3-yl)-3-azabicyclo[3.1.0]hexan-6-yl)-1H-pyrazol-3-yl)pyridin-2-amine | (400 MHz, CD₃OD): δ 8.08 (s, 1 H), 7.88 (s, 1 H), 6.25 (s, 1 H), 4.79-4.73 (m, 3 H), 4.66-4.63 (m, 2 H), 3.88-3.81 (m, 1 H), 3.26 (d, J = 9.2 Hz, 2 H), 2.58-2.56 (m, 2 H), 2.33-2.31 (m, 1 H), 1.90-1.88 (m, 2 H), 1.80-1.73 (m, 1 H), 1.53 (d, J = 6.8 Hz, 6 H), 1.09-1.06 (m, 2 H), 0.78-0.70 (m, 2 H) | 380.0 | A |
| 141 | 3-(difluoromethoxy)-5-(1-isopropyl-5-((1R,5S,6r)-3-(oxetan-3-yl)-3-azabicyclo[3.1.0]hexan-6-yl)-1H-pyrazol-3-yl)pyridin-2-amine | (400 MHz, CD₃OD): δ 8.16 (s, 1 H), 7.73 (s, 1 H), 6.88 (t, J = 73.6 Hz, 1 H), 6.19 (s, 1 H), 4.80-4.72 (m, 3 H), 4.66-4.63 (m, 2 H), 3.85-3.80 (m, 1 H), 3.23 (d, J = 9.2 Hz, 2 H), 2.54-2.52 (m, 2 H), 2.32-2.30 (m, 1 H), 1.88-1.87 (m, 2 H), 1.53 (d, J = 6.4 Hz, 6 H) | 406.0 | A |
| 140 | 3-chloro-5-(1-isopropyl-5-((1R,5S,6r)-3-(oxetan-3-yl)-3-azabicyclo[3.1.0]hexan-6-yl)-1H-pyrazol-3-yl)pyridin-2-amine | (400 MHz, CD₃OD): δ 8.22 (s, 1 H), 7.93 (s, 1 H), 8.17 (s, 1 H), 4.76-4.70 (m, 3 H), 4.63-4.60 (m, 2 H), 3.86-3.79 (m, 1 H), 3.24 (d, J = 9.2 Hz, 2H), 2.56-2.54 (m, 2 H), 2.28-2.27 (m, 1 H), 1.88-1.86 (m, 2 H), 1.50 (d, J = 6.8 Hz, 6 H) | 373.9 | A |

TABLE A-continued

| No. | Structure | ¹H NMR | MS [MH]⁺ | Method |
|---|---|---|---|---|
| 139 | 5-(1-cyclopentyl-5-((1R,5S,6r)-3-(oxetan-3-yl)-3-azabicyclo[3.1.0]hexan-6-yl)-1H-pyrazol-3-yl)-3-cyclopropylpyridin-2-amine | (400 MHz, DMSO-d6) δ: 8.14 (s, 1H), 7.39 (s, 1H), 6.25 (s, 1H), 5.89 (s, 2H), 4.94-4.74 (m, 1H), 4.52 (dt, J = 28.8, 6.4 Hz, 4H), 3.83-3.68 (m, 1H), 3.12 (d, J = 8.7 Hz, 2H), 2.46-2.35 (m, 2H), 2.21-2.11 (m, 1H), 2.12-1.57 (m, 11H), 0.96-0.83 (m, 2H), 0.63-0.41 (m, 2H) | 406.3 | C |
| 138 | 2-amino-5-(1-cyclopentyl-5-((1R,5S,6r)-3-(oxetan-3-yl)-3-azabicyclo[3.1.0]hexan-6-yl)-1H-pyrazol-3-yl)nicotinonitrile | (400 MHz, DMSO-d₆) δ: 8.56 (s, 1H), 8.07 (s, 1H), 6.91 (s, 2H), 6.36 (s, 1H), 4.89-4.77 (m, 1H), 4.60-4.44 (m, 4H), 3.81-3.70 (m, 1H), 3.12 (d, J = 8.8 Hz, 2H), 2.43 (dd, J = 8.4, 2.1 Hz, 2H), 2.21-2.14 (m, 1H), 2.11-1.75 (m, 8H), 1.73-1.61 (m, 2H) | 391.2 | C |
| 137 | 5-(1-cyclopentyl-5-((1R,5S,6r)-3-(oxetan-3-yl)-3-azabicyclo[3.1.0]hexan-6-yl)-1H-pyrazol-3-yl)-3-(difluoromethoxy)pyridin-2-amine | (400 MHz, CD₃OD): δ 8.13 (s, 1 H), 7.73 (s, 1 H), 6.87 (t, J = 73.6 Hz, 1 H), 6.19 (s, 1 H), 4.91-4.89 (m, 1 H), 4.76-4.73 (m, 2 H), 4.65-4.62 (m, 2 H), 3.91-3.88 (m, 1 H), 3.31 (s, 2 H), 2.65-2.63 (m, 2 H), 2.32-2.30 (m, 1 H), 2.15-2.08 (m, 4 H), 2.00-1.91 (m, 2 H), 1.90-1.89 (m, 2 H), 1.76-1.72 (m, 2 H) | 432.0 | C |
| 136 | 3-chloro-5-(1-cyclopentyl-5-((1R,5S,6r)-3-(oxetan-3-yl)-3-azabicyclo[3.1.0]hexan-6-yl)-1H-pyrazol-3-yl)pyridin-2-amine | (400 MHz, CD₃OD): δ 8.23 (s, 1 H), 7.93 (s, 1 H), 6.17 (s, 1 H), 4.92-4.85 (m, 1 H), 4.74-4.70 (m, 2 H), 4.64-4.61 (m, 2 H), 3.84-3.78 (m, 1 H), 3.22 (d, J = 9.2 Hz, 2 H), 2.54-2.52 (m, 2 H), 2.31-2.29 (m, 1 H), 2.14-2.07 (m, 4 H), 2.00-1.96 (m, 2 H), 1.85 (s, 2 H), 1.76-1.72 (m, 2 H) | 399.9 | C |

TABLE A-continued

| No. | Structure | ¹H NMR | MS [MH]⁺ | Method |
|---|---|---|---|---|
| 41 | 5-(1-isopropyl-5-(1-methylpiperidin-4-yl)-1H-pyrazol-3-yl)-3-(trifluoromethyl)pyridin-2-amine | (400 MHz, CD$_3$OD): δ 8.55 (s, 1 H), 8.14 (s, 1 H), 6.45 (s, 1 H), 4.66-4.59 (m, 1 H), 3.55-3.52 (m, 2 H), 3.32-3.31 (m, 3 H), 2.85 (s, 3 H), 2.17-2.14 (m, 2 H), 2.01-1.98 (m, 2 H), 1.51 (d, J = 7.6 Hz, 6 H) | 367.9 | O |
| 99 | 3-(difluoromethoxy)-5-(1-isopropyl-5-(1-(oxetan-3-yl)piperidin-4-yl)-1H-pyrazol-3-yl)pyridin-2-amine | (400 MHz, CD$_3$OD): δ 8.18 (s, 1 H), 7.74 (s, 1 H), 6.88 (t, J = 73.6 Hz, 1H), 6.35 (s, 1 H), 4.72-4.69 (m, 2 H), 4.64-4.61 (m, 2 H), 4.59-4.54 (m, 1H), 3.57-3.51 (m, 1 H), 2.91-2.88 (m, 2 H), 2.81-2.73 (m, 1 H), 2.06-2.00 (m, 2 H), 1.99-1.89 (m, 2 H), 1.82-1.73 (m, 2 H), 1.49 (d, J = 6.8 Hz, 6 H) | 408.0 | L |
| 98 | 3-cyclopropyl-5-(1-isopropyl-5-(1-(oxetan-3-yl)piperidin-4-yl)-1H-pyrazol-3-yl)pyridin-2-amine | (400 MHz, CD$_3$OD): δ 8.14 (s, 1 H), 7.65 (s, 1 H), 6.31 (s, 1 H), 4.73-4.69 (m, 2 H), 4.64-4.60 (m, 2 H), 4.59-4.54 (m, 1 H), 3.58-3.51 (m, 1 H), 2.92-2.89 (m, 2 H), 2.81-2.73 (m, 1 H), 2.06-2.00 (m, 2 H), 1.95-1.92 (m, 2 H), 1.84-1.67 (m, 3 H), 1.49 (d, J = 6.4 Hz, 6 H), 1.01-0.96 (m, 2 H), 0.68-0.62 (m, 2 H) | 382.2 | L |
| 102 | 5-(5-(1-cyclobutylpiperidin-4-yl)-1-isopropyl-1H-pyrazol-3-yl)-3-(trifluoromethyl)pyridin-2-amine | (400 MHz, CD$_3$OD): δ 8.54 (s, 1 H), 8.14 (s, 1 H), 6.44 (s, 1 H), 4.63-4.60 (m, 1 H), 3.66-3.62 (m, 1 H), 3.54-3.50 (m, 2 H), 3.15-3.07 (m, 1H), 2.92-2.85 (m, 2 H), 2.38-2.32 (m, 2 H), 2.27-2.17 (m, 4 H), 1.97-1.86 (m, 4 H), 1.51 (d, J = 6.4 Hz, 6 H) | 408.0 | N |

TABLE A-continued

| No. | Structure | ¹H NMR | MS [MH]⁺ | Method |
|---|---|---|---|---|
| 53 | 5-(1-isopropyl-5-(1-(2-methoxyethyl)piperidin-4-yl)-1H-pyrazol-3-yl)-3-(trifluoromethyl)pyridin-2-amine | (400 MHz, CD₃OD): δ 8.56 (s, 1 H), 8.16 (s, 1 H), 6.44 (s, 1 H), 4.67-4.60 (m, 1 H), 3.73-3.70 (m, 2 H), 3.52-3.49 (m, 2 H), 3.43 (s, 3 H), 3.17-3.14 (m, 2 H), 3.07-3.02 (m, 1 H), 3.02-3.87 (m, 2 H), 2.13-2.10 (m, 2 H), 2.02-1.91 (m, 2 H), 1.53 (d, J = 6.8 Hz, 6 H) | 412.0 | M |
| 52 | 2-(4-(3-(6-amino-5-(trifluoromethyl)pyridin-3-yl)-1-isopropyl-1H-pyrazol-5-yl)piperidin-1-yl)acetonitrile | (400 MHz, CD₃OD): 8.54 (s, 1 H), 8.14 (s, 1 H), 6.39 (s, 1 H), 4.61-4.58 (m, 1 H), 3.70 (s, 2 H), 3.00-2.97 (m, 2 H), 2.80-2.74 (m, 1 H), 2.52-2.46 (m, 2 H), 2.03-1.96 (m, 2 H), 1.84-1.81 (m, 2 H), 1.50 (d, J = 6.8 Hz, 6 H) | 393.1 | P |
| 7 | 5-(1-isopropyl-5-(1-methylazetidin-3-yl)-1H-pyrazol-3-yl)-3-(trifluoromethyl)pyridin-2-amine | (400 MHz, CDCl3): δ 8.61 (s, 1 H), 8.15 (s, 1 H), 6.33 (s, 1 H), 4.96 (s, 2 H), 4.29-4.22 (m, 1 H), 3.81-3.78 (m, 2 H), 3.73-3.65 (m, 1 H), 3.17-3.14 (m, 2 H), 2.38 (s, 3 H), 1.47 (d, J = 6.8 Hz, 6 H) | 339.9 | D |
| 97 | 5-(5-(1-(oxetan-3-yl)piperidin-4-yl)-1-(tetrahydrofuran-3-yl)-1H-pyrazol-3-yl)-3-(trifluoromethyl)pyridin-2-amine | (400 MHz, CD₃OD): δ 8.58 (s, 1 H), 8.18 (s, 1 H), 6.49 (s, 1 H), 5.16-5.10 (m, 1 H), 4.81-4.77 (m, 2 H), 4.72-4.68 (m, 2 H), 4.29-4.27 (m, 1 H), 4.25-4.23 (m, 1 H), 4.17-3.96 (m, 2 H), 3.81-3.77 (m, 1 H), 3.11-3.08 (m, 2 H), 2.98-2.92 (m, 1 H), 2.45-2.39 (m, 2 H), 2.38-2.28 (m, 2 H), 2.09-2.01 (m, 2 H), 1.91-1.80 (m, 2 H) | 438.2 | U |

TABLE A-continued

| No. | Structure | ¹H NMR | MS [MH]⁺ | Method |
|---|---|---|---|---|
| 95 | 5-(1-isopropyl-5-(1-(oxetan-3-yl)piperidin-4-yl)-1H-pyrazol-3-yl)-3,3-dimethyl-2,3-dihydro-1H-pyrrolo[2,3-b]pyridine | (400 MHz, DMSO-d₆) δ: 8.09 (s, 1H), 7.70 (s, 1H), 7.01 (s, 1H), 6.40 (s, 1H), 4.75-4.70 (m, 2H), 4.70-4.62 (m, 2H), 4.62-4.50 (m, 1H), 4.08 (s, 1H), 2.99-2.94 (m, 1H), 2.02-1.94 (m, 2H), 1.90-1.85 (m, 2H), 1.41 (d, J = 6.4 Hz, 6H), 1.30 (s, 6H) | 396.3 | AG |
| 93 | 2-amino-5-(1-cyclopentyl-5-(1-(oxetan-3-yl)piperidin-4-yl)-1H-pyrazol-3-yl) nicotinonitrile | (400 MHz, DMSO-d₆) δ: 8.61 (s, 1H), 8.12 (s, 1H), 6.91 (s, 2H), 6.49 (s, 1H), 4.77-4.65 (m, 1H), 4.59-4.51 (m, 2H), 4.49-4.42 (m, 2H), 3.45-3.40 (m, 1H), 2.79-2.74 (m, 2H), 2.06-1.80 (m, 11H), 1.69-1.57 (m, 4H) | 393.3 | S |
| 92 | 2-amino-5-(1-isopropyl-5-(1-(oxetan-3-yl)piperidin-4-yl)-1H-pyrazol-3-yl) nicotinonitrile | (400 MHz, DMSO-d₆) δ: 8.61 (s, 1H), 8.13 (s, 1H), 6.91 (s, 2H), 6.49 (s, 1H), 4.59-4.48 (m, 3H), 4.48-4.40 (m, 2H), 3.46-3.38 (m, 1H), 2.81-2.66 (m, 3H), 1.97-1.78 (m, 4H), 1.70-1.55 (m, 2H), 1.40 (d, J = 6.4 Hz, 6H) | 367.2 | L |
| 135 | 5-(1-cyclopentyl-5-((1R,5S,6r)-3-(oxetan-3-yl)-3-azabicyclo[3.1.0]hexan-6-yl)-1H-pyrazol-3-yl)-3-(trifluoromethyl) pyridin-2-amine | (400 MHz, CD₃OD): δ 8.52 (s, 1 H), 8.12 (s, 1 H), 6.24 (s, 1 H), 4.94-4.90 (m, 1 H), 4.76-4.73 (m, 2 H), 4.67-4.64 (m, 2 H), 3.88-3.82 (m, 1 H), 3.26 (d, J = 9.2 Hz, 2 H), 2.59-2.56 (m, 2 H), 2.34-2.32 (m, 1 H), 2.18-2.09 (m, 4 H), 2.04-1.98 (m, 2 H), 1.90 (s, 2 H), 1.89-1.74 (m, 2 H) | 433.9 | C |

TABLE A-continued

| No. | Structure | ¹H NMR | MS [MH]⁺ | Method |
|---|---|---|---|---|
| 91 | 3-chloro-5-(1-(3,3-difluorocyclopentyl)-5-(1-(oxetan-3-yl)piperidin-4-yl)-1H-pyrazol-3-yl)pyridin-2-amine | (400 MHz, CD$_3$OD): δ 8.28 (s, 1 H), 7.98 (s, 1 H), 6.40 (s, 1 H), 4.97-4.93 (m, 1 H), 4.71 (t, J = 6.8 Hz, 2 H), 4.63 (t, J = 6.8 Hz, 2 H), 3.58-3.53 (m, 1 H), 2.92-2.89 (m, 2 H), 2.84-2.71 (m, 2 H), 2.63-2.51 (m, 2 H), 2.34-2.14 (m, 3 H), 2.08-2.01 (m, 2 H), 1.95-1.92 (m, 2 H), 1.83-1.73 (m, 2 H) | 438.2 | T |
| 106 | 5-(5-((1R,5S,6s)-3-oxabicyclo[3.1.0]hexan-6-yl)-1-isopropyl-1H-pyrazol-3-yl)-3-fluoro-1H-pyrrolo[2,3-b]pyridine | | 327.2 | K |
| 105 | 5-(5-((1R,5S,6s)-3-oxabicyclo[3.1.0]hexan-6-yl)-1-cyclopentyl-1H-pyrazol-3-yl)-3-chloropyridin-2-amine | | 345.1 | K |
| 90 | 5-(1-cyclopentyl-5-(1-(oxetan-3-yl)piperidin-4-yl)-1H-pyrazol-3-yl)-3-isopropoxypyridin-2-amine | (400 MHz, DMSO-d$_6$) δ: 7.91 (s, 1H), 7.44 (s, 1H), 6.46 (s, 1H), 6.24 (s, 2H), 4.78-4.61 (m, 6H), 3.01-2.96 (m, 2H), 2.09-1.81 (m, 12H), 1.70-1.58 (m, 2H), 1.32 (d, J = 5.9 Hz, 6H) | 426.3 | S |

TABLE A-continued

| No. | Structure | ¹H NMR | MS [MH]⁺ | Method |
|---|---|---|---|---|
| 89 | 5-(1-isopropyl-5-(1-(oxetan-3-yl)piperidin-4-yl)-1H-pyrazol-3-yl)-3-methoxypyridin-2-amine | (400 MHz, DMSO-d₆) δ: 7.92 (s, 1H), 7.53 (s, 1H), 6.99 (s, 2H), 6.51 (s, 1H), 4.87-4.82 (m, 2H), 4.73-4.54 (m, 3H), 3.94 (s, 3H), 3.36 (s, 1H), 3.08-3.03 (m, 2H), 2.88-2.83 (m, 2H), 2.04-1.99 (m, 4H), 1.42 (d, J = 6.4 Hz, 6H) | 372.3 | L |
| 88 | 5-(1-cyclopentyl-5-(1-(oxetan-3-yl)piperidin-4-yl)-1H-pyrazol-3-yl)-3-methoxypyridin-2-amine | (400 MHz, DMSO-d₆) δ: 7.92 (s, 1H), 7.34 (s, 1H), 6.42 (s, 1H), 5.89 (s, 2H), 4.84-4.65 (m, 1H), 4.64-4.40 (m, 2H), 3.84 (s, 3H), 2.90-2.85 (m, 2H), 2.08-1.82 (m, 8H), 1.75-1.70 (m, 2H), 1.72-1.59 (m, 2H) | 398.3 | S |
| 101 | 5-(5-(1-cyclobutylpiperidin-4-yl)-1-isopropyl-1H-pyrazol-3-yl)-3-(trifluoromethyl)-1H-pyrrolo[2,3-b]pyridine | (400 MHz, CD₃OD): δ 8.76 (s, 1 H), 8.38 (s, 1 H), 7.86 (s, 1 H), 6.54 (s, 1 H), 4.67-4.58 (m, 1 H), 3.41-3.38 (m, 3 H), 3.07-3.02 (m, 1 H), 2.68-2.65 (m, 2 H), 2.33-2.25 (m, 2 H), 2.17-2.12 (m, 4 H), 1.94-1.84 (m, 4 H), 1.54 (d, J = 6.8 Hz, 6 H) | 432.0 | N |
| 134 | 5-(1-isopropyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine | (400 MHz, DMSO-d₆): δ 8.54 (d, J = 2.1 Hz, 1 H), 7.98 (d, J = 2.1 Hz, 1 H), 6.50 (br s, 2 H), 6.39 (s, 1 H), 4.67 (m, 1 H), 4.56 (t, J = 6.6 Hz, 2 H), 4.48 (t, J = 6.0 Hz, 2 H), 3.75 (m, 1 H), 3.12 (d, J = 8.7 Hz, 2 H), 2.42 (m, 2 H), 2.15 (m, 1 H), 1.81 (m, 2 H), 1.42 (d, J = 6.5 Hz, 6 H) | 408.0 | A |

| No. | Structure | ¹H NMR | MS [MH]⁺ | Method |
|---|---|---|---|---|
| 87 | 3-(cyclopropylmethoxy)-5-(1-(3,3-difluorocyclopentyl)-5-(1-(oxetan-3-yl)piperidin-4-yl)-1H-pyrazol-3-yl)pyridin-2-amine | (400 MHz, CD₃OD): δ 7.90 (s, 1 H), 7.44 (s, 1 H), 6.38 (s, 1 H), 4.96-4.87 (m, 1 H), 4.73-4.70 (m, 2 H), 4.65-4.62 (m, 2 H), 3.95 (d, J = 6.8 Hz, 2 H), 3.57-3.54 (m, 1 H), 2.92-2.89 (m, 2 H), 2.84-2.74 (m, 2 H), 2.62-2.42 (m, 2 H), 2.34-2.16 (m, 3 H), 2.08-2.02 (m, 2 H), 1.95-1.83 (m, 2 H), 1.83-1.74 (m, 2 H), 1.36-1.32 (m, 1 H), 0.68-0.64 (m, 2 H), 0.44-0.41 (m, 2 H) | 474.1 | T |
| 86 | 5-(1-(3,3-difluorocyclopentyl)-5-(1-(oxetan-3-yl)piperidin-4-yl)-1H-pyrazol-3-yl)-3-isopropoxypyridin-2-amine | (400 MHz, CD₃OD): δ 7.89 (s, 1 H), 7.46 (s, 1 H), 6.37 (s, 1 H), 4.93-4.91 (m, 1 H), 4.73-4.69 (m, 3 H), 4.64-4.61 (m, 2 H), 3.56-3.53 (m, 1 H), 2.90-2.88 (m, 2 H), 2.83-2.70 (m, 2 H), 2.64-2.47 (m, 2 H), 2.34-2.16 (m, 3 H), 2.07-2.01 (m, 2 H), 1.95-1.92 (m, 2 H), 1.83-1.70 (m, 2 H), 1.38 (d, J = 6.8 Hz, 6H) | 462.0 | T |
| 85 | 5-(1-(3,3-difluorocyclopentyl)-5-(1-(oxetan-3-yl)piperidin-4-yl)-1H-pyrazol-3-yl)-3-ethoxypyridin-2-amine | (400 MHz, CD₃OD): δ 7.89 (s, 1 H), 7.44 (s, 1 H), 6.38 (s, 1 H), 4.95-4.93 (m, 1 H), 4.73-4.69 (m, 2 H), 4.64-4.61 (m, 2 H), 4.19-4.13 (m, 2 H), 3.56-3.53 (m, 1 H), 2.91-2.88 (m, 2 H), 2.83-2.72 (m, 2 H), 2.63-2.47 (m, 2 H), 2.32-2.20 (m, 3 H), 2.07-2.01 (m, 2 H), 1.95-1.92 (m, 2 H), 1.79-1.74 (m, 2 H), 1.50-1.42 (m, 3 H) | 448.2 | T |

TABLE A-continued

| No. | Structure | ¹H NMR | MS [MH]⁺ | Method |
|---|---|---|---|---|
| 84 | 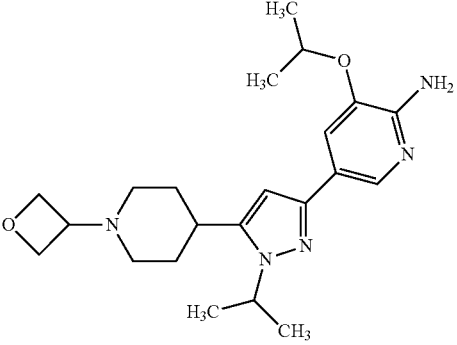 [SMILES: CC(C)Oc1cc(-c2cc(C3CCN(C4COC4)CC3)n(C(C)C)n2)cnc1N]<br>3-isopropoxy-5-(1-isopropyl-5-(1-(oxetan-3-yl)piperidin-4-yl)-1H-pyrazol-3-yl)pyridin-2-amine | (400 MHz, CD₃OD): δ 7.86 (s, 1 H), 7.57 (s, 1 H), 6.41 (s, 1 H), 4.82-4.75 (m, 3 H), 4.69-4.66 (m, 2 H), 4.63-4.60 (m, 1 H), 3.72-3.65 (m, 1 H), 3.03-3.00 (m, 2 H), 2.89-2.83 (m, 1 H), 2.22-2.16 (m, 2 H), 2.02-1.99 (m, 2 H), 1.89-1.82 (m, 2 H), 1.51 (d, J = 6.4 Hz, 6 H), 1.43 (d, J = 6.0 Hz, 6 H) | 400.1 | L |
| 83 | 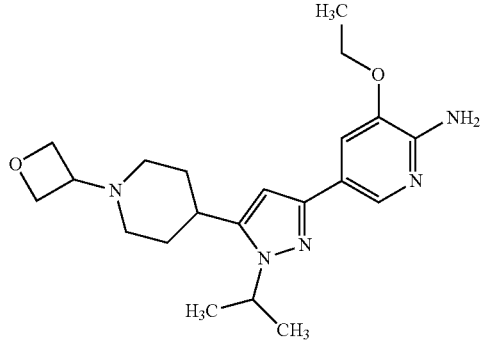 [SMILES: CCOc1cc(-c2cc(C3CCN(C4COC4)CC3)n(C(C)C)n2)cnc1N]<br>3-ethoxy-5-(1-isopropyl-5-(1-(oxetan-3-yl)piperidin-4-yl)-1H-pyrazol-3-yl)pyridin-2-amine | (400 MHz, CDCl₃): δ 8.33 (s, 2 H), 7.74 (s, 1 H), 7.51 (s, 1H), 6.19 (s, 1 H), 4.69 (d, J = 6.4 Hz, 4 H), 4.45-4.38 (m, 1 H), 4.24-4.19 (m, 2 H), 3.61-3.54 (m, 1 H), 2.94-2.92 (m, 2 H), 2.66-2.59 (m, 1 H), 2.04-2.00 (m, 2 H), 1.98-1.82 (m, 4 H), 1.52-1.49 (m, 9 H) | 386.1 | L |
| 81 | 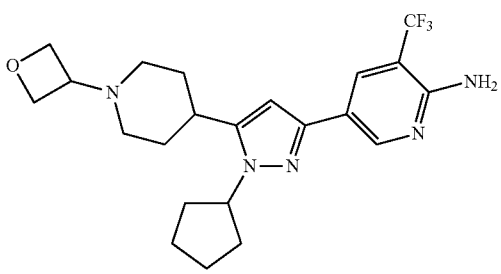 [SMILES: Nc1ncc(-c2cc(C3CCN(C4COC4)CC3)n(C3CCCC3)n2)cc1C(F)(F)F]<br>5-(1-cyclopentyl-5-(1-(oxetan-3-yl)piperidin-4-yl)-1H-pyrazol-3-yl)-3-(trifluoromethyl)pyridin-2-amine | (400 MHz, CD₃OD) δ 8.54 (s, 1 H), 8.13 (s, 1 H), 6.42 (s, 1 H), 4.78-4.74 (m, 3 H), 4.69-4.66 (m, 2 H), 3.77-3.70 (m, 1 H), 3.06-3.03 (m, 2 H), 2.94-2.86 (m, 1 H), 2.28-2.23 (m, 2 H), 2.16-1.97 (m, 8 H), 1.88-1.81 (m, 4 H) | 436.0 | S |

TABLE A-continued

| No. | Structure | ¹H NMR | MS [MH]⁺ | Method |
|---|---|---|---|---|
| 133 | 5-(1-isopropyl-5-((1R,5S,6r)-3-(oxetan-3-yl)-3-azabicyclo[3.1.0]hexan-6-yl)-1H-pyrazol-3-yl)-3-(trifluoromethyl)-1H-pyrrolo[2,3-b]pyridine | (400 MHz, CD₃OD): δ 8.73 (s, 1 H), 8.35 (s, 1 H), 7.84 (s, 1 H), 6.34 (s, 1 H), 4.82-4.78 (m, 1 H), 4.73-4.70 (m, 2 H), 4.64-4.61 (m, 2 H), 3.84-3.78 (m, 1 H), 3.23 (d, J = 8.8 Hz, 2 H), 2.54-2.52 (m, 2 H), 2.33-2.31 (m, 1 H), 1.90 (s, 2 H), 1.56 (d, J = 6.4 Hz, 6 H) | 432.1 | A |
| 104 | 5-(5-((1R,5S,6s)-3-oxabicyclo[3.1.0]hexan-6-yl)-1-isopropyl-1H-pyrazol-3-yl)-3-(trifluoromethyl)pyridin-2-amine | 1H NMR (400 MHz, Chloroform-d) δ 8.56 (s, 1 H), 8.12 (s, 1H), 6.07 (s, 1 H), 4.99 (br.s, 2 H), 4.70-4.60 (m, 2 H), 4.06 (d, J = 8.8 Hz, 2 H), 3.82 (d, J = 8.8 Hz, 2 H), 1.96 (s, 2 H), 1.79-1.75 (m, 1 H), 1.53 (d, J = 6.4 Hz, 6 H) | 352.8 | K |
| 46 | 5-(1-isopropyl-5-(1-(2,2,2-trifluoroethyl)piperidin-4-yl)-1H-pyrazol-3-yl)-1H-pyrrolo[2,3-b]pyridine-3-carbonitrile | (400 MHz, CD₃OD): δ 8.82 (s, 1 H), 8.43 (s, 1 H), 8.13 (s, 1 H), 6.55 (s, 1 H), 4.65-4.61 (m, 1 H), 3.16-3.08 (m, 4 H), 2.80-2.76 (m, 1 H), 2.59-2.54 (m, 2 H), 1.94-1.84 (m, 4 H), 1.54 (d, J = 6.4 Hz, 6 H) | 416.9 | Q |
| 40 | 5-(1-isopropyl-5-(1-methylpiperidin-4-yl)-1H-pyrazol-3-yl)-3-(trifluoromethyl)-1H-pyrrolo[2,3-b]pyridine | (400 MHz, CD₃OD): δ 8.90 (s, 1 H), 8.67 (s, 1 H), 8.06 (s, 1 H), 6.72 (s, 1 H), 4.76-4.70 (m, 1 H), 3.69-3.65 (m, 2 H), 3.28-3.20 (m, 3 H), 2.97 (s, 3 H), 2.28-2.21 (m, 2 H), 2.13-1.99 (m, 2 H), 1.58 (d, J = 6.8 Hz, 6 H) | 391.9 | O |

TABLE A-continued

| No. | Structure | ¹H NMR | MS [MH]⁺ | Method |
|---|---|---|---|---|
| 67 | 5-(1-isopropyl-5-(1-(oxetan-3-yl)pyrrolidin-3-yl)-1H-pyrazol-3-yl)-3-(trifluoromethyl)pyridin-2-amine | (400 MHz, DMSO-d₆) δ: 8.60 (s, 1H), 8.02 (s, 1H), 6.57 (s, 1H), 6.46 (s, 2H), 4.63-4.46 (m, 5H), 3.71-3.60 (m, 1H), 3.55-3.42 (m, 1H), 2.99 (t, J = 8.4 Hz, 1H), 2.74-2.64 (m, 1H), 2.61-2.51 (m, 1H), 2.50-2.41 (m, 1H), 2.36-2.22 (m, 1H), 1.87-1.73 (m, 1H), 1.40 (dd, J = 6.7, 1.3 Hz, 6H) | 396.2 | |
| 51 | 2-(4-(1-isopropyl-3-(3-(trifluoromethyl)-1H-pyrrolo[2,3-b]pyridin-5-yl)-1H-pyrazol-5-yl)piperidin-1-yl)acetonitrile | (400 MHz, CD₃OD): δ 8.75 (s, 1 H), 8.38 (s, 1 H), 7.85 (s, 1 H), 6.50 (s, 1 H), 4.67-4.60 (m, 1 H), 3.71 (s, 2 H), 3.01-2.98 (m, 2 H), 2.83-2.72 (m, 1 H), 2.53-2.47 (m, 2 H), 1.99-1.97 (m, 2 H), 1.89-1.80 (m, 2 H), 1.53 (d, J = 6.4 Hz, 6 H) | 417.1 | P |
| 60 | 5-(1-isopropyl-5-(1-(oxetan-3-yl)azetidin-3-yl)-1H-pyrazol-3-yl)-3-(trifluoromethyl)pyridin-2-amine | (400 MHz, CD₃OD): δ 8.58 (s, 1 H), 8.17 (s, 1 H), 6.70 (s, 1 H), 4.87-4.85 (m, 2 H), 4.59-4.56 (m, 2 H), 4.41-4.37 (m, 1 H), 4.32-4.27 (m, 3 H), 4.19-4.15 (m, 1 H), 3.93-3.89 (m, 2 H), 1.47 (d, J = 6.8 Hz, 6 H) | 381.9 | E |
| 1 | 5-(5-isopropyl-1-(1-(oxetan-3-yl)azetidin-3-yl)-1H-pyrazol-3-yl)-3-(trifluoromethyl)-1H-pyrrolo[2,3-b]pyridine | | 406.2 | AH |

TABLE A-continued

| No. | Structure | ¹H NMR | MS [MH]⁺ | Method |
|---|---|---|---|---|
| 132 | 5-(1-isopropyl-5-((1R,5S,6r)-3-(oxetan-3-yl)-3-azabicyclo[3.1.0]hexan-6-yl)-1H-pyrazol-3-yl)-1H-pyrrolo[2,3-b]pyridine-3-carbonitrile | (400 MHz, CD₃OD): δ 8.81 (s, 1 H), 8.42 (s, 1 H), 8.15 (s, 1 H), 6.42 (s, 1 H), 4.77-4.73 (m, 2 H), 4.67-4.61 (m, 3 H), 3.86-3.83 (m, 1 H), 3.26 (d, J = 9.2 Hz, 2 H), 2.57-2.55 (m, 2 H), 2.36-2.35 (m, 1 H), 1.94 (s, 2 H), 1.59 (d, J = 6.4 Hz, 6 H) | 389.0 | A |
| 78 | 3-chloro-5-(1-isopropyl-5-(1-(oxetan-3-yl)piperidin-4-yl)-1H-pyrazol-3-yl)pyridin-2-amine | (400 MHz, CDCl₃): δ 8.33 (s, 1 H), 7.96 (s, 1 H), 6.19 (s, 1 H), 4.84 (s, 2 H), 4.69-4.62 (m, 4 H), 4.42-4.39 (m, 1 H), 3.52-3.49 (m, 1 H), 2.88-2.85 (m, 2 H), 2.64-2.58 (m, 1 H), 1.98-1.90 (m, 4 H), 1.83-1.80 (m, 2 H), 1.50 (d, J = 6.8 Hz, 6 H) | 376.0 | L |
| 77 | 5-(1-isopropyl-5-(1-(oxetan-3-yl)piperidin-4-yl)-1H-pyrazol-3-yl)-1H-pyrrolo[2,3-b]pyridine-3-carbonitrile | (400 MHz, CD₃OD): δ 8.82 (s, 1 H), 8.43 (s, 1 H), 8.14 (s, 1 H), 6.58 (s, 1 H), 4.73-4.71 (m, 2 H), 4.66-4.65 (m, 3 H), 3.60-3.48 (m, 1 H), 2.95-2.92 (m, 2 H), 2.86-2.80 (m, 1 H), 2.10-1.97 (m, 4 H), 1.89-1.82 (m, 2 H), 1.54 (d, J = 6.8 Hz, 6 H) | 391.0 | L |

TABLE A-continued

| No. | Structure | ¹H NMR | MS [MH]⁺ | Method |
|---|---|---|---|---|
| 59 | 5-(1-isopropyl-5-(1-(oxetan-3-yl)azetidin-3-yl)-1H-pyrazol-3-yl)-1H-pyrrolo[2,3-b]pyridine-3-carbonitrile | (400 MHz, CD$_3$OD): δ 8.85 (s, 1 H), 8.46 (s, 1 H), 8.15 (s, 1 H), 6.76 (s, 1 H), 4.79-4.76 (m, 3 H), 4.56-4.53 (m, 2 H), 4.47-4.44 (m, 1 H), 3.91-3.87 (m, 3 H), 3.49-3.39 (m, 2 H), 1.50 (d, J = 6.8 Hz, 6 H) | 362.9 | E |
| 76 | 5-(1-isopropyl-5-(1-(oxetan-3-yl)piperidin-4-yl)-1H-pyrazol-3-yl)-3-(trifluoromethyl)pyridin-2-amine | (400 MHz, CD$_3$OD): δ 8.53 (s, 1 H), 8.13 (s, 1 H), 6.42 (s, 1 H), 4.79-4.76 (m, 2 H), 4.72-4.69 (m, 2 H), 4.62-4.55 (m, 1 H), 3.92-3.86 (m, 1 H), 3.18-3.15 (m, 2 H), 2.97-2.87 (m, 1 H), 2.46-2.39 (m, 2 H), 2.06-2.03 (m, 2 H), 1.92-1.82 (m, 2 H), 1.48 (d, J = 6.8 Hz, 6 H) | 410.0 | L |
| 58 | 3-fluoro-5-(1-isopropyl-5-(1-(oxetan-3-yl)azetidin-3-yl)-1H-pyrazol-3-yl)-1H-pyrrolo[2,3-b]pyridine | (400 MHz, CDCl$_3$): δ 9.14 (br s, 1 H), 8.77 (s, 1 H), 8.39 (s, 1 H), 7.11 (s, 1 H), 6.49 (s, 1 H), 4.95-4.91 (m, 2 H), 4.75-4.71 (m, 2 H), 4.46-4.39 (m, 2 H), 4.25-4.14 (m, 5 H), 1.53 (d, J = 6.8 Hz, 6 H) | 356.1 | E |
| 57 | 3-chloro-5-(1-isopropyl-5-(1-(oxetan-3-yl)azetidin-3-yl)-1H-pyrazol-3-yl)-1H-pyrrolo[2,3-b]pyridine | (400 MHz, DMSO-d$_6$): δ 8.80 (s, 1 H), 8.24 (s, 1 H), 7.69 (s, 1 H), 7.11 (s, 1 H), 4.77-4.73 (m, 2 H), 4.69-4.66 (m, 2 H), 4.44-4.39 (m, 2 H), 4.38-4.32 (m, 3 H), 4.09-4.07 (m, 2 H), 1.41 (d, J = 6.4 Hz, 6 H) | 372.1 | E |

TABLE A-continued

| No. | Structure | ¹H NMR | MS [MH]⁺ | Method |
|---|---|---|---|---|
| 75 | 3-fluoro-5-(1-isopropyl-5-(1-(oxetan-3-yl)piperidin-4-yl)-1H-pyrazol-3-yl)-1H-pyrrolo[2,3-b]pyridine | (400 MHz, DMSO-d₆): δ 11.45 (s, 1 H), 8.71-8.70 (m, 1 H), 8.25-8.23 (m, 1 H), 1.43-7.42 (m, 1 H), 6.59 (s, 1 H), 4.57-4.52 (m, 2 H), 4.42 (t, J = 6.4 Hz, 1 H), 3.41-3.36 (m, 1 H), 3.07-3.04 (m, 1 H), 2.78-2.69 (m, 2 H), 2.52-2.51 (m, 1 H), 2.48-2.36 (m, 2 H), 1.92-1.87 (m, 3 H), 1.84-1.71 (m, 2 H), 1.40 (d, J = 6.8 Hz, 6 H) | 384.0 | L |
| 56 | 5-(1-(3,3-difluorocyclopentyl)-5-(1-(oxetan-3-yl)azetidin-3-yl)-1H-pyrazol-3-yl)-3-(trifluoromethyl)-1H-pyrrolo[2,3-b]pyridine | (400 MHz, CDCl₃): δ 9.87 (s, 1 H), 8.90 (s, 1 H), 8.39 (s, 1 H), 7.70 (s, 1 H), 6.52 (s, 1 H), 4.74 (t, J = 6.8 Hz, 2 H), 4.59-4.56 (m, 3 H), 3.89-3.80 (m, 4 H), 3.36-3.35 (m, 2 H), 2.94-2.82 (m, 1 H), 2.61-2.40 (m, 3 H), 2.27-2.18 (m, 2 H) | 468.0 | H |
| 66 | 3-fluoro-5-(1-isopropyl-5-(1-(oxetan-3-yl)pyrrolidin-3-yl)-1H-pyrazol-3-yl)-1H-pyrrolol[2,3-b]pyridine | | 370.2 | |
| 74 | 3-chloro-5-(5-(1-(oxetan-3-yl)piperidin-4-yl)-1-(tetrahydrofuran-3-yl)-1H-pyrazol-3-yl)pyridin-2-amine | (400 MHz, CD₃OD): δ 8.27 (m, 1 H), 7.99 (s, 1 H), 6.40 (s, 1 H), 5.11-5.05 (m, 1 H), 4.73-4.70 (m, 2 H), 4.64-4.61 (m, 2 H), 4.24-4.19 (m, 1 H), 4.13-4.09 (m, 1 H), 3.98-3.92 (m, 2 H), 3.60-3.58 (m, 1 H), 2.95-2.92 (m, 2 H), 2.87-2.81 (m, 1 H), 2.40-2.33 (m, 2 H), 2.12-2.06 (m, 2 H), 2.02-1.91 (m, 2 H), 1.82-1.73 (m, 2 H) | 404.0 | U |

TABLE A-continued

| No. | Structure | ¹H NMR | MS [MH]⁺ | Method |
|---|---|---|---|---|
| 65 | 3-chloro-5-(1-isopropyl-5-(1-(oxetan-3-yl)pyrrolidin-3-yl)-1H-pyrazol-3-yl)-1H-pyrrolo[2,3-b]pyridine | | 386.2 | |
| 72 | 3-chloro-5-(1-isopropyl-5-(1-(oxetan-3-yl)piperidin-4-yl)-1H-pyrazol-3-yl)-1H-pyrrolo[2,3-b]pyridine | (400 MHz, CD$_3$OD): δ 8.72 (s, 1 H), 8.32 (s, 1 H), 7.45 (s, 1 H), 6.55 (s, 1 H), 4.75 (t, J = 6.8 Hz, 2 H), 4.68-4.61 (m, 3 H), 3.60-3.57 (m, 1 H), 2.97-2.94 (m, 2 H), 2.88-2.82 (m, 1 H), 2.11-1.99 (m, 4 H), 1.91-1.82 (m, 2 H), 1.56 (d, J = 6.4 Hz, 6 H) | 399.9 | L |
| 55 | 5-(5-(1-(oxetan-3-yl)azetidin-3-yl)-1-(tetrahydrofuran-3-yl)-1H-pyrazol-3-yl)-3-(trifluoromethyl)-1H-pyrrolo[2,3-b]pyridine | (400 MHz, CD$_3$OD): δ 8.83 (s, 1 H), 8.43 (s, 1 H), 7.87 (s, 1 H), 6.78 (s, 1 H), 4.99-4.95 (m, 1 H), 4.77 (t, J = 6.8 Hz, 2 H), 4.56-4.55 (m, 2 H), 4.28-4.22 (m, 1 H), 4.14-4.10 (m, 1 H), 4.05-3.88 (m, 6 H), 3.46-3.41 (m, 2 H), 2.44-2.39 (m, 2 H) | 433.8 | G |
| 54 | 5-(1-isopropyl-5-(1-(oxetan-3-yl)azetidin-3-yl)-1H-pyrazol-3-yl)-3-(trifluoromethyl)-1H-pyrrolo[2,3-b]pyridine | (400 MHz, CD$_3$OD): δ 8.87 (s, 1 H), 8.42 (s, 1 H), 7.87 (s, 1 H), 6.72 (s, 1 H), 4.78-4.76 (m, 3 H), 4.56-4.53 (m, 2 H), 4.47-4.43 (m, 1 H), 3.94-3.90 (m, 3 H); 3.48-3.41 (m, 2 H), 1.50 (d, J = 6.8 Hz, 6 H) | 405.9 | E |

TABLE A-continued

| No. | Structure | ¹H NMR | MS [MH]⁺ | Method |
|---|---|---|---|---|
| 33 | 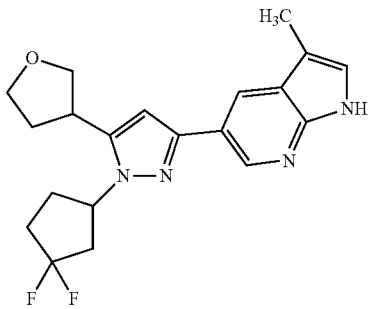 [SMILES: Cc1c[nH]c2ncc(-c3cc(C4CCOC4)n(C4CCC(F)(F)C4)n3)cc12]<br>5-(1-(3,3-difluorocyclopentyl)-5-(tetrahydrofuran-3-yl)-1H-pyrazol-3-yl)-3-methyl-1H-pyrrolo[2,3-b]pyridine<br>(Stereoisomer 4) | $R_T$ = 1.02<br>(Berger MG II, 21.1 ×<br>150 mm, 5 uM, 70 mL/min,<br>20% methanol in 0.1%<br>ammonium hydroxide)<br>Column: Chiralpak AD | 373.2 | AC |
| 32 | 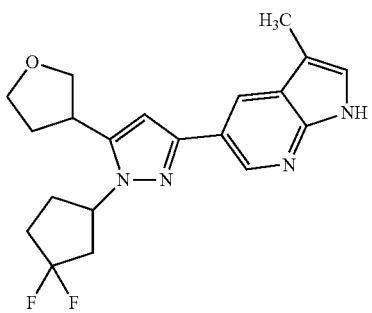 [SMILES: Cc1c[nH]c2ncc(-c3cc(C4CCOC4)n(C4CCC(F)(F)C4)n3)cc12]<br>5-(1-(3,3-difluorocyclopentyl)-5-(tetrahydrofuran-3-yl)-1H-pyrazol-3-yl)-3-methyl-1H-pyrrolo[2,3-b]pyridine<br>(Stereoisomer 3) | $R_T$ = 0.86<br>(Berger MG II, 21.1 ×<br>150 mm, 5 uM, 70 mL/min,<br>20% methanol in 0.1%<br>ammonium hydroxide)<br>Column: Chiralpak AD | 373.2 | AC |
| 31 | 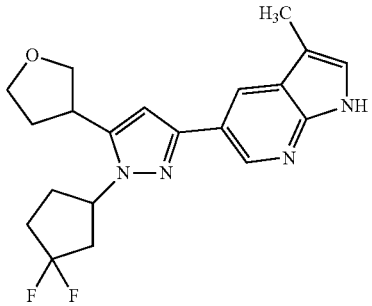 [SMILES: Cc1c[nH]c2ncc(-c3cc(C4CCOC4)n(C4CCC(F)(F)C4)n3)cc12]<br>5-(1-(3,3-difluorocyclopentyl)-5-(tetrahydrofuran-3-yl)-1H-pyrazol-3-yl)-3-methyl-1H-pyrrolo[2,3-b]pyridine<br>(Stereoisomer 1) | $R_T$ = 0.67<br>(Berger MG II, 21.1 ×<br>150 mm, 5 uM, 70 mL/min,<br>20% methanol in 0.1%<br>ammonium hydroxide)<br>Column: Chiralpak AD | 373.2 | AC |

TABLE A-continued

| No. | Structure | ¹H NMR | MS [MH]⁺ | Method |
|---|---|---|---|---|
| 30 | 5-(1,5-bis(tetrahydrofuran-3-yl)-1H-pyrazol-3-yl)-3-(trifluoromethyl)-1H-pyrrolo[2,3-b]pyridine (Stereoisomer 4) | $R_T$ = 0.56 (Berger MG II, 21.1 × 150 mm, 5 uM, 70 mL/min, 25% methanol in 0.1% ammonium hydroxide) Column: Chiralpak AD | 393.2 | AD |
| 29 | 5-(1,5-bis(tetrahydrofuran-3-yl)-1H-pyrazol-3-yl)-3-(trifluoromethyl)-1H-pyrrolo[2,3-b]pyridine (Stereoisomer 3) | $R_T$ = 0.52 (Berger MG II, 21.1 × 150 mm, 5 uM, 70 mL/min, 25% methanol in 0.1% ammonium hydroxide) Column: Chiralpak AD | 393.2 | AD |
| 28 | 5-(1,5-bis(tetrahydrofuran-3-yl)-1H-pyrazol-3-yl)-3-(trifluoromethyl)-1H-pyrrolo[2,3-b]pyridine (Stereoisomer 1) | $R_T$ = 0.4 (Berger MG II, 21.1 × 150 mm, 5 uM, 70 mL/min, 25% methanol in 0.1% ammonium hydroxide) Column: Chiralpak AD | 393.2 | AD |

TABLE A-continued

| No. | Structure | ¹H NMR | MS [MH]⁺ | Method |
|---|---|---|---|---|
| 27 | 5-(1-(3,3-difluorocyclopentyl)-5-(tetrahydrofuran-3-yl)-1H-pyrazol-3-yl)-3-methyl-1H-pyrrolo[2,3-b]pyridine (Stereoisomer 2) | $R_T$ = 0.79 (Berger MG II, 21.1 × 150 mm, 5 uM, 70 mL/min, 20% methanol in 0.1% ammonium hydroxide) Column: Chiralpak AD | 373.2 | AC |
| 26 | 5-(1,5-bis(tetrahydrofuran-3-yl)-1H-pyrazol-3-yl)-3-(trifluoromethyl)-1H-pyrrolo[2,3-b]pyridine (Stereoisomer 2) | $R_T$ = 0.45 (Berger MG II, 21.1 × 150 mm, 5 uM, 70 mL/min, 20% methanol in 0.1% ammonium hydroxide) Column: Chiralpak AD | 393.2 | AD |
| 71 | 3-chloro-5-(1-cyclopentyl-5-(1-(oxetan-3-yl)piperidin-4-yl)-1H-pyrazol-3-yl)pyridin-2-amine | ¹H NMR (400 MHz, DMSO-d6) δ 8.30 (s, 1H), 7.86 (s, 1H), 6.45 (s, 1H), 6.28 (s, 2H), 4.75-4.64 (m, 1H), 4.54 (t, J = 6.5 Hz, 2H), 4.44 (t, J = 6.2 Hz, 2H), 3.47-3.37 (m, 1H), 2.82-2.69 (m, 3H), 2.05-1.79 (m, 11H), 1.69-1.57 (m, 4H). | 402 | S |
| 39 | 3-chloro-5-(1-(3,3-difluorocyclobutyl)-5-(tetrahydro-2H-pyran-4-yl)-1H-pyrazol-3-yl)pyridin-2-amine | (400 MHz, DMSO-d₆), δ: 8.36 (d, J = 2.0 Hz, 1 H), 7.94 (d, J = 2.0 Hz, 1H), 6.55 (s, 1 H), 6.36 (s, 1 H), 5.75 (s, 1 H), 4.95 (m, 1 H), 3.91 (dd, J = 11.1, 4.0 Hz, 2 H), 3.48 (t, J = 11.5 Hz, 2 H), 3.02-3.25 (m, 6 H), 1.74 (m, 2 H), 1.60 (m, 2 H) | 369.2 | |

TABLE A-continued

| No. | Structure | ¹H NMR | MS [MH]⁺ | Method |
|---|---|---|---|---|
| 45 | 4-(1-(3,3-difluorocyclobutyl)-3-(3-(trifluoromethyl)-1H-pyrrolo[2,3-b]pyridin-5-yl)-1H-pyrazol-5-yl)-1-methylpiperidin-2-one | (400 MHz, DMSO-d₆), δ: 8.87 (s, 1 H), 8.34 (s, 1 H), 8.16 (s, 1 H), 6.82 (s, 1 H), 5.02 (m, 1 H), 3.16-3.49 (m, 3 H), 2.87 (s, 3 H), 2.82-2.89 (m, 2 H), 2.33-2.58 (m, 2 H), 2.08 (m, 1 H), 1.89 (m, 1 H), 1.15 (m, 1 H), 0.98 (t, J = 7.1 Hz, 2 H) | 454.2 | |
| 43 | 4-(3-(6-amino-5-chloropyridin-3-yl)-1-(3,3-difluorocyclobutyl)-1H-pyrazol-5-yl)-1-methylpiperidin-2-one | (400 MHz, DMSO-d₆), δ: 8.34 (d, J = 2.0 Hz, 1 H), 7.93 (d, J = 2.2 Hz, 1 H), 6.57 (s, 1 H), 6.38 (br s, 2 H), 4.95 (m, 1 H), 3.12-3.47 (m, 5 H), 2.86 (s, 3 H), 2.58 (m, 1 H), 2.32 (m, 1 H), 2.03 (m, 1 H), 1.83 (m, 1 H), 0.99 (t, J = 7.3 Hz, 2 H) | 396.2 | |
| 38 | 5-(1-(3,3-difluorocyclobutyl)-5-(tetrahydro-2H-pyran-4-yl)-1H-pyrazol-3-yl)-3-(trifluoromethyl)-1H-pyrrolo[2,3-b]pyridine | (400 MHz, DMSO-d₆), δ: 12.54 (br s, 1 H), 8.88 (d, J = 2.0 Hz, 1 H), 8.35 (s, 1 H), 8.16 (s, 1 H), 6.79 (s, 1 H), 5.01 (m, 1 H), 3.94 (m, 2 H), 3.50 (t, J = 11.5 Hz, 2 H), 3.07-3.26 (m, 4 H), 1.78 (m, 2 H), 1.67 (m, 2 H), 1.04 (t, J = 7.4 Hz, 1 H) | 427.2 | |
| 25 | 3-chloro-5-(1-(3,3-difluorocyclobutyl)-5-(tetrahydrofuran-3-yl)-1H-pyrazol-3-yl)pyridin-2-amine | (400 MHz, CD₃OD): δ 8.57 (s, 1 H), 8.28 (s, 1 H), 6.62 (s, 1 H), 4.98-4.95 (m, 1 H), 4.14-4.10 (m, 1 H), 4.04-3.89 (m, 2 H), 3.77-3.73 (m, 1 H), 3.66-3.61 (m, 1 H), 3.37-3.35 (m, 1 H), 3.31-3.25 (m, 1 H), 3.16-3.09 (m, 3 H), 2.47-2.39 (m, 1 H), 2.05-1.95 (m, 1 H) | 354.9 | |

TABLE A-continued

| No. | Structure | ¹H NMR | MS [MH]⁺ | Method |
|---|---|---|---|---|
| 23 | 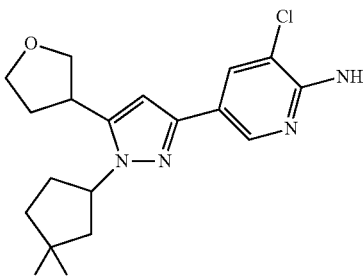<br>3-chloro-5-(1-(3,3-difluorocyclopentyl)-5-(tetrahydrofuran-3-yl)-1H-pyrazol-3-yl)pyridin-2-amine | (400 MHz, CD$_3$OD): δ 8.27 (s, 1 H), 7.97 (s, 1 H), 6.42 (s, 1 H), 5.00-4.92 (m, 1 H), 4.14-4.08 (m, 1 H), 4.03-3.97 (m, 1 H), 3.93-3.88 (m, 1 H), 3.76-3.71 (m, 1 H), 3.63-3.59 (m, 1 H), 2.78-2.60 (m, 2 H), 2.55-2.38 (m, 2 H), 2.32-2.19 (m, 3 H), 2.03-1.97 (m, 1 H) | 369.0 | AC |
| 64 | 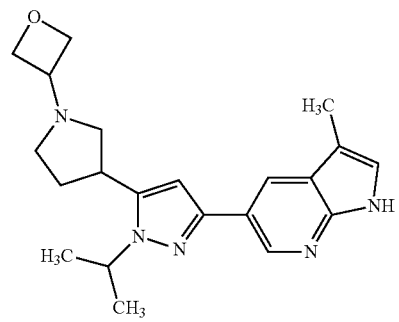 [SMILES: Cc1c[nH]c2ncc(-c3cc(C4CCN(C5COC5)C4)n(C(C)C)n3)cc12]<br>5-(1-isopropyl-5-(1-(oxetan-3-yl)pyrrolidin-3-yl)-1H-pyrazol-3-yl)-3-methyl-1H-pyrrolo[2,3-b]pyridine | (400 MHz, DMSO-d$_6$), δ: 11.22 (s, 1 H), 8.64 (d, J = 1.9 Hz, 1 H), 8.20 (d, J = 1.9 Hz, 1 H), 7.20 (s, 1 H), 6.61 (s, 1 H), 4.55-4.62 (m, 3 H), 4.51 (t, J = 5.8 Hz, 2 H), 3.67 (m, 1 H), 3.51 (m, 1 H), 3.02 (t, J = 8.4 Hz, 1 H), 2.70 (m, 1 H), 2.58 (m, 1 H), 2.47 (m, 1 H), 2.33 (m, 1 H), 2.29 (s, 3 H), 1.84 (m, 1 H), 1.44 (d, J = 6.6 Hz, 6 H) | 366.3 | |
| 20 | 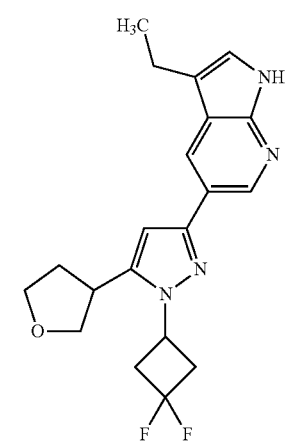 [SMILES: CCc1c[nH]c2ncc(-c3cc(C4CCOC4)n(C4CC(F)(F)C4)n3)cc12]<br>5-(1-(3,3-difluorocyclobutyl)-5-(tetrahydrofuran-3-yl)-1H-pyrazol-3-yl)-3-ethyl-1H-pyrrolo[2,3-b]pyridine | (400 MHz, CD$_3$OD): δ 8.63 (s, 1 H), 8.35 (s, 1 H), 7.17 (s , 1 H), 6.61 (s, 1 H), 5.05-4.96 (m, 1 H), 4.18-4.14 (m, 1 H), 4.05-4.03 (m, 1 H), 3.96-3.93 (m, 1 H), 3.81-3.78 (m, 1 H), 3.67-3.64 (m, 1 H), 3.50-3.30 (m, 2 H), 3.13-3.11 (m, 2 H), 2.83-2.79 (m, 2 H), 2.45-2.40 (m, 1 H), 2.08-2.03 (m, 1 H), 1.37-1.34 (m, 3 H) | 373.2 | AB |

TABLE A-continued

| No. | Structure | ¹H NMR | MS [MH]⁺ | Method |
|---|---|---|---|---|
| 19 | 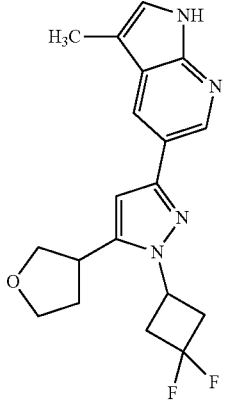 [SMILES: Cc1c[nH]c2ncc(-c3cc(C4CCOC4)n(C4CC(F)(F)C4)n3)cc12] 5-(1-(3,3-difluorocyclobutyl)-5-(tetrahydrofuran-3-yl)-1H-pyrazol-3-yl)-3-methyl-1H-pyrrolo[2,3-b]pyridine | (400 MHz, CD₃OD): δ 9.02 (s, 1 H), 8.81 (s, 1 H), 7.48 (s, 1 H), 6.82 (s, 1 H), 5.10-4.90 (m, 1 H), 4.18-4.14 (m, 1 H), 4.05-4.03 (m, 1 H), 3.97-3.94 (m, 1 H), 3.80-3.79 (m, 1 H), 3.77-3.68 (m, 1 H), 3.50-3.30 (m, 2 H), 3.17-3.14 (m, 2 H), 2.60-2.40 (m, 4 H), 2.07-2.03 (m, 1 H) | 358.9 | AB |
| 18 | 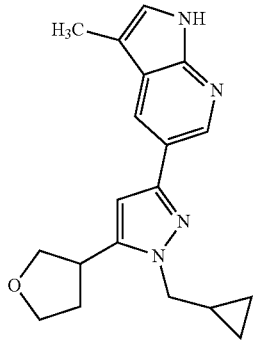 [SMILES: Cc1c[nH]c2ncc(-c3cc(C4CCOC4)n(CC4CC4)n3)cc12] 5-(1-(cyclopropylmethyl)-5-(tetrahydrofuran-3-yl)-1H-pyrazol-3-yl)-3-methyl-1H-pyrrolo[2,3-b]pyridine (enantiomer 2) | (400 MHz, DMSO-d₆) δ: 11.23 (s, 1H), 8.63 (s, 1H), 8.21 (d, J = 2.0 Hz, 1H), 7.21 (d, 1H), 6.67 (s, 1H), 4.13-3.90 (m, 4H), 3.89-3.78 (m, 1H), 3.68-3.50 (m, 2H), 2.43-2.31 (m, 1H), 2.28 (s, 3H), 2.03-1.88 (m, 1H), 1.34-1.22 (m, 1H), 0.58-0.44 (m, 2H), 0.45-0.36 (m, 2H) | 323.2 | X |
| 17 | 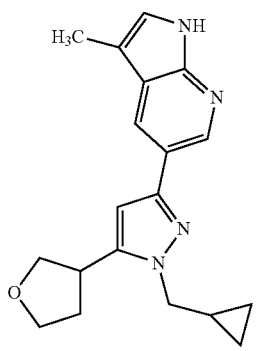 [SMILES: Cc1c[nH]c2ncc(-c3cc(C4CCOC4)n(CC4CC4)n3)cc12] 5-(1-(cyclopropylmethyl)-5-(tetrahydrofuran-3-yl)-1H-pyrazol-3-yl)-3-methyl-1H-pyrrolo[2,3-b]pyridine (enantiomer 1) | (400 MHz, DMSO-d₆) δ: 11.23 (s, 1H), 8.63 (s, 1H), 8.21 (s, 1H), 7.21 (d, 1H), 6.67 (s, 1H), 4.13-3.90 (m, 4H), 3.89-3.78 (m, 1H), 3.68-3.50 (m, 2H), 2.46-2.31 (m, 1H), 2.28 (s, 3H), 2.04-1.90 (m, 1H), 1.35-1.20 (m, 1H), 0.58-0.44 (m, 2H), 0.45-0.36 (m, 2H) | 323.2 | X |

TABLE A-continued

| No. | Structure | ¹H NMR | MS [MH]⁺ | Method |
|---|---|---|---|---|
| 35 | 5-(1-(3,3-difluorocyclobutyl)-5-(tetrahydro-2H-pyran-4-yl)-1H-pyrazol-3-yl)-3-methyl-1H-pyrrolo[2,3-b]pyridine | (400 MHz, DMSO-d₆): δ 11.28 (s, 1 H), 8.68 (d, J = 2.2 Hz, 1 H), 8.25 (d, J = 2.0 (Hz, 1 H), 7.22 (s, 1 H), 6.67 (s, 1 H), 4.99 (m, 1 H), 3.94 (m, 2 H), 3.50 (m, 2 H), 3.05-3.22 (m, 4 H), 2.30 (s, 3 H), 1.80 (m, 2 H), 1.68 (m, 2 H), 0.99 (m, 1 H) | 373.2 | |
| 16 | 5-(1-(3,3-difluorocyclopentyl)-5-(tetrahydrofuran-3-yl)-1H-pyrazol-3-yl)-3-(trifluoromethyl)-1H-pyrrolo[2,3-b]pyridine | (400 MHz, CD₃OD): δ 8.83 (s, 1 H), 8.42 (s, 1 H), 7.88 (s, 1 H), 6.64 (s, 1 H), 5.09-5.05 (m, 1 H), 4.21-4.17 (m, 1 H), 4.10-4.04 (m, 1 H), 3.99-3.93 (m, 1 H), 3.85-3.80 (m, 1 H), 3.71-3.67 (m, 1 H), 2.88-2.81 (m, 1 H), 2.79-2.66 (m, 1 H), 2.60-2.45 (m, 2 H), 2.43-2.22 (m, 3 H), 2.11-2.06 (m, 1 H) | 427.0 | AC |
| 12 | 1-(3-(1-isopropyl-3-(3-methyl-1H-pyrrolo[2,3-b]pyridin-5-yl)-1H-pyrazol-5-yl)azetidin-1-yl)ethanone | (400 MHz, CDCl3): δ 9.48 (s, 1 H), 8.74 (s, 1 H), 8.28 (s, 1 H), 7.10 (s, 1 H), 6.55 (s, 1 H), 4.58 (t, J = 8.4 Hz, 1 H), 4.47 (t, J = 8.8 Hz, 1 H), 4.30-4.23 (m, 2 H), 4.19-4.15 (m, 1 H), 3.97-3.91 (m, 1 H), 2.36 (s, 3 H), 1.94 (s, 3 H), 1.55 (d, J = 6.8 Hz, 6 H) | 337.9 | F |
| 11 | 1-(3-(1-methyl-3-(3-(trifluoromethyl)-1H-pyrrolo[2,3-b]pyridin-5-yl)-1H-pyrazol-5-yl)azetidin-1-yl)ethanone | (400 MHz, CD₃OD): δ 8.79 (s, 1 H), 8.43 (s, 1 H), 7.88 (s, 1 H), 6.87 (s, 1 H), 4.70-4.66 (m, 1 H), 4.49-4.43 (m, 1 H), 4.38-4.34 (m, 1 H), 4.11-4.06 (m, 2 H), 3.83 (s, 3 H), 1.93 (s, 3 H) | 363.9 | J |

TABLE A-continued

| No. | Structure | ¹H NMR | MS [MH]⁺ | Method |
|---|---|---|---|---|
| 42 | 4-(1-(3,3-difluorocyclobutyl)-3-(3-methyl-1H-pyrrolo[2,3-b]pyridin-5-yl)-1H-pyrazol-5-yl)-1-methylpiperidin-2-one | (400 MHz, DMSO-d₆), δ: 11.29 (s, 1 H), 8.66 (d, J = 2.0 Hz, 1 H), 8.24 (d, J = 1.8 Hz, 1 H), 7.23 (s, 1 H), 6.69 (s, 1 H), 5.00 (m, 1 H), 3.15-3.48 (m, 6 H), 2.87 (s, 3 H), 2.64 (m, 1 H), 2.29 (s, 3 H), 2.07 (m, 1 H), 1.88 (m, 1 H), 1.00 (t, J = 7.2 Hz, 2 H) | 400.2 | |
| 63 | 3-methyl-5-(1-methyl-5-(1-(oxetan-3-yl)pyrrolidin-3-yl)-1H-pyrazol-3-yl)-1H-pyrrolo[2,3-b]pyridine | (400 MHz, DMSO-d₆), δ: 11.22 (s, 1 H), 8.62 (d, J = 2.0 Hz, 1 H), 8.20 (d, J = 2.01 Hz, 1 H), 7.20 (m, 1 H), 6.66 (s, 1 H), 4.60 (m, 2 H), 4.51 (t, J = 6.0 Hz, 2 H), 3.81 (s, 3 H), 3.67 (m, 1 H), 3.48 (m, 1 H), 3.02 (t, J = 8.4 Hz, 1 H), 2.69 (m, 1 H), 2.58 (m, 1 H), 2.48 (m, 1 H), 2.33 (m, 1 H), 2.28 (s, 3 H), 1.85 (m, 1 H) | 338.2 | |
| 15 | 5-(1,5-bis(tetrahydrofuran-3-yl)-1H-pyrazol-3-yl)-3-(trifluoromethyl)-1H-pyrrolo[2,3-b]pyridine | (400 MHz, CD₃OD): δ 8.78 (s, 1 H), 8.39 (s, 1 H), 7.84 (s, 1 H), 6.61 (s, 1 H), 5.18-5.16 (m, 1 H), 4.29-4.24 (m, 1 H), 4.20-4.13 (m, 2 H), 4.08-3.90 (m, 4 H), 3.80-3.77 (m, 1 H), 3.69-3.65 (m, 1 H), 2.45-2.40 (m, 3 H), 2.07-2.04 (m, 1 H) | 392.8 | AD |

TABLE A-continued

| No. | Structure | ¹H NMR | MS [MH]⁺ | Method |
|---|---|---|---|---|
| 10 | 1-(3-(1-isopropyl-3-(3-(trifluoromethyl)-1H-pyrrolo[2,3-b]pyridin-5-yl)-1H-pyrazol-5-yl)azetidin-1-yl)ethanone | (400 MHz, CDCl3): δ 10.97 (s, 1 H), 8.91 (s, 1 H), 8.43 (s, 1 H), 7.73 (s, 1 H), 6.59 (s, 1 H), 4.58 (t, J = 8.4 Hz, 1 H), 4.47 (t, J = 9.2 Hz, 1 H), 4.28-4.17 (m, 3 H), 3.95-3.91 (m, 1 H), 1.93 (s, 3 H), 1.55 (d, J = 6.4 Hz, 6 H) | 392.1 | F |
| 14 | 5-(1-(3,3-difluorocyclopentyl)-5-(tetrahydrofuran-3-yl)-1H-pyrazol-3-yl)-3-methyl-1H-pyrrolo[2,3-b]pyridine | (400 MHz, CD3OD): δ 8.60 (s, 1 H), 8.29 (s, 1 H), 7.13 (s, 1 H), 6.55 (s, 1 H), 5.03-4.99 (m, 1 H), 4.17-4.13 (m, 1 H), 4.06-4.00 (m, 1 H), 3.95-3.90 (m, 1 H), 3.81-3.76 (m, 1 H), 3.66-3.62 (m, 1 H), 2.85-2.78 (m, 1 H), 2.66-2.51 (m, 2 H), 2.49-2.20 (m, 7 H), 2.07-2.01 (m, 1 H) | 373.0 | AC |
| 9 | 1-(3-(1-(cyclopropylmethyl)-3-(3-methyl-1H-pyrrolo[2,3-b]pyridin-5-yl)-1H-pyrazol-5-yl)azetidin-1-yl)ethanone | (400 MHz, CDCl3): δ 10.24 (s, 1 H), 8.68 (s, 1 H), 8.30 (s, 1 H), 7.09 (s, 1 H), 6.61 (s, 1 H), 4.57-4.43 (m, 2 H), 4.24-4.12 (m, 2 H), 3.95-3.88 (m, 3 H), 2.34 (s, 3H), 1.92 (s, 3 H), 1.22-1.19 (m, 1 H), 0.60 (d, J = 7.2 Hz, 2 H), 0.39-0.36 (m, 2 H) | 349.9 | I |
| 13 | Racemic-5-(1-(cyclopropylmethyl)-5-(tetrahydrofuran-3-yl)-1H-pyrazol-3-yl)-3-methyl-1H-pyrrolo[2,3-b]pyridine | (400 MHz, CD3OD): δ 8.60 (s, 1 H), 8.31 (s, 1 H), 7.17 (s, 1 H), 6.60 (s, 1 H), 4.16 (t, J = 8.0 Hz, 1 H), 4.10-4.05 (m, 3 H), 3.97-3.92 (m, 1 H), 3.82-3.79 (m, 1 H), 3.64-3.60 (m, 1 H), 2.49-2.35 (m, 1 H), 2.25 (s, 3 H), 2.12-2.03 (m, 1 H), 1.35-1.29 (m, 1 H), 0.65-0.58 (m 2 H), 0.49-0.38 (m, 2 H) | 323.0 | X |

TABLE A-continued

| No. | Structure | ¹H NMR | MS [MH]⁺ | Method |
|---|---|---|---|---|
| 70 | 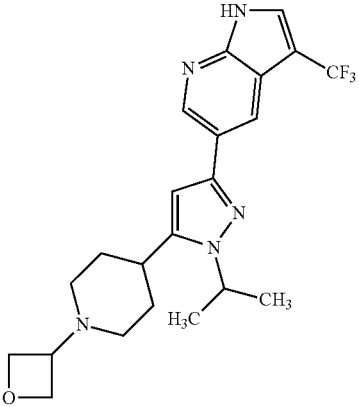 [SMILES: CC(C)n1nc(-c2cnc3[nH]cc(C(F)(F)F)c3c2)cc1C1CCN(C2COC2)CC1]<br>5-(1-isopropyl-5-(1-(oxetan-3-yl)piperidin-4-yl)-1H-pyrazol-3-yl)-3-(trifluoromethyl)-1H-pyrrolo[2,3-b]pyridine | (400 MHz, CD$_3$OD): δ 8.78 (s, 1 H), 8.40 (s, 1 H), 7.88 (s, 1 H), 6.55 (s, 1 H), 4.79-4.75 (m, 2 H), 4.69-4.64 (m, 3 H), 3.74-3.71 (m, 1 H), 3.07-302 (m, 2 H), 2.93-2.87 (m, 1 H), 2.45-2.20 (m, 2 H), 2.06-2.03 (m, 2 H), 1.89-1.86 (m, 2 H), 1.54 (d, J = 6.4 Hz, 6 H) | 433.9 | L |
| 69 | 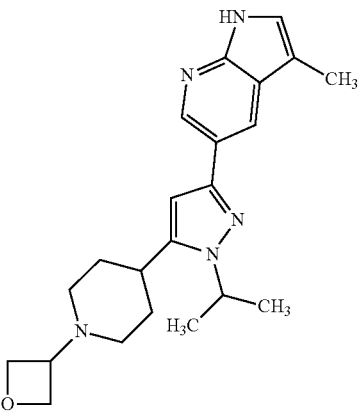 [SMILES: Cc1c[nH]c2ncc(-c3cc(C4CCN(C5COC5)CC4)n(C(C)C)n3)cc12]<br>5-(1-isopropyl-5-(1-(oxetan-3-yl)piperidin-4-yl)-1H-pyrazol-3-yl)-3-methyl-1H-pyrrolo[2,3-b]pyridine | (400 MHz, CD$_3$OD): δ 9.03 (s, 1 H), 8.81 (s, 1 H), 7.50 (s, 1 H), 6.85 (s, 1 H), 4.97-4.88 (m, 2 H), 4.79-4.76 (m, 1 H), 4.18-4.09 (m, 2 H), 3.90-3.80 (m, 1 H), 3.69-3.56 (m, 3 H), 3.25-3.13 (m, 1 H), 3.10-2.94 (m, 1 H), 2.46 (s, 3 H), 2.26-2.24 (m, 4 H), 1.57 (d, J = 6.0 Hz, 6 H) | 380.0 | L |
| 68 | 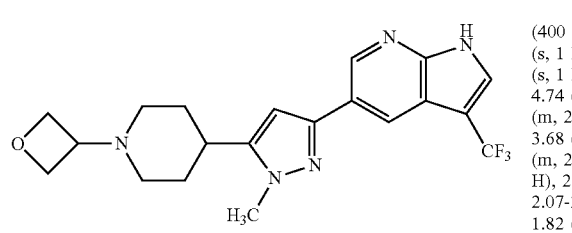<br>5-(1-methyl-5-(1-(oxetan-3-yl)piperidin-4-yl)-1H-pyrazol-3-yl)-3-(trifluoromethyl)-1H-pyrrolo[2,3-b]pyridine | (400 MHz, CD$_3$OD): δ 8.75 (s, 1 H), 8.39 (s, 1 H), 7.84 (s, 1 H), 6.58 (s, 1 H), 4.77-4.74 (m, 2 H), 4.69-4.66 (m, 2 H), 3.89 (s, 3 H), 3.71-3.68 (m, 1 H), 3.04-3.01 (m, 2 H), 2.88-2.82 (m, 1 H), 2.24-2.17 (m, 2 H), 2.07-2.04 (m, 2 H), 1.89-1.82 (m, 2 H) | 405.9 | V |

TABLE A-continued

| No. | Structure | ¹H NMR | MS [MH]⁺ | Method |
|---|---|---|---|---|
| 50 | 1-(4-(1-isopropyl-3-(3-(trifluoromethyl)-1H-pyrrolo[2,3-b]pyridin-5-yl)-1H-pyrazol-5-yl)piperidin-1-yl)ethanone | (400 MHz, CD₃OD): δ 8.95 (s, 1 H), 8.91 (s, 1 H), 8.21 (s, 1 H), 6.80 (s, 1 H), 4.83-4.78 (m, 1H), 4.69-4.66 (m, 1 H), 4.09-4.06 (m, 1 H), 3.37-3.31 (m, 1 H), 3.20-3.14 (m, 1 H), 2.87-2.81 (m, 1 H), 2.18 (s, 3 H), 2.07-1.99 (m, 2 H), 1.79-1.64 (m, 2 H), 1.57 (d, J = 6.4 Hz, 6 H) | 419.9 | R |
| 49 | 1-(4-(1-isopropyl-3-(3-methyl-1H-pyrrolo[2,3-b]pyridin-5-yl)-1H-pyrazol-5-yl)piperidin-1-yl)ethanone | (400 MHz, CD₃OD): δ 8.59 (s, 1 H), 8.32 (s, 1 H), 7.18 (s, 1 H), 6.49 (s, 1 H), 4.72-4.68 (m, 2 H), 4.10-4.01 (m, 1 H), 3.50-3.47 (m, 1 H), 3.10-3.02 (m, 1 H), 2.85-2.75 (m, 1 H), 2.37 (s, 3H), 2.17 (s, 3 H), 2.03-1.95 (m, 2 H), 1.80-1.60 (m, 2 H), 1.57 (d, J = 6.0 Hz, 6 H) | 366.0 | R |
| 8 | 1-(3-(1-(cyclopropylmethyl)-3-(3-(trifluoromethyl)-1H-pyrrolo[2,3-b]pyridin-5-yl)-1H-pyrazol-5-yl)azetidin-1-yl)ethanone | (400 MHz, DMSO-d₆): δ 12.53 (s, 1 H), 8.86 (s, 1 H), 8.34 (s, 1 H), 8.16 (s, 1 H), 7.09 (s, 1 H), 4.55 (t, J = 8.4 Hz, 1 H), 4.30-4.19 (m, 2 H), 4.06-4.01 (m, 1 H), 3.95-3.90 (m, 3 H), 1.81 (s, 3H), 1.22-1.19 (m, 1 H), 0.52-0.50 (m, 2 H), 0.37-0.36 (m, 2 H) | 404.2 | I |
| 48 | 1-(4-(1-methyl-3-(3-(trifluoromethyl)-1H-pyrrolo[2,3-b]pyridin-5-yl)-1H-pyrazol-5-yl)piperidin-1-yl)ethanone | (400 MHz, CD₃OD): δ 8.77 (s, 1 H), 8.41 (s, 1 H), 7.89 (s, 1 H), 6.61 (s, 1 H), 4.71-4.68 (m, 1 H), 4.10-4.05 (m, 1 H), 3.94 (s, 3 H), 3.33-3.29 (m, 1 H), 3.12-3.05 (m, 1 H), 2.85-2.79 (m, 1 H), 2.17 (s, 3 H), 2.10-2.03 (m, 2 H), 1.80-1.64 (m, 2 H) | 392.2 | W |

TABLE A-continued

| No. | Structure | ¹H NMR | MS [MH]⁺ | Method |
|---|---|---|---|---|
| 47 | 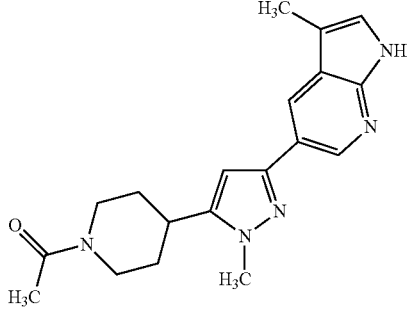 [SMILES: CC(=O)N1CCC(c2cc(-c3cnc4[nH]cc(C)c4c3)nn2C)CC1] 1-(4-(1-methyl-3-(3-methyl-1H-pyrrolo[2,3-b]pyridin-5-yl)-1H-pyrazol-5-yl)piperidin-1-yl)ethanone | (400 MHz, CD₃OD): δ 8.58 (s, 1 H), 8.30 (s, 1 H), 7.18 (s, 1 H), 6.56 (s, 1 H), 4.70-4.68 (m, 1 H), 4.10-4.07 (m, 1 H), 3.93 (s, 3 H), 3.35-3.30 (m, 1 H), 3.20-3.05 (m, 1 H), 2.90-2.80 (m, 1 H), 2.36 (s, 3 H), 2.17 (s, 3 H), 2.06-2.02 (m, 2 H), 1.80-1.55 (m, 2 H) | 338.2 | W |
| 154 | 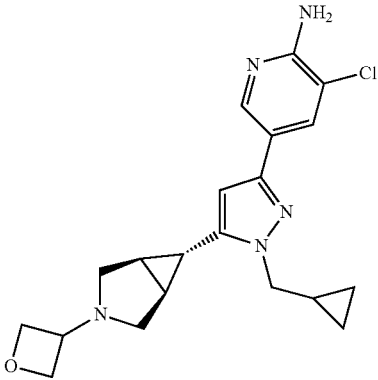 [SMILES: Nc1ncc(-c2cc([C@H]3[C@@H]4CN(C5COC5)C[C@@H]43)n(CC3CC3)n2)cc1Cl] 3-chloro-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine | (400 MHz, CDCl3): δ 8.30 (d, J = 2.0 Hz, 1H), 7.95 (d, J = 2.0 Hz, 1H), 6.01 (s, 1H), 4.88 (s, 2H), 4.71 (t, J = 6.6 Hz, 2H), 4.63 (t, J = 6.1 Hz, 2H), 4.07 (d, J = 6.8 Hz, 2H), 3.81 (p, J = 6.3 Hz, 1H), 3.16 (d, J = 8.8 Hz, 2H), 2.50 (d, J = 8.7 Hz, 2H), 2.29-2.19 (m, 1H), 1.83-1.74 (m, 2H), 1.44-1.23 (m, 1H), 0.65-0.53 (m, 2H), 0.47-0.38 (m, 2H) | 386 | Y |
| 166 | 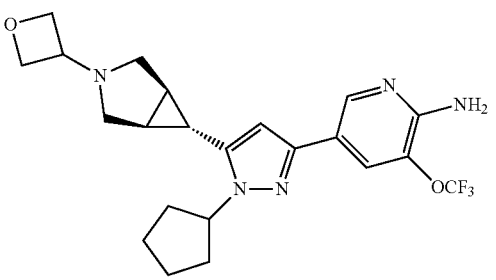 [SMILES: Nc1ncc(-c2cc([C@H]3[C@@H]4CN(C5COC5)C[C@@H]43)n(C3CCCC3)n2)cc1OC(F)(F)F] 5-(1-cyclopentyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine | (400 MHz, CD₃OD): δ 8.25 (s, 1 H), 7.82-7.81 (m, 1 H), 6.19 (s, 1 H), 4.92-4.90 (m, 1 H), 4.74-4.70 (m, 2 H), 4.64-4.61 (m, 2 H), 3.83-3.77 (m, 1 H), 3.22-3.20 (m, 2 H), 2.52-2.49 (m, 2 H), 2.32-2.30 (m, 1 H), 2.15-2.08 (m, 4 H), 2.00-1.96 (m, 2 H), 1.86-1.85 (m, 2 H), 1.80-1.72 (m, 2 H). | 450.2 | C |

TABLE A-continued

| No. | Structure | ¹H NMR | MS [MH]⁺ | Method |
|---|---|---|---|---|
| 171 | 5-(1-cyclopentyl-5-((1R,5S,6r)-3-(oxetan-3-yl)-3-azabicyclo[3.1.0]hexan-6-yl)-1H-pyrazol-3-yl)-3-(difluoromethyl)pyridin-2-amine | (400 MHz, CD₃)D): δ 8.40 (s, 1 H), 8.01 (s, 1 H), 6.82 (t, J = 55.2 Hz, 1 H), 6.19 (s, 1 H), 4.92-4.88 (m, 1 H), 4.73-4.70 (m, 2 H), 4.64-4.61 (m, 2 H), 3.83-3.77 (m, 1 H), 3.22-3.20 (m, 2 H), 2.52-2.50 (m, 2 H), 2.32-2.30 (m, 1 H), 2.15-2.09 (m, 4 H), 2.02-1.96 (m, 2 H), 1.86-1.85 (m, 2 H), 1.80-1.72 (m, 2 H) | 416.2 | C |
| 157 | 5-(1-cyclopentyl-5-((1R,5S,6r)-3-(oxetan-3-yl)-3-azabicyclo[3.1.0]hexan-6-yl)-1H-pyrazol-3-yl)-3-methoxypyridin-2-amine | (400 MHz, CD₃OD): δ 7.83 (s, 1 H), 7.43 (s, 1 H), 6.17 (s, 1 H), 4.91-4.89 (m, 1 H), 4.73-4.70 (m, 2 H), 4.64-4.61 (m, 2 H), 3.92 (s, 3 H), 3.81-3.78 (m, 1 H), 3.22-3.20 (m, 2 H), 2.51-2.49 (m, 2 H), 2.35-2.98 (m, 1 H), 2.12-2.05 (m, 4 H), 2.03-1.97 (m, 2 H), 1.90-1.82 (m, 2 H), 1.80-1.68 (m, 2 H) | 396.2 | C |
| 156 | 5-(1-cyclopentyl-5-((1R,5S,6r)-3-(oxetan-3-yl)-3-azabicyclo[3.1.0]hexan-6-yl)-1H-pyrazol-3-yl)-3-isopropoxypyridin-2-amine | (400 MHz, CD₃OD): δ 7.82 (s, 1 H), 7.73 (s, 1 H), 6.16 (s, 1 H), 4.91-4.88 (m, 1 H), 4.73-4.67 (m, 3 H), 4.64-4.61 (m, 2 H), 3.81-3.78 (m, 1 H), 3.22-3.20 (m, 2 H), 2.51-2.49 (m, 2 H), 2.32-2.28 (m, 1 H), 2.19-2.06 (m, 4 H), 2.01-1.97 (m, 2 H), 1.90-1.80 (m, 2 H), 1.78-1.70 (m, 2 H), 1.38 (d, J = 6.0 Hz, 6 H) | 424.1 | C |
| 155 | 5-(1-cyclopentyl-5-((1R,5S,6r)-3-(oxetan-3-yl)-3-azabicyclo[3.1.0]hexan-6-yl)-1H-pyrazol-3-yl)-3-(methylsulfonyl)pyridin-2-amine | (400 MHz, CD₃OD): δ 8.60 (s, 1 H), 8.31 (s, 1 H), 6.24 (s, 1 H), 4.92-4.89 (m, 1 H), 4.77-4.73 (m, 2 H), 4.66-4.63 (m, 2 H), 3.84-3.88 (m, 1 H), 3.33-3.31 (m, 2 H), 3.14 (s, 3 H), 2.69-2.66 (m, 2 H), 2.33-2.32 (m, 1 H), 2.16-2.07 (m, 4 H), 2.02-1.98 (m, 2 H), 1.96-1.93 (m, 2 H), 1.77-1.74 (m, 2 H) | 444.0 | C |

TABLE A-continued

| No. | Structure | ¹H NMR | MS [MH]⁺ | Method |
|---|---|---|---|---|
| 169 | 5-(1-(cyclopropylmethyl)-5-((1R,5S,6r)-3-(oxetan-3-yl)-3-azabicyclo[3.1.0]hexan-6-yl)-1H-pyrazol-3-yl)-3-(difluoromethyl)pyridin-2-amine | (400 MHz, Methanol-d₄): δ 8.41 (s, 1 H), 8.01 (s, 1 H), 6.83 (t, J = 55.2 Hz, 1 H), 6.22 (s, 1 H), 4.74-4.71 (m, 2 H), 4.64-4.61 (m, 2 H), 4.10 (d, J = 6.8 Hz, 2 H), 3.83-3.77 (m, 1 H), 3.21 (d, J = 9.2 Hz, 2 H), 2.53-2.51 (m, 2 H), 2.33-2.32 (m, 1 H), 1.89-1.88 (m, 2 H), 1.36-1.29 (m, 1 H), 0.62-0.58 (m, 2 H), 0.48-0.45 (m, 2 H) | 402.2 | Y |
| 161 | 3-cyclopropyl-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine | (400 MHz, Methanol-d₄): δ 8.11 (s, 1 H), 7.63 (s, 1 H), 6.16 (s, 1 H), 4.73-4.70 (m, 2 H), 4.63-4.60 (m, 2 H), 4.08 (d, J = 6.8 Hz, 2 H), 3.81-3.78 (m, 1 H), 3.20 (d, J = 9.2 Hz, 2 H), 2.52-2.50 (m, 2 H), 2.31-2.30 (m, 1 H), 1.87 (s, 2 H), 1.72-1.66 (m, 1 H), 1.36-1.28 (m, 1 H), 1.00-0.98 (m, 2 H), 0.68-0.55 (m, 4 H), 0.50-0.42 (m, 2 H) | 392.2 | Y |
| 165 | 5-(1-isopropyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine | (400 MHz, Methanol-d₄): δ 8.25 (s, 1 H), 7.83 (s, 1 H), 6.19 (s, 1 H), 4.80-4.75 (m, 1 H), 4.73-4.70 (m, 2 H), 4.64-4.61 (m, 2 H), 3.83-3.76 (m, 1 H), 3.21 (d, J = 8.8 Hz, 2 H), 2.51-2.49 (m, 2 H), 2.30-2.28 (m, 1 H), 1.87-1.85 (m, 2 H), 1.52 (d, J = 6.4 Hz, 6 H) | 424.1 | A |
| 119 | 3-(difluoromethoxy)-5-(1-isopropyl-5-((1R,5S,6r)-3-(2-methoxyethyl)-3-azabicyclo[3.1.0]hexan-6-yl)-1H-pyrazol-3-yl)pyridin-2-amine | (400 MHz, Methanol-d₄): δ 8.14 (s, 1 H), 7.71 (s, 1 H), 6.87 (t, J = 72.0 Hz, 1 H), 6.16 (s, 1 H), 4.79-4.72 (m, 1 H), 3.54-3.52 (m, 2 H), 3.36 (s, 3 H), 3.32-3.28 (m, 2 H), 2.78-2.75 (m, 2 H), 2.64-2.62 (m, 2 H), 2.30-2.28 (m, 1 H), 1.85 (s, 2 H), 1.51 (d, J = 6.8 Hz, 6 H) | 408.1 | AE |

TABLE A-continued

| No. | Structure | ¹H NMR | MS [MH]⁺ | Method |
|---|---|---|---|---|
| 158 | 3-(difluoromethyl)-5-(1-isopropyl-5-((1R,5S,6r)-3-(oxetan-3-yl)-3-azabicyclo[3.1.0]hexan-6-yl)-1H-pyrazol-3-yl)pyridin-2-amine | (400 MHz, Methanol-d₄): δ 8.40 (s, 1 H), 8.03 (s, 1 H), 6.83 (t, J = 54.8 Hz, 1 H), 6.21 (s, 1 H), 4.76-4.73 (m, 3 H), 4.67-4.65 (m, 2 H), 3.94-3.91 (m, 1 H), 3.34-3.32 (m, 1 H), 3.31-3.30 (m, 1 H), 2.69-2.67 (m, 2 H), 2.32-2.30 (m, 1 H), 1.94-1.93 (m, 2 H), 1.52 (d, J = 6.4 Hz, 6 H) | 390.2 | A |
| 118 | 3-chloro-5-(1-isopropyl-5-((1R,5S,6r)-3-(2-methoxyethyl)-3-azabicyclo[3.1.0]hexan-6-yl)-1H-pyrazol-3-yl)pyridin-2-amine | (400 MHz, Methanol-d₄): δ 8.25 (s, 1 H), 7.96 (s, 1 H), 6.26 (s, 1 H), 4.78-4.71 (m, 1 H), 3.75-3.67 (m, 4 H), 3.53-3.50 (m, 2 H), 3.44 (s, 3 H), 3.36-3.33 (m, 2 H), 2.36-2.35 (m, 1 H), 2.22 (s, 2H), 1.54 (d, J = 6.8 Hz, 6 H) | 375.9 | AE |
| 163 | 5-(1-cyclobutyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine | NMR (400 MHz, Methanol-d₄): δ 8.27 (s, 1 H), 7.86 (s, 1 H), 6.21 (s, 1 H), 5.03-4.96 (m, 1 H), 4.75-4.72 (m, 2 H), 4.65-4.62 (m, 2 H), 3.87-3.81 (m, 1 H), 3.25 (d, J = 9.2 Hz, 2 H), 2.75-2.67 (m, 2 H), 2.57-2.55 (m, 2 H), 2.48-2.44 (m, 2 H), 2.27-2.25 (m, 1 H), 2.00-1.90 (m, 2 H), 1.88-1.82 (m, 2 H) | 436.1 | B |
| 159 | 5-(1-cyclobutyl-5-((1R,5S,6r)-3-(oxetan-3-yl)-3-azabicyclo[3.1.0]hexan-6-yl)-1H-pyrazol-3-yl)-3-methoxypyridin-2-amine | (400 MHz, Methanol-d₄): δ 7.82 (s, 1 H), 7.59 (s, 1 H), 6.24 (s, 1 H), 5.04-5.00 (m, 1 H), 4.75-4.71 (m, 2 H), 4.65-4.62 (m, 2 H), 3.99 (s, 3 H), 3.85-3.82 (m, 1 H), 3.28 (d, J = 18.0 Hz, 2 H), 2.77-2.66 (m, 2 H), 2.57-2.50 (m, 2 H), 2.48-2.43 (m, 2 H), 2.28-2.27 (m, 1 H), 1.95-1.90 (m, 2 H), 1.88-1.82 (m, 2 H) | 382.2 | B |

EXAMPLE 4

DLK TR-FRET inhibition assay: DLK kinase reactions (20 µL) containing 5 nM N-terminally GST-tagged DLK (catalytic domain amino acid 1-520) (Carna Bioscience), 40 nM N-terminally HIS-tagged MKK4 K131M substrate, and 30 µM ATP in kinase reaction buffer (50 mM HEPES, pH 7.5, 0.01% Triton X-100, 0.01% Bovine γ-Globulins, 2 mM DTT, 10 mM MgCl$_2$ and 1 mM EGTA), and testing compound 1:3 serial diluted starting at 20 uM were incubated at ambient temperature for 60 minutes in 384 well OptiPlate (Perkin Elmer). To quench kinase reactions and detect phosphorylated MKK4, 15 μL of TR-FRET antibody mixture containing 2 nM anti-phosphorylated MKK4 labeled with Europium cryptate (Cisbio) and 23 nM anti-HIS labeled with D2 (Cisbio) in detection buffer (25 mM Tris pH 7.5, 100 mM NaCl, 100 mM EDTA, 0.01% Tween-20, and 200 mM KF) was added to the reaction mixture. The detection mixture was incubated for 3 hours at ambient temperature and the TR-FRET was detected with an EnVision multilabel plate reader (Perkin-Elmer) using the LANCE/DELFIA Dual Enh label from Perkin-Elmer (excitation filter: UV2 (TRF) 320 and emission filters: APC 665 and Europium 615). Compounds of formula I as set forth in Table 1 inhibited the DLK kinase with the K$_i$s in micromolar (μM) as provided in Table 2 below.

TABLE 2

| No | DLK (K$_i$) μM |
| --- | --- |
| 1 | 0.034 |
| 2 | 0.11 |
| 3 | 0.14 |
| 4 | 0.78 |
| 5 | >1 |
| 6 | 0.14 |
| 7 | 0.47 |
| 8 | 0.01 |
| 9 | 0.076 |
| 10 | 0.0064 |
| 11 | 0.034 |
| 12 | 0.026 |
| 13 | 0.029 |
| 14 | 0.074 |
| 15 | 0.035 |
| 16 | 0.013 |
| 17 | 0.030 or 0.026 |
| 18 | 0.030 or 0.026 |
| 19 | 0.082 |
| 20 | 0.025 |
| 21 | >1 |
| 22 | >1 |
| 23 | 0.35 |
| 24 | >1 |
| 25 | 0.55 |
| 26 | 0.032, 0.0096 or 0.0062 |
| 27 | 0.03, 0.041, 0.026 or 0.0071 |
| 28 | 0.032, 0.0096 or 0.0062 |
| 29 | 0.032, 0.0096 or 0.0062 |
| 30 | 0.032, 0.0096 or 0.0062 |
| 31 | 0.03, 0.041, 0.026 or 0.0071 |
| 32 | 0.03, 0.041, 0.026 or 0.0071 |
| 33 | 0.03, 0.041, 0.026 or 0.0071 |
| 34 | 0.16 |
| 35 | 0.10 |
| 36 | >1 |
| 37 | >1 |
| 38 | 0.058 |
| 39 | 0.46 |
| 40 | 0.00017 |
| 41 | 0.045 |
| 42 | 0.25 |
| 43 | 0.06 |
| 44 | >1 |
| 45 | 0.14 |
| 46 | 0.028 |
| 47 | 0.047 |
| 48 | 0.012 |
| 49 | 0.019 |
| 50 | 0.0037 |
| 51 | 0.00017 |
| 52 | 0.056 |
| 53 | 0.056 |
| 54 | 0.00048 |
| 55 | 0.019 |
| 56 | 0.013 |
| 57 | 0.034 |
| 58 | 0.64 |
| 59 | 0.31 |
| 60 | 0.027 |
| 61 | >1 |
| 62 | >1 |
| 63 | 0.034 |
| 64 | 0.0045 |
| 65 | 0.022 |
| 66 | 0.11 |
| 67 | 0.030 |
| 68 | 0.015 |
| 69 | 0.0037 |
| 70 | 0.0023 |
| 71 | 0.27 |
| 72 | 0.015 |
| 73 | >1 |
| 74 | 0.98 |
| 75 | 0.096 |
| 76 | 0.15 |
| 77 | 0.12 |
| 78 | 1 |
| 79 | >1 |
| 80 | >1 |
| 81 | 0.084 |
| 82 | >1 |
| 83 | 0.39 |
| 84 | 0.26 |
| 85 | 0.99 |
| 86 | 0.91 |
| 87 | 0.64 |
| 88 | 0.26 |
| 89 | 0.14 |
| 90 | 0.12 |
| 91 | 1.0 |
| 92 | 0.94 |
| 93 | 0.17 |
| 94 | >1 |
| 95 | 1.2 |
| 96 | >1 |
| 97 | 0.81 |
| 98 | 0.36 |
| 99 | 0.069 |
| 100 | >1 |
| 101 | 0.001 |
| 102 | 0.034 |
| 103 | >1 |
| 104 | 0.091 |
| 105 | 0.096 |
| 106 | 0.13 |
| 107 | 0.0024 |
| 108 | 0.0049 |
| 109 | 0.001 |
| 110 | 0.0045 |
| 111 | 0.18 |
| 112 | >1 |
| 113 | 0.064 |
| 114 | 0.96 |
| 115 | 0.0056 |
| 116 | 0.011 |
| 117 | 0.0094 |
| 118 | 0.034 |
| 119 | 0.0055 |
| 120 | 0.030 |
| 121 | 0.09 |
| 122 | 0.0079 |
| 123 | 0.027 |
| 124 | 0.027 |
| 125 | 0.0058 |
| 126 | 0.0019 |
| 127 | 0.0059 |
| 128 | 0.011 |
| 129 | 0.0013 |
| 130 | 0.0056 |
| 131 | 0.0044 |
| 132 | 0.025 |

TABLE 2-continued

| No | DLK ($K_i$) μM |
|---|---|
| 133 | 0.0004 |
| 134 | 0.0027 |
| 135 | 0.0089 |
| 136 | 0.024 |
| 137 | 0.0074 |
| 138 | 0.031 |
| 139 | 0.037 |
| 140 | 0.04 |
| 141 | 0.008 |
| 142 | 0.022 |
| 143 | 0.074 |
| 144 | 0.022 |
| 145 | 0.0074 |
| 146 | 0.014 |
| 147 | 0.018 |
| 148 | 0.0012 |
| 149 | 0.011 |
| 150 | 0.022 |
| 151 | 0.0055 |
| 152 | 0.00017 |
| 153 | 0.011 |
| 154 | 0.025 |
| 155 | 0.3 |
| 156 | 0.032 |
| 157 | 0.035 |
| 158 | 0.035 |
| 159 | 0.02 |
| 160 | 0.0081 |
| 161 | 0.021 |
| 162 | 0.066 |
| 163 | 0.013 |
| 164 | 0.013 |
| 165 | 0.0019 |
| 166 | 0.0047 |
| 167 | 0.027 |
| 168 | 0.0047 |
| 169 | 0.041 |
| 170 | 0.012 |
| 171 | 0.016 |
| 172 | 0.27 |
| 173 | 0.0039 |
| 174 | 0.0016 |
| 175 | 0.0092 |
| 176 | 0.13 |
| 177 | 0.00067 |
| 178 | 0.18 |
| 179 | 1 |
| 180 | >1 |
| 181 | >1 |
| 182 | >1 |

The invention claimed is:

1. A method for inhibiting degeneration of a central nervous system (CNS) neuron in a patient having a neurodegenerative disease or condition; or for decreasing one or more symptoms of a neurodegenerative disease or condition in a patient suffering therefrom; or for decreasing the progression of a neurodegenerative disease or condition in a patient suffering therefrom; wherein said neurodegenerative disease or condition is selected from the group consisting of: Alzheimer's disease, Huntington's disease, Parkinson's disease, amyotrophic lateral sclerosis (ALS), and glaucoma; comprising administering to said patient a therapeutically effective amount of a compound of Formula (I)

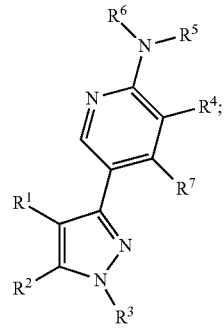

(I)

or a pharmaceutically acceptable salt thereof;

wherein in Formula (I)

$R^1$ is selected from the group consisting of hydrogen, —F, —Cl, —Br, —I, —$NO_2$, —CN, $C_{1-12}$ alkyl and $C_{1-12}$ haloalkyl;

$R^2$ is selected from the group consisting of 3 to 12 membered cycloalkyl, C-linked 3 to 12 membered heterocycloalkyl and —C($R^{42}$)($C_{1-6}$(halo)alkyl)$_2$, wherein $R^{42}$ is hydrogen, —F, —Cl, —Br, —I, —CN, —OH, —$NH_2$, —$SF_5$, —$OSF_5$, $C_{1-12}$ alkylthio, $C_{1-12}$ alkoxy, $C_{1-12}$ alkylamino and $C_{1-12}$ dialkylamino; and wherein $R^2$ is optionally substituted 1 to 5 $R^{2-A}$ substituents selected from the group consisting of $C_{1-12}$ alkyl, $C_{1-12}$ haloalkyl, $C_{1-12}$ heteroalkyl, $C_{2-12}$ alkenyl, $C_{2-12}$ alkynyl, —F, —Cl, —Br, —I, —$(X^2)_{0-1}$—CN, —$(X^2)_{0-1}$—$NO_2$, —$(X^2)_{0-1}$—$SF_5$, —$(X^2)_{0-1}$—$OSF_5$, —$(X^2)_{0-1}$—$OR^{2A}$, —$(X^2)_{0-1}$—$N(R^{2A})_2$, —$(X^2)_{0-1}$—$SR^{2A}$, —$(X^2)_{0-1}$—$CF_3$, 3 to 12 membered cycloalkyl-$(X^2)_{0-1}$—, 3 to 12 membered heterocycloalkyl-$(X^2)_{0-1}$—, 5 to 6 membered heteroaryl-$(X^2)_{0-1}$—, phenyl-$(X^2)_{0-1}$—, —$(X^2)_{0-1}$—C(=O)N($R^{2A}$)($R^{2A}$), —$(X^2)_{0-1}$—C(=O)$OR^{2A}$, —$(X^2)_{0-1}$—N($R^{2A}$)C(=O)($R^{2A}$), —$(X^2)_{0-1}$—N($R^{2A}$)C(=O)$OR^{2A}$, —$(X^2)_{0-1}$—S(=O)$_{1-2}$—$R^{2A}$, —$(X^2)_{0-1}$—N($R^{2A}$)S(=O)$_{1-2}$—$R^{2A}$, —$(X^2)_{0-1}$—S(=O)$_{1-2}$N($R^{2A}$)$_2$, —$(X^2)_{0-1}$—C(=O)$R^{2A}$, —$(X^2)_{0-1}$—C(=NO$R^{2A}$)$R^{2A}$, —$(X^2)_{0-1}$—N($R^{2A}$)C(=O)N($R^{2A}$)$_2$ and —$(X^2)_{0-1}$—OC(=O)$R^{2A}$, —$(X^2)_{0-1}$—OP(=O)(O$R^{2A}$)$_2$, —$(X^2)$—SC(=O)$OR^{2A}$ and —$(X^2)$—SC(=O)N($R^{2A}$)$_2$; wherein $X^2$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{2A}$ at each occurrence is each independently selected from the group consisting of hydrogen, $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl, 3-7 membered heterocycloalkyl, 3-7 membered heterocycloalkyl-$C_{1-4}$ alkyl, 5-6 membered heteroaryl, 5-6 membered heteroaryl-$C_{1-4}$ alkyl, phenyl and phenyl-$C_{1-4}$ alkyl, or any two $R^{2A}$ groups attached to the same nitrogen atom are optionally combined to form a 3 to 6 membered heterocyclic ring comprising 1 to 2 additional heteroatom selected from N, O and S; and wherein a $R^{2-A}$ substituent at each occurrence is independently optionally further substituted with 1 to 5 $R^{2A-1}$ substituents selected from the group consisting of —F, —Cl, —Br, —I, —OH, —CN, —$NO_2$, —$SF_5$, —$NH_2$, $C_{1-6}$ alkoxy, $C_{1-6}$ alkylamino, $C_{1-6}$ dialkylamino;

$R^3$ is selected from the group consisting of $C_{1-12}$ alkyl-, $C_{1-12}$ haloalkyl-, $C_{1-12}$ heteroalkyl-(L)$_{0-1}$-, $C_{2-12}$ alkenyl-(L)$_{0-1}$-, $C_{2-12}$ alkynyl-(L)$_{0-1}$-, 3 to 12 membered cycloalkyl-(L)$_{0-1}$-, 3 to 12 membered heterocycloalkyl-(L)$_{0-1}$-, wherein L is selected from the group consisting of C$_{1-4}$ alkylene, C$_{1-4}$ haloalkylene, C$_{1-4}$ heteroalkylene, C$_{2-4}$ alkenylene, C$_{2-4}$ alkynylene, —C(=O)—, —C(=O)—N(H)—, —C(=O)N(C$_{1-6}$ alkyl)-, —C(=O)O—, —S(O)$_{1-2}$— and —S(O)$_{1-2}$—N(H)—; wherein a R$^3$ group is optionally further substituted with 1 to 5 R$^{3A}$ substituents selected from the group consisting of —F, —Cl, —Br, —I, —OH, —CN, —NO$_2$, —SF$_5$, —OSF$_5$, —NH$_2$, C$_{1-6}$ alkyl, C$_{1-6}$ haloalkyl, 3 to 5 membered cycloalkyl, 3 to 5 membered heterocycloalkyl, C$_{1-6}$ alkoxy, C$_{1-6}$ alkylthio, C$_{1-6}$ alkylamino and C$_{1-6}$ dialkylamino;

R$^4$ is selected from the group consisting of C$_{1-12}$ alkyl, C$_{1-12}$ haloalkyl, C$_{2-12}$ alkenyl, C$_{2-12}$ alkynyl, —F, —Cl, —Br, —I, —(X$^4$)$_{0-1}$—CN, —(X$^4$)$_{0-1}$—NO$_2$, —(X$^4$)$_{0-1}$—SF$_5$, —(X$^4$)$_{0-1}$—OSF$_5$, —(X$^4$)$_{0-1}$—OR$^{4A}$, —(X$^4$)$_{0-1}$—N(R$^{4A}$)$_2$, —(X$^4$)$_{0-1}$—SR$^{4A}$, —(X$^4$)$_{0-1}$—CF$_3$, 3 to 7 membered cycloalkyl-(X$^4$)$_{0-1}$—, 3 to 7 membered heterocycloalkyl-(X$^4$)$_{0-1}$—, 5 to 6 membered heteroaryl-(X$^4$)$_{0-1}$—, phenyl-(X$^4$)$_{0-1}$—, —(X$^4$)$_{0-1}$—C(=O)N(R$^{4A}$)(R$^{4A}$), —(X$^4$)$_{0-1}$—C(=O)OR$^{4A}$, —(X$^4$)$_{0-1}$—N(R$^{4A}$)C(=O)(R$^{4A}$), —(X$^4$)$_{0-1}$—N(R$^{4A}$)C(=O) OR$^{4A}$, —(X$^4$)$_{0-1}$—S(=O)$_{1-2}$—R$^{4A}$, —(X$^4$)$_{0-1}$—N(R$^{4A}$)S(=O)$_{1-2}$—R$^{4A}$, —(X$^4$)$_{0-1}$—S(=O)$_{1-2}$N(R$^{4A}$)$_2$, —(X$^4$)$_{0-1}$—C(=O)R$^{4A}$, —(X$^4$)$_{0-1}$—C(=NOR$^{4A}$)R$^{4A}$, —(X$^4$)$_{0-1}$—N(R$^{4A}$)C(=O)N(R$^{4A}$)$_2$, —(X$^4$)$_{0-1}$—OC(=O)R$^{4A}$, —(X$^4$)$_{0-1}$—OP(=O)(OR$^{4A}$)$_2$, —(X$^4$)—SC(=O)OR$^{4A}$ and —(X$^4$)—SC(=O)N(R$^{4A}$)$_2$, X$^4$ is selected from the group consisting of C$_{1-4}$ alkylene, C$_{1-4}$ haloalkylene, C$_{1-4}$ heteroalkylene, C$_{2-4}$ alkenylene, and C$_{2-4}$ alkynylene, R$^{4A}$ at each occurrence is each independently selected from the group consisting of hydrogen, C$_{1-6}$ alkyl, C$_{1-6}$ haloalkyl and C$_{1-6}$ heteroalkyl, or any two R$^{4A}$ groups attached to the same nitrogen atom are optionally combined to form a 3 to 6 membered heterocyclic ring comprising 1 to 2 additional heteroatom selected from N, O and S; and wherein a R$^4$ group is independently optionally further substituted with 1 to 5 R$^{4A-1}$ substituents selected from the group consisting of —F, —Cl, —Br, —I, —OH, —CN, —NO$_2$, —SF$_5$, —NH$_2$, C$_{1-6}$ alkoxy, C$_{1-6}$ alkylamino and C$_{1-6}$ dialkylamino;

R$^5$ and R$^6$ are each independently selected from the group consisting of hydrogen, C$_{1-12}$ alkyl, and C$_{1-12}$ haloalkyl; and in the alternative R$^4$ and R$^5$ are combined to form a 5 to 7 membered heteroaryl or 5 to 7 membered heterocycloalkyl ring optionally comprising 1 additional heteroatom selected from N, O and S, and wherein said 5 to 7 membered heteroaryl or 5 to 7 membered heterocycloalkyl ring is further optionally substituted with 1 to 3 R$^{4/5cy}$ substituents selected from the group consisting of C$_{1-12}$ alkyl, C$_{1-12}$ haloalkyl, C$_{2-12}$ alkenyl, C$_{2-12}$ alkynyl, —F, —Cl, —Br, —I, —(X$^{4/5}$)$_{0-1}$—CN, —(X$^{4/5}$)$_{0-1}$—NO$_2$, —(X$^{4/5}$)$_{0-1}$—SF$_5$, —(X$^{4/5}$)$_{0-1}$—OSF$_5$, —(X$^{4/5}$)$_{0-1}$—OR$^{45A}$, —(X$^{4/5}$)$_{0-1}$—N(R$^{45A}$)$_2$, —(X$^{4/5}$)$_{0-1}$—SR$^{45A}$, —(X$^{4/5}$)$_{0-1}$—CF$_3$, 3 to 12 membered cycloalkyl-(X$^{45}$)$_{0-1}$—, 3 to 12 membered heterocycloalkyl-(X$^{4/5}$)$_{0-1}$—, 5 to 6 membered heteroaryl-(X$^{4/5}$)$_{0-1}$—, phenyl-(X$^{4/5}$)$_{0-1}$—, —(X$^{4/5}$)$_{0-1}$—C(=O)N(R$^{45A}$)(R$^{45A}$), —(X$^{4/5}$)$_{0-1}$—C(=O)OR$^{45A}$, —(X$^{4/5}$)$_{0-1}$—N(R$^{45A}$)C(=O)(R$^{45A}$), —(X$^{4/5}$)$_{0-1}$—N(R$^{45A}$)C(=O)OR$^{45A}$, —(X$^{4/5}$)$_{0-1}$—S(=O)$_{1-2}$—R$^{45A}$, —(X$^{4/5}$)$_{0-1}$—N(R$^{45A}$)S(=O)$_{1-2}$—R$^{45A}$, —(X$^{4/5}$)$_{0-1}$—S(=O)$_{1-2}$N(R$^{45A}$)$_2$, —(X$^{4/5}$)$_{0-1}$—C(=O)R$^{45A}$, —(X$^{4/5}$)$_{0-1}$—C(=NOR$^{45A}$)R$^{45A}$, —(X$^{4/5}$)$_{0-1}$—N(R$^{45A}$)C(=O)N(R$^{45A}$)$_2$ and —(X$^{4/5}$)$_{0-1}$—OC(=O)R$^{45A}$, —(X$^{4/5}$)$_{0-1}$—OP(=O)(OR$^{45A}$)$_2$, —(X$^{4/5}$)—SC(=O)OR$^{45A}$ and —(X$^{4/5}$)—SC(=O)N(R$^{45A}$)$_2$, X$^{4/5}$ is selected from the group consisting of C$_{1-4}$ alkylene, C$_{1-4}$ haloalkylene, C$_{1-4}$ heteroalkylene, C$_{2-4}$ alkenylene, and C$_{2-4}$ alkynylene, R$^{45A}$ at each occurrence is each independently selected from the group consisting of hydrogen, C$_{1-6}$ alkyl, C$_{1-6}$ haloalkyl and C$_{1-6}$ heteroalkyl; or any two R$^{45A}$ groups attached to the same nitrogen atom are optionally combined to form a 3 to 6 membered heterocyclic ring comprising 1 to 2 additional heteroatom selected from N, O and S; and wherein a R$^{4/5cy}$ substituent at each occurrence is independently optionally further substituted with 1 to 5 R$^{4/5cy-1}$ substituents selected from the group consisting of —F, —Cl, —Br, —I, —OH, —CN, —NO$_2$, —SF$_5$, —NH$_2$, C$_{1-6}$ alkoxy, C$_{1-6}$ alkylamino and C$_{1-6}$ dialkylamino; and R$^7$ is hydrogen, or in the alternative R$^4$ and R$^7$ are optionally combined to form a 5 to 7 membered heteroaryl or 5 to 7 membered heterocycloalkyl ring optionally comprising 1 additional heteroatom selected from N, O and S.

2. The method of claim 1, wherein R$^5$ and R$^6$ are each H.

3. The method of claim 1, wherein R$^4$ is selected from the group consisting of C$_{1-12}$ alkyl, C$_{1-12}$ haloalkyl, —F, —Cl, —(X$^4$)$_{0-1}$—CN, —(X$^4$)$_{0-1}$—OR$^{4A}$, —(X$^4$)$_{0-1}$—SR$^{4A}$, 3 to 7 membered cycloalkyl-(X$^4$)$_{0-1}$—, —(X$^4$)$_{0-1}$—S(=O)$_{1-2}$—R$^{4A}$ and is further optionally substituted.

4. The method of claim 1, wherein R$^4$ is selected from the group consisting of —F, —Cl, C$_{1-4}$ alkyl, C$_{1-4}$ haloalkyl, —(C$_{1-4}$ alkylene)$_{0-1}$-CN, C$_{1-4}$ alkyloxy, C$_{1-4}$ haloalkyloxy, C$_{1-4}$ alkylthio, C$_{1-4}$ haloalkylthio, 3 to 5 membered cycloalkyl-(C$_{1-4}$ alkyloxy)-, 3 to 6 membered cycloalkyl, and (C$_{1-4}$ alkyl)-S(O)$_2$—, wherein R$^4$ is further optionally substituted.

5. The method of claim 1, wherein R$^4$ is selected from the group consisting of —F, Cl, —CN, methyl, monofluoromethyl, difluoromethyl, trifluoromethyl, ethyl, 2-fluoroeth-1-yl, 1-fluoroeth-1-yl, 2,2-difluoroeth-1-yl, 1,2-difluoroeth-1-yl, 1,1-difluoroeth-1-yl, 2,2,2-trifluoroeth-1-yl, 1,2,2-trifluoroeth-1-yl, 1,1,2-trifluoroeth-1-yl, methoxy, monofluoromethoxy, difluoromethoxy, trifluoromethoxy, 2-fluoroethan-1-oxy, 2,2-difluoroethan-1oxy, 1,2-difluoroethan-1-oxy, 1,1-difluoroethan-1-oxy, 2,2,2-trifluoroethan-1-oxy, 1,2,2-trifluoroethan-1-oxy, 1,1,2-trifluoroethan-1-oxy, isopropoxy, 1-fluoro-propan-2-oxy, 1,1-difluoro-propan-2-oxy, 1,3-difluoro-propan-2-oxy, 1,1,1-trifluoro-propan-2-oxy, 1,1,3-trifluoro-propan-2-oxy, 1,1,1,3,3,3-hexafluoropropan-2-oxy, monofluoromethylthio, difluoromethylthio, trifluromethylthio, cyclopropylmethoxy and cyclopropyl.

6. The method of claim 1, wherein R$^6$ is H; and R$^4$ and R$^5$ are combined to form a 5 to 7 membered ring selected from the group consisting of pyrrole, imidazole, pyrazole, pyrrolidone, pyrrolidine, morpholine, piperdine and piperazine, wherein R$^4$ and R$^5$ combined are optionally substituted with 1 to 3 R$^{4/5cy}$ substituents.

7. The method of claim 1, wherein R$^{4/5cy}$ is selected from the group consisting of C$_{1-12}$ alkyl, C$_{1-12}$ haloalkyl, —F, —Cl, —(X$^{4/5}$)$_{0-1}$—CN, —(X$^{4/5}$)$_{0-1}$—OR$^{45A}$, 3 to 7 membered cycloalkyl-(X$^{4/5}$)$_{0-1}$—, —(X$^{4/5}$)$_{0-1}$—S(=O)$_{1-2}$—R$^{45A}$, wherein R$^{4/5cy}$ is optionally substituted with 1 to 3 R$^{4/5cy-1}$ substituents.

8. The method of claim 1, wherein R$^{4/5cy}$ is selected from the group consisting of —F, —Cl, C$_{1-4}$ alkyl, C$_{1-4}$ haloalkyl, —(C$_{1-4}$ alkylene)$_{0-1}$-CN, C$_{1-4}$ alkyloxy, C$_{1-4}$ haloalkyloxy, C$_{1-4}$ alkylthio, C$_{1-4}$ haloalkylthio, 3-6 membered cycloalkyl- ($C_{1-4}$ alkyloxy)-, 3 to 6 membered cycloalkyl, and ($C_{1-4}$ alkyl)-$S(O)_2$—, wherein $R^{4/5cy}$ is optionally substituted with 1 to 5 $R^{4/5cy-1}$ substituents.

9. The method of claim 1, wherein $R^{4/5cy}$ is selected from the group consisting of —F, Cl, —CN, methyl, monofluoromethyl, difluoromethyl, trifluoromethyl, ethyl, 2-fluoroeth-1-yl, 1-fluoroeth-1-yl, 2,2-difluoroeth-1-yl, 1,2-difluoroeth-1-yl, 1,1-difluoroeth-1-yl, 2,2,2-trifluoroeth-1-yl, 1,2,2-trifluoroeth-1-yl, 1,1,2-trifluoroeth-1-yl, methoxy, monofluoromethoxy, difluoromethoxy, trifluoromethoxy, 2-fluoroethan-1-oxy, 2,2-difluoroethan-1oxy, 1,2-difluoroethan-1-oxy, 1,1-difluoroethan-1-oxy, 2,2,2-trifluoroethan-1-oxy, 1,2,2-trifluoroethan-1-oxy, 1,1,2-trifluoroethan-1-oxy, isopropoxy, 1-fluoro-propan-2-oxy, 1,1-difluoro-propan-2-oxy, 1,3-difluoro-propan-2-oxy, 1,1,1-trifluoro-propan-2-oxy, 1,1,3-trifluoro-propan-2-oxy, 1,1,1,3,3,3-hexafluoropropan-2-oxy, monofluoromethylthio, difluoromethylthio, trifluromethylthio, cyclopropylmethoxy and cyclopropyl.

10. The method of claim 1, wherein $R^1$ is selected from the group consisting of hydrogen, $C_{1-4}$ alkyl and $C_{1-4}$ haloalkyl.

11. The method of claim 1, wherein $R^1$ is hydrogen, monofluoromethyl, difluoromethyl, trifluormethyl and methyl.

12. The method of claim 1, wherein $R^1$ is hydrogen.

13. The method of claim 1, wherein $R^2$ is a fused or bridged 3 to 12 membered cycloalkyl or a fused or bridged bicyclic or tricyclic C-linked 3 to 12 membered heterocycloalkyl ring, wherein $R^2$ is optionally substituted with 1-5 $R^{2-A}$ substituents.

14. The method of claim 1, wherein $R^2$ is selected from the group consisting of 3-azabicyclo[3.1.0]hexane, 3-azabicyclo[3.2.1]octane, 3-azabicyclo[3.1.1]heptane, 1,1a,5,5a-tetrahydro-4a-aza-cyclopropa[a]pentalene, 1,1a,5,5a-tetrahydro-2,4a-diaza-cyclopropa[a]pentalene, 1,1a,5,5a-tetrahydro-3,4a-diaza-cyclopropa[a]pentalene, 1,1a,5,5a-tetrahydro-2,3,4a-triaza-cyclopropa[a]pentalene, 1,1a,5,5a-tetrahydro-4,4a-diaza-cyclopropa[a]pentalene, octahydro-4a-aza-cyclopropa[a]pentalene, 3-oxabicyclo[3.2.1]octane, 3-oxabicyclo[3.1.1]heptane and 3-oxabicyclo[3.1.0]hexane, and wherein $R^2$ is optionally substituted with 1 to 5 $R^{2-A}$ substituents.

15. The method of claim 1, wherein $R^2$ is selected from the group consisting of

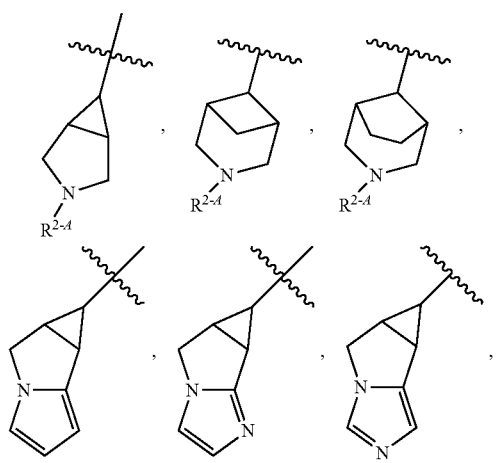

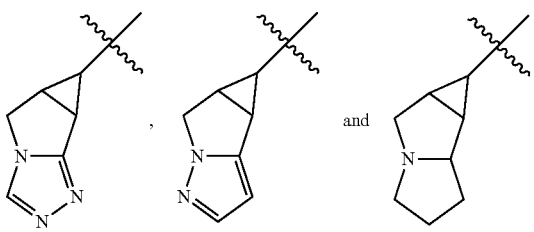

16. The method of claim 1, wherein $R^2$ is selected from the group consisting of

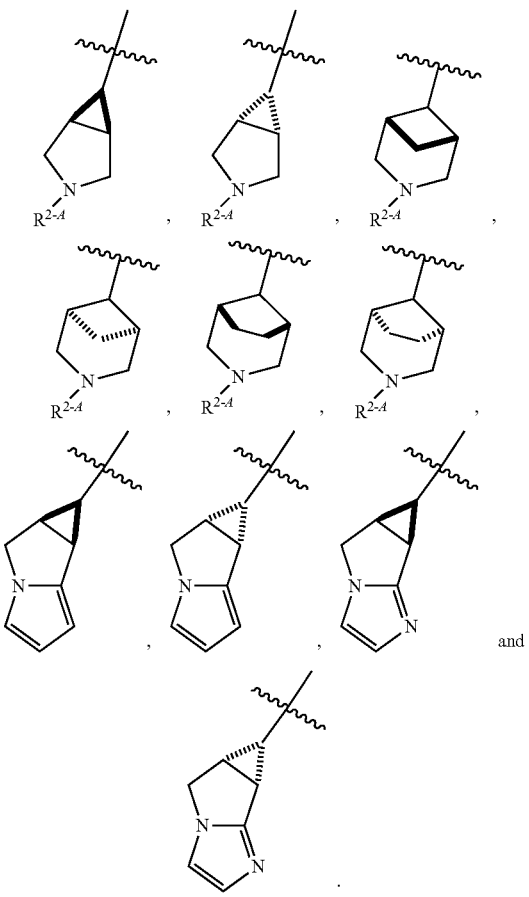

17. The method of claim 1, wherein $R^2$ is a monocyclic ring, wherein $R^2$ is optionally substituted with 1 to 5 $R^{2-A}$ substituents.

18. The method of claim 1, wherein $R^2$ is a monocyclic ring selected from the group consisting of azetidine, pyrrolidine, pyrrolidone, piperidine, piperidone, azepane, azepanone, tetrahydrofuran, tetrahydrofuranone, tetrahydropyan, tetrahydropyanone, oxetane, oxetanone, oxepane and oxepanone, wherein $R^2$ is optionally substituted with 1 to 5 $R^{2-A}$ substituents and wherein $R^{2-A}$ is further optionally substituted.

19. The method of claim 1, wherein $R^2$ is selected from the group consisting of

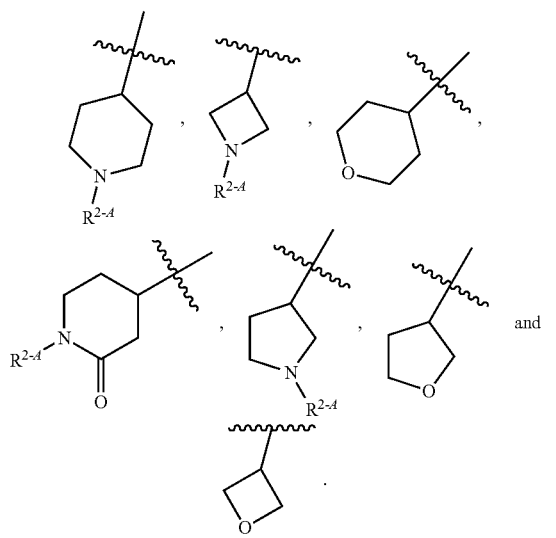

20. The method of claim 1, wherein $R^{2-A}$ is selected from the group consisting of $C_{1-12}$ alkyl, $C_{1-12}$ haloalkyl, $C_{1-12}$ heteroalkyl, $-(X^2)_{0-1}-CN$, $-(X^2)_{0-1}-OR^{2A}$, 3 to 12 membered cycloalkyl-$(X^2)_{0-1}-$, 3 to 12 membered heterocycloalkyl-$(X^2)_{0-1}-$, $-(X^2)_{0-1}-S(=O)_{1-2}-R^{2A}$ and $-(X^2)_{0-1}-C(=O)R^{2A}$, wherein $R^{2-A}$ is optionally substituted.

21. The method of claim 1, wherein $R^{2-A}$ is selected from the group consisting of OH, ($C_{1-6}$ alkyl)-C(=O)—, ($C_{1-6}$ alkyl)-S(=O)$_2$—, oxepane, azetidine, $C_{1-6}$ alkyl, $C_{1-6}$ haloalkyl, $C_{1-6}$ heteroalkyl and —($C_{1-6}$ alkyl)-CN, wherein $R^{2-A}$ is optionally substituted.

22. The method of claim 1, wherein $R^{2-A}$ is selected from the group consisting of $CH_3$—C(=O)—, oxetanyl, methyl, monofluoromethyl, difluoromethyl, trifluoromethyl, ethyl, 2-fluoroeth-1-yl, 1-fluoroeth-1-yl, 1,2-difluoroeth-1-yl, 2,2-difluoroeth-1-yl, 1,1,2-trifluoroeth-1-yl 2,2,2-trifluoroeth-1-yl, 1,2,2-trifluoroeth-1-yl, cyanomethyl, cyanoethyl, methoxyethyl, hydroxy, $(CH_3)_2(OH)CC(H)_2$—, $CH_3OCH_2C(H)(CH_3)$—, $CH_3OC(CH_3)_2CH_2$—, NCC(H)$(CH_3)CH_2$—, $NCC(H)(CH_3)_2CH_2$—, $CH_3OC(H)(CH_3)$ $CH_2$—, $NCCH_2C(H)(CH_3)$—, $NCCCH_2C(CH_3)_2$—, $CH_3$—$S(O)_2$— and isopropyl-OC(=O)—.

23. The method of claim 1, wherein $R^2$ is —C($R^{A2}$)($C_{1-6}$ alkyl)$_2$, wherein $R^{A2}$ is hydrogen, —F, —Cl, —Br, —I, —CN, —OH, —NH$_2$, —SF$_5$, —OSF$_5$, $C_{1-4}$ alkylthio, $C_{1-4}$ alkoxy, $C_{1-4}$ alkylamino and $C_{1-4}$ dialkylamino and wherein $R^2$ is optionally substituted with 1 to 5 $R^{2-A}$ substituents.

24. The method of claim 1, wherein $R^3$ is selected from the group consisting of $C_{1-6}$ alkyl, 3 to 6 membered cycloalkyl-$C_{1-4}$ alkyl, 3 to 6 membered cycloalkyl, 3 to 6 membered heterocycloalkyl-$C_{1-4}$ alkyl, and 3-6 membered heterocycloalkyl, wherein $R^3$ is optionally substituted with $R^{3A}$.

25. The method of claim 1, wherein $R^3$ is selected from the group consisting of methyl, monofluoromethyl, difluoromethyl, ethyl, 1,1,1-trifluoroeth-2-yl, propyl, isopropyl, butyl, sec-butyl, tert-butyl, cyclopropyl, cyclopropylmethyl, cyclobutyl, cyclobutylmethyl, cyclopentyl, cyclopentylmethyl, cyclohexyl, cyclohexylmethyl, 1,1-difluorocyclobut-3-yl, 1,1-difluorocyclopent-3-yl, oxetan-2-yl, oxetan-2-yl-methyl, oxetan-3-yl, oxetan-3-yl-methyl, tetrahydrofuran-3-yl, tetrahydrofuran-3-yl-methyl, tetrahydropyran-3-yl, tetrahydropyran-3-yl-methyl, tetrahydropyran-4-yl, tetrahydropyran-4-yl-methyl, azetindin-3-yl, azetindin-3-yl-methyl, pyrrolidin-3-yl, pyrrolidin-3-yl-methyl, piperidin-4yl, piperidin-4-yl-methyl, piperidin-3-yl and piperidin-3-yl-methyl.

26. The method of claim 1, wherein said compound has a formula selected from the group consisting of:

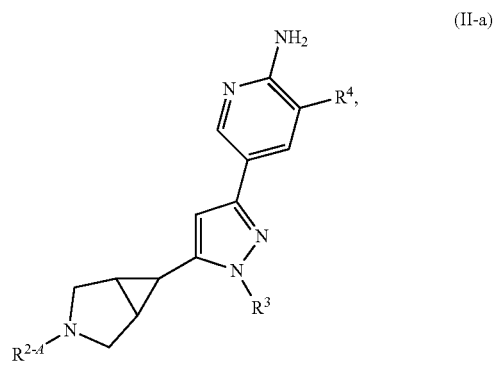

(II-a)

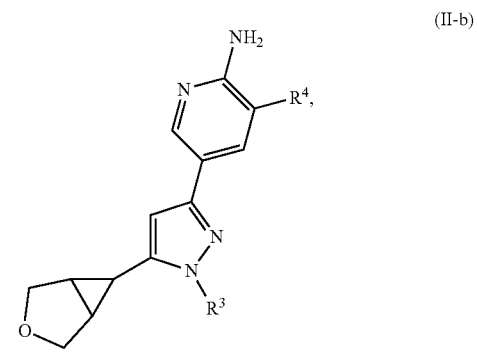

(II-b)

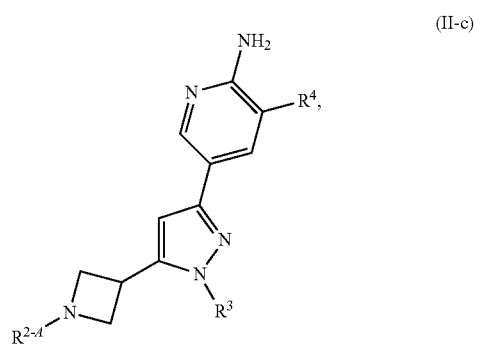

(II-c)

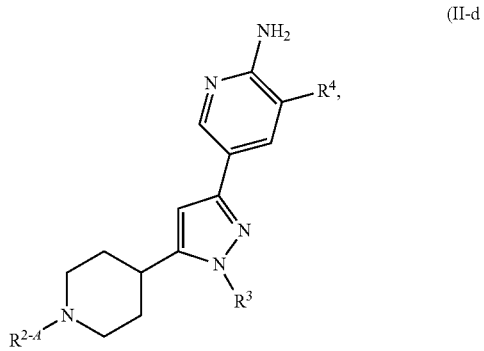

(II-d)

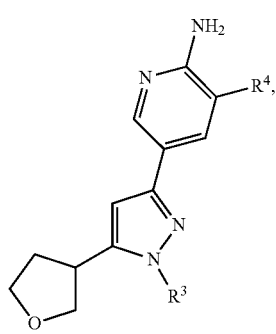
(II-e)
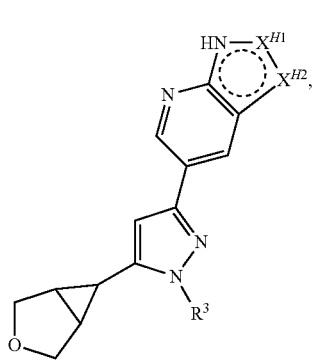
(III-b)
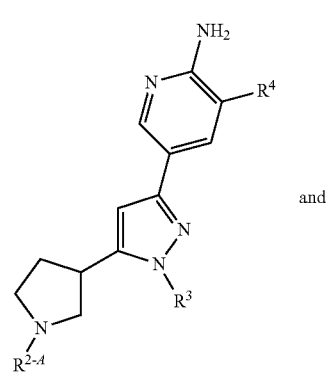
and
(II-f)
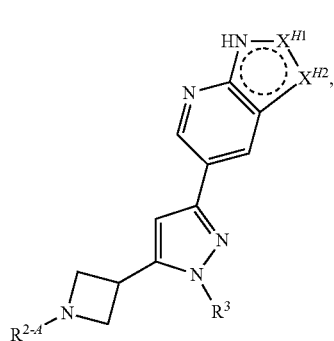
(III-c)
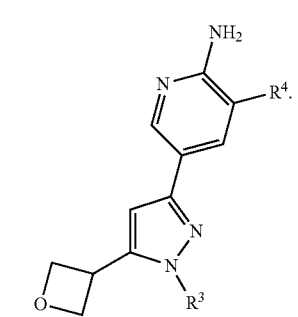
(II-g)
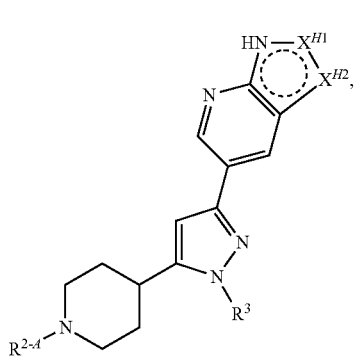
(III-d)
27. The method of claim 1, wherein said compound has the formula selected from the group consisting of
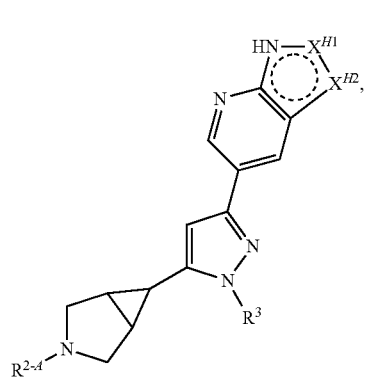
(III-a)
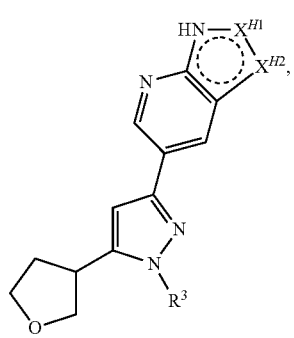
(III-e)

-continued

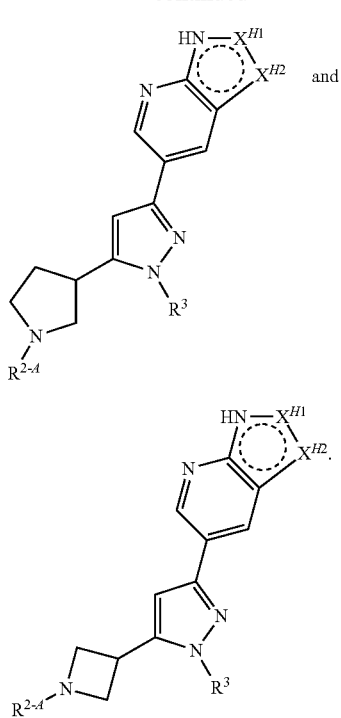

(III-f)

(III-g)

wherein in formula III-a, III-b, III-c, III-d, III-e, III-f and III-g, $X^{H1}$ and $X^{H2}$ at each occurrence is independently selected from the group consisting of N, NH, N($R^{4/5cy}$), CH or C($R^{4/5cy}$).

28. The method of claim 27, wherein $X^{H1}$ and $X^{H2}$ are independently CH or C($R^{4/5cy}$).

29. The method of claim 1, wherein said compound of Formula (I) is selected from the group consisting of
5-(5-isopropyl-1-(1-(oxetan-3-yl)azetidin-3-yl)-1H-pyrazol-3-yl)-3-(trifluoromethyl)-1H-pyrrolo[2,3-b]pyridine,
2-(3-(6-amino-5-(trifluoromethyl)pyridin-3-yl)-1-isopropyl-1H-pyrazol-5-yl)propan-2-ol,
2-(3-(6-amino-5-(difluoromethoxy)pyridin-3-yl)-1-isopropyl-1H-pyrazol-5-yl)propan-2-ol,
2-(3-(6-amino-5-(trifluoromethyl)pyridin-3-yl)-1-isopropyl-1H-pyrazol-5-yl)-2-methylpropanenitrile,
2-(3-(6-amino-5-(difluoromethoxy)pyridin-3-yl)-1-isopropyl-1H-pyrazol-5-yl)-2-methylpropanenitrile,
2-(3-(6-amino-5-(trifluoromethoxy)pyridin-3-yl)-1-isopropyl-1H-pyrazol-5-yl)-2-methylpropanenitrile,
5-(1-isopropyl-5-(1-methylazetidin-3-yl)-1H-pyrazol-3-yl)-3-(trifluoromethyl)pyridin-2-amine,
1-(3-(1-(cyclopropylmethyl)-3-(3-(trifluoromethyl)-1H-pyrrolo[2,3-b]pyridin-5-yl)-1H-pyrazol-5-yl)azetidin-1-yl)ethanone,
1-(3-(1-(cyclopropylmethyl)-3-(3-methyl-1H-pyrrolo[2,3-b]pyridin-5-yl)-1H-pyrazol-5-yl)azetidin-1-yl)ethanone,
1-(3-(1-isopropyl-3-(3-(trifluoromethyl)-1H-pyrrolo[2,3-b]pyridin-5-yl)-1H-pyrazol-5-yl)azetidin-1-yl)ethanone,
1-(3-(1-methyl-3-(3-(trifluoromethyl)-1H-pyrrolo[2,3-b]pyridin-5-yl)-1H-pyrazol-5-yl)azetidin-1-yl)ethanone,
1-(3-(1-isopropyl-3-(3-methyl-1H-pyrrolo[2,3-b]pyridin-5-yl)-H-pyrazol-5-yl)azetidin-1-yl)ethanone,
racemic-5-(1-(cyclopropylmethyl)-5-(tetrahydrofuran-3-yl)-1H-pyrazol-3-yl)-3-methyl-1H-pyrrolo[2,3-b]pyridine,
5-(1-(3,3-difluorocyclopentyl)-5-(tetrahydrofuran-3-yl)-1H-pyrazol-3-yl)-3-methyl-1H-pyrrolo[2,3-b]pyridine,
5-(1,5-bis(tetrahydrofuran-3-yl)-1H-pyrazol-3-yl)-3-(trifluoromethyl)-1H-pyrrolo[2,3-b]pyridine
5-(1-(3,3-difluorocyclopentyl)-5-(tetrahydrofuran-3-yl)-1H-pyrazol-3-yl)-3-(trifluoromethyl)-1H-pyrrolo[2,3-b]pyridine,
(R)-5-(1-(cyclopropylmethyl)-5-(tetrahydrofuran-3-yl)-1H-pyrazol-3-yl)-3-methyl-1H-pyrrolo[2,3-b]pyridine,
(S)-5-(1-(cyclopropylmethyl)-5-(tetrahydrofuran-3-yl)-1H-pyrazol-3-yl)-3-methyl-1H-pyrrolo[2,3-b]pyridine,
5-(1-(3,3-difluorocyclobutyl)-5-(tetrahydrofuran-3-yl)-1H-pyrazol-3-yl)-3-methyl-1H-pyrrolo[2,3-b]pyridine,
5-(1-(3,3-difluorocyclobutyl)-5-(tetrahydrofuran-3-yl)-1H-pyrazol-3-yl)-3-ethyl-1H-pyrrolo[2,3-b]pyridine,
5-(1,5-bis(tetrahydrofuran-3-yl)-1H-pyrazol-3-yl)-3-chloropyridin-2-amine,
5-(1,5-bis(tetrahydrofuran-3-yl)-1H-pyrazol-3-yl)-3-fluoropyridin-2-amine,
3-chloro-5-(1-(3,3-difluorocyclopentyl)-5-(tetrahydrofuran-3-yl)-1H-pyrazol-3-yl)pyridin-2-amine,
5-(1-(3,3-difluorocyclopentyl)-5-(tetrahydrofuran-3-yl)-1H-pyrazol-3-yl)-3-fluoropyridin-2-amine,
3-chloro-5-(1-(3,3-difluorocyclobutyl)-5-(tetrahydrofuran-3-yl)-1H-pyrazol-3-yl)pyridin-2-amine,
5-(1-((R)-tetrahydrofuran-3-yl)-5-((S)-tetrahydrofuran-3-yl)-1H-pyrazol-3-yl)-3-(trifluoromethyl)-1H-pyrrolo[2,3-b]pyridine,
5-(1-((R)-3,3-difluorocyclopentyl)-5-((R)-tetrahydrofuran-3-yl)-1H-pyrazol-3-yl)-3-methyl-1H-pyrrolo[2,3-b]pyridine,
5-(5-((R)-tetrahydrofuran-3-yl)-1-((S)-tetrahydrofuran-3-yl)-1H-pyrazol-3-yl)-3-(trifluoromethyl)-1H-pyrrolo[2,3-b]pyridine,
5-(1,5-bis((S)-tetrahydrofuran-3-yl)-1H-pyrazol-3-yl)-3-(trifluoromethyl)-1H-pyrrolo[2,3-b]pyridine,
5-(1,5-bis((R)-tetrahydrofuran-3-yl)-1H-pyrazol-3-yl)-3-(trifluoromethyl)-1H-pyrrolo[2,3-b]pyridine,
5-(1-((S)-3,3-difluorocyclopentyl)-5-((S)-tetrahydrofuran-3-yl)-1H-pyrazol-3-yl)-3-methyl-1H-pyrrolo[2,3-b]pyridine,
5-(1-((R)-3,3-difluorocyclopentyl)-5-((S)-tetrahydrofuran-3-yl)-1H-pyrazol-3-yl)-3-methyl-1H-pyrrolo[2,3-b]pyridine,
5-(1-((S)-3,3-difluorocyclopentyl)-5-((R)-tetrahydrofuran-3-yl)-1H-pyrazol-3-yl)-3-methyl-1H-pyrrolo[2,3-b]pyridine,
1-(3-(6-amino-5-(trifluoromethyl)pyridin-3-yl)-1-isopropyl-1H-pyrazol-5-yl)cyclopentanol,
5-(1-(3,3-difluorocyclobutyl)-5-(tetrahydro-2H-pyran-4-yl)-1H-pyrazol-3-yl)-3-methyl-1H-pyrrolo[2,3-b]pyridine,
5-(1-(3,3-difluorocyclobutyl)-5-(tetrahydro-2H-pyran-4-yl)-1H-pyrazol-3-yl)-3-ethyl-1H-pyrazolo[3,4-b]pyridine,
5-(1-(3,3-difluorocyclobutyl)-5-(tetrahydro-2H-pyran-4-yl)-1H-pyrazol-3-yl)-3-fluoropyridin-2-amine,
5-(1-(3,3-difluorocyclobutyl)-5-(tetrahydro-2H-pyran-4-yl)-1H-pyrazol-3-yl)-3-(trifluoromethyl)-1H-pyrrolo[2,3-b]pyridine,
3-chloro-5-(1-(3,3-difluorocyclobutyl)-5-(tetrahydro-2H-pyran-4-yl)-1H-pyrazol-3-yl)pyridin-2-amine,
5-(1-isopropyl-5-(1-methylpiperidin-4-yl)-1H-pyrazol-3-yl)-3-(trifluoromethyl)-1H-pyrrolo[2,3-b]pyridine, 5-(1-isopropyl-5-(1-methylpiperidin-4-yl)-1H-pyrazol-3-yl)-3-(trifluoromethyl)pyridin-2-amine,
4-(1-(3,3-difluorocyclobutyl)-3-(3-methyl-1H-pyrrolo[2,3-b]pyridin-5-yl)-1H-pyrazol-5-yl)-1-methylpiperidin-2-one,
4-(3-(6-amino-5-chloropyridin-3-yl)-1l-(3,3-difluorocyclobutyl)-1H-pyrazol-5-yl)-1-methylpiperidin-2-one,
4-(3-(6-amino-5-fluoropyridin-3-yl)-1-(3,3-difluorocyclobutyl)-1H-pyrazol-5-yl)-1-methylpiperidin-2-one,
4-(1-(3,3-difluorocyclobutyl)-3-(3-(trifluoromethyl)-1H-pyrrolo[2,3-b]pyridin-5-yl)-1H-pyrazol-5-yl)-1-methylpiperidin-2-one,
5-(1-isopropyl-5-(1-(2,2,2-trifluoroethyl)piperidin-4-yl)-1H-pyrazol-3-yl)-1H-pyrrolo[2,3-b]pyridine-3-carbonitrile,
1-(4-(1-methyl-3-(3-methyl-1H-pyrrolo[2,3-b]pyridin-5-yl)-1H-pyrazol-5-yl)piperidin-1-yl)ethanone,
1-(4-(1-methyl-3-(3-(trifluoromethyl)-1H-pyrrolo[2,3-b]pyridin-5-yl)-1H-pyrazol-5-yl)piperidin-1-yl)ethanone,
1-(4-(1-isopropyl-3-(3-methyl-1H-pyrrolo[2,3-b]pyridin-5-yl)-1H-pyrazol-5-yl)piperidin-1-yl)ethanone,
1-(4-(1-isopropyl-3-(3-(trifluoromethyl)-1H-pyrrolo[2,3-b]pyridin-5-yl)-1H-pyrazol-5-yl)piperidin-1-yl)ethanone,
2-(4-(1-isopropyl-3-(3-(trifluoromethyl)-1H-pyrrolo[2,3-b]pyridin-5-yl)-1H-pyrazol-5-yl)piperidin-1-yl)acetonitrile,
2-(4-(3-(6-amino-5-(trifluoromethyl)pyridin-3-yl)-1-isopropyl-1H-pyrazol-5-yl)piperidin-1-yl)acetonitrile,
5-(1-isopropyl-5-(1-(2-methoxyethyl)piperidin-4-yl)-1H-pyrazol-3-yl)-3-(trifluoromethyl)pyridin-2-amine,
5-(1-isopropyl-5-(1-(oxetan-3-yl)azetidin-3-yl)-1H-pyrazol-3-yl)-3-(trifluoromethyl)-1H-pyrrolo[2,3-b]pyridine,
5-(5-(1-(oxetan-3-yl)azetidin-3-yl)-1-(tetrahydrofuran-3-yl)-1H-pyrazol-3-yl)-3-(trifluoromethyl)-1H-pyrrolo[2,3-b]pyridine,
5-(1-(3,3-difluorocyclopentyl)-5-(1-(oxetan-3-yl)azetidin-3-yl)-1H-pyrazol-3-yl)-3-(trifluoromethyl)-1H-pyrrolo[2,3-b]pyridine,
3-chloro-5-(1-isopropyl-5-(1-(oxetan-3-yl)azetidin-3-yl)-1H-pyrazol-3-yl)-1H-pyrrolo[2,3-b]pyridine,
3-fluoro-5-(1-isopropyl-5-(1-(oxetan-3-yl)azetidin-3-yl)-1H-pyrazol-3-yl)-1H-pyrrolo[2,3-b]pyridine,
5-(1-isopropyl-5-(1-(oxetan-3-yl)azetidin-3-yl)-1H-pyrazol-3-yl)-1H-pyrrolo[2,3-b]pyridine-3-carbonitrile,
5-(1-isopropyl-5-(1-(oxetan-3-yl)azetidin-3-yl)-1H-pyrazol-3-yl)-3-(trifluoromethyl)pyridin-2-amine,
5-(1-isopropyl-5-(1-(oxetan-3-yl)azetidin-3-yl)-H-pyrazol-3-yl)-3,3-dimethyl-1H-pyrrolo[2,3-b]pyridin-2(3H)-one,
6-(1-isopropyl-5-(1-(oxetan-3-yl)azetidin-3-yl)-1H-pyrazol-3-yl)-3H-imidazo[4,5-b]pyridine,
3-methyl-5-(1-methyl-5-(1-(oxetan-3-yl)pyrrolidin-3-yl)-1H-pyrazol-3-yl)-1H-pyrrolo[2,3-b]pyridine,
5-(1-isopropyl-5-(1-(oxetan-3-yl)pyrrolidin-3-yl)-1H-pyrazol-3-yl)-3-methyl-1H-pyrrolo[2,3-b]pyridine,
3-chloro-5-(1-isopropyl-5-(1-(oxetan-3-yl)pyrrolidin-3-yl)-1H-pyrazol-3-yl)-1H-pyrrolo[2,3-b]pyridine,
3-fluoro-5-(1-isopropyl-5-(1-(oxetan-3-yl)pyrrolidin-3-yl)-1H-pyrazol-3-yl)-1H-pyrrolo[2,3-b]pyridine,
5-(1-isopropyl-5-(1-(oxetan-3-yl)pyrrolidin-3-yl)-1H-pyrazol-3-yl)-3-(trifluoromethyl)pyridin-2-amine,
5-(1-methyl-5-(1-(oxetan-3-yl)piperidin-4-yl)-1H-pyrazol-3-yl)-3-(trifluoromethyl)-1H-pyrrolo[2,3-b]pyridine,
5-(1-isopropyl-5-(1-(oxetan-3-yl)piperidin-4-yl)-1H-pyrazol-3-yl)-3-methyl-1H-pyrrolo[2,3-b]pyridine,
5-(1-isopropyl-5-(1-(oxetan-3-yl)piperidin-4-yl)-1H-pyrazol-3-yl)-3-(trifluoromethyl)-1H-pyrrolo[2,3-b]pyridine,
3-chloro-5-(1-cyclopentyl-5-(1-(oxetan-3-yl)piperidin-4-yl)-1H-pyrazol-3-yl)pyridin-2-amine,
3-chloro-5-(1-isopropyl-5-(1-(oxetan-3-yl)piperidin-4-yl)-1H-pyrazol-3-yl)-1H-pyrrolo[2,3-b]pyridine,
5-(1-isopropyl-5-(1-(oxetan-3-yl)piperidin-4-yl)-1H-pyrazol-3-yl)-1H-pyrrolo[2,3-b]pyridin-2(3H)-one,
3-chloro-5-(5-(1-(oxetan-3-yl)piperidin-4-yl)-1-(tetrahydrofuran-3-yl)-1H-pyrazol-3-yl)pyridin-2-amine,
3-fluoro-5-(1-isopropyl-5-(1-(oxetan-3-yl)piperidin-4-yl)-1H-pyrazol-3-yl)-1H-pyrrolo[2,3-b]pyridine,
5-(1-isopropyl-5-(1-(oxetan-3-yl)piperidin-4-yl)-1H-pyrazol-3-yl)-3-(trifluoromethyl)pyridin-2-amine,
5-(1-isopropyl-5-(1-(oxetan-3-yl)piperidin-4-yl)-1H-pyrazol-3-yl)-1H-pyrrolo[2,3-b]pyridine-3-carbonitrile,
3-chloro-5-(1-isopropyl-5-(1-(oxetan-3-yl)piperidin-4-yl)-1H-pyrazol-3-yl)pyridin-2-amine,
6-(1-isopropyl-5-(1-(oxetan-3-yl)piperidin-4-yl)-1H-pyrazol-3-yl)-3H-imidazo[4,5-b]pyridine,
5-(1-isopropyl-5-(1-(oxetan-3-yl)piperidin-4-yl)-1H-pyrazol-3-yl)-3,3-dimethyl-1H-pyrrolo[2,3-b]pyridin-2(3H)-one,
5-(1-cyclopentyl-5-(1-(oxetan-3-yl)piperidin-4-yl)-1H-pyrazol-3-yl)-3-(trifluoromethyl)pyridin-2-amine,
5-(1-isopropyl-5-(1-(oxetan-3-yl)piperidin-4-yl)-1H-pyrazol-3-yl)-3-methylpyridin-2-amine,
3-ethoxy-5-(1-isopropyl-5-(1-(oxetan-3-yl)piperidin-4-yl)-1H-pyrazol-3-yl)pyridin-2-amine,
3-isopropoxy-5-(1-isopropyl-5-(1-(oxetan-3-yl)piperidin-4-yl)-1H-pyrazol-3-yl)pyridin-2-amine,
5-(1-(3,3-difluorocyclopentyl)-5-(1-(oxetan-3-yl)piperidin-4-yl)-1H-pyrazol-3-yl)-3-ethoxypyridin-2-amine,
5-(1-(3,3-difluorocyclopentyl)-5-(1-(oxetan-3-yl)piperidin-4-yl)-1H-pyrazol-3-yl)-3-isopropoxypyridin-2-amine,
3-(cyclopropylmethoxy)-5-(1-(3,3-difluorocyclopentyl)-5-(1-(oxetan-3-yl)piperidin-4-yl)-1H-pyrazol-3-yl)pyridin-2-amine,
5-(1-cyclopentyl-5-(1-(oxetan-3-yl)piperidin-4-yl)-1H-pyrazol-3-yl)-3-methoxypyridin-2-amine,
5-(1-isopropyl-5-(1-(oxetan-3-yl)piperidin-4-yl)-1H-pyrazol-3-yl)-3-methoxypyridin-2-amine,
5-(1-cyclopentyl-5-(1-(oxetan-3-yl)piperidin-4-yl)-1H-pyrazol-3-yl)-3-isopropoxypyridin-2-amine,
3-chloro-5-(1-(3,3-difluorocyclopentyl)-5-(1-(oxetan-3-yl)piperidin-4-yl)-1H-pyrazol-3-yl)pyridin-2-amine,
2-amino-5-(1-isopropyl-5-(1-(oxetan-3-yl)piperidin-4-yl)-1H-pyrazol-3-yl)nicotinonitrile,
2-amino-5-(1-cyclopentyl-5-(1-(oxetan-3-yl)piperidin-4-yl)-1H-pyrazol-3-yl)nicotinonitrile,
7-(1-isopropyl-5-(1-(oxetan-3-yl)piperidin-4-yl)-1H-pyrazol-3-yl)-3,4-dihydro-2H-pyrido[3,2-b][1,4]oxazine,
5-(1-isopropyl-5-(1-(oxetan-3-yl)piperidin-4-yl)-1H-pyrazol-3-yl)-3,3-dimethyl-2,3-dihydro-1H-pyrrolo[2,3-b]pyridine,
6-(1-isopropyl-5-(1-(oxetan-3-yl)piperidin-4-yl)-1H-pyrazol-3-yl)-1,2,3,4-tetrahydro-1,8-naphthyridine,
5-(5-(1-(oxetan-3-yl)piperidin-4-yl)-1-(tetrahydrofuran-3-yl)-H-pyrazol-3-yl)-3-(trifluoromethyl)pyridin-2-amine, 3-cyclopropyl-5-(1-isopropyl-5-(1-(oxetan-3-yl)piperidin-4-yl)-1H-pyrazol-3-yl)pyridin-2-amine,
3-(difluoromethoxy)-5-(1-isopropyl-5-(1-(oxetan-3-yl)piperidin-4-yl)-1H-pyrazol-3-yl)pyridin-2-amine,
5-(1-(3,3-difluorocyclopentyl)-5-(1-(oxetan-3-yl)piperidin-4-yl)-1H-pyrazol-3-yl)-3-methoxypyridin-2-amine,
5-(5-(1-cyclobutylpiperidin-4-yl)-1-isopropyl-1H-pyrazol-3-yl)-3-(trifluoromethyl)-1H-pyrrolo[2,3-b]pyridine,
5-(5-(1-cyclobutylpiperidin-4-yl)-1-isopropyl-1H-pyrazol-3-yl)-3-(trifluoromethyl)pyridin-2-amine,
5-(1-isopropyl-5-(4-methoxy-1-(oxetan-3-yl)piperidin-4-yl)-1H-pyrazol-3-yl)-3-(trifluoromethyl)pyridin-2-amine,
5-(5-((1R,5S,6s)-3-oxabicyclo[3.1.0]hexan-6-yl)-1-isopropyl-1H-pyrazol-3-yl)-3-(trifluoromethyl)pyridin-2-amine,
5-(5-((1R,5S,6s)-3-oxabicyclo[3.1.0]hexan-6-yl)-1-cyclopentyl-1H-pyrazol-3-yl)-3-chloropyridin-2-amine,
5-(5-((1R,5S,6s)-3-oxabicyclo[3.1.0]hexan-6-yl)-1-isopropyl-1H-pyrazol-3-yl)-3-fluoro-1H-pyrrolo[2,3-b]pyridine,
5-(5-((1R,5S,6r)-3-azabicyclo[3.1.0]hexan-6-yl)-1-(2,2,2-trifluoroethyl)-1H-pyrazol-3-yl)-3-(trifluoromethyl)pyridin-2-amine,
5-(1-isopropyl-5-((1R,5S,6r)-3-(methylsulfonyl)-3-azabicyclo[3.1.0]hexan-6-yl)-1H-pyrazol-3-yl)-3-(trifluoromethyl)pyridin-2-amine
5-(5-((1R,5S,6r)-3-(2,2-difluoroethyl)-3-azabicyclo[3.1.0]hexan-6-yl)-1-isopropyl-1H-pyrazol-3-yl)-3-(trifluoromethyl)pyridin-2-amine,
3-(difluoromethoxy)-5-(1-isopropyl-5-((1R,5S,6r)-3-(2,2,2-trifluoroethyl)-3-azabicyclo[3.1.0]hexan-6-yl)-1H-pyrazol-3-yl)pyridin-2-amine,
3-chloro-5-(1-(oxetan-3-yl)-5-((1R,5S,6r)-3-(2,2,2-trifluoroethyl)-3-azabicyclo[3.1.0]hexan-6-yl)-1H-pyrazol-3-yl)pyridin-2-amine,
3-chloro-5-(1-((3-methyloxetan-3-yl)methyl)-5-((1R,5S,6r)-3-(2,2,2-trifluoroethyl)-3-azabicyclo[3.1.0]hexan-6-yl)-1H-pyrazol-3-yl)pyridin-2-amine,
2-amino-5-(1-(cyclopropylmethyl)-5-((1R,5S,6r)-3-(2,2,2-trifluoroethyl)-3-azabicyclo[3.1.0]hexan-6-yl)-1H-pyrazol-3-yl)nicotinonitrile,
7-(1-isopropyl-5-((1R,5S,6r)-3-(2,2,2-trifluoroethyl)-3-azabicyclo[3.1.0]hexan-6-yl)-1H-pyrazol-3-yl)-1H-pyrazolo[4,3-c]pyridin-4-amine,
1-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)ethanone,
3-chloro-5-(5-((1R,5S,6r)-3-(2-methoxyethyl)-3-azabicyclo[3.1.0]hexan-6-yl)-1-(2,2,2-trifluoroethyl)-1H-pyrazol-3-yl)pyridin-2-amine,
5-(1-isopropyl-5-((1R,5S,6r)-3-(2-methoxyethyl)-3-azabicyclo[3.1.0]hexan-6-yl)-1H-pyrazol-3-yl)-3-(trifluoromethyl)pyridin-2-amine,
3-chloro-5-(1-isopropyl-5-((1R,5S,6r)-3-(2-methoxyethyl)-3-azabicyclo[3.1.0]hexan-6-yl)-1H-pyrazol-3-yl)pyridin-2-amine,
3-(difluoromethoxy)-5-(1-isopropyl-5-((1R,5S,6r)-3-(2-methoxyethyl)-3-azabicyclo[3.1.0]hexan-6-yl)-1H-pyrazol-3-yl)pyridin-2-amine,
3-chloro-5-(1-isobutyl-5-((1R,5S,6r)-3-(2-methoxyethyl)-3-azabicyclo[3.1.0]hexan-6-yl)-1H-pyrazol-3-yl)pyridin-2-amine,
3-chloro-5-(1-((2,2-difluorocyclopropyl)methyl)-5-((1R,5S,6r)-3-(2-methoxyethyl)-3-azabicyclo[3.1.0]hexan-6-yl)-1H-pyrazol-3-yl)pyridin-2-amine,
5-(1-(cyclopropylmethyl)-5-((1R,5S,6r)-3-(2-methoxyethyl)-3-azabicyclo[3.1.0]hexan-6-yl)-1H-pyrazol-3-yl)-3-(trifluoromethyl)pyridin-2-amine,
3-chloro-5-(1-(cyclopropylmethyl)-5-((1R,5S,6r)-3-(2-methoxyethyl)-3-azabicyclo[3.1.0]hexan-6-yl)-1H-pyrazol-3-yl)pyridin-2-amine,
5-(1-(cyclobutylmethyl)-5-((1R,5S,6r)-3-(2-methoxyethyl)-3-azabicyclo[3.1.0]hexan-6-yl)-1H-pyrazol-3-yl)-3-(trifluoromethyl)pyridin-2-amine,
5-(1-isopropyl-5-((1R,5S,6r)-3-(2-methoxyethyl)-3-azabicyclo[3.1.0]hexan-6-yl)-1H-pyrazol-3-yl)-3-(trifluoromethoxy)pyridin-2-amine,
5-(5-((1R,5S,6r)-3-(2-methoxyethyl)-3-azabicyclo[3.1.0]hexan-6-yl)-1-(2,2,2-trifluoroethyl)-1H-pyrazol-3-yl)-3-(trifluoromethyl)pyridin-2-amine,
3-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)propanenitrile,
1-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)-2-methylpropan-2-ol,
5-(1-isopropyl-5-((1R,5S,6r)-3-(1-methoxypropan-2-yl)-3-azabicyclo[3.1.0]hexan-6-yl)-1H-pyrazol-3-yl)-3-(trifluoromethyl)pyridin-2-amine,
(1R,5S,6r)-isopropyl 6-(3-(6-amino-5-(trifluoromethyl)pyridin-3-yl)-1-isopropyl-1H-pyrazol-5-yl)-3-azabicyclo[3.1.0]hexane-3-carboxylate,
3-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)butanenitrile,
5-(1-isopropyl-5-((1R,5S,6r)-3-(oxetan-3-yl)-3-azabicyclo[3.1.0]hexan-6-yl)-1H-pyrazol-3-yl)-1H-pyrrolo[2,3-b]pyridine-3-carbonitrile,
5-(1-isopropyl-5-((1R,5S,6r)-3-(oxetan-3-yl)-3-azabicyclo[3.1.0]hexan-6-yl)-1H-pyrazol-3-yl)-3-(trifluoromethyl)-1H-pyrrolo[2,3-b]pyridine,
5-(1-isopropyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine,
5-(1-cyclopentyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine,
3-chloro-5-(1-cyclopentyl-5-((1R,5S,6r)-3-(oxetan-3-yl)-3-azabicyclo[3.1.0]hexan-6-yl)-1H-pyrazol-3-yl)pyridin-2-amine,
5-(1-cyclopentyl-5-((1R,5S,6r)-3-(oxetan-3-yl)-3-azabicyclo[3.1.0]hexan-6-yl)-1H-pyrazol-3-yl)-3-(difluoromethoxy)pyridin-2-amine,
2-amino-5-(1-cyclopentyl-5-((1R,5S,6r)-3-(oxetan-3-yl)-3-azabicyclo[3.1.0]hexan-6-yl)-1H-pyrazol-3-yl)nicotinonitrile,
5-(1-cyclopentyl-5-((1R,5S,6r)-3-(oxetan-3-yl)-3-azabicyclo[3.1.0]hexan-6-yl)-1H-pyrazol-3-yl)-3-cyclopropylpyridin-2-amine,
3-chloro-5-(1-isopropyl-5-((1R,5S,6r)-3-(oxetan-3-yl)-3-azabicyclo[3.1.0]hexan-6-yl)-1H-pyrazol-3-yl)pyridin-2-amine,
3-(difluoromethoxy)-5-(1-isopropyl-5-((1R,5S,6r)-3-(oxetan-3-yl)-3-azabicyclo[3.1.0]hexan-6-yl)-1H-pyrazol-3-yl)pyridin-2-amine,
3-cyclopropyl-5-(1-isopropyl-5-((1R,5S,6r)-3-(oxetan-3-yl)-3-azabicyclo[3.1.0]hexan-6-yl)-1H-pyrazol-3-yl)pyridin-2-amine, 5-(1-isopropyl-5-((1R,5S,6r)-3-(oxetan-3-yl)-3-azabicyclo[3.1.0]hexan-6-yl)-1H-pyrazol-3-yl)-3,3-dimethyl-2,3-dihydro-1H-pyrrolo[2,3-b]pyridine, 2-amino-5-(1-isopropyl-5-((1R,5S,6r)-3-(oxetan-3-yl)-3-azabicyclo[3.1.0]hexan-6-yl)-1H-pyrazol-3-yl)nicotinonitrile, 5-(1-isopropyl-5-((1R,5S,6r)-3-(oxetan-3-yl)-3-azabicyclo[3.1.0]hexan-6-yl)-1H-pyrazol-3-yl)-3-methoxypyridin-2-amine, 3-isopropoxy-5-(1-isopropyl-5-((1R,5S,6r)-3-(oxetan-3-yl)-3-azabicyclo[3.1.0]hexan-6-yl)-1H-pyrazol-3-yl)pyridin-2-amine, 3-chloro-5-(1-cyclobutyl-5-((1R,5S,6r)-3-(oxetan-3-yl)-3-azabicyclo[3.1.0]hexan-6-yl)-1H-pyrazol-3-yl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-isopropoxypyridin-2-amine, 3-chloro-5-(5-((1R,5S,6r)-3-(oxetan-3-yl)-3-azabicyclo[3.1.0]hexan-6-yl)-1-(2,2,2-trifluoroethyl)-1H-pyrazol-3-yl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-(difluoromethoxy)pyridin-2-amine, 5-(1-(cyclopropylmethyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-cyclopropylpyridin-2-amine, 3-chloro-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-(methylsulfonyl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-isopropoxypyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-methoxypyridin-2-amine, 3-(difluoromethyl)-5-(1-isopropyl-5-((1R,5S,6r)-3-(oxetan-3-yl)-3-azabicyclo[3.1.0]hexan-6-yl)-1H-pyrazol-3-yl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-methoxypyridin-2-amine, 5-(1-(cyclobutylmethyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 3-cyclopropyl-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine, 5-(1-(cyclobutylmethyl)-5-((1R,5S,6r)-3-(oxetan-3-yl)-3-azabicyclo[3.1.0]hexan-6-yl)-1H-pyrazol-3-yl)-3-cyclopropylpyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine, 5-(1-(cyclopropylmethyl)-5-((1R,5S,6r)-3-(oxetan-3-yl)-3-azabicyclo[3.1.0]hexan-6-yl)-1H-pyrazol-3-yl)-3-(difluoromethoxy)pyridin-2-amine, 5-(1-isopropyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine, 5-(1-(tert-butyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(1-cyclopropyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(1-(cyclopropylmethyl)-5-((1R,5S,6r)-3-(oxetan-3-yl)-3-azabicyclo[3.1.0]hexan-6-yl)-1H-pyrazol-3-yl)-3-(difluoromethyl)pyridin-2-amine, 5-(1-cyclopropyl-5-((1R,5S,6r)-3-(oxetan-3-yl)-3-azabicyclo[3.1.0]hexan-6-yl)-1H-pyrazol-3-yl)-3-(difluoromethyl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-(difluoromethyl)pyridin-2-amine, 7-(1-isopropyl-5-((1R,5S,6r)-3-(oxetan-3-yl)-3-azabicyclo[3.1.0]hexan-6-yl)-1H-pyrazol-3-yl)-1H-pyrazolo[4,3-c]pyridin-4-amine, 5-(1-(cyclopropylmethyl)-5-((1R,5S,6r)-3-(oxetan-3-yl)-3-azabicyclo[3.1.0]hexan-6-yl)-1H-pyrazol-3-yl)-3-(difluoromethoxy)pyridin-2-amine, 5-(5-((1R,5S,6r)-3-(oxetan-3-yl)-3-azabicyclo[3.1.0]hexan-6-yl)-1-(2,2,2-trifluoroethyl)-1H-pyrazol-3-yl)-3-(trifluoromethyl)pyridin-2-amine, 3-(1,1-difluoroethyl)-5-(1-isopropyl-5-((1R,5S,6r)-3-(oxetan-3-yl)-3-azabicyclo[3.1.0]hexan-6-yl)-1H-pyrazol-3-yl)pyridin-2-amine, 3-(1,1-difluoroethoxy)-5-(1-isopropyl-5-((1R,5S,6r)-3-(oxetan-3-yl)-3-azabicyclo[3.1.0]hexan-6-yl)-1H-pyrazol-3-yl)pyridin-2-amine, 5-(1-(((1-methylcyclopropyl)methyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(5-((1R,5S,6r)-3-cyclobutyl-3-azabicyclo[3.1.0]hexan-6-yl)-1-cyclopentyl-1H-pyrazol-3-yl)-3-(methylsulfonyl)pyridin-2-amine, 5-(1-isopropyl-5-(3-(oxetan-3-yl)-3-azabicyclo[3.1.1]heptan-6-yl)-1H-pyrazol-3-yl)-3-(trifluoromethyl)pyridin-2-amine, 3-chloro-5-(1-isopropyl-5-(3-(oxetan-3-yl)-3-azabicyclo[3.1.1]heptan-6-yl)-1H-pyrazol-3-yl)pyridin-2-amine, 3-(difluoromethoxy)-5-(1-isopropyl-5-(3-(oxetan-3-yl)-3-azabicyclo[3.1.1]heptan-6-yl)-1H-pyrazol-3-yl)pyridin-2-amine, and 5-(1-isopropyl-5-(3-(oxetan-3-yl)-3-azabicyclo[3.1.1]heptan-6-yl)-1H-pyrazol-3-yl)-3-(trifluoromethoxy)pyridin-2-amine, and pharmaceutically acceptable salts thereof.

30. The method of claim 1, wherein said neurodegenerative disease or condition is selected from the group consisting of: Alzheimer's disease, Parkinson's disease, and amyotrophic lateral sclerosis (ALS).

31. The method of claim 1, wherein the compound of Formula (I) is administered in combination with one or more additional pharmaceutical agents.

32. A method for inhibiting degeneration of a central nervous system (CNS) neuron or a portion thereof, the method comprising administering to the CNS neuron a compound of Formula (I)

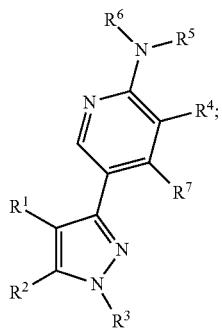

(I)

or a salt thereof;
wherein in Formula (I)
  $R^1$ is selected from the group consisting of hydrogen, —F, —Cl, —Br, —I, —NO$_2$, —CN, $C_{1-12}$ alkyl and $C_{1-12}$ haloalkyl;
  $R^2$ is selected from the group consisting of 3 to 12 membered cycloalkyl, C-linked 3 to 12 membered heterocycloalkyl and —C(R$^{A2}$)(C$_{1-6}$ (halo)alkyl)$_2$, wherein $R^{A2}$ is hydrogen, —F, —Cl, —Br, —I, —CN, —OH, —NH$_2$, —SF$_5$, —OSF$_5$, $C_{1-12}$ alkylthio, $C_{1-12}$ alkoxy, $C_{1-12}$ alkylamino and $C_{1-12}$ dialkylamino; and wherein $R^2$ is optionally substituted 1 to 5 $R^{2-A}$ substituents selected from the group consisting of $C_{1-12}$ alkyl, $C_{1-12}$ haloalkyl, $C_{1-12}$ heteroalkyl, $C_{2-12}$ alkenyl, $C_{2-12}$ alkynyl, —F, —Cl, —Br, —I, —(X$^2$)$_{0-1}$—CN, —(X$^2$)$_{0-1}$—NO$_2$, —(X$^2$)$_{0-1}$—SF$_5$, —(X$^2$)$_{0-1}$—OSF$_5$, —(X$^2$)$_{0-1}$—OR$^{2A}$, —(X$^2$)$_{0-1}$—N(R$^{2A}$)$_2$, —(X$^2$)$_{0-1}$—SR$^{2A}$, —(X$^2$)$_{0-1}$—CF$_3$, 3 to 12 membered cycloalkyl-(X$^2$)$_{0-1}$—, 3 to 12 membered heterocycloalkyl-(X$^2$)$_{0-1}$—, 5 to 6 membered heteroaryl-(X$^2$)$_{0-1}$—, phenyl-(X$^2$)$_{0-1}$—, —(X$^2$)$_{0-1}$—C(=O)N(R$^{2A}$)(R$^{2A}$), —(X$^2$)$_{0-1}$—C(=O)OR$^{2A}$, —(X$^2$)$_{0-1}$—N(R$^{2A}$)C(=O)(R$^{2A}$), —(X$^2$)$_{0-1}$—N(R$^{2A}$)C(=O)OR$^{2A}$, —(X$^2$)$_{0-1}$—S(=O)$_{1-2}$—R$^{2A}$, —(X$^2$)$_{0-1}$—N(R$^{2A}$)S(=O)$_{1-2}$—R$^{2A}$, —(X$^2$)$_{0-1}$—S(=O)$_{1-2}$N(R$^{2A}$)$_2$, —(X$^2$)$_{0-1}$—C(=O)R$^{2A}$, —(X$^2$)$_{0-1}$—C(=NOR$^{2A}$)R$^{2A}$, —(X$^2$)$_{0-1}$—N(R$^{2A}$)C(=O)N(R$^{2A}$)$_2$ and —(X$^2$)$_{0-1}$—OC(=O)R$^{2A}$, —(X$^2$)$_{0-1}$—OP(=O)(OR$^{2A}$)$_2$, —(X$^2$)—SC(=O)OR$^{2A}$ and —(X$^2$)—SC(=O)N(R$^{2A}$)$_2$; wherein X$^2$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, R$^{2A}$ at each occurrence is each independently selected from the group consisting of hydrogen, $C_{1-6}$ alkyl, $C_{1-6}$ haloalkyl, $C_{1-6}$ heteroalkyl, 3-7 membered cycloalkyl, 3-7 membered cycloalkyl-C$_{1-4}$ alkyl, 3-7 membered heterocycloalkyl, 3-7 membered heterocycloalkyl-C$_{1-4}$ alkyl, 5-6 membered heteroaryl, 5-6 membered heteroaryl-C$_{1-4}$ alkyl, phenyl and phenyl-C$_{1-4}$ alkyl, or any two R$^{2A}$ groups attached to the same nitrogen atom are optionally combined to form a 3 to 6 membered heterocyclic ring comprising 1 to 2 additional heteroatom selected from N, O and S; and wherein a R$^{2-A}$ substituent at each occurrence is independently optionally further substituted with 1 to 5 R$^{2A-1}$ substituents selected from the group consisting of —F, —Cl, —Br, —I, —OH, —CN, —NO$_2$, —SF$_5$, —NH$_2$, $C_{1-6}$ alkoxy, $C_{1-6}$ alkylamino, $C_{1-6}$ dialkylamino;
  $R^3$ is selected from the group consisting of $C_{1-12}$ alkyl-, $C_{1-12}$ haloalkyl-, $C_{1-12}$ heteroalkyl-(L)$_{0-1}$-, $C_{2-12}$ alkenyl-(L)$_{0-1}$-, $C_{2-12}$ alkynyl-(L)$_{0-1}$-, 3 to 12 membered cycloalkyl-(L)$_{0-1}$-, 3 to 12 membered heterocycloalkyl-(L)$_{0-1}$-, wherein L is selected from the group consisting of $C_{1-4}$ alkylene, $C_{1-4}$ haloalkylene, $C_{1-4}$ heteroalkylene, $C_{2-4}$ alkenylene, $C_{2-4}$ alkynylene, —C(=O)—, —C(=O)—N(H)—, —C(=O)N(C$_{1-6}$ alkyl)-, —C(=O)O—, —S(O)$_{1-2}$— and —S(O)$_{1-2}$—N(H)—; wherein a $R^3$ group is optionally further substituted with 1 to 5 R$^{3A}$ substituents selected from the group consisting of —F, —Cl, —Br, —I, —OH, —CN, —NO$_2$, —SF$_5$, —OSF$_5$, —NH$_2$, $C_{1-6}$ alkyl, $C_{1-6}$ haloalkyl, 3 to 5 membered cycloalkyl, 3 to 5 membered heterocycloalkyl, $C_{1-6}$ alkoxy, $C_{1-6}$ alkylthio, $C_{1-6}$ alkylamino and $C_{1-6}$ dialkylamino;
  $R^4$ is selected from the group consisting of $C_{1-12}$ alkyl, $C_{1-12}$ haloalkyl, $C_{2-12}$ alkenyl, $C_{2-12}$ alkynyl, —F, —Cl, —Br, —I, —(X$^4$)$_{0-1}$—CN, —(X$^4$)$_{0-1}$—NO$_2$, —(X$^4$)$_{0-1}$—SF$_5$, —(X$^4$)$_{0-1}$—OSF$_5$, —(X$^4$)$_{0-1}$—OR$^{4A}$, —(X$^4$)$_{0-1}$—N(R$^{4A}$)$_2$, —(X$^4$)$_{0-1}$—SR$^{4A}$, —(X$^4$)$_{0-1}$—CF$_3$, 3 to 7 membered cycloalkyl-(X$^4$)$_{0-1}$—, 3 to 7 membered heterocycloalkyl-(X$^4$)$_{0-1}$—, 5 to 6 membered heteroaryl-(X$^4$)$_{0-1}$—, phenyl-(X$^4$)$_{0-1}$—, —(X$^4$)$_{0-1}$—C(=O)N(R$^{4A}$)(R$^{4A}$), —(X$^4$)$_{0-1}$—C(=O)OR$^{4A}$, —(X$^4$)$_{0-1}$—N(R$^{4A}$)C(=O)(R$^{4A}$), —(X$^4$)$_{0-1}$—N(R$^{4A}$)C(=O) OR$^{4A}$, —(X$^4$)$_{0-1}$—S(=O)$_{1-2}$—R$^{4A}$, —(X$^4$)$_{0-1}$—N(R$^{4A}$)S(=O)$_{1-2}$—R$^{4A}$, —(X$^4$)$_{0-1}$—S(=O)$_{1-2}$—N(R$^{4A}$)$_2$, —(X$^4$)$_{0-1}$—C(=O)R$^{4A}$, —(X$^4$)$_{0-1}$—C(=NOR$^{4A}$)R$^{4A}$, —(X$^4$)$_{0-1}$—N(R$^{4A}$)C(=O)N(R$^{4A}$)$_2$, —(X$^4$)$_{0-1}$—OC(=O)R$^{4A}$, —(X$^4$)$_{0-1}$—OP(=O)(OR$^{4A}$)$_2$, —(X$^4$)—SC(=O)OR$^{4A}$ and —(X$^4$)—SC(=O)N(R$^{4A}$)$_2$, X$^4$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, R$^{4A}$ at each occurrence is each independently selected from the group consisting of hydrogen, $C_{1-6}$ alkyl, $C_{1-6}$ haloalkyl and $C_{1-6}$ heteroalkyl, or any two R$^{4A}$ groups attached to the same nitrogen atom are optionally combined to form a 3 to 6 membered heterocyclic ring comprising 1 to 2 additional heteroatom selected from N, O and S; and wherein a $R^4$ group is independently optionally further substituted with 1 to 5 R$^{4A-1}$ substituents selected from the group consisting of —F, —Cl, —Br, —I, —OH, —CN, —NO$_2$, —SF$_5$, —NH$_2$, $C_{1-6}$ alkoxy, $C_{1-6}$ alkylamino and $C_{1-6}$ dialkylamino;
  $R^5$ and $R^6$ are each independently selected from the group consisting of hydrogen, $C_{1-12}$ alkyl, and $C_{1-12}$ haloalkyl; and
  in the alternative $R^4$ and $R^5$ are combined to form a 5 to 7 membered heteroaryl or 5 to 7 membered heterocycloalkyl ring optionally comprising 1 additional heteroatom selected from N, O and S, and wherein said 5 to 7 membered heteroaryl or 5 to 7 membered heterocycloalkyl ring is further optionally substituted with 1 to 3 R$^{4/5cy}$ substituents selected from the group consisting of $C_{1-12}$ alkyl, $C_{1-12}$ haloalkyl, $C_{2-12}$ alkenyl, $C_{2-12}$ alkynyl, —F, —Cl, —Br, —I, —(X$^{4/5}$)$_{0-1}$—CN, —(X$^{4/5}$)$_{0-1}$—NO$_2$, —(X$^{4/5}$)$_{0-1}$—SF$_5$, —(X$^{4/5}$)$_{0-1}$—OSF$_5$, —(X$^{4/5}$)$_{0-1}$—OR$^{45A}$, —(X$^{4/5}$)$_{0-1}$—N(R$^{45A}$)$_2$, —(X$^{4/5}$)$_{0-1}$—SR$^{45A}$, —(X$^{4/5}$)$_{0-1}$—CF$_3$, 3 to 12 membered cycloalkyl-(X$^{4/5}$)$_{0-1}$—, 3 to 12 membered heterocycloalkyl-(X$^{4/5}$)$_{0-1}$—, 5 to 6 membered heteroaryl-(X$^{4/5}$)$_{0-1}$—, phenyl-(X$^{4/5}$)$_{0-1}$—, —(X$^{4/5}$)$_{0-1}$—C(=O)N(R$^{45A}$)(R$^{45A}$), —(X$^{4/5}$)$_{0-1}$—C(=O)OR$^{45A}$, —(X$^{4/5}$)$_{0-1}$—N(R$^{45A}$)C(=O)(R$^{45A}$), —(X$^{4/5}$)$_{0-1}$—N(R$^{45A}$)C(=O)OR$^{45A}$, —(X$^{4/5}$)$_{0-1}$—S(=O)$_{1-2}$—R$^{45A}$, —(X$^{4/5}$)$_{0-1}$—N(R$^{45A}$)S(=O)$_{1-2}$—R$^{45A}$, —(X$^{4/5}$)$_{0-1}$—S(=O)$_{1-2}$N(R$^{45A}$)$_2$, —(X$^{4/5}$)$_{0-1}$—C(=O)R$^{45A}$, —(X$^{4/5}$)$_{0-1}$—C(=NOR$^{45A}$)R$^{45A}$, —(X$^{4/5}$)$_{0-1}$—N ($R^{45A}$)C(=O)N($R^{45A}$)$_2$ and —($X^{4/5}$)$_{0-1}$—OC(=O)$R^{45A}$, —($X^{4/5}$)$_{0-1}$—OP(=O)(O$R^{45A}$)$_2$, —($X^{4/5}$)—SC(=O)O$R^{45A}$ and —($X^{4/5}$)—SC(=O)N($R^{45A}$)$_2$, $X^{4/5}$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{45A}$ at each occurrence is each independently selected from the group consisting of hydrogen, $C_{1-6}$ alkyl, $C_{1-6}$ haloalkyl and $C_{1-6}$ heteroalkyl; or any two $R^{45A}$ groups attached to the same nitrogen atom are optionally combined to form a 3 to 6 membered heterocyclic ring comprising 1 to 2 additional heteroatom selected from N, O and S; and wherein a $R^{4/5cy}$ substituent at each occurrence is independently optionally further substituted with 1 to 5 $R^{4/5cy-1}$ substituents selected from the group consisting of —F, —Cl, —Br, —I, —OH, —CN, —NO$_2$, —SF$_5$, —NH$_2$, $C_{1-6}$ alkoxy, $C_{1-6}$ alkylamino and $C_{1-6}$ dialkylamino; and $R^7$ is hydrogen, or in the alternative $R^4$ and $R^7$ are optionally combined to form a 5 to 7 membered heteroaryl or 5 to 7 membered heterocycloalkyl ring optionally comprising 1 additional heteroatom selected from N, O and S.

33. The method of claim 32, wherein $R^5$ and $R^6$ are each H.

34. The method of claim 32, wherein $R^4$ is selected from the group consisting of $C_{1-12}$ alkyl, $C_{1-12}$ haloalkyl, —F, —Cl, —($X^4$)$_{0-1}$—CN, —($X^4$)$_{0-1}$—O$R^{4A}$, —($X^4$)$_{0-1}$—S$R^{4A}$, 3 to 7 membered cycloalkyl-($X^4$)$_{0-1}$—, —($X^4$)$_{0-1}$—S(=O)$_{1-2}$—$R^{4A}$ and is further optionally substituted.

35. The method of claim 32, wherein $R^4$ is selected from the group consisting of —F, —Cl, $C_{1-4}$ alkyl, $C_{1-4}$ haloalkyl, —($C_{1-4}$ alkylene)$_{0-1}$-CN, $C_{1-4}$ alkyloxy, $C_{1-4}$ haloalkyloxy, $C_{1-4}$ alkylthio, $C_{1-4}$ haloalkylthio, 3 to 5 membered cycloalkyl-($C_{1-4}$ alkyloxy)-, 3 to 6 membered cycloalkyl, and ($C_{1-4}$ alkyl)-S(O)$_2$—, wherein $R^4$ is further optionally substituted.

36. The method of claim 32, wherein $R^4$ is selected from the group consisting of —F, Cl, —CN, methyl, monofluoromethyl, difluoromethyl, trifluoromethyl, ethyl, 2-fluoroeth-1-yl, 1-fluoroeth-1-yl, 2,2-difluoroeth-1-yl, 1,2-difluoroeth-1-yl, 1,1-difluoroeth-1-yl, 2,2,2-trifluoroeth-1-yl, 1,2,2-trifluoroeth-1-yl, 1,1,2-trifluoroeth-1-yl, methoxy, monofluoromethoxy, difluoromethoxy, trifluoromethoxy, 2-fluoroethan-1-oxy, 2,2-difluoroethan-1oxy, 1,2-difluoroethan-1-oxy, 1,1-difluoroethan-1-oxy, 2,2,2-trifluoroethan-1-oxy, 1,2,2-trifluoroethan-1-oxy, 1,1,2-trifluoroethan-1-oxy, isopropoxy, 1-fluoro-propan-2-oxy, 1,1-difluoro-propan-2-oxy, 1,3-difluoro-propan-2-oxy, 1,1,1-trifluoro-propan-2-oxy, 1,1,3-trifluoro-propan-2-oxy, 1,1,1,3,3,3-hexafluoro-propan-2-oxy, monofluoromethylthio, difluoromethylthio, trifluromethylthio, cyclopropylmethoxy and cyclopropyl.

37. The method of claim 32, wherein $R^6$ is H; and $R^4$ and $R^5$ are combined to form a 5 to 7 membered ring selected from the group consisting of pyrrole, imidazole, pyrazole, pyrrolidone, pyrrolidine, morpholine, piperdine and piperazine, wherein $R^4$ and $R^5$ combined are optionally substituted with 1 to 3 $R^{4/5cy}$ substituents.

38. The method of claim 32, wherein $R^{4/5cy}$ is selected from the group consisting of $C_{1-12}$ alkyl, $C_{1-12}$ haloalkyl, —F, —Cl, —($X^{4/5}$)$_{0-1}$—CN, —($X^{4/5}$)$_{0-1}$—O$R^{45A}$, 3 to 7 membered cycloalkyl-($X^{4/5}$)$_{0-1}$—, —($X^{4/5}$)$_{0-1}$—S(=O)$_{1-2}$—$R^{45A}$, wherein $R^{4/5cy}$ is optionally substituted with 1 to 3 $R^{4/5cy-1}$ substituents.

39. The method of claim 32, wherein $R^{4/5cy}$ is selected from the group consisting of —F, —Cl, $C_{1-4}$ alkyl, $C_{1-4}$ haloalkyl, —($C_{1-4}$ alkylene)$_{0-1}$-CN, $C_{1-4}$ alkyloxy, $C_{1-4}$ haloalkyloxy, $C_{1-4}$ alkylthio, $C_{1-4}$ haloalkylthio, 3-6 membered cycloalkyl-($C_{1-4}$ alkyloxy)-, 3 to 6 membered cycloalkyl, and ($C_{1-4}$ alkyl)-S(O)$_2$—, wherein $R^{4/5cy}$ is optionally substituted with 1 to 5 $R^{4/5cy-1}$ substituents.

40. The method of claim 32, wherein $R^{4/5cy}$ is selected from the group consisting of —F, Cl, —CN, methyl, monofluoromethyl, difluoromethyl, trifluoromethyl, ethyl, 2-fluoroeth-1-yl, 1-fluoroeth-1-yl, 2,2-difluoroeth-1-yl, 1,2-difluoroeth-1-yl, 1,1-difluoroeth-1-yl, 2,2,2-trifluoroeth-1-yl, 1,2,2-trifluoroeth-1-yl, 1,1,2-trifluoroeth-1-yl, methoxy, monofluoromethoxy, difluoromethoxy, trifluoromethoxy, 2-fluoroethan-1-oxy, 2,2-difluoroethan-1oxy, 1,2-difluoroethan-1-oxy, 1,1-difluoroethan-1-oxy, 2,2,2-trifluoroethan-1-oxy, 1,2,2-trifluoroethan-1-oxy, 1,1,2-trifluoroethan-1-oxy, isopropoxy, 1-fluoro-propan-2-oxy, 1,1-difluoro-propan-2-oxy, 1,3-difluoro-propan-2-oxy, 1,1,1-trifluoro-propan-2-oxy, 1,1,3-trifluoro-propan-2-oxy, 1,1,1,3,3,3-hexafluoro-propan-2-oxy, monofluoromethylthio, difluoromethylthio, trifluroromethylthio, cyclopropylmethoxy and cyclopropyl.

41. The method of claim 32, wherein $R^1$ is selected from the group consisting of hydrogen, $C_{1-4}$ alkyl and $C_{1-4}$ haloalkyl.

42. The method of claim 32, wherein $R^1$ is hydrogen, monofluoromethyl, difluoromethyl, trifluormethyl and methyl.

43. The method of claim 32, wherein $R^1$ is hydrogen.

44. The method of claim 32, wherein $R^2$ is a fused or bridged 3 to 12 membered cycloalkyl or a fused or bridged bicyclic or tricyclic C-linked 3 to 12 membered heterocycloalkyl ring, wherein $R^2$ is optionally substituted with 1-5 $R^{2-A}$ substituents.

45. The method of claim 32, wherein $R^2$ is selected from the group consisting of 3-azabicyclo[3.1.0]hexane, 3-azabicyclo[3.2.1]octane, 3-azabicyclo[3.1.1]heptane, 1,1a,5,5a-tetrahydro-4a-aza-cyclopropa[a]pentalene, 1,1a,5,5a-tetrahydro-2,4a-diaza-cyclopropa[a]pentalene, 1,1a,5,5a-tetrahydro-3,4a-diaza-cyclopropa[a]pentalene, 1,1a,5,5a-tetrahydro-2,3,4a-triaza-cyclopropa[a]pentalene, 1,1a,5,5a-tetrahydro-4,4a-diaza-cyclopropa[a]pentalene, octahydro-4a-aza-cyclopropa[a]pentalene, 3-oxabicyclo[3.2.1]octane, 3-oxabicyclo[3.1.1]heptane and 3-oxabicyclo[3.1.0]hexane, and wherein $R^2$ is optionally substituted with 1 to 5 $R^{2-A}$ substituents.

46. The method of claim 32, wherein $R^2$ is selected from the group consisting of

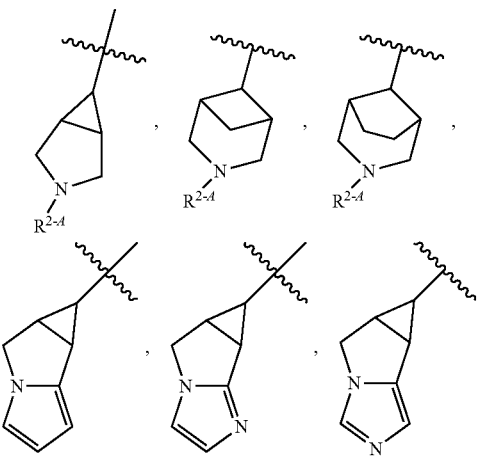

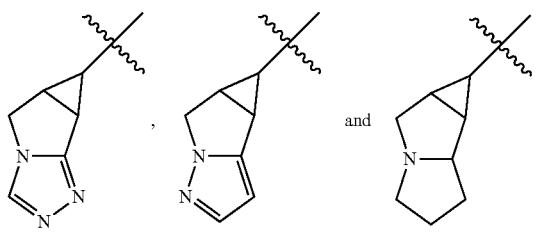

47. The method of claim 32, wherein R² is selected from the group consisting of

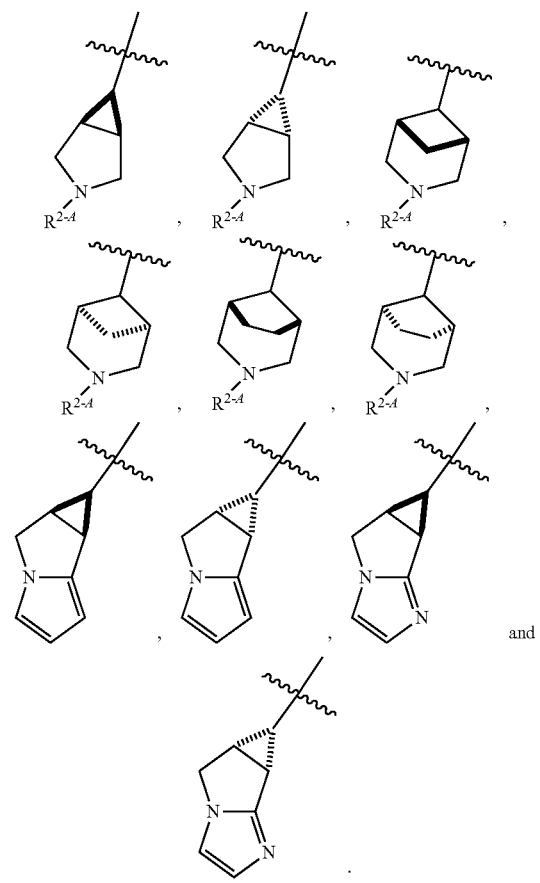

48. The method of claim 32, wherein R² is a monocyclic ring, wherein R² is optionally substituted with 1 to 5 R²⁻ᴬ substituents.

49. The method of claim 32, wherein R² is a monocyclic ring selected from the group consisting of azetidine, pyrrolidine, pyrrolidone, piperidine, piperidone, azepane, azepanone, tetrahydrofuran, tetrahydrofuranone, tetrahydropyan, tetrahydropyanone, oxetane, oxetanone, oxepane and oxepanone, wherein R² is optionally substituted with 1 to 5 R²⁻ᴬ substituents and wherein R²⁻ᴬ is further optionally substituted.

50. The method of claim 32, wherein R² is selected from the group consisting of

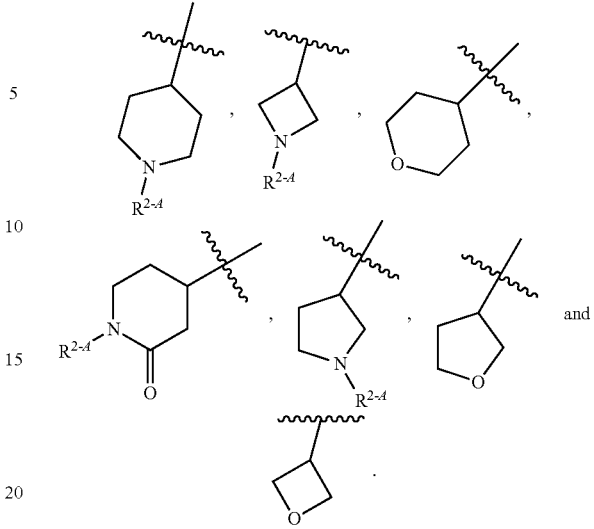

51. The method of claim 32, wherein R²⁻ᴬ is selected from the group consisting of $C_{1-12}$ alkyl, $C_{1-12}$ haloalkyl, $C_{1-12}$ heteroalkyl, —(X²)$_{0-1}$—CN, —(X²)$_{0-1}$—OR²ᴬ, 3 to 12 membered cycloalkyl-(X²)$_{0-1}$—, 3 to 12 membered heterocycloalkyl-(X²)$_{0-1}$—, —(X²)$_{0-1}$—S(=O)$_{1-2}$—R²ᴬ and —(X²)$_{0-1}$—C(=O)R²ᴬ, wherein R²⁻ᴬ is optionally substituted.

52. The method of claim 32, wherein R²⁻ᴬ is selected from the group consisting of OH, ($C_{1-6}$ alkyl)-C(=O)—, ($C_{1-6}$ alkyl)-S(=O)₂—, oxepane, azetidine, $C_{1-6}$ alkyl, $C_{1-6}$ haloalkyl, $C_{1-6}$ heteroalkyl and —($C_{1-6}$ alkyl)-CN, wherein R²⁻ᴬ is optionally substituted.

53. The method of claim 32, wherein R²⁻ᴬ is selected from the group consisting of CH₃—C(=O)—, oxetanyl, methyl, monofluoromethyl, difluoromethyl, trifluoromethyl, ethyl, 2-fluoroeth-1-yl, 1-fluoroeth-1-yl, 1,2-difluoroeth-1-yl, 2,2-difluoroeth-1-yl, 1,1,2-trifluoroeth-1-yl 2,2,2-trifluoroeth-1-yl, 1,2,2-trifluoroeth-1-yl, cyanomethyl, cyanoethyl, methoxyethyl, hydroxy, (CH₃)₂(OH)CC(H)₂—, CH₃OCH₂C(H)(CH₃)—, CH₃OC(CH₃)₂CH₂—, NCC(H)(CH₃)CH₂—, NCC(H)(CH₃)₂CH₂—, CH₃OC(H)(CH₃)CH₂—, NCCH₂C(H)(CH₃)—, NCCCH₂C(CH₃)₂—, CH₃—S(O)₂— and isopropyl-OC(=O)—.

54. The method of claim 32, wherein R² is —C(R⁴²)(C$_{1-6}$ alkyl)₂, wherein R⁴² is hydrogen, —F, —Cl, —Br, —I, —CN, —OH, —NH₂, —SF₅, —OSF₅, $C_{1-4}$ alkylthio, $C_{1-4}$ alkoxy, $C_{1-4}$ alkylamino and $C_{1-4}$ dialkylamino and wherein R² is optionally substituted with 1 to 5 R²⁻ᴬ substituents.

55. The method of claim 32, wherein R³ is selected from the group consisting of $C_{1-6}$ alkyl, 3 to 6 membered cycloalkyl-$C_{1-4}$ alkyl, 3 to 6 membered cycloalkyl, 3 to 6 membered heterocycloalkyl-$C_{1-4}$ alkyl, and 3-6 membered heterocycloalkyl, wherein R³ is optionally substituted with R³ᴬ.

56. The method of claim 32, wherein R³ is selected from the group consisting of methyl, monofluoromethyl, difluoromethyl, ethyl, 1,1,1-trifluoroeth-2-yl, propyl, isopropyl, butyl, sec-butyl, tert-butyl, cyclopropyl, cyclopropylmethyl, cyclobutyl, cyclobutylmethyl, cyclopentyl, cyclopentylmethyl, cyclohexyl, cyclohexylmethyl, 1,1-difluorocyclobut-3-yl, 1,1-difluorocyclopent-3-yl, oxetan-2-yl, oxetan-2-yl-methyl, oxetan-3-yl, oxetan-3-yl-methyl, tetrahydrofuran-3-yl, tetrahydrofuran-3-yl-methyl, tetrahydropyran-3-yl, tetrahydropyran-3-yl-methyl, tetrahydropyran-4-yl, tetrahydropyran-4-yl-methyl, azetindin-3-yl, azetindin-3-yl-methyl, pyrrolidin-3-yl, pyrrolidin-3-yl-methyl, piperidin-4yl, piperidin-4-yl-methyl, piperidin-3-yl and piperidin-3-yl-methyl.

57. The method of claim 32, wherein said compound has a formula selected from the group consisting of:

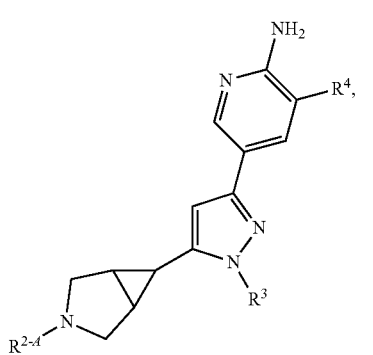
(II-a)

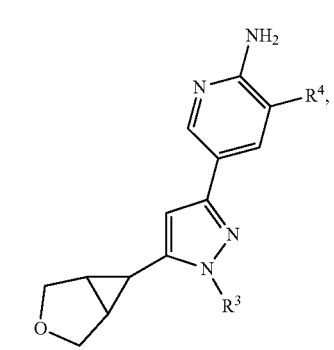
(II-b)

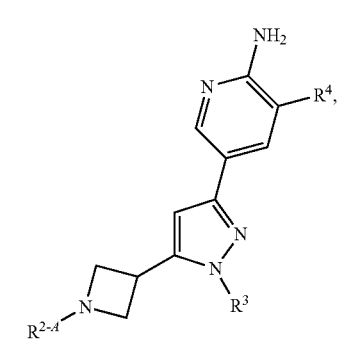
(II-c)

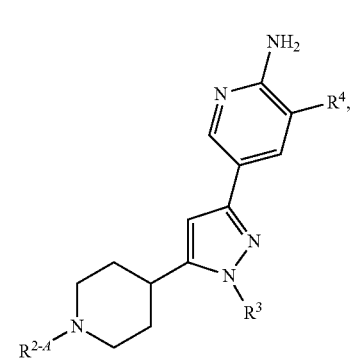
(II-d)

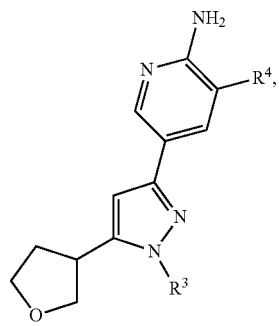
(II-e)

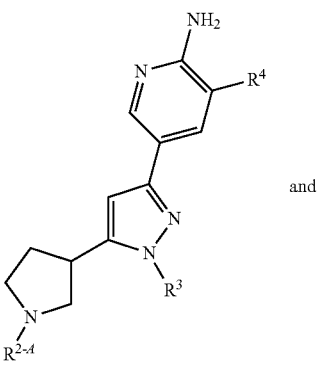
and
(II-f)

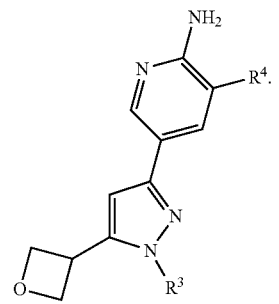
(II-g)

58. The method of claim 32, wherein said compound has the formula selected from the group consisting of (III-a)

-continued

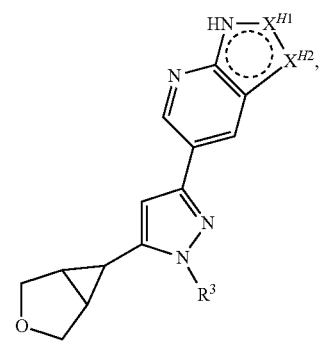
(III-b)

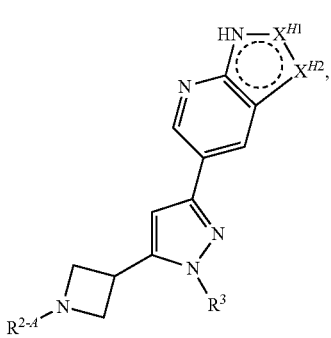
(III-c)

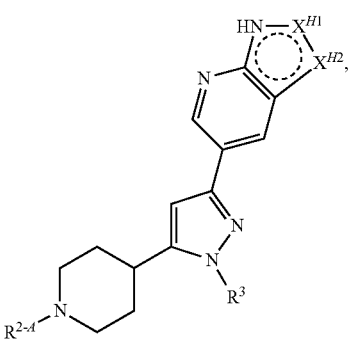
(III-d)

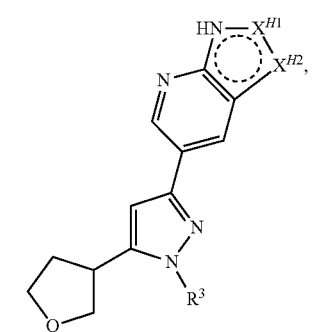
(III-e)

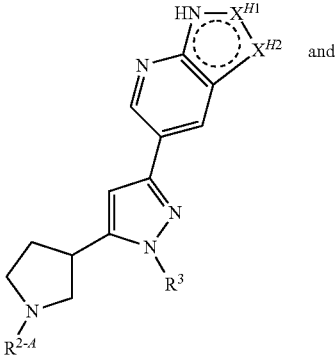
(III-f)

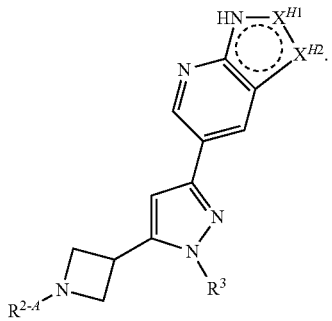
(III-g)

wherein in formula III-a, III-b, III-c, III-d, III-e, III-f and III-g, $X^{H1}$ and $X^{H2}$ at each occurrence is independently selected from the group consisting of N, NH, N($R^{4/5cy}$), CH or C($R^{4/5cy}$).

59. The method of claim 58, wherein $X^{H1}$ and $X^{H2}$ are independently CH or C($R^{4/5cy}$).

60. The method of claim 32, wherein said compound of Formula (I) is selected from the group consisting of
5-(5-isopropyl-1-(1-(oxetan-3-yl)azetidin-3-yl)-1H-pyrazol-3-yl)-3-(trifluoromethyl)-1H-pyrrolo[2,3-b]pyridine,
2-(3-(6-amino-5-(trifluoromethyl)pyridin-3-yl)-1-isopropyl-1H-pyrazol-5-yl)propan-2-ol,
2-(3-(6-amino-5-(difluoromethoxy)pyridin-3-yl)-1-isopropyl-1H-pyrazol-5-yl)propan-2-ol,
2-(3-(6-amino-5-(trifluoromethyl)pyridin-3-yl)-1-isopropyl-1H-pyrazol-5-yl)-2-methylpropanenitrile,
2-(3-(6-amino-5-(difluoromethyl)pyridin-3-yl)-1-isopropyl-1H-pyrazol-5-yl)-2-methylpropanenitrile,
2-(3-(6-amino-5-(trifluoromethoxy)pyridin-3-yl)-1-isopropyl-1H-pyrazol-5-yl)-2-methylpropanenitrile,
5-(1-isopropyl-5-(1-methylazetidin-3-yl)-1H-pyrazol-3-yl)-3-(trifluoromethyl)pyridin-2-amine,
1-(3-(1-(cyclopropylmethyl)-3-(3-(trifluoromethyl)-1H-pyrrolo[2,3-b]pyridin-5-yl)-1H-pyrazol-5-yl)azetidin-1-yl)ethanone,
1-(3-(1-(cyclopropylmethyl)-3-(3-methyl-1H-pyrrolo[2,3-b]pyridin-5-yl)-1H-pyrazol-5-yl)azetidin-1-yl)ethanone,
1-(3-(1-isopropyl-3-(3-(trifluoromethyl)-1H-pyrrolo[2,3-b]pyridin-5-yl)-1H-pyrazol-5-yl)azetidin-1-yl)ethanone,
1-(3-(1-methyl-3-(3-(trifluoromethyl)-1H-pyrrolo[2,3-b]pyridin-5-yl)-1H-pyrazol-5-yl)azetidin-1-yl)ethanone,
1-(3-(1-isopropyl-3-(3-methyl-1H-pyrrolo[2,3-b]pyridin-5-yl)-H-pyrazol-5-yl)azetidin-1-yl)ethanone, racemic-5-(1-(cyclopropylmethyl)-5-(tetrahydrofuran-3-yl)-1H-pyrazol-3-yl)-3-methyl-1H-pyrrolo[2,3-b]pyridine,
5-(1-(3,3-difluorocyclopentyl)-5-(tetrahydrofuran-3-yl)-1H-pyrazol-3-yl)-3-methyl-1H-pyrrolo[2,3-b]pyridine,
5-(1,5-bis(tetrahydrofuran-3-yl)-1H-pyrazol-3-yl)-3-(trifluoromethyl)-1H-pyrrolo[2,3-b]pyridine
5-(1-(3,3-difluorocyclopentyl)-5-(tetrahydrofuran-3-yl)-1H-pyrazol-3-yl)-3-(trifluoromethyl)-1H-pyrrolo[2,3-b]pyridine,
(R)-5-(1-(cyclopropylmethyl)-5-(tetrahydrofuran-3-yl)-1H-pyrazol-3-yl)-3-methyl-1H-pyrrolo[2,3-b]pyridine,
(S)-5-(1-(cyclopropylmethyl)-5-(tetrahydrofuran-3-yl)-1H-pyrazol-3-yl)-3-methyl-1H-pyrrolo[2,3-b]pyridine,
5-(1-(3,3-difluorocyclobutyl)-5-(tetrahydrofuran-3-yl)-1H-pyrazol-3-yl)-3-methyl-1H-pyrrolo[2,3-b]pyridine,
5-(1-(3,3-difluorocyclobutyl)-5-(tetrahydrofuran-3-yl)-1H-pyrazol-3-yl)-3-ethyl-1H-pyrrolo[2,3-b]pyridine,
5-(1,5-bis(tetrahydrofuran-3-yl)-1H-pyrazol-3-yl)-3-chloropyridin-2-amine,
5-(1,5-bis(tetrahydrofuran-3-yl)-1H-pyrazol-3-yl)-3-fluoropyridin-2-amine,
3-chloro-5-(1-(3,3-difluorocyclopentyl)-5-(tetrahydrofuran-3-yl)-1H-pyrazol-3-yl)pyridin-2-amine,
5-(1-(3,3-difluorocyclopentyl)-5-(tetrahydrofuran-3-yl)-1H-pyrazol-3-yl)-3-fluoropyridin-2-amine,
3-chloro-5-(1-(3,3-difluorocyclobutyl)-5-(tetrahydrofuran-3-yl)-1H-pyrazol-3-yl)pyridin-2-amine,
5-(1-((R)-tetrahydrofuran-3-yl)-5-((S)-tetrahydrofuran-3-yl)-1H-pyrazol-3-yl)-3-(trifluoromethyl)-1H-pyrrolo[2,3-b]pyridine,
5-(1-((R)-3,3-difluorocyclopentyl)-5-((R)-tetrahydrofuran-3-yl)-1H-pyrazol-3-yl)-3-methyl-1H-pyrrolo[2,3-b]pyridine,
5-(5-((R)-tetrahydrofuran-3-yl)-1-((S)-tetrahydrofuran-3-yl)-1H-pyrazol-3-yl)-3-(trifluoromethyl)-1H-pyrrolo[2,3-b]pyridine,
5-(1,5-bis((S)-tetrahydrofuran-3-yl)-1H-pyrazol-3-yl)-3-(trifluoromethyl)-1H-pyrrolo[2,3-b]pyridine,
5-(1,5-bis((R)-tetrahydrofuran-3-yl)-1H-pyrazol-3-yl)-3-(trifluoromethyl)-1H-pyrrolo[2,3-b]pyridine,
5-(1-((S)-3,3-difluorocyclopentyl)-5-((S)-tetrahydrofuran-3-yl)-1H-pyrazol-3-yl)-3-methyl-1H-pyrrolo[2,3-b]pyridine,
5-(1-((R)-3,3-difluorocyclopentyl)-5-((S)-tetrahydrofuran-3-yl)-1H-pyrazol-3-yl)-3-methyl-1H-pyrrolo[2,3-b]pyridine,
5-(1-((S)-3,3-difluorocyclopentyl)-5-((R)-tetrahydrofuran-3-yl)-1H-pyrazol-3-yl)-3-methyl-1H-pyrrolo[2,3-b]pyridine,
1-(3-(6-amino-5-(trifluoromethyl)pyridin-3-yl)-1-isopropyl-1H-pyrazol-5-yl)cyclopentanol,
5-(1-(3,3-difluorocyclobutyl)-5-(tetrahydro-2H-pyran-4-yl)-1H-pyrazol-3-yl)-3-methyl-1H-pyrrolo[2,3-b]pyridine,
5-(1-(3,3-difluorocyclobutyl)-5-(tetrahydro-2H-pyran-4-yl)-1H-pyrazol-3-yl)-3-ethyl-1H-pyrazolo[3,4-b]pyridine,
5-(1-(3,3-difluorocyclobutyl)-5-(tetrahydro-2H-pyran-4-yl)-1H-pyrazol-3-yl)-3-fluoropyridin-2-amine,
5-(1-(3,3-difluorocyclobutyl)-5-(tetrahydro-2H-pyran-4-yl)-1H-pyrazol-3-yl)-3-(trifluoromethyl)-1H-pyrrolo[2,3-b]pyridine,
3-chloro-5-(1-(3,3-difluorocyclobutyl)-5-(tetrahydro-2H-pyran-4-yl)-1H-pyrazol-3-yl)pyridin-2-amine,
5-(1-isopropyl-5-(1-methylpiperidin-4-yl)-1H-pyrazol-3-yl)-3-(trifluoromethyl)-1H-pyrrolo[2,3-b]pyridine,
5-(1-isopropyl-5-(1-methylpiperidin-4-yl)-1H-pyrazol-3-yl)-3-(trifluoromethyl)pyridin-2-amine,
4-(1-(3,3-difluorocyclobutyl)-3-(3-methyl-1H-pyrrolo[2,3-b]pyridin-5-yl)-1H-pyrazol-5-yl)-1-methylpiperidin-2-one,
4-(3-(6-amino-5-chloropyridin-3-yl)-1-(3,3-difluorocyclobutyl)-1H-pyrazol-5-yl)-1-methylpiperidin-2-one,
4-(3-(6-amino-5-fluoropyridin-3-yl)-1-(3,3-difluorocyclobutyl)-1H-pyrazol-5-yl)-1-methylpiperidin-2-one,
4-(1-(3,3-difluorocyclobutyl)-3-(3-(trifluoromethyl)-1H-pyrrolo[2,3-b]pyridin-5-yl)-1H-pyrazol-5-yl)-1-methylpiperidin-2-one,
5-(1-isopropyl-5-(1-(2,2,2-trifluoroethyl)piperidin-4-yl)-1H-pyrazol-3-yl)-1H-pyrrolo[2,3-b]pyridine-3-carbonitrile,
1-(4-(1-methyl-3-(3-methyl-1H-pyrrolo[2,3-b]pyridin-5-yl)-1H-pyrazol-5-yl)piperidin-1-yl)ethanone,
1-(4-(1-methyl-3-(3-(trifluoromethyl)-1H-pyrrolo[2,3-b]pyridin-5-yl)-1H-pyrazol-5-yl)piperidin-1-yl)ethanone,
1-(4-(1-isopropyl-3-(3-methyl-1H-pyrrolo[2,3-b]pyridin-5-yl)-1H-pyrazol-5-yl)piperidin-1-yl)ethanone,
1-(4-(1-isopropyl-3-(3-(trifluoromethyl)-1H-pyrrolo[2,3-b]pyridin-5-yl)-1H-pyrazol-5-yl)piperidin-1-yl)ethanone,
2-(4-(1-isopropyl-3-(3-(trifluoromethyl)-1H-pyrrolo[2,3-b]pyridin-5-yl)-1H-pyrazol-5-yl)piperidin-1-yl)acetonitrile,
2-(4-(3-(6-amino-5-(trifluoromethyl)pyridin-3-yl)-1-isopropyl-1H-pyrazol-5-yl)piperidin-1-yl)acetonitrile,
5-(1-isopropyl-5-(1-(2-methoxyethyl)piperidin-4-yl)-1H-pyrazol-3-yl)-3-(trifluoromethyl)pyridin-2-amine,
5-(1-isopropyl-5-(1-(oxetan-3-yl)azetidin-3-yl)-1H-pyrazol-3-yl)-3-(trifluoromethyl)-1H-pyrrolo[2,3-b]pyridine,
5-(5-(1-(oxetan-3-yl)azetidin-3-yl)-1-(tetrahydrofuran-3-yl)-1H-pyrazol-3-yl)-3-(trifluoromethyl)-1H-pyrrolo[2,3-b]pyridine,
5-(1-(3,3-difluorocyclopentyl)-5-(1-(oxetan-3-yl)azetidin-3-yl)-1H-pyrazol-3-yl)-3-(trifluoromethyl)-1H-pyrrolo[2,3-b]pyridine,
3-chloro-5-(1-isopropyl-5-(1-(oxetan-3-yl)azetidin-3-yl)-1H-pyrazol-3-yl)-1H-pyrrolo[2,3-b]pyridine,
3-fluoro-5-(1-isopropyl-5-(1-(oxetan-3-yl)azetidin-3-yl)-1H-pyrazol-3-yl)-1H-pyrrolo[2,3-b]pyridine,
5-(1-isopropyl-5-(1-(oxetan-3-yl)azetidin-3-yl)-1H-pyrazol-3-yl)-1H-pyrrolo[2,3-b]pyridine-3-carbonitrile,
5-(1-isopropyl-5-(1-(oxetan-3-yl)azetidin-3-yl)-1H-pyrazol-3-yl)-3-(trifluoromethyl)pyridin-2-amine,
5-(1-isopropyl-5-(1-(oxetan-3-yl)azetidin-3-yl)-H-pyrazol-3-yl)-3,3-dimethyl-1H-pyrrolo[2,3-b]pyridin-2(3H)-one,
6-(1-isopropyl-5-(1-(oxetan-3-yl)azetidin-3-yl)-1H-pyrazol-3-yl)-3H-imidazo[4,5-b]pyridine,
3-methyl-5-(1-methyl-5-(1-(oxetan-3-yl)pyrrolidin-3-yl)-1H-pyrazol-3-yl)-1H-pyrrolo[2,3-b]pyridine,
5-(1-isopropyl-5-(1-(oxetan-3-yl)pyrrolidin-3-yl)-1H-pyrazol-3-yl)-3-methyl-1H-pyrrolo[2,3-b]pyridine,
3-chloro-5-(1-isopropyl-5-(1-(oxetan-3-yl)pyrrolidin-3-yl)-1H-pyrazol-3-yl)-1H-pyrrolo[2,3-b]pyridine,
3-fluoro-5-(1-isopropyl-5-(1-(oxetan-3-yl)pyrrolidin-3-yl)-1H-pyrazol-3-yl)-1H-pyrrolo[2,3-b]pyridine,
5-(1-isopropyl-5-(1-(oxetan-3-yl)pyrrolidin-3-yl)-1H-pyrazol-3-yl)-3-(trifluoromethyl)pyridin-2-amine,
5-(1-methyl-5-(1-(oxetan-3-yl)piperidin-4-yl)-1H-pyrazol-3-yl)-3-(trifluoromethyl)-1H-pyrrolo[2,3-b]pyridine, 5-(1-isopropyl-5-(1-(oxetan-3-yl)piperidin-4-yl)-1H-pyrazol-3-yl)-3-methyl-1H-pyrrolo[2,3-b]pyridine, 5-(1-isopropyl-5-(1-(oxetan-3-yl)piperidin-4-yl)-1H-pyrazol-3-yl)-3-(trifluoromethyl)-1H-pyrrolo[2,3-b]pyridine, 3-chloro-5-(1-cyclopentyl-5-(1-(oxetan-3-yl)piperidin-4-yl)-1H-pyrazol-3-yl)pyridin-2-amine, 3-chloro-5-(1-isopropyl-5-(1-(oxetan-3-yl)piperidin-4-yl)-1H-pyrazol-3-yl)-1H-pyrrolo[2,3-b]pyridine, 5-(1-isopropyl-5-(1-(oxetan-3-yl)piperidin-4-yl)-1H-pyrazol-3-yl)-1H-pyrrolo[2,3-b]pyridin-2(3H)-one, 3-chloro-5-(5-(1-(oxetan-3-yl)piperidin-4-yl)-1-(tetrahydrofuran-3-yl)-1H-pyrazol-3-yl)pyridin-2-amine, 3-fluoro-5-(1-isopropyl-5-(1-(oxetan-3-yl)piperidin-4-yl)-1H-pyrazol-3-yl)-1H-pyrrolo[2,3-b]pyridine, 5-(1-isopropyl-5-(1-(oxetan-3-yl)piperidin-4-yl)-1H-pyrazol-3-yl)-3-(trifluoromethyl)pyridin-2-amine, 5-(1-isopropyl-5-(1-(oxetan-3-yl)piperidin-4-yl)-1H-pyrazol-3-yl)-1H-pyrrolo[2,3-b]pyridine-3-carbonitrile, 3-chloro-5-(1-isopropyl-5-(1-(oxetan-3-yl)piperidin-4-yl)-1H-pyrazol-3-yl)pyridin-2-amine, 6-(1-isopropyl-5-(1-(oxetan-3-yl)piperidin-4-yl)-1H-pyrazol-3-yl)-3H-imidazo[4,5-b]pyridine, 5-(1-isopropyl-5-(1-(oxetan-3-yl)piperidin-4-yl)-1H-pyrazol-3-yl)-3,3-dimethyl-1H-pyrrolo[2,3-b]pyridin-2(3H)-one, 5-(1-cyclopentyl-5-(1-(oxetan-3-yl)piperidin-4-yl)-1H-pyrazol-3-yl)-3-(trifluoromethyl)pyridin-2-amine, 5-(1-isopropyl-5-(1-(oxetan-3-yl)piperidin-4-yl)-1H-pyrazol-3-yl)-3-methylpyridin-2-amine, 3-ethoxy-5-(1-isopropyl-5-(1-(oxetan-3-yl)piperidin-4-yl)-1H-pyrazol-3-yl)pyridin-2-amine, 3-isopropoxy-5-(1-isopropyl-5-(1-(oxetan-3-yl)piperidin-4-yl)-1H-pyrazol-3-yl)pyridin-2-amine, 5-(1-(3,3-difluorocyclopentyl)-5-(1-(oxetan-3-yl)piperidin-4-yl)-1H-pyrazol-3-yl)-3-ethoxypyridin-2-amine, 5-(1-(3,3-difluorocyclopentyl)-5-(1-(oxetan-3-yl)piperidin-4-yl)-1H-pyrazol-3-yl)-3-isopropoxypyridin-2-amine, 3-(cyclopropylmethoxy)-5-(1-(3,3-difluorocyclopentyl)-5-(1-(oxetan-3-yl)piperidin-4-yl)-1H-pyrazol-3-yl)pyridin-2-amine, 5-(1-cyclopentyl-5-(1-(oxetan-3-yl)piperidin-4-yl)-1H-pyrazol-3-yl)-3-methoxypyridin-2-amine, 5-(1-isopropyl-5-(1-(oxetan-3-yl)piperidin-4-yl)-1H-pyrazol-3-yl)-3-methoxypyridin-2-amine, 5-(1-cyclopentyl-5-(1-(oxetan-3-yl)piperidin-4-yl)-1H-pyrazol-3-yl)-3-isopropoxypyridin-2-amine, 3-chloro-5-(1-(3,3-difluorocyclopentyl)-5-(1-(oxetan-3-yl)piperidin-4-yl)-1H-pyrazol-3-yl)pyridin-2-amine, 2-amino-5-(1-isopropyl-5-(1-(oxetan-3-yl)piperidin-4-yl)-1H-pyrazol-3-yl)nicotinonitrile, 2-amino-5-(1-cyclopentyl-5-(1-(oxetan-3-yl)piperidin-4-yl)-1H-pyrazol-3-yl)nicotinonitrile, 7-(1-isopropyl-5-(1-(oxetan-3-yl)piperidin-4-yl)-1H-pyrazol-3-yl)-3,4-dihydro-2H-pyrido[3,2-b][1,4]oxazine, 5-(1-isopropyl-5-(1-(oxetan-3-yl)piperidin-4-yl)-1H-pyrazol-3-yl)-3,3-dimethyl-2,3-dihydro-1H-pyrrolo[2,3-b]pyridine, 6-(1-isopropyl-5-(1-(oxetan-3-yl)piperidin-4-yl)-1H-pyrazol-3-yl)-1,2,3,4-tetrahydro-1,8-naphthyridine, 5-(5-(1-(oxetan-3-yl)piperidin-4-yl)-1-(tetrahydrofuran-3-yl)-H-pyrazol-3-yl)-3-(trifluoromethyl)pyridin-2-amine, 3-cyclopropyl-5-(1-isopropyl-5-(1-(oxetan-3-yl)piperidin-4-yl)-1H-pyrazol-3-yl)pyridin-2-amine, 3-(difluoromethoxy)-5-(1-isopropyl-5-(1-(oxetan-3-yl)piperidin-4-yl)-1H-pyrazol-3-yl)pyridin-2-amine, 5-(1-(3,3-difluorocyclopentyl)-5-(1-(oxetan-3-yl)piperidin-4-yl)-1H-pyrazol-3-yl)-3-methoxypyridin-2-amine, 5-(5-(1-cyclobutylpiperidin-4-yl)-1-isopropyl-1H-pyrazol-3-yl)-3-(trifluoromethyl)-1H-pyrrolo[2,3-b]pyridine, 5-(5-(1-cyclobutylpiperidin-4-yl)-1-isopropyl-1H-pyrazol-3-yl)-3-(trifluoromethyl)pyridin-2-amine, 5-(1-isopropyl-5-(4-methoxy-1-(oxetan-3-yl)piperidin-4-yl)-1H-pyrazol-3-yl)-3-(trifluoromethyl)pyridin-2-amine, 5-(5-((1R,5S,6s)-3-oxabicyclo[3.1.0]hexan-6-yl)-1-isopropyl-1H-pyrazol-3-yl)-3-(trifluoromethyl)pyridin-2-amine, 5-(5-((1R,5S,6s)-3-oxabicyclo[3.1.0]hexan-6-yl)-1-cyclopentyl-1H-pyrazol-3-yl)-3-chloropyridin-2-amine, 5-(5-((1R,5S,6s)-3-oxabicyclo[3.1.0]hexan-6-yl)-1-isopropyl-1H-pyrazol-3-yl)-3-fluoro-1H-pyrrolo[2,3-b]pyridine, 5-(5-((1R,5S,6r)-3-azabicyclo[3.1.0]hexan-6-yl)-1-(2,2,2-trifluoroethyl)-1H-pyrazol-3-yl)-3-(trifluoromethyl)pyridin-2-amine, 5-(1-isopropyl-5-((1R,5S,6r)-3-(methylsulfonyl)-3-azabicyclo[3.1.0]hexan-6-yl)-1H-pyrazol-3-yl)-3-(trifluoromethyl)pyridin-2-amine 5-(5-((1R,5S,6r)-3-(2,2-difluoroethyl)-3-azabicyclo[3.1.0]hexan-6-yl)-1-isopropyl-1H-pyrazol-3-yl)-3-(trifluoromethyl)pyridin-2-amine, 3-(difluoromethoxy)-5-(1-isopropyl-5-((1R,5S,6r)-3-(2,2,2-trifluoroethyl)-3-azabicyclo[3.1.0]hexan-6-yl)-1H-pyrazol-3-yl)pyridin-2-amine, 3-chloro-5-(1-(oxetan-3-yl)-5-((1R,5S,6r)-3-(2,2,2-trifluoroethyl)-3-azabicyclo[3.1.0]hexan-6-yl)-1H-pyrazol-3-yl)pyridin-2-amine, 3-chloro-5-(1-((3-methyloxetan-3-yl)methyl)-5-((1R,5S,6r)-3-(2,2,2-trifluoroethyl)-3-azabicyclo[3.1.0]hexan-6-yl)-1H-pyrazol-3-yl)pyridin-2-amine, 2-amino-5-(1-(cyclopropylmethyl)-5-((1R,5S,6r)-3-(2,2,2-trifluoroethyl)-3-azabicyclo[3.1.0]hexan-6-yl)-1H-pyrazol-3-yl)nicotinonitrile, 7-(1-isopropyl-5-((1R,5S,6r)-3-(2,2,2-trifluoroethyl)-3-azabicyclo[3.1.0]hexan-6-yl)-1H-pyrazol-3-yl)-1H-pyrazolo[4,3-c]pyridin-4-amine, 1-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)ethanone, 3-chloro-5-(5-((1R,5S,6r)-3-(2-methoxyethyl)-3-azabicyclo[3.1.0]hexan-6-yl)-1-(2,2,2-trifluoroethyl)-1H-pyrazol-3-yl)pyridin-2-amine, 5-(1-isopropyl-5-((1R,5S,6r)-3-(2-methoxyethyl)-3-azabicyclo[3.1.0]hexan-6-yl)-1H-pyrazol-3-yl)-3-(trifluoromethyl)pyridin-2-amine, 3-chloro-5-(1-isopropyl-5-((1R,5S,6r)-3-(2-methoxyethyl)-3-azabicyclo[3.1.0]hexan-6-yl)-1H-pyrazol-3-yl)pyridin-2-amine, 3-(difluoromethoxy)-5-(1-isopropyl-5-((1R,5S,6r)-3-(2-methoxyethyl)-3-azabicyclo[3.1.0]hexan-6-yl)-1H-pyrazol-3-yl)pyridin-2-amine, 3-chloro-5-(1-isobutyl-5-((1R,5S,6r)-3-(2-methoxyethyl)-3-azabicyclo[3.1.0]hexan-6-yl)-1H-pyrazol-3-yl)pyridin-2-amine, 3-chloro-5-(1-((2, 2-difluorocyclopropyl)methyl)-5-((1R,5S,6r)-3-(2-methoxyethyl)-3-azabicyclo[3.1.0]hexan-6-yl)-1H-pyrazol-3-yl)pyridin-2-amine, 5-(1-(cyclopropylmethyl)-5-((1R,5S,6r)-3-(2-methoxyethyl)-3-azabicyclo[3.1.0]hexan-6-yl)-1H-pyrazol-3-yl)-3-(trifluoromethyl)pyridin-2-amine, 3-chloro-5-(1-(cyclopropylmethyl)-5-((1R,5S,6r)-3-(2-methoxyethyl)-3-azabicyclo[3.1.0]hexan-6-yl)-1H-pyrazol-3-yl)pyridin-2-amine, 5-(1-(cyclobutylmethyl)-5-((1R,5S,6r)-3-(2-methoxyethyl)-3-azabicyclo[3.1.0]hexan-6-yl)-1H-pyrazol-3-yl)-3-(trifluoromethyl)pyridin-2-amine, 5-(1-isopropyl-5-((1R,5S,6r)-3-(2-methoxyethyl)-3-azabicyclo[3.1.0]hexan-6-yl)-1H-pyrazol-3-yl)-3-(trifluoromethoxy)pyridin-2-amine, 5-(5-((1R,5S,6r)-3-(2-methoxyethyl)-3-azabicyclo[3.1.0]hexan-6-yl)-1-(2,2,2-trifluoroethyl)-1H-pyrazol-3-yl)-3-(trifluoromethyl)pyridin-2-amine, 3-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)propanenitrile, 1-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)-2-methylpropan-2-ol, 5-(1-isopropyl-5-((1R,5S,6r)-3-(1-methoxypropan-2-yl)-3-azabicyclo[3.1.0]hexan-6-yl)-1H-pyrazol-3-yl)-3-(trifluoromethyl)pyridin-2-amine, (1R,5S,6r)-isopropyl 6-(3-(6-amino-5-(trifluoromethyl)pyridin-3-yl)-1-isopropyl-1H-pyrazol-5-yl)-3-azabicyclo[3.1.0]hexane-3-carboxylate, 3-((1R,5S,6r)-6-(3-(6-amino-5-(trifluoromethyl)pyridin-3-yl)-1-isopropyl-1H-pyrazol-5-yl)-3-azabicyclo[3.1.0]hexan-3-yl)butanenitrile, 5-(1-isopropyl-5-((1R,5S,6r)-3-(oxetan-3-yl)-3-azabicyclo[3.1.0]hexan-6-yl)-1H-pyrazol-3-yl)-1H-pyrrolo[2,3-b]pyridine-3-carbonitrile, 5-(1-isopropyl-5-((1R,5S,6r)-3-(oxetan-3-yl)-3-azabicyclo[3.1.0]hexan-6-yl)-1H-pyrazol-3-yl)-3-(trifluoromethyl)-1H-pyrrolo[2,3-b]pyridine, 5-(1-isopropyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 3-chloro-5-(1-cyclopentyl-5-((1R,5S,6r)-3-(oxetan-3-yl)-3-azabicyclo[3.1.0]hexan-6-yl)-1H-pyrazol-3-yl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-(difluoromethoxy)pyridin-2-amine, 2-amino-5-(1-cyclopentyl-5-((1R,5S,6r)-3-(oxetan-3-yl)-3-azabicyclo[3.1.0]hexan-6-yl)-1H-pyrazol-3-yl)nicotinonitrile, 5-(1-cyclopentyl-5-((1R,5S,6r)-3-(oxetan-3-yl)-3-azabicyclo[3.1.0]hexan-6-yl)-1H-pyrazol-3-yl)-3-cyclopropylpyridin-2-amine, 3-chloro-5-(1-isopropyl-5-((1R,5S,6r)-3-(oxetan-3-yl)-3-azabicyclo[3.1.0]hexan-6-yl)-1H-pyrazol-3-yl)pyridin-2-amine, 3-(difluoromethoxy)-5-(1-isopropyl-5-((1R,5S,6r)-3-(oxetan-3-yl)-3-azabicyclo[3.1.0]hexan-6-yl)-1H-pyrazol-3-yl)pyridin-2-amine, 3-cyclopropyl-5-(1-isopropyl-5-((1R,5S,6r)-3-(oxetan-3-yl)-3-azabicyclo[3.1.0]hexan-6-yl)-1H-pyrazol-3-yl)pyridin-2-amine, 5-(1-isopropyl-5-((1R,5S,6r)-3-(oxetan-3-yl)-3-azabicyclo[3.1.0]hexan-6-yl)-1H-pyrazol-3-yl)-3,3-dimethyl-2,3-dihydro-1H-pyrrolo[2,3-b]pyridine, 2-amino-5-(1-isopropyl-5-((1R,5S,6r)-3-(oxetan-3-yl)-3-azabicyclo[3.1.0]hexan-6-yl)-1H-pyrazol-3-yl)nicotinonitrile, 5-(1-isopropyl-5-((1R,5S,6r)-3-(oxetan-3-yl)-3-azabicyclo[3.1.0]hexan-6-yl)-1H-pyrazol-3-yl)-3-methoxypyridin-2-amine, 3-isopropoxy-5-(1-isopropyl-5-((1R,5S,6r)-3-(oxetan-3-yl)-3-azabicyclo[3.1.0]hexan-6-yl)-1H-pyrazol-3-yl)pyridin-2-amine, 3-chloro-5-(1-cyclobutyl-5-((1R,5S,6r)-3-(oxetan-3-yl)-3-azabicyclo[3.1.0]hexan-6-yl)-1H-pyrazol-3-yl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-isopropoxypyridin-2-amine, 3-chloro-5-(5-((1R,5S,6r)-3-(oxetan-3-yl)-3-azabicyclo[3.1.0]hexan-6-yl)-1-(2,2,2-trifluoroethyl)-1H-pyrazol-3-yl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-(difluoromethoxy)pyridin-2-amine, 5-(1-(cyclopropylmethyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-cyclopropylpyridin-2-amine, 3-chloro-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-(methylsulfonyl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-isopropoxypyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-methoxypyridin-2-amine, 3-(difluoromethyl)-5-(1-isopropyl-5-((1R,5S,6r)-3-(oxetan-3-yl)-3-azabicyclo[3.1.0]hexan-6-yl)-1H-pyrazol-3-yl)pyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-methoxypyridin-2-amine, 5-(1-(cyclobutylmethyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 3-cyclopropyl-5-(1-(cyclopropylmethyl)-5-((1R,5S,6r)-3-(oxetan-3-yl)-3-azabicyclo[3.1.0]hexan-6-yl)-1H-pyrazol-3-yl)pyridin-2-amine, 5-(1-(cyclobutylmethyl)-5-((1R,5S,6r)-3-(oxetan-3-yl)-3-azabicyclo[3.1.0]hexan-6-yl)-1H-pyrazol-3-yl)-3-cyclopropylpyridin-2-amine, 5-(1-cyclobutyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine, 5-(1-(cyclobutylmethyl)-5-((1R,5S,6r)-3-(oxetan-3-yl)-3-azabicyclo[3.1.0]hexan-6-yl)-1H-pyrazol-3-yl)-3-(difluoromethoxy)pyridin-2-amine, 5-(1-isopropyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-(trifluoromethoxy)pyridin-2-amine, 5-(1-(tert-butyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(1-cyclopropyl-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(1-(cyclopropylmethyl)-5-((1R,5S,6r)-3-(oxetan-3-yl)-3-azabicyclo[3.1.0]hexan-6-yl)-1H-pyrazol-3-yl)-3-(difluoromethyl)pyridin-2-amine, 5-(1-cyclopropyl-5-((1R,5S,6r)-3-(oxetan-3-yl)-3-azabicyclo[3.1.0]hexan-6-yl)-1H-pyrazol-3-yl)-3-(difluoromethyl)pyridin-2-amine, 5-(1-cyclopentyl-5-((1R,5S,6r)-3-(oxetan-3-yl)-3-azabicyclo[3.1.0]hexan-6-yl)-1H-pyrazol-3-yl)-3-(difluoromethyl)pyridin-2-amine, 7-(1-isopropyl-5-((1R,5S,6r)-3-(oxetan-3-yl)-3-azabicyclo[3.1.0]hexan-6-yl)-1H-pyrazol-3-yl)-1H-pyrazolo[4,3-c]pyridin-4-amine, 5-(1-(cyclopropylmethyl)-5-((1R,5S,6r)-3-(oxetan-3-yl)-3-azabicyclo[3.1.0]hexan-6-yl)-1H-pyrazol-3-yl)-3-(difluoromethoxy)pyridin-2-amine, 5-(5-((1R,5S,6r)-3-(oxetan-3-yl)-3-azabicyclo[3.1.0]hexan-6-yl)-1-(2,2,2-trifluoroethyl)-1H-pyrazol-3-yl)-3-(trifluoromethyl)pyridin-2-amine, 3-(1,1-difluoroethyl)-5-(1-isopropyl-5-((1R,5S,6r)-3-(oxetan-3-yl)-3-azabicyclo[3.1.0]hexan-6-yl)-1H-pyrazol-3-yl)pyridin-2-amine, 3-(1,1-difluoroethoxy)-5-(1-isopropyl-5-((1R,5S,6r)-3-(oxetan-3-yl)-3-azabicyclo[3.1.0]hexan-6-yl)-1H-pyrazol-3-yl)pyridin-2-amine, 5-(1-((1-methylcyclopropyl)methyl)-5-((1R,5S,6r)-3-(oxetan-3-yl)-3-azabicyclo[3.1.0]hexan-6-yl)-1H-pyrazol-3-yl)-3-(trifluoromethyl)pyridin-2-amine, 5-(5-((1R,5S,6r)-3-cyclobutyl-3-azabicyclo[3.1.0]hexan-6-yl)-1-cyclopentyl-1H-pyrazol-3-yl)-3-(methylsulfonyl)pyridin-2-amine, 5-(1-isopropyl-5-(3-(oxetan-3-yl)-3-azabicyclo[3.1.1]heptan-6-yl)-1H-pyrazol-3-yl)-3-(trifluoromethyl)pyridin-2-amine, 3-chloro-5-(1-isopropyl-5-(3-(oxetan-3-yl)-3-azabicyclo[3.1.1]heptan-6-yl)-1H-pyrazol-3-yl)pyridin-2-amine, 3-(difluoromethoxy)-5-(1-isopropyl-5-(3-(oxetan-3-yl)-3-azabicyclo[3.1.1]heptan-6-yl)-1H-pyrazol-3-yl)pyridin-2-amine, and 5-(1-isopropyl-5-(3-(oxetan-3-yl)-3-azabicyclo[3.1.1]heptan-6-yl)-1H-pyrazol-3-yl)-3-(trifluoromethoxy)pyridin-2-amine, and salts thereof.

61. The method of claim 32, wherein said administering to the CNS neuron is performed in vitro.

62. The method of claim 61, wherein the method further comprises grafting or implanting the CNS neuron into a human patient after administration of the agent.

63. The method of claim 32, wherein the CNS neuron is present in a human patient.

64. The method of claim 32, wherein administering to the CNS neuron comprises administration of said compound of formula I in a pharmaceutically acceptable carrier, diluent or excipient.

65. The method of claim 32, wherein administering to the CNS neuron is carried out by an administration route selected from the group consisting of parenteral, subcutaneous, intravenous, intraperitoneal, intracerebral, intralesional, intramuscular, intraocular, intraarterial interstitial infusion and implanted delivery device.

66. The method of claim 32 further comprising administering one or more additional pharmaceutical agents.

67. The method of claim 32, wherein the administering of a compound of Formula (I) results in a decrease in JNK phosphorylation, JNK activity and/or JNK expression.

68. The method of claim 32, wherein the administering of a compound of Formula (I) results in a decrease of cJun phosphorylation, cJun activity, and/or cJun expression.

69. The method of claim 32, wherein the administering of a compound of Formula (I) results in a decrease in p38 phosphorylation, p38 activity, and/or p38 expression.

\* \* \* \* \*